United States Patent
Zhu et al.

(10) Patent No.: US 7,700,603 B2
(45) Date of Patent: *Apr. 20, 2010

(54) HETEROCYCLIC ASPARTYL PROTEASE INHIBITORS

(75) Inventors: Zhaoning Zhu, Plainsboro, NJ (US); Brian A McKittrick, New Vernon, NJ (US); Zhong-Yue Sun, Parlin, NJ (US); Yuanzan C Ye, Edison, NJ (US); Johannes H Voigt, Cranford, NJ (US); Corey Strickland, Martinsville, NJ (US); Elizabeth M. Smith, Verona, NJ (US); Andrew Stamford, Chatham Township, NJ (US); William J. Greenlee, Teaneck, NJ (US); Robert Mazzola, Stewartsville, NJ (US); John Caldwell, Ringwood, NJ (US); Jared N. Cumming, Garwood, NJ (US); Lingyan Wang, East Brunswick, NJ (US); Yusheng Wu, New York, NY (US); Ulrich Iserloh, Hoboken, NJ (US); Tao Guo, Dayton, NJ (US); Thuy X. H. Le, Monmouth Junction, NJ (US); Kurt W. Saionz, Cranford, NJ (US); Suresh D. Babu, Plainsboro, NJ (US); Rachael C. Hunter, Princeton, NJ (US); Michelle L. Morris, Lawrenceville, NJ (US); Gang Qian, Kendall Park, NJ (US); Dawit Tadesse, East Windsor, NJ (US)

(73) Assignee: Schering Corporation, Kenilworth, NJ (US)

( * ) Notice: Subject to any disclaimer, the term of this patent is extended or adjusted under 35 U.S.C. 154(b) by 525 days.

This patent is subject to a terminal disclaimer.

(21) Appl. No.: 11/149,027

(22) Filed: Jun. 9, 2005

(65) Prior Publication Data
US 2006/0111370 A1 May 25, 2006

Related U.S. Application Data

(63) Continuation-in-part of application No. 11/010,772, filed on Dec. 13, 2004.

(60) Provisional application No. 60/529,535, filed on Dec. 15, 2003.

(51) Int. Cl.
*A01N 43/54* (2006.01)
*C07D 239/02* (2006.01)
*C07D 239/42* (2006.01)
*C07D 401/04* (2006.01)

(52) U.S. Cl. .................. 514/256; 544/320; 544/321

(58) Field of Classification Search .......... 514/256; 544/320, 321
See application file for complete search history.

(56) References Cited

U.S. PATENT DOCUMENTS 5,883,096 A 3/1999 Lowe et al.
5,889,006 A 3/1999 Lowe et al.

(Continued)

FOREIGN PATENT DOCUMENTS

EP 0 231 919 3/1987

(Continued)

OTHER PUBLICATIONS

Barton, H.J, et al., "On the Structure of some Substituted 4,6-Pyrimidinediones", Polish J. Chem., 1995, pp. 235-245, vol. 69.

(Continued)

*Primary Examiner*—James O Wilson
*Assistant Examiner*—Erich A Leeser
(74) *Attorney, Agent, or Firm*—Keith D. MacMillan; William Y. Lee

(57) ABSTRACT

Disclosed are compounds of the formula I

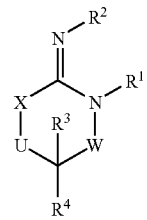

or a stereoisomer, tautomer, or pharmaceutically acceptable salt or solvate thereof, wherein
W is a bond, —C(=S)—, —S(O)—, —S(O)$_2$—, —C(=O)—, —O—, —C(R$^6$)(R$^7$)—, —N(R$^5$)— or —C(=N(R$^5$))—;
X is —O—, —N(R$^5$)— or —C(R$^6$)(R$^7$)—; provided that when X is —O—, U is not —O—, —S(O)—, —S(O)$_2$—, —C(=O)— or —C(=NR$^5$)—;
U is a bond, —S(O)—, —S(O)$_2$—, —C(O)—, —O—, —P(O)(OR$^{15}$)—, —C(=NR$^5$)—, —(C(R$^6$)(R$^7$))$_b$— or —N(R$^5$)—; wherein b is 1 or 2; provided that when W is —S(O)—, —S(O)$_2$—, —O—, or —N(R$^5$)—, U is not —S(O)—, —S(O)$_2$—, —O—, or —N(R$^5$)—; provided that when X is —N(R$^5$)— and W is —S(O)—, —S(O)$_2$—, —O—, or —N(R$^5$)—, then U is not a bond; and R$^1$, R$^2$, R$^3$, R$^4$, R$^5$, R$^6$, and R$^7$ are as defined in the specification; and pharmaceutical compositions comprising the compounds of formula I.

Also disclosed is the method of inhibiting aspartyl protease, and in particular, the methods of treating cardiovascular diseases, cognitive and neurodegenerative diseases, and the methods of inhibiting of Human Immunodeficiency Virus, plasmepins, cathepsin D and protozoal enzymes.

Also disclosed are methods of treating cognitive or neurodegenerative diseases using the compounds of formula I in combination with a cholinesterase inhibitor or a muscarinic m$_1$ agonist or m$_2$ antagonist.

8 Claims, No Drawings

U.S. PATENT DOCUMENTS

| | | | |
|---|---|---|---|
| 5,935,958 | A | 8/1999 | Kozlowski et al. |
| 5,952,349 | A | 9/1999 | Asberom et al. |
| 5,977,138 | A | 11/1999 | Wang et al. |
| 6,037,352 | A | 3/2000 | Lowe et al. |
| 6,043,255 | A | 3/2000 | Lowe et al. |
| 6,066,636 | A | 5/2000 | Kozlowski et al. |
| 6,294,554 | B1 | 9/2001 | Clader et al. |
| 6,458,812 | B1 | 10/2002 | McKittrick et al. |
| 2005/0282825 | A1 | 12/2005 | Malamas et al. |
| 2005/0282826 | A1 | 12/2005 | Malamas et al. |
| 2007/0072852 | A1* | 3/2007 | Zhu et al. ............... 514/229.2 |
| 2007/0072925 | A1 | 3/2007 | Malamas et al. |
| 2007/0299087 | A1 | 12/2007 | Berg et al. |

FOREIGN PATENT DOCUMENTS

| | | |
|---|---|---|
| EP | 0 361 341 | 4/1990 |
| EP | 0 763 054 | 3/1997 |
| EP | 0 969 011 | 1/2000 |
| WO | WO 89/03842 | 5/1989 |
| WO | WO 90/04917 | 5/1990 |
| WO | WO01/07440 | 2/2001 |
| WO | WO 02/02512 | 1/2002 |
| WO | WO 02/02518 | 1/2002 |
| WO | WO 02/02520 | 1/2002 |
| WO | WO 02/07419 | 1/2002 |
| WO | WO02/12243 | 2/2002 |
| WO | WO 02/088101 | 11/2002 |
| WO | WO 03/031412 | 4/2003 |
| WO | WO03/035613 | 5/2003 |
| WO | WO 03/106405 | 12/2003 |
| WO | WO 2005/013020 | 2/2005 |
| WO | WO2005/014540 | 2/2005 |
| WO | WO2005/016876 | 2/2005 |
| WO | WO 2005/058311 | 6/2005 |
| WO | WO 2005/097767 | 10/2005 |
| WO | WO 2005/103043 | 11/2005 |
| WO | WO2005108391 | 11/2005 |
| WO | WO 2005/113484 | 12/2005 |
| WO | WO 2006/002004 | 1/2006 |
| WO | WO 2006/009653 | 1/2006 |
| WO | WO2006/014762 | 2/2006 |
| WO | WO2006/014944 | 2/2006 |
| WO | WO 2006/017836 | 2/2006 |
| WO | WO 2006/017844 | 2/2006 |
| WO | WO 2006/024932 | 3/2006 |
| WO | WO 2006/041404 | 4/2006 |
| WO | WO 2006/044497 | 4/2006 |
| WO | WO2006/138192 | 12/2006 |
| WO | WO2006/138195 | 12/2006 |
| WO | WO2006/138217 | 12/2006 |
| WO | WO2006/138230 | 12/2006 |
| WO | WO2006/138264 | 12/2006 |
| WO | WO2006/138265 | 12/2006 |
| WO | WO2006/138266 | 12/2006 |
| WO | WO 2007/005366 | 1/2007 |
| WO | WO 2007/005404 | 1/2007 |
| WO | WO 2007/016012 | 2/2007 |
| WO | WO 2007/038271 | 4/2007 |
| WO | WO2007/050721 | 5/2007 |
| WO | WO2007/053506 | 5/2007 |
| WO | WO 2007/114771 | 10/2007 |
| WO | WO 2007/145568 | 12/2007 |
| WO | WO 2007/145569 | 12/2007 |
| WO | WO 2007/145570 | 12/2007 |
| WO | WO 2007/145571 | 12/2007 |
| WO | WO2007/146225 | 12/2007 |
| WO | WO 2007/149033 | 12/2007 |
| WO | WO2008/073365 | 6/2008 |
| WO | WO2008/073370 | 6/2008 |
| WO | WO2008/103351 | 8/2008 |

OTHER PUBLICATIONS

Berge, Stephen M, et al., "Pharmaceutical Salts", Journal of Pharmaceutical Sciences, 1977, pp. 1-19, vol. 66, No. 1.

Bingham, Ann L, et al., "Over one hundred solvates of sulfathiazole†", Chem. Commun., 2001, pp. 603-604.

Caira, Mino R, et al., "Preparation and Crystal Characterization of a Polymorph, a Monohydrate, and an Ethyl Acetate Solvate of the Antifungal Fluconazole", Journal of Pharmaceutical Sciences, 2004, pp. 601-611, vol. 93, No. 3.

Coldham, Iain, et al., "Synthesis of the ABC Ring System of Manzamine A", J. Org. Chem., 2002, pp. 6181-6187, vol. 67, No. 17.

Garratt, Peter J, et al., "A Novel Synthesis of Dihydropyrimidines", J. Chem. Soc., Chem. Commun., 1987, pp. 568-569.

Gould, Philip L, "Salt selection for basic drugs", International Journal of Pharmaceutics, 1986, pp. 201-217, vol. 33.

Hasegawa, Kiyoshi, et al., "The Synthesis of the 1,2,4-Thiadiazine-1,1-dioxides[1]", Bulletin of The Chemical Society of Japan, 1972, pp. 1893-1896, vol. 45, No. 6.

Hussein, Ahmad Q, et al., "Synthesen von α-Bromisothiocyanaten" Chem. Ber. 1979, pp. 1948-1955, vol. 112, (abstract included).

Kwon, Chul-Hoon, et al., "Facile Synthesis of Substituted 2-Iminohydantoins", Synthetic Communications, 1987, pp. 1677-1682, vol. 17, No. 14.

Merten, Rudolf, et al., "Notiz über eine neue Synthese von Derivaten des 1.4.2-Diazaphospholidins", Chem. Ber. 1969, pp. 2143-2145, vol. 102, (abstract not included).

Moloney, Gerard P, et al., "A Novel Series of 2,5-Substituted Tryptamine Derivatives as Vascular $5HT_{1B/1D}$ Receptor Antagonists", J. Med. Chem., 1997, pp. 2347-2362, vol. 40, No. 15.

Na, Byoung-Kuk, et al., "Aspartic proteases of Plasmodium vivax are highly conserved in wild isolates", The Korean Journal of Parasitology, 2004, pp. 61-66, vol. 42, No. 2.

Oparil, Suzanne, et al., "The Renin-Angiotensin System (Second of Two Parts)", The New England Journal of Medicine, 1974, pp. 446-457, vol. 291, No. 9.

Page, Philip C. Bulman, et al., "A Convenient Preparation of Symmetrical and Unsymmetrical 1,2-Diketones: Application to Fluorinated Phenytoin Synthesis", Tetrahedron, 1992, pp. 7265-7274, vol. 48, No. 35.

Paik, Seunguk, et al., "α-Aminosulfonopeptides as Possible Functional Analogs of Penicillin; Evidence for their Extreme Instability", Tetrahedron, 1996, pp. 5303-5318, vol. 52, No. 15.

Ugi, Ivar, Novel Methods of Preparative Organic Chemistry IV, "The α-Addition of Immonium Ions and Anions to Isonitriles Accompanied by Secondary Reactions", Angew. Chem. Internat. Edit., 1962, pp. 8-21, vol. 1, No. 1.

Van Tonder, Elsa C, et al., "Preparation and Physicochemical Characterization of 5 Niclosamide Solvates and 1 Hemisolvate", AAPS PharmSciTech, 2004, pp. 1-10, vol. 5, No. 1, Article 12.

Varga, László, et al., "Solution-phase parallel synthesis of 4,6-diarylpyrimidine-2-ylamines and 2-amino-5,5-disubstituted-3,5-dihydro-imidazol-4-ones via a rearrangement", Tetrahedron, 2003, pp. 655-662, vol. 59.

Wang, Ying, et al., "Use of Polymer-Supported Pd Reagents for Rapid and Efficient Suzuki Reactions Using Microwave Heating", American Chemical Society, Organic Letters, 2004, pp. 2793-2796, vol. 6, No. 16.

Weber, W. et al., "First synthesis of the main metabolite of secobarbital", Pharmazie, 1998, pp. 771-775, vol. 53, No. 11.

Winkler, Jeffrey D, et al., Stereoselective Synthesis of the Tetracyclic Core of Manzamine via the Vinylogous Amide Photocycloaddition Cascade§, Tetrahedron, 1998, pp. 7045-7056, vol. 54.

Yu, Jin-Quan, et al., "Diverse Pathways for the Palladium(II)-Mediated Oxidation of Olefins by *tert*-Butylhydroperoxide", American Chemical Society, Organic Letters, 2002, pp. 2727-2730, vol. 4, No. 16.

Intellectual Search Report for PCT/US 2004/041700, mailed Jun. 1, 2005 (6 pages) for CN06136.

Intellectual Search Report for PCT/US 2005/020446, mailed Jul. 26, 2006 (6 pages) for CN06136-01.

ROC (Taiwan) Patent Application No. 093138776 Search Report—1 page Translation, Sep. 17, 2007.

Barton, H.J., et al., "On the Structure of some Substituted 4,6-Pyrimidinediones", Polish J. Chem., 1995, pp. 235-245, vol. 69.

Garratt, Peter J., et al., "A Novel Synthesis of Dihydropyrimidines", J. Chem. Soc., Chem. Commun., 1987, pp. 568-569.

Kwon, Chul-Hoon, et al., "Facile Synthesis of Substituted 2-Iminohydantoins", Synthetic Communications, 1987, pp. 1677-1682, vol. 17, No. 14.

Lin, Peishan, et al., "Synthesis of Novel Guanidinoglycoside: 2-Glycosylamino 4,5-dihydro-6-pyrimidinone", J. Org. Chem., 2001, pp. 8243-8247, vol. 66, No. 24.

Talaty, Erach R., et al., "Preparation of Substituted Imidazolidinones and Hydantoins by Ring-Expansion of Aziridinones", Synlett, 1997, pp. 683-684. vol. 6.

Weber, W. et al., "First synthesis of the main metabolite of secobarbital", Pharmazie, 1998, pp. 771-775, vol. 53, No. 11.

Yusoff, Mashitah M., et al., "Ring-Expansion of an Aziridinone to a Hexahydrotriazine through the Agency of a Novel Rearrangement", Tetrahedron Letters, 1996, pp. 8695-8698, vol. 37, No. 48.

U.S. Appl. No. 11/010,772 Non-Final Office Action mailed Feb. 28, 2008, 10 pages.

U.S. Appl. No. 11/010,772, Applicants' response to Office Action, filed Jun. 27, 2008, 34 pages.

U.S. Appl. No. 11/010,772 Non-Final Office Action mailed Sep. 19, 2008, 8 pages.

\* cited by examiner

HETEROCYCLIC ASPARTYL PROTEASE INHIBITORS

REFERENCE TO RELATED APPLICATIONS

This application claims priority to U.S. Ser. No. 11/010,772 filed on Dec. 13, 2004, which claims the benefit of U.S. Provisional Application No. 60/529,535 filed Dec. 15, 2003.

FIELD OF THE INVENTION

This invention relates to heterocyclic aspartyl protease inhibitors, pharmaceutical compositions comprising said compounds, their use in the treatment of cardiovascular diseases, cognitive and neurodegenerative diseases, and their use as inhibitors of the Human Immunodeficiency Virus, plasmepsins, cathepsin D and protozoal enzymes.

BACKGROUND

Eight human aspartic proteases of the A1 (pepsin-like) family are known to date: pepsin A and C, renin, BACE, BACE 2, Napsin A, cathepsin D in pathological conditions.

The role of renin-angiotensin system (RAS) in regulation of blood pressure and fluid electrolyte has been well established (Oparil, S, et al. N Engl J Med 1974; 291:381-401/446-57). The octapeptide Angiotensin-II, a potent vasoconstrictor and stimulator for release of adrenal aldosterone, was processed from the precursor decapeptide Angiotensin-I, which in turn was processed from angiotensinogen by the renin enzyme. Angiotensin-II was also found to play roles in vascular smooth muscle cell growth, inflammation, reactive oxygen species generation and thrombosis, influence atherogenesis and vascular damage. Clinically, the benefit of interruption of the generation of angiotensin-II through antagonism of conversion of angiotensin-I has been well known and there are a number of ACE inhibitor drugs on the market. The blockade of the earlier conversion of angiotensinogen to angiotensin-I, i.e. the inhibition of renin enzyme, is expected to have similar but not identical effects. Since renin is an aspartyl protease whose only natural substrate is angiotensinogen, it is believed that there would be less frequent adverse effect for controlling high blood pressure and related symptoms regulated by angiotensin-II through its inhibition.

Another protease, Cathepsin-D, is involved in lysosomal biogenesis and protein targeting, and may also be involved in antigen processing and presentation of peptide fragments. It has been linked to numerous diseases including, Alzheimer's, disease, connective tissue disease, muscular dystrophy and breast cancer.

Alzheimer's disease (AD) is a progressive neurodegenerative disease that is ultimately fatal. Disease progression is associated with gradual loss of cognitive function related to memory, reasoning, orientation and judgment. Behavioral changes including confusion, depression and aggression also manifest as the disease progresses. The cognitive and behavioral dysfunction is believed to result from altered neuronal function and neuronal loss in the hippocampus and cerebral cortex. The currently available AD treatments are palliative, and while they ameliorate the cognitive and behavioral disorders, they do not prevent disease progression. Therefore there is an unmet medical need for AD treatments that halt disease progression.

Pathological hallmarks of AD are the deposition of extracellular β-amyloid (Aβ) plaques and intracellular neurofibrillary tangles comprised of abnormally phosphorylated protein tau. Individuals with AD exhibit characteristic Aβ deposits, in brain regions known to be important for memory and cognition. It is believed that Aβ is the fundamental causative agent of neuronal cell loss and dysfunction which is associated with cognitive and behavioral decline. Amyloid plaques consist predominantly of Aβ peptides comprised of 40-42 amino acid residues, which are derived from processing of amyloid precursor protein (APP). APP is processed by multiple distinct protease activities. Aβ peptides result from the cleavage of APP by β-secretase at the position corresponding to the N-terminus of Aβ, and at the C-terminus by γ-secretase activity. APP is also cleaved by α-secretase activity resulting in the secreted, non-amyloidogenic fragment known as soluble APP.

An aspartyl protease known as BACE-1 has been identified as the β-secretase activity responsible for cleavage of APP at the position corresponding to the N-terminus of Aβ peptides.

Accumulated biochemical and genetic evidence supports a central role of Aβ in the etiology of AD. For example, Aβ has been shown to be toxic to neuronal cells in vitro and when injected into rodent brains. Furthermore inherited forms of early-onset AD are known in which well-defined mutations of APP or the presenilins are present. These mutations enhance the production of Aβ and are considered causative of AD.

Since Aβ peptides are formed as a result β-secretase activity, inhibition of BACE-1 should inhibit formation of Aβ peptides. Thus inhibition of BACE-1 is a therapeutic approach to the treatment of AD and other cognitive and neurodegenerative diseases caused by Aβ plaque deposition.

Human immunodeficiency virus (HIV), is the causative agent of acquired immune deficiency syndrome (AIDS). It has been clinically demonstrated that compounds such as indinavir, ritonavir and saquinavir which are inhibitors of the HIV aspartyl protease result in lowering of viral load. As such, the compounds described herein would be expected to be useful for the treatment of AIDS. Traditionally, a major target for researchers has been HIV-1 protease, an aspartyl protease related to renin.

In addition, Human T-cell leukemia virus type I (HTLV-I) is a human retrovirus that has been clinically associated with adult T-cell leukemia and other chronic diseases. Like other retroviruses, HTLV-I requires an aspartyl protease to process viral precursor proteins, which produce mature virions. This makes the protease an attractive target for inhibitor design. (Moore, et al. Purification of HTLV-I Protease and Synthesis of Inhibitors for the treatment of HTLV-I Infection 55th Southeast Regional Meeting of the American Chemical Society, Atlanta, Ga., US Nov. 16-19, 2003 (2003), 1073. CODEN; 69EUCH Conference, AN 2004:137641 CAPLUS.)

Plasmepsins are essential aspartyl protease enzymes of the malarial parasite. Compounds for the inhibition of aspartyl proteases plasmepsins, particularly I, II, IV and HAP, are in development for the treatment of malaria. (Freire, et al. WO 2002074719. Na Byoung-Kuk, et al. Aspartic proteases of *Plasmodium vivax* are highly conserved in wild isolates Korean Journal of Prasitology (2004 June), 42(2) 61-6. Journal code: 9435800) Furthermore, compounds used to target aspartyl proteases plasmepsins (e.g. I, II, IV and HAP), have been used to kill malarial parasites, thus treating patients thus afflicted.

SUMMARY OF THE INVENTION

The present invention relates to compounds having the structural formula I

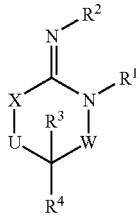

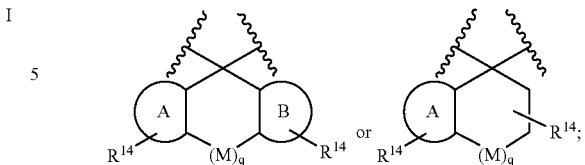

or a stereoisomer, tautomer, or pharmaceutically acceptable salt or solvate thereof, wherein W is a bond, —C(=S)—, —S(O)—, —S(O)$_2$—, —C(=O)—, —O—, —C(R$^6$)(R$^7$)—, —N(R$^5$)— or —C(=N(R$^5$))—;

X is —O—, —N(R$^5$)— or —C(R$^6$)(R$^7$)—; provided that when X is —O—, U is not —O—, —S(O)—, —S(O)$_2$—, —C(=O)— or —C(=NR$^5$)—;

U is a bond, —S(O)—, —S(O)$_2$—, —C(O)—, —O—, —P(O)(OR$^{15}$)—, —C(=NR$^5$)—, —(C(R$^6$)(R$^7$))$_b$— or —N(R$^5$)—; wherein b is 1 or 2; provided that when W is —S(O)—, —S(O)$_2$—, —O—, or —N(R$^5$)—, U is not —S(O)—, —S(O)$_2$—, —O—, or —N(R$^5$)—; provided that when X is —N(R$^5$)— and W is —S(O)—, —S(O)$_2$—, —O—, or —N(R$^5$)—, then U is not a bond;

R$^1$, R$^2$ and R$^5$ are independently selected from the group consisting of H, alkyl, alkenyl, cycloalkyl, cycloalkylalkyl, heterocycloalkyl, heterocycloalkylalkyl, aryl, arylalkyl, heteroaryl, heteroarylalkyl, arylcycloalkyl, —OR$^{15}$, —CN, —C(O)R$^8$, —C(O)OR$^9$, —S(O)R$^{10}$, —S(O)$_2$R$^{10}$, —C(O)N(R$^{11}$)(R$^{12}$), —S(O)N(R$^{11}$)(R$^{12}$), —S(O)$_2$N(R$^{11}$)(R$^{12}$), —NO$_2$, —N=C(R$^8$)$_2$ and —N(R$^8$)$_2$, provided that R$^1$ and R$^5$ are not both selected from —NO$_2$, —N=C(R$^8$)$_2$ and —N(R$^8$)$_2$;

R$^3$, R$^4$, R$^6$ and R$^7$ are independently selected from the group consisting of H, alkyl, cycloalkyl, cycloalkylalkyl, heterocycloalkyl, heterocycloalkylalkyl, aryl, arylalkyl, heteroaryl, heteroarylalkyl, halo, —CH$_2$—O—Si(R$^9$)(R$^{10}$)(R$^{19}$), —SH, —CN, —OR$^9$, —C(O)R$^8$, —C(O)OR$^9$, —C(O)N(R$^1$)(R$^{12}$), —SR$^{19}$, —S(O)N(R$^{11}$)(R$^{12}$), —S(O)$_2$N(R$^{11}$)(R$^{12}$), —N(R$^{11}$)(R$^{12}$), —N(R$^{11}$)C(O)R$^8$, —N(R$^{11}$)S(O)R$^{10}$, —N(R$^{11}$)C(O)N(R$^{12}$)(R$^{13}$), —N(R$^1$)C(O)OR$^9$ and —C(=NOH)R$^8$; provided that when U is —O— or —N(R$^5$)—, then R$^3$, R$^4$, R$^6$ and R$^7$ are not halo, —SH, —OR$^9$, —SR$^{19}$, —S(O)N(R$^1$)(R$^{12}$), —S(O)$_2$N(R$^{11}$)(R$^{12}$), —N(R$^1$)(R$^{12}$), —N(R$^{11}$)C(O)R$^8$, —N(R$^{11}$)S(O)R$^{10}$, —N(R$^{11}$)C(O)N(R$^{12}$)(R$^{13}$), or —N(R$^{11}$)C(O)OR$^9$; provided that when W is —O— or —N(R$^5$)—, then R$^3$ and R$^4$ are not halo, —SH, —OR$^9$, —SR$^{19}$, —S(O)N(R$^{11}$)(R$^{12}$), —S(O)$_2$N(R$^{11}$)(R$^{12}$), —N(R$^{11}$)(R$^{12}$), —N(R$^{11}$)C(O)R$^8$, —N(R$^{11}$)S(O)R$^{10}$, —N(R$^{11}$)C(O)N(R$^{12}$)(R$^{13}$), or —N(R$^{11}$)C(O)OR$^9$; and provided that when X is —N(R$^5$)—, W is —C(O)— and U is a bond; —R$^3$ and R$^4$ are not halo, —CN, —SH, —OR$^9$, —SR$^{19}$, —S(O)N(R$^{11}$)(R$^{12}$) or —S(O)$_2$N(R$^{11}$)(R$^{12}$); or R$^3$, R$^4$, R$^6$ and R$^7$, together with the carbon to which they are attached, form a 3-7 membered cycloalkyl group optionally substituted by R$^{14}$ or a 3-7 membered cycloalkylether optionally substituted by R$^{14}$;

or R$^3$ and R$^4$ or R$^6$ and R$^7$ together with the carbon to which they are attached, are combined to form multicyclic groups such as

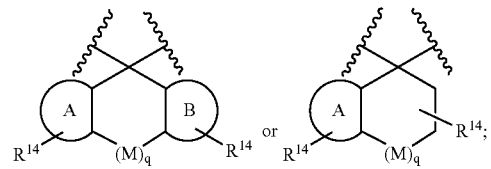

wherein M is —CH$_2$—, S, —N(R$^{19}$)— or O, A and B are independently aryl or heteroaryl and q is 0, 1 or 2 provided that when q is 2, one M must be a carbon atom and when q is 2, M is optionally a double bond; and with the proviso that when R$^3$, R$^4$, R$^6$ and R$^7$ form said multicyclic groups then adjacent R$^3$ and R$^4$ or R$^6$ and R$^7$ groups cannot be combined to form said multicyclic groups;

R$^8$ is independently selected from the group consisting of H, alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, —OR$^{15}$, —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$) and —N(R$^{15}$)C(O)OR$^{16}$;

R$^9$ is independently selected from the group consisting of H, alkyl, cycloalkyl, cycloalkylalkyl, heterocycloalkyl, heterocycloalkylalkyl, aryl, arylalkyl, heteroaryl and heteroarylalkyl;

R$^{10}$ is independently selected from the group consisting of H, alkyl, alkenyl, cycloalkyl, cycloalkylalkyl, cycloalkenyl, heterocycloalkyl, heterocycloalkylalkyl, aryl, arylalkyl, heteroaryl, heteroarylalkyl and —N(R$^{15}$)(R$^{16}$);

R$^{11}$, R$^{12}$ and R$^{13}$ are independently selected from the group consisting of H, alkyl, cycloalkyl, cycloalkylalkyl, heterocycloalkyl, heterocycloalkylalkyl, aryl, arylalkyl, heteroaryl, heteroarylalkyl, —C(O)R$^8$, —C(O)OR$^9$, —S(O)R$^{10}$, —S(O)$_2$R$^{10}$, —C(O)N(R$^{15}$)(R$^{16}$), —S(O)N(R$^{15}$)(R$^{16}$), —S(O)$_2$N(R$^{15}$)(R$^{16}$) and —CN;

R$^{14}$ is 1-5 substituents independently selected from the group consisting of alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —S(O)$_2$N(R$^{15}$)(R$^{15}$), —C(=NOR$^{15}$)R$^{16}$, —P(O)(OR$^{15}$)(OR$^{16}$), —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$) and —N(R$^{15}$)C(O)OR$^{16}$;

R$^{15}$, R$^{16}$ and R$^{17}$ are independently selected from the group consisting of H, alkyl, alkenyl, alkynyl, cycloalkyl, cycloalkylalkyl, heterocycloalkyl, heterocycloalkylalkyl, aryl, arylalkyl, heteroaryl, heteroarylalkyl, arylcycloalkyl, arylheterocycloalkyl, R$^{18}$-alkyl, R$^{18}$-cycloalkyl, R$^{18}$-cycloalkylalkyl, R$^{18}$-heterocycloalkyl, R$^{18}$-heterocycloalkylalkyl, R$^{18}$-aryl, R$^8$-arylalkyl, R$^{18}$-heteroaryl and R$^{18}$-heteroarylalkyl; or $R^{15}$, $R^{16}$ and $R^{17}$ are

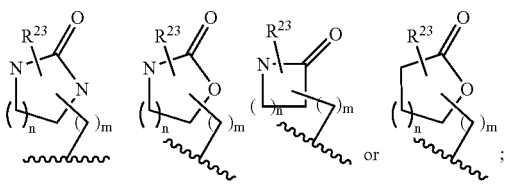

wherein $R^{23}$ numbers 0 to 5 substituents, m is 0 to 6 and n is 1 to 5;

$R^{18}$ is 1-5 substituents independently selected from the group consisting of alkyl, alkenyl, aryl, arylalkyl, arylalkenyl, arylalkynyl, —$NO_2$, halo, heteroaryl, HO-alkyoxyalkyl, —$CF_3$, —CN, alkyl-CN, —C(O)$R^{19}$, —C(O)OH, —C(O)O$R^{19}$, —C(O)NH$R^{20}$, —C(O)$NH_2$, —C(O)$NH_2$—C(O)N(alkyl)$_2$, —C(O)N(alkyl)(aryl), —C(O)N(alkyl)(heteroaryl), —S$R^{19}$, —S(O)$R^{20}$, —S(O)$NH_2$, —S(O)NH(alkyl), —S(O)N(alkyl)(alkyl), —S(O)NH(aryl), —S(O)$_2NH_2$, —S(O)$_2$NH$R^{19}$, —S(O)$_2$NH(heterocycloalkyl), —S(O)$_2$N(alkyl)$_2$, —S(O)$_2$N(alkyl)(aryl), —O$CF_3$, —OH, —O$R^{20}$, —O-heterocycloalkyl, —O-cycloalkylalkyl, —O-heterocycloalkylalkyl, —$NH_2$, —NH$R^{20}$, —N(alkyl)$_2$, —N(arylalkyl)$_2$, —N(arylalkyl)-(heterylalkyl), —NHC(O)$R^{20}$, —NHC(O)$NH_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2R^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or two $R^{18}$ moieties on adjacent carbons can be linked together to form

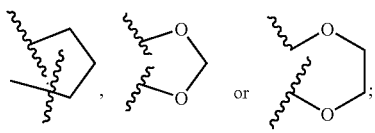

$R^{19}$ is alkyl, cycloalkyl, aryl, arylalkyl or heteroarylalkyl;

$R^{20}$ is alkyl, cycloalkyl, aryl, halo substituted aryl, arylalkyl, heteroaryl or heteroarylalkyl;

and wherein each of the alkyl, cycloalkyl, cycloalkylalkyl, heterocycloalkyl, heterocycloalkylalkyl, aryl, arylalkyl, heteroaryl, heteroarylalkyl, alkenyl and alkynyl groups in $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are independently unsubstituted or substituted by 1 to 5 $R^{21}$ groups independently selected from the group consisting of alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —O$R^{15}$, —C(O)$R^{15}$, —C(O)O$R^{15}$, —C(O)N($R^{15}$)($R^{16}$), —S$R^{15}$, —S(O)N($R^{15}$)($R^{16}$), —CH($R^{15}$)($R^{16}$), —S(O)$_2$N($R^{15}$)($R^{16}$), —C(=NO$R^{15}$)$R^{16}$, —P(O)($R^{15}$)(O$R^{16}$), —N($R^{15}$)($R^{16}$), -alkyl-N($R^{15}$)($R^{16}$), —N($R^{15}$)C(O)$R^{16}$, —$CH_2$—N($R^{15}$)C(O)$R^{16}$, —$CH_2$—N($R^{15}$)C(O)N($R^{16}$)($R^{17}$), —$CH_2$—$R^{15}$; —$CH_2$N($R^{15}$)($R^{16}$), —N($R^{15}$)S(O)$R^{16}$, —N($R^{15}$)S(O)$_2R^{16}$, —$CH_2$—N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —$CH_2$—N($R^{15}$)C(O)N($R^{16}$)($R^{17}$) —N($R^{15}$)C(O)O$R^{16}$, —$CH_2$—N($R^{15}$)C(O)O$R^{16}$, —S(O)$R^{15}$, =NO$R^{15}$, —$N_3$, —$NO_2$ and —S(O)$_2R^{15}$; and wherein each of the alkyl, cycloalkenyl, cycloalkyl, cycloalkylalkyl, heterocycloalkyl, heterocycloalkylalkyl, aryl, arylalkyl, heteroaryl, heteroarylalkyl, alkenyl and alkynyl groups in $R^{21}$ are independently unsubstituted or substituted by 1 to 5 $R^{22}$ groups independently selected from the group consisting of alkyl, cycloalkyl, cycloalkenyl, heterocycloalkyl, aryl, heteroaryl, halo, —$CF_3$, —CN, —O$R^{15}$, —C(O)$R^{15}$, —C(O)O$R^{15}$, -alkyl-C(O)O$R^{15}$, C(O)N($R^{15}$)($R^{16}$), —S$R^{15}$, —S(O)N($R^{15}$)($R^{16}$), —S(O)$_2$N($R^{15}$)($R^{16}$), —(=NO$R^{15}$)$R^{16}$, —P(O)(O$R^{15}$)($R^{16}$), —N($R^{15}$) ($R^{16}$), -alkyl-N($R^{15}$)($R^{16}$), —N($R^{15}$)C(O)$R^{16}$, —$CH_2$—N($R^{15}$)C(O)$R^{16}$, —N($R^{15}$)S(O)$R^{16}$, —N($R^{15}$)S(O)$_2R^{16}$, —$CH_2$—N($R^{15}$)S(O)$_2R^{16}$, —N($R^{15}$)S(O)$_2$N($R^{16}$)($R^{17}$), —N($R^{15}$)S(O)N($R^{16}$)($R^{17}$); —N($R^{15}$)C(O)N($R^{16}$)($R^{17}$), —$CH_2$—N($R^{15}$)C(O)N($R^{16}$)($R^{17}$), —N($R^{15}$)C(O)O$R^{16}$, —$CH_2$—N($R^{15}$)C(O)O$R^{16}$, —$N_3$, =NO$R^{15}$, —$NO_2$, —S(O)$R^{15}$ and —S(O)$_2R^{15}$;

or two $R^{21}$ or two $R^{22}$ moieties on adjacent carbons can be linked together to form

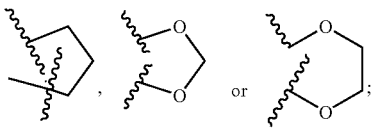

and when $R^{21}$ or $R^{22}$ are selected from the group consisting of —C(=NO$R^{15}$)$R^{16}$, —N($R^{15}$)C(O)$R^{16}$, —$CH_2$—N($R^{15}$)C(O)$R^{16}$, —N($R^{15}$)S(O)$R^{16}$, —N($R^{15}$)S(O)$_2R^{16}$, —$CH_2$—N($R^{15}$)S(O)$_2R^{16}$, —N($R^{15}$)S(O)$_2$N($R^{16}$) ($R^{17}$), —N($R^{15}$)S(O)N($R^{16}$)($R^{17}$), —N($R^{15}$)C(O)N($R^{16}$)($R^{17}$), —$CH_2$—N($R^{15}$)C(O)N($R^{16}$)($R^{17}$), —N($R^{15}$)C(O)O$R^{16}$ and —$CH_2$—N($R^{15}$)C(O)O$R^{16}$, $R^{15}$ and $R^{16}$ together can be a $C_2$ to $C_4$ chain wherein, optionally, one, two or three ring carbons can be replaced by —C(O)— or —N(H)— and $R^{15}$ and $R^{16}$, together with the atoms to which they are attached, form a 5 to 7 membered ring, optionally substituted by $R^{23}$;

$R^{23}$ is 1 to 5 groups independently selected from the group consisting of alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —O$R^{24}$, —C(O)$R^{24}$, —C(O)O$R^{24}$, —C(O)N($R^{24}$)($R^{25}$), —S$R^{24}$, —S(O)N($R^{24}$)($R^{25}$), —S(O)$_2$N($R^{24}$)($R^{25}$), —C(=NO$R^{24}$)$R^{25}$—P(O)(O$R^{24}$)($R^{25}$)—N($R^{24}$)($R^{25}$)-alkyl-N($R^{24}$)($R^{25}$), —N($R^{24}$)C(O)$R^{25}$—$CH_2$—N($R^{24}$)C(O)$R^{25}$, —N($R^{24}$)S(O)$R^{25}$, —N($R^{24}$)S(O)$_2R^{25}$, —$CH_2$—N($R^{24}$)S(O)$_2R^{25}$, —N($R^{24}$)S(O)$_2$N($R^{25}$)($R^{26}$), —N($R^{24}$)S(O)N($R^{25}$)($R^{26}$), —N($R^{24}$)C(O)N($R^{25}$)($R^{26}$), —$CH_2$—N($R^{24}$)C(O)N($R^{25}$)($R^{26}$), —N($R^{24}$)C(O)O$R^{25}$, —$CH_2$—N($R^{24}$)C(O)O$R^{25}$, —S(O)$R^{24}$ and —S(O)$_2R^{24}$; and wherein each of the alkyl, cycloalkyl, cycloalkylalkyl, heterocycloalkyl, heterocycloalkylalkyl, aryl, arylalkyl, heteroaryl, heteroarylalkyl, alkenyl and alkynyl groups in $R^{23}$ are independently unsubstituted or substituted by 1 to 5 $R^{27}$ groups independently selected from the group consisting of alkyl, cycloalkyl, heterocycloalkyl, aryl, heteroaryl, halo, —$CF_3$, —CN, —O$R^{24}$, —C(O)$R^{24}$, —C(O)O$R^{24}$, alkyl-C(O)O$R^{24}$, C(O)N($R^{24}$)($R^{25}$)—S$R^{24}$—S(O)N($R^{24}$)($R^{25}$), —S(O)$_2$N($R^{24}$)($R^{25}$), (=NO$R^{24}$)$R^{25}$—P(O)(O$R^{24}$)(O$R^{25}$), —N($R^{24}$)($R^{25}$), -alkyl-N($R^{24}$)($R^{25}$), —N($R^{24}$)C(O)$R^{25}$, —$CH_2$—N($R^{24}$)C(O)$R^{25}$, —N($R^{24}$)S(O)$R^{25}$, —N($R^{24}$)S(O)$_2R^{25}$, —$CH_2$—N($R^{24}$)S(O)$_2R^{25}$, —N($R^{24}$)S(O)$_2$N($R^{25}$)($R^{26}$), —N($R^{24}$)S(O)N($R^{25}$) ($R^{26}$), —N($R^{24}$)C(O)N($R^{25}$)($R^{26}$), —$CH_2$—N($R^{24}$)C(O)N ($R^{25}$)($R^{26}$), —N($R^{24}$)C(O)O$R^{25}$, —$CH_2$—N($R^{24}$)C(O)O$R^{25}$, —S(O)$R^{24}$ and —S(O)$_2R^{24}$;

$R^{24}$, $R^{25}$ and $R^{26}$ are independently selected from the group consisting of H, alkyl, cycloalkyl, cycloalkylalkyl, heterocycloalkyl, heterocycloalkylalkyl, aryl, arylalkyl, heteroaryl, heteroarylalkyl, arylcycloalkyl, R²⁷-alkyl, R²⁷-cycloalkyl, R²⁷-cycloalkylalkyl, R²⁷-heterocycloalkyl, R²⁷-heterocycloalkylalkyl, R²⁷-aryl, R²⁷-arylalkyl, R²⁷-heteroaryl and R²⁷-heteroarylalkyl;

R²⁷ is 1-5 substituents independently selected from the group consisting of alkyl, aryl, arylalkyl, —NO₂, halo, —CF₃, —CN, alkyl-CN, —C(O)R²⁸, —C(O)OH, —C(O)OR²⁸, —C(O)NHR²⁹, —C(O)N(alkyl)₂, —C(O)N(alkyl)(aryl), —C(O)N(alkyl)(heteroaryl), —SR²⁸, —S(O)₂R²⁹, —S(O)NH₂, —S(O)NH(alkyl), —S(O)N(alkyl)(alkyl), —S(O)NH(aryl), —S(O)₂NH₂, —S(O)₂NH R²⁸, —S(O)₂NH(aryl), —S(O)₂NH(heterocycloalkyl), —S(O)₂N(alkyl)₂, —S(O)₂N(alkyl)(aryl), —OH, —OR²⁹, —O-heterocycloalkyl, —O-cycloalkylalkyl, —O-heterocycloalkylalkyl, —NH₂, —NHR²⁹, —N(alkyl)₂, —N(arylalkyl)₂, —N(arylalkyl)(heteroarylalkyl), —NHC(O)R²⁹, —NHC(O)NH₂, —NHC(O)NH(alkyl), —NHC(O)N(alkyl)(alkyl), —N(alkyl)C(O)NH(alkyl), —N(alkyl)C(O)N(alkyl)(alkyl), —NHS(O)₂R²⁹, —NHS(O)₂NH(alkyl), —NHS(O)₂N(alkyl)(alkyl), —N(alkyl)S(O)₂NH(alkyl) and —N(alkyl)S(O)₂N(alkyl)(alkyl);

R²⁸ is alkyl, cycloalkyl, arylalkyl or heteroarylalkyl; and
R²⁹ is alkyl, cycloalkyl, aryl, arylalkyl, heteroaryl or heteroarylalkyl;

provided that when W is —C(O)— and U is a bond, R¹ is not optionally substituted phenyl, and that when U is —C(O)— and W is a bond, R⁵ is not optionally substituted phenyl;

provided that neither R¹ nor R⁵ is —C(O)-alkyl-azetidinone or alkyl di-substituted with (—COOR¹⁵ or —C(O)N(R¹⁵)(R¹⁶)) and (—N(R¹⁵)(R¹⁶), —N(R¹⁵)C(O)R¹⁶, —N(R¹⁵)S(O)R¹⁶, —N(R¹⁵)S(O)₂R¹⁶, —N(R¹⁵)S(O)₂N(R¹⁶)(R¹⁷), —N(R¹⁵)S(O)N(R¹⁶)(R¹⁷), —N(R¹⁵)C(O)N(R¹⁶)(R¹⁷) or —N(R¹⁵)C(O)OR¹⁶);

provided that when R¹ is methyl, X is —N(R⁵)—, R² is H, W is —C(O)— and U is a bond, (R³, R⁴) is not (H, H), (phenyl, phenyl), (H, phenyl), (benzyl, H), (benzyl, phenyl), (i-butyl, H), (i-butyl, phenyl), (OH-phenyl, phenyl), (halophenyl, phenyl), or (CH₃O-phenyl, NO₂-phenyl); and when W is a bond and U is —C(O)—, (R³, R⁴) is not (H, H), (phenyl, phenyl), (H, phenyl), (benzyl, H), (benzyl, phenyl), (i-butyl, H), (i-butyl, phenyl), (OH-phenyl, phenyl), (halophenyl, phenyl), or (CH₃O-phenyl, NO₂-phenyl);

provided that when X is —N(R⁵)—, R¹ and R⁵ are each H, W is C(O)— and U is a bond, (R³, R⁴) is not (optionally substituted phenyl, optionally substituted benzyl), (optionally substituted phenyl, heteroarylalkyl) or (heteroaryl, heteroarylalkyl);

provided that when U is a bond, W is —C(O)—, and R³ and R⁴ form a ring with the carbon to which they are attached, R¹ is not 2-CF₃-3-CN-phenyl;

provided that when X is —N(R⁵)—, U is —O— and W is a bond or —C(R⁶)(R⁷)—, (R³, R⁴) is not (H, —NHC(O)-alkyl-heteroaryl) or (H, alkyl-NHC(O)-alkyl-heteroaryl); and provided that when X is —N(R⁵)—, R¹ and R⁵ are not -alkylaryl-aryl-SO₂—N(R¹⁵)(R¹⁶) wherein R¹⁵ is H and R¹⁶ is heteroaryl;

provided that when R¹ is R²¹-aryl or R²¹-arylalkyl, wherein R²¹ is —OCF₃, —S(O)CF₃, —S(O)₂CF₃, —S(O)alkyl, —S(O)₂alkyl, —S(O)₂CHF₂, —S(O)₂CF₂CF₃, —OCF²CHF₂, —OCHF₂, —OCH₂CF₃, —SF₅ or —S(O)₂NR¹⁵R¹⁶;

wherein R¹⁵ and R¹⁶ are independently selected from the group consisting of H, alkyl, alkenyl, cycloalkyl, heterocycloalkyl, aryl and heteroaryl, R¹⁸-alkyl, R¹⁸-cycloalkyl, R¹⁸-heterocycloalkyl, R¹⁸-aryl and R¹⁸-heteroaryl; U is a bond or —CH₂; and X is —N(R⁵)—; then R⁵ is H;

provided that when U is a bond,
R³ and R⁴ are alkyl,

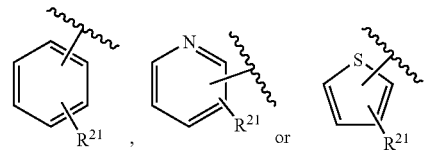

where R²¹ is halo, —CN, alkyl, alkoxy, haloalkyl or haloalkoxy, or R³ and R⁴, together with the carbon to which they are attached, form a 3-7 membered cycloalkyl group, and R¹ is

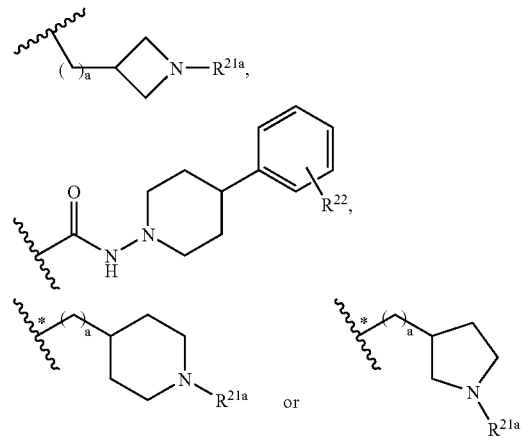

where a is 0 to 6 and R²² is alkyl, alkoxy, halo, —CN, —OH, —NO₂ or haloalkyl;

then R²¹ᵃ is not H, —C(O)₂R¹⁵, wherein R¹⁵ is selected from the group consisting of alkyl, cycloalkyl and alkyl substituted with phenyl, alkyl or alkyl-R²² wherein R²² is selected from the group consisting of phenyl, phenyl substituted with alkyl, and

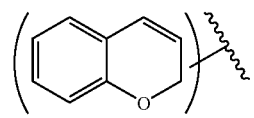

wherein R²² is selected from the group consisting of H, methoxy, nitro, oxo, —OH, halo and alkyl,

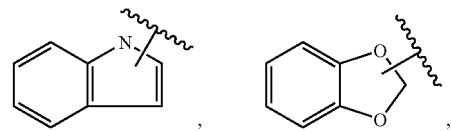

-continued

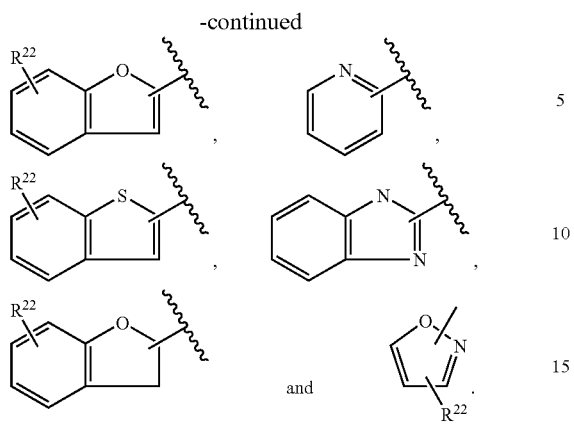

In another aspect, the invention relates to a pharmaceutical composition comprising at least one compound of formula I and a pharmaceutically acceptable carrier.

In another aspect, the invention comprises the method of inhibiting aspartyl protease comprising administering at least one compound of formula I to a patient in need of such treatment.

More specifically, the invention comprises: the method of treating a cardiovascular disease such as hypertension, renal failure, or a disease modulated by renin inhibition; the method of treating Human Immunodeficiency Virus; the method of treating a cognitive or neurodegenerative disease such as Alzheimer's Disease; the method of inhibiting plasmepins I and II for treatment of malaria; the method of inhibiting Cathepsin D for the treatment of Alzheimer's Disease, breast cancer, and ovarian cancer; and the method of inhibiting protozoal enzymes, for example inhibition of *plasmodium falciparnum*, for the treatment of fungal infections. Said method of treatment comprise administering at least one compound of formula I to a patient in need of such treatment. In particular, the invention comprises the method of treating Alzheimer's disease comprising administering at least one compound of formula I to a patient in need of such treatment.

In another aspect, the invention comprises the method of treating Alzheimer's disease comprising administering to a patient I need of such treatment a combination of at least one compound of formula I and a cholinesterase inhibitor or a muscarinic $m_1$ agonist or $m_2$ antagonist.

In a final aspect, the invention relates to a kit comprising in separate containers in a single package pharmaceutical compositions for use in combination, in which one container comprises a compound of formula I in a pharmaceutically acceptable carrier and a second container comprises a cholinesterase inhibitor or a muscarinic $m_1$ agonist or $m_2$ antagonist in a pharmaceutically acceptable carrier, the combined quantities being an effective amount to treat a cognitive disease or neurodegenerative disease such as Alzheimer's disease.

DETAILED DESCRIPTION

Compounds of formula I wherein X, W and U are as defined above include the following independently preferred structures:

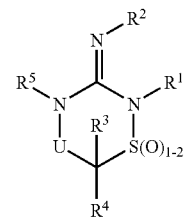

IA

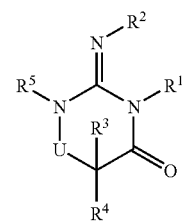

IB

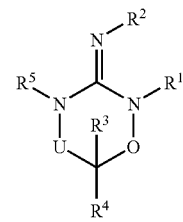

IC

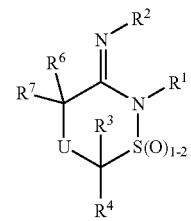

ID

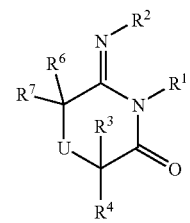

IE

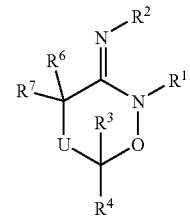

IF

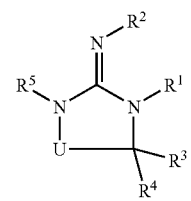

IG

-continued

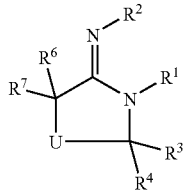

IH

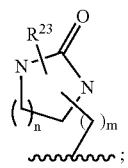

In compounds of formulas IA to IF, U is preferably a bond or —C(R$^6$)(R$^7$)—. In compounds of formula IG and IH, U is preferably —C(O)—.

It will be understood that since the definition of R$^1$ is the same as the definition of R$^5$, when X is —N(R$^5$)—, compounds of formula I wherein W is a bond and U is a bond, —S(O)—, —S(O)$_2$—, —C(O)—, —O—, —C(R$^6$)(R$^7$)— or —N(R$^5$)— are equivalent to compounds of formula I wherein U is a bond and W is a bond, —S(O)—, —S(O)$_2$—, —C(O)—, —O—, —C(R$^6$)(R$^7$)— or —N(R$^5$)—.

More preferred compounds of the invention are those of formula IB wherein U is a bond or those of formula IB wherein U is —C(R$^6$)(R$^7$)—.

Another group of preferred compounds of formula I is that wherein R$^2$ is H.

R$^3$, R$^4$, R$^6$ and R$^7$ are preferably selected from the group consisting of alkyl, cycloalkyl, cycloalkylalkyl, heterocycloalkyl, heterocycloalkylalkyl, aryl, arylalkyl, heteroaryl, heteroarylalkyl, halo, —CH$_2$—O—Si(R$^9$)(R$^{10}$)(R$^{19}$), —SH, —CN, —OR$^9$, —C(O)R$^8$, —C(O)OR$^9$, —C(O)N(R$^{11}$)(R$^{12}$), —SR$^{19}$, —S(O)N(R$^{11}$)(R$^{12}$), —S(O)$_2$N(R$^{11}$)(R$^{12}$), —N(R$^{11}$)(R$^{12}$), —N(R$^{11}$)C(O)R$^8$, —N(R$^{11}$)S(O)R$^{10}$, —N(R$^{11}$)C(O)N(R$^{12}$)(R$^{13}$), —N(R$^{11}$)C(O)OR$^9$ and —C(=NOH)R$^8$.

R$^3$, R$^4$, R$^6$ and R$^7$ are preferably selected from the group consisting of aryl, heteroaryl, heteroarylalkyl, arylalkyl, cycloalkyl, heterocycloalkyl, heterocycloalkylalkyl, alkyl and cycloalkylalkyl.

In a group of preferred compounds
U is a bond or —C(O)—;
W is a bond or —C(O)—;
X is —N(R$^5$);
R$^1$ is H, alkyl, R$^{21}$-alkyl, arylalkyl, R$^{21}$-arylalkyl, cycloalkylalkyl, R$^{21}$-cycloalkylalkyl, heterocycloalkyalkyl or R$^{21}$-heterocycloalkylalkyl,
R$^2$ is H;
R$^3$ is alkyl, cycloalkylalkyl, cycloalkyl, aryl, arylalkyl, R$^{21}$-alkyl, R$^{21}$-cycloalkylalkyl, R$^{21}$-cycloalkyl, R$^{21}$-aryl or R$^{21}$-arylalkyl;
R$^4$ is alkyl, cycloalkylalkyl, cycloalkyl, aryl, arylalkyl, R$^{21}$-alkyl, R$^{21}$-cycloalkylalkyl, R$^{21}$-cycloalkyl, R$^{21}$-aryl or R$^{21}$-arylalkyl;
R$^5$ is H, alkyl, R$^{21}$-alkyl, arylalkyl, R$^{21}$-arylalkyl, cycloalkylalkyl, R$^{21}$-cycloalkylalkyl, heterocycloalkyalkyl or R$^{21}$-heterocycloalkylalkyl;
R$^6$ is alkyl cycloalkylalkyl, cycloalkyl, aryl, arylalkyl, R$^{21}$-alkyl, R$^{21}$-cycloalkylalkyl, R$^{21}$-cycloalkyl, R$^{21}$-aryl or R$^{21}$-arylalkyl;
R$^7$ is alkyl, cycloalkylalkyl, cycloalkyl, aryl, arylalkyl, R$^{21}$-alkyl, R$^{21}$-cycloalkylalkyl, R$^{21}$-cycloalkyl, R$^{21}$-aryl or R$^{21}$-arylalkyl;
R$^{15}$, R$^{16}$ and R$^{17}$ is H, R$^{18}$-alkyl, alkyl or R$^{21}$ is alkyl, aryl, halo, —OR$^{15}$, —NO$_2$, —C(O)R$^{15}$, —CH$_2$—N(R$^{15}$)C(O)N(R$^{16}$)(R$^{17}$) or —CH(R$^{15}$)(R$^{16}$);
n is 1;
m is 1;
R$^1$ is —OR$^{20}$
R$^{20}$ is aryl; and
R$^{23}$ is alkyl.
In a group of preferred compounds
R$^3$, R$^4$, R$^6$ and R$^7$ are

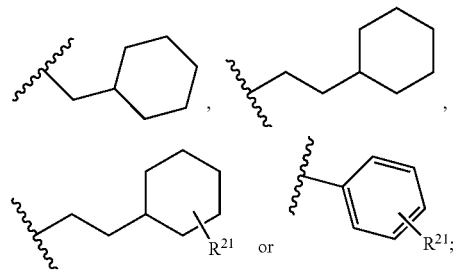

and R$^1$ and R$^5$ is H, CH$_3$,

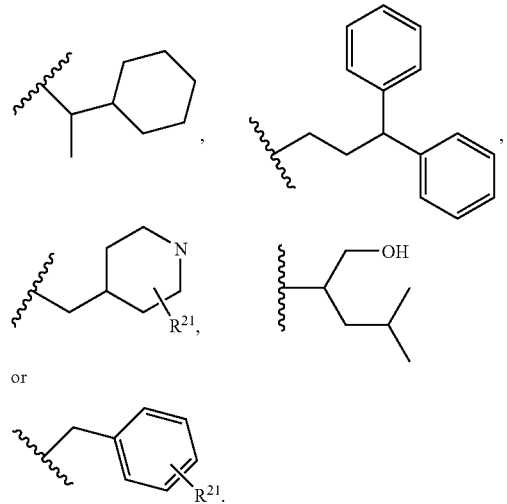

In an additional group of preferred compounds;
U is a bond or —C(O)—;
W is a bond or —C(O)—;
X is —N(R$^5$)—;
R$^1$ is H, alkyl, R$^{21}$-alkyl, arylalkyl, R$^{21}$-arylalkyl, cycloalkylalkyl, R$^{21}$-cycloalkylalkyl, heterocycloalkyalkyl or R$^{21}$-heterocycloalkylalkyl,
R$^2$ is H;
R$^3$ is alkyl, cycloalkylalkyl, cycloalkyl, aryl, arylalkyl, R$^{21}$-alkyl, R$^{21}$-cycloalkylalkyl, R$^{21}$-cycloalkyl, R$^{21}$-aryl, R$^{21}$-arylalkyl, heteroarylalkyl, heteroaryl, heterocycloalkyl, heterocycloalkylalkyl, $R^{21}$-heteroarylalkyl, $R^{21}$-heteroaryl, $R^{21}$-heterocycloalkyl or $R^{21}$-heterocycloalkylalkyl;

$R^4$ is alkyl, cycloalkylalkyl, cycloalkyl, aryl, arylalkyl, $R^{21}$-alkyl, $R^{21}$-cycloalkylalkyl, $R^{21}$-cycloalkyl, $R^{21}$-aryl, $R^{21}$-arylalkyl, heteroarylalkyl, heteroaryl, heterocycloalkyl, heterocycloalkylalkyl, $R^{21}$-heteroarylalkyl, $R^{21}$-heteroaryl, $R^{21}$-heterocycloalkyl or $R^{21}$-heterocycloalkylalkyl;

$R^5$ is H, alkyl, $R^{21}$-alkyl, arylalkyl, $R^{21}$-arylalkyl, cycloalkylalkyl, $R^{21}$-cycloalkylalkyl, heterocycloalkyalkyl or $R^{21}$-heterocycloalkylalkyl;

$R^6$ is alkyl, cycloalkylalkyl, cycloalkyl, aryl, arylalkyl, $R^{21}$-alkyl, $R^{21}$ cycloalkylalkyl, $R^{21}$-cycloalkyl, $R^{21}$-aryl, $R^{21}$-arylalkyl, heteroarylalkyl, heteroaryl, heterocycloalkyl, heterocycloalkylalkyl, $R^{21}$-heteroarylalkyl, $R^{21}$-heteroaryl, $R^{21}$-heterocycloalkyl or $R^{21}$-heterocycloalkylalkyl;

$R^7$ is alkyl, cycloalkylalkyl, cycloalkyl, aryl, arylalkyl, $R^{21}$-alkyl, $R^{21}$-cycloalkylalkyl, $R^{21}$-cycloalkyl, $R^{21}$-aryl, $R^{21}$-arylalkyl, heteroarylalkyl, heteroaryl, heterocycloalkyl, heterocycloalkylalkyl, $R^{21}$-heteroarylalkyl, $R^{21}$-heteroaryl, $R^{21}$-heterocycloalkyl or $R^{21}$-heterocycloalkylalkyl;

$R^{15}$, $R^{16}$ and $R^{17}$ is H, cycloalkyl, cycloalkylalkyl, $R^{18}$-alkyl, alkyl, aryl, $R^{18}$-aryl, $R^{18}$-arylalkyl, arylalkyl,

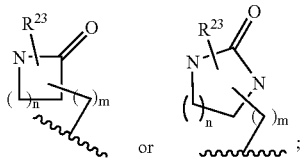

n is 1 or 2;
m is 0 or 1;
$R^{18}$ is —$OR^{20}$ or halo;
$R^{20}$ is aryl or halo substituted aryl;
$R^{21}$ is alkyl, aryl, heteroaryl, $R^{22}$-alkyl, $R^{22}$-aryl, $R^{22}$-heteroaryl, halo, heterocycloalkyl, —$N(R^{15})(R^{16})$, —$OR^{15}$, —$NO_2$, —$C(O)R^{15}$, —$N(R^{15})C(O)R^{16}$, —$N(R^{15})S(O)_2R^1$, —$CH_2$—$N(R^{15})C(O)N(R^{16})(R^{17})$, —$N(R^{15})C(O)N(R^{16})(R^{17})$ or —$CH(R^{15})(R^{16})$;

$R^{22}$ is —$OR^{15}$ or halo and
$R^{23}$ is H or alkyl.

It is noted that the carbons of formula I may be replaced with 1 to 3 silicon atoms so long as all valency requirements are satisfied.

As used above, and throughout the specification, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, isopropyl, n-butyl, t-butyl, n-pentyl, heptyl, nonyl and decyl. $R^2$-substituted alkyl groups include fluoromethyl, trifluoromethyl and cyclopropylmethyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl.

"Aryl" means an aromatic monocyclic or multicyclic ring system comprising about 6 to about 14 carbon atoms, preferably about 6 to about 10 carbon atoms. The aryl group can be optionally substituted with one or more substituents (e.g., $R^{18}$, $R^{21}$, $R^{22}$, etc.) which may be the same or different, and are as defined herein or two substituents on adjacent carbons can be linked together to form

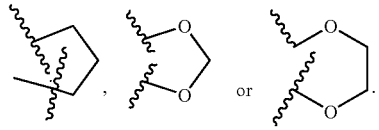

Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one to eight of the ring atoms is an element other than carbon, for example nitrogen, oxygen or sulfur, alone or in combination. Preferred heteroaryls contain about 5 to about 6 ring atoms. The "heteroaryl" can be optionally substituted by one or more $R^{21}$ substituents which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more $R^{21}$ substituents which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like. Further non-limiting examples of cycloalkyl include the following

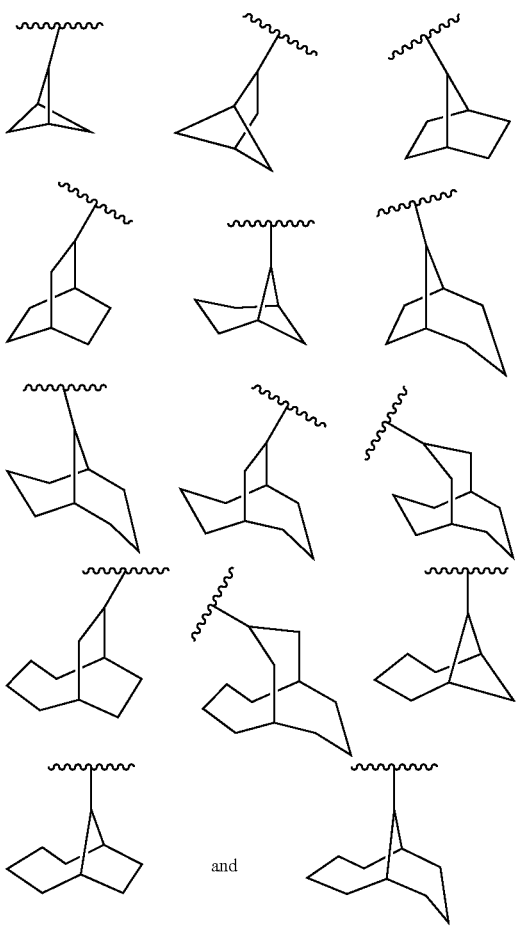

"Cycloalkylether" means a non-aromatic ring of 3 to 7 members comprising an oxygen atom and 2 to 7 carbon atoms. Ring carbon atoms can be substituted, provided that substituents adjacent to the ring oxygen do not include halo or substituents joined to the ring through an oxygen, nitrogen or sulfur atom.

"Cycloalkenyl" means a non-aromatic mono or multicyclic ring system comprising about 3 to about 10 carbon atoms, preferably about 5 to about 10 carbon atoms which contains at least one carbon-carbon double bond. The cycloalkenyl ring can be optionally substituted with one or more $R^{21}$ substituents which may be the same or different, and are as defined above. Preferred cycloalkenyl rings contain about 5 to about 7 ring atoms. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclenyl" means a non-aromatic monocyclic or multicyclic ring system comprising about 3 to about 14 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Halo" means fluoro, chloro, bromo, or iodo groups. Preferred are fluoro, chloro or bromo, and more preferred are fluoro and chloro.

"Haloalkyl" means an alkyl as defined above wherein one or more hydrogen atoms on the alkyl is replaced by a halo group defined above.

"Heterocyclyl" (or heterocycloalkyl) means a non-aromatic saturated monocyclic or multicyclic ring system comprising about 3 to about 14 ring atoms, preferably about 5 to about 10 ring atoms, in which 1-3, preferably 1 or 2 of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more $R^{21}$ substituents which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Arylcycloalkyl" means a group derived from a fused aryl and cycloalkyl as defined herein. Preferred arylcycloalkyls are those wherein aryl is phenyl and cycloalkyl consists of about 5 to about 6 ring atoms. The arylcycloalkyl can be optionally substituted by 1-5 $R^{21}$ substituents. Non-limiting examples of suitable arylcycloalkyls include indanyl and 1,2,3,4-tetrahydronaphthyl and the like. The bond to the parent moiety is through a non-aromatic carbon atom.

"Arylheterocycloalkyl" means a group derived from a fused aryl and heterocycloalkyl as defined herein. Preferred arylcycloalkyls are those wherein aryl is phenyl and heterocycloalkyl consists of about 5 to about 6 ring atoms. The arylheterocycloalkyl can be optionally substituted by 1-5 $R^{21}$ substituents. Non-limiting examples of suitable arylheterocycloalkyls include

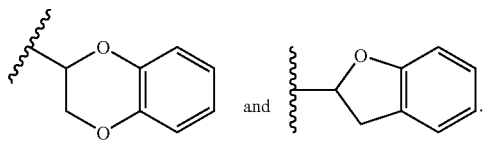

The bond to the parent moiety is through a non-aromatic carbon atom.

Similarly, "heteroarylalkyl" "cycloalkylalkyl" and "heterocycloalkylalkyl" mean a heteroaryl-, cycloalkyl- or heterocycloalkyl-alkyl-group in which the heteroaryl, cycloalkyl, heterocycloalkyl and alkyl are as previously described. Preferred groups contain a lower alkyl group. The bond to the parent moiety is through the alkyl.

"Acyl" means an H—C(O)—, alkyl-C(O)—, alkenyl-C(O)—, alkynyl-C(O)— or cycloalkyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Alkyoxyalkyl" means a group derived from an alkoxy and alkyl as defined herein. The bond to the parent moiety is through the alkyl.

"Arylalkenyl" means a group derived from an aryl and alkenyl as defined herein. Preferred arylalkenyls are those wherein aryl is phenyl and the alkenyl consists of about 3 to about 6 atoms. The arylalkenyl can be optionally substituted by one or more $R^{27}$ substituents. The bond to the parent moiety is through a non-aromatic carbon atom.

"Arylalkynyl" means a group derived from a aryl and alkynyl as defined herein. Preferred arylalkynyls are those wherein aryl is phenyl and the alkynyl consists of about 3 to about 6 atoms. The arylalkynyl can be optionally substituted by one or more $R^{27}$ substituents. The bond to the parent moiety is through a non-aromatic carbon atom.

The suffix "ene" on alkyl, aryl, hetercycloalkyl, etc. indicates a divalent moiety, e.g., —CH$_2$CH$_2$— is ethylene, and

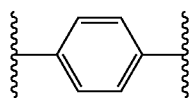

is para-phenylene.

The term "optionally substituted" means optional substitution with the specified groups, radicals or moieties, in available position or positions.

Substitution on a cycloalkylalkyl, heterocycloalkylalkyl, arylalkyl, or heteroarylalkyl moiety includes substitution on the ring portion and/or on the alkyl portion of the group.

When a variable appears more than once in a group, e.g., $R^8$ in —N($R^8$)$_2$, or a variable appears more than once in the structure of formula I, e.g., $R^{15}$ may appear in both $R^1$ and $R^3$, the variables can be the same or different.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art. With respect to the compositions and methods comprising the use of "at least one compound of formula I," one to three compounds of formula I can be administered at the same time, preferably one.

As used herein, the term "composition" is intended to encompass a product comprising the specified ingredients in the specified amounts, as well as any product which results, directly or indirectly, from combination of the specified ingredients in the specified amounts.

The wavy line ~~~ as a bond generally indicates a mixture of, or either of, the possible isomers, e.g., containing (R)- and (S)-stereochemistry. For example,

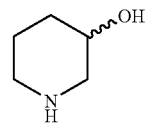

means containing both

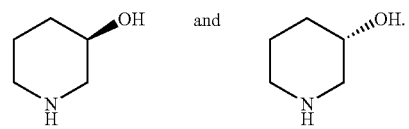

Lines drawn into the ring systems, such as, for example:

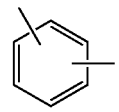

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

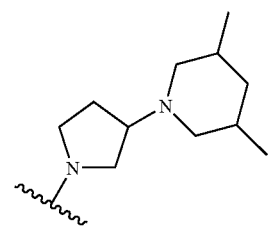

represents

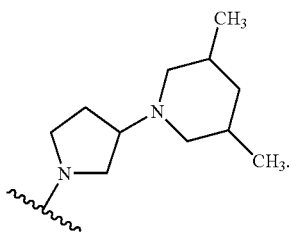

It should also be noted that any heteroatom with unsatisfied valences in the text, schemes, examples, structural formulae, and any Tables herein is assumed to have the hydrogen atom or atoms to satisfy the valences.

Those skilled in the art will recognize that certain compounds of formula I are tautomeric, and all such tautomeric forms are contemplated herein as part of the present invention. For example, a compound wherein X is —N($R^5$)— and $R^1$ and $R^5$ are each H can be represented by any of the following structures:

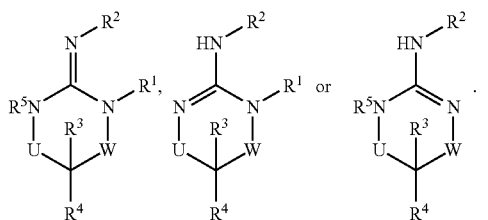

When $R^{21}$ and $R^{22}$, are, for example, —N($R^{15}$)C(O)N($R^{16}$)($R^{17}$) and $R^{15}$ and $R^{16}$ form a ring, the moiety formed, is, for example,

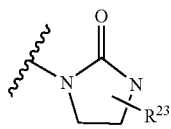

or

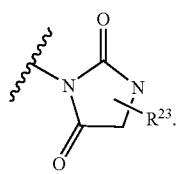

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting aspartyl protease and/or inhibiting BACE-1 and thus producing the desired therapeutic effect in a suitable patient.

The compounds of formula I form salts which are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Polymorphic forms of the compounds of formula I, and of the salts, solvates and prodrugs of the compounds of formula I, are intended to be included in the present invention Compounds of formula I can be made using procedures known in the art. Preparative methods for preparing starting materials and compounds of formula I are show below as general reaction schemes (Method A, Method B, etc.) followed by specific procedures, but those skilled in the art will recognize that other procedures can also be suitable. In the Schemes and in the Examples below, the following abbreviations are used:

methyl: Me; ethyl: Et; propyl: Pr; butyl: Bu; benzyl: Bn; tertiary butyloxycarbonyl: Boc or BOC
  high pressure liquid chromatography: HPLC
  liquid chromatography mass spectroscopy: LCMS
  room temperature: RT or rt
  day: d; hour: h; minute: min
  retention time: Rt
  microwave: gW
  saturated: sat.; anhydrous: anhyd.
  1-hydroxybenzotriazole: HOBt
  1-(3-dimethylaminopropyl)-3-ethylcarbodiimide hydrochloride: EDCI
  ethyl acetate: EtOAc
  Benzyloxycarbonyl: CBZ
  [1-(chloromethyl)-4-fluoro-1,4-diazoniabicyclo[2.2.2]octane bis(tetrafluoroborate)]: Selectfluor
  1,8-diazabicyclo[5,4,0]undec-7-ene: DBU tetrahydrofuran: THF; N,N-dimethylformamide: DMF; methanol: MeOH; diethyl ether: $Et_2O$; acetic acid: AcOH; acetonitrile: MeCN; trifluoroacetic acid: TFA; dichloromethane: DCM; dimethoxyethane: DME; diphenylphosphinoferrocene (dppf);
  n-butyllithium: n-BuLi; lithium diisopropylamide: LDA
  1-hydroxy-7-azabenzotriazole: HOAt
  4-N,N-dimethylaminopyridine: DMAP; diisopropylethylamine: DIEA; N-methylmorpholine: NMM.
  Microporous Toluene sulfonic acid resin (MP-TsOH resin)
  tris-(2-aminoethyl)aminomethyl polystyrene (PS-trisamine)
  methylisocyanate polystyrene (PS-NCO)
  Saturated (sat.); anhydrous. (anhyd); room temperature (rt); hour (h); Minutes (Min), Retention Time (Rt); molecular weight (MW); milliliter (mL); gram (g). milligram (mg); equivalent (eq); day (d); microwave (μW); microliter (μL);

All NMR data were collected on 400 MHz NMR spectrometers unless otherwise indicated. LC-Electrospray-Mass spectroscopy with a C-18 column and 5% to 95% MeCN in water as the mobile phase was used to determine the molecular mass and retention time. The tables contain the compounds with retention time/observed MW and/or NMR data.

For internal consistency in the reaction schemes shown in Methods A to DF, the product of each method is shown as structure A4, B4, C3, etc., wherein certain variables are as defined for that method, but it will be apparent that, for example, A4 has the same structure as C3. That is, different methods can be used to prepare similar compounds.

The compounds in the invention may be produced by processes known to those skilled in the art and as shown in the following reaction schemes and in the preparations and examples described below. The tables contain the compounds with observed m/e values from mass spectroscopy and/or NMR data. These compounds can be obtained with synthetic methods similar to these listed in the last column using appropriate reagents.

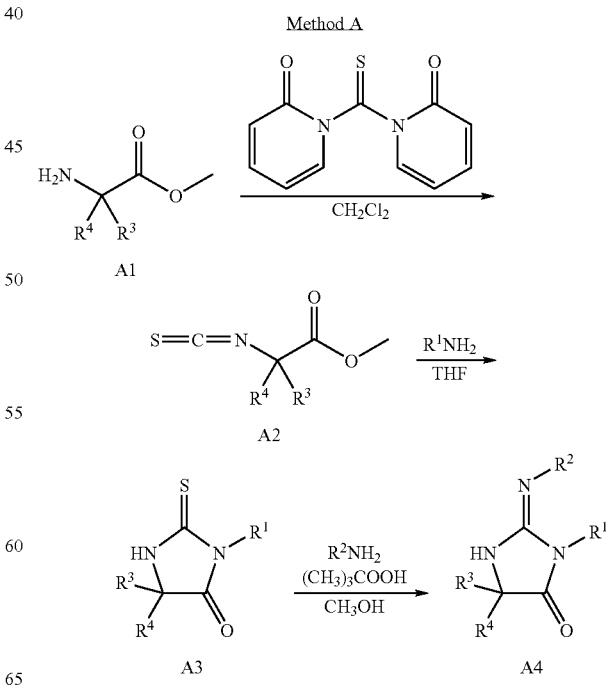

Method A

Method A, Step 1:

To a solution of A1 ($R^3$=$CH_3$ & $R^4$=$CH_2CH(CH_3)_2$) (10 mmol, 1 eq) in 30 ml of anhyd. $CH_2Cl_2$ was added thiocarbonyl dipyridone (1.2 eq). After stirring overnight the solution was diluted with $CH_2Cl_2$, washed with 1N HCl, $H_2O$ (2×), and a saturated aqueous NaCl solution (2×). The organic solution was dried over $Na_2SO_4$, filtered and concentrated. The crude material was purified via flash chromatography to afford A2 ($R^3$=$CH_3$ & $R^4$=$CH_2CH(CH_3)_2$).

Method A, Step 2:

A solution of 3,5-difluorobenzyl amine (0.15 mmol, 1.5 eq) in THF (0.15 mL) was added to a solution of A2 ($R^3$=$CH_3$ & $R^4$=$CH_2CH(CH_3)_2$) (0.1 mmol, 1 eq) in anhydrous $CH_2Cl_2$ (1 mL). The reaction mixture was refluxed overnight. The reaction solution was added to MP-TsOH resin (2-3 eq) and diluted with $CH_3CN$. The suspension was agitated overnight. The mixture was filtered and the filtrate was concentrated to afford A3 ($R^1$=3,5-difluorobenzyl, $R^3$=$CH_3$, & $R^4$=$CH_2CH(CH_3)_2$).

Method A, Step 3:

To a solution of A3 ($R^1$=3,5-difluorobenzyl, $R^3$=$CH_3$, & $R^4$=$CH_2CH(CH_3)_2$) (10 mg) in $CH_3OH$ (1 mL) was added $NH_4OH$ (0.44 mL) and t-butyl hydrogen peroxide (0.1 mL) and the reaction mixture was agitated for 2 d. The solution was concentrated, the resulting residue was dissolved in $CH_3OH$ (1.2 mL) and was treated with sulfonic acid resin. The suspension was agitated overnight and the resin was washed with $CH_3OH$ (4×10 min) before it was treated with 2 N $NH_3$ in $CH_3OH$ for 1 h. The suspension was filtered and the filtrate was concentrated to give the crude material which was purified by preparative HPLC/LCMS eluting with a $CH_3CN$/$H_2O$ gradient to afford A4 ($R^1$=3,5-difluorobenzyl, $R^2$=H, $R^3$=$CH_3$, & $R^4$=$CH_2CH(CH_3)_2$). NMR ($CD_3OD$): δ6.9, m, 3H, δ4.8-4.9, m; δ1.75, d, 2H, δ1.5, m, 1H, δ1.42, s, 3H, δ0.85, d, 3H, δ0.65, d, 3H. ES_LCMS (m/e) 296.1.

The following compounds were synthesized using similar methods:

| # | Structure | MW | Obs. m/e |
|---|-----------|-----|----------|
| 1 | 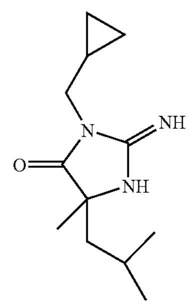 | 223 | 224 |
| 2 | 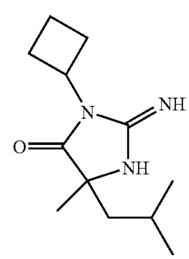 | 223 | 224 |
| 3 | 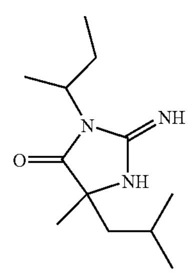 | 225 | 226 |
| 4 | 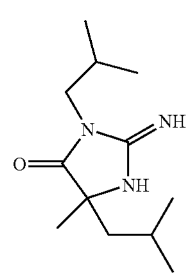 | 225 | 226 |

-continued

| # | Structure | MW | Obs. m/e |
|---|---|---|---|
| 5 | 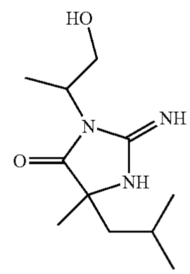 | 227 | 228 |
| 6 | 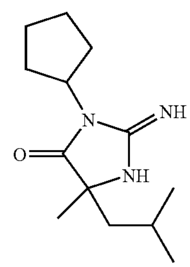 | 237 | 238 |
| 7 | 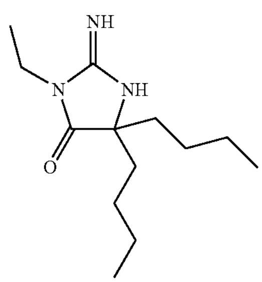 | 239 | 240 |
| 8 | 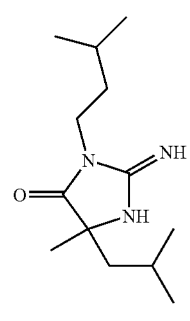 | 239 | 240 |
| 9 | 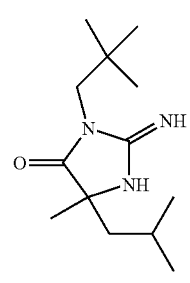 | 239 | 240 |

-continued

| # | Structure | MW | Obs. m/e |
|---|---|---|---|
| 10 | 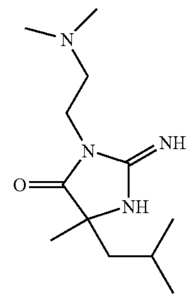 | 240 | 241 |
| 11 | 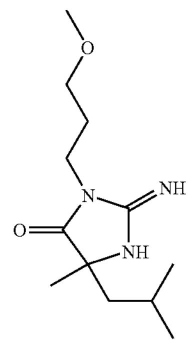 | 241 | 242 |
| 12 | 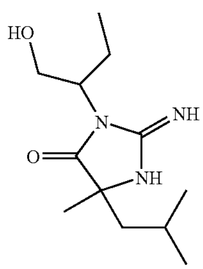 | 241 | 242 |
| 13 | 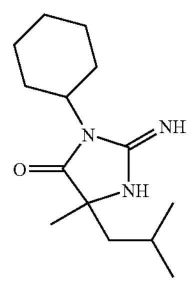 | 251 | 252 |
| 14 | 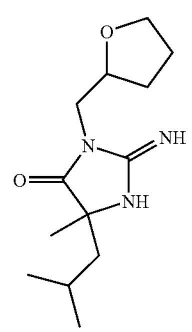 | 253 | 254 |

-continued

| # | Structure | MW | Obs. m/e |
|---|---|---|---|
| 15 | 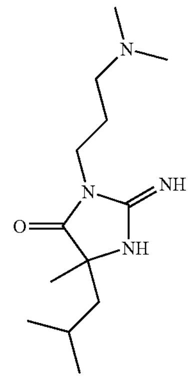 | 254 | 255 |
| 16 | 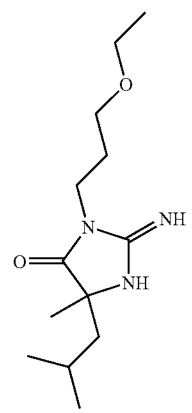 | 255 | 256 |
| 17 | 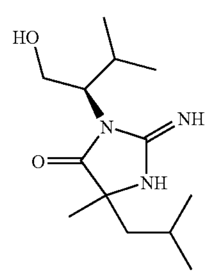 | 255 | 256 |
| 18 | 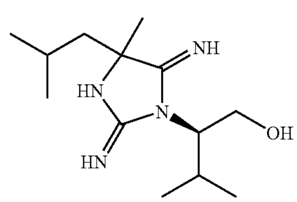 | 255 | 256 |
| 19 | 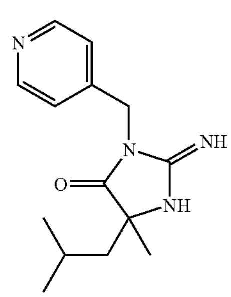 | 260 | 261 |

-continued

| # | Structure | MW | Obs. m/e |
|---|---|---|---|
| 20 | 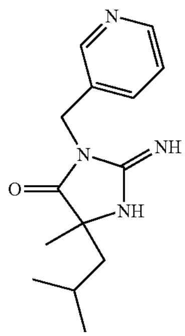 | 260 | 261 |
| 21 | 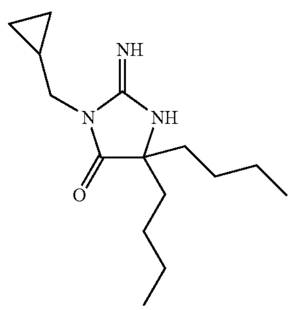 | 265 | 266 |
| 22 | 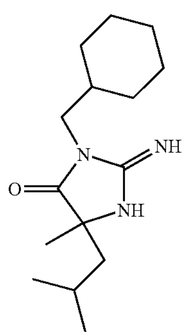 | 265 | 266 |
| 23 | 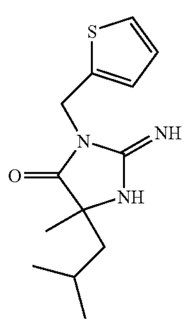 | 265 | 266 |
| 24 | 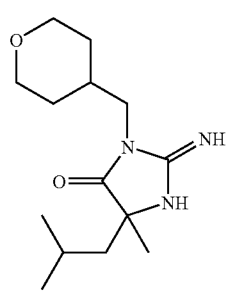 | 267 | 268 |

-continued
| # | Structure | MW | Obs. m/e |
|---|---|---|---|
| 25 | 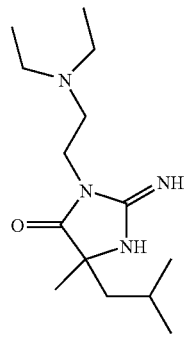 | 268 | 269 |
| 26 | 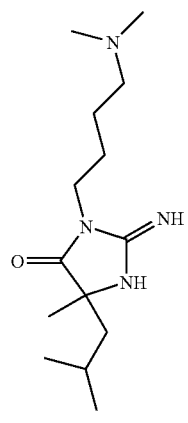 | 268 | 269 |
| 27 | 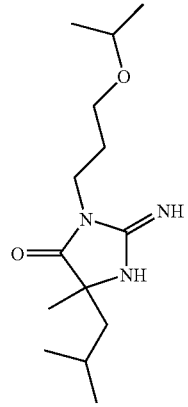 | 269 | 270 |
| 28 | 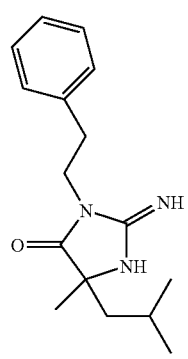 | 273 | 274 |

-continued

| # | Structure | MW | Obs. m/e |
|---|---|---|---|
| 29 | 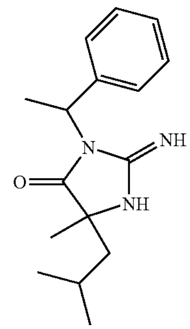 | 273 | 274 |
| 30 | 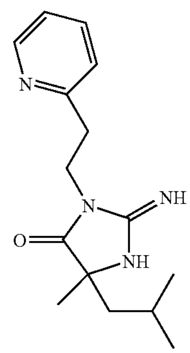 | 274 | 275 |
| 31 | 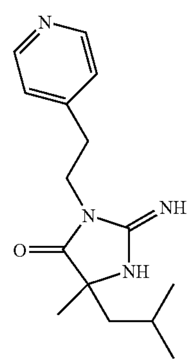 | 274 | 275 |
| 32 | 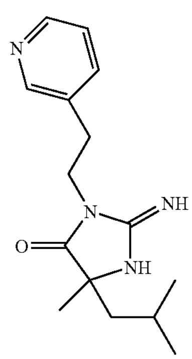 | 274 | 275 |

-continued
| # | Structure | MW | Obs. m/e |
|---|---|---|---|
| 33 | 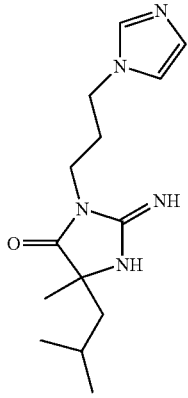 | 277 | 278 |
| 34 | 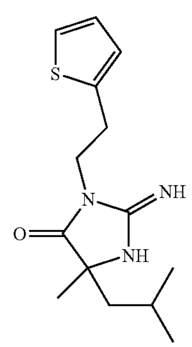 | 279 | 280 |
| 35 | 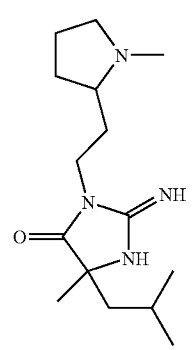 | 280 | 281 |
| 36 | 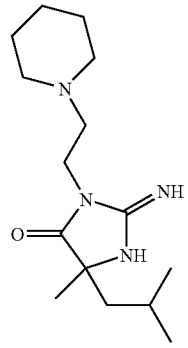 | 280 | 281 |

-continued
| # | Structure | MW | Obs. m/e |
|---|---|---|---|
| 37 | 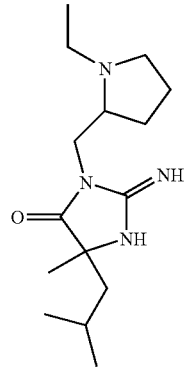 | 280 | 281 |
| 38 | 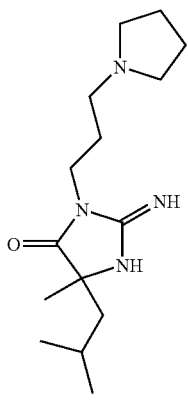 | 280 | 281 |
| 39 | 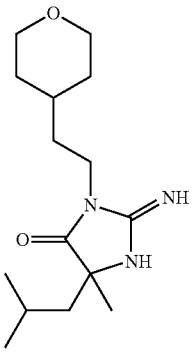 | 281 | 282 |
| 40 | 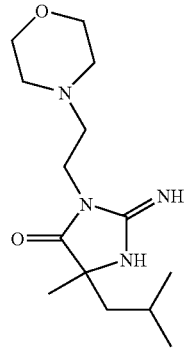 | 282 | 283 |

-continued

| # | Structure | MW | Obs. m/e |
|---|---|---|---|
| 41 | 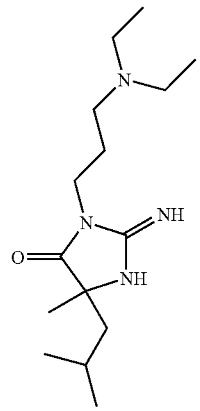 | 282 | 283 |
| 42 | 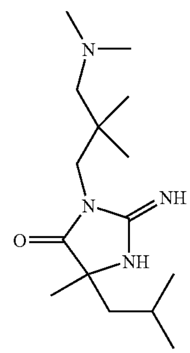 | 282 | 283 |
| 43 | 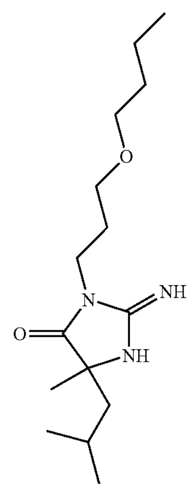 | 283 | 284 |
| 44 | 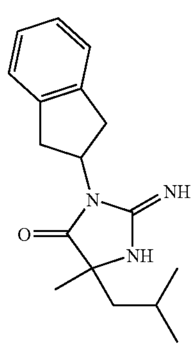 | 285 | 286 |

-continued
| # | Structure | MW | Obs. m/e |
|---|---|---|---|
| 45 | 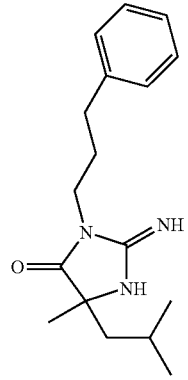 | 287 | 288 |
| 46 | 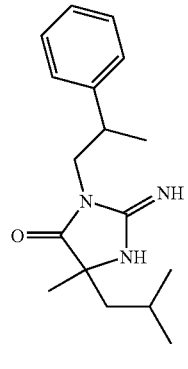 | 287 | 288 |
| 47 | 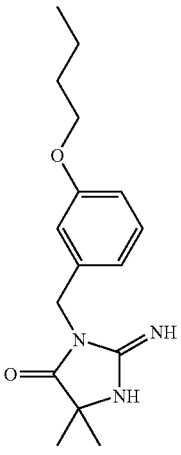 | 289 | 290 |
| 48 | 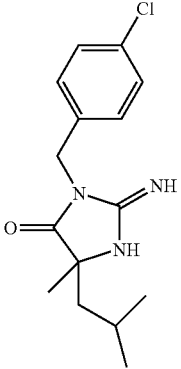 | 293 | 294 |

-continued
| # | Structure | MW | Obs. m/e |
|---|---|---|---|
| 49 | 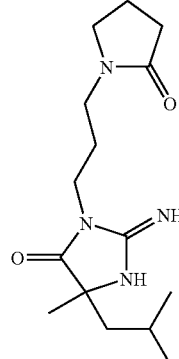 | 294 | 295 |
| 50 | 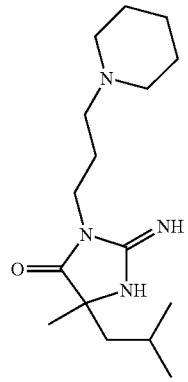 | 294 | 295 |
| 51 | 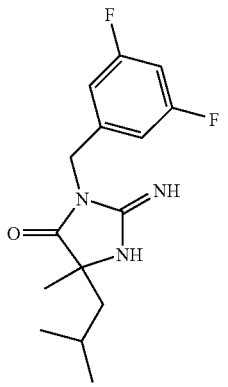 | 295 | 296 |
| 52 | 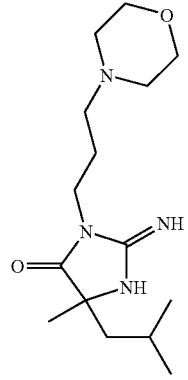 | 296 | 297 |

-continued

| # | Structure | MW | Obs. m/e |
|---|-----------|-----|----------|
| 53 | 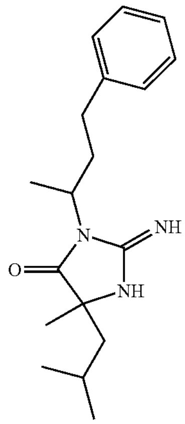 | 301 | 302 |
| 54 | 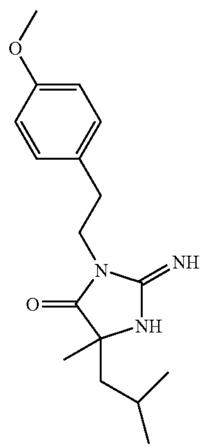 | 303 | 304 |
| 55 | 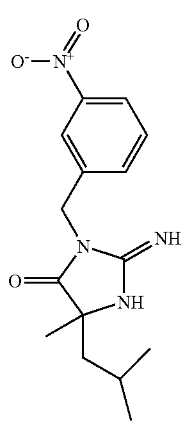 | 304 | 305 |

-continued

| # | Structure | MW | Obs. m/e |
|---|---|---|---|
| 56 | 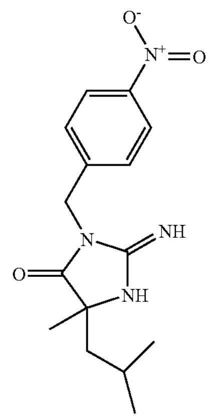 | 304 | 305 |
| 57 | 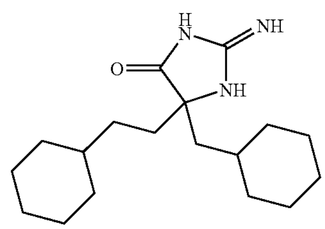 | 305 | 306 |
| 58 | 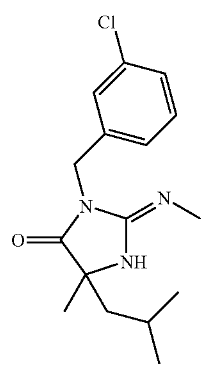 | 307 | 308 |
| 59 | 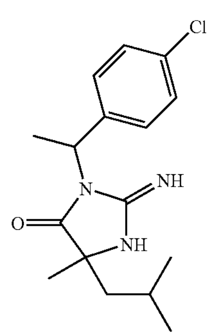 | 307 | 308 |

-continued
| # | Structure | MW | Obs. m/e |
|---|---|---|---|
| 60 | 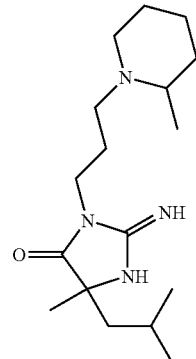 | 308 | 309 |
| 61 | 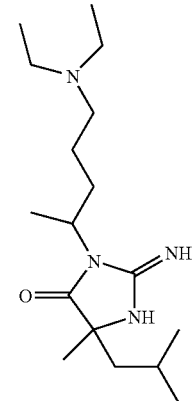 | 310 | 311 |
| 62 | 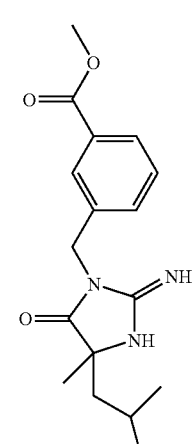 | 317 | 318 |
| 63 | 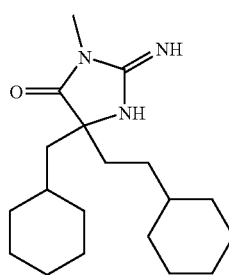 | 319 | 320 |

-continued

| # | Structure | MW | Obs. m/e |
|---|-----------|----|----|
| 64 | 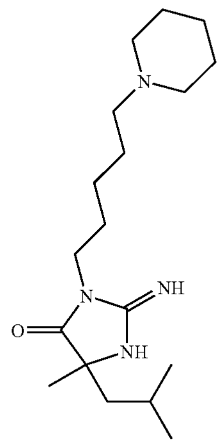 | 322 | 323 |
| 65 | 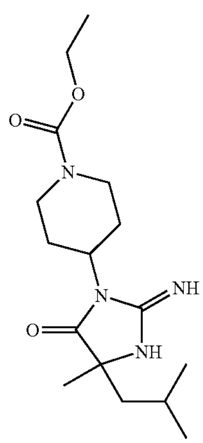 | 324 | 325 |
| 66 | 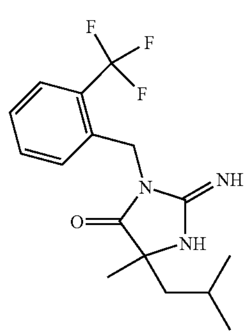 | 327 | 328 |

-continued
| # | Structure | MW | Obs. m/e |
|---|---|---|---|
| 67 | 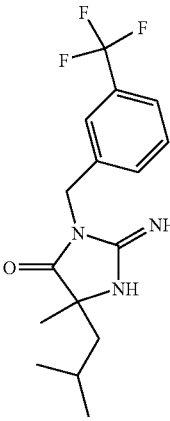 | 327 | 328 |
| 68 | 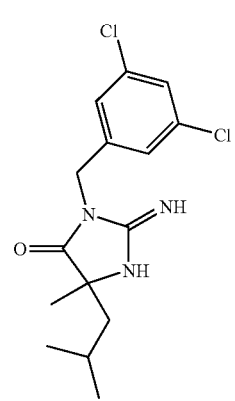 | 327 | 328 |
| 69 | 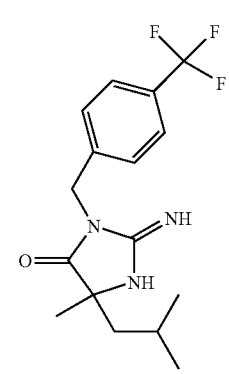 | 327 | 328 |
| 70 | 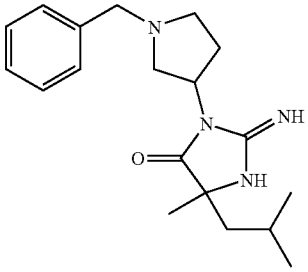 | 328 | 329 |

-continued

| # | Structure | MW | Obs. m/e |
|---|---|---|---|
| 71 | 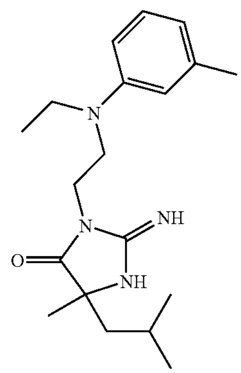 | 330 | 331 |
| 72 | 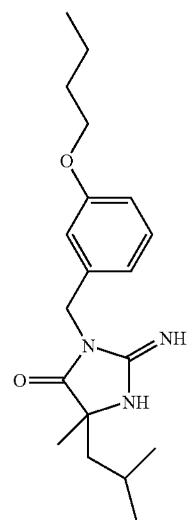 | 331 | 332 |
| 73 | 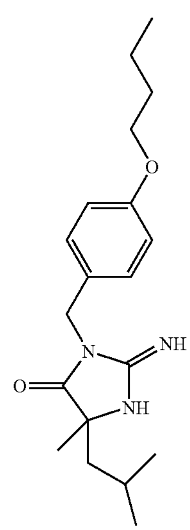 | 331 | 332 |

| # | Structure | MW | Obs. m/e |
|---|---|---|---|
| 74 | 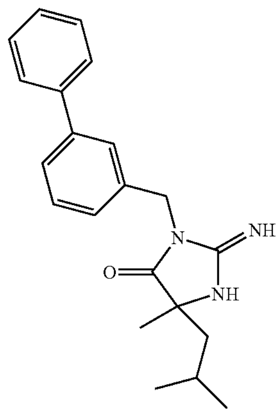 | 335 | 336 |
| 75 | 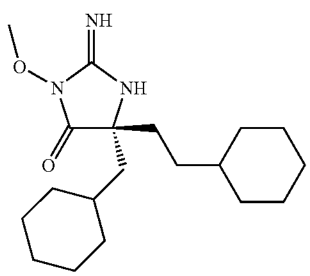 | 335 | 336 |
| 76 | 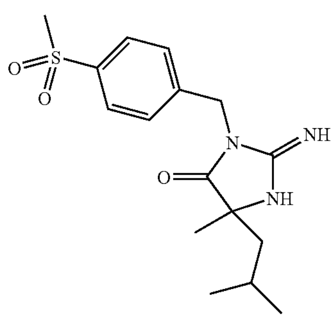 | 337 | 338 |
| 77 | 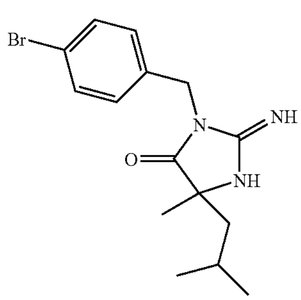 | 337 | 338 |

-continued

| # | Structure | MW | Obs. m/e |
|---|-----------|-----|----------|
| 78 | 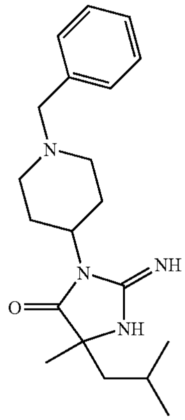 | 342 | 343 |
| 79 | 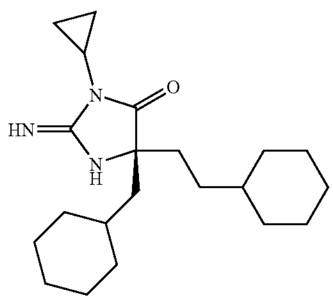 | 345 | 346 |
| 80 | 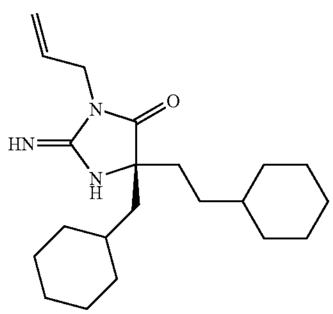 | 345 | 346 |
| 81 | 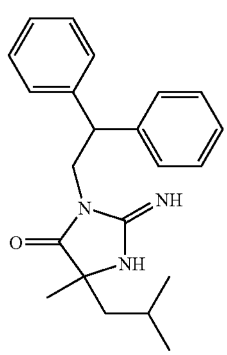 | 349 | 350 |

-continued

| # | Structure | MW | Obs. m/e |
|---|---|---|---|
| 82 | 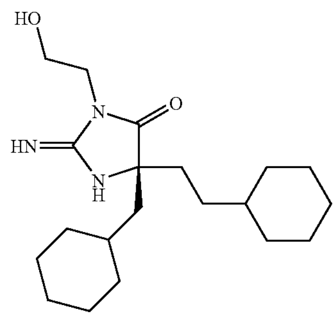 | 349 | 350 |
| 83 | 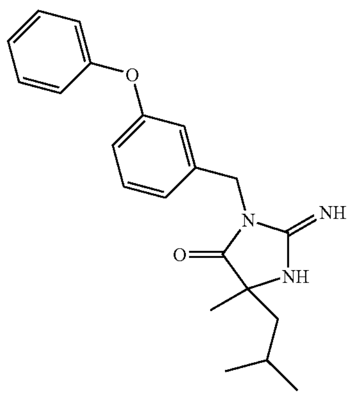 | 351 | 352 |
| 84 | 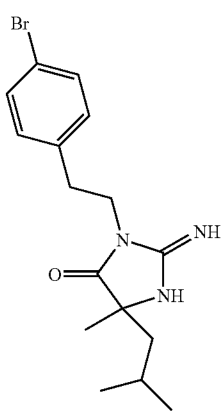 | 351 | 352 |
| 85 | 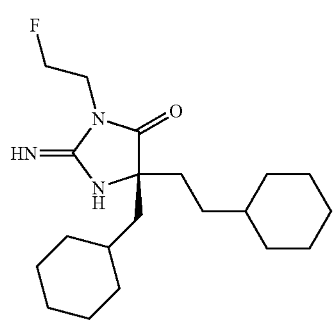 | 351 | 352 |

-continued
| # | Structure | MW | Obs. m/e |
|---|---|---|---|
| 86 | 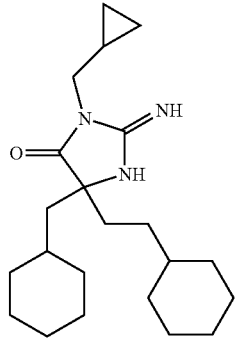 | 359 | 360 |
| 87 | 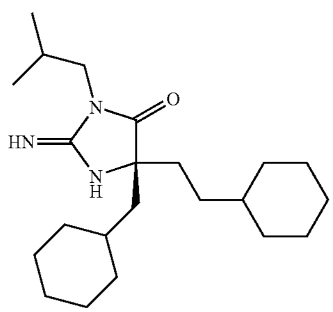 | 361 | 362 |
| 88 | 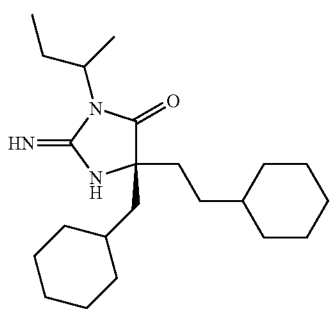 | 361 | 362 |
| 89 | 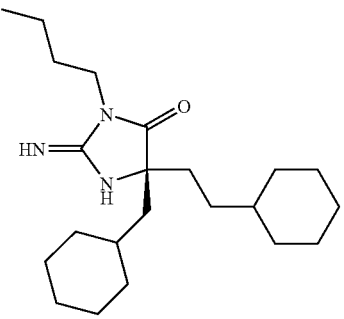 | 361 | 362 |

-continued

| # | Structure | MW | Obs. m/e |
|---|-----------|-----|----------|
| 90 | 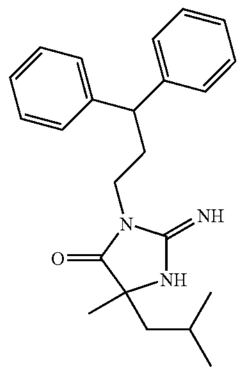 | 363 | 364 |
| 91 | 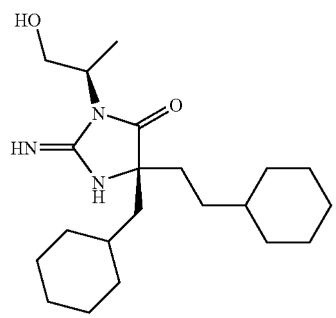 | 363 | 364 |
| 92 | 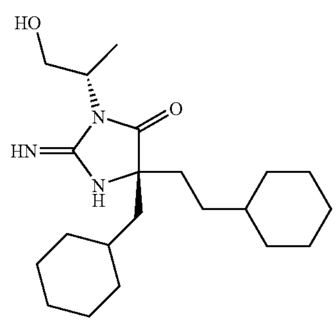 | 363 | 364 |
| 93 | 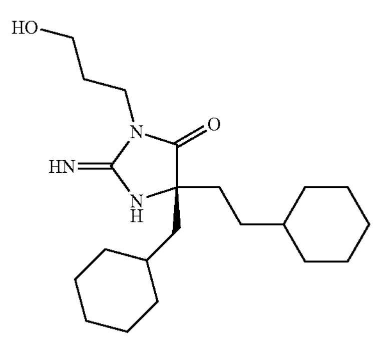 | 363 | 364 |

-continued

| # | Structure | MW | Obs. m/e |
|---|---|---|---|
| 94 | 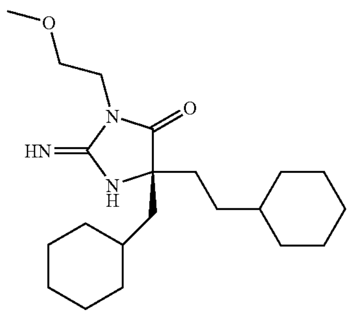 | 363 | 364 |
| 95 | 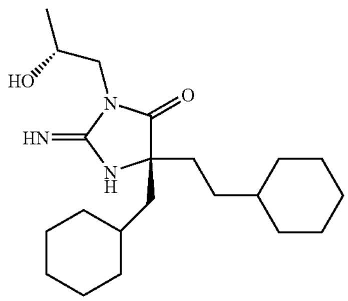 | 363 | 364 |
| 96 | 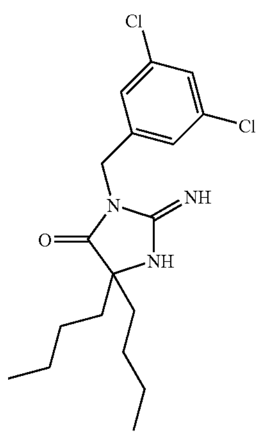 | 369 | 370 |
| 97 | 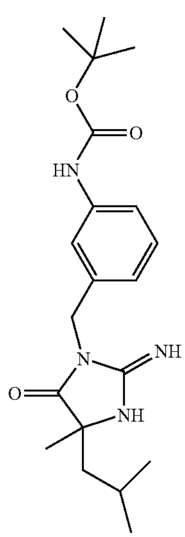 | 374 | 375 |

-continued

| # | Structure | MW | Obs. m/e |
|---|---|---|---|
| 98 | 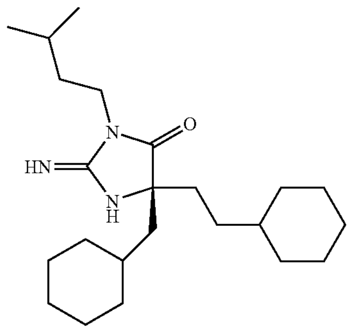 | 375 | 376 |
| 99 | 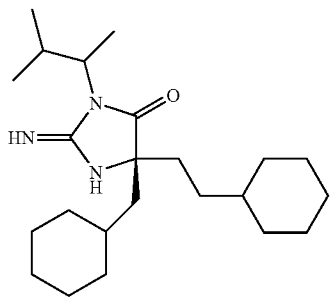 | 375 | 376 |
| 100 | 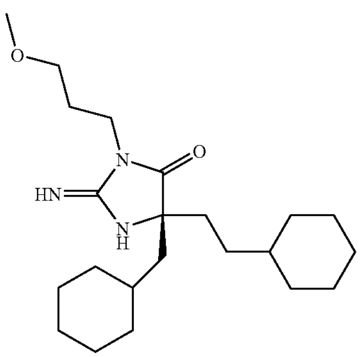 | 377 | 378 |
| 101 | 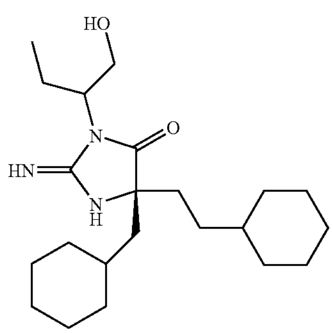 | 377 | 378 |

-continued

| # | Structure | MW | Obs. m/e |
|---|---|---|---|
| 102 | 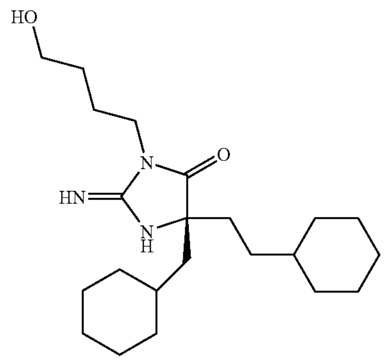 | 377 | 378 |
| 103 | 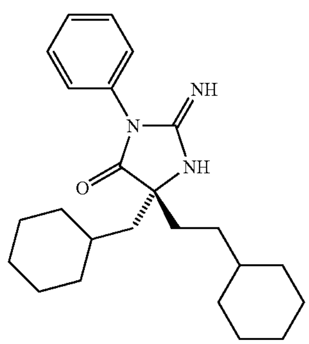 | 381 | 382 |
| 104 | 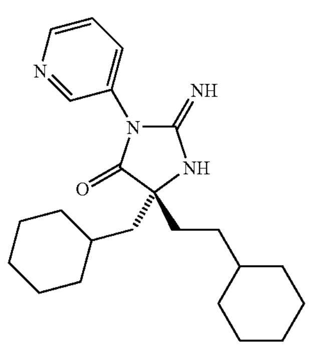 | 382 | 383 |
| 105 | 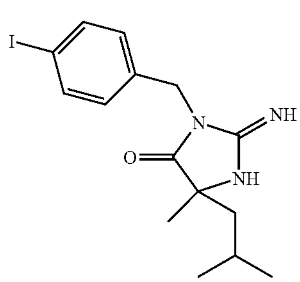 | 385 | 386 |

| # | Structure | MW | Obs. m/e |
|---|---|---|---|
| 106 | 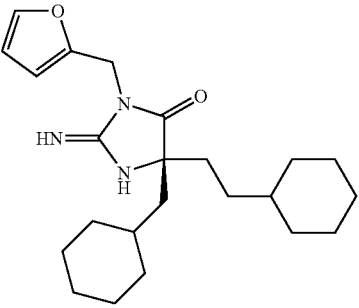 | 385 | 386 |
| 107 | 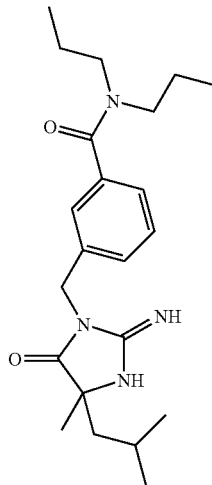 | 386 | 387 |
| 108 | 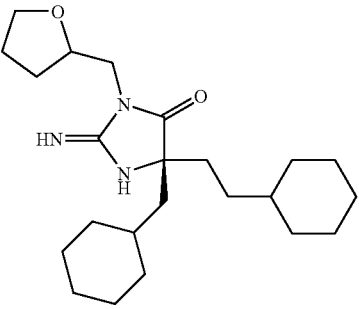 | 389 | 390 |
| 109 | 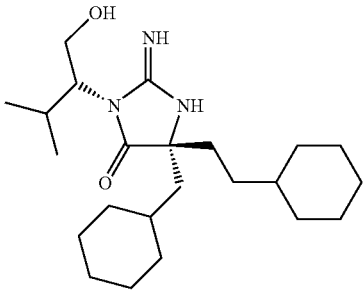 | 391 | 392 |

-continued

| # | Structure | MW | Obs. m/e |
|---|---|---|---|
| 110 | 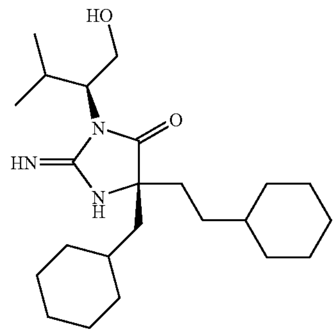 | 391 | 392 |
| 111 | 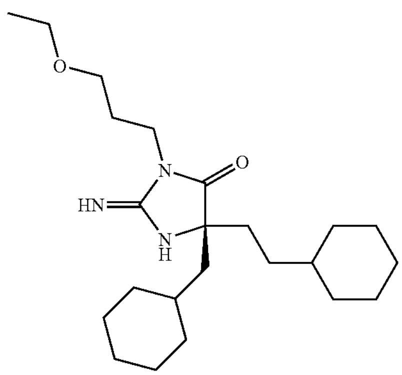 | 391 | 392 |
| 112 | 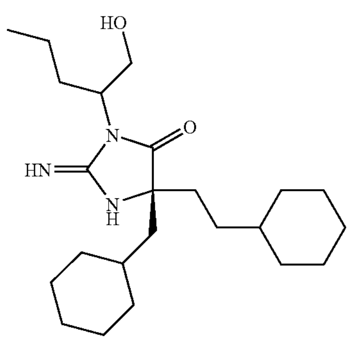 | 391 | 392 |
| 113 | 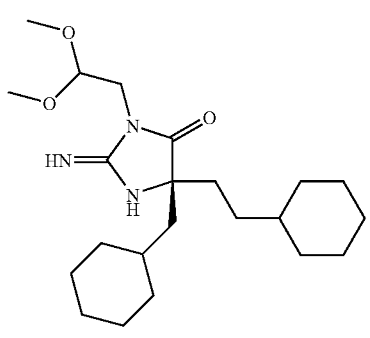 | 393 | 394 |

-continued

| # | Structure | MW | Obs. m/e |
|---|---|---|---|
| 114 | 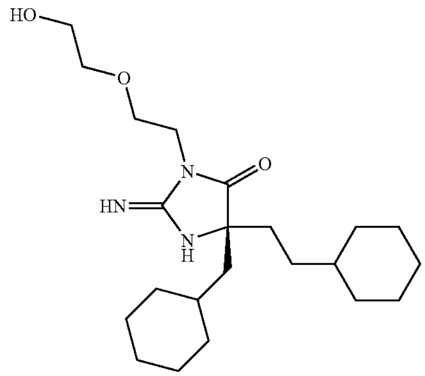 | 393 | 394 |
| 115 | 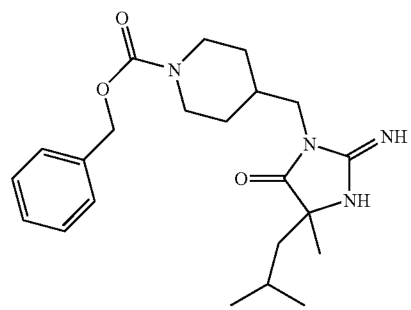 | 400 | 401 |
| 116 | 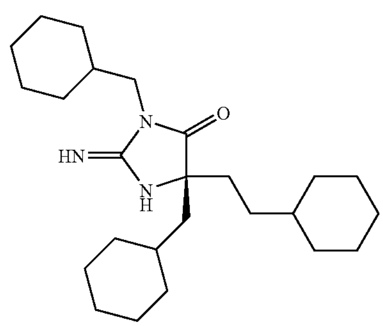 | 401 | 402 |
| 117 | 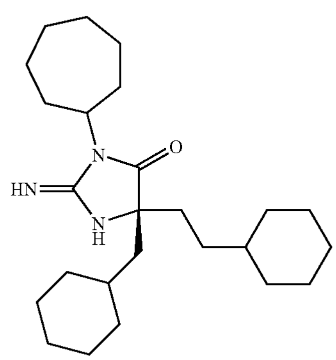 | 401 | 402 |

-continued

| # | Structure | MW | Obs. m/e |
|---|---|---|---|
| 118 | 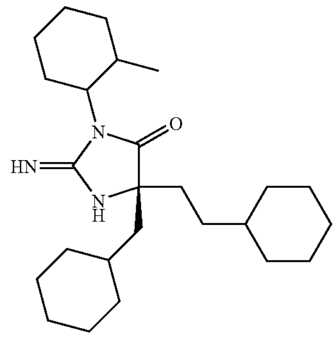 | 401 | 402 |
| 119 | 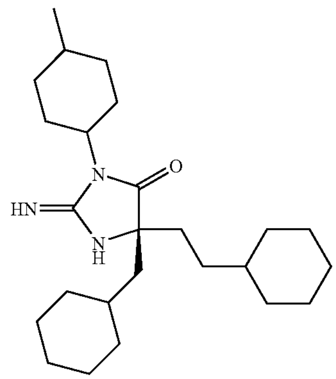 | 401 | 402 |
| 120 | 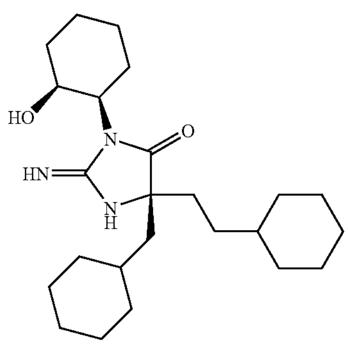 | 403 | 404 |
| 121 | 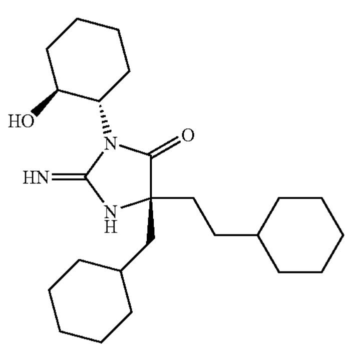 | 403 | 404 |

-continued

| # | Structure | MW | Obs. m/e |
|---|---|---|---|
| 122 | 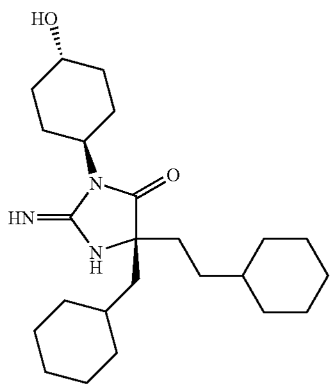 | 403 | 404 |
| 123 | 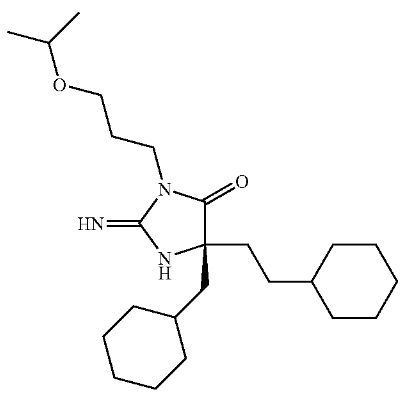 | 405 | 406 |
| 124 | 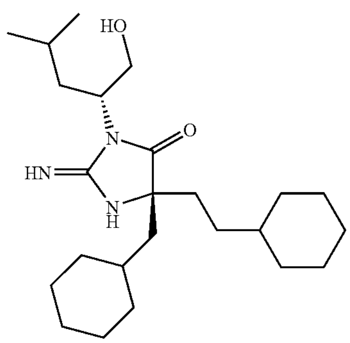 | 405 | 406 |
| 125 | 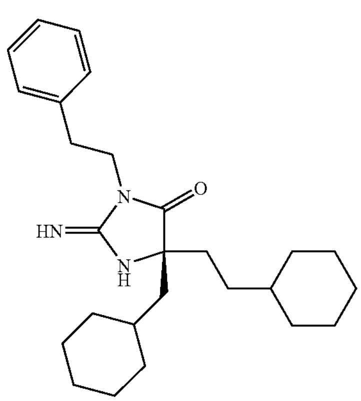 | 409 | 410 |

-continued
| # | Structure | MW | Obs. m/e |
|---|---|---|---|
| 126 | 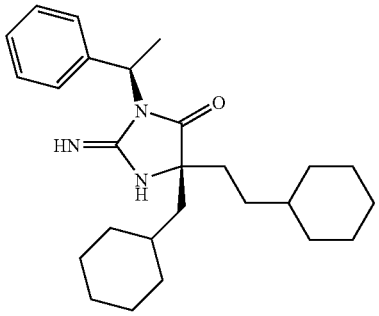 | 409 | 410 |
| 127 | 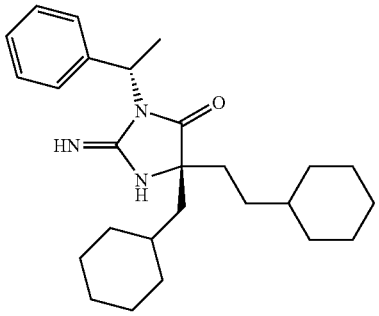 | 409 | 410 |
| 128 | 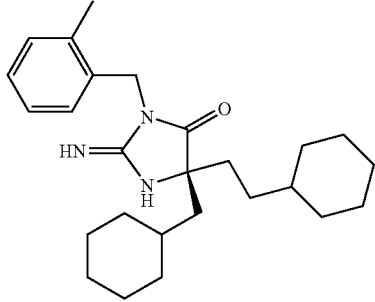 | 409 | 410 |
| 129 | 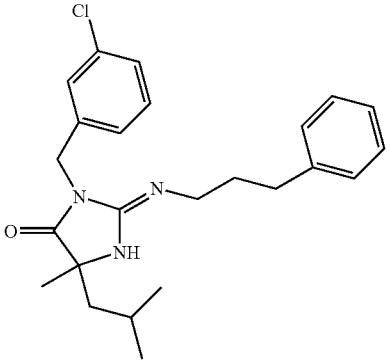 | 411 | 412 |

-continued

| # | Structure | MW | Obs. m/e |
|---|---|---|---|
| 130 | 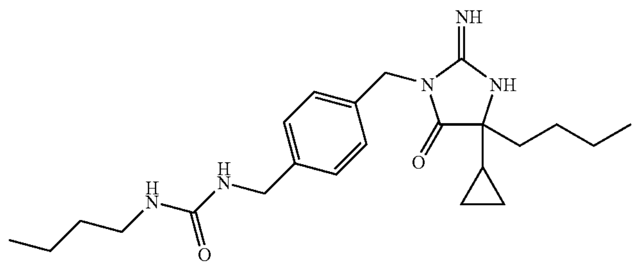 | 413 | 414 |
| 131 | 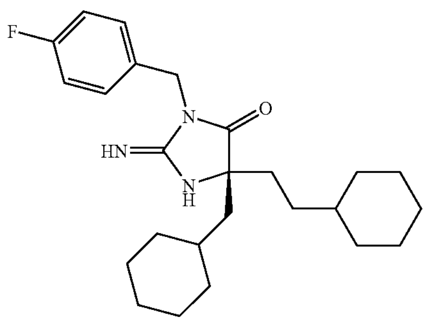 | 413 | 414 |
| 132 | 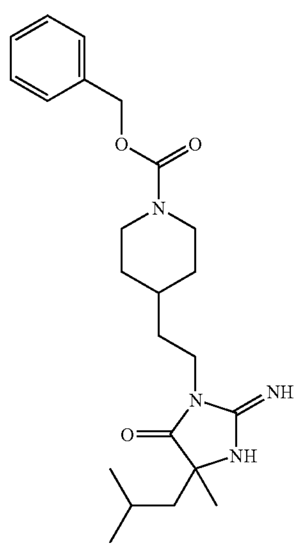 | 414 | 415 |
| 133 | 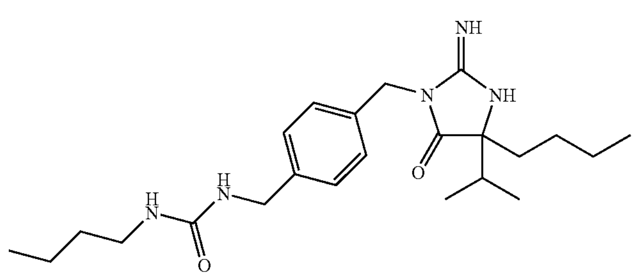 | 415 | 416 |

-continued

| # | Structure | MW | Obs. m/e |
|---|---|---|---|
| 134 | 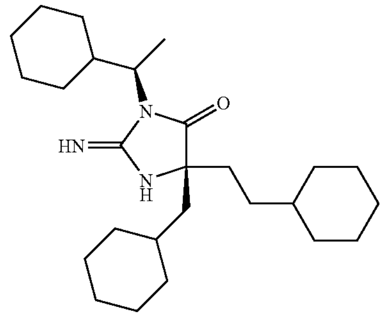 | 415 | 416 |
| 135 | 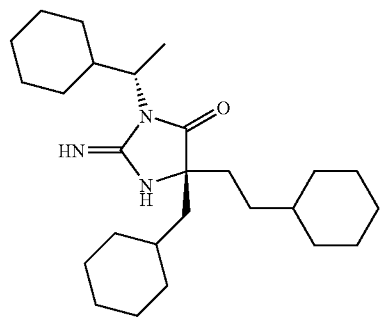 | 415 | 416 |
| 136 | 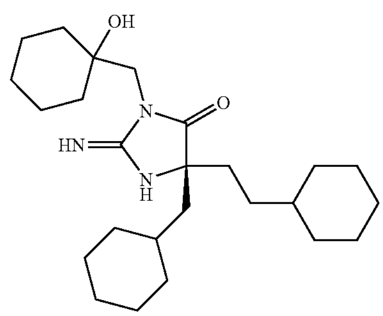 | 417 | 418 |
| 137 | 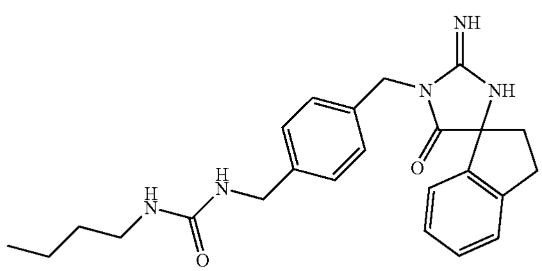 | 419 | 420 |
| 138 | 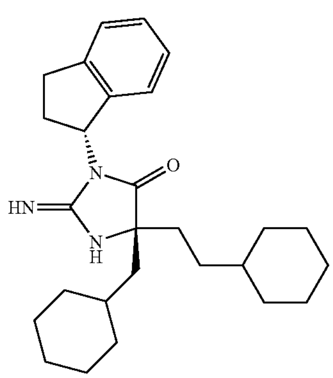 | 421 | 422 |

| # | Structure | MW | Obs. m/e |
|---|---|---|---|
| 139 | 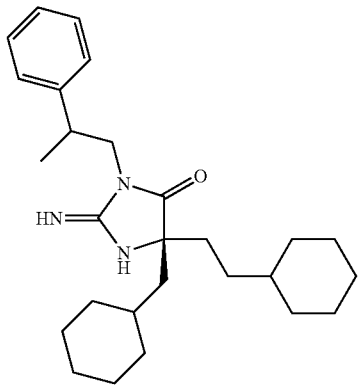 | 423 | 424 |
| 140 | 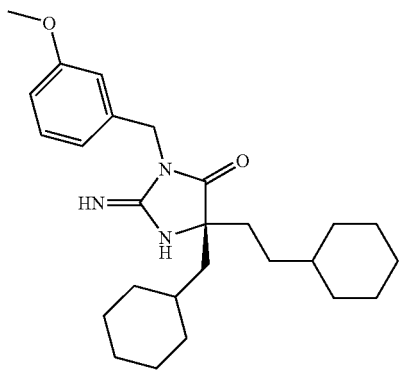 | 425 | 426 |
| 141 | 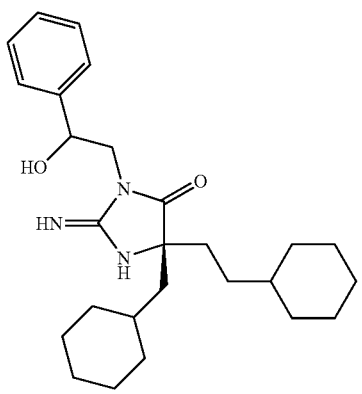 | 425 | 426 |

| # | Structure | MW | Obs. m/e |
|---|---|---|---|
| 142 | 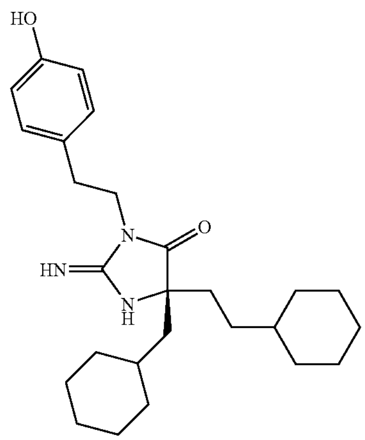 | 425 | 426 |
| 143 | 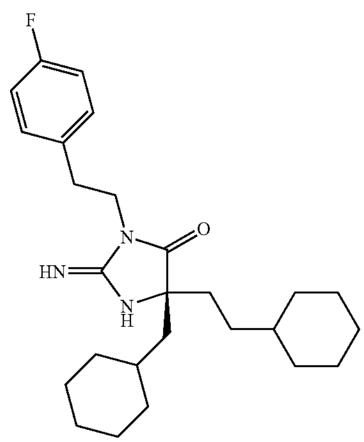 | 427 | 428 |
| 144 | 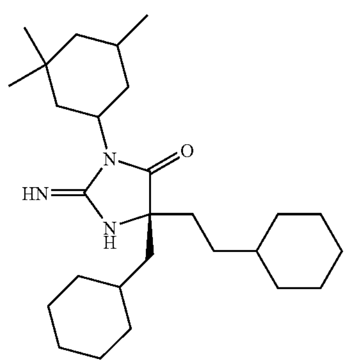 | 429 | 430 |
| 145 | 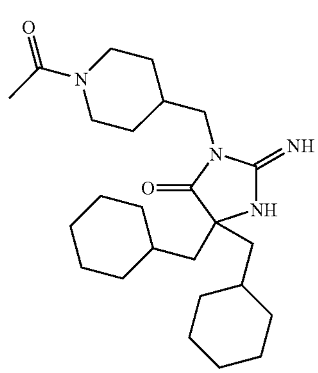 | 430 | 431 |

| # | Structure | MW | Obs. m/e |
|---|-----------|-----|----------|
| 146 | 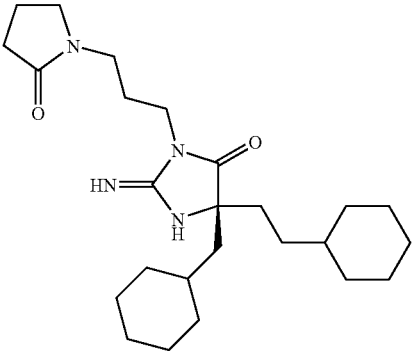 | 430 | 431 |
| 147 | 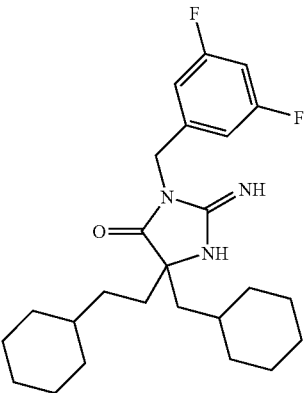 | 431 | 432 |
| 148 | 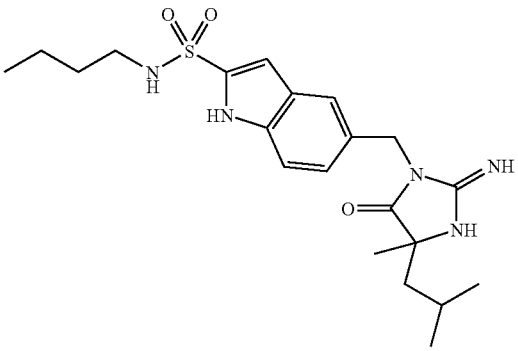 | 433 | 434 |
| 149 | 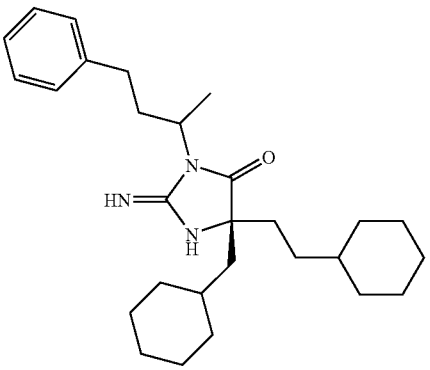 | 437 | 438 |

-continued

| # | Structure | MW | Obs. m/e |
|---|---|---|---|
| 150 | 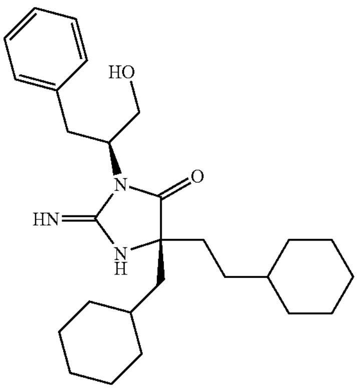 | 439 | 440 |
| 151 | 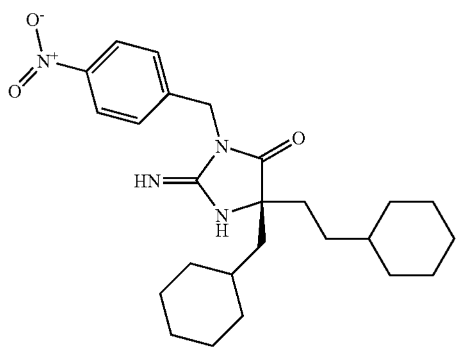 | 440 | 441 |
| 152 | 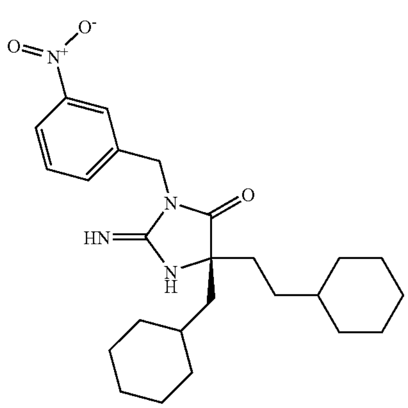 | 440 | 441 |

-continued

| # | Structure | MW | Obs. m/e |
|---|---|---|---|
| 153 | 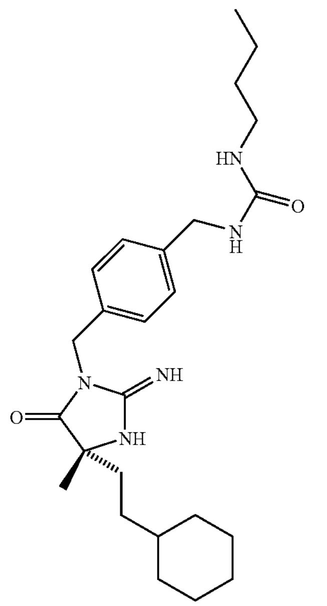 | 441 | 442 |
| 154 | 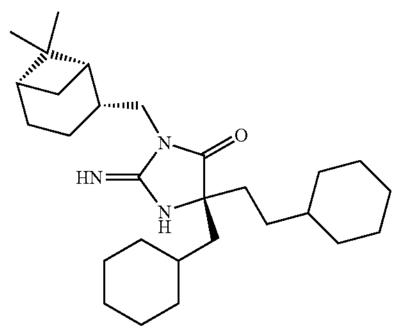 | 441 | 442 |
| 155 | 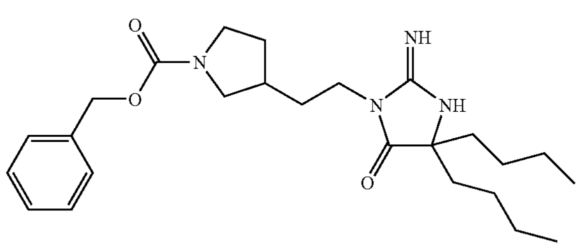 | 442 | 443 |
| 156 | 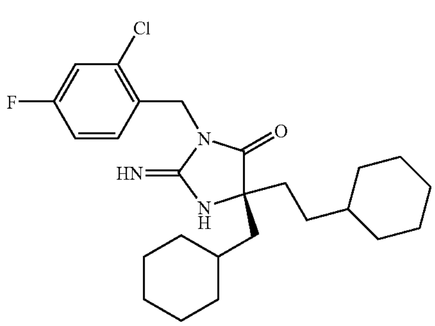 | 447 | 448 |

-continued

| # | Structure | MW | Obs. m/e |
|---|---|---|---|
| 157 | 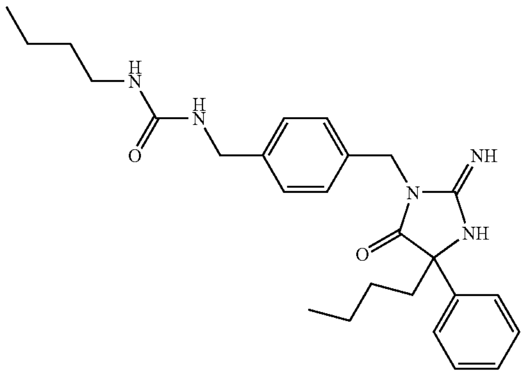 | 449 | 450 |
| 158 | 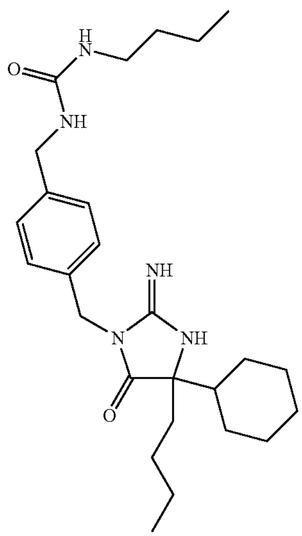 | 455 | 456 |
| 159 | 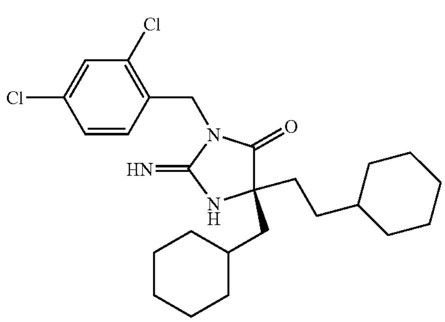 | 463 | 464 |
| 160 | 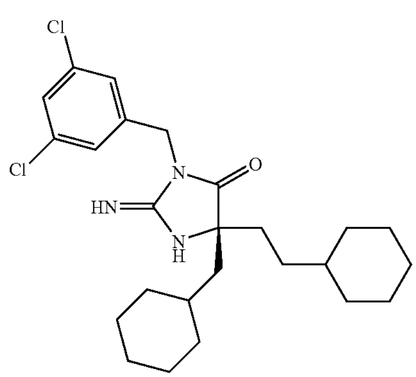 | 463 | 464 |

-continued

| # | Structure | MW | Obs. m/e |
|---|---|---|---|
| 161 | 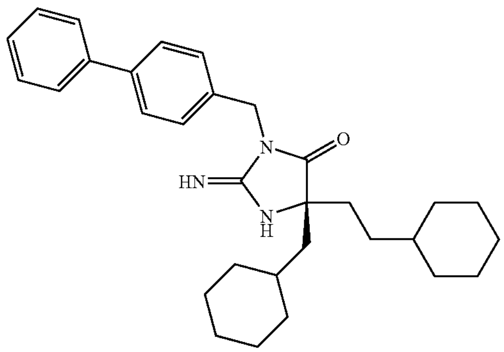 | 471 | 472 |
| 162 | 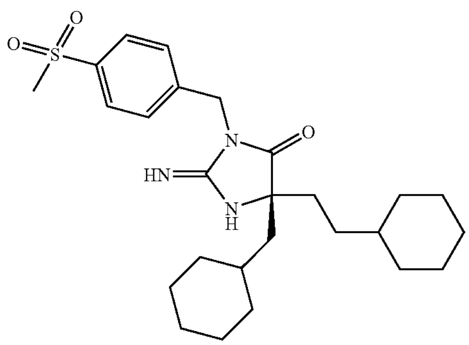 | 473 | 474 |
| 163 | 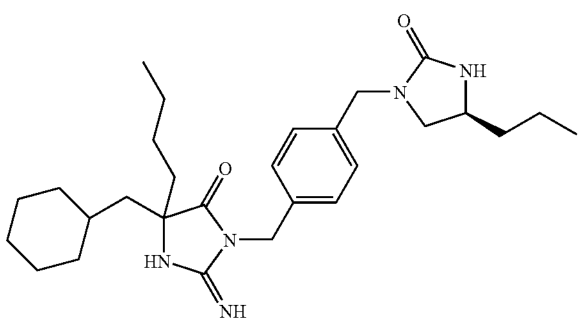 | 481 | 482 |
| 164 | 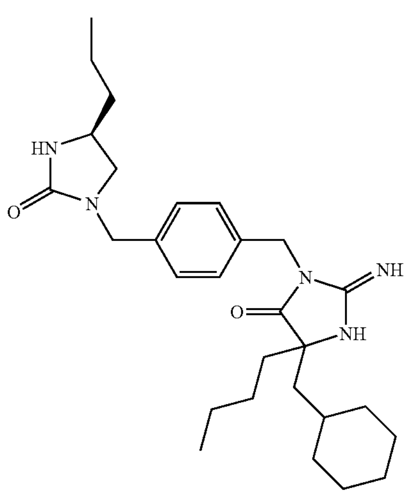 | 481 | 482 |

| # | Structure | MW | Obs. m/e |
|---|---|---|---|
| 165 | 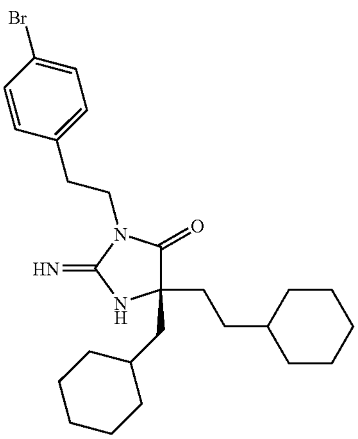 | 487 | 488 |
| 166 | 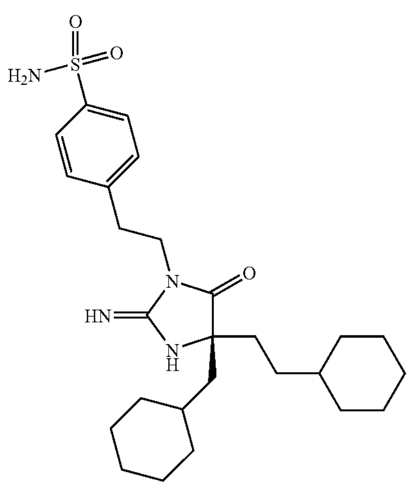 | 488 | 489 |
| 167 | 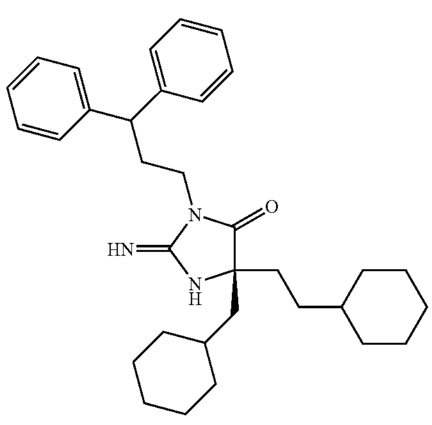 | 499 | 500 |

-continued
| # | Structure | MW | Obs. m/e |
|---|---|---|---|
| 168 | 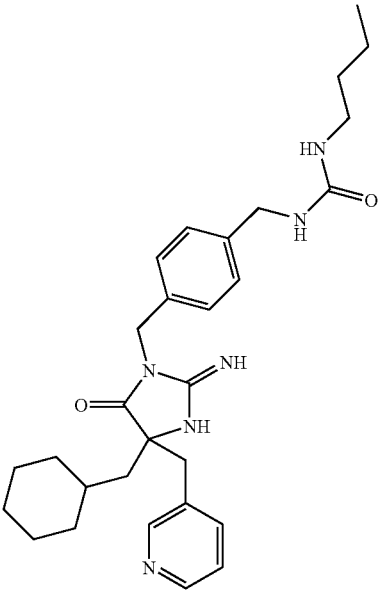 | 504 | 505 |
| 169 | 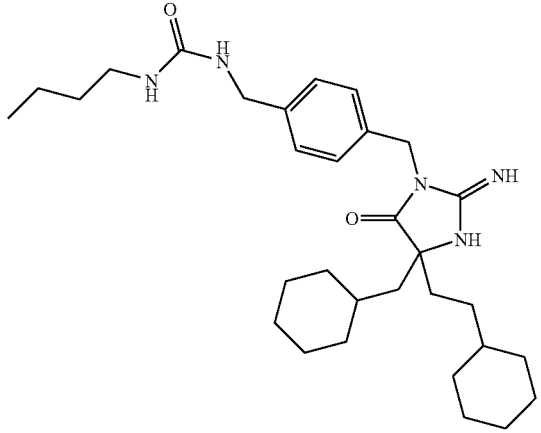 | 523 | 524 |
| 170 | 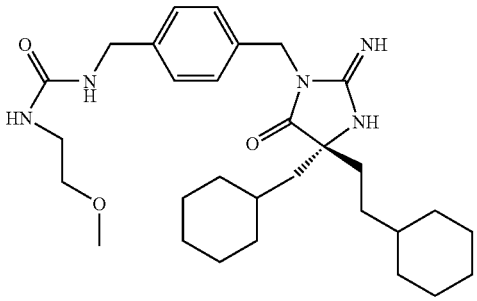 | 525 | 526 |

-continued

| # | Structure | MW | Obs. m/e |
|---|---|---|---|
| 171 | 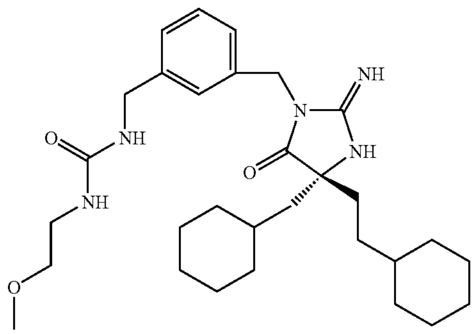 | 525 | 526 |
| 172 | 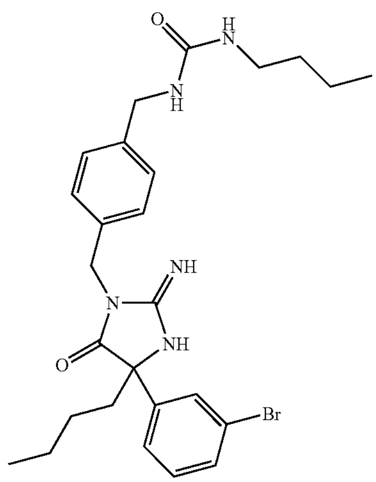 | 527 | 528 |
| 173 | 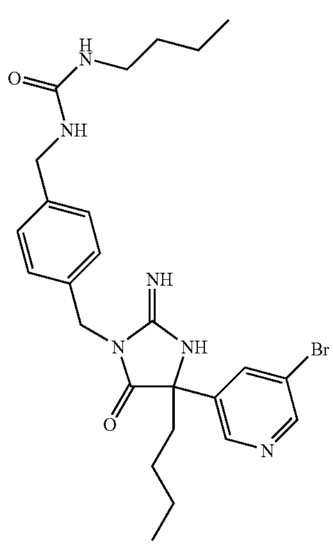 | 528 | 529 |

-continued

| # | Structure | MW | Obs. m/e |
|---|---|---|---|
| 174 | 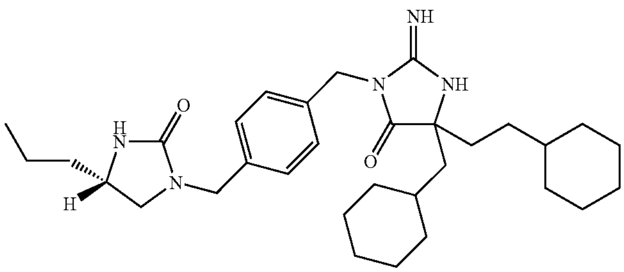 | 535 | 536 |
| 175 | 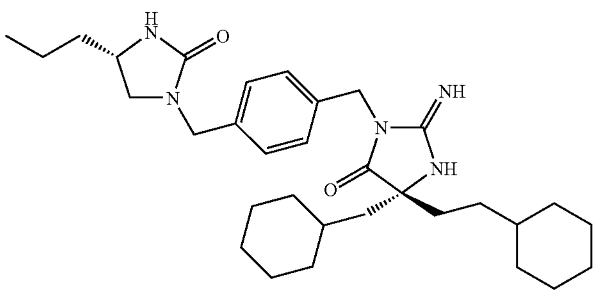 | 535 | 536 |
| 176 | 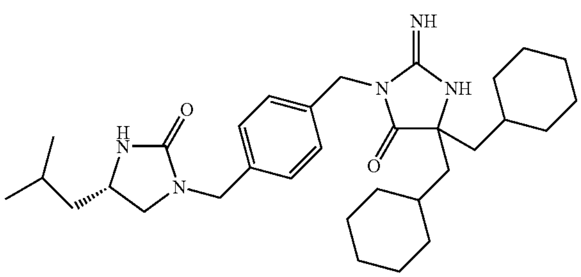 | 535 | 536 |
| 177 | 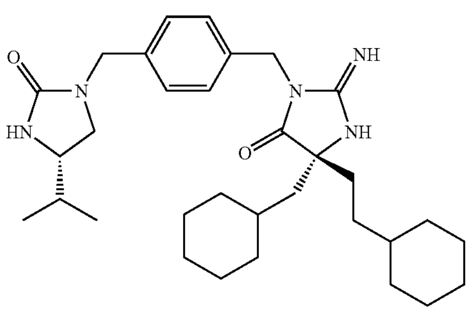 | 535 | 536 |
| 178 | 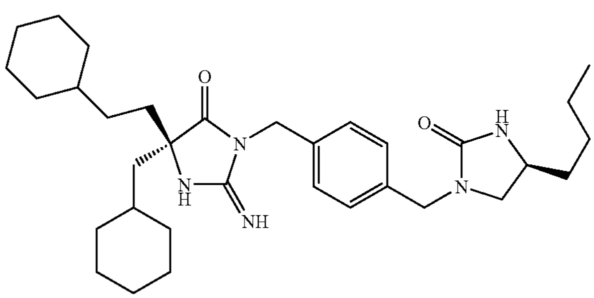 | 550 | 551 |

-continued
| # | Structure | MW | Obs. m/e |
|---|---|---|---|
| 179 | 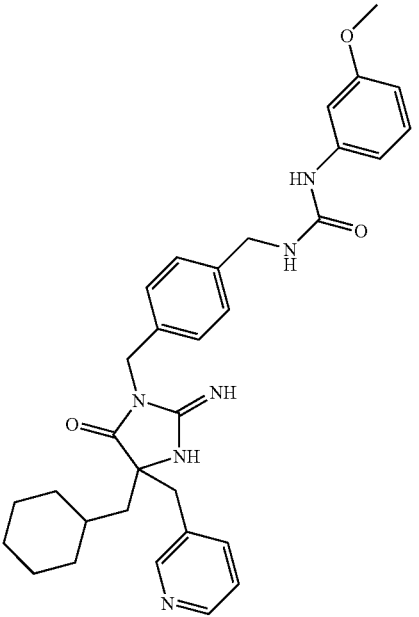 | 554 | 555 |
| 180 | 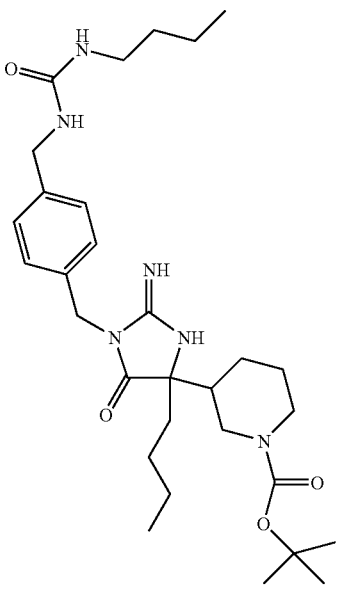 | 556 | 557 |
| 181 | 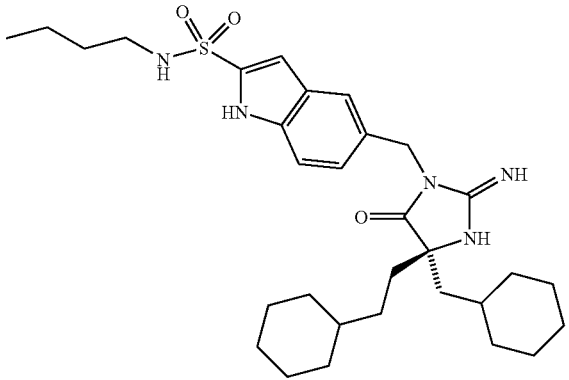 | 569 | 570 |

-continued

| # | Structure | MW | Obs. m/e |
|---|---|---|---|
| 182 | 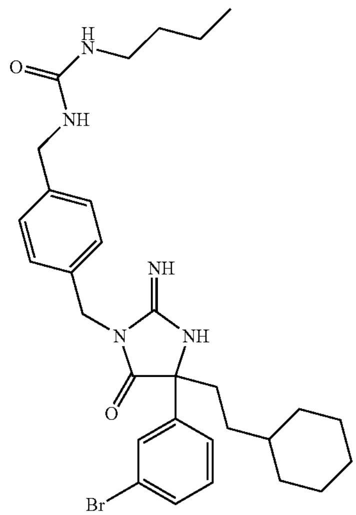 | 581 | 582 |
| 183 | 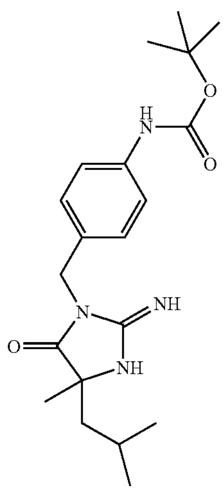 | 374 | NA |
| 184 | 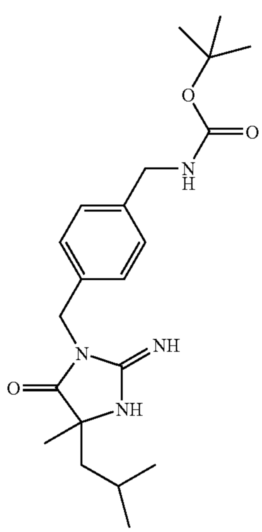 | 388 | NA |

| # | Structure | MW | Obs. m/e |
|---|---|---|---|
| 185 | 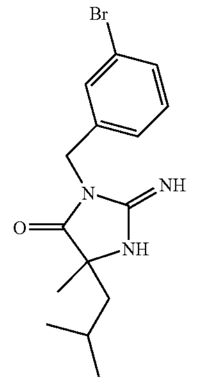 | 337 | NMR |
| 186 | 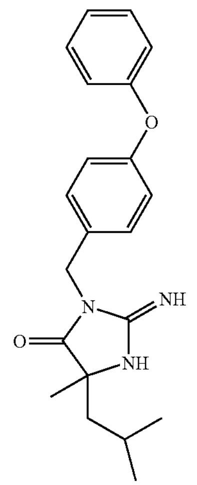 | 351 | NMR |

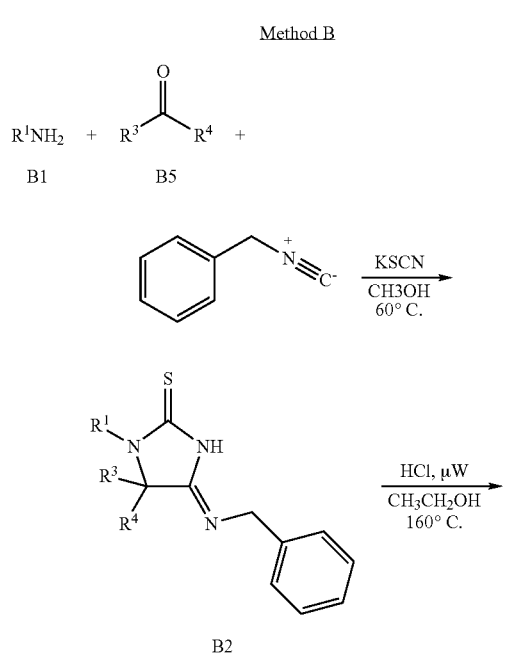

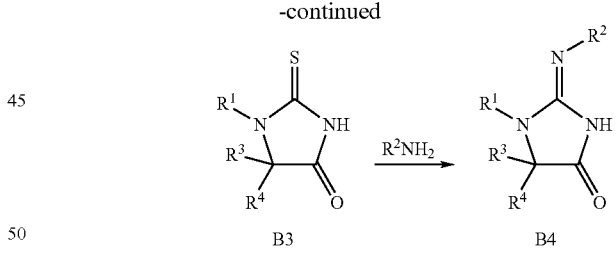

A modified literature procedure was used (Ugi, I. *Angew. Chem.* 1962, 74 9-22).

Method B, Step 1:

To a solution of B1 (HCl salt, $R^1$=3-chlorophenethyl) (1.1 g, 5.73 mmol) in anhydrous $CH_3OH$ (15 mL) was added potassium thiocyanate (0.56 g, 5.73 mmol). The reaction mixture was heated to 60° C. for 1 h. The suspension was filtered and the filtrate was added to B5 ($R^3$=Me, $R^4$=$^i$Bu) (0.72 mL, 5.73 mmol) and benzyl isocyanide (0.77 mL, 6.3 mmol). The mixture was stirred overnight before the solution was concentrated and the residue was purified via flash chromatography eluting with ethyl acetate in hexane to yield 0.28 g of B2 ($R^3$=$CH_3$, $R^4$=$CH_2CH(CH_3)_2$, and $R^1$=3-Chlorophenethyl).

Method B, Step 2:

A solution of 40% concentrated HCl in $CH_3CH_2OH$ was added to B2 ($R^3=CH_3$, $R^4=CH_2CH(CH_3)_2$, and $R^1$=3-Chlorophenethyl) and the solution was heated in a microwave at 160° C. for 30 min. The solution was concentrated and purified via reverse phase preparative HPLC eluting with a $CH_3CN/H_2O$ (with 0.1% formic acid) gradient to afford B3 ($R^3=CH_3$, $R^4=CH_2CH(CH_3)_2$, and $R^1$=3-Chlorophenethyl).

Method B, Step 3:

Compound B4 ($R^2$=H, $R_3$=$CH_3$, $R^4$=$CH_2CH(CH_3)_2$, and $R^1$=3-Chlorophenethyl) was prepared from B3 ($R^3$=$CH_3$, $R^4$=$CH_2CH(CH_3)_2$, and $R^1$=3-Chlorophenethyl) following a procedure similar to Method A, Step 3. NMR($CD_3OD$): δ 8.1, br, 1H; δ 7.35, s, 1H; δ 7.25, m, 3H; δ 3.6, m, 1H; δ 3.4, m, 1 H, δ 3.0, m, 1H, δ 2.8, m, 1 H, δ 1.75, m, 1H, δ 1.6, m, 1H, δ 1.35, m, 1H, δ 1.2 s, 3H; δ 0.8, m, 6H. ES_LCMS (m/e): 308.1

The following compounds were prepared using similar methods

| # | Structure | MW | Obs. m/e |
|---|---|---|---|
| 545 | 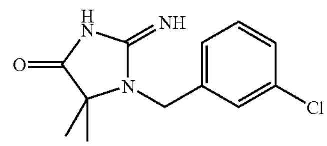 | 251 | 252 |
| 546 | 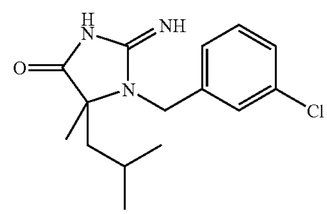 | 293 | 294 |
| 547 | 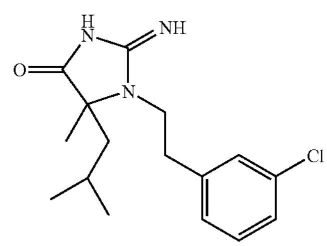 | 307 | 308 |
| 548 | 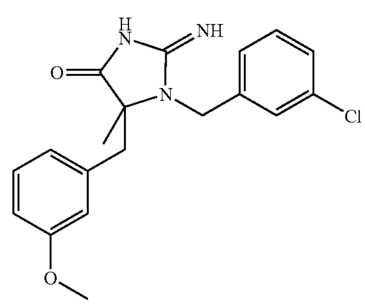 | 357 | 358 |
| 549 | 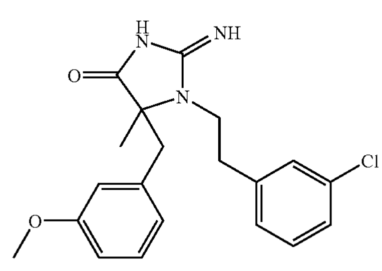 | 371 | 372 |

-continued

| # | Structure | MW | Obs. m/e |
|---|-----------|----|----|
| 550 | (structure: 1-[2-(3-chlorophenyl)ethyl]-5-isobutyl-5-methyl-4-(benzylimino)-2-thioxoimidazolidine) | 413 | |
| 551 | (structure: 1-[2-(3-chlorophenyl)ethyl]-5,5-dimethyl-2-imino-imidazolidin-4-one) | 265 | |

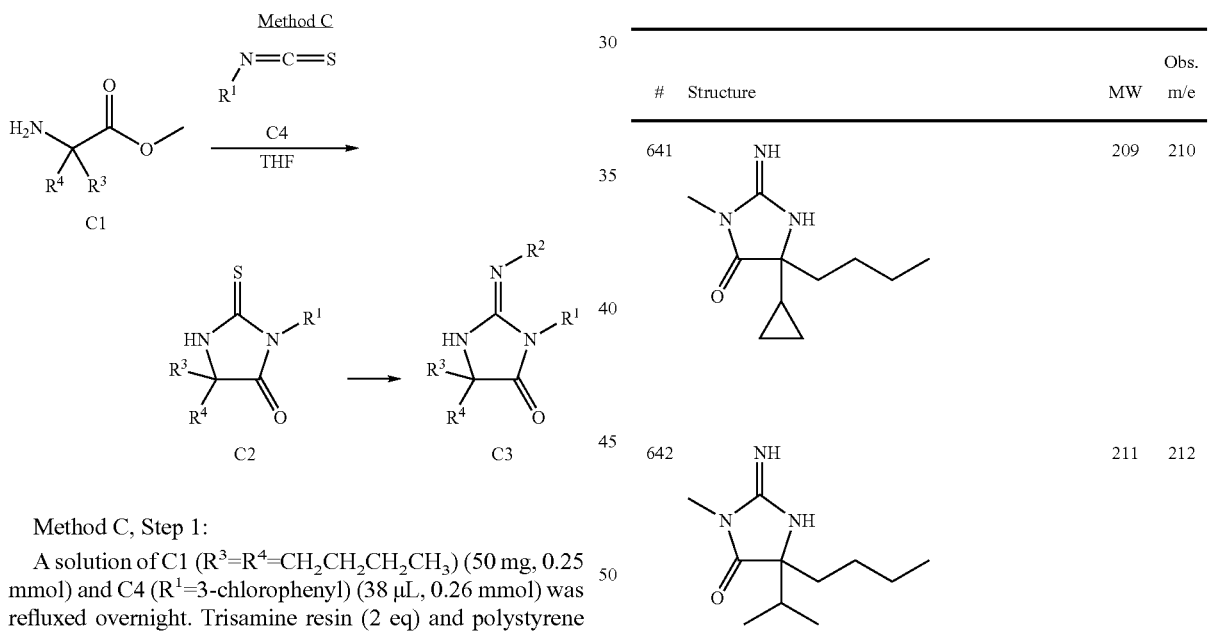

Method C, Step 1:

A solution of C1 ($R^3=R^4=CH_2CH_2CH_2CH_3$) (50 mg, 0.25 mmol) and C4 ($R^1$=3-chlorophenyl) (38 μL, 0.26 mmol) was refluxed overnight. Trisamine resin (2 eq) and polystyrene isocyanate resin (2 eq) was added and the mixture was agitated. After 3 h, the suspension was filtered and the resin was washed with $CH_2Cl_2$ (3×) and $CH_3OH$ (3×). The filtrate was concentrated to afford C2 ($R^1$=3-Cl—$C_6H_4$, $R^3=R^4=CH_2CH_2CH_2CH_3$) (60 mg, 68%).

Method C, Step 2:

Compound C3 ($R^1$=3-$C_1$-$C_6H_4$, $R^2$=H, $R^3=R^4=CH_2CH_2CH_2CH_3$) was prepared from C2 ($R^1$=3-$C_1$-$C_6H_4$, $R^3=R^4=CH_2CH_2CH_2CH_3$) following a procedure similar to Method A, Step 3. NMR(CDCl3): δ 7.4, m, 2H; δ 7.2, m, 2H; δ 5.0, s, 2H; δ 1.7, m, 4H; δ 1.1, m, 8H; δ 0.7; m, 6H. ES-LCMS (m/e): 336.1.

The following compounds were prepared using similar method.

| # | Structure | MW | Obs. m/e |
|---|-----------|----|----|
| 641 | (2-imino-3-methyl-5-butyl-5-cyclopropyl-imidazolidin-4-one) | 209 | 210 |
| 642 | (2-imino-3-methyl-5-butyl-5-isopropyl-imidazolidin-4-one) | 211 | 212 |
| 643 | (2-imino-3-methyl-spiro-indane-imidazolidin-4-one) | 215 | 216 |

-continued

| # | Structure | MW | Obs. m/e |
|---|---|---|---|
| 644 | 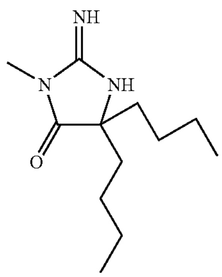 | 225 | 226 |
| 645 | 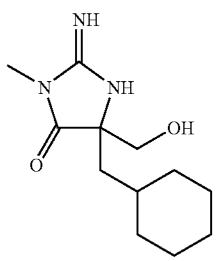 | 239 | 240 |
| 646 | 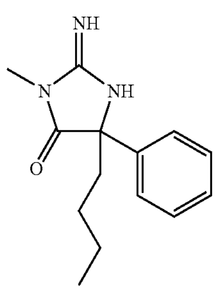 | 245 | 246 |
| 647 | 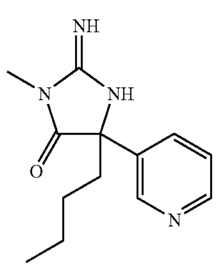 | 246 | 247 |
| 648 | 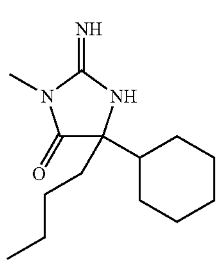 | 251 | 252 |

-continued

| # | Structure | MW | Obs. m/e |
|---|---|---|---|
| 649 | 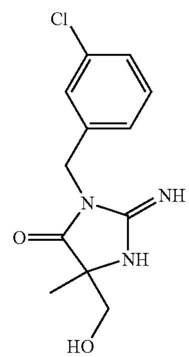 | 267 | 268 |
| 650 | 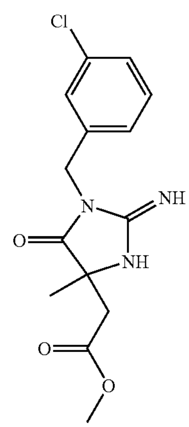 | 309 | 310 |
| 651 | 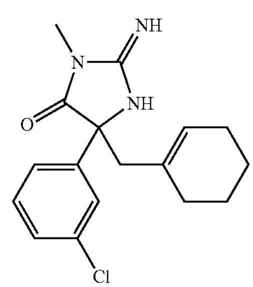 | 317 | 318 |
| 652 | 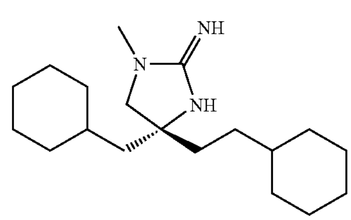 | 319 | 320 |
| 653 | 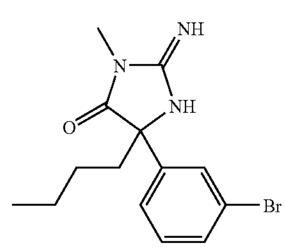 | 323 | 324 |

| # | Structure | MW | Obs. m/e |
|---|---|---|---|
| 654 | 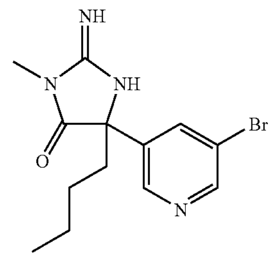 | 324 | 325 |
| 655 | 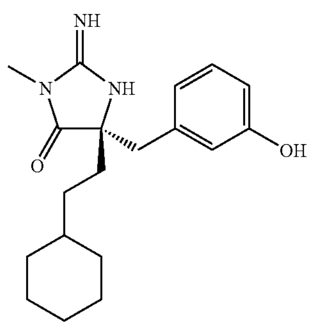 | 329 | 330 |
| 656 | 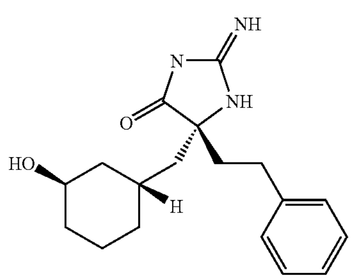 | 329 | 330 |
| 657 | 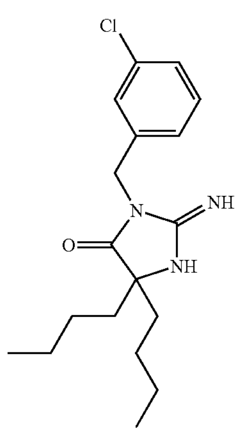 | 335 | 336 |
| 658 | 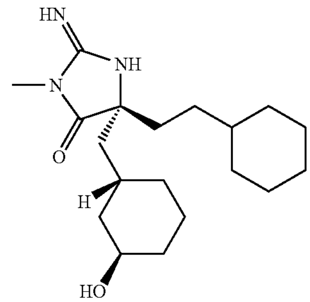 | 335 | 336 |
| 659 | 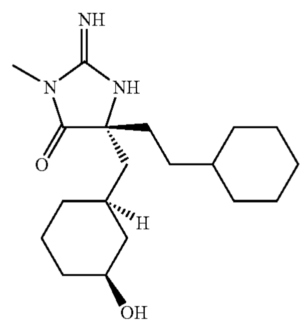 | 335 | 336 |
| 660 | 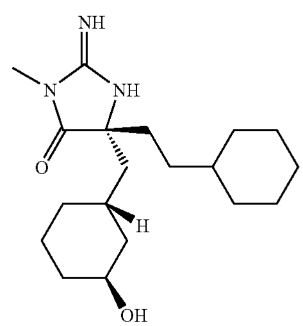 | 335 | 336 |
| 661 | 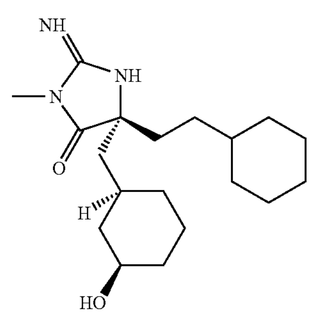 | 335 | 336 |

-continued

| # | Structure | MW | Obs. m/e |
|---|---|---|---|
| 662 | 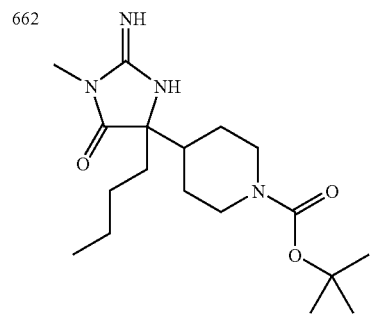 | 352 | 353 |
| 663 | 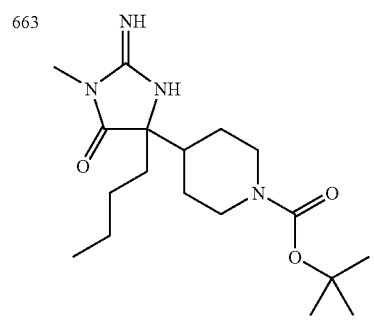 | 352 | 353 |
| 664 | 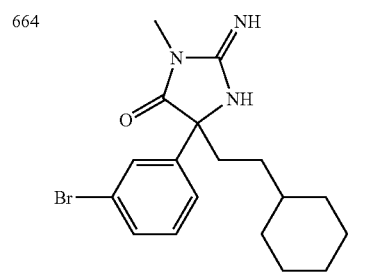 | 377 | 378 |
| 665 | 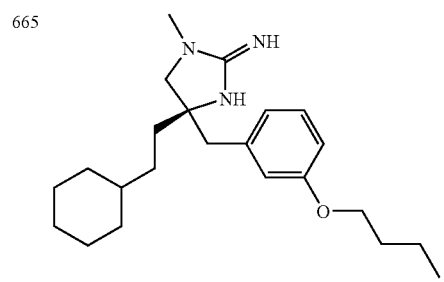 | 385 | 386 |
| 666 | 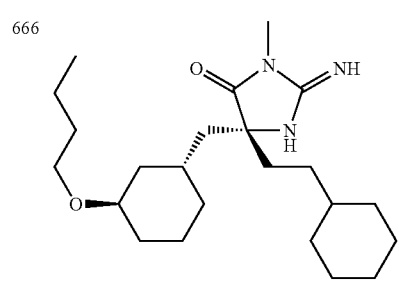 | 391 | 392 |

-continued

| # | Structure | MW | Obs. m/e |
|---|---|---|---|
| 667 | 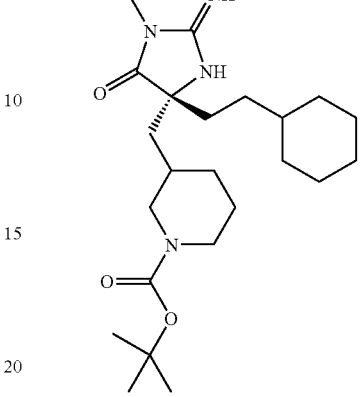 | 420 | 421 |
| 668 | 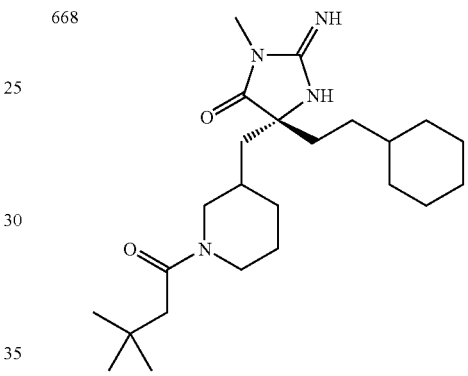 | 420 | 421 |

Method D

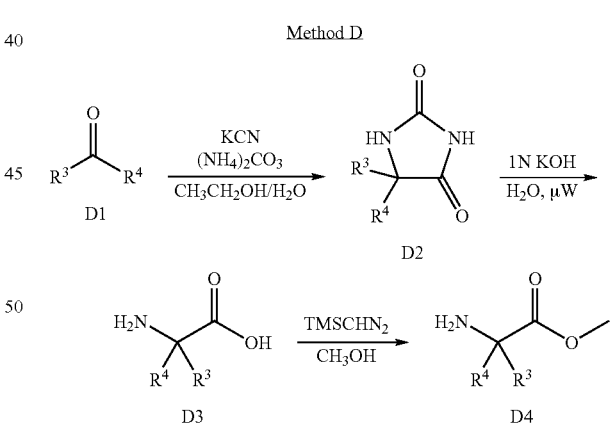

Method D, Step 1:

A mixture of D1 ($R^3=R^4=CH_2C_6H_5$) (20 g), potassium cyanide (40 g) and ammonium carbonate (15 g) in ethanol (100 mL) and $H_2O$ (200 mL) was heated in a sealed flask at 130° C. overnight to yield 25 g of D2 ($R^3=R^4=CH_2C_6H_5$) after filtration followed by washing with water.

Method D, Step 2:

A solution of 2 N KOH (3 eq) was added to D2 ($R^3=R^4=CH_2C_6H_5$) (1 eq) and irradiated via microwave at 185° C. for 3 h followed by addition of concentrated HCl to the solution until a pH=2-3 was obtained. The solid was filtered and washed with water to afford D3 ($R^3=R^4=CH_2C_6H_5$).

Method D, Step 3:

A solution of trimethylsilyldiazomethane in hexane (2 N) (2 eq) was added drop wise to a solution of D3 ($R^3=R^4=CH_2C_6H_5$) (1 eq) in anhydrous $CH_3OH$ (30 mL). After 1 h, an additional 2 eq of trimethylsilyldiazomethane in hexane (2 N) was added and the reaction was stirred for 20 minutes before it was was concentrated. The residue was dissolved in a 0.2 N HCl solution (25 mL) and washed with ether (3×). A saturated solution of $Na_2CO_3$ was added to the aqueous phase until the pH of the solution was basic. The solution was extracted with ethyl acetate (3×). The organic extracts were combined, dried over $Na_2SO_4$, and concentrated to afford D4 ($R^3=R^4=CH_2C_6H_5$).

The following amino esters were prepared using a similar method.

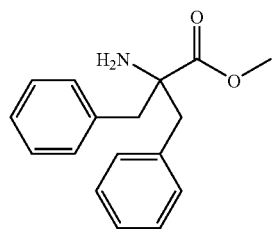

D5

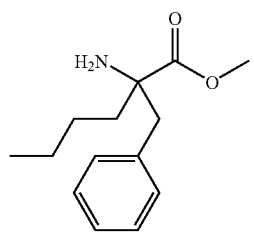

D6

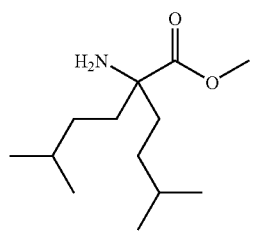

D7

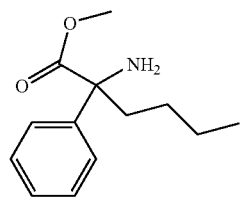

D8

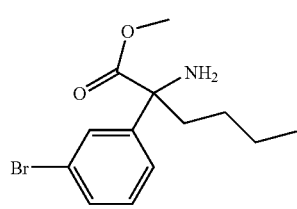

D9

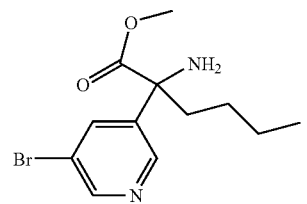

D10

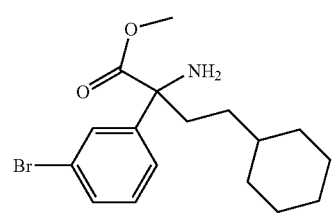

D11

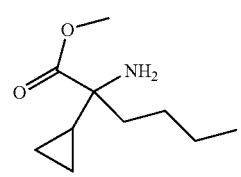

D12

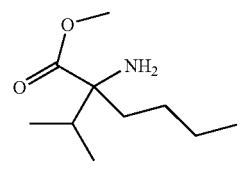

D13

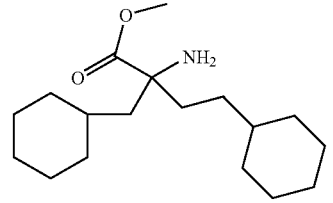

D14

Method E

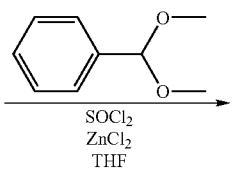

E1

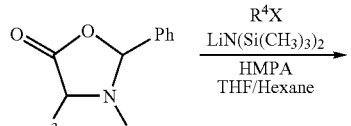

E2

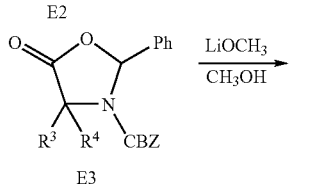

E3

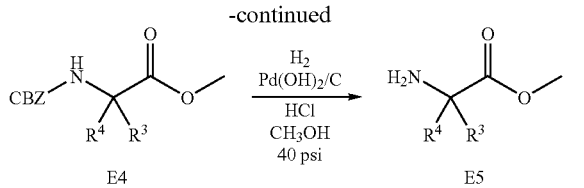

Method E, Step 1:

Thionyl chloride (0.47, 6.38 mmol) was added drop wise to a solution of E1 (R³=CH₂CH₂C₆H₅) (2 g, 6.38 mmol) and benzaldehyde dimethyl acetal (0.96 mL, 6.38 mmol) in anhydrous THF at 0° C. under N₂. After 5 min, ZnCl₂ (0.87 g, 6.38 mmol) was added and the reaction mixture was stirred at 0° C. After 3 h, an additional amount of ZnCl₂ (0.18 g, 1.28 mmol) and thionyl chloride (0.1 mL, 1.28 mmol) were added and stirred for 1 h at 0° C. The reaction mixture was poured into a stirred suspension of ice/H₂O. The mixture was stirred occasionally until the ice melted. The aqueous solution was extracted with ether (3×). The combined organic extracts were washed with H₂O (3×), a sat. aqueous solution of NaHCO₃ (1×), and H₂O (2×). The organic solution was dried over Na₂SO₄, filtered and concentrated. The crude material was purified via flash chromatography eluting with ethyl acetate in hexane to yield compound E2 (R³=CH₂CH₂C₆H₅).

Method E, Step 2:

A solution of lithium hexamethyldisilazide in hexane (1.0 M, 1.65 mL, 1.64 mmol) was added drop wise to a solution of E2 (R³=CH₂CH₂C₆H₅) (600 mg, 1.49 mmol) and HMPA (0.85 mL) in THF (6.5 mL) cooled at −78° C. under N₂. After 15 min, isobutyl iodide (0.52 mL, 4.48 mmol) was added drop wise and the reaction mixture was stirred at −78° C. for 3 h. The reaction was warmed to −65° C., stirred for 2 h and warmed to rt overnight. The reaction solution was poured into a mixture of sat. NaHCO₃ (aq)/ether/ice. The aqueous layer was extracted with ether (3×). The organic extracts were combined and washed with brine (2×). The organic solution was dried over Na₂SO₄, filtered and concentrated. The crude material was purified via flash chromatography eluting with ethyl acetate in hexane to yield compound E3 (R³=CH₂CH₂C₆H₅, R⁴=CH₂CH(CH₃)₂).

Method E, Step 3:

A solution of lithium methoxide (1 N in CH₃OH) (0.36 mL, 0.36 mmol) was added to compound E3 (R³=CH₂CH₂C₆H₅, R⁴=CH₂CH(CH₃)₂). The reaction mixture was shaken at rt for 50 min. An additional 0.55 eq of lithium methoxide were added. After 2.5 h, a sat. aqueous solution of NaHSO₃ (0.75 mL) and ethyl acetate (3 mL) was added to the reaction mixture and shaken for 15 min. The suspension was filtered. The resulting white solid was washed with a sat. aqueous solution of NaHSO₃ (1×) and ethyl acetate (1×). The aqueous phase of the filtrate was separated and extracted with ethyl acetate (2×). The organic extracts were combined and washed with a sat. aqueous solution of NaHSO₃ (8×). The organic solution was dried over Na₂SO₄, filtered and concentrated to afford E4 (R³=CH₂CH₂C₆H₅, R⁴=CH₂CH(CH₃)₂) (109 mg, 87%).

Method E, Step 4:

To a solution of E4 (R³=CH₂CH₂C₆H₅, R⁴=CH₂CH(CH₃)₂) (109 mg, 0.28 mmol) in CH₃OH (4 mL) was added 1 N HCl (0.28 mL, 0.28 mmol) and 20% palladium hydroxide on carbon (22 mg). The reaction mixture was hydrogenated at 40 psi. After 2.5 h, the reaction was filtered and the catalyst was washed with CH₃OH (3×). The filtrate was concentrated to afford E5 (R³=CH₂CH₂C₆H₅, R⁴=CH₂CH(CH₃)₂) (78 mg, 96%).

The following aminoesters were prepared using similar method.

E6

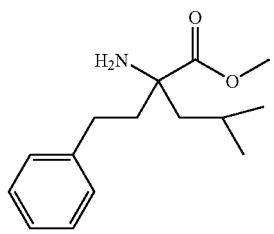

E7

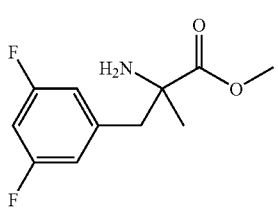

E8

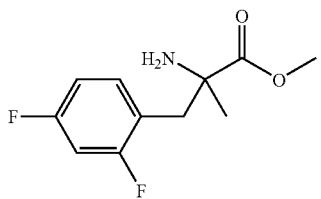

E9

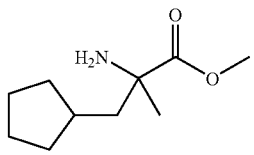

E10

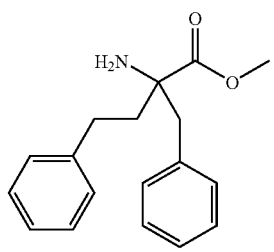

E11

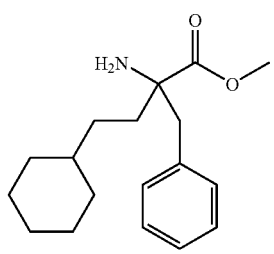

-continued

E12 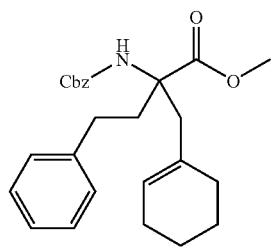

E13 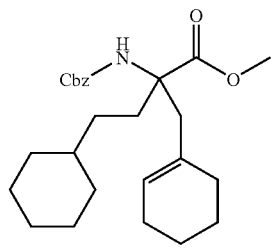

E14

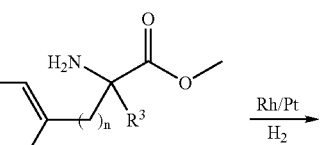

E15

Method F

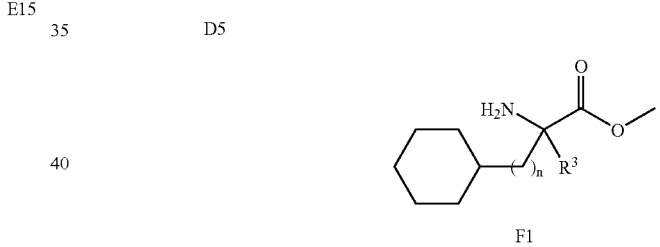

E16

A 500 mL methanol solution of 20 g of D5 ($R^3$=benzyl, n=1) with 1.5 eq of HCl was hydrogenated with 1 g of Rh/C (5% w/w) and 2 g of Pt/C (5% w/w) at 60 psi for 2 days. The solid was filtered and washed with excessive methanol. The combined solution was evaporated to give 20 g of F1 ($R^3$=cyclohexylmethyl, n=1) as HCl salt.

The following amino esters were examples prepared using similar method.

E17

F2

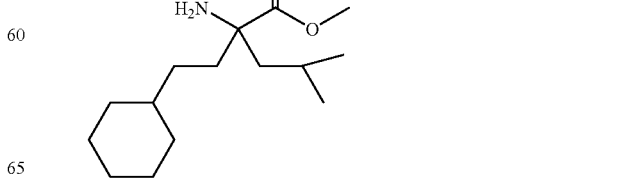

-continued

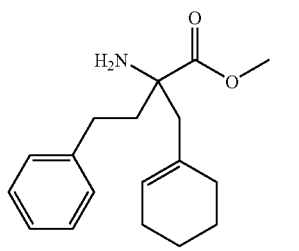

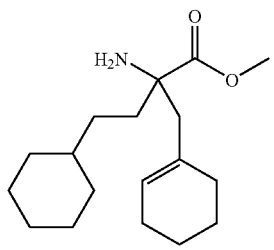

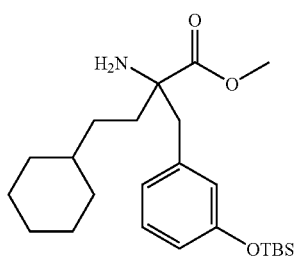

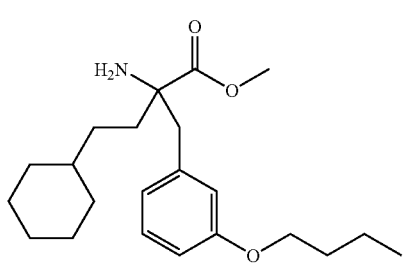

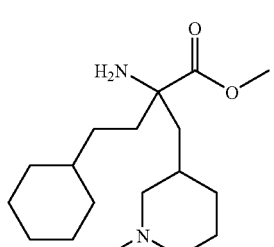

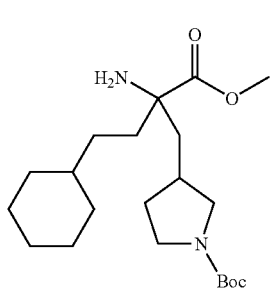

-continued

F3 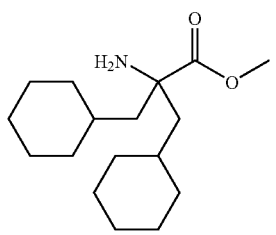

F4 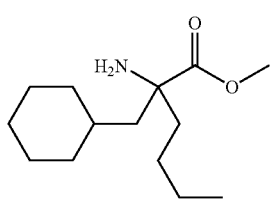

F5 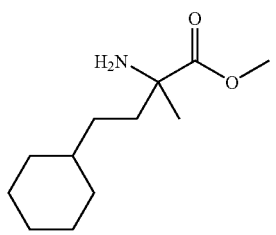

F6 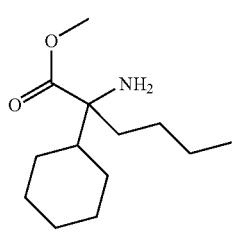

F7 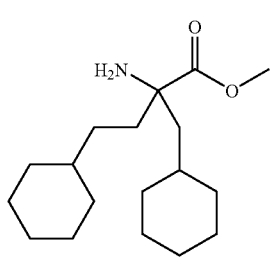

F8 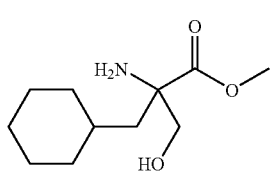

F9 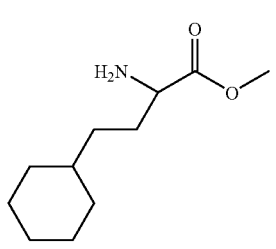

-continued

F10 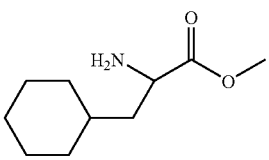

Method G

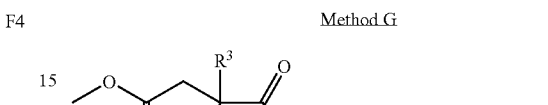
G1

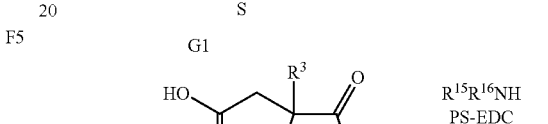
G2

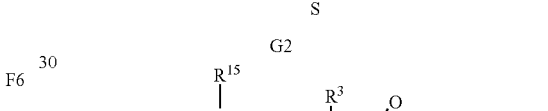
G3

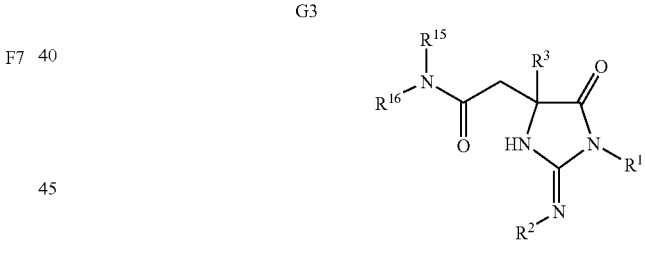
G4

Method G, Step 1:

To a solution of G1 ($R^1$=CH$_2$(3-ClC$_6$H$_4$) and $R^3$=CH$_3$) (400 mg, 1.23 mmol, generated following a procedure similar to Method C, Step 1) in ethanol (5 mL) was added lithium hydroxide monohydrate (100 mg, 2.45 mmol) in H$_2$O (0.5 mL). After 2.5 h, another portion of lithium hydroxide monohydrate (100 mg, 2.45 mmol) was added. After 5.5 h, the reaction mixture was diluted with H$_2$O (15 mL) and extracted with ether (2×). A solution of 30% HCl was added to the aqueous phase until its pH=1 to 2. The solution was saturated with NaCl and extracted with ethyl acetate (3×). The organic solution was dried over Na$_2$SO$_4$, filtered and concentrated to afford G2 ($R^1$=CH$_2$(3-ClC$_6$H$_4$) and $R^3$=CH$_3$) (357 mg, 93%).

Method G, Step 2:

A solution of benzyl amine (1.2 eq) was added to G2 ($R^1$=CH$_2$(3-ClC$_6$H$_4$) and $R^3$=CH$_3$) (1 eq), HOBT (1.5 eq)

and polystyrene EDC resin (94 mg, 1.53 mmol/g, 3 eq) in 1:1 THF:CH$_3$CN (1 mL). The reaction mixture was shaken overnight at rt. Trisamine resin (85 mg, 3.38 mmol/g, 6 eq) and isocyanate resin (100 mg, 1.47 mmol/g, 3 eq) was added. After 6 h, the suspension was filtered and the filtrate was concentrated to afford G3 (R$^1$=CH$_2$(3-ClC$_6$H$_4$), R$^3$=CH$_3$, R$^{15}$=CH$_2$C$_6$H$_5$ and R$^{16}$=H).

Method G, Step 3:

Compound G4 (R$^1$=CH$_2$(3-ClC$_6$H$_4$), R$^2$=H, R$^3$=CH$_3$, R$^{15}$=CH$_2$C$_6$H$_5$ and R$^{15}$=H) was prepared from G3 (R$^1$=CH$_2$(3-ClC$_6$H$_4$), R$^3$=CH$_3$, R$^{15}$=CH$_2$C$_6$H$_5$ and R$^{16}$=H) following a procedure similar to Method A, Step 3.

The following compounds were prepared using similar methods.

| # | Structure | MW | Obs. m/e |
|---|-----------|-----|----------|
| 669 | 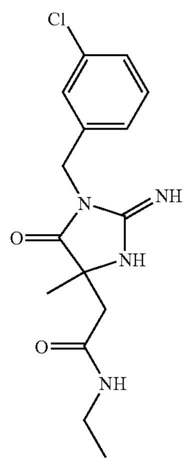 | 322 | 323 |
| 670 | 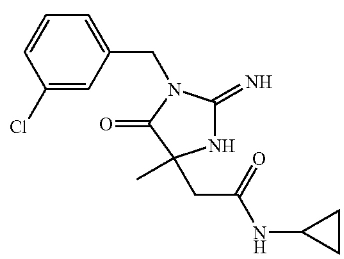 | 334 | 335 |
| 671 | 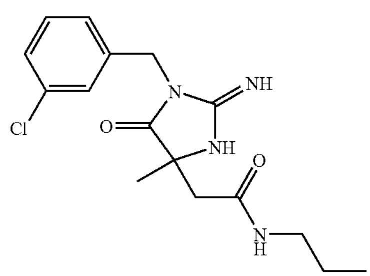 | 336 | 337 |
| 672 | 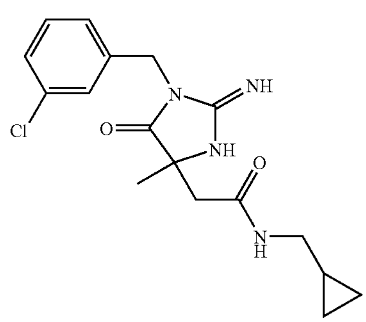 | 348 | 349 |

-continued

| # | Structure | MW | Obs. m/e |
|---|---|---|---|
| 673 | 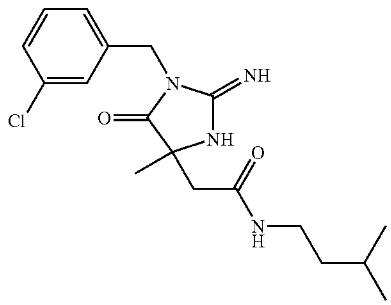 | 364 | 365 |
| 674 | 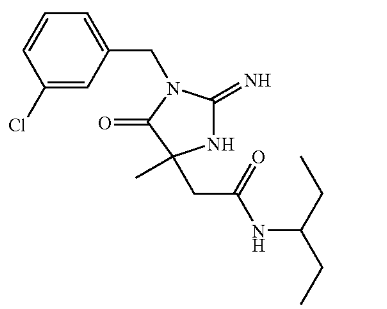 | 364 | 365 |
| 675 | 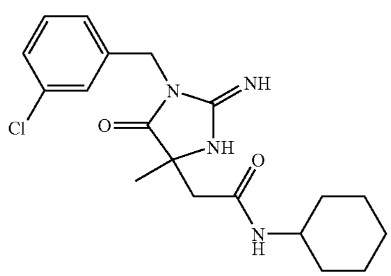 | 376 | 377 |
| 676 | 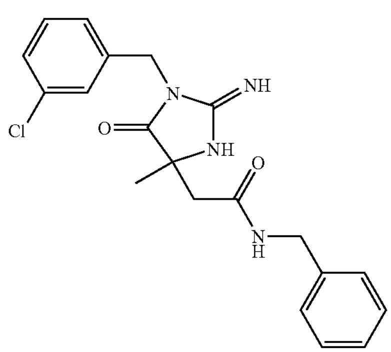 | 384 | 385 |

-continued

| # | Structure | MW | Obs. m/e |
|---|---|---|---|
| 677 | 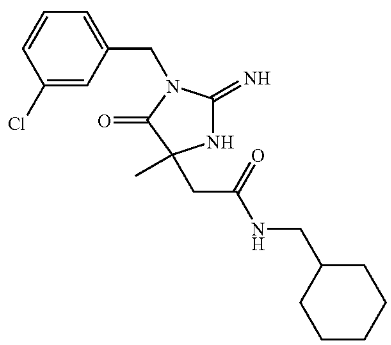 | 390 | 391 |
| 678 | 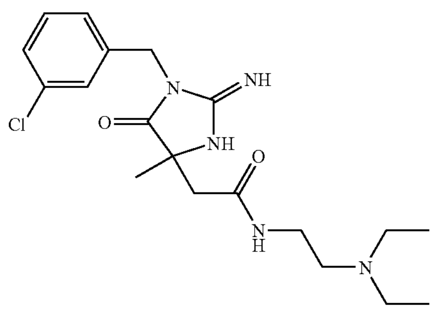 | 393 | 394 |
| 679 | 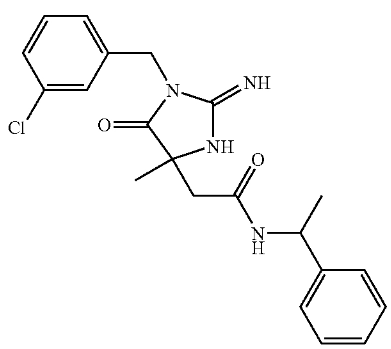 | 398 | 399 |
| 680 | 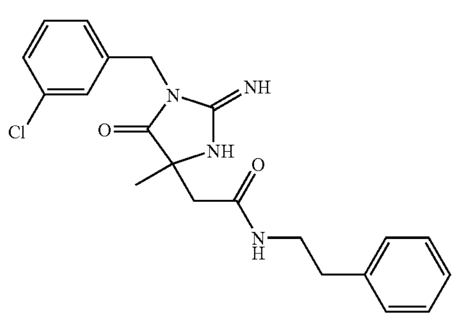 | 398 | 399 |

-continued

| # | Structure | MW | Obs. m/e |
|---|---|---|---|
| 681 | 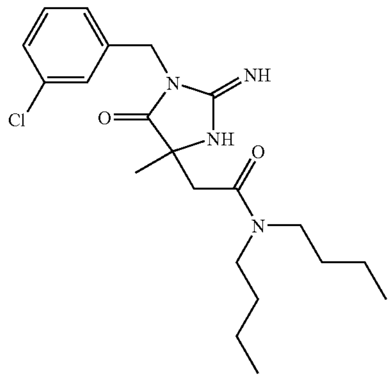 | 406 | 407 |
| 682 | 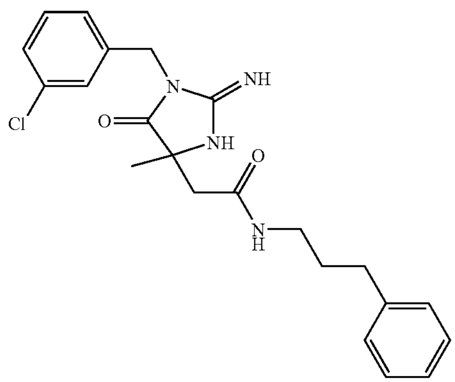 | 412 | 413 |
| 683 | 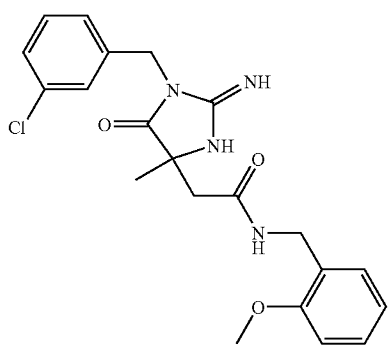 | 414 | 415 |
| 684 | 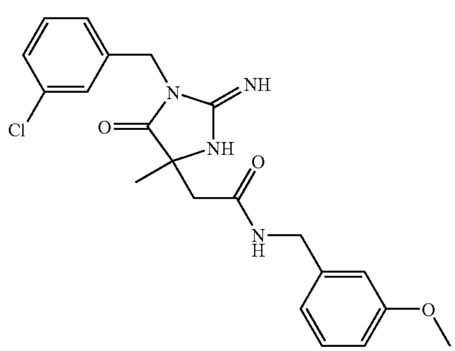 | 414 | 415 |

-continued

| # | Structure | MW | Obs. m/e |
|---|---|---|---|
| 685 | 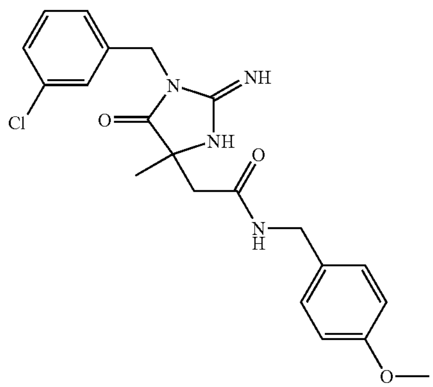 | 414 | 415 |
| 686 | 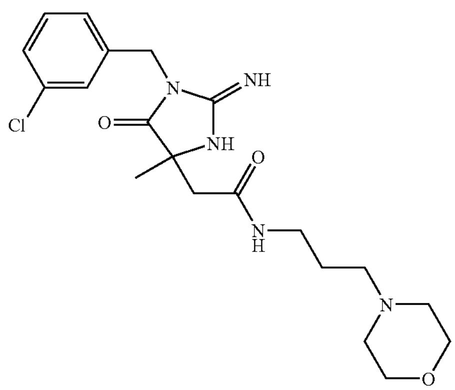 | 421 | 422 |
| 687 | 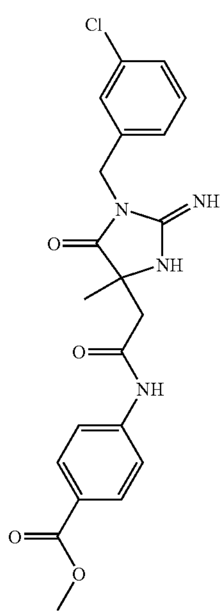 | 428 | 429 |

-continued

| # | Structure | MW | Obs. m/e |
|---|---|---|---|
| 688 | 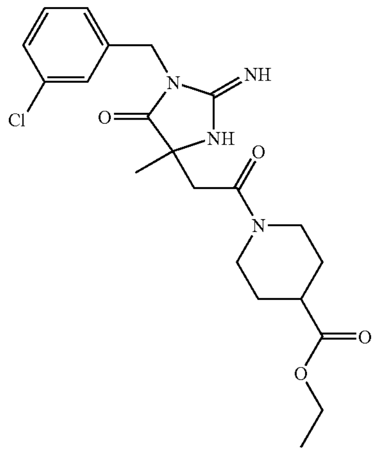 | 434 | 435 |
| 689 | 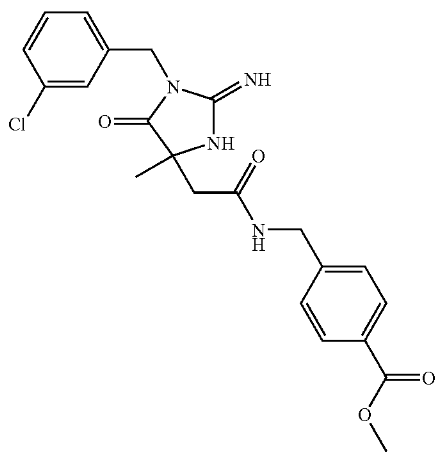 | 442 | 443 |
| 690 | 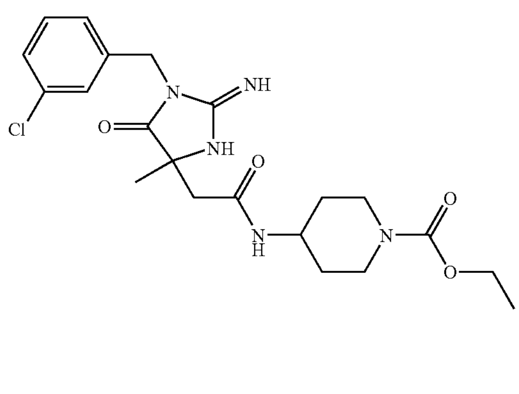 | 449 | 450 |

-continued
| # | Structure | MW | Obs. m/e |
|---|---|---|---|
| 691 | 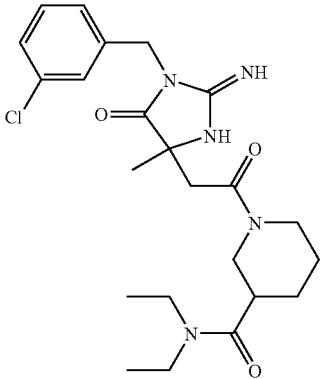 | 461 | 462 |
| 692 | 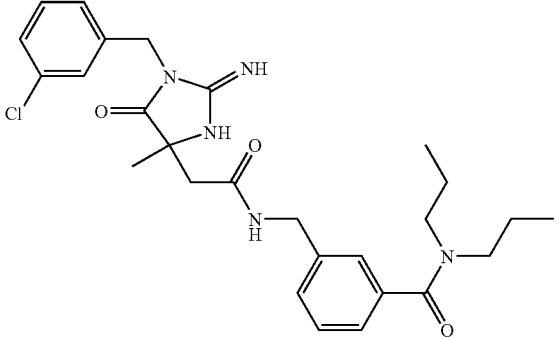 | 511 | 512 |
| 693 | 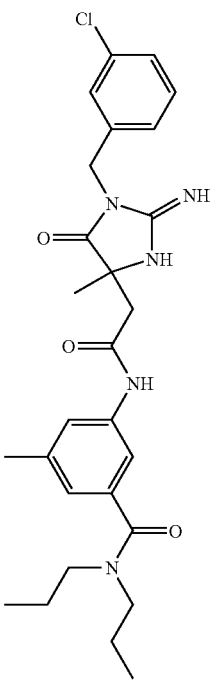 | 511 | 512 |

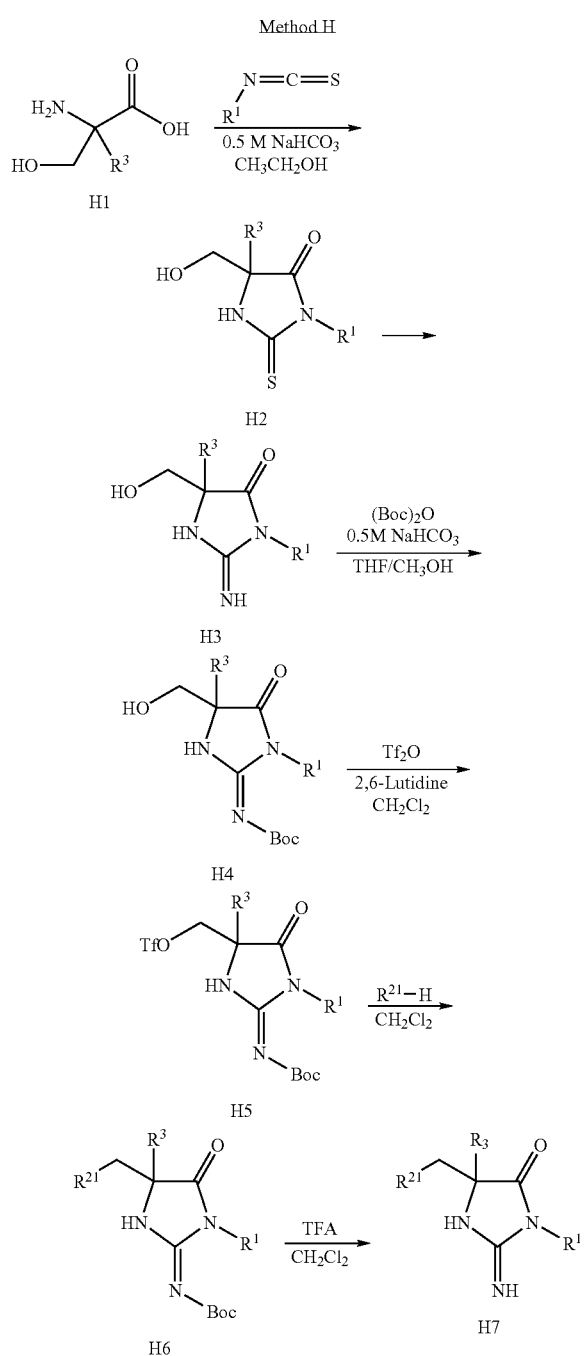

Method H, Step 1:

To a solution of H1 ($R^3$=$CH_3$) (5 g, 39 mmol) in a 1:1 mixture of 0.5 M $NaHCO_3$:$CH_3CH_2OH$ was added $R^1$-NCS ($R^1$=3-chlorobenzyl) (11.5 mL, 78 mmol). The reaction mixture was heated at 50° C. overnight. The reaction was cooled and diluted with water. The aqueous phase was extracted with ethyl acetate (5×). The organic extracts were combined, washed with water (2×) and dried over $Na_2SO_4$. The solution was filtered and solvent was removed to give a small volume of solution. Hexane was added and the resulting suspension was filtered to yield 6.8 g of a solid H2 ($R^3$=$CH_3$, $R^1$=$CH_2$(3-$ClC_6H_4$)) (61%).

Method H, Step 2:

Compound H3 ($R^3$=$CH_3$, $R^1$=$CH_2$(3-$ClC_6H_4$)) was synthesized from H2 ($R^3$=$CH_3$, $R^1$=$CH_2$(3-$ClC_6H_4$)) following a procedure similar to Method A, Step 3.

Method H, Step 3:

To a solution of crude H3 ($R^3$=$CH_3$, $R^1$=$CH_2$(3-$ClC_6H_4$)) (14 mmol) in a 1:3 mixture of $CH_3OH$:THF was added 0.5 M $NaHCO_3$ in $H_2O$ (28 mL, 14 mmol) and di-tert-butyl dicarbonate (3.69 g, 16.9 mmol). The reaction was stirred at rt for 2.5 h and then stored at −10° C. overnight. The reaction was diluted with brine and extracted with ethyl acetate (4×). The organic extracts were combined and washed with brine (1×). The organic solution was dried over $Na_2SO_4$, filtered and concentrated. The crude material was purified via flash chromatography eluting with ethyl acetate in hexane to afford 1.5 g of H4 ($R^1$=$CH_2$(3-$ClC_6H_4$) and $R^3$=$CH_3$).

Method H, Step 4:

A solution of triflic anhydride (128 μL, 0.76 mmol) in $CH_2Cl_2$ (5 mL) was added drop wise to a solution of H4 ($R^1$=$CH_2$(3-$ClC_6H_4$) and $R^3$=$CH_3$) (200 mg, 0.55 mmol) and 2,6-lutidine (176 μL, 2.18 mmol) at −30° C. The reaction mixture was stirred for 1.5 h. Water (10 mL) was added at −20° C. and the ice bath was removed. The reaction was stirred until it reached 0° C. The organic layer was separated, dried over $Na_2SO_4$, filtered and concentrated to afford 310 mg of H5 ($R^1$=$CH_2$(3-$ClC_6H_4$) and $R^3$=$CH_3$).

Method H, Step 5:

A solution of crude H5 ($R^1$=$CH_2$(3-$ClC_6H_4$) and $R^3$=$CH_3$) (0.11 mmol) and 7N ammonia in Methanol ($R^{21}$—H=$NH_2$—H) (10 eq) was stirred overnight at rt. The reaction solution was concentrated. The crude material was purified using reverse phase preparative HPLC eluting with a $CH_3CN$/$H_2O$ gradient with 0.1% formic acid to yield H6 ($R^1$=$CH_2$(3-$ClC_6H_4$), $R^3$=$CH_3$, $R^{21}$=$NH_2$).

Method H, Step 6:

A solution of 50% trifluoroacetic acid in $CH_2Cl_2$ (2 mL) was added to H6 ($R^1$=$CH_2$(3-$ClC_6H_4$), $R^3$=$CH_3$, $R^{21}$=$NH_2$). After 40 min the solvent was evaporated and residue purified by preparative HPLC/LCMS eluting with a $CH_3CN$/$H_2O$ gradient to afford H7 ($R^1$=$CH_2$(3-$ClC_6H_4$), $R_3$=$CH_3$, $R^{21}$=$NH_2$). NMR ($CDCl_3$), δ 7.45, m, 3H; δ 7.35, m, 1H; δ 4.9, m, 2H; δ 3.5, m, 2H; δ 1.65, s, 3H. ES_LCMS (m/e) 267.07.

The following compounds were prepared using similar methods.

| # | Structure | MW | Obs. m/e |
|---|---|---|---|
| 694 | 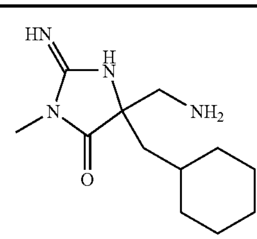 | 238 | 239 |

-continued

| # | Structure | MW | Obs. m/e |
|---|---|---|---|
| 695 | 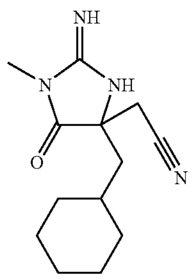 | 248 | 249 |
| 696 | 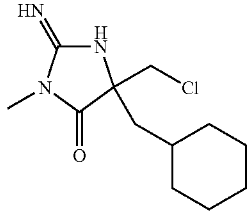 | 257 | 258 |
| 697 | 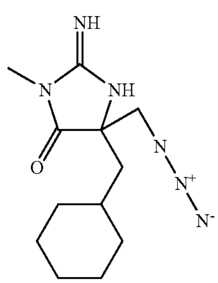 | 264 | 265 |
| 698 | 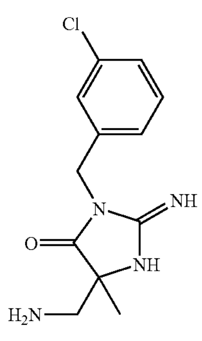 | 266 | 267 |
| 699 | 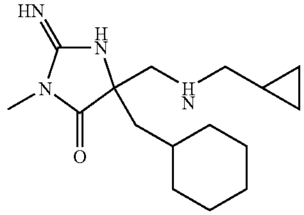 | 292 | 293 |

-continued

| # | Structure | MW | Obs. m/e |
|---|---|---|---|
| 700 | | 308 | 309 |
| 701 | | 314 | 315 |
| 702 | | 320 | 321 |
| 703 | | 328 | 329 |
| 704 | | 334 | 335 |

-continued

| # | Structure | MW | Obs. m/e |
|---|---|---|---|
| 705 | 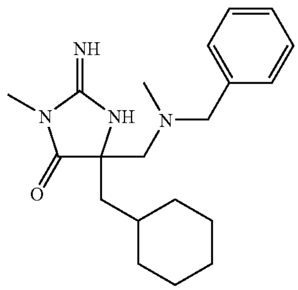 | 342 | 343 |
| 706 | 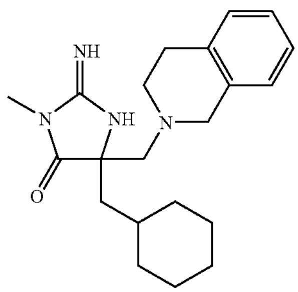 | 354 | 355 |
| 707 | 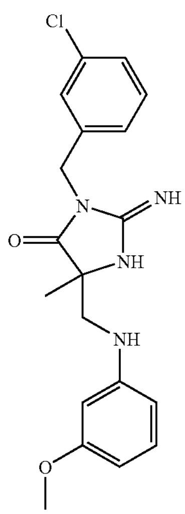 | 372 | 373 |
| 708 | 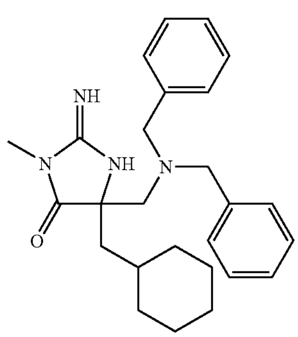 | 418 | 419 |

-continued

| # | Structure | MW | Obs. m/e |
|---|---|---|---|
| 709 | 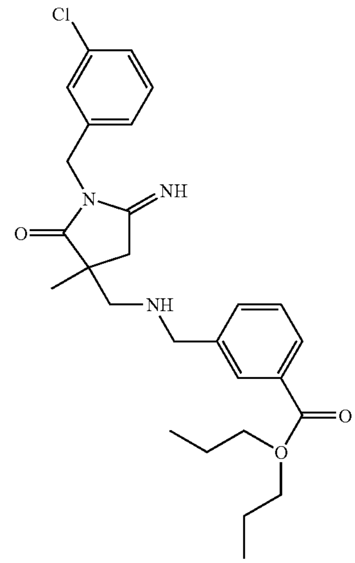 | 483 | 484 |

Method I

Method I, Step 1:

Diethylaminomethyl polystyrene resin (5 eq) was added to a solution of the formate salt of I1 ($R^1$=CH$_2$(3-ClC$_6$H$_4$), $R^3$=CH$_3$ and $R^{16}$=H) in CH$_2$Cl$_2$ and the suspension was agitated. After 15 min, the mixture was filtered and the resin was washed with CH$_2$Cl$_2$ (4×). The filtrate was concentrated to afford the free base I1 ($R^1$=CH$_2$(3-ClC$_6$H$_4$), $R^3$=CH$_3$ and $R^6$=H).

A solution of $R^{15}$COOH($R^5$=Phenethyl) (1.3 eq) was added to a mixture of EDC resin (41 mg, 1.53 mmol/g, 3 eq), HOBT (1.5 eq), and the free base of I1 (R$^1$=CH$_2$(3-ClC$_6$H$_4$), R$^3$=CH$_3$ and R$^{16}$=H) (0.021 mmol) in 1:1 CH$_3$CN:THF. The suspension was agitated overnight. Polystyrene isocyanate resin (45 mg, 3 eq), polystyrene trisamine resin (40 mg, 6 eq) and a 1:1 mixture of CH$_3$CN:THF (0.5 mL) was added. The mixture was agitated for 6 h. The suspension was filtered and the filtrate was concentrated to afford 12 (R$^1$=CH$_2$(3-ClC$_6$H$_4$), R$^3$=CH$_3$, R$^{16}$=H and R$^{15}$=CH$_2$CH$_2$C$_6$H$_5$).

Method I, Step 2:

I3 (R$^1$=CH$_2$(3-ClC$_6$H$_4$), R$^3$=CH$_3$, R$^{16}$=H and R$^{15}$=CH$_2$CH$_2$C$_6$H$_5$) was prepared from I2 (R$^1$=CH$_2$(3-ClC$_6$H$_4$), R$^3$=CH$_3$, R$^{16}$=H and R$^{15}$=CH$_2$CH$_2$C$_6$H$_5$) using method similar to method H step 6.

The following compounds were prepared using similar method.

| # | Structure | MW | Obs. m/e |
|---|-----------|----|----|
| 710 | 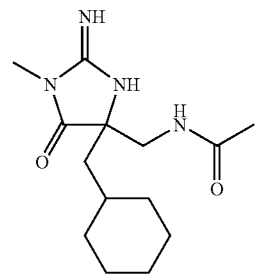 | 280 | 281 |
| 711 | 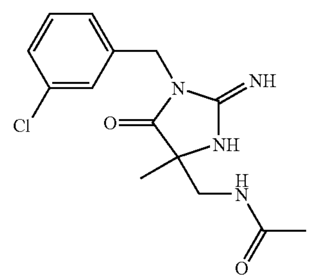 | 308 | 309 |
| 712 | 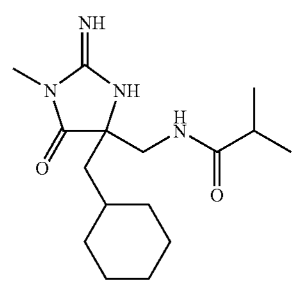 | 308 | 309 |
| 713 | 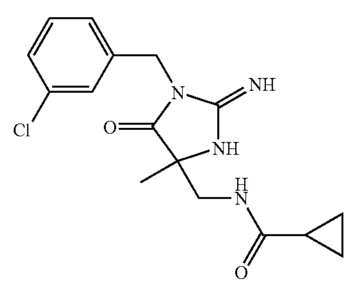 | 334 | 335 |

-continued
| # | Structure | MW | Obs. m/e |
|---|---|---|---|
| 714 | 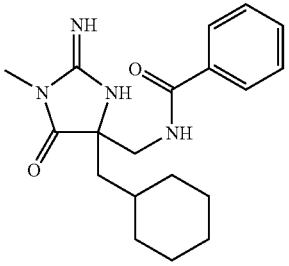 | 342 | 343 |
| 715 | 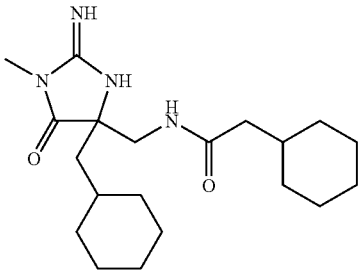 | 362 | 363 |
| 716 | 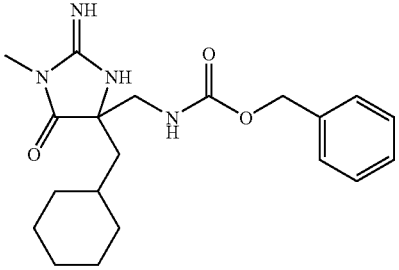 | 372 | 373 |
| 717 | 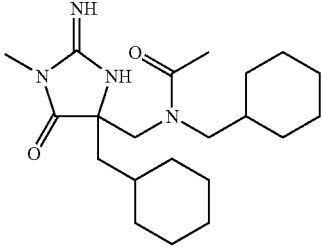 | 376 | 377 |
| 718 | 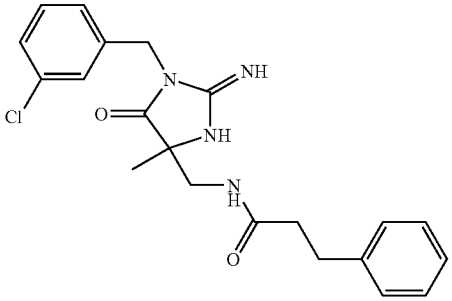 | 398 | 399 |

| # | Structure | MW | Obs. m/e |
|---|---|---|---|
| 719 | 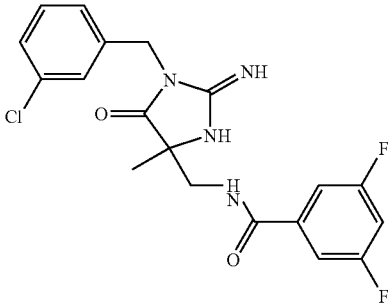 | 406 | 407 |
| 720 | 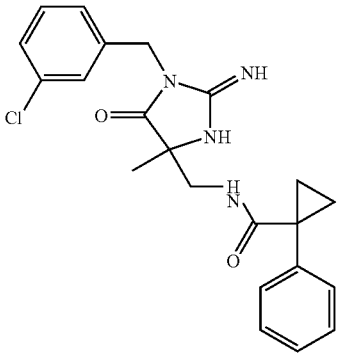 | 410 | 11 |
| 721 | 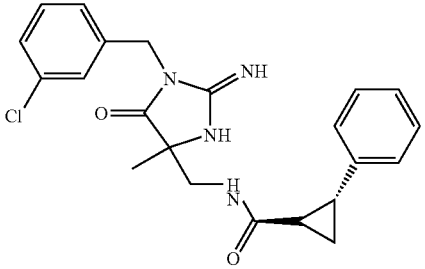 | 410 | 11 |
| 722 | 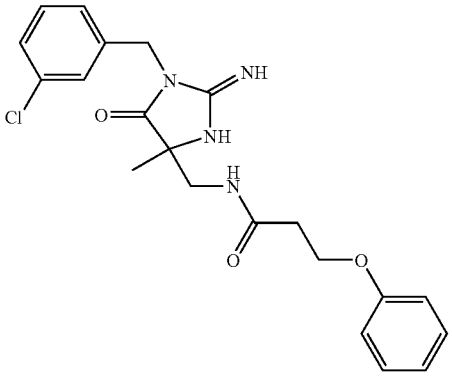 | 414 | 15 |

-continued

| # | Structure | MW | Obs. m/e |
|---|---|---|---|
| 723 | 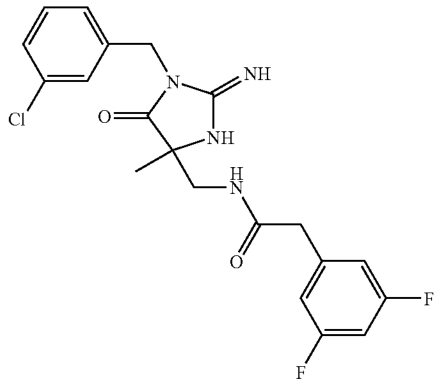 | 420 | 21 |
| 724 | 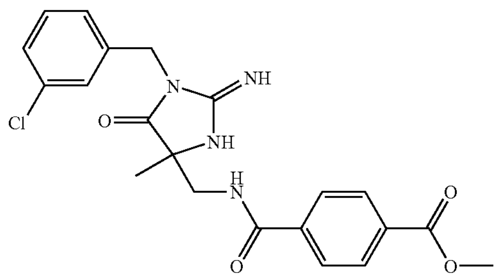 | 428 | 29 |
| 725 | 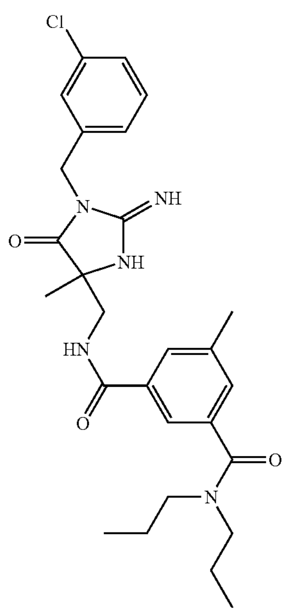 | 511 | 12 |

Method J

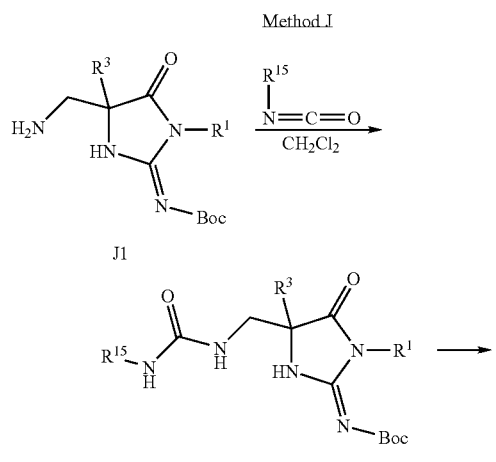

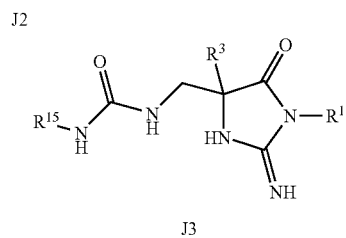

Method J, Step 1:

Diethylaminomethyl polystyrene resin (5 eq) was added to a solution of J1 (TFA salt, $R^1=CH_2(3\text{-}ClC_6H_4)$ and $R^3=CH_3$) in $CH_2Cl_2$ and the suspension was agitated. After 15 min, the mixture was filtered and the resin was washed with $CH_2Cl_2$ (4×). The filtrate was concentrated to afford the free base. A solution of $R^{15}NCO$ ($R^{15}$=butyl) (2 eq) in $CH_2Cl_2$ was added to the free base of J1 ($R^1=CH_2(3\text{-}ClC_6H_4)$ and $R^3=CH_3$) (0.021 mmol) in 1:1 $CH_3CN$:THF. The suspension was agitated overnight. Polystyrene isocyanate resin (45 mg, 3 eq), polystyrene trisamine resin (40 mg, 6 eq) and a 1:1 mixture of $CH_3CN$:THF (0.5 mL) was added. The mixture was agitated for 6 h. The suspension was filtered and the filtrate was concentrated to afford J2 ($R^1=CH_2(3\text{-}ClC_6H_4)$, $R^3=CH_3$, and $R^{15}=CH_2CH_2CH_2CH_3$).

Method J, Step 2:

Compound J3 ($R^1=CH_2(3\text{-}ClC_6H_4)$, $R^3=CH_3$, and $R^{15}=CH_2CH_2CH_2CH_3$) was prepared from J2 ($R^1=CH_2(3\text{-}ClC_6H_4)$, $R^3=CH_3$, and $R^{15}=CH_2CH_2CH_2CH_3$) following the procedure described in Method H, Step 2.

The following compounds were prepared using similar method.

| # | Structure | MW | Obs. m/e |
|---|---|---|---|
| 726 | 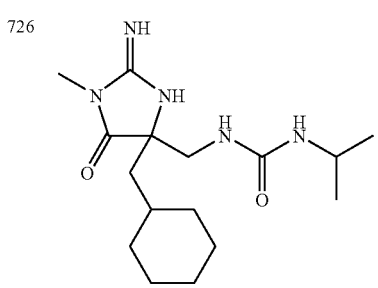 | 323 | 324 |
| 727 | 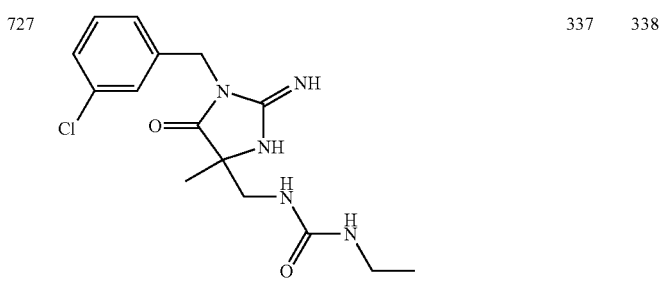 | 337 | 338 |

| # | Structure | MW | Obs. m/e |
|---|---|---|---|
| 728 | 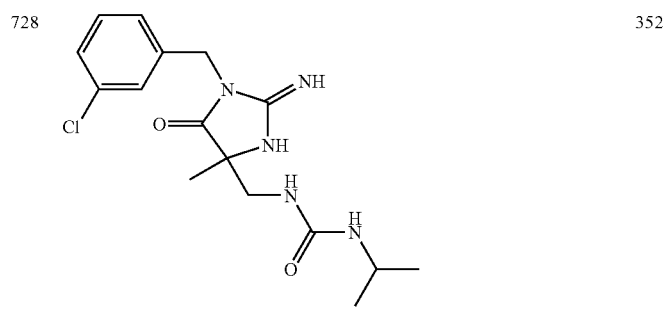 | | 352 |
| 729 | 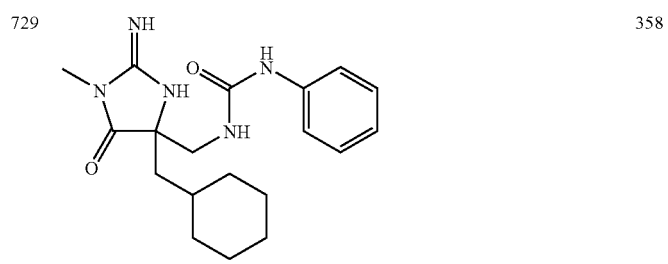 | | 358 |
| 730 | 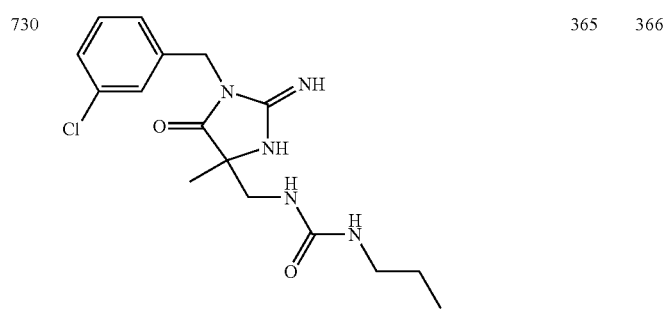 | 365 | 366 |
| 731 | 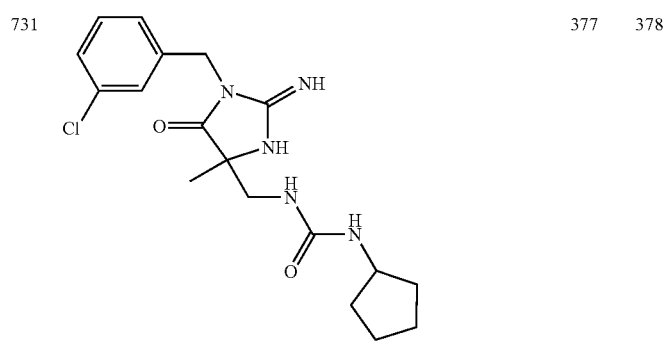 | 377 | 378 |

| # | Structure | MW | Obs. m/e |
|---|---|---|---|
| 732 | 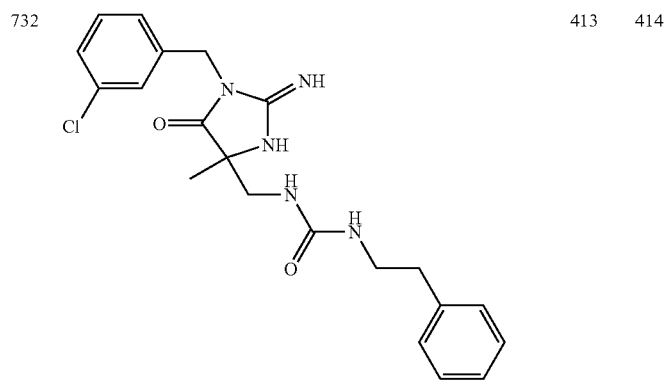 | 413 | 414 |
| 733 | 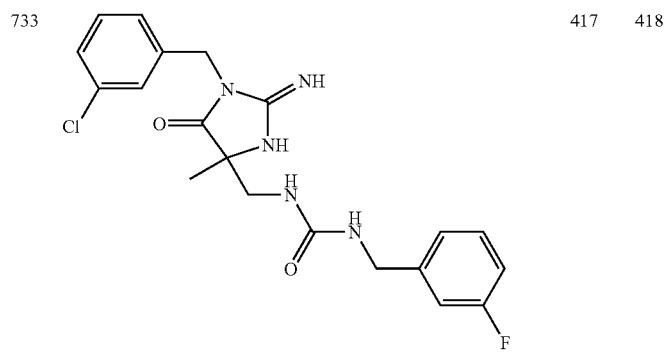 | 417 | 418 |
| 734 | 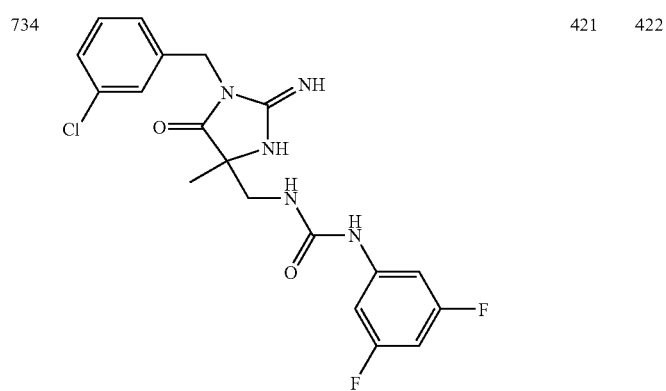 | 421 | 422 |

-continued

| # | Structure | MW | Obs. m/e |
|---|---|---|---|
| 735 | 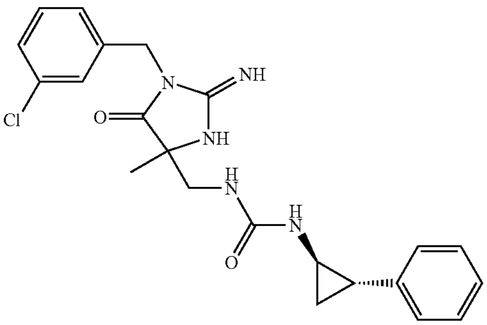 | 425 | 426 |

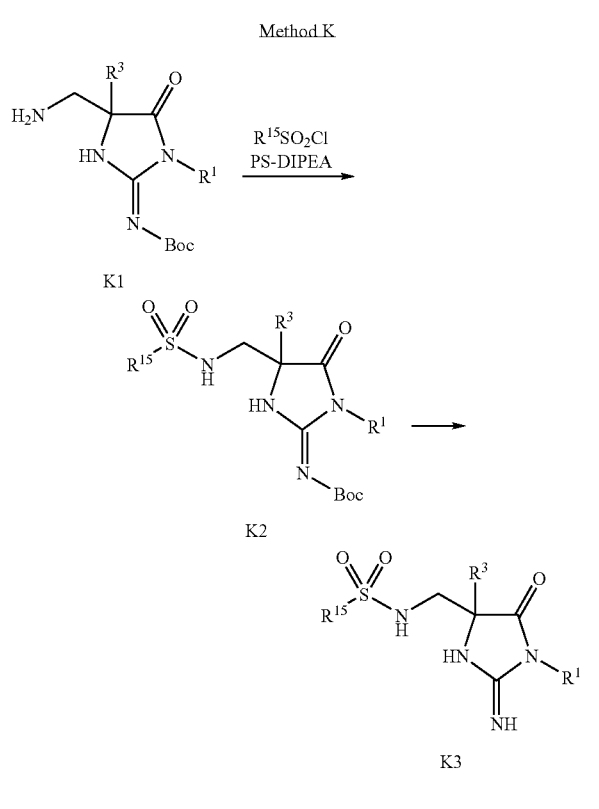

Method K, Step 1:

A solution of $R^{15}SO_2Cl$ ($R^{15}$=Propyl)(1.5 eq) was added to a suspension of polystyrene diisopropylethylamine resin (18 mg, 3.45 mmol/g, 3 eq) and the free base of K1 prepared using method H ($R^1$=$CH_2$(3-$ClC_6H_4$) and $R^3$=$CH_3$) (0.021 mmol) in 1:1 $CH_3CN$:THF. The suspension was agitated overnight. Polystyrene isocyanate resin (45 mg, 3 eq), polystyrene trisamine resin (40 mg, 6 eq) and a 1:1 mixture of $CH_3CN$:THF (0.5 mL) was added. The mixture was agitated for 6 h. The suspension was filtered and the filtrate was concentrated to afford K2 ($R^1$=$CH_2$(3-$ClC_6H_4$), $R^3$=$CH_3$, and $R^{15}$=$CH_2CH_2CH_3$).

Method K, Step 2:

Compound K3 ($R^1$=$CH_2$(3-$ClC_6H_4$), $R^3$=$CH_3$, and $R^{15}$=$CH_2CH_2CH_3$) was prepared from K2 ($R^1$=$CH_2$(3-$ClC_6H_4$), $R^3$=$CH_3$, and $R^{15}$=$CH_2CH_2CH_3$) following the procedure described in Method H, Step 6.

The following compounds were prepared using similar method.

| # | Structure | MW | Obs. m/e |
|---|---|---|---|
| 736 | 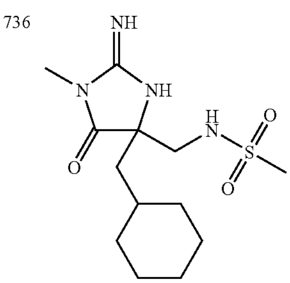 | 316 | 317 |
| 737 | 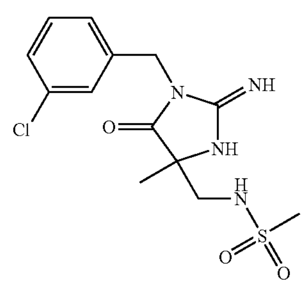 | 344 | 345 |
| 738 | 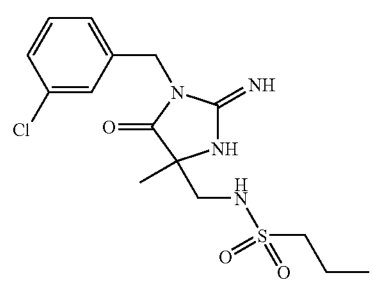 | 372 | 373 |

-continued

| # | Structure | MW | Obs. m/e |
|---|---|---|---|
| 739 | 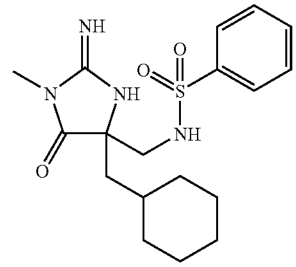 | 378 | 379 |
| 740 | 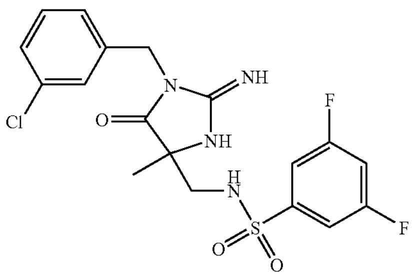 | 442 | 443 |
| 741 | 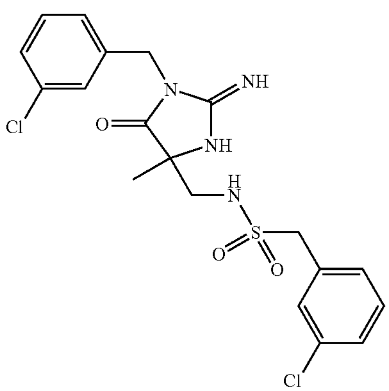 | 454 | 455 |
| 742 | 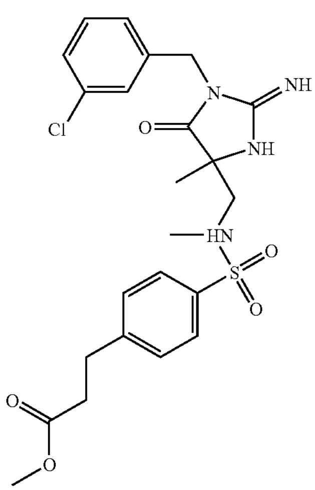 | 492 | 493 |

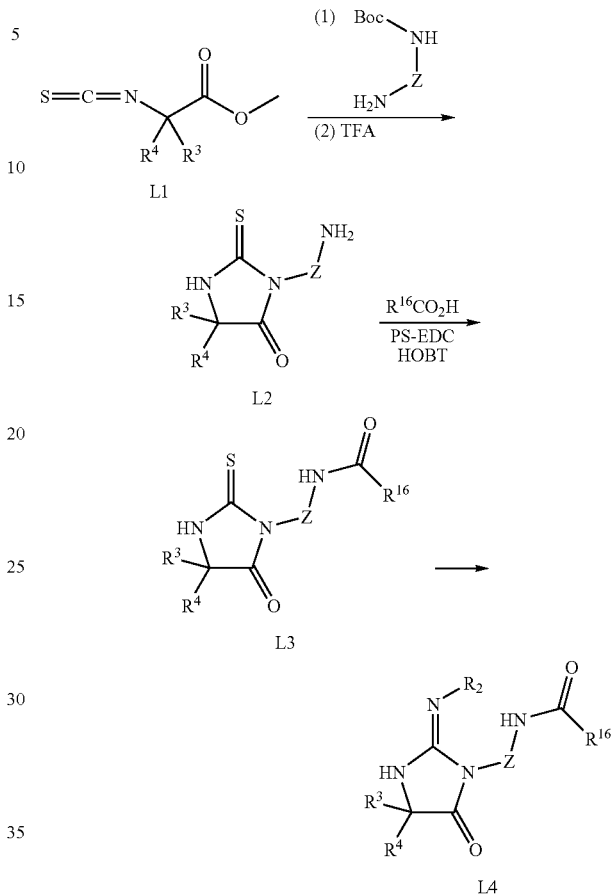

Method L (In the scheme, -Z-NH—C(O)R$^{16}$— is equivalent to R$^{51}$ substituted by R$^{21}$, or R$^1$ Subsitituted by alkyl-R$^{22}$, wherein R$^{21}$ and R$^{22}$ are —N(R$^{15}$)C(O)R$^{16}$ and R$^{15}$ is H, and wherein Z is optionally substituted alkylene-arylene, alkylene-arylene-alkylene, alkylene-heteroarylene, alkylene-heteroarylene-alkylene, alkylene-cycloalkylene, alkylene-cycloalkylene-alkylene, alkylene-heterocycloalkylene, alkylene-heterocycloalkylene-alkylene, arylene, heteroarylene, cycloalkylene or heterocycloalkylene)

Method L, Step 1:

A solution of L1 (R$^3$=CH$_3$ and R$^4$=CH$_2$CH(CH$_3$)$_2$) (1 eq) and Z=-paramethylene-benzyl) (1.05 eq) in CH$_2$Cl$_2$ was stirred at rt. The reaction solution was concentrated and purified via flash chromatography. The material was treated with 50% trifluoroacetic acid in CH$_2$Cl$_2$ for 30 min. The solution was concentrated. The residue was dissolved in 1 N HCl (10 mL) and washed with ether (2×). A saturated solution of Na$_2$CO$_3$ in H$_2$O was added to the aqueous phase until the solution became basic. The solution was extracted with CH$_2$Cl$_2$ (3×). The CH$_2$Cl$_2$ extracts were combined, dried over Na$_2$SO$_4$, filtered and concentrated to yield L2 (R$^3$=CH$_3$, R$^4$=CH$_2$CH(CH$_3$)$_2$, Z=para-(CH$_2$)C$_6$H$_4$(CH$_2$)—).

Method L, Step 2:

Compound L3 (R$^3$=CH$_3$, R$^4$=CH$_2$CH(CH$_3$)$_2$, Z=para-(CH$_2$)C$_6$H$_4$(CH$_2$)—, R$^{16}$=CH$_2$CH$_2$CH$_2$CH$_3$) was prepared from L2 (R$^3$=CH$_3$, R$^4$=CH$_2$CH(CH$_3$)$_2$, Z=para-(CH$_2$)C$_6$H$_4$(CH$_2$)—) following the procedure described in Method I, Step 1.

Method L, Step 3:

Compound L4 (R³=CH₃, R⁴=CH₂CH(CH₃)₂, Z=para-(CH₂)C₆H₄(CH₂)—, R¹=CH₂CH₂CH₂CH₃) was prepared from (R³=CH₃, R⁴=CH₂CH(CH₃)₂, Z=para-(CH₂)C₆H₄(CH₂)—, R¹⁶=CH₂CH₂CH₂CH₃) following the procedure described in Method A, Step 3.

The following compounds were prepared using similar method.

| # | Structure | MW | Obs. m/e |
|---|---|---|---|
| 743 | 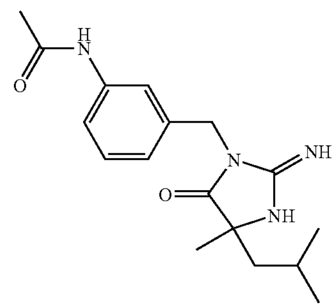 | 316 | 317 |
| 744 | 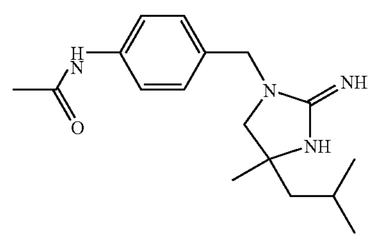 | 316 | 317 |
| 745 | 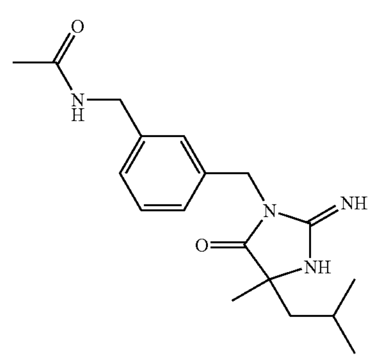 | 330 | 331 |
| 746 | 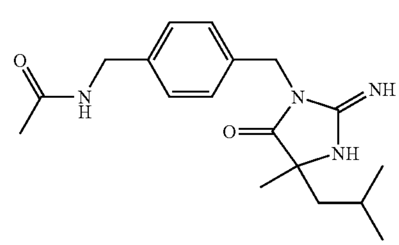 | 330 | 331 |

-continued

| # | Structure | MW | Obs. m/e |
|---|---|---|---|
| 747 | 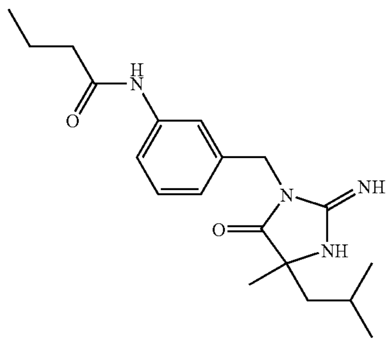 | 344 | 345 |
| 748 | 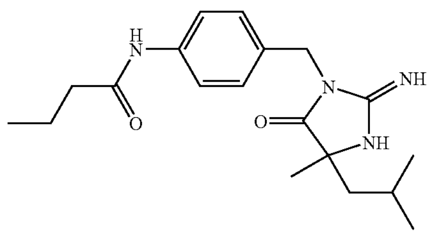 | 344 | 345 |
| 749 | 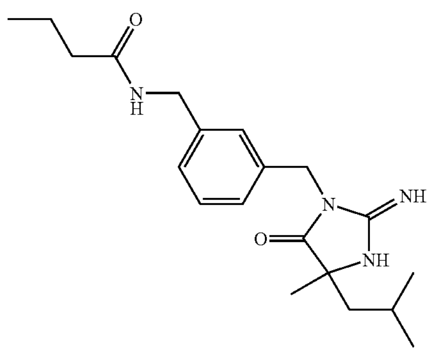 | 358 | 359 |
| 750 | 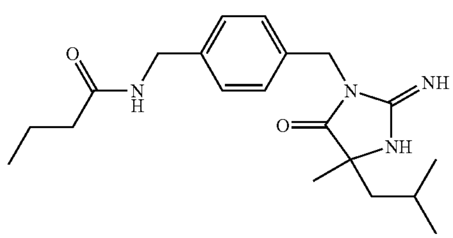 | 358 | 359 |
| 751 | 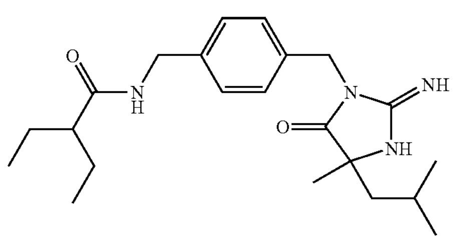 | 386 | 387 |

| # | Structure | MW | Obs. m/e |
|---|---|---|---|
| 752 | 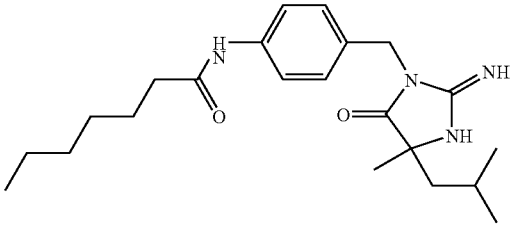 | 386 | 387 |
| 753 | 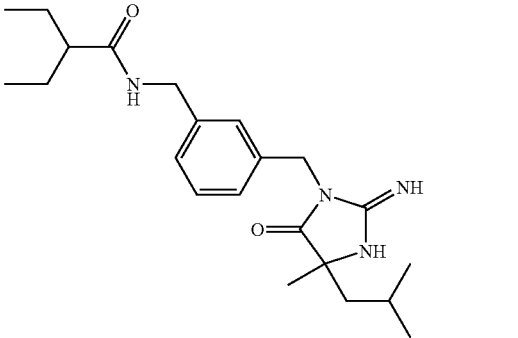 | 386 | 387 |
| 754 | 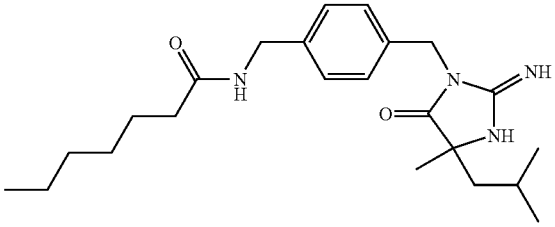 | 400 | 401 |
| 755 | 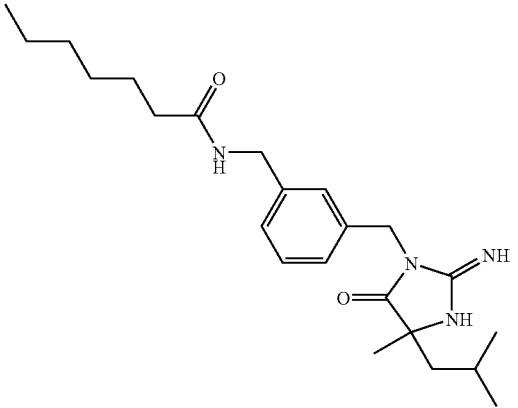 | 400 | 401 |
| 756 | 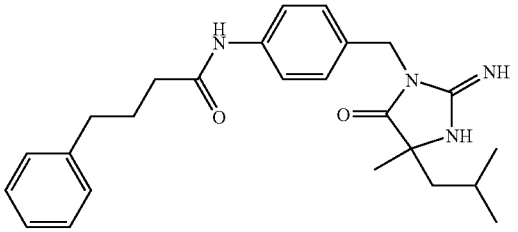 | 420 | 421 |

-continued

| # | Structure | MW | Obs. m/e |
|---|---|---|---|
| 757 | 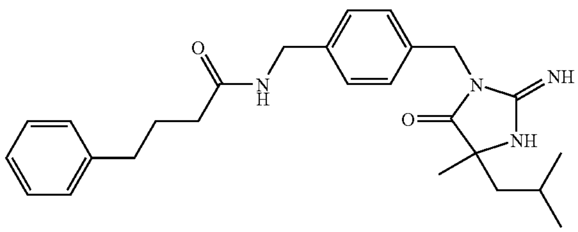 | 434 | 435 |
| 758 | 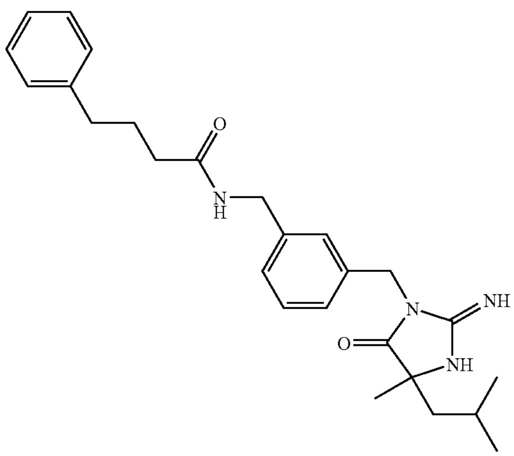 | 434 | 435 |
| 759 | 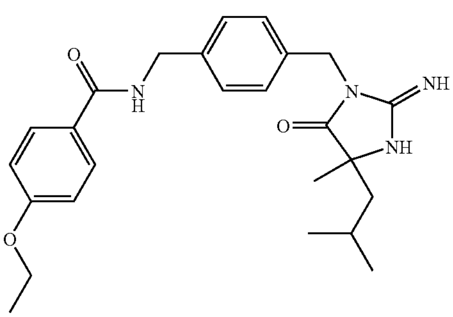 | 436 | 437 |
| 760 | 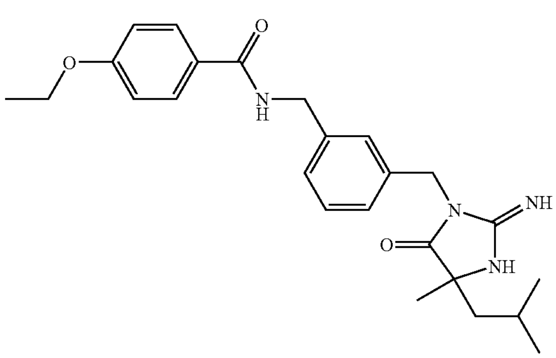 | 436 | 437 |

-continued

| # | Structure | MW | Obs. m/e |
|---|---|---|---|
| 761 | 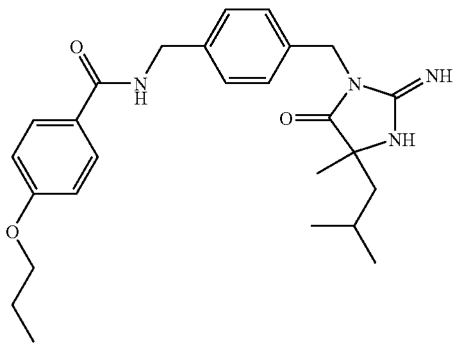 | 450 | 451 |
| 762 | 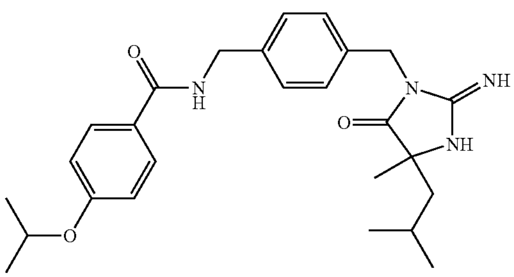 | 450 | 451 |
| 763 | 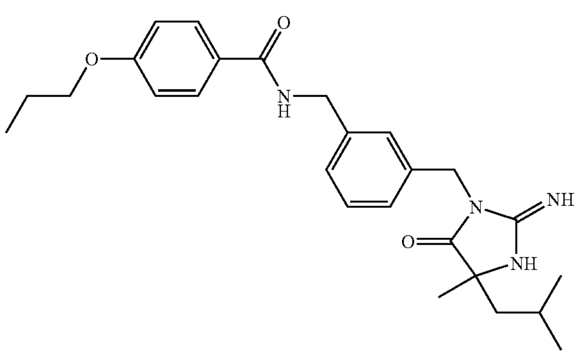 | 450 | 451 |
| 764 | 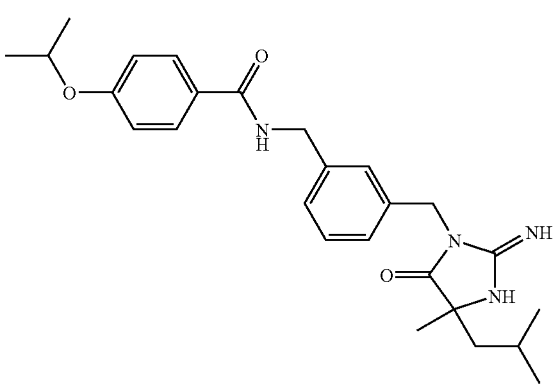 | 450 | 451 |

| # | Structure | MW | Obs. m/e |
|---|---|---|---|
| 765 | 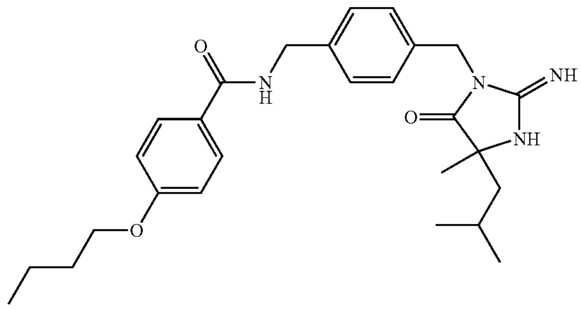 | 464 | 465 |
| 766 | 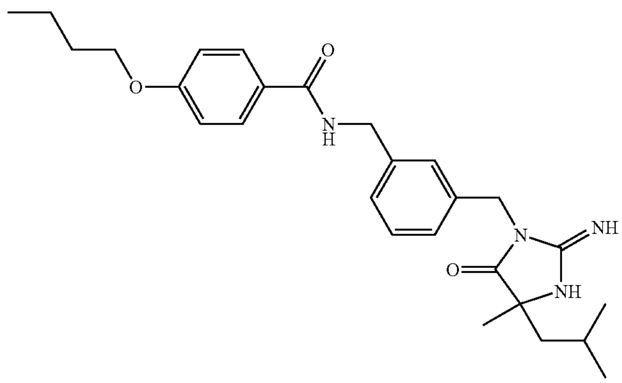 | 464 | 465 |
| 767 | 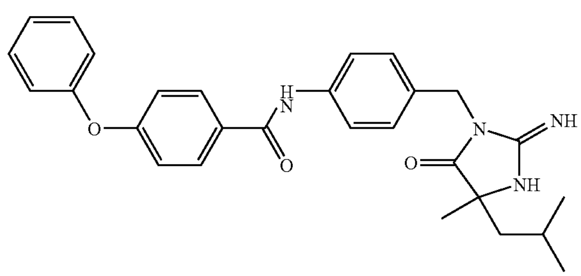 | 470 | 471 |
| 768 | 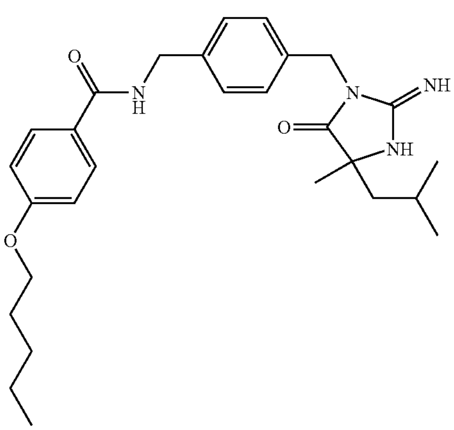 | 478 | 479 |

-continued

| # | Structure | MW | Obs. m/e |
|---|---|---|---|
| 769 | 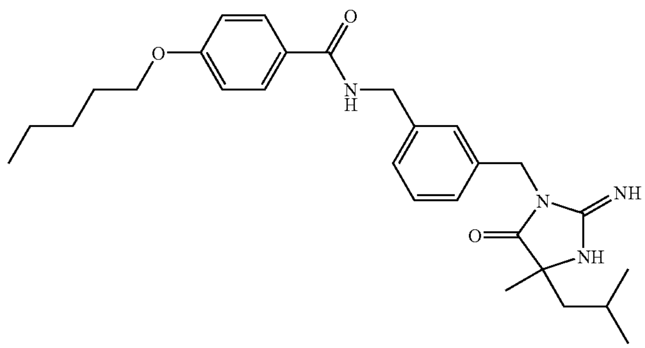 | 478 | 479 |
| 770 | 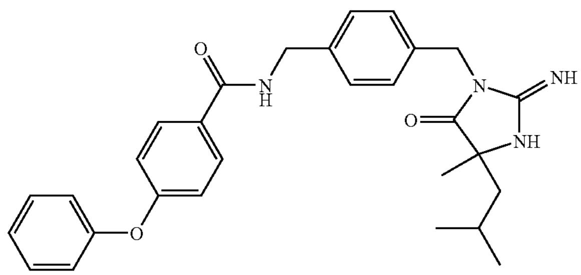 | 484 | 485 |
| 771 | 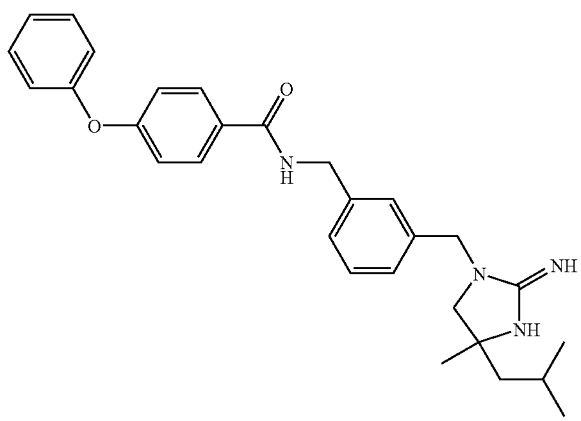 | 484 | 485 |
| 772 | 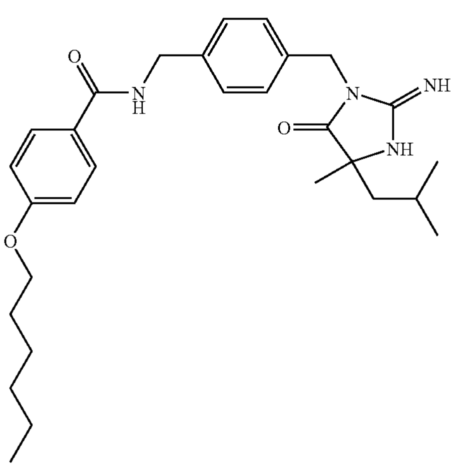 | 492 | 493 |

-continued

| # | Structure | MW | Obs. m/e |
|---|---|---|---|
| 773 | 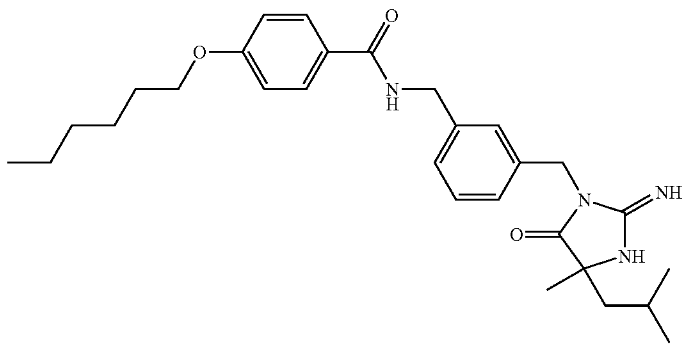 | 492 | 493 |
| 774 | 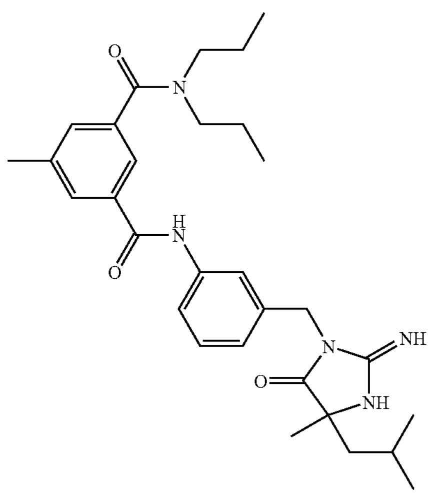 | 519 | 520 |
| 775 | 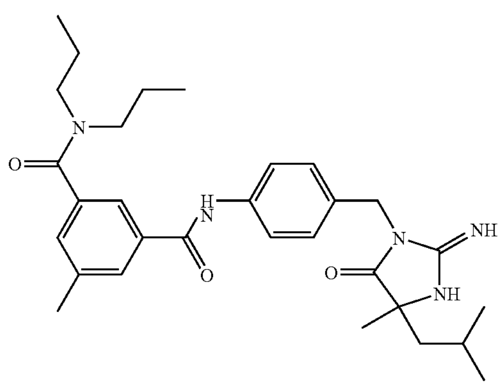 | 519 | 520 |

-continued

| # | Structure | MW | Obs. m/e |
|---|---|---|---|
| 776 | (structure) | 533 | 534 |
| 777 | (structure) | 533 | 534 |

Method M (M1 + R$^{15}$-N=C=O → M2 → M3)

(In the scheme, -Z-NH—C(O)—NHR$^{15}$— is equivalent to R$^1$ substituted by R$^{21}$, or R$^1$ Subsitituted by alkyl-R$^{22}$, wherein R$^{21}$ and R$^{22}$ are —N(R$^{16}$)—C(O)—NHR$^{15}$ and R$^{16}$ is H, and wherein Z is optionally substituted alkylene-arylene, alkylene-arylene-alkylene, alkylene-heteroarylene, alkylene-heteroarylene-alkylene, alkylene-cycloalkylene, alkylene-cycloalkylene-alkylene, alkylene-heterocycloalkylene, alkylene-heterocycloalkylene-alkylene, arylene, heteroarylene, cycloalkylene or heterocycloalkylene)

Method M, Step 1:

Compound M2 (R$^3$=CH$_3$, R$^4$=CH$_2$CH(CH$_3$)$_2$, Z=para-(CH$_2$)C$_6$H$_4$(CH$_2$)—, R$^{15}$=3,4-difluorophenyl) was prepared from M1 (R$^3$=CH$_3$, R$^4$=CH$_2$CH(CH$_3$)$_2$, Z=para-(CH$_2$)C$_6$H$_4$(CH$_2$)—) following the procedure described in Method J, Step 1.

Method M, Step 2:

Compound M3 (R$^3$=CH$_3$, R$^4$=CH$_2$CH(CH$_3$)$_2$, Z=para-(CH$_2$)C$_6$H$_4$(CH$_2$)—, R$^{15}$=3,4-difluorophenyl) was prepared from M2 (R$^3$=CH$_3$, R$^4$=CH$_2$CH(CH$_3$)$_2$, Z=para-(CH$_2$)C$_6$H$_4$(CH$_2$)—, R$^{15}$=3,4-difluorophenyl) following the procedure described in Method A, Step 3. NMR(CD$_3$OD) δ 7.45, m, 1H; δ 7.26, m, 4H; 7.24, m, 1H, δ 6.96, m, 1H, δ 4.8, m; δ 4.3, s, 2H; δ 1.69, m, 2H, δ 1.44, m, 1H; δ 1,37, s, 3H; δ 0.8, m, 3H; δ 0.63, m, 3H. ES_LCMS (m/e) 430.27

The following compounds were prepared using similar method.

| # | Structure | MW | Obs. m/e |
|---|-----------|-----|----------|
| 778 | 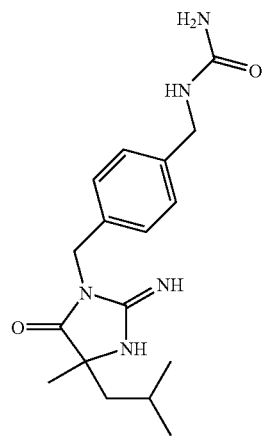 | 331 | 332 |
| 779 | 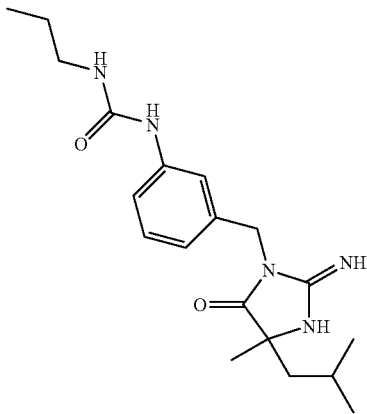 | 359 | 360 |
| 780 | 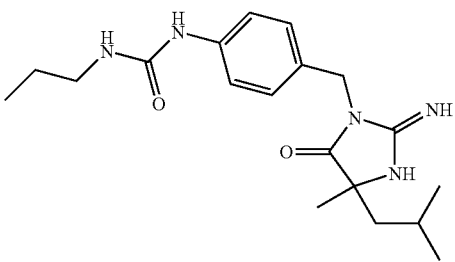 | 359 | 360 |

| # | Structure | MW | Obs. m/e |
|---|---|---|---|
| 781 | 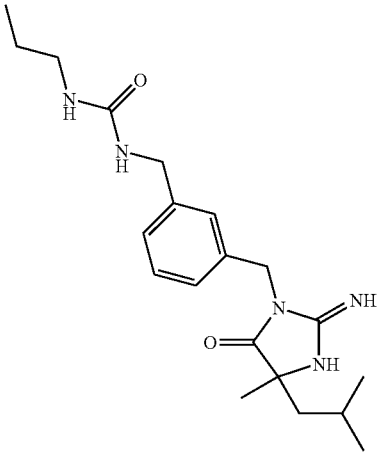 | 373 | 374 |
| 782 | 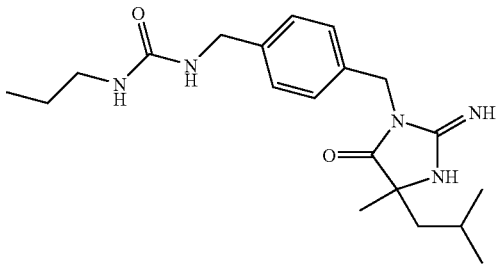 | 373 | 374 |
| 783 | 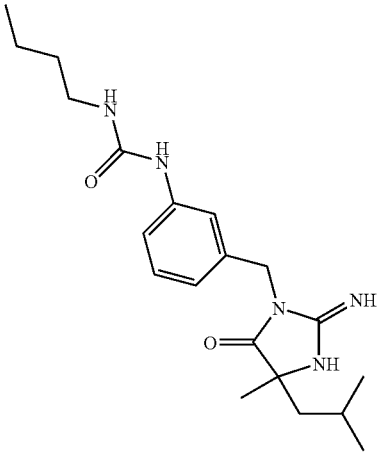 | 373 | 374 |
| 784 | 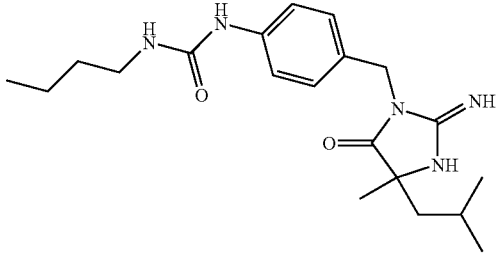 | 373 | 374 |

| # | Structure | MW | Obs. m/e |
|---|-----------|-----|----------|
| 785 | 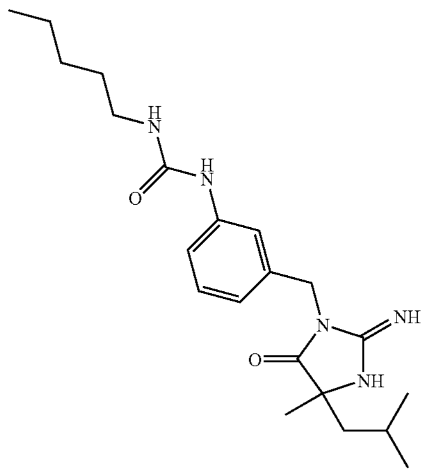 | 387 | 388 |
| 786 | 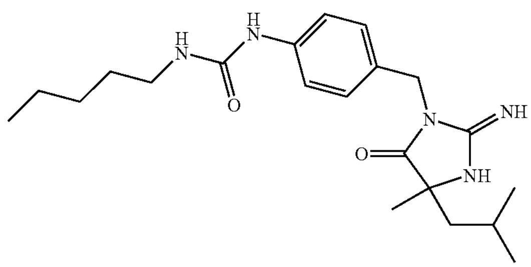 | 387 | 388 |
| 787 | 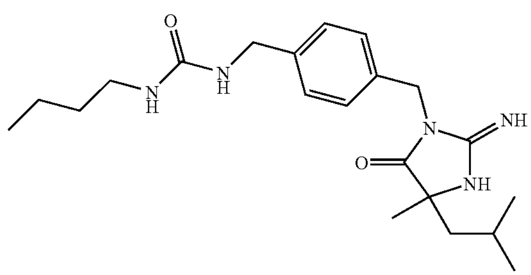 | 387 | 388 |
| 788 | 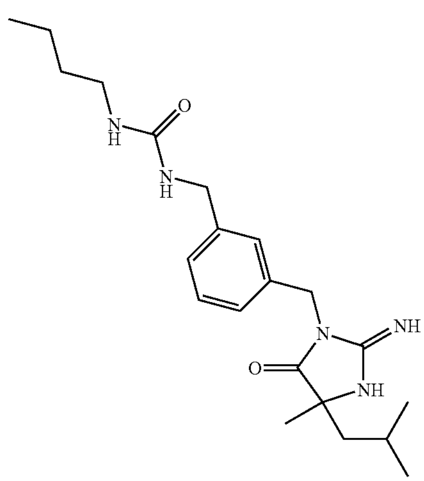 | 387 | 388 |

-continued

| # | Structure | MW | Obs. m/e |
|---|-----------|-----|----------|
| 789 | 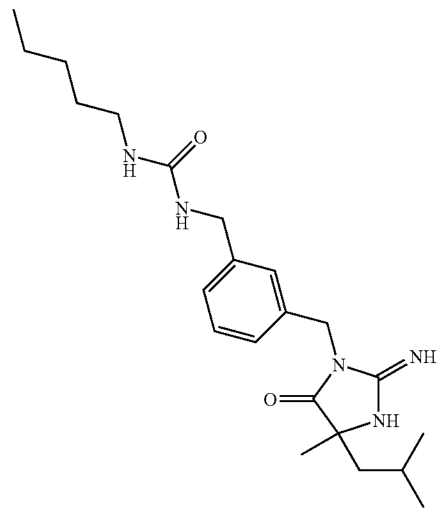 | 401 | 402 |
| 790 | 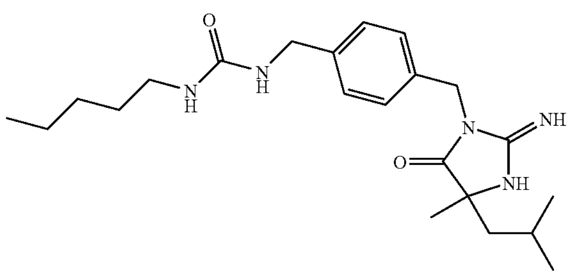 | 401 | 402 |
| 791 | 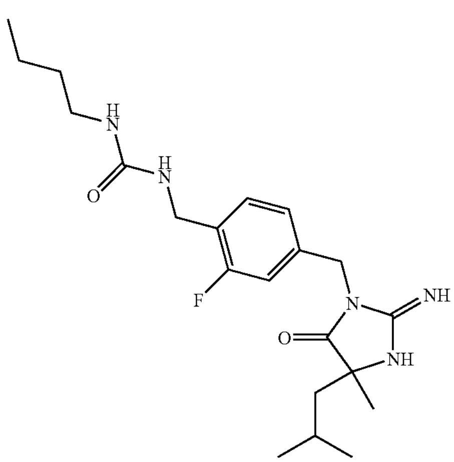 | 405 | 406 |

| # | Structure | MW | Obs. m/e |
|---|---|---|---|
| 792 | 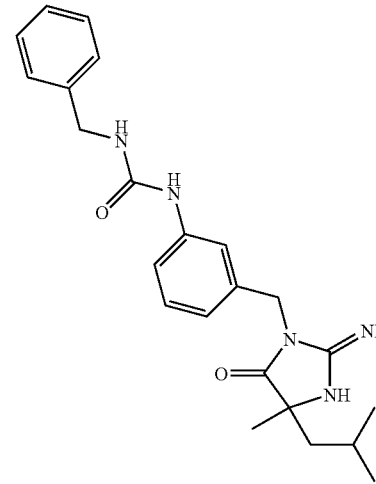 | 407 | 408 |
| 793 | 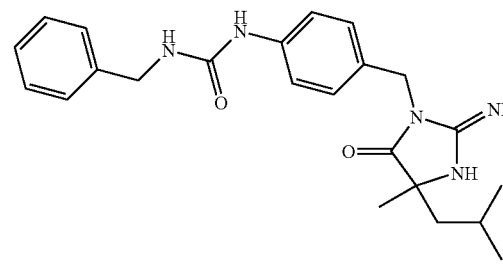 | 407 | 408 |
| 794 | 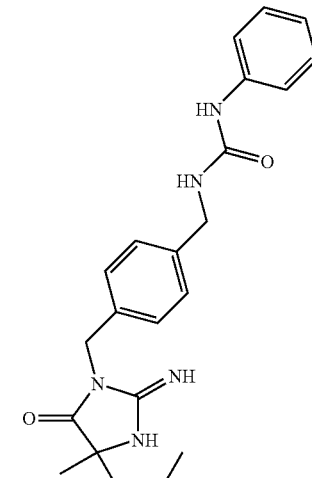 | 407 | 408 |

-continued
| # | Structure | MW | Obs. m/e |
|---|---|---|---|
| 795 | 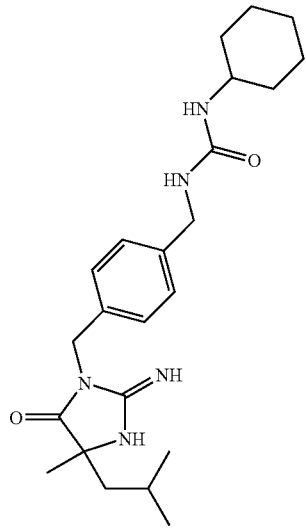 | 413 | 414 |
| 796 | 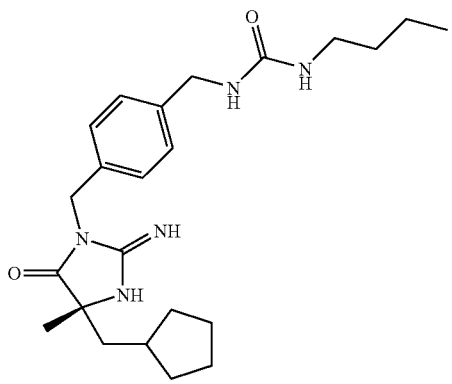 | 413 | 414 |
| 797 | 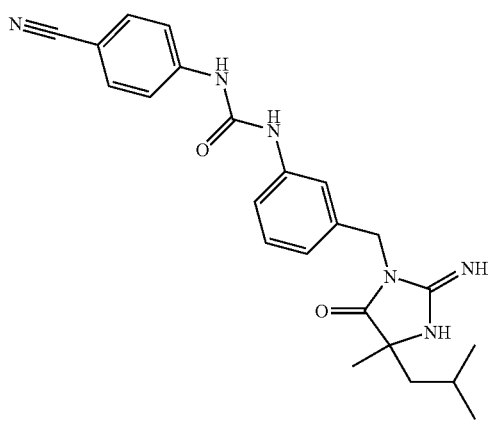 | 418 | 419 |

-continued

| # | Structure | MW | Obs. m/e |
|---|---|---|---|
| 798 | 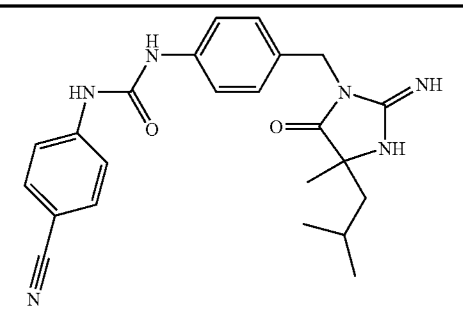 | 418 | 419 |
| 799 | 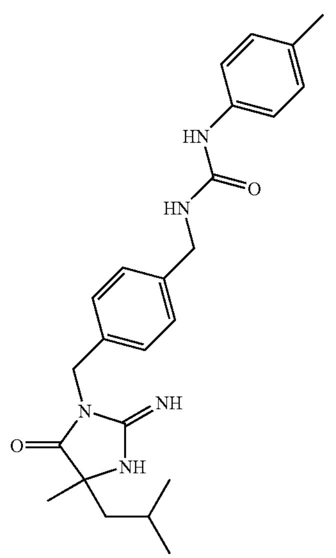 | 421 | 422 |
| 800 | 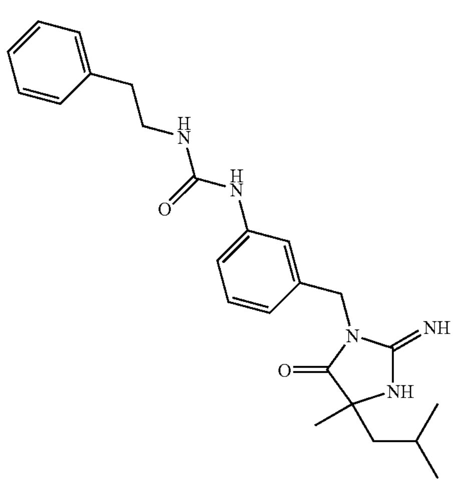 | 421 | 422 |

| # | Structure | MW | Obs. m/e |
|---|---|---|---|
| 801 | 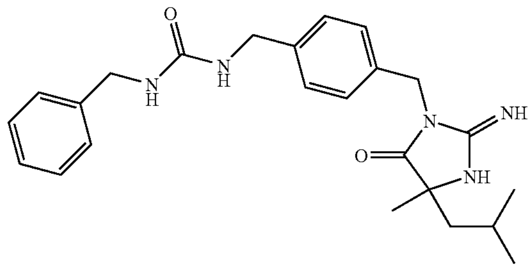 | 421 | 422 |
| 802 | 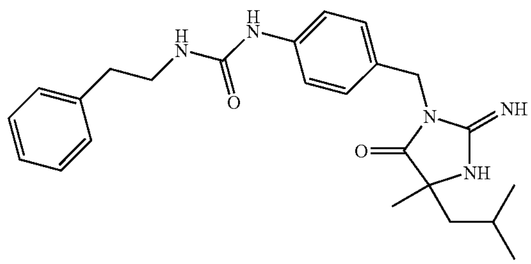 | 421 | 422 |
| 803 | 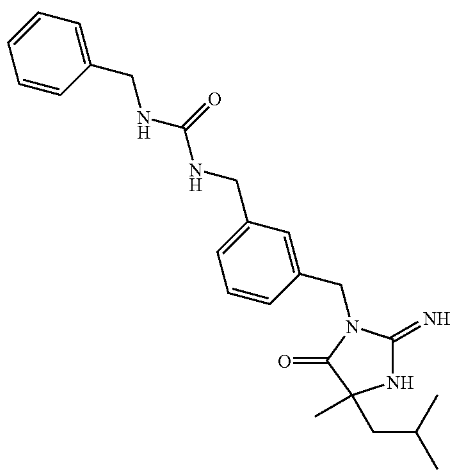 | 421 | 422 |
| 804 | 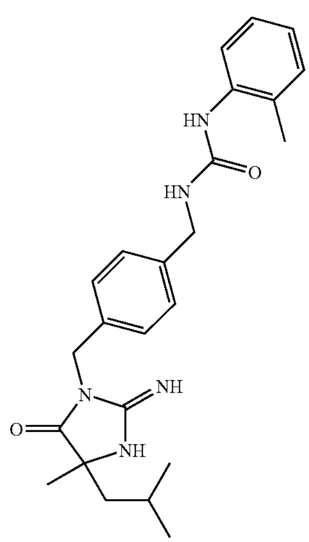 | 421 | 422 |

-continued

| # | Structure | MW | Obs. m/e |
|---|---|---|---|
| 805 | 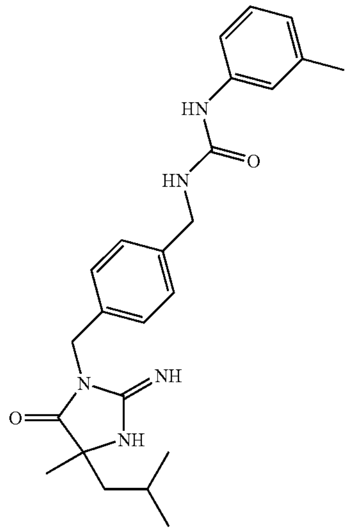 | 421 | 422 |
| 806 | 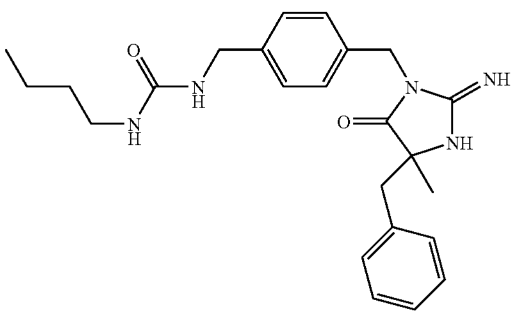 | 421 | 422 |
| 807 | 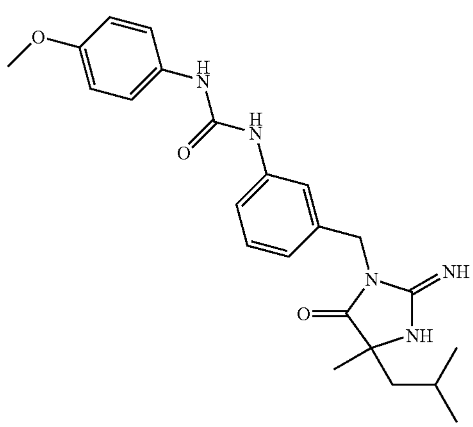 | 423 | 424 |

-continued

| # | Structure | MW | Obs. m/e |
|---|---|---|---|
| 808 | 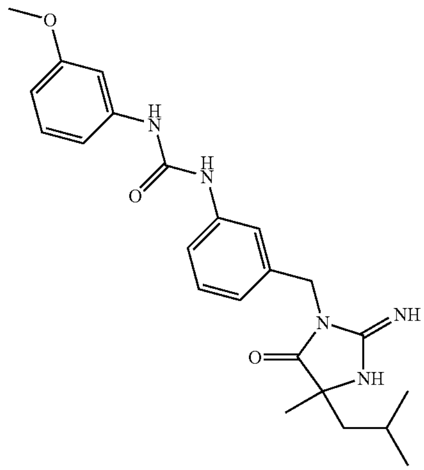 | 423 | 424 |
| 809 | 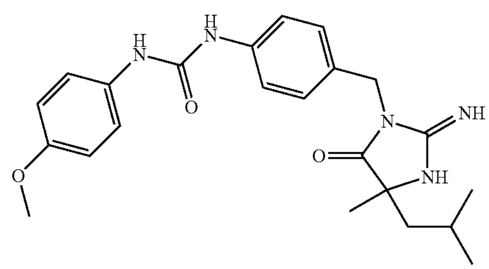 | 423 | 424 |
| 810 | 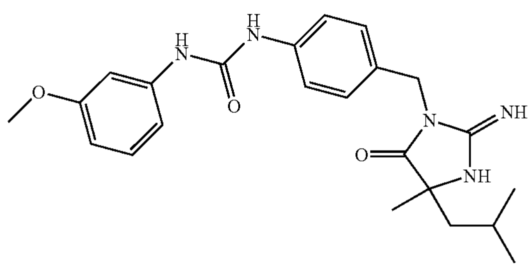 | 423 | 424 |
| 811 | 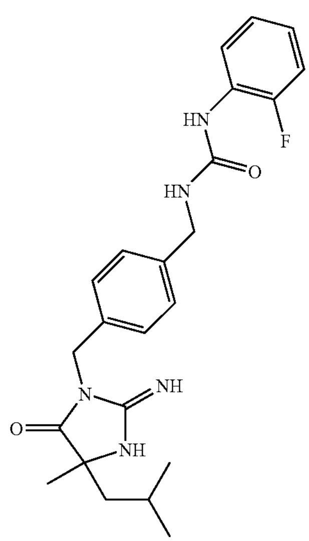 | 425 | 426 |

-continued

| # | Structure | MW | Obs. m/e |
|---|---|---|---|
| 812 | 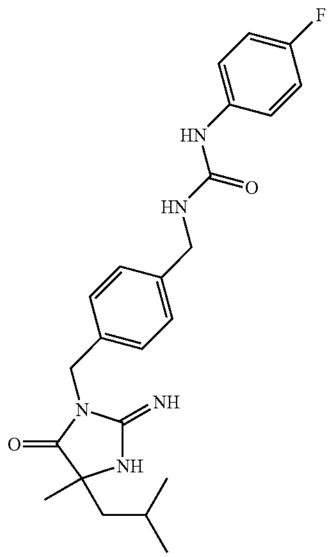 | 425 | 426 |
| 813 | 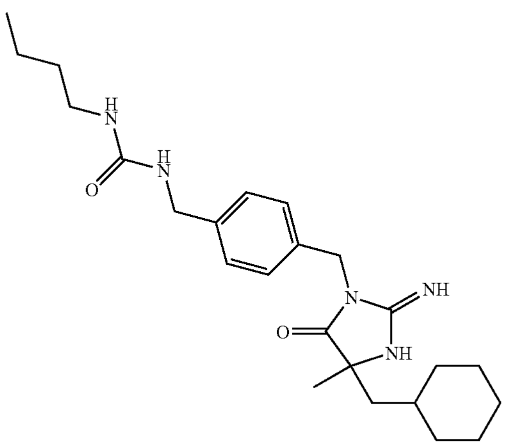 | 427 | 428 |
| 814 | 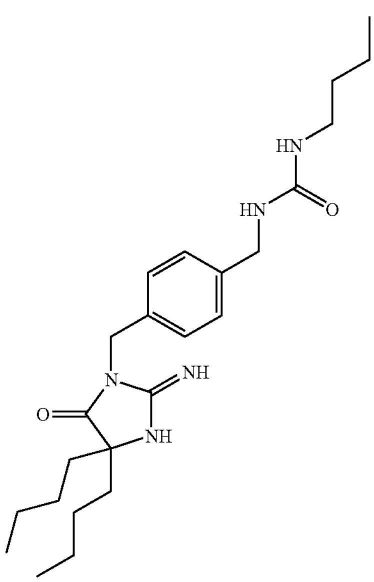 | 429 | 430 |

-continued

| # | Structure | MW | Obs. m/e |
|---|---|---|---|
| 815 | 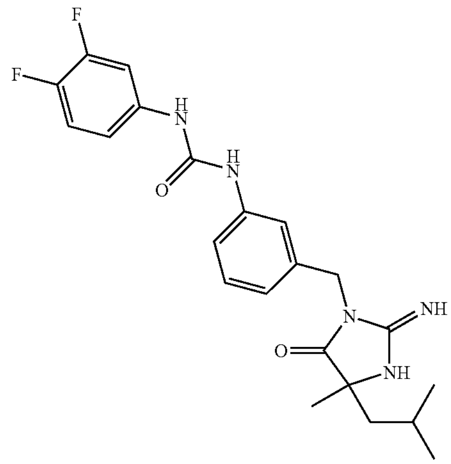 | 429 | 430 |
| 816 | 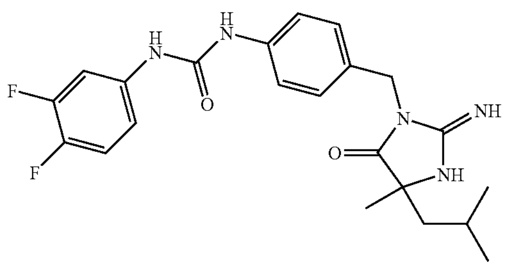 | 429 | 430 |
| 817 | 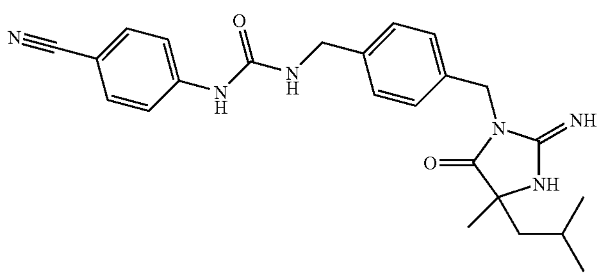 | 432 | 433 |
| 818 | 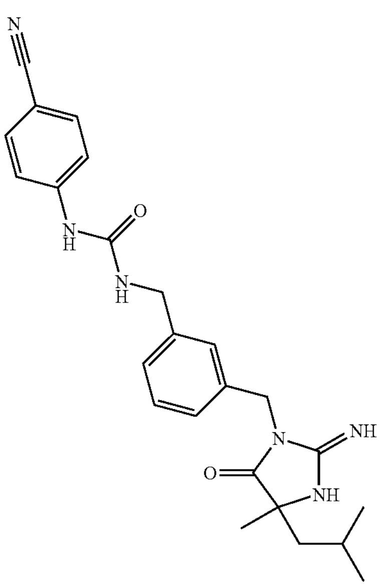 | 432 | 433 |

-continued
| # | Structure | MW | Obs. m/e |
|---|---|---|---|
| 819 | 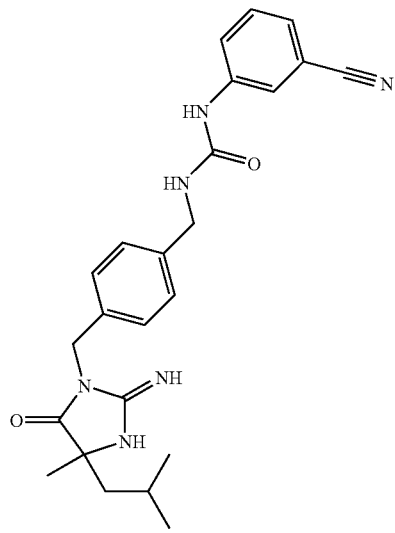 | 432 | 433 |
| 820 | 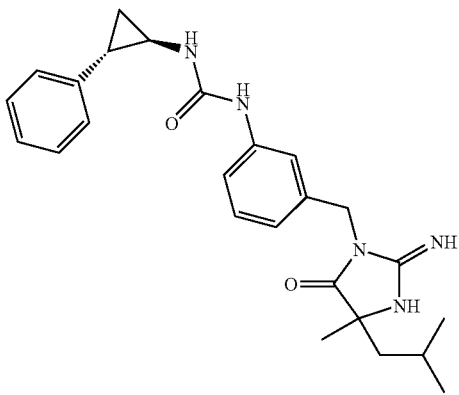 | 433 | 434 |
| 821 | 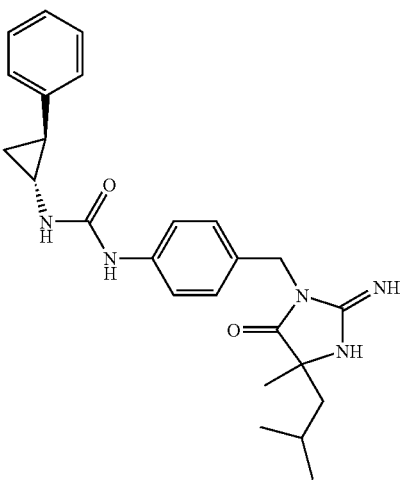 | 433 | 434 |

-continued

| # | Structure | MW | Obs. m/e |
|---|---|---|---|
| 822 | 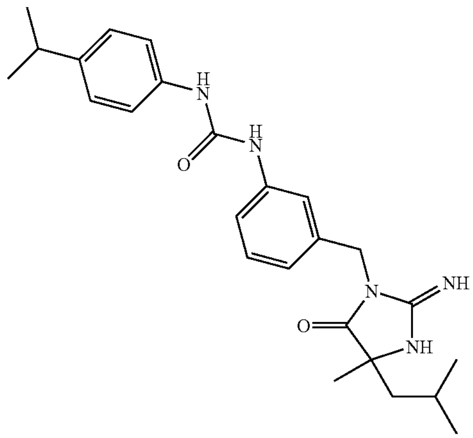 | 435 | 436 |
| 823 | 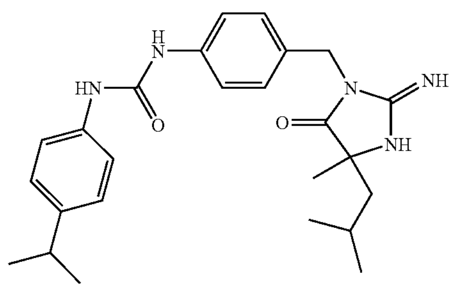 | 435 | 436 |
| 824 | 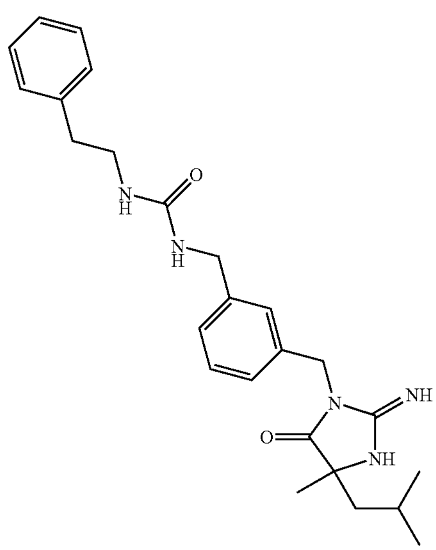 | 435 | 436 |

-continued
| # | Structure | MW | Obs. m/e |
|---|-----------|----|----|
| 825 | 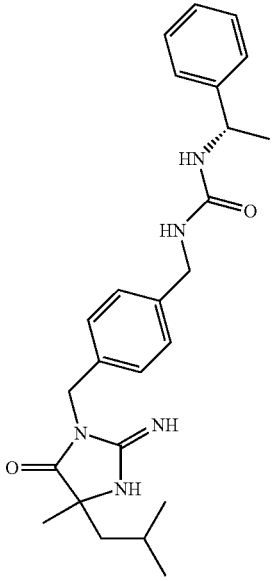 | 435 | 436 |
| 826 | 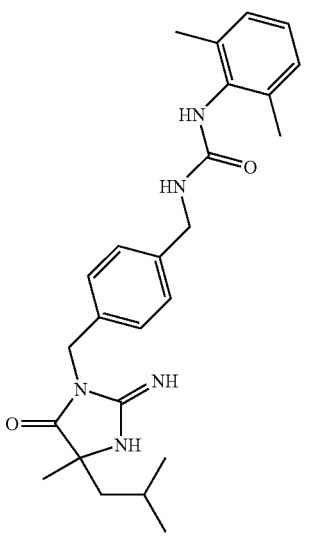 | 435 | 436 |

-continued
| # | Structure | MW | Obs. m/e |
|---|---|---|---|
| 827 | 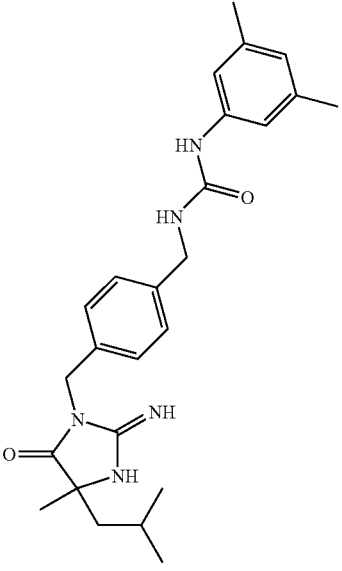 | 435 | 436 |
| 828 | 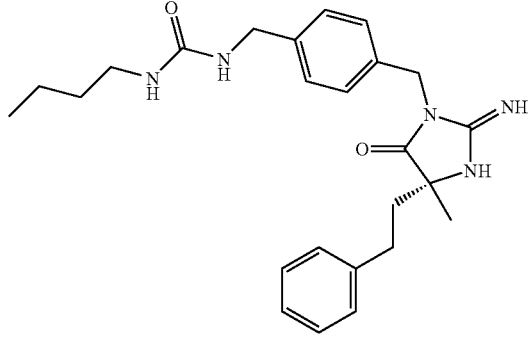 | 435 | 436 |
| 829 | 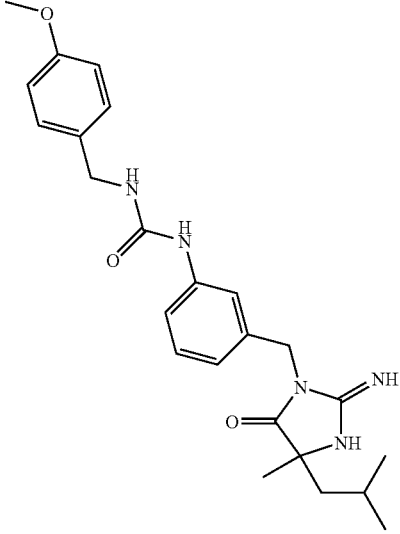 | 437 | 438 |

-continued

| # | Structure | MW | Obs. m/e |
|---|-----------|-----|----------|
| 830 | 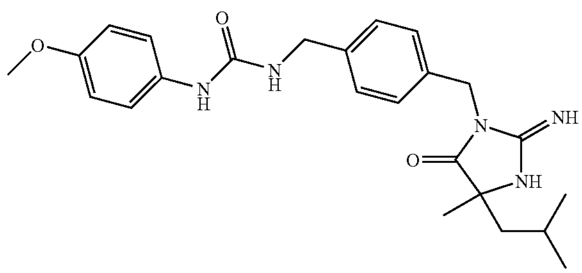 | 437 | 438 |
| 831 | 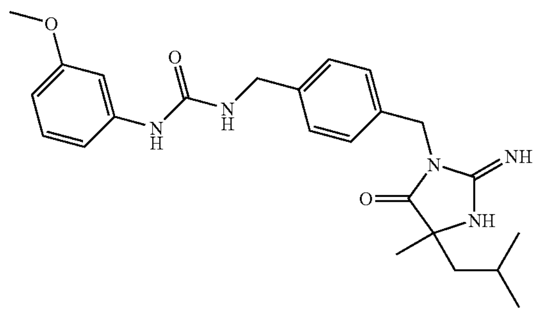 | 437 | 438 |
| 832 | 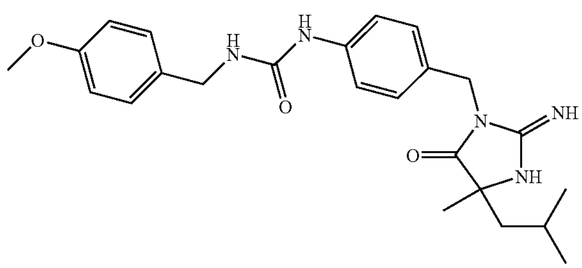 | 437 | 438 |
| 833 | 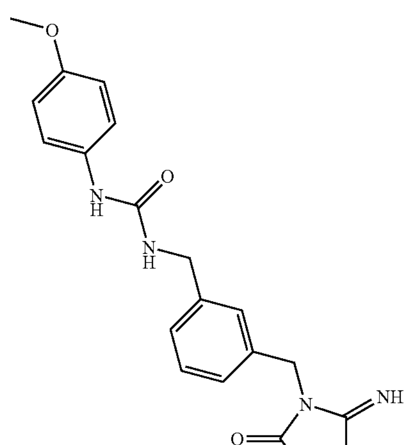 | 437 | 438 |

-continued
| # | Structure | MW | Obs. m/e |
|---|---|---|---|
| 834 | 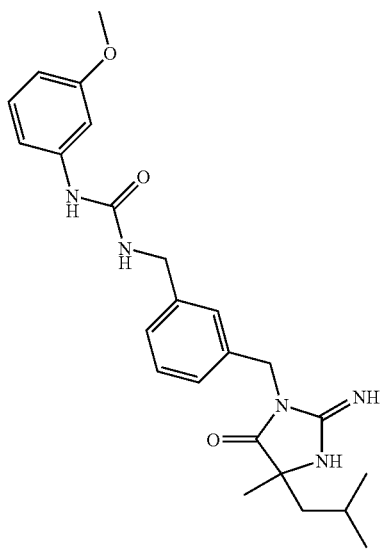 | 437 | 438 |
| 835 | 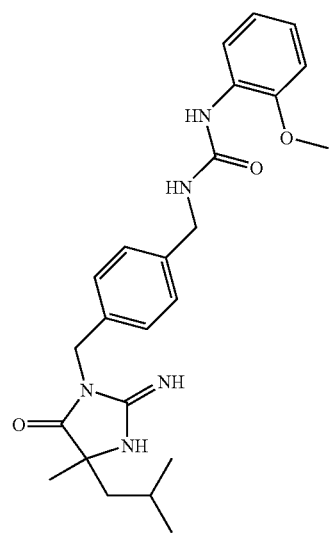 | 437 | 438 |

-continued

| # | Structure | MW | Obs. m/e |
|---|---|---|---|
| 836 | 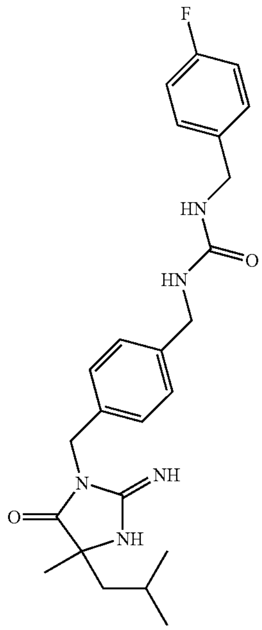 | 439 | 440 |
| 837 | 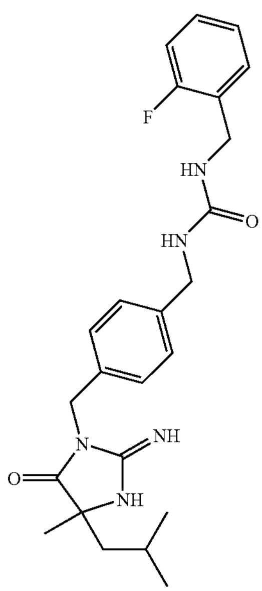 | 439 | 440 |
| 838 | 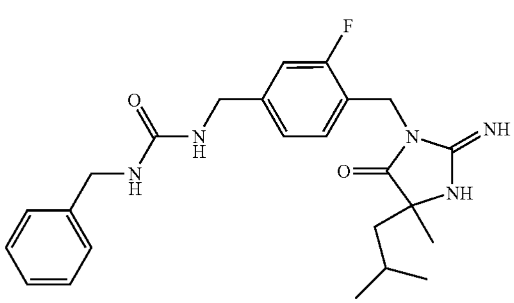 | 439 | 440 |

-continued
| # | Structure | MW | Obs. m/e |
|---|---|---|---|
| 839 | 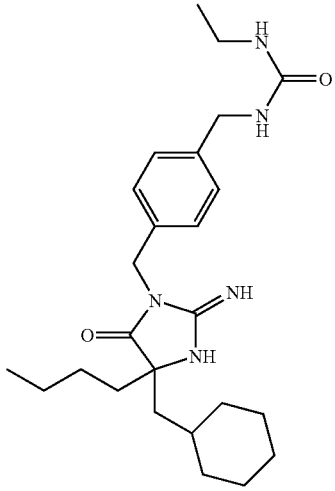 | 441 | 442 |
| 840 | 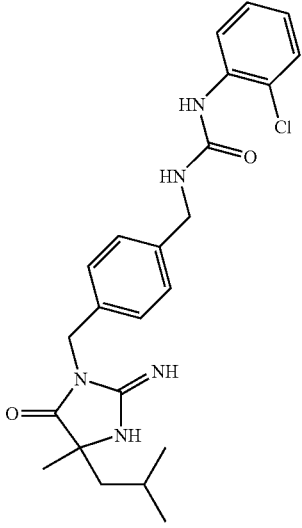 | 441 | 442 |
| 841 | 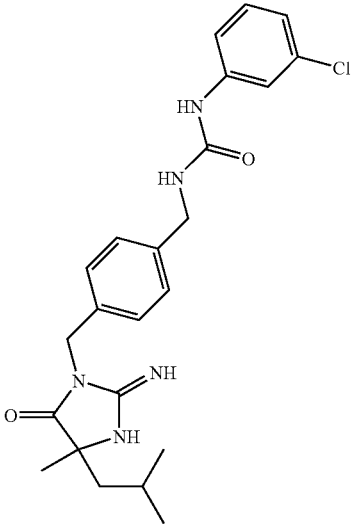 | 441 | 442 |

-continued
| # | Structure | MW | Obs. m/e |
|---|---|---|---|
| 842 | 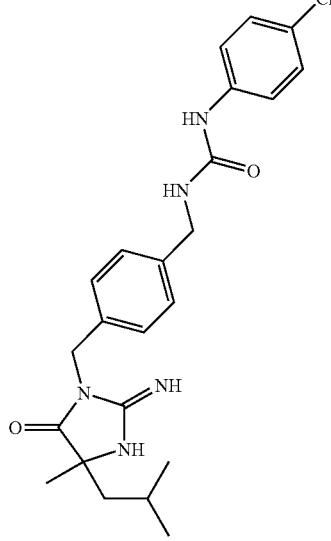 | 441 | 442 |
| 843 | 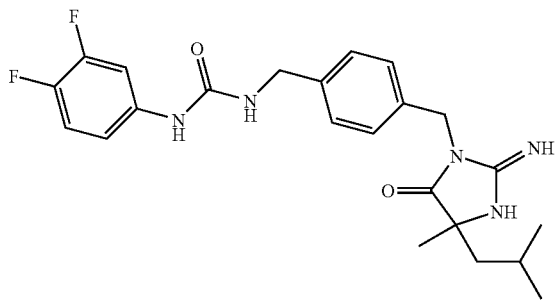 | 443 | 444 |
| 844 | 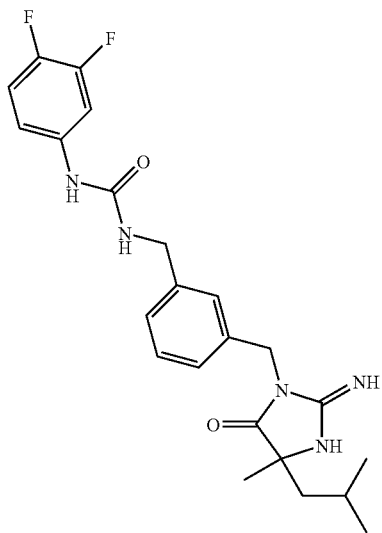 | 443 | 444 |

-continued

| # | Structure | MW | Obs. m/e |
|---|---|---|---|
| 845 | 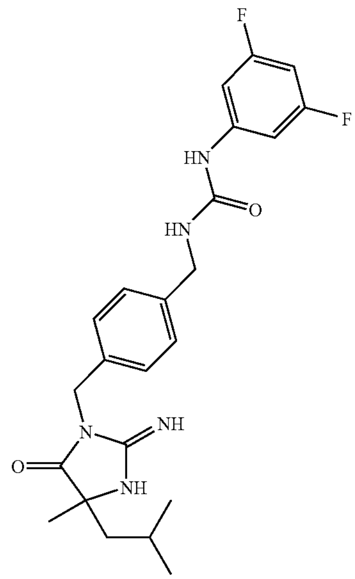 | 443 | 444 |
| 846 | 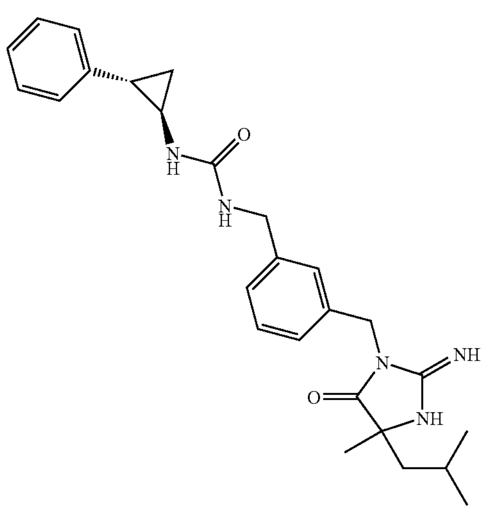 | 447 | 448 |

-continued

| # | Structure | MW | Obs. m/e |
|---|---|---|---|
| 847 | 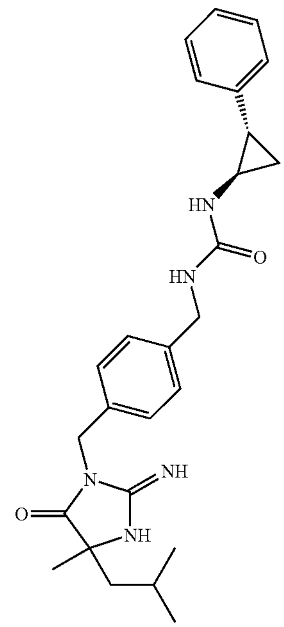 | 447 | 448 |
| 848 | 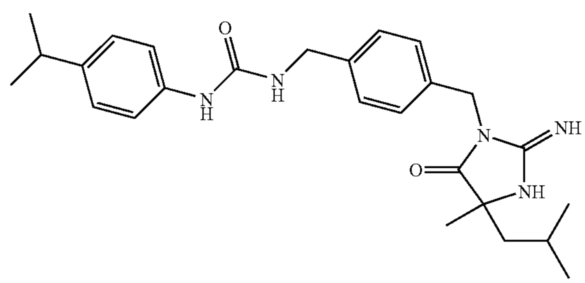 | 449 | 450 |
| 849 | 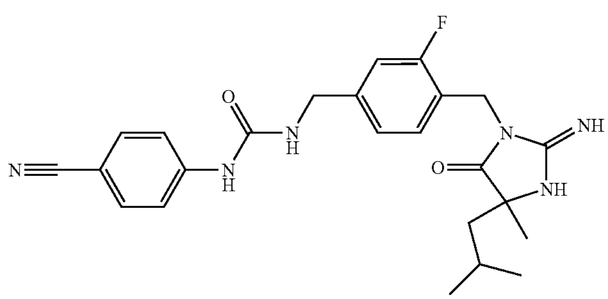 | 450 | 451 |
| 850 | 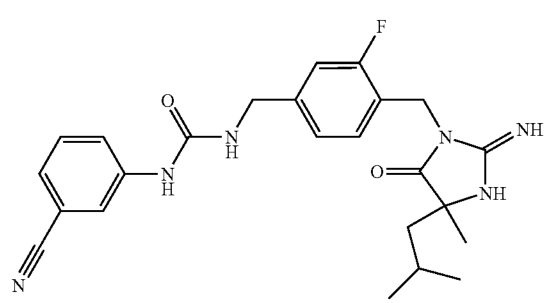 | 450 | 451 |

-continued

| # | Structure | MW | Obs. m/e |
|---|---|---|---|
| 851 | 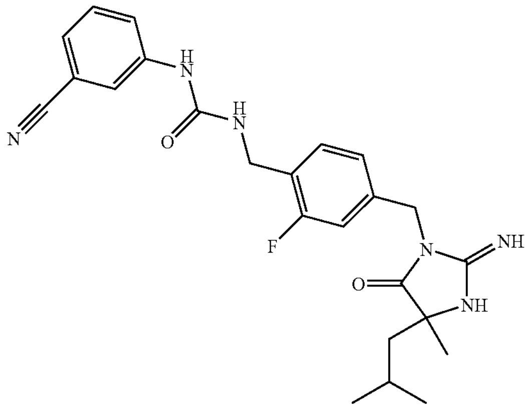 | 450 | 451 |
| 852 | 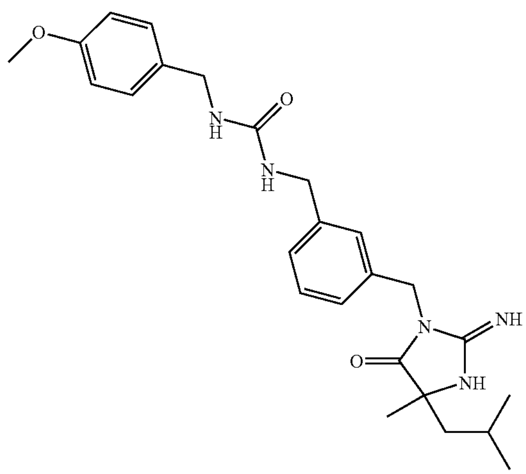 | 451 | 452 |
| 853 | 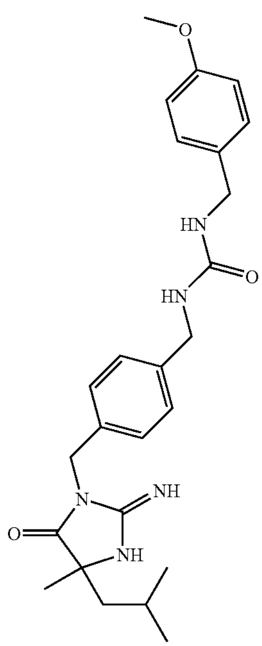 | 451 | 452 |

-continued
| # | Structure | MW | Obs. m/e |
|---|---|---|---|
| 854 | 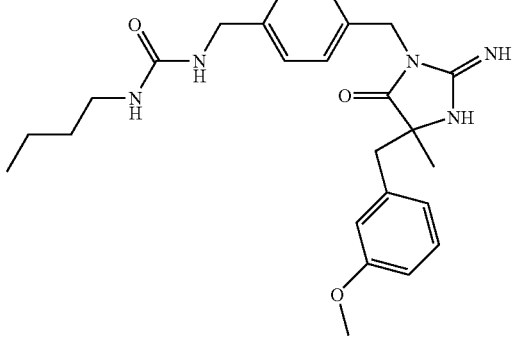 | 451 | 452 |
| 855 | 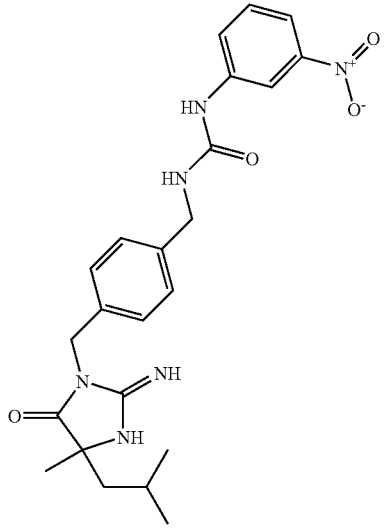 | 452 | 453 |
| 856 | 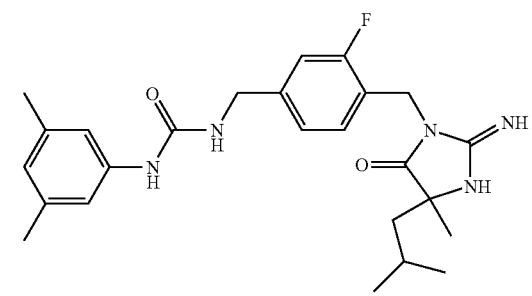 | 453 | 454 |

-continued

| # | Structure | MW | Obs. m/e |
|---|---|---|---|
| 857 | 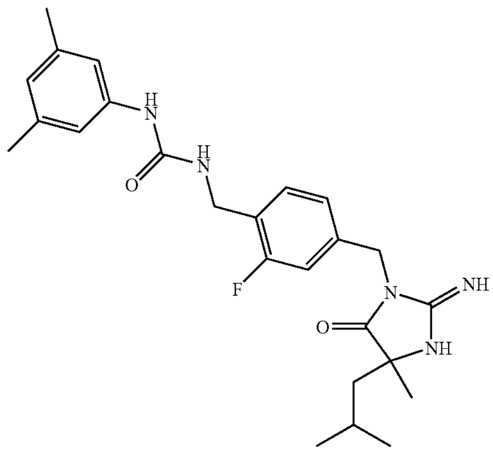 | 453 | 454 |
| 858 | 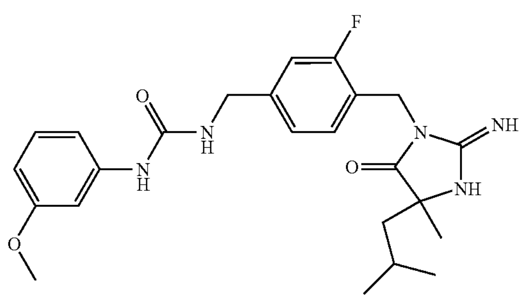 | 455 | 456 |
| 859 | 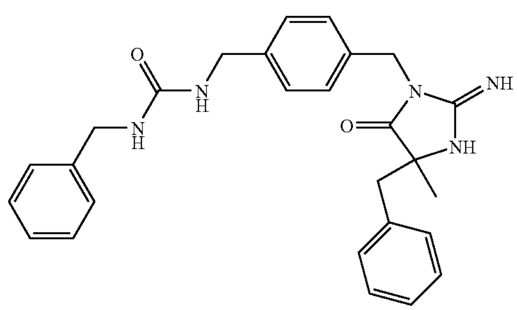 | 455 | 456 |
| 860 | 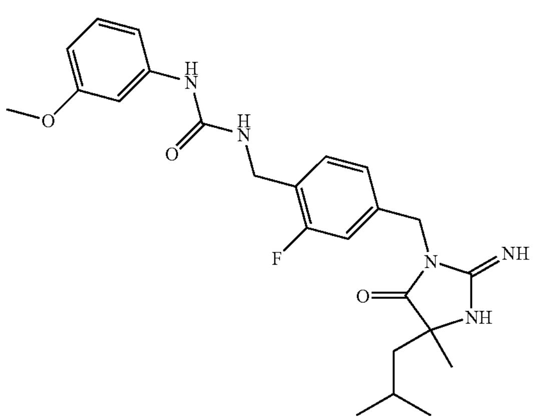 | 455 | 456 |

-continued
| # | Structure | MW | Obs. m/e |
|---|-----------|----|----|
| 861 | 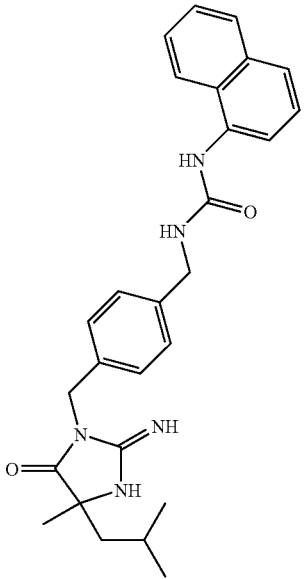 | 457 | 458 |
| 862 | 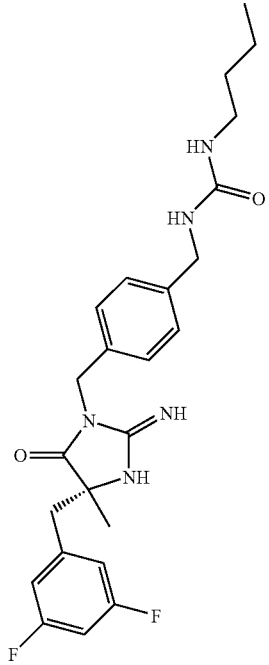 | 457 | 458 |

-continued
| # | Structure | MW | Obs. m/e |
|---|---|---|---|
| 863 | 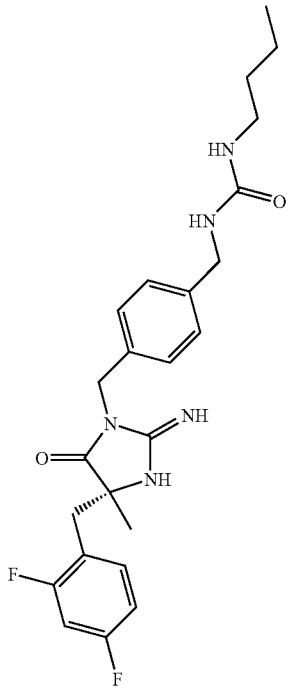 | 457 | 458 |
| 864 | 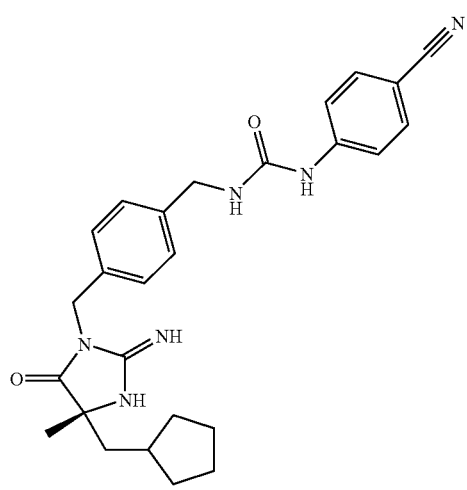 | 458 | 459 |

-continued
| # | Structure | MW | Obs. m/e |
|---|---|---|---|
| 865 | 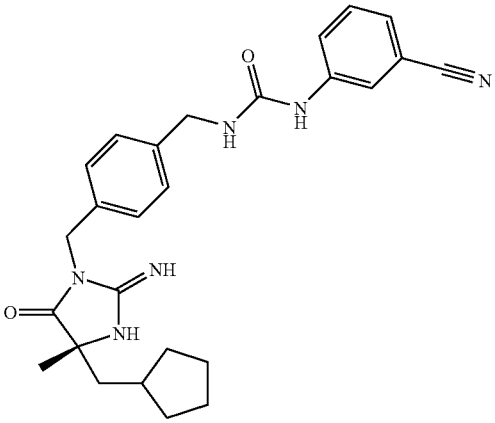 | 458 | 459 |
| 866 | 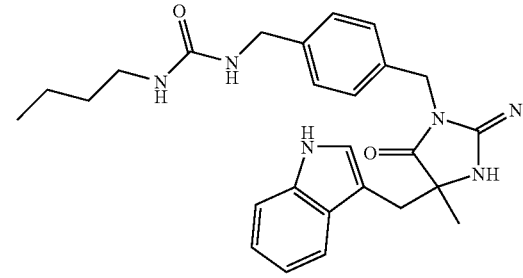 | 460 | 461 |
| 867 | 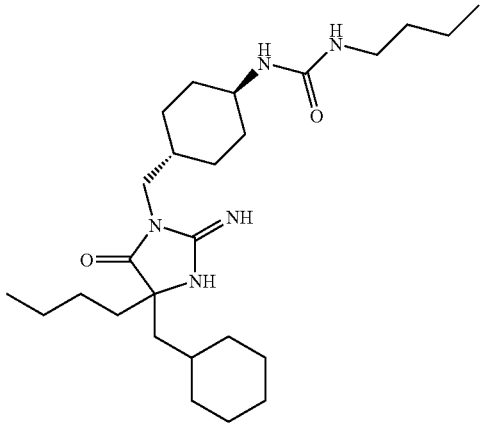 | 461 | 462 |
| 868 | 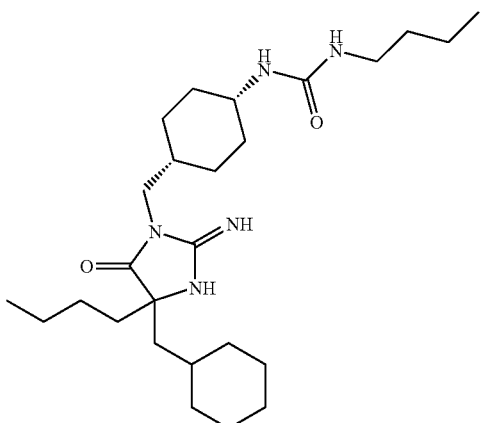 | 461 | 462 |

-continued

| # | Structure | MW | Obs. m/e |
|---|---|---|---|
| 869 | 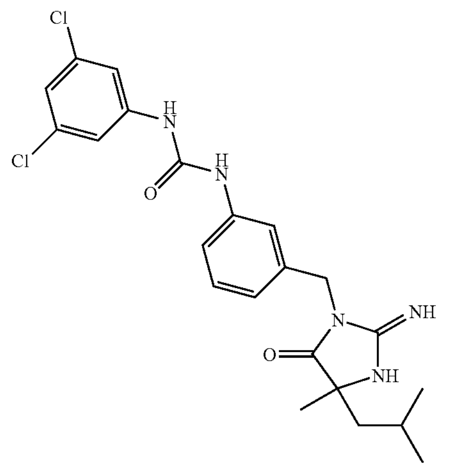 | 461 | 462 |
| 870 | 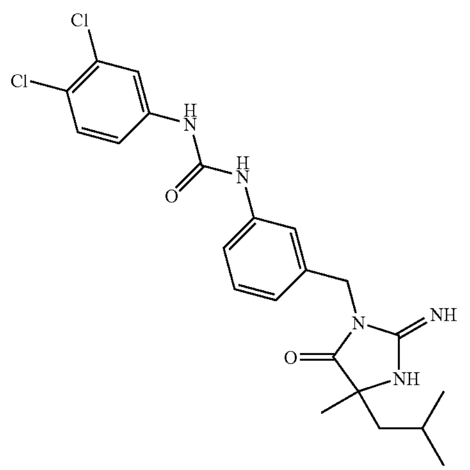 | 461 | 462 |
| 871 | 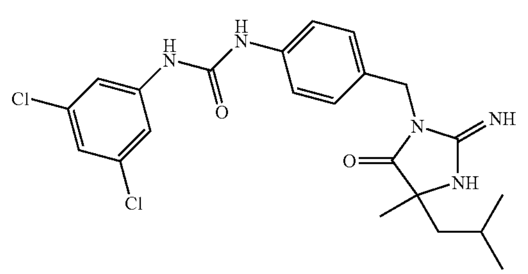 | 461 | 462 |
| 872 | 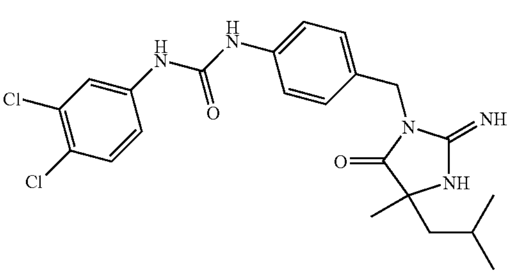 | 461 | 462 |

-continued

| # | Structure | MW | Obs. m/e |
|---|---|---|---|
| 873 | 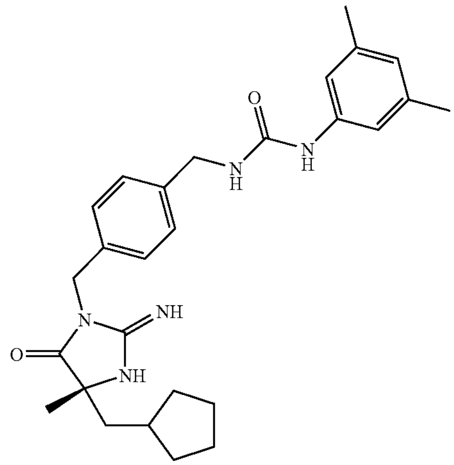 | 461 | 462 |
| 874 | 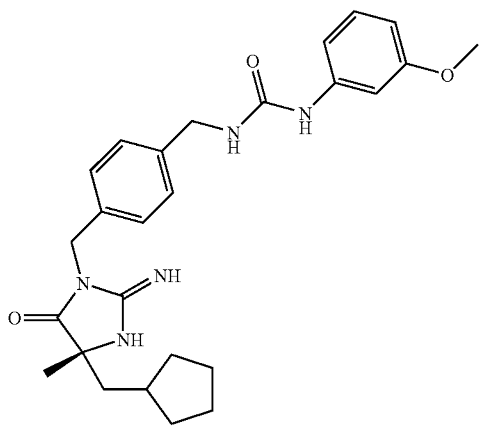 | 463 | 464 |
| 875 | 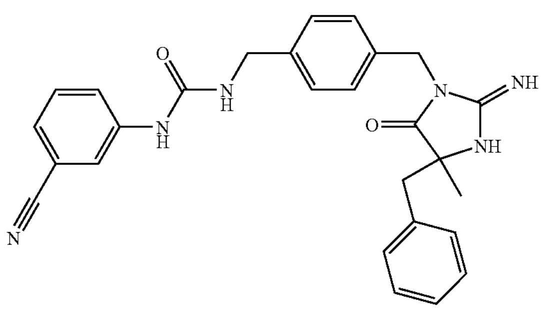 | 466 | 467 |
| 876 | 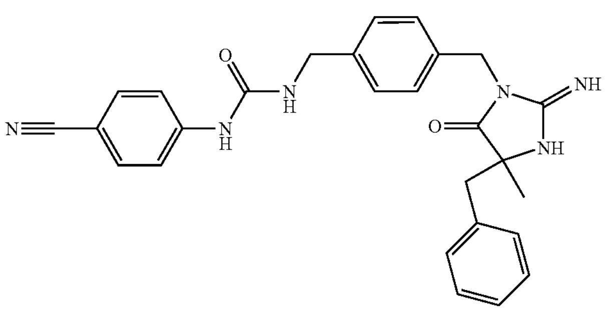 | 466 | 467 |

| # | Structure | MW | Obs. m/e |
|---|-----------|----|----------|
| 877 | 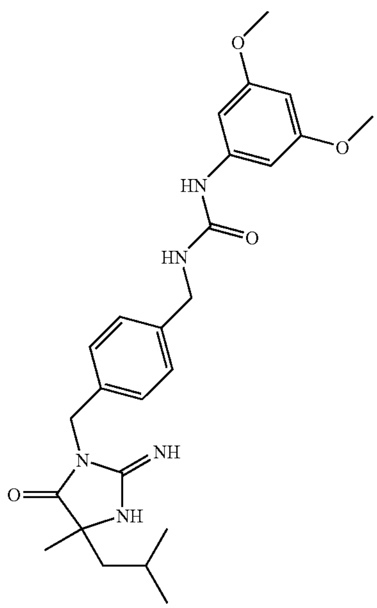 | 467 | 468 |
| 878 | 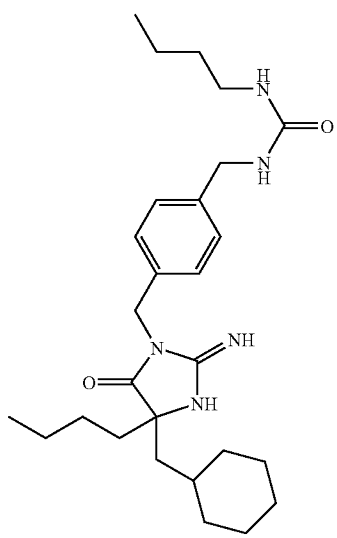 | 469 | 470 |
| 879 | 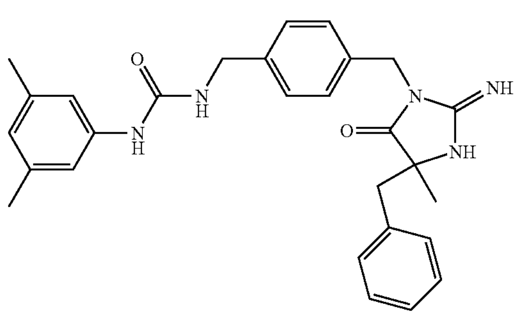 | 469 | 470 |

-continued

| # | Structure | MW | Obs. m/e |
|---|---|---|---|
| 880 | 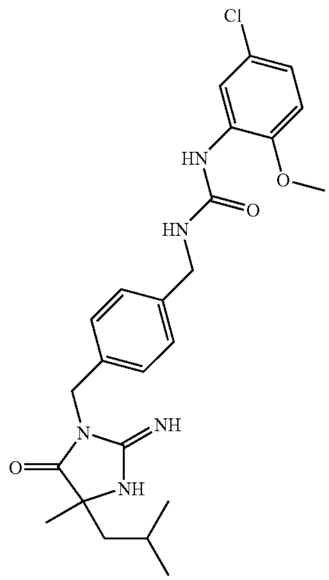 | 471 | 472 |
| 881 | 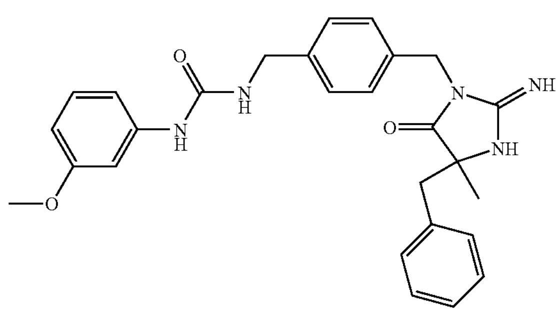 | 471 | 472 |
| 882 | 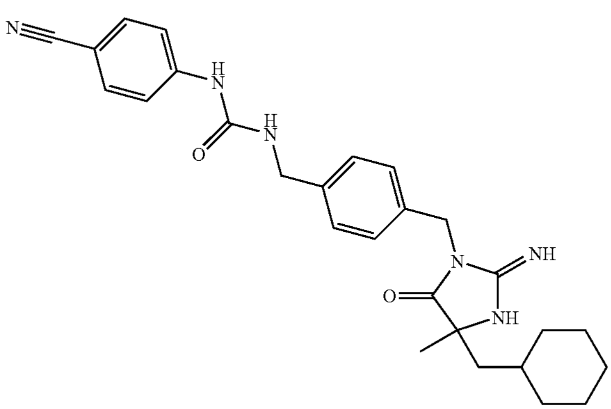 | 472 | 473 |

-continued
| # | Structure | MW | Obs. m/e |
|---|---|---|---|
| 883 | 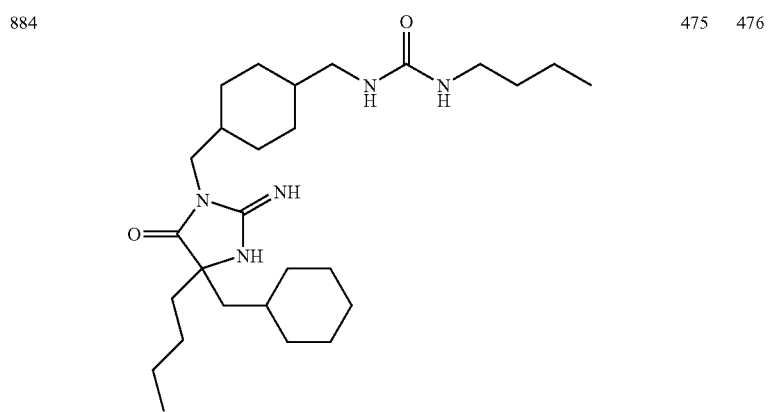 | 472 | 473 |
| 884 | 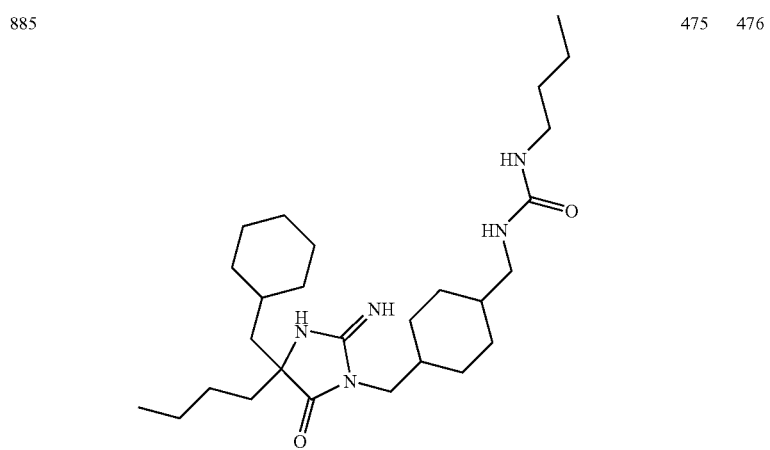 | 475 | 476 |
| 885 | 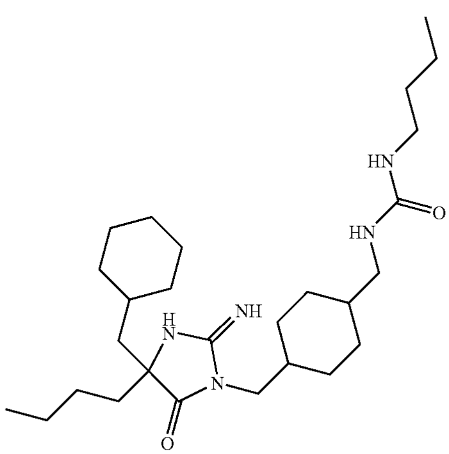 | 475 | 476 |

-continued

| # | Structure | MW | Obs. m/e |
|---|-----------|-----|----------|
| 886 | 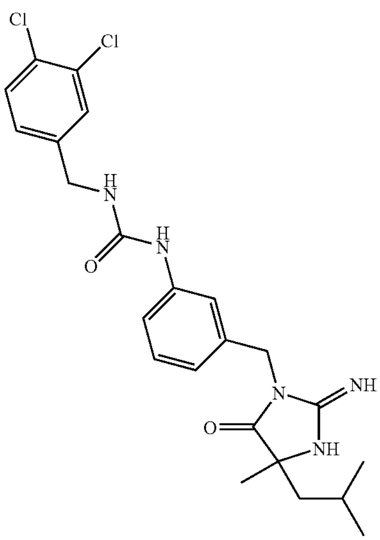 | 475 | 476 |
| 887 | 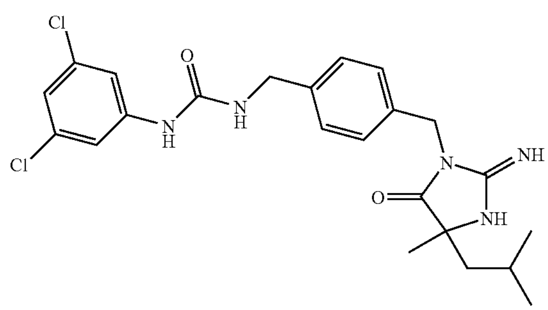 | 475 | 476 |
| 888 | 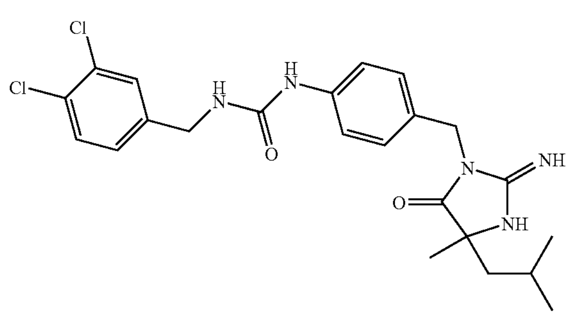 | 475 | 476 |

-continued

| # | Structure | MW | Obs. m/e |
|---|-----------|-----|----------|
| 889 | 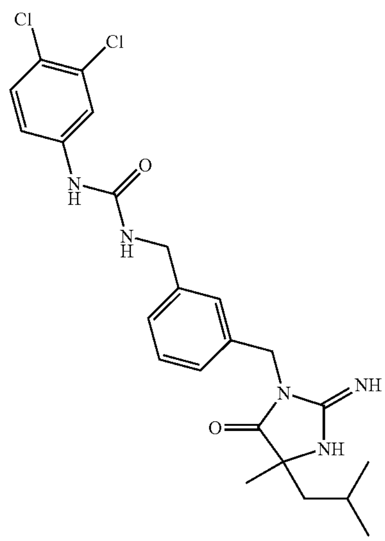 | 475 | 476 |
| 890 | 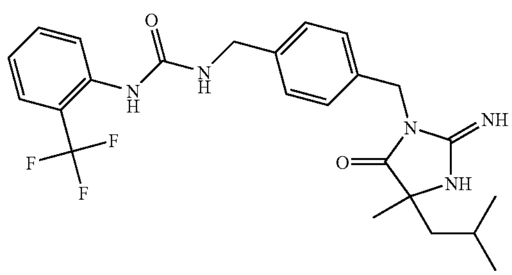 | 475 | 476 |
| 891 | 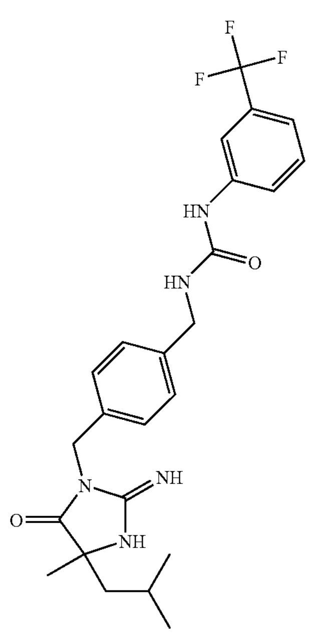 | 475 | 476 |

-continued
| # | Structure | MW | Obs. m/e |
|---|---|---|---|
| 892 | 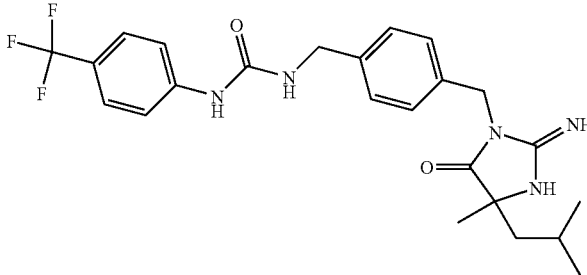 | 475 | 476 |
| 893 | 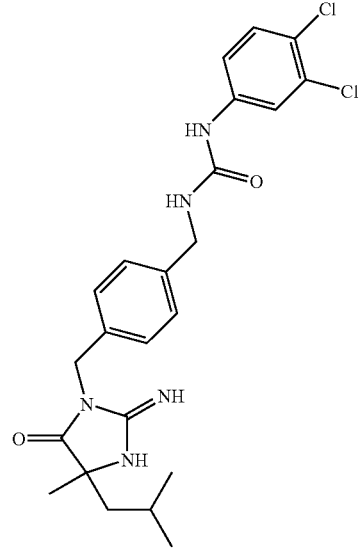 | 475 | 476 |
| 894 | 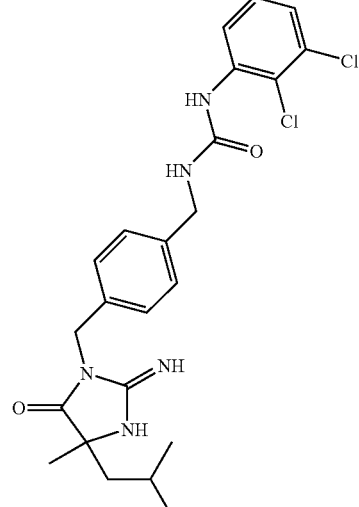 | 475 | 476 |

-continued
| # | Structure | MW | Obs. m/e |
|---|---|---|---|
| 895 | 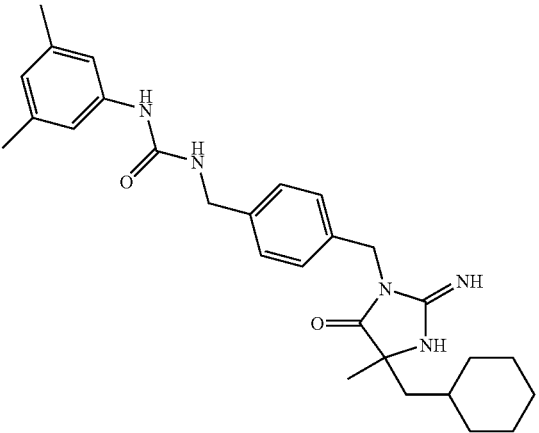 | 475 | 476 |
| 896 | 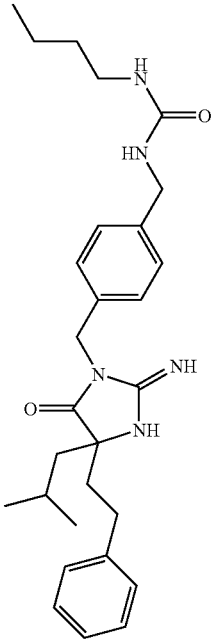 | 477 | 478 |
| 897 | 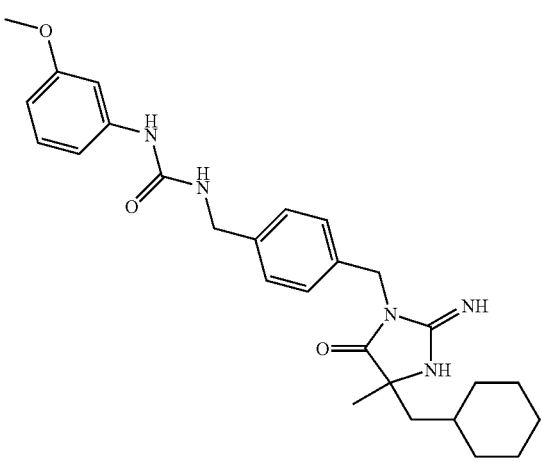 | 477 | 478 |

-continued

| # | Structure | MW | Obs. m/e |
|---|-----------|-----|----------|
| 898 | 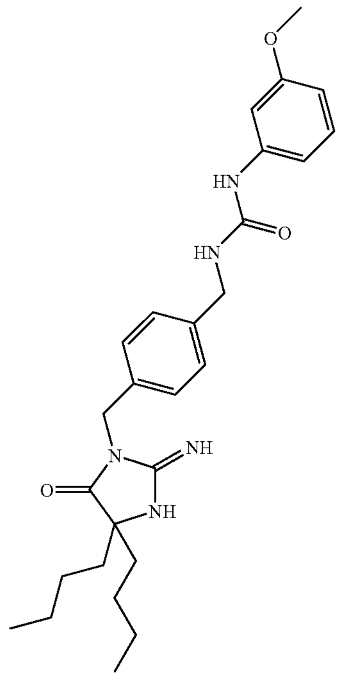 | 479 | 480 |
| 899 | 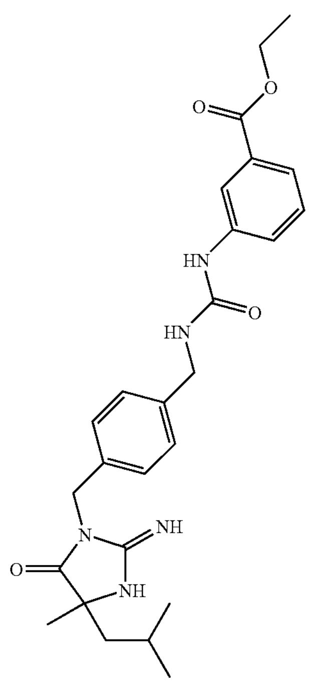 | 479 | 480 |

-continued

| # | Structure | MW | Obs. m/e |
|---|---|---|---|
| 900 | 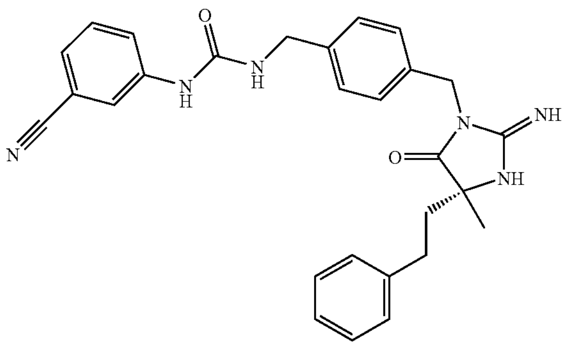 | 480 | 481 |
| 901 | 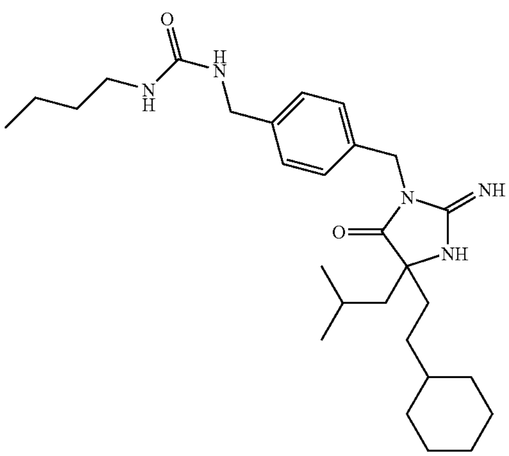 | 483 | 484 |
| 902 | 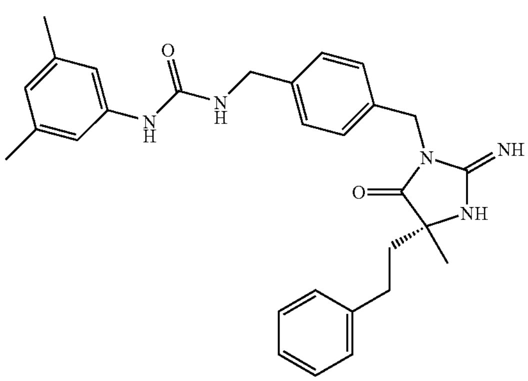 | 483 | 484 |

-continued

| # | Structure | MW | Obs. m/e |
|---|---|---|---|
| 903 | 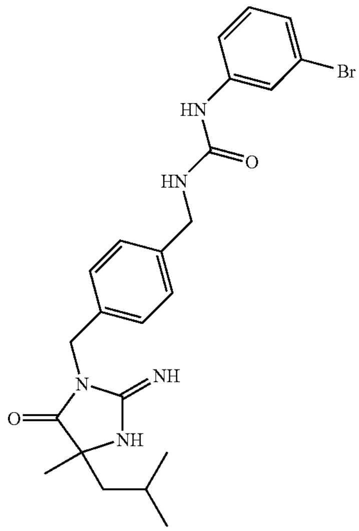 | 485 | 486 |
| 904 | 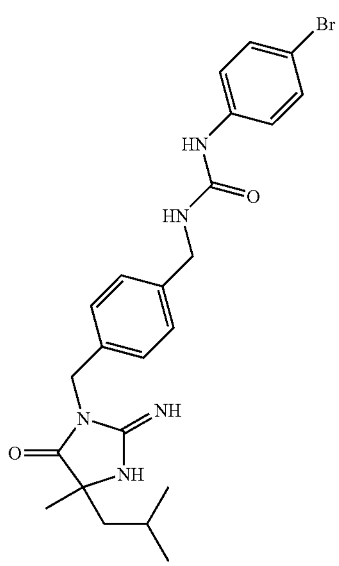 | 485 | 486 |

-continued
| # | Structure | MW | Obs. m/e |
|---|---|---|---|
| 905 | 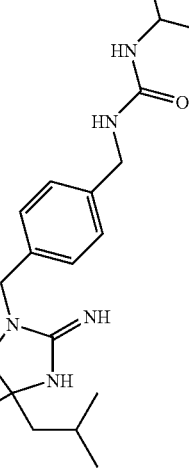 | 485 | 486 |
| 906 | 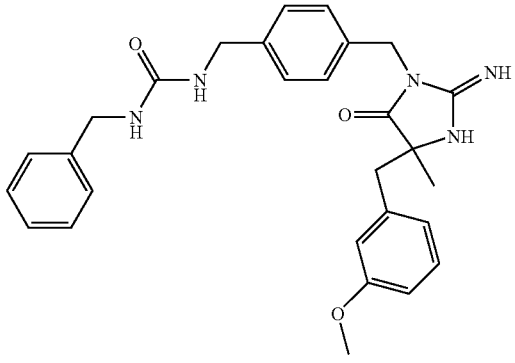 | 485 | 486 |
| 907 | 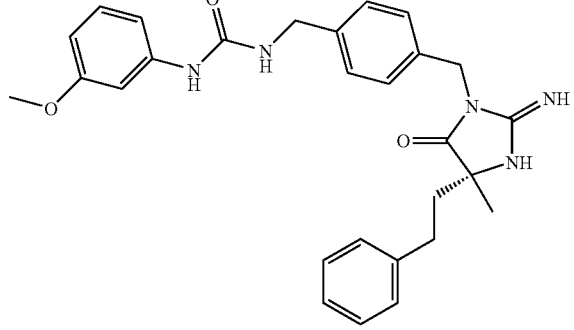 | 485 | 486 |
| 908 | 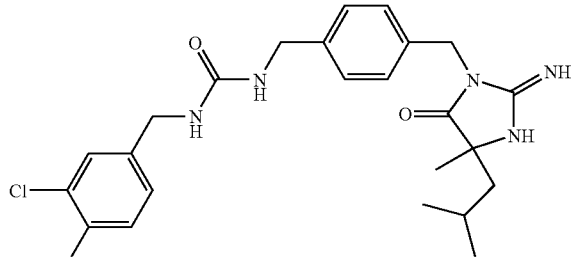 | 489 | 490 |

-continued
| # | Structure | MW | Obs. m/e |
|---|---|---|---|
| 909 | 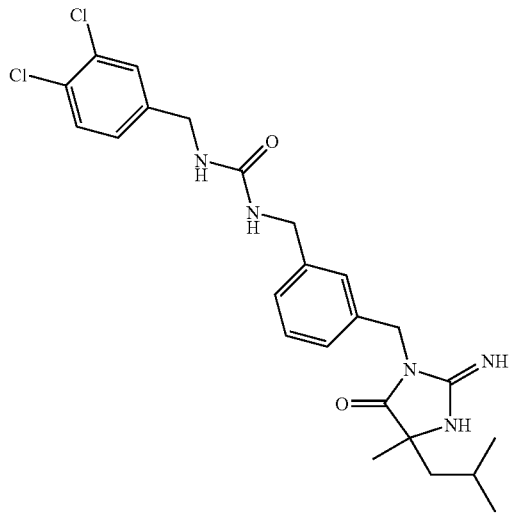 | 489 | 490 |
| 910 | 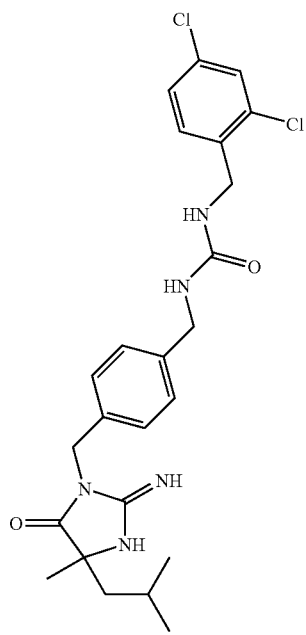 | 489 | 490 |

-continued
| # | Structure | MW | Obs. m/e |
|---|---|---|---|
| 911 | 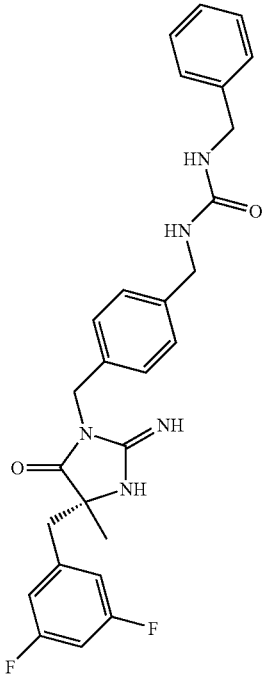 | 491 | 492 |
| 912 | 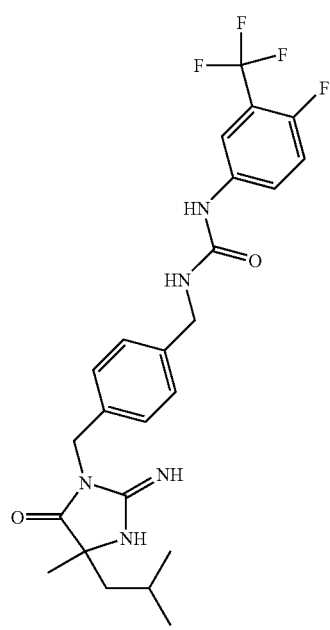 | 493 | 494 |

-continued

| # | Structure | MW | Obs. m/e |
|---|---|---|---|
| 913 | 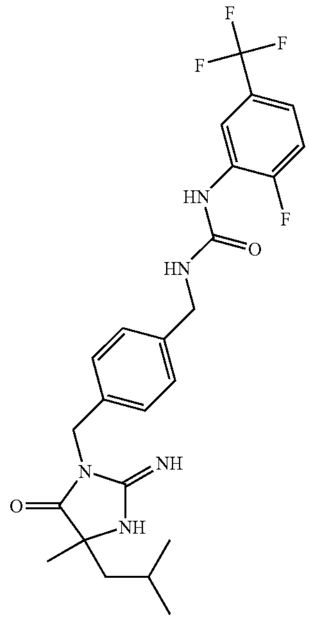 | 493 | 494 |
| 914 | 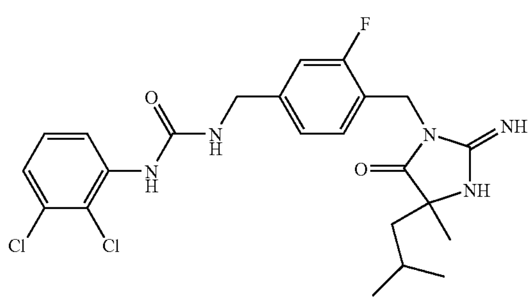 | 493 | 494 |
| 915 | 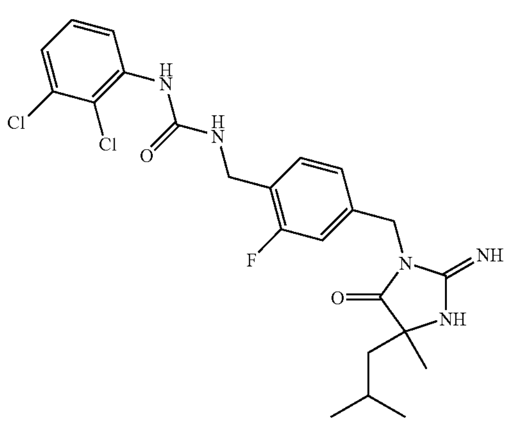 | 493 | 494 |

-continued

| # | Structure | MW | Obs. m/e |
|---|---|---|---|
| 916 | 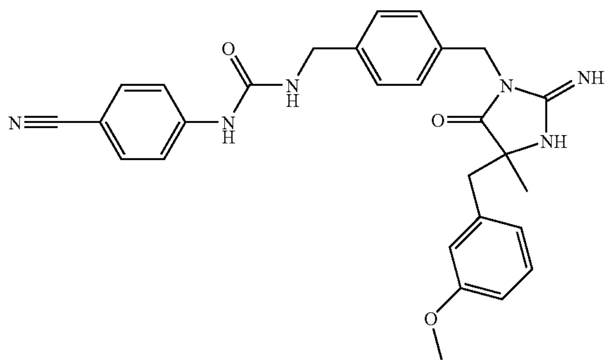 | 496 | 497 |
| 917 | 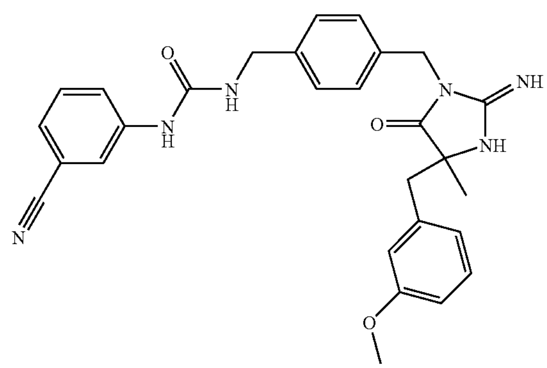 | 496 | 497 |
| 918 | 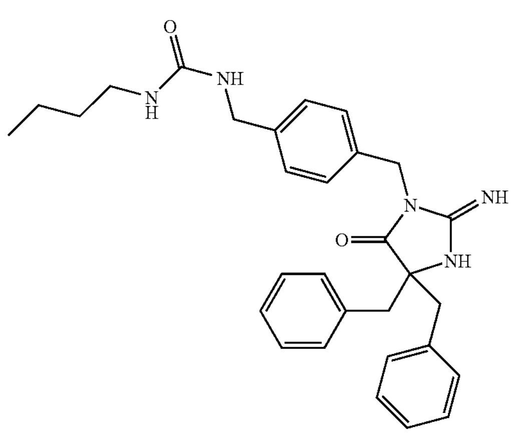 | 497 | 498 |

-continued
| # | Structure | MW | Obs. m/e |
|---|---|---|---|
| 919 | 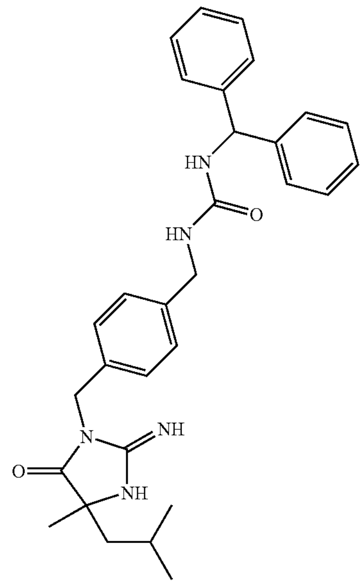 | 497 | 498 |
| 920 | 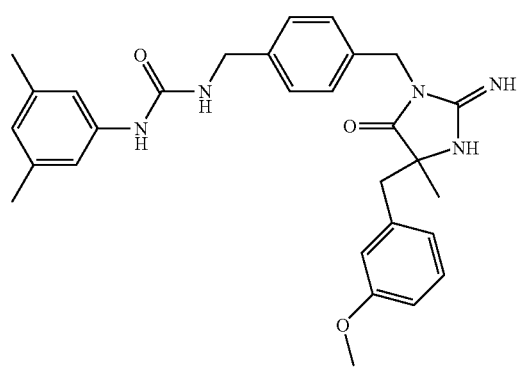 | 499 | 500 |
| 921 | 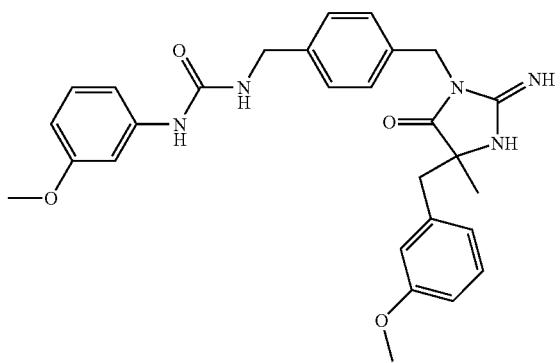 | 501 | 502 |

-continued

| # | Structure | MW | Obs. m/e |
|---|-----------|-----|----------|
| 922 | 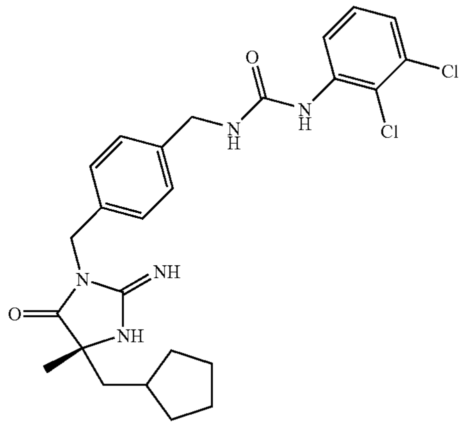 | 501 | 502 |
| 923 | 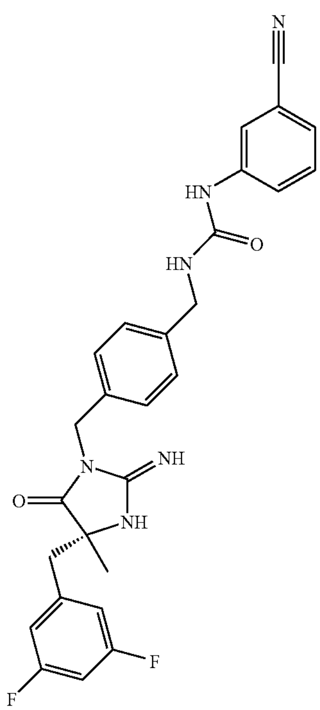 | 502 | 503 |

-continued
| # | Structure | MW | Obs. m/e |
|---|-----------|-----|----------|
| 924 | 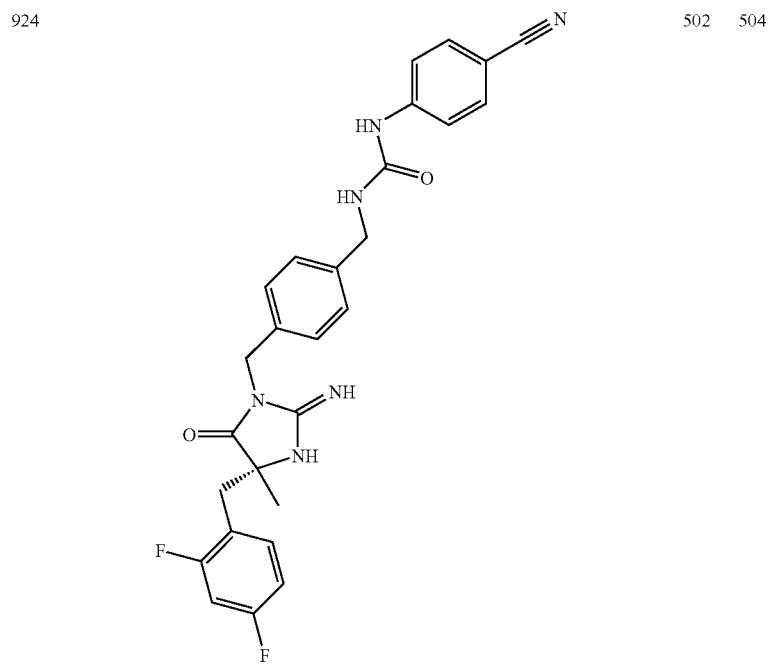 | 502 | 504 |
| 925 | 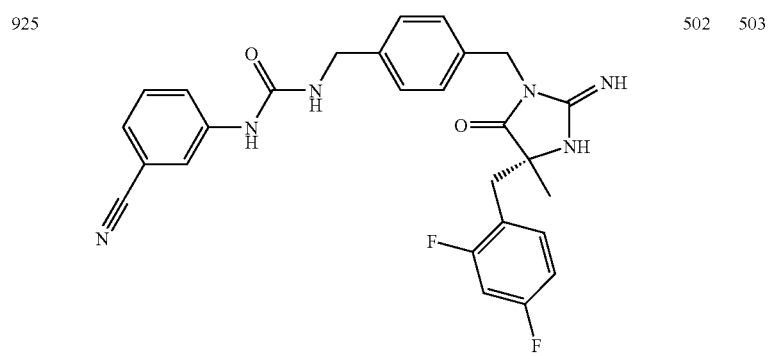 | 502 | 503 |

-continued

| # | Structure | MW | Obs. m/e |
|---|---|---|---|
| 926 | 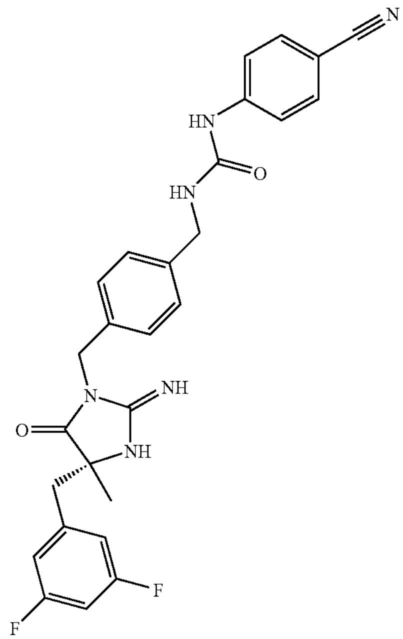 | 502 | 503 |
| 927 | 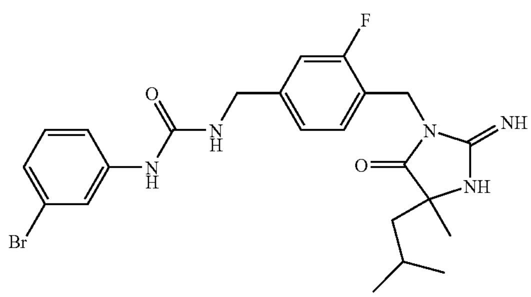 | 503 | 504 |
| 928 | 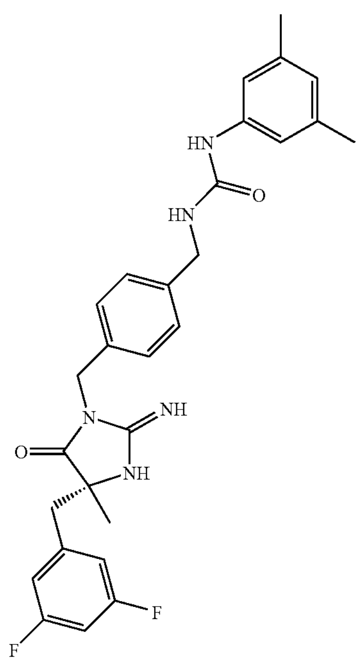 | 505 | 506 |

-continued
| # | Structure | MW | Obs. m/e |
|---|---|---|---|
| 929 | 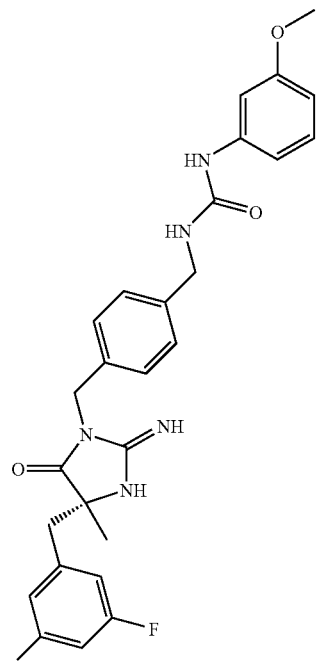 | 507 | 508 |
| 930 | 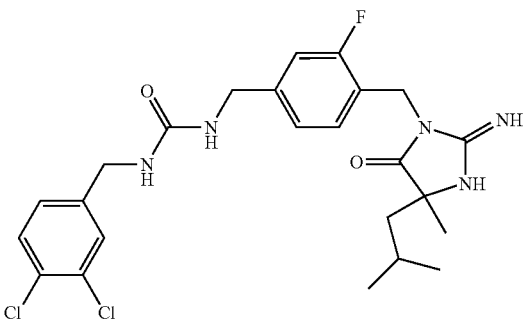 | 507 | 508 |
| 931 | 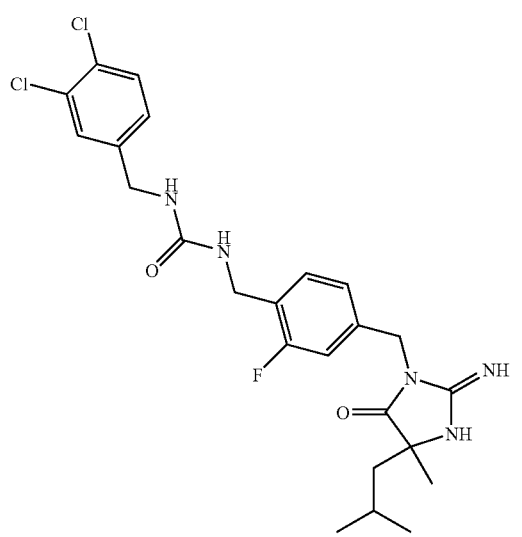 | 507 | 508 |

-continued

| # | Structure | MW | Obs. m/e |
|---|---|---|---|
| 932 | 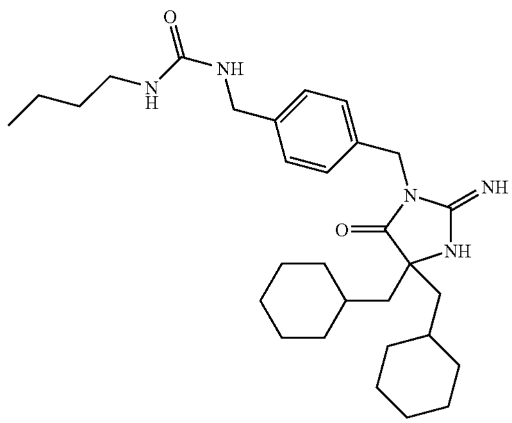 | 509 | 510 |
| 933 | 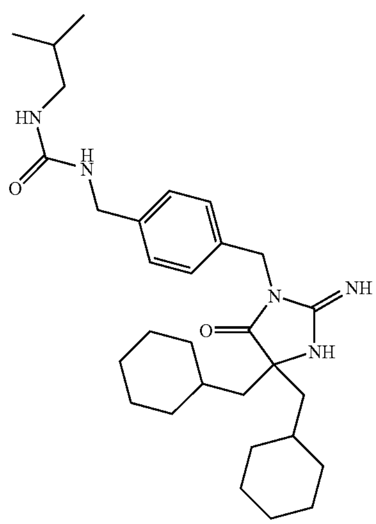 | 509 | 510 |
| 934 | 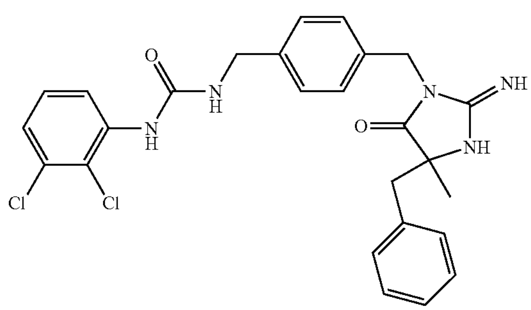 | 509 | 510 |
| 935 | 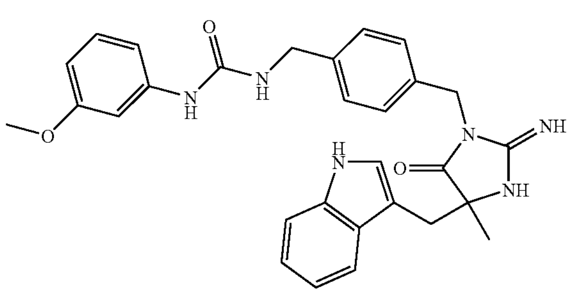 | 510 | 511 |

-continued
| # | Structure | MW | Obs. m/e |
|---|---|---|---|
| 936 | 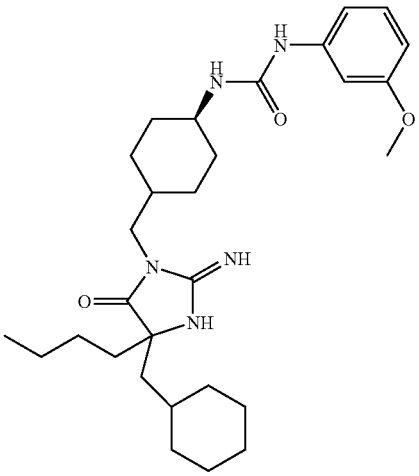 | 511 | 512 |
| 937 | 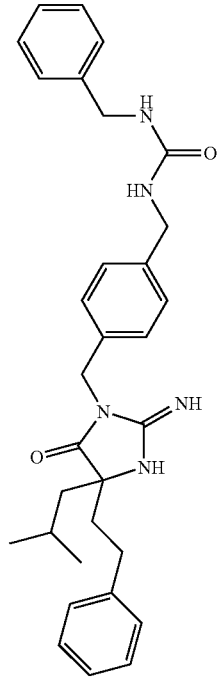 | 511 | 512 |

-continued

| # | Structure | MW | Obs. m/e |
|---|---|---|---|
| 938 | 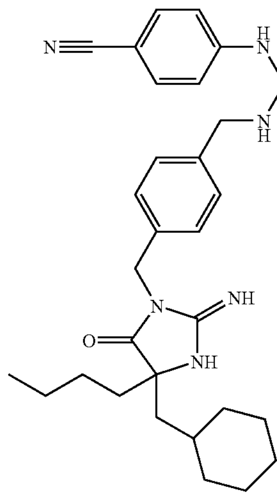 | 514 | 515 |
| 939 | 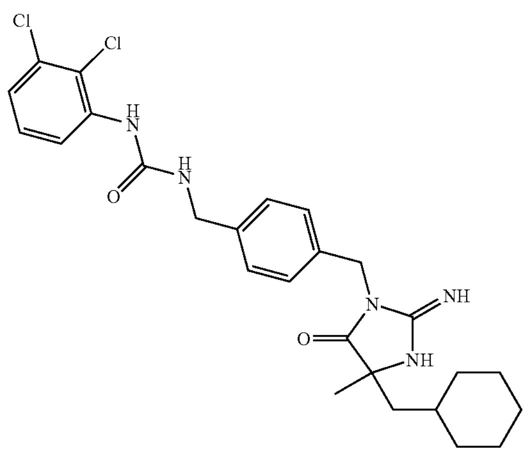 | 515 | 516 |
| 940 | 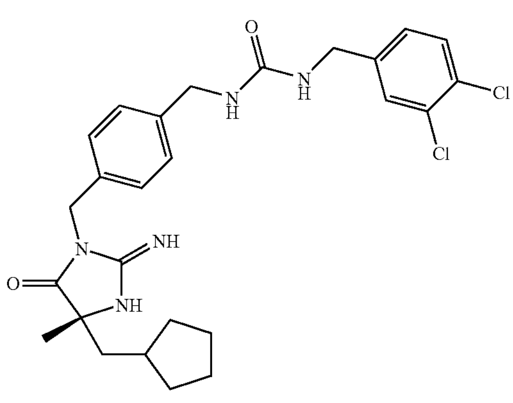 | 515 | 516 |

-continued

| # | Structure | MW | Obs. m/e |
|---|---|---|---|
| 941 | 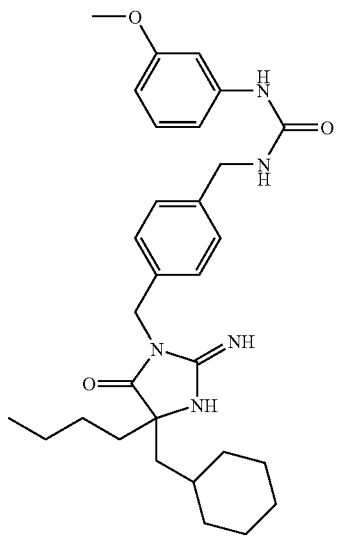 | 519 | 520 |
| 942 | 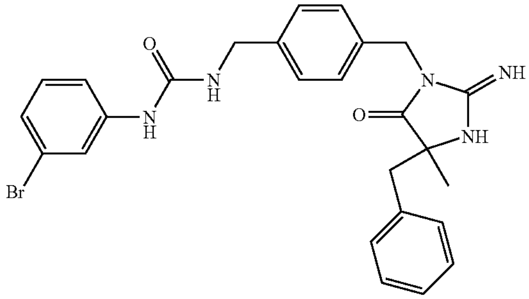 | 519 | 520 |
| 943 | 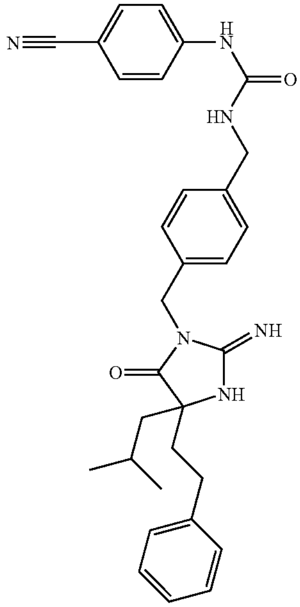 | 522 | 523 |

-continued

| # | Structure | MW | Obs. m/e |
|---|-----------|-----|----------|
| 944 | 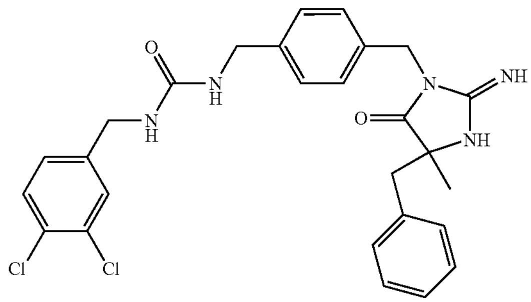 | 523 | 524 |
| 945 | 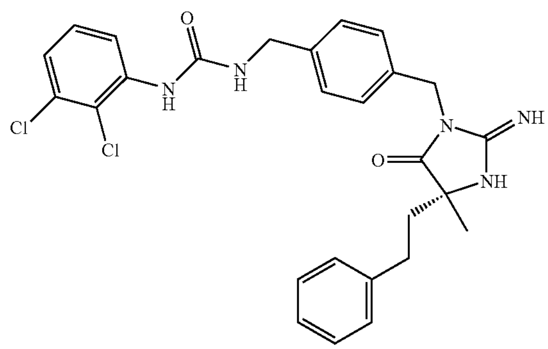 | 545 | 524 |
| 946 | 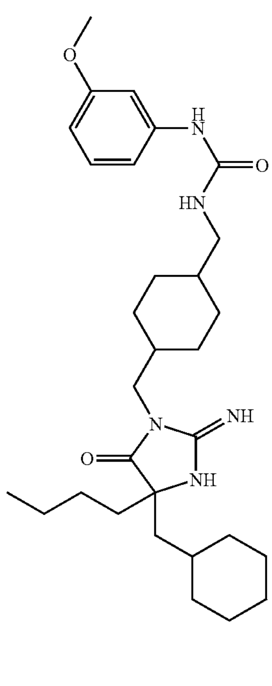 | 525 | 526 |

-continued

| # | Structure | MW | Obs. m/e |
|---|---|---|---|
| 947 | 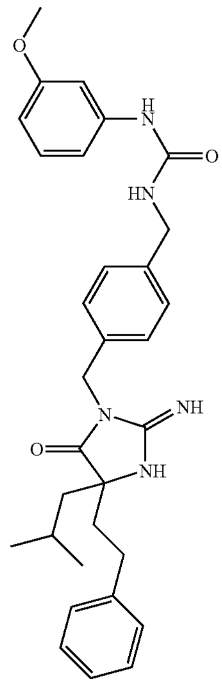 | 527 | 528 |
| 948 | 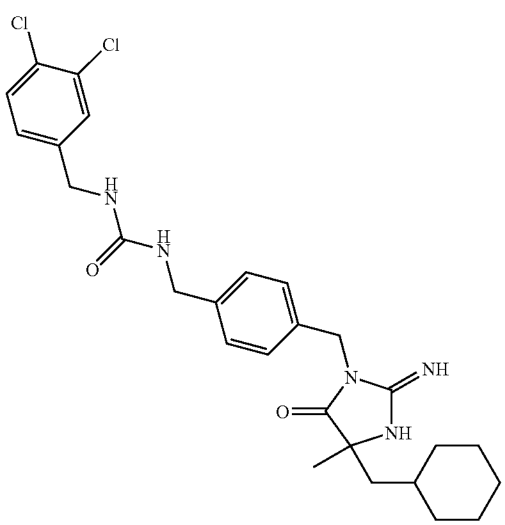 | 529 | 530 |

-continued

| # | Structure | MW | Obs. m/e |
|---|---|---|---|
| 949 | 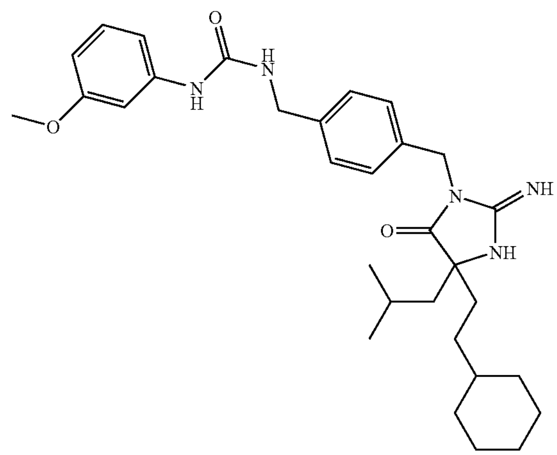 | 533 | 534 |
| 950 | 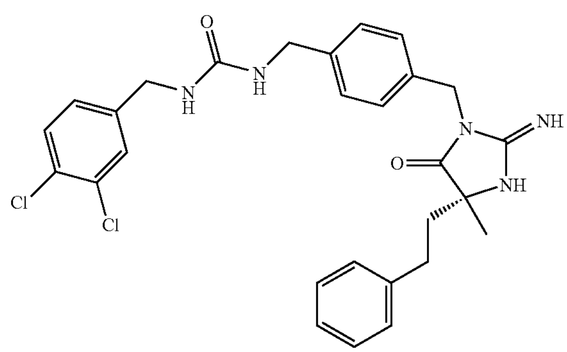 | 537 | 538 |
| 951 | 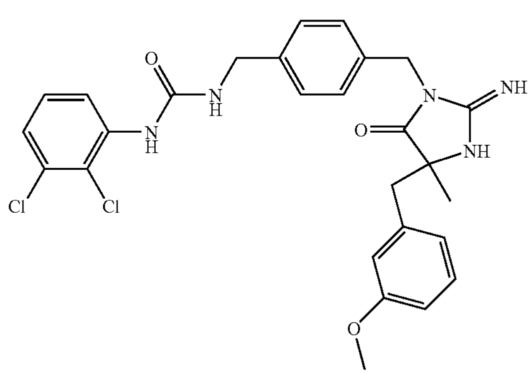 | 539 | 540 |

-continued
| # | Structure | MW | Obs. m/e |
|---|---|---|---|
| 952 | 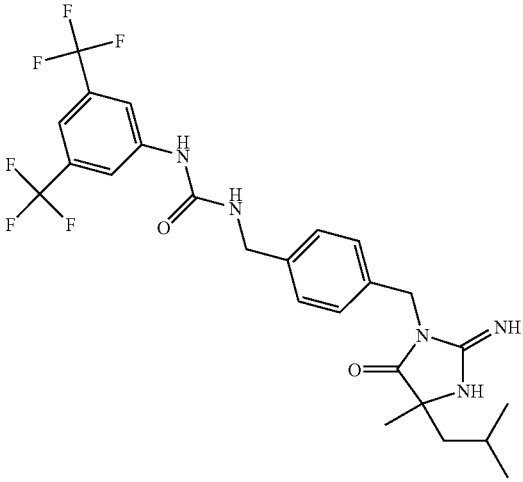 | 543 | 544 |
| 953 | 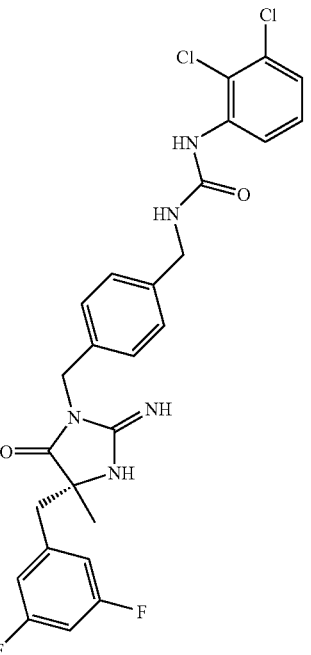 | 545 | 546 |
| 954 | 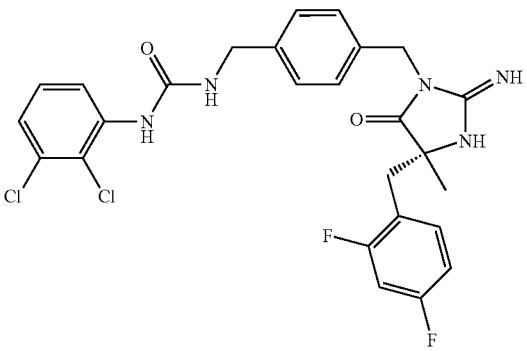 | 545 | 546 |

-continued
| # | Structure | MW | Obs. m/e |
|---|---|---|---|
| 955 | 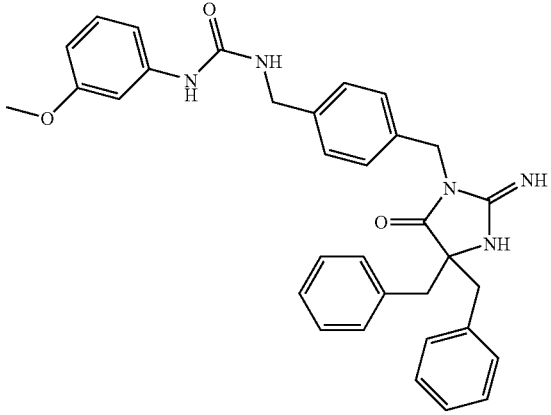 | 547 | 548 |
| 956 | 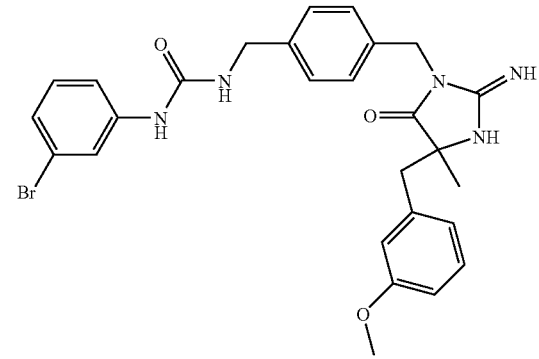 | 549 | 550 |
| 957 | 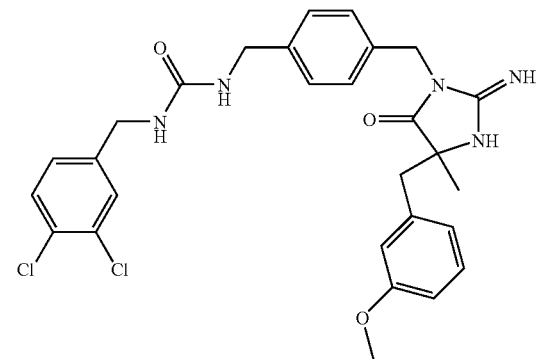 | 553 | 554 |

-continued
| # | Structure | MW | Obs. m/e |
|---|---|---|---|
| 958 | 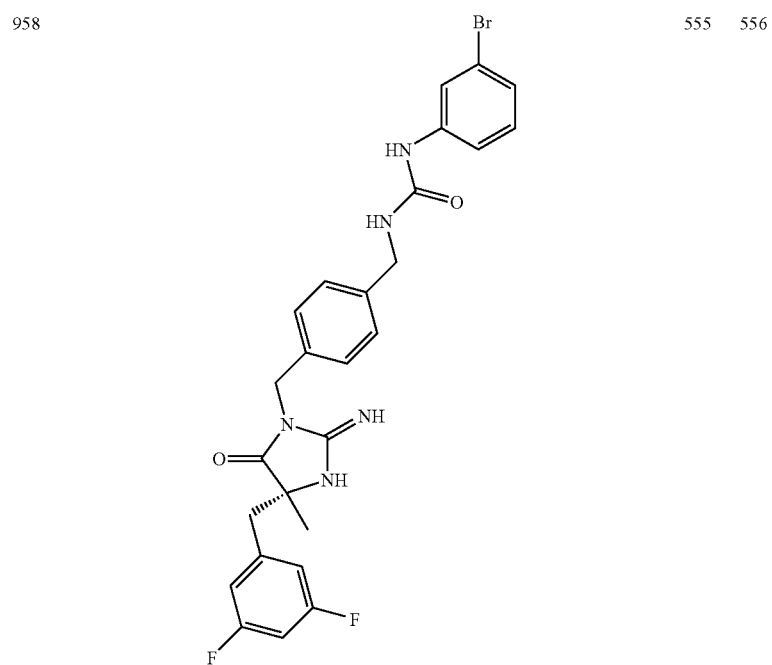 | 555 | 556 |
| 959 | 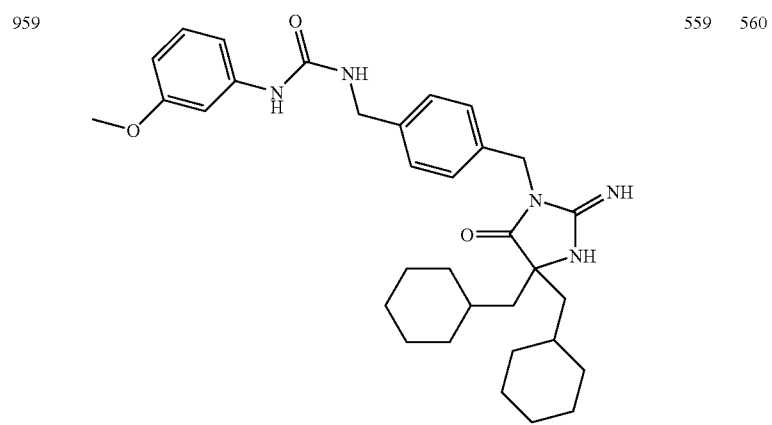 | 559 | 560 |

-continued

| # | Structure | MW | Obs. m/e |
|---|---|---|---|
| 960 | 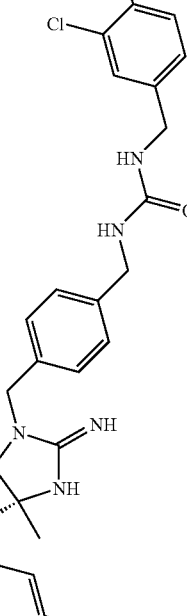 | 559 | 560 |
| 961 | 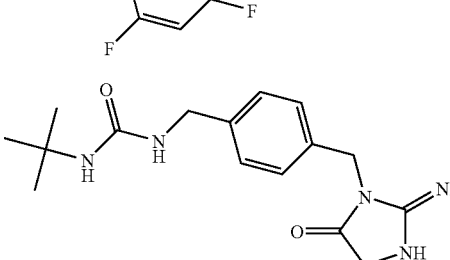 | 387 | |

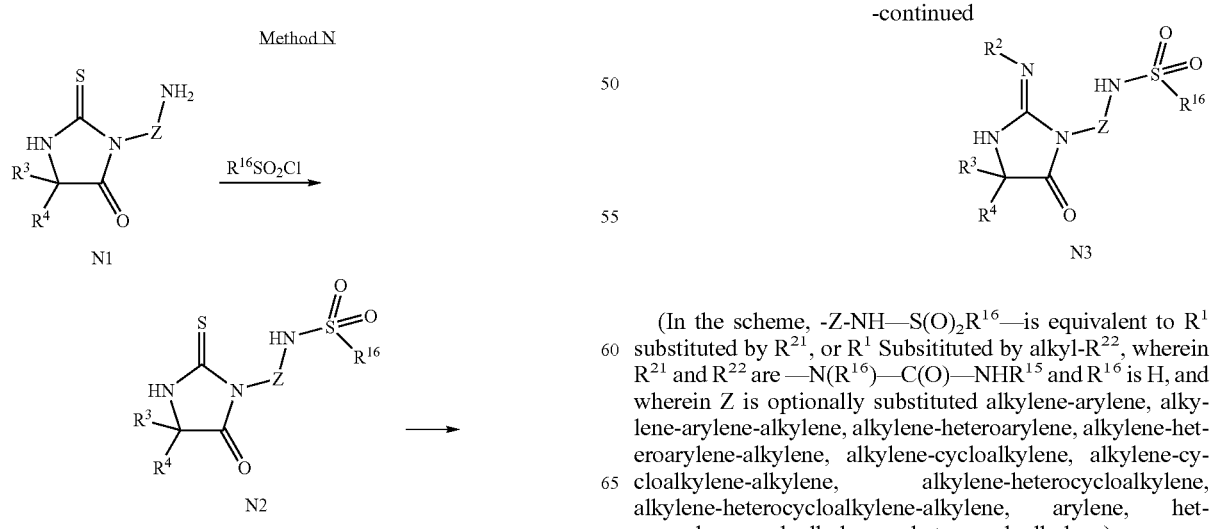

(In the scheme, -Z-NH—S(O)$_2$R$^{16}$—is equivalent to R$^1$ substituted by R$^{21}$, or R$^1$ Subsitituted by alkyl-R$^{22}$, wherein R$^{21}$ and R$^{22}$ are —N(R$^{16}$)—C(O)—NHR$^{15}$ and R$^{16}$ is H, and wherein Z is optionally substituted alkylene-arylene, alkylene-arylene-alkylene, alkylene-heteroarylene, alkylene-heteroarylene-alkylene, alkylene-cycloalkylene, alkylene-cycloalkylene-alkylene, alkylene-heterocycloalkylene, alkylene-heterocycloalkylene-alkylene, arylene, heteroarylene, cycloalkylene or heterocycloalkylene)

Method N, Step 1:

Compound N2 (R³=CH₃, R⁴=CH₂CH(CH₃)₂, Z=para-(CH₂)C₆H₄(CH₂)—, R¹⁶=CH₂CH(CH₃)₂) was prepared from N1 (R³=CH₃, R⁴=CH₂CH(CH₃)₂, Z=para-(CH₂)C₆H₄(CH₂)—) following the procedure described in Method K, Step 1.

Method N, Step 2:

Compound N3 (R³=CH₃, R⁴=CH₂CH(CH₃)₂, Z=para-(CH₂)C₆H₄(CH₂)—, R¹⁶=CH₂CH(CH₃)₂) was prepared from N2 (R³=CH₃, R⁴=CH₂CH(CH₃)₂, Z=para-(CH₂)C₆H₄(CH₂)—, R¹⁶=CH₂CH(CH₃)₂) following the procedure described in Method A, Step 3.

The following compounds were prepared using similar method.

| # | Structure | MW | Obs. m/e |
|---|---|---|---|
| 962 | 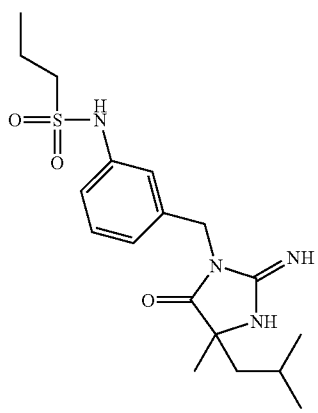 | 380 | 381 |
| 963 | 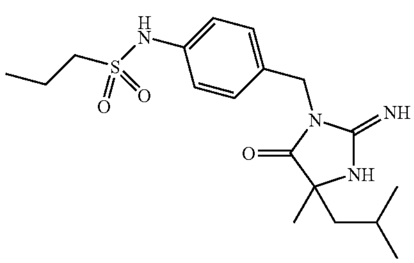 | 380 | 381 |
| 964 | 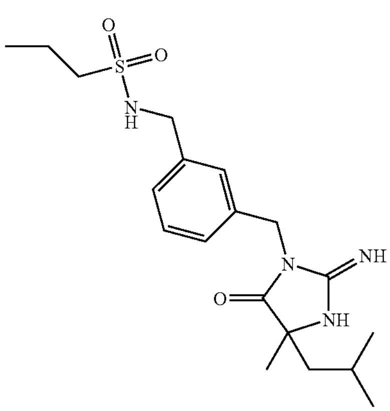 | 394 | 395 |
| 965 | | 394 | 395 |
| 966 | | 451 | 452 |
| 967 | | 484 | 485 |

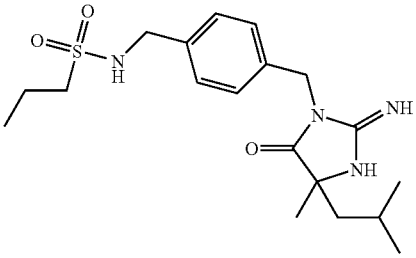

319
-continued
| # | Structure | MW | Obs. m/e |
|---|---|---|---|
| 968 | 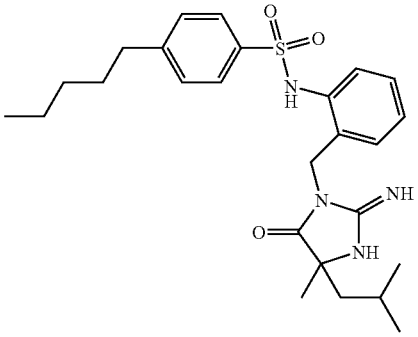 | 484 | 485 |
| 969 | 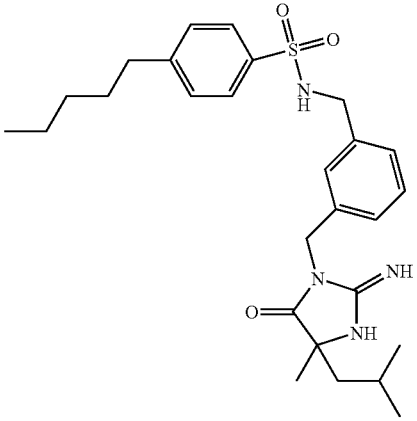 | 498 | 499 |
| 970 | 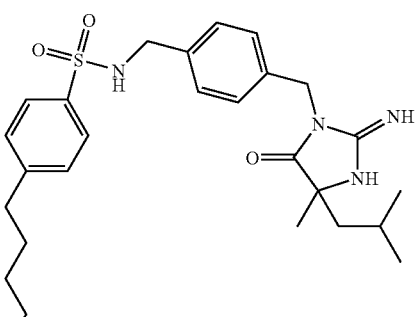 | 498 | 499 |
Method O
320
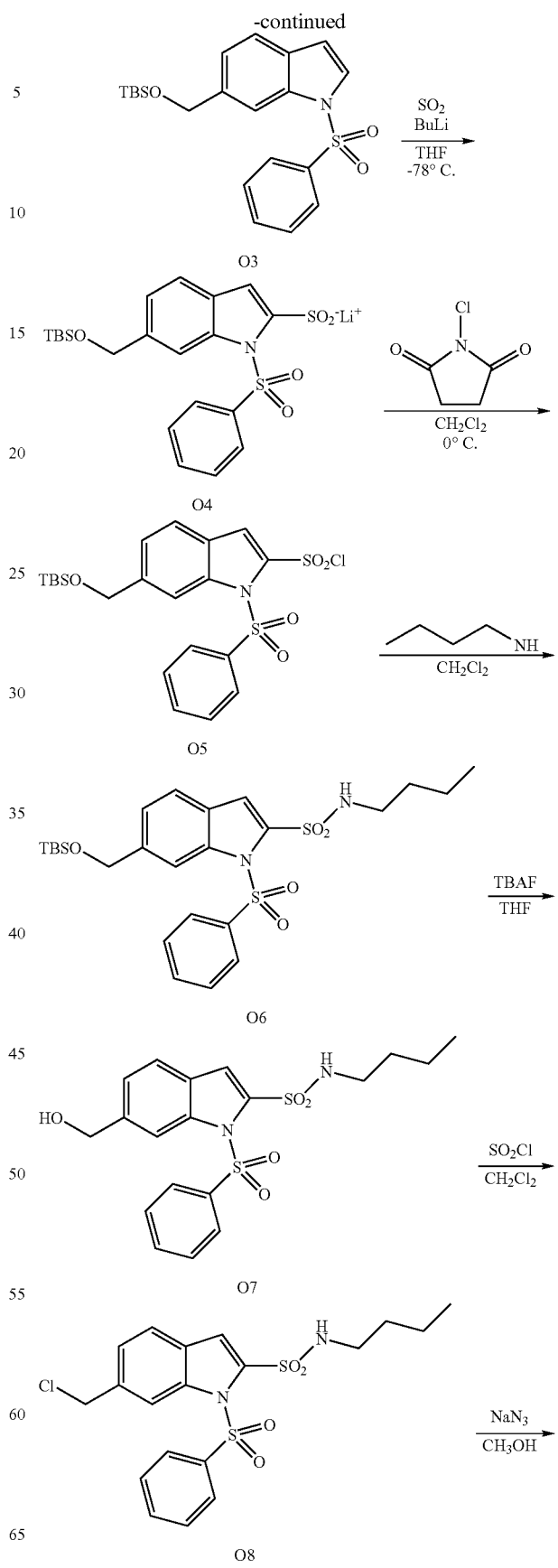

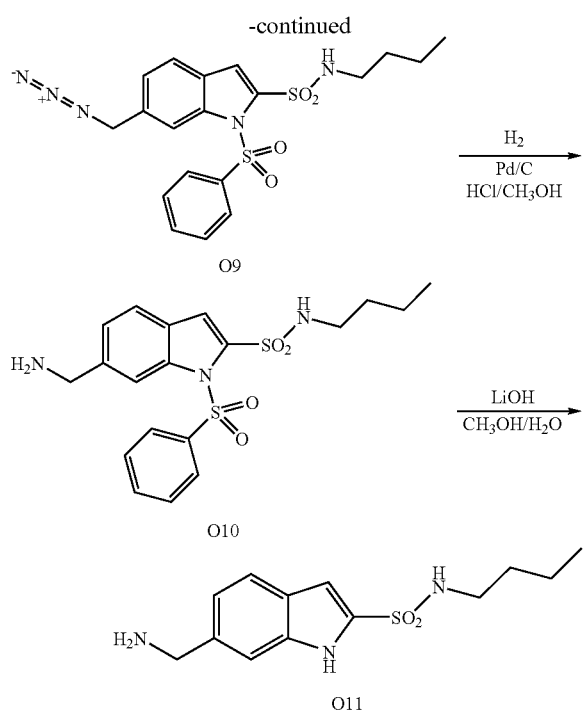

Method O, Step 1:

A solution of indole-6-methanol (400 mg, 2.72 mmol), tert-butyldimethysilyl choride (816 mg, 5.41 mmol) and imidazole (740 mg, 10.9 mmol) in $CH_2Cl_2$ was stirred at rt. overnight before the solvent was evaporated and residue chromatographed using ethylacetate/hexane to give product O2.

Method O, Step 2:

To a solution of O2 (200 mg, 0.77 mmol) in THF (10 mL) at −78° C. was added butyl lithium (1.2 eq). The solution was stirred at −78° C. for 5 min and then warmed to rt. The reaction mixture was cooled to −78° C. and p-toluenesulfonyl chloride was added. The solution was warmed to rt and stirred overnight. The reaction was quenched with a saturated aqueous $K_2CO_3$ solution, extracted with ethyl acetate and $CH_2Cl_2$. The crude material was purified via flash chromatography using ethylacetate/hexane to afford 360 mg of O3.

Method O, Step 3:

A solution butyl lithium (1.2 eq) was added to a solution of O3 (340 mg, 0.829 mmol) in THF (20 mL). The reaction mixture was stirred for 15 min at −78° C. then sulfur dioxide was bubbled through the solution for 15 min. Hexane (100 mL) was added to the reaction mixture. The reaction mixture was evaporated to afford O4 which was used in the next step without further purification.

Method O, Step 4:

To a solution of O4 (0.829 mmol) in $CH_2Cl_2$ cooled to 0° C. was added N-chlorosuccinimide (220 mg, 1.66 mmol). After 2 h of stirring, the solution was filtered through a Celite plug. The filtrate was concentrated to afford O5.

Method O, Step 5:

To a solution of O5 in anhydrous pyridine (3 mL) was added butyl amine (100 μL). The reaction was agitated at rt for 4 d. The reaction mixture was partitioned between 1 N HCl and $CH_2Cl_2$. The organic layer was separated and washed with 1 N HCl (3×). The organic solution was dried over $Na_2SO_4$, filtered and concentrated. The crude material was purified via flash chromatography using ethylacetate/hexane to yield O6.

Method O, Step 6:

To a solution of O6 (70 mg) in THF was added TBAF. The reaction was stirred at rt. before the reaction mixture was chromatographed using ethylacetate/hexane to afforded 50 mg of O7 (95%).

Method O, Step 7:

To a solution of O7 (50 mg) in $CH_2Cl_2$ (5 mL) was added thionyl chloride (1 mL) the reaction was stirred for 5 min and then evaporated to afford O8.

Method O, Step 8:

To a solution of O8 in $CH_3OH$ (5 mL) was added sodium azide (50 mg). The solution was stirred at rt overnight and solvent evaporated. The residue was chromatographed using ethylacetate/hexane to afforded O9 after purification.

Method O, Step 9:

To a suspension of O9 (70 mg) in $CH_3OH$ was added 1 eq HCl (aq) and palladium on carbon. The reaction mixture was hydrogenated at 1 atm for 20 min to yield 90 mg of crude product O10.

Method O, Step 10:

A solution of lithium hydroxide (30 mg) in $H_2O$ was added to a solution of O10 (40 mg) in $CH_3OH$ (3 mL). The reaction was stirred at rt for 2 h and an additional portion of LiOH (40 mg) was added and solution was stirred for 2 more hours. The solvent was evaporated and residue chromatographed using ethylacetate/hexane to afforded O11.

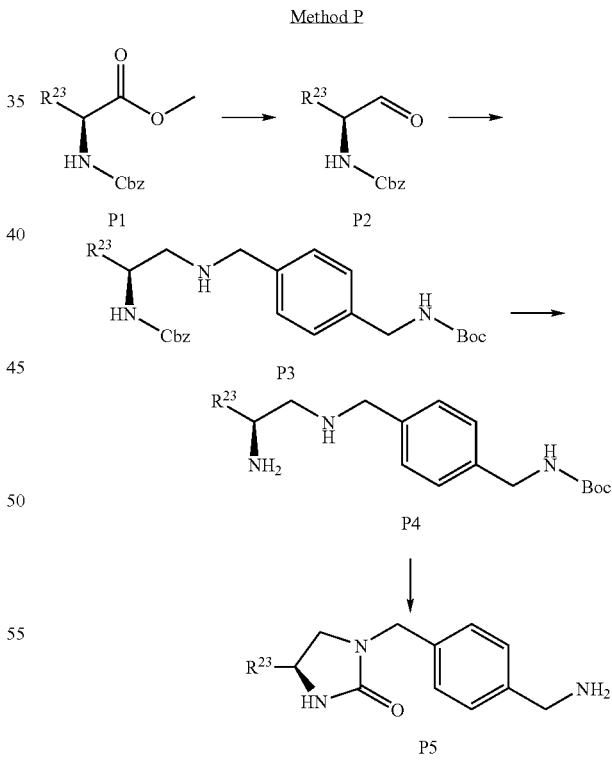

Method P, Step 1:

A 300 mL of THF solution of 100 g of P1 ($R^{23}$=n-Pr) was added to a suspension of 38 g of LAH in 2 L of anhydrous THF at 0 C. The reaction mixture is stirred at r.t. for 1 h before 30 ml of $H_2O$, 90 ml of 15% NaOH was added at 0° C. The mixture was stirred at r.t. for one hour before $Na_2SO_4$ (anh)

was added, the mixture was filtered, and the solution evaporated to give a product which was dried under vacuo overnight. This product was dissolved in 600 ml of DCM and the solution was added into a solution of oxalyl chloride (37.3 ml) and DMSO (60.8 ml) in 1.4 L of DCM at −78° C. over 40 min before Diisopropylethylamine (299 ml) was added at −78° C. The reaction was allowed to reach −10° C. The reaction was quenched with 1 L H$_2$O at −10° C. and the mixture was extracted with DCM. After removal of solvent, P2 (R$^{23}$=Pr, 106 g) was obtained. The crude material was used for next step without purification.

Method P, Step 2:

To a 1.5 L DCM solution of P2 (R$^{23}$=Pr, 106 g) was added p-Boc-aminomethylbenzylamine (1.1 eq) and sodium triacetoxyborohydride (1.1 eq) and the reaction was stirred at r.t. overnight. The reaction was quenched with H$_2$O and content extracted with DCM. After removal of solvents the residue was chromatographed using a silica gel column eluted with 3% MeOH in DCM to give 42.5 g of P3 (R$^{23}$=Pr).

Method P, Step 3:

A 10 ml MeOH solution of P3 (R$^{23}$=Pr, 110 mg) was hydrogenated using Pd/C (5%, 11 mg) at 1 atm of hydrogen to give product P4 (R$^{23}$=Pr) after removal of solvent and catalyst.

Method P, Step 4:

To a 10 ml DCM solution of P4 at 0° C. (R$_{23}$=Pr) was added triphosgene 1.2 eq) and triethylamine (2.4 eq) and the solution was stirred at 0 C for 2 h before the reaction was extracted with DCM/H$_2$O. After removal of the solvent, the residue was chromatographed using a silica gel column eluted with EtOAc/Hexane to give a white solid which was treated with 2N HCl in dioxane for 2 h. After removal of the solvent, compound P5 (R$^{23}$=Pr) as a white solid was obtained (80 mg).

The following compounds were synthesized using similar methods:

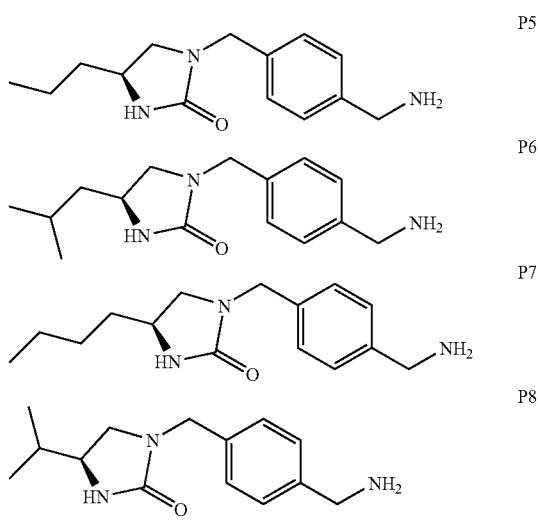

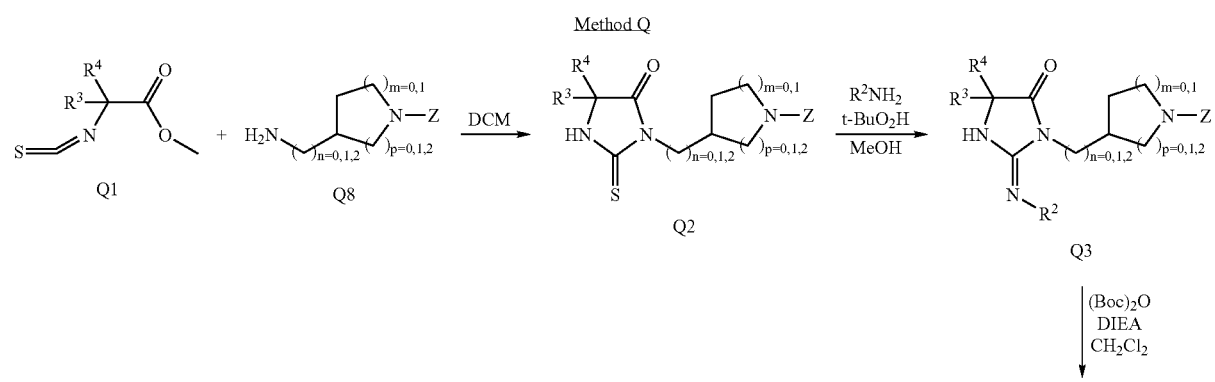

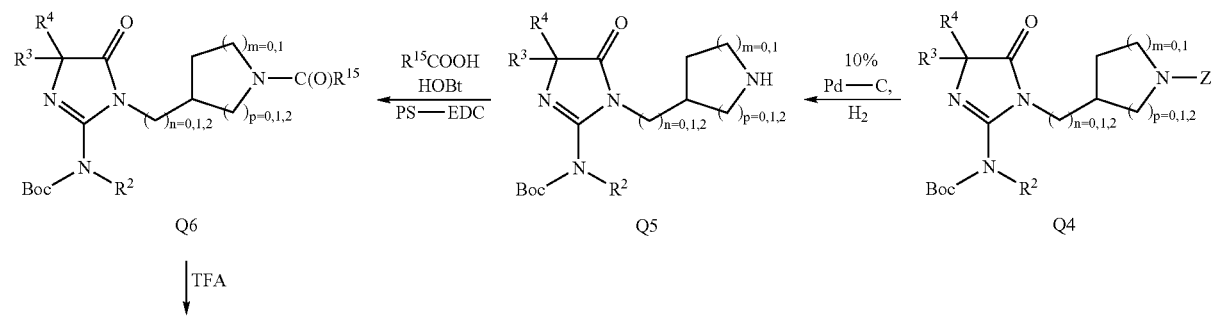

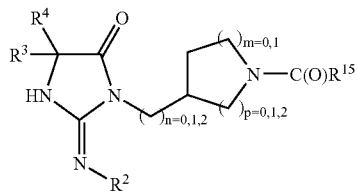

Q7

Method Q, Step 1

At room temperature, Q1 ($R^3$=Me; $R^4$=iBu) (1.00 g) and 08 (n=1, p=2, m=1) (1.24 g) in dichloromethane (30 mL) were stirred for 42 h. This mixture was concentrated in vacuo to give an amber oil which was purified on a column of silica gel (200 mL) eluted with ethylacetate/hexane to give Q2 (n=1, p=2, m=1, $R^3$=Me; $R^4$=iBu), a colorless oil (1.59 g).

Method Q, Step 2

Compound Q3 (n=1, p=2, m=1, $R^2$=H, $R^3$=Me; $R^4$=iBu) was prepared from Q2 (n=1, p=2, m=1, $R^3$=Me; $R^4$=iBu) using method similar to method A step 3.

Method Q, Step 3

Compound Q3 (n=1, p=2, m=1, $R^2$=H, $R^3$=Me; $R^4$=iBu) (1.37 g) in anhydrous dichloromethane (25 mL) was treated with di-tert-butyl dicarbonate (0.68 g, 1.1 equiv.) and diisopropylethylamine (0.66 mL, 1.1.equiv.). The resulting solution was stirred at room temperature for 20 h before it was diluted with dichloromethane and washed with 1N hydrochloric acid. The dried dichloromethane solution was concentrated in vacuo to give a colorless film (1.32 g) which was purified on a column of silica gel (125 mL) and eluted with hexane:ethyl acetate to give compound Q4 (n=1, p=2, m=1, $R^2$=H, $R^3$=Me; $R^4$=i-Bu) as a white foam (0.74 g).

Method Q, Step 4

Compound Q4 (n=1, p=2, m=1, $R^2$=H, $R^3$=Me; $R^4$=$^i$Bu) (0.540 g) in absolute EtOH (20 mL) was hydrogenated with 10% Pd/C (0.400 g) at 1 atm for 2 h. The reaction mixture was filtered and the filtrate was concentrated in vacuo to give Q5 (n=1, p=2, m=1, $R^2$=H, $R^3$=Me; $R^4$=$^i$Bu) as a colorless oil (0.35 g).

Method Q, Step 5

Compound Q5 (n=1, p=2, m=1, $R^2$=H, $R^3$=Me; $R^4$=iBu) (0.012 g) and HOBt (0.005 g) dissolved in acetonitrile (0.8 mL) and tetrahydrofuran (0.25 mL) was treated with EDC resin (0.080 g, 3 eq., 1.53 mmol/g) in a microtiter plate well followed by addition of a 1M dichloroethane solution of $R^{15}$—COOH (40 uL, 1.25 eq.). After the well was capped and shaken for 18 h, the mixture was filtered and the resin washed with acetonitrile (0.5 mL). The combined solution was treated with Trisamine resin (0.050 g, 6 eq., 4.23 mmol/g) and Isocyanate resin (0.067 g, 3 eq., 1.53 mmol/g) for 18 h before the solution was filtered and the solvent was removed in vacuo to give Q6 (n=1, p=2, m=1, $R^2$=H, $R^3$=Me; $R^4$=Bu, $R^{15}$=Me).

Method Q, Step 6.

A dichloromethane solution (1.0 mL) of Q6 (n=1, p=2, m=1, $R^2$=H, $R^3$=Me; $R^4$=$^i$Bu, $R^{16}$=Me) was mixed with trifluoroacetic acid (1.0 mL) and the solution was shaken for 2 h before it was concentrated. Diethyl ether (0.5 mL) was added and then concentrated in vacuo to give a residue, which was was purified on a Prep LCMS unit to give Q7 (=1, p=2, m=1, $R^2$=H, $R_3$=Me; $R_4$=iBu, $R_{15}$=Me). NMR (CDCl$_3$): δ 8.38, br, 2H; δ 4.56, m, 1H; δ 3.79, m, 1H; δ 3.57, m, 2H, δ 2.99, m, 1H, δ 2.48, m, 1H, δ 2.04, s, 3H, δ 1.95, m, 1H, δ 1.5-1.8, m, 5H; δ 1.5, s, 3H, 1.25, m, 2H; δ 0.95, m, 3H; δ 0.85, m, 3H. ES_LCMS (m/e) 309.17.

The following compounds were prepared using similar methods:

| # | Structure | MW | Obs. m/e |
|---|---|---|---|
| 971 | 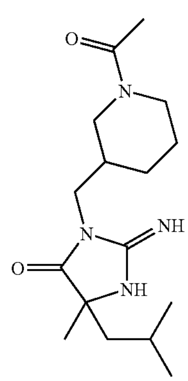 | 308 | 309 |

-continued

| # | Structure | MW | Obs. m/e |
|---|---|---|---|
| 972 | 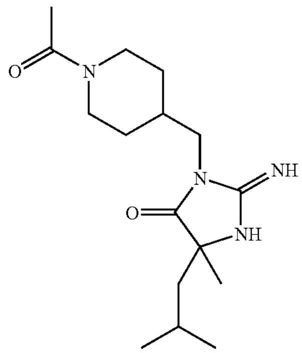 | 308 | 309 |
| 973 | 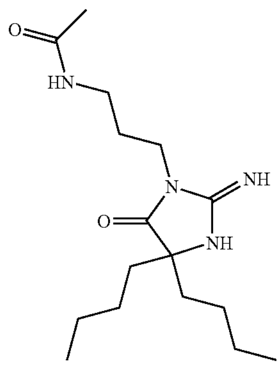 | 310 | 311 |
| 974 | 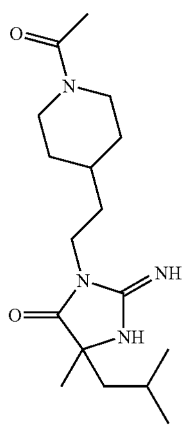 | 322 | 323 |
| 975 | 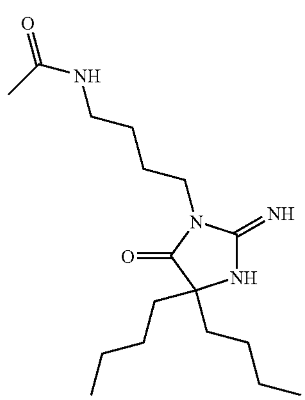 | 324 | 325 |

-continued

| # | Structure | MW | Obs. m/e |
|---|---|---|---|
| 976 | 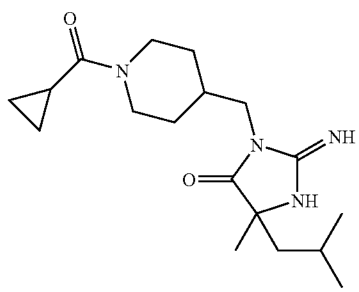 | 334 | 335 |
| 977 | 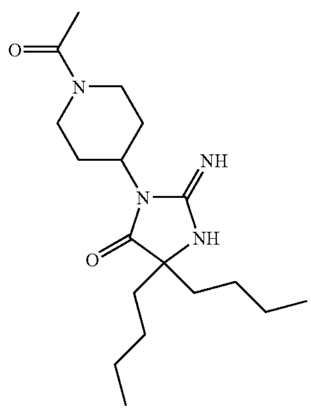 | 336 | 337 |
| 978 | 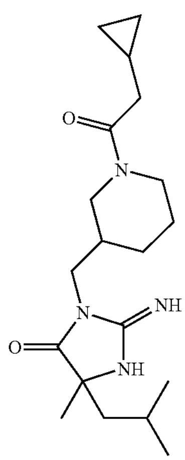 | 348 | 349 |
| 979 | 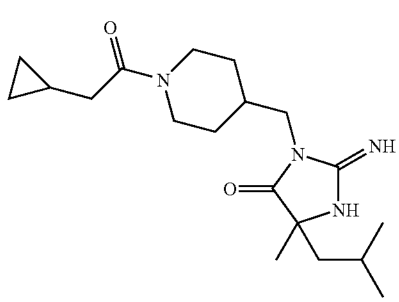 | 348 | 349 |

-continued

| # | Structure | MW | Obs. m/e |
|---|---|---|---|
| 980 | 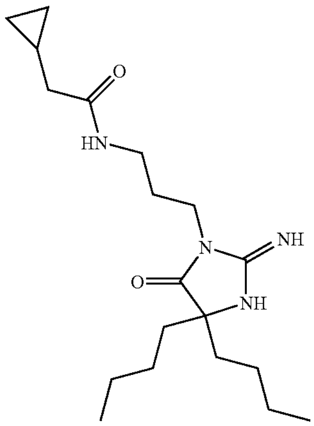 | 0 | 351 |
| 981 | 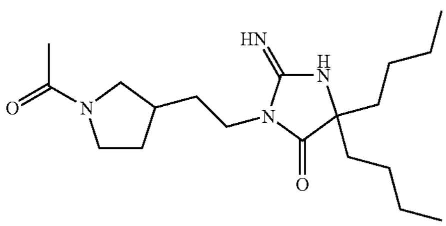 | 350 | 351 |
| 982 | 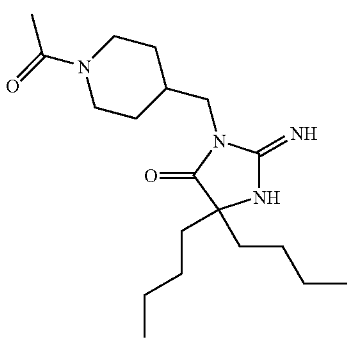 | 350 | 351 |
| 983 | 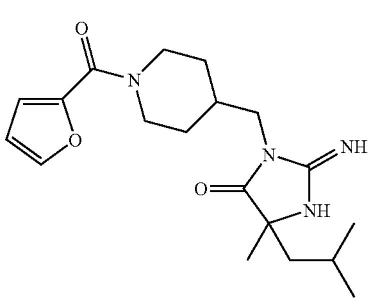 | 360 | 361 |

-continued

| # | Structure | MW | Obs. m/e |
|---|---|---|---|
| 984 | 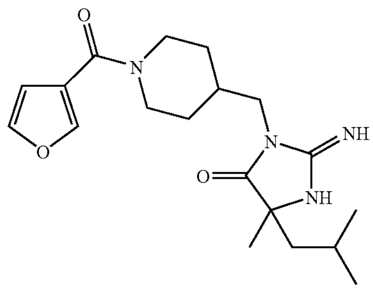 | 360 | 361 |
| 985 | 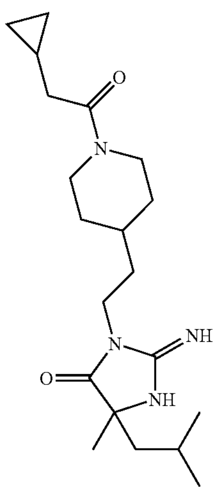 | 362 | 363 |
| 986 | 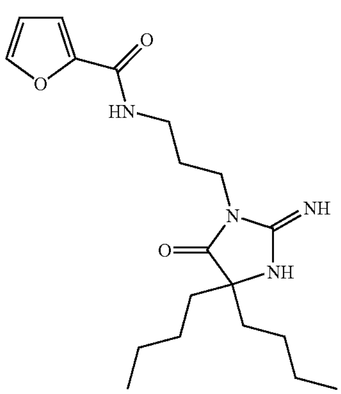 | 362 | 363 |

-continued

| # | Structure | MW | Obs. m/e |
|---|---|---|---|
| 987 | 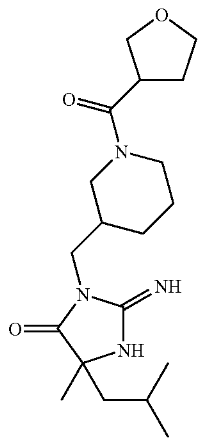 | 364 | 365 |
| 988 | 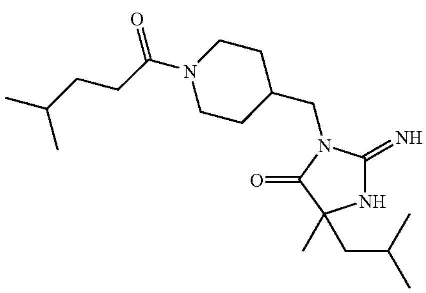 | 364 | 365 |
| 989 | 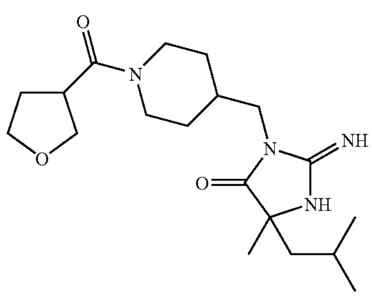 | 364 | 365 |
| 990 | 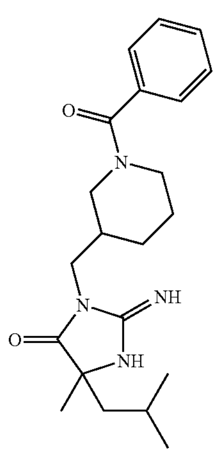 | 370 | 371 |

-continued

| # | Structure | MW | Obs. m/e |
|---|---|---|---|
| 991 | 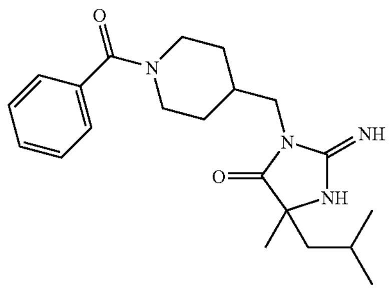 | 370 | 371 |
| 992 | 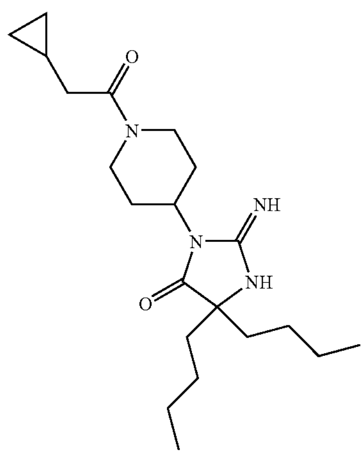 | 376 | 377 |
| 993 | 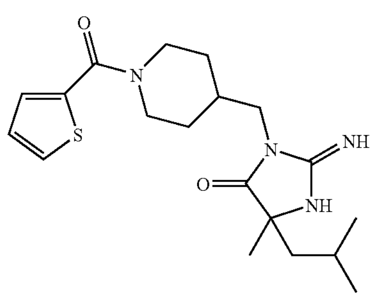 | 376 | 377 |
| 994 | 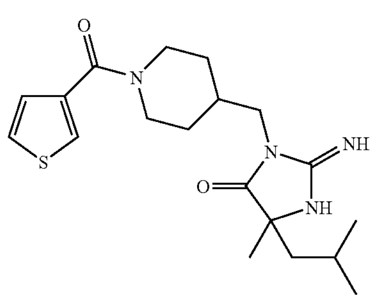 | 376 | 377 |

-continued
| # | Structure | MW | Obs. m/e |
|---|---|---|---|
| 995 | 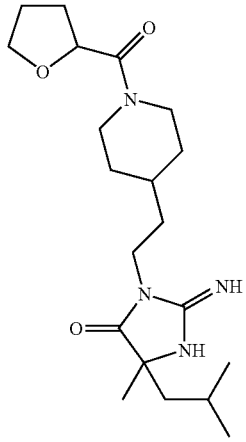 | 378 | 379 |
| 996 | 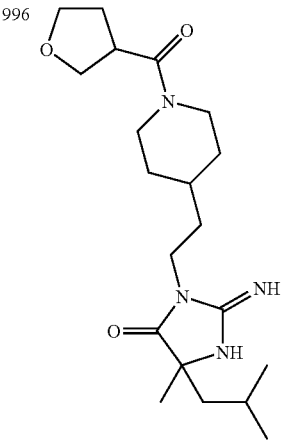 | 378 | 379 |
| 997 | 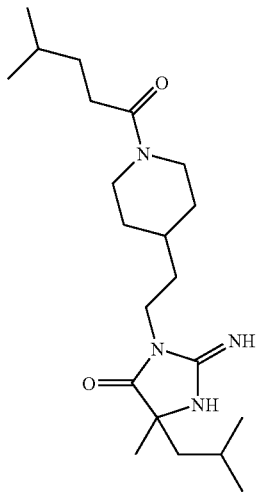 | 378 | 379 |

|  #  | Structure | MW | Obs. m/e |
|-----|-----------|-----|----------|
| 998 | 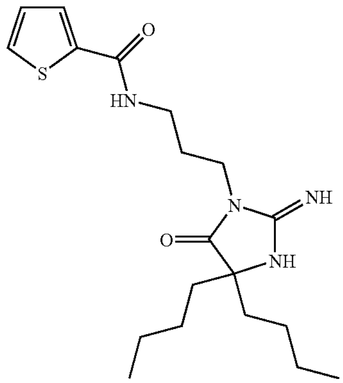 | 378 | 379 |
| 999 | 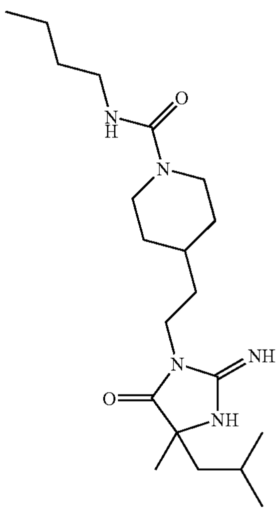 | 379 | 380 |
| 1000 | 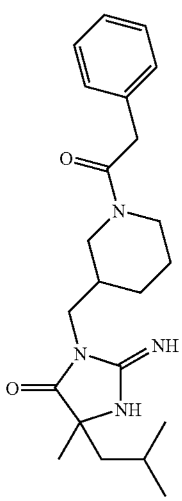 | 384 | 385 |

-continued
| # | Structure | MW | Obs. m/e |
|---|---|---|---|
| 1001 | 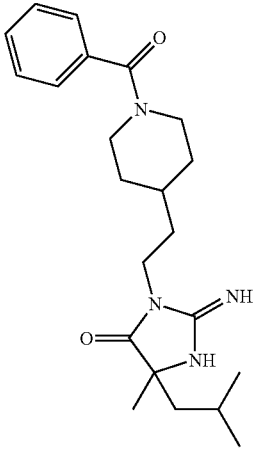 | 384 | 385 |
| 1002 | 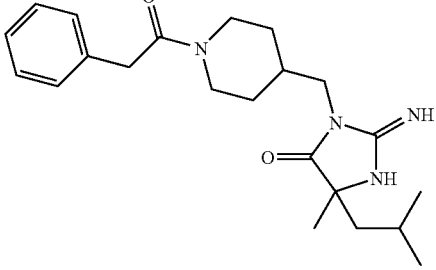 | 384 | 385 |
| 1003 | 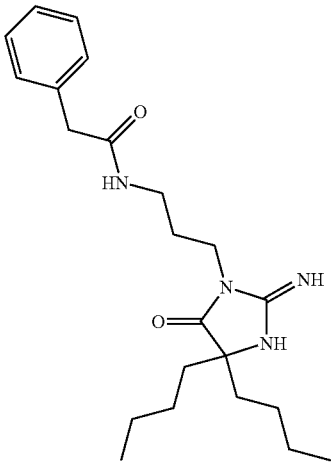 | 386 | 387 |

-continued

| # | Structure | MW | Obs. m/e |
|---|---|---|---|
| 1004 | 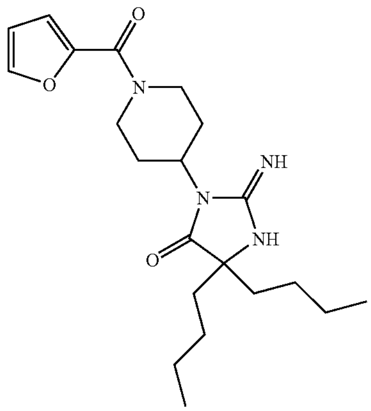 | 388 | 389 |
| 1005 | 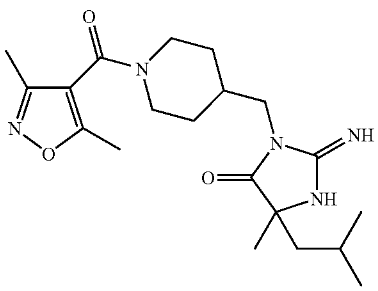 | 389 | 390 |
| 1006 | 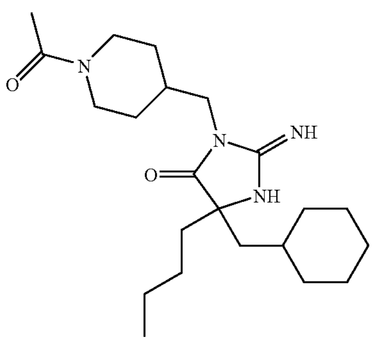 | 390 | 391 |
| 1007 | 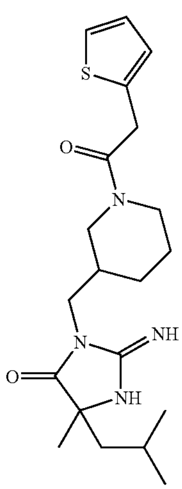 | 390 | 391 |

-continued

| # | Structure | MW | Obs. m/e |
|---|---|---|---|
| 1008 | 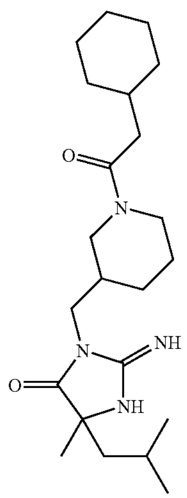 | 390 | 391 |
| 1009 | 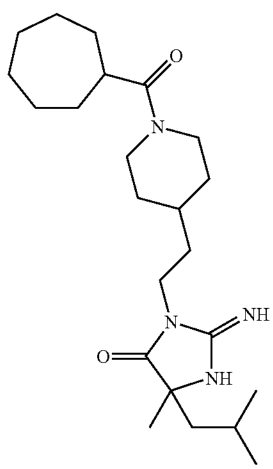 | 390 | 391 |
| 1010 | 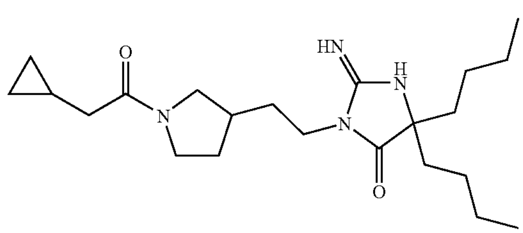 | 390 | 391 |
| 1011 | 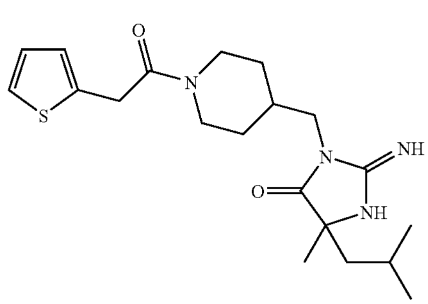 | 390 | 391 |

-continued

| # | Structure | MW | Obs. m/e |
|---|---|---|---|
| 1012 | 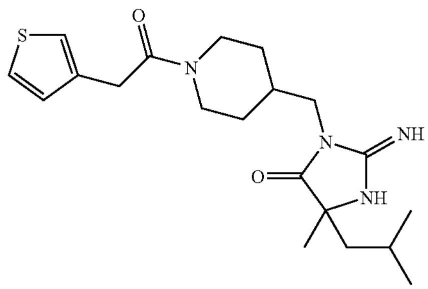 | 390 | 391 |
| 1013 | 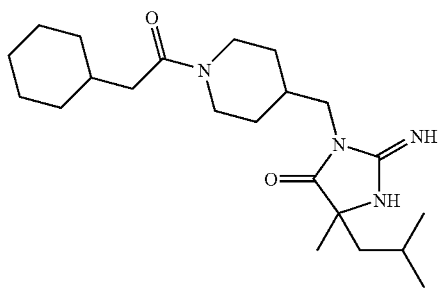 | 390 | 391 |
| 1014 | 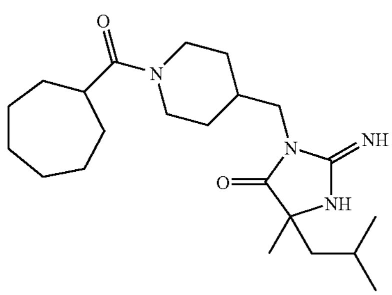 | 390 | 391 |
| 1015 | 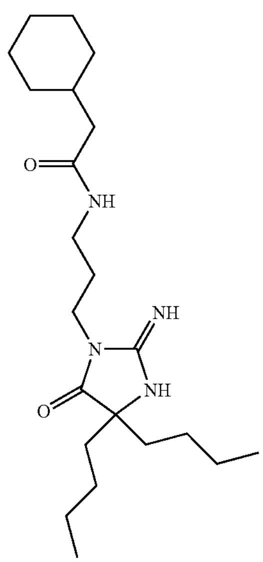 | 392 | 393 |

-continued

| # | Structure | MW | Obs. m/e |
|---|---|---|---|
| 1016 | 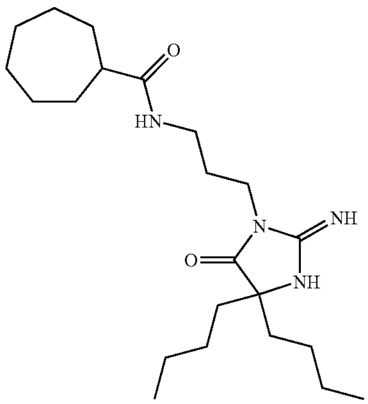 | 392 | 393 |
| 1017 | 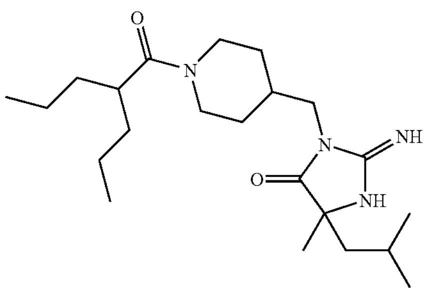 | 392 | 393 |
| 1018 | 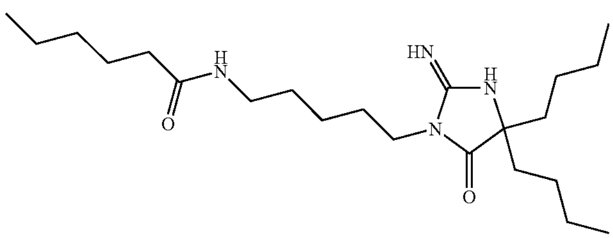 | 394 | 395 |
| 1019 | 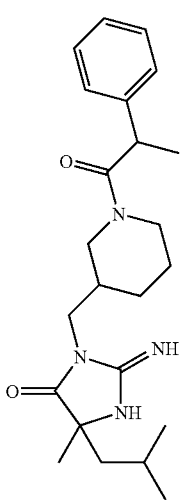 | 398 | 399 |

-continued
| # | Structure | MW | Obs. m/e |
|---|---|---|---|
| 1020 | 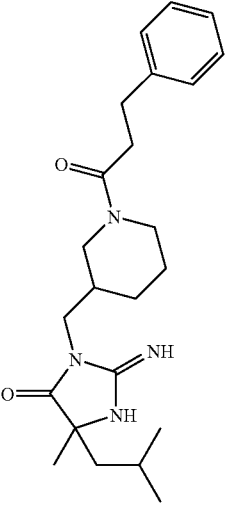 | 398 | 399 |
| 1021 | 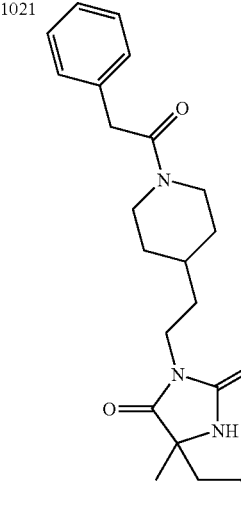 | 398 | 399 |
| 1022 | 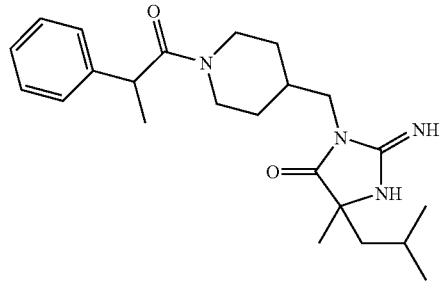 | 398 | 399 |

-continued
| # | Structure | MW | Obs. m/e |
|---|---|---|---|
| 1023 | 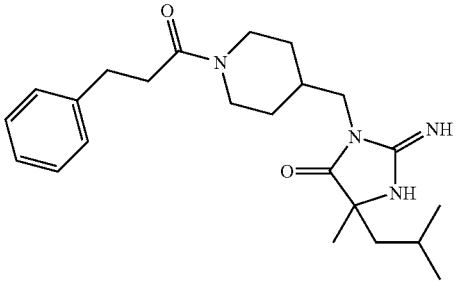 | 398 | 399 |
| 1024 | 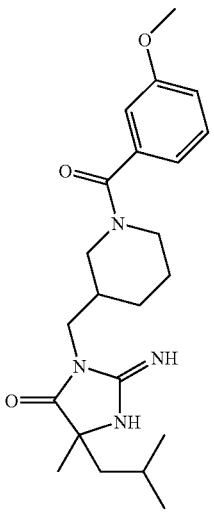 | 400 | 401 |
| 1025 | 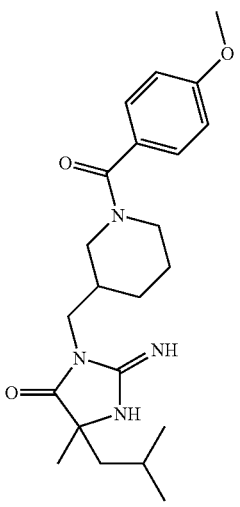 | 400 | 401 |

-continued

| # | Structure | MW | Obs. m/e |
|---|---|---|---|
| 1025 | 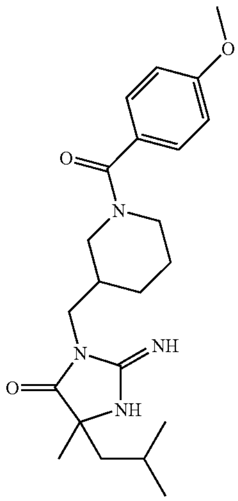 | 400 | 401 |
| 1026 | 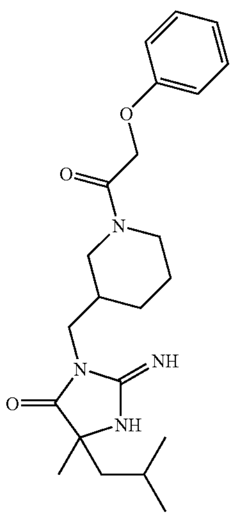 | 400 | 401 |
| 1027 | 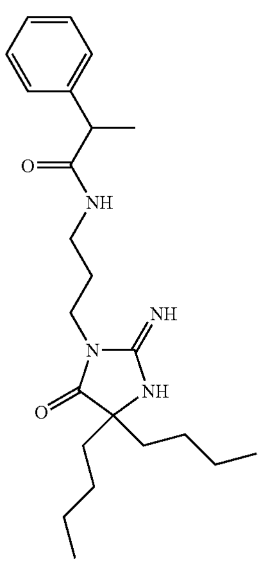 | 400 | 401 |

| # | Structure | MW | Obs. m/e |
|---|---|---|---|
| 1028 | 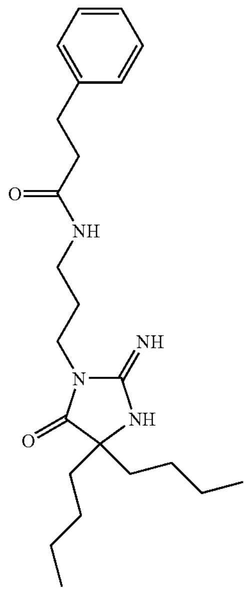 | 400 | 401 |
| 1029 | 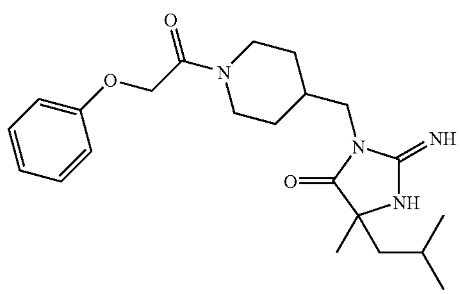 | 400 | 401 |
| 1030 | 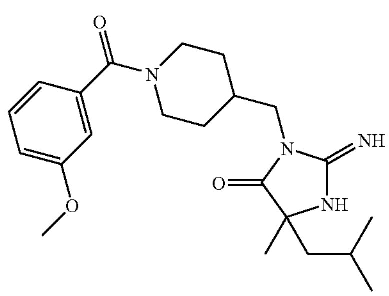 | 400 | 401 |
| 1031 | 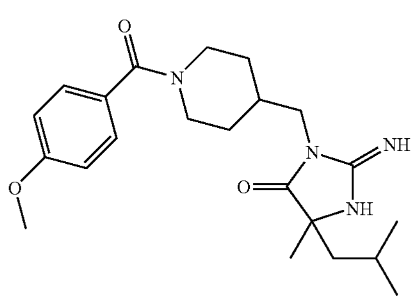 | 400 | 401 |

-continued
| # | Structure | MW | Obs. m/e |
|---|---|---|---|
| 1032 | 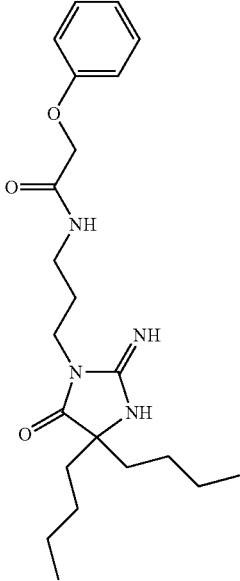 | 402 | 403 |
| 1033 | 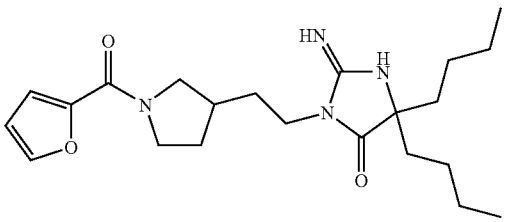 | 402 | 403 |
| 1034 | 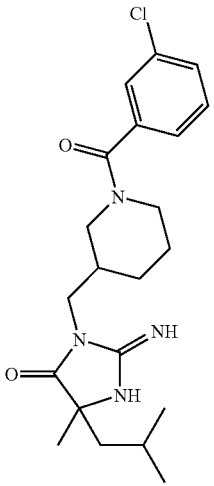 | 404 | 405 |

-continued

| # | Structure | MW | Obs. m/e |
|---|---|---|---|
| 1035 | 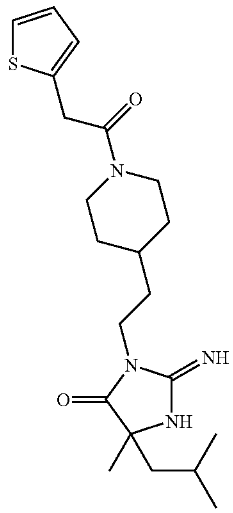 | 404 | 404 |
| 1036 | 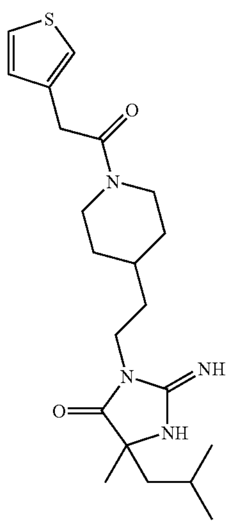 | 404 | 405 |
| 1037 | 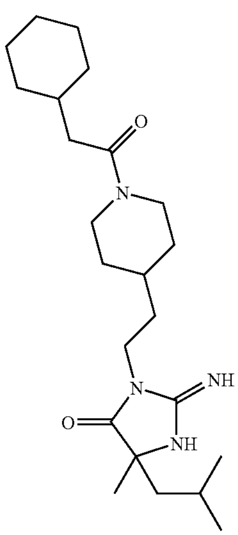 | 404 | 405 |

-continued

| # | Structure | MW | Obs. m/e |
|---|---|---|---|
| 1038 | 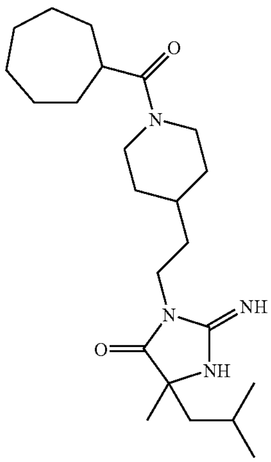 | 404 | 405 |
| 1039 | 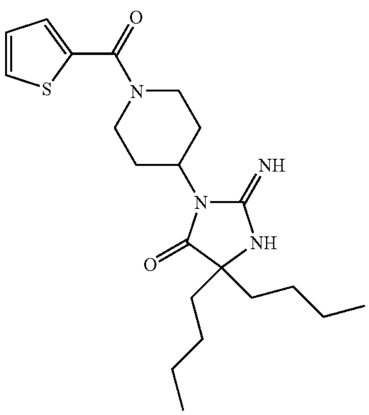 | 404 | 405 |
| 1040 | 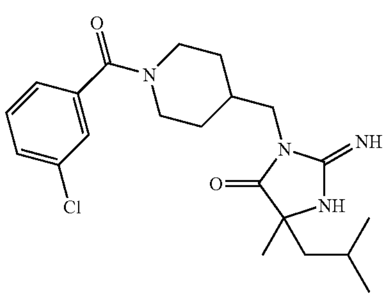 | 404 | 405 |
| 1041 | 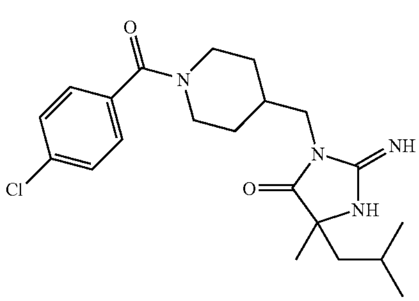 | 404 | 405 |

-continued

| # | Structure | MW | Obs. m/e |
|---|---|---|---|
| 1042 | 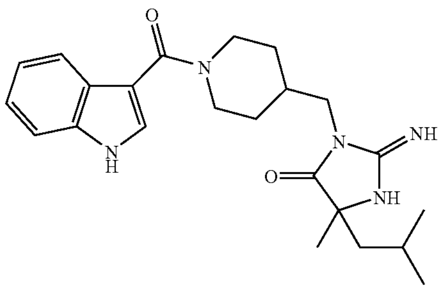 | 409 | 410 |
| 1043 | 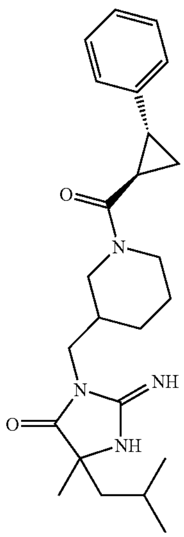 | 410 | 411 |
| 1044 | 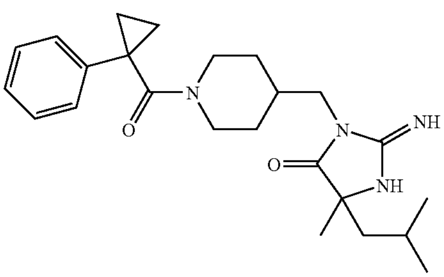 | 0 | 411 |
| 1045 | 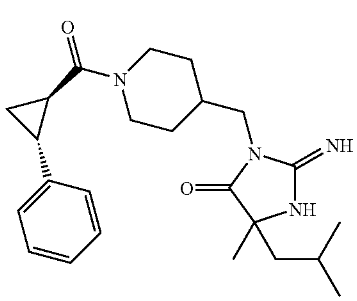 | 410 | 411 |

-continued

| # | Structure | MW | Obs. m/e |
|---|---|---|---|
| 1046 | 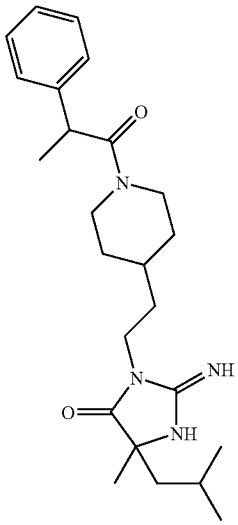 | 412 | 413 |
| 1047 | 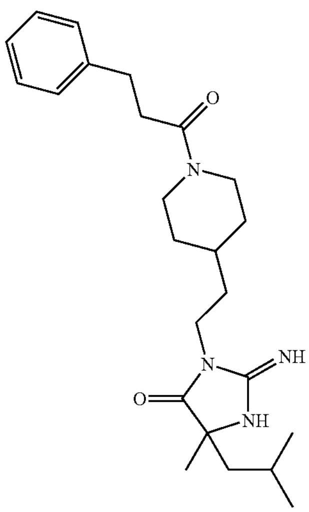 | 412 | 413 |
| 1048 | 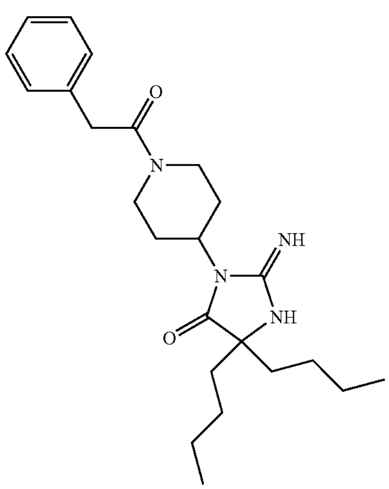 | 412 | 413 |

| # | Structure | MW | Obs. m/e |
|---|---|---|---|
| 1049 | 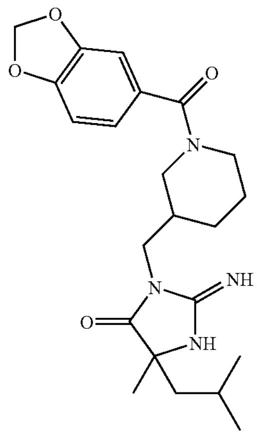 | 414 | 415 |
| 1050 | 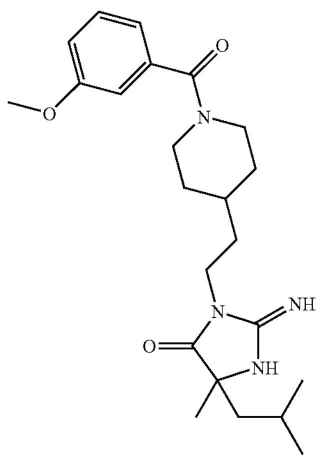 | 414 | 415 |
| 1051 | 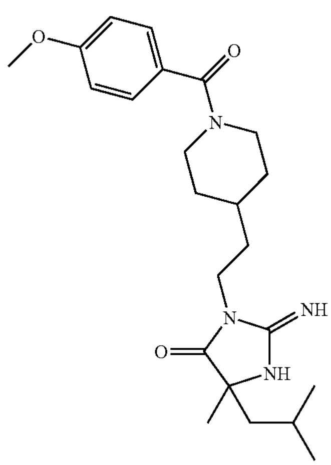 | 414 | 415 |

-continued

| # | Structure | MW | Obs. m/e |
|---|---|---|---|
| 1052 | 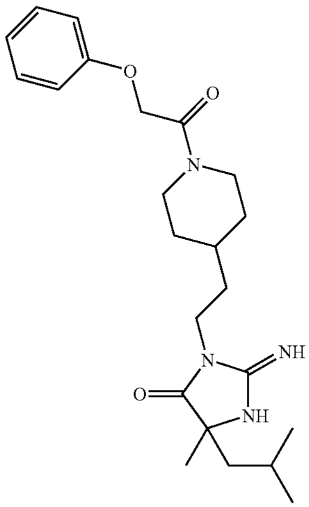 | 414 | 415 |
| 1053 | 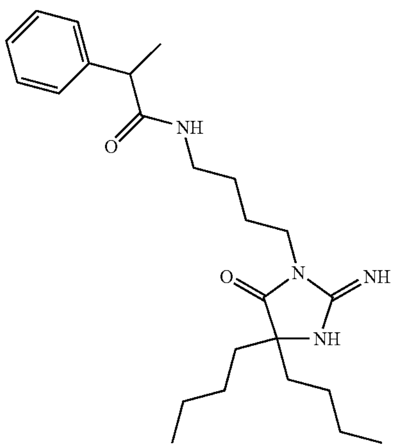 | 414 | 415 |
| 1054 | 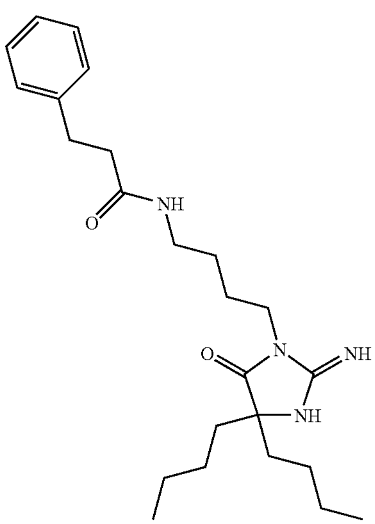 | 414 | 415 |

-continued

| # | Structure | MW | Obs. m/e |
|---|---|---|---|
| 1055 | 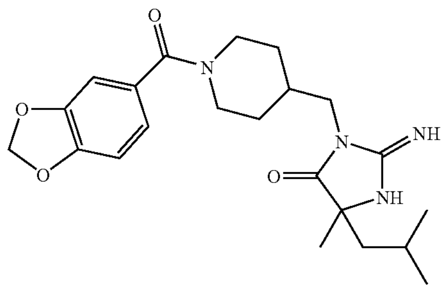 | 414 | 415 |
| 1056 | 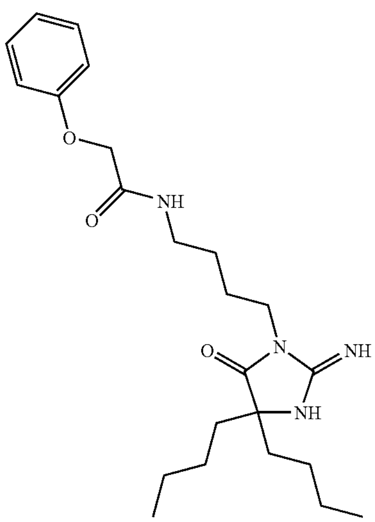 | 416 | 417 |
| 1057 | 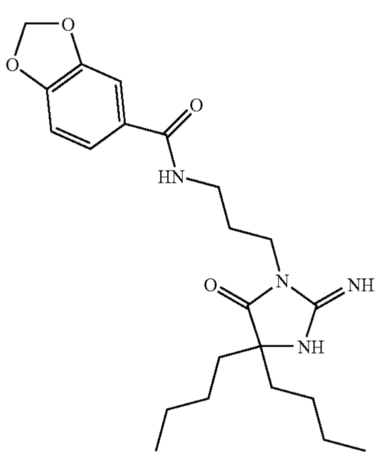 | 416 | 417 |

-continued
| # | Structure | MW | Obs. m/e |
|---|---|---|---|
| 1058 | 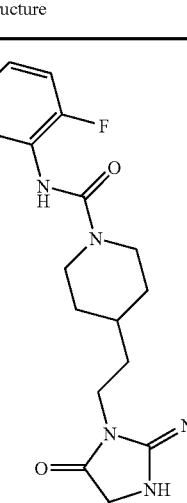 | 417 | 418 |
| 1059 | 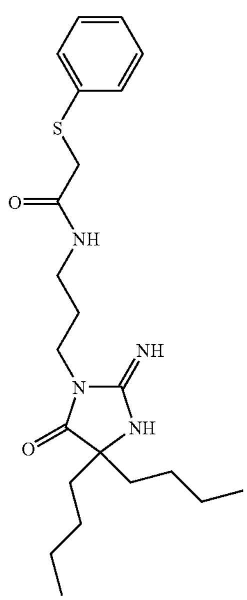 | 418 | 419 |

-continued
| # | Structure | MW | Obs. m/e |
|---|---|---|---|
| 1060 | 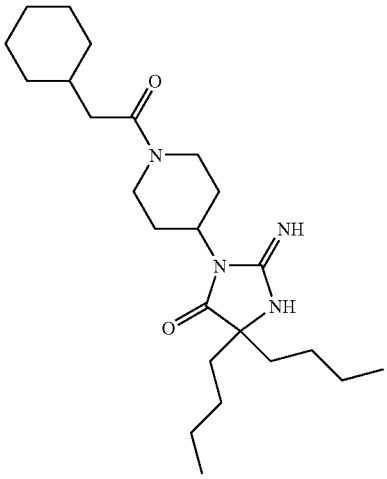 | 418 | 419 |
| 1061 | 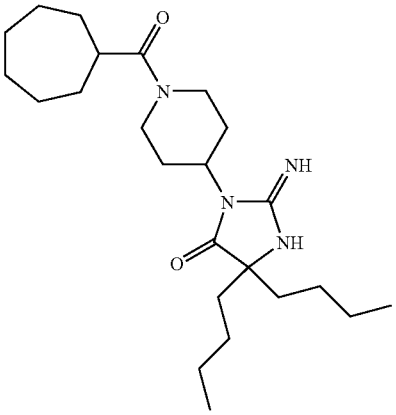 | 418 | 419 |
| 1062 | 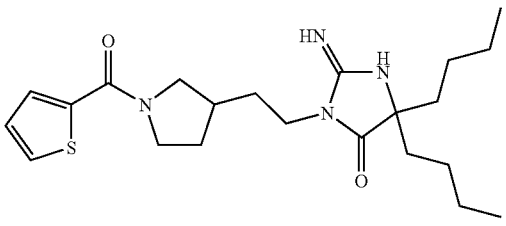 | 418 | 419 |
| 1063 | 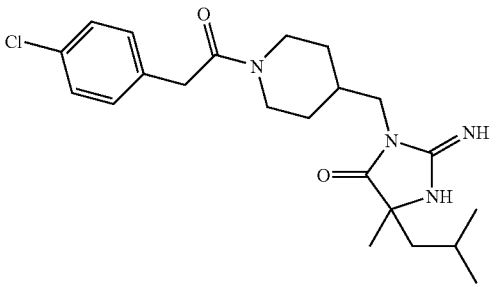 | 418 | 419 |

-continued
| # | Structure | MW | Obs. m/e |
|---|---|---|---|
| 1064 | 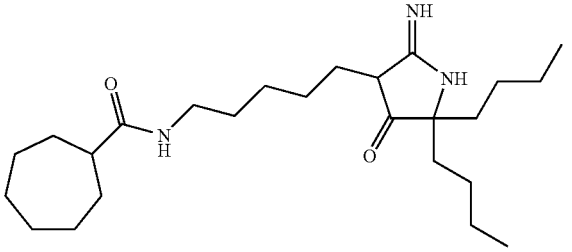 | 420 | 421 |
| 1065 | 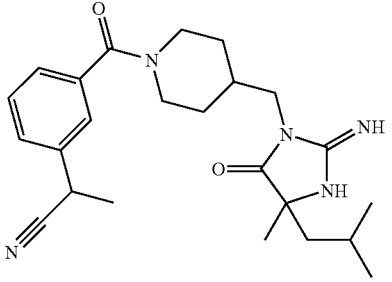 | 423 | 424 |
| 1066 | 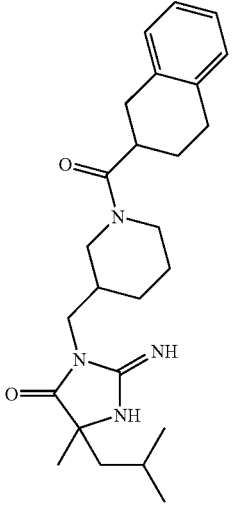 | 424 | 415 |
| 1067 | 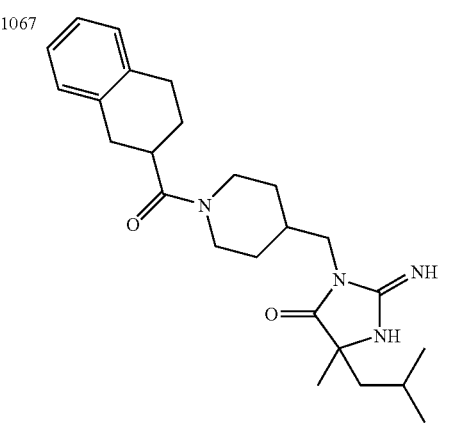 | 424 | 425 |

-continued

| # | Structure | MW | Obs. m/e |
|---|---|---|---|
| 1068 | 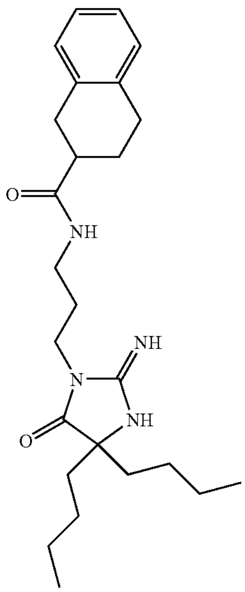 | 426 | 427 |
| 1069 | 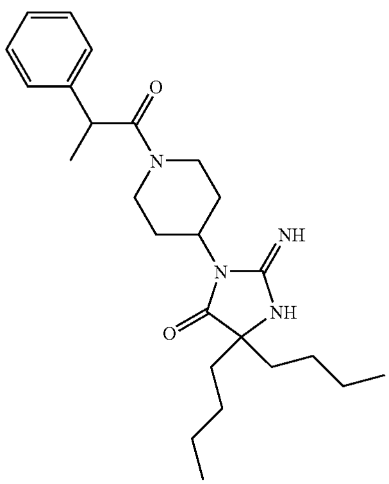 | 426 | 427 |
| 1070 | 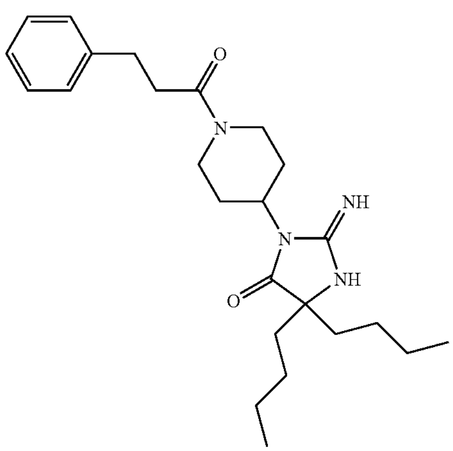 | 426 | 427 |

-continued

| # | Structure | MW | Obs. m/e |
|---|---|---|---|
| 1071 | 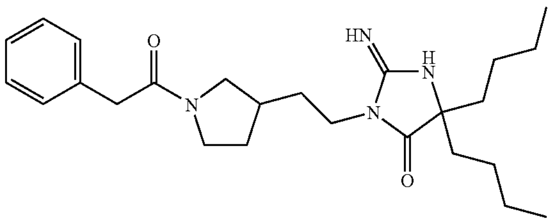 | 426 | 427 |
| 1072 | 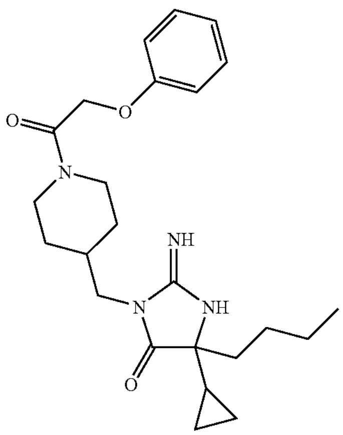 | 426 | 427 |
| 1073 | 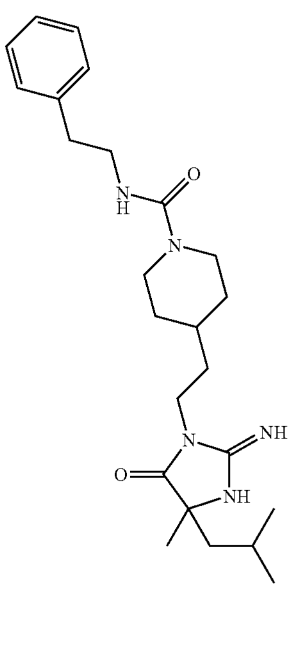 | 427 | 428 |

-continued
| # | Structure | MW | Obs. m/e |
|---|---|---|---|
| 1074 | 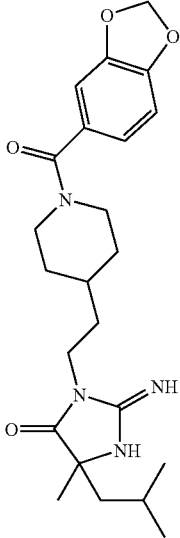 | 428 | 429 |
| 1075 | 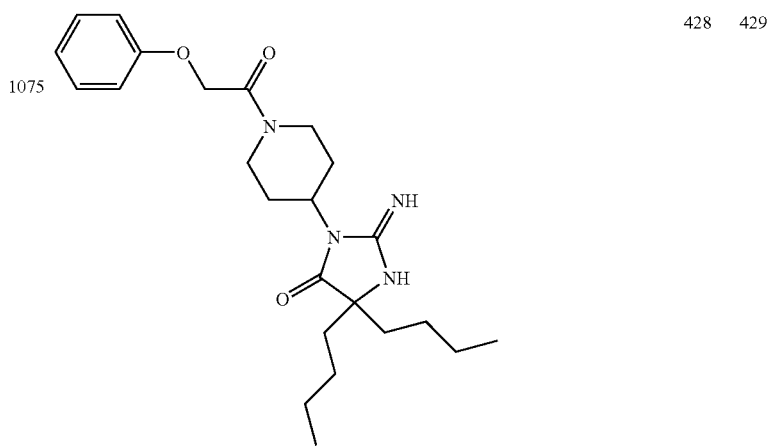 | 428 | 429 |
| 1076 | 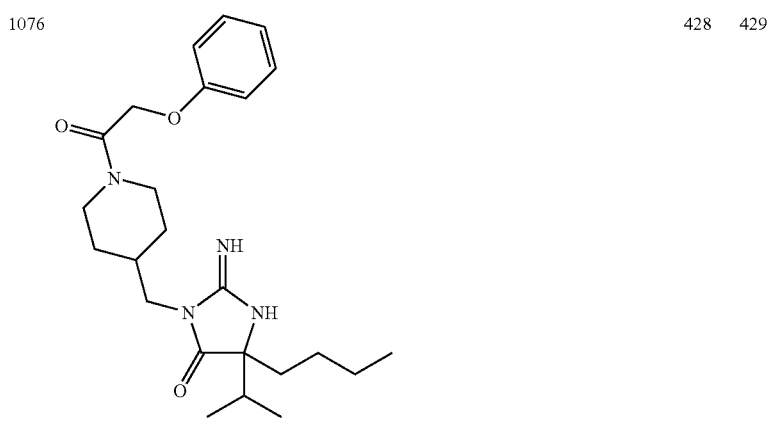 | 428 | 429 |

-continued

| # | Structure | MW | Obs. m/e |
|---|---|---|---|
| 1077 | 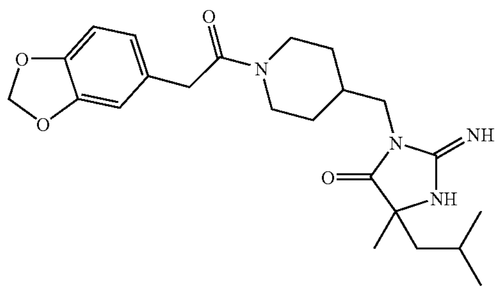 | 428 | 429 |
| 1078 | 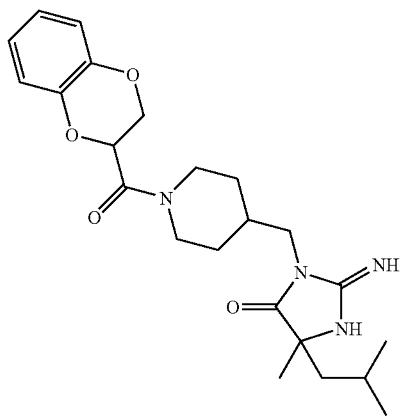 | 428 | 429 |
| 1079 | 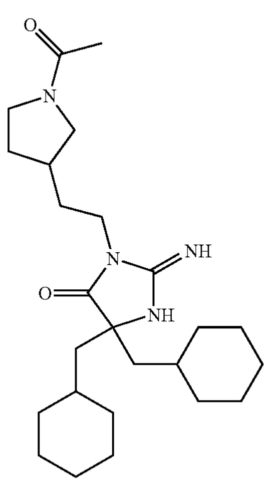 | 430 | 431 |

| # | Structure | MW | Obs. m/e |
|---|---|---|---|
| 1080 | 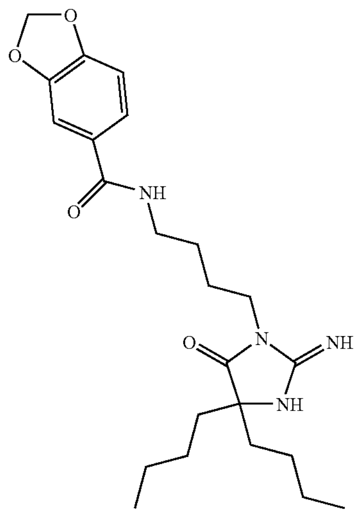 | 430 | 431 |
| 1081 | 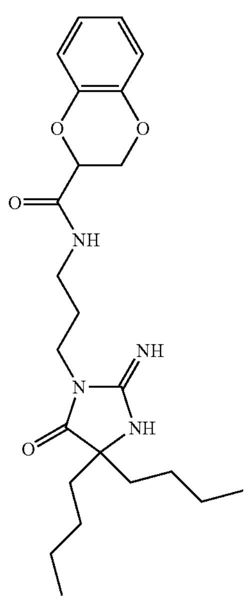 | 430 | 431 |

-continued
| # | Structure | MW | Obs. m/e |
|---|---|---|---|
| 1082 | 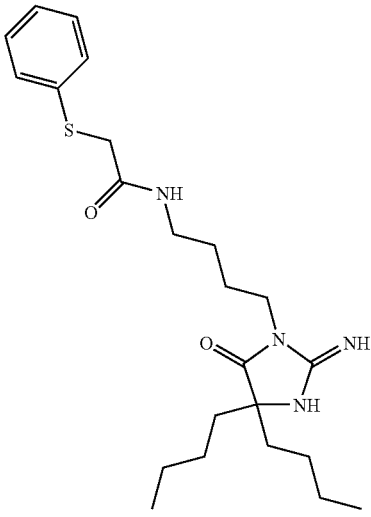 | 432 | 433 |
| 1083 | 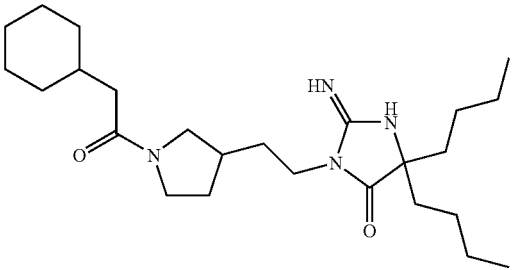 | 432 | 433 |
| 1084 | 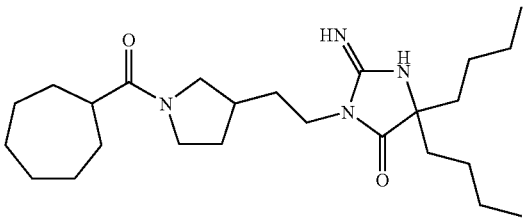 | 432 | 433 |
| 1085 | 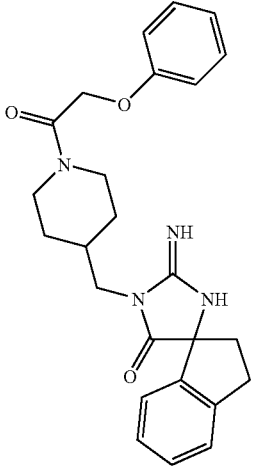 | 432 | 433 |

-continued

| # | Structure | MW | Obs. m/e |
|---|---|---|---|
| 1086 | 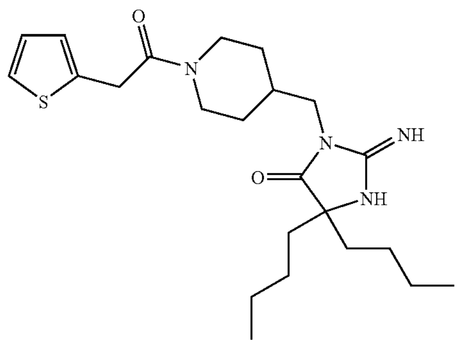 | 432 | 433 |
| 1087 | 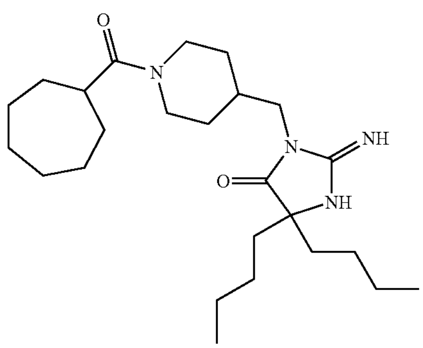 | 432 | 433 |
| 1088 | 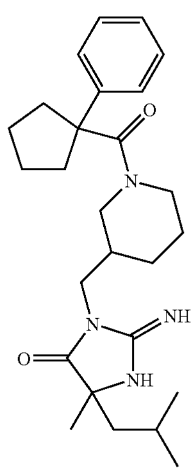 | 438 | 439 |

-continued

| # | Structure | MW | Obs. m/e |
|---|---|---|---|
| 1089 | 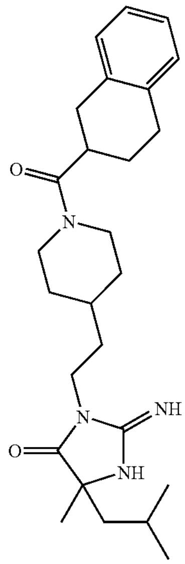 | 438 | 439 |
| 1090 | 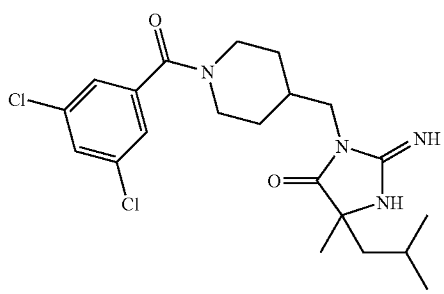 | 438 | 439 |
| 1091 | 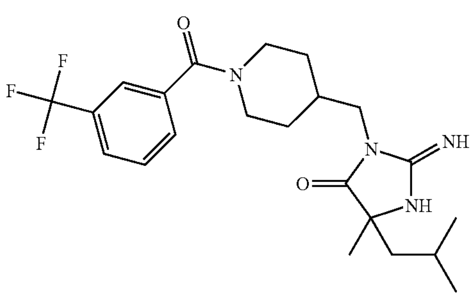 | 438 | 439 |
| 1092 | 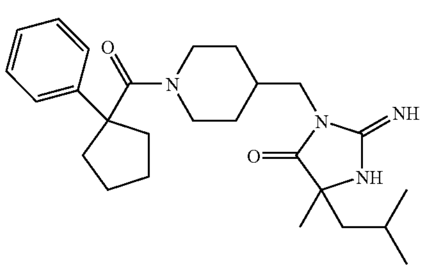 | 438 | 439 |

-continued

| # | Structure | MW | Obs. m/e |
|---|---|---|---|
| 1093 | 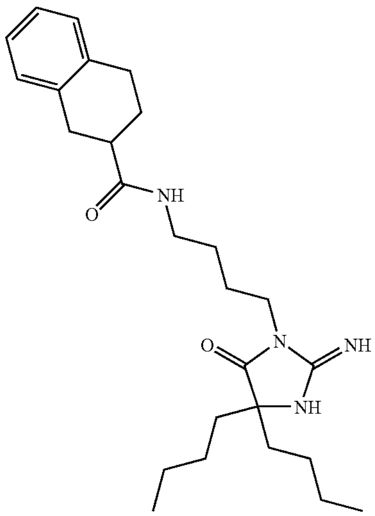 | 440 | 441 |
| 1094 | 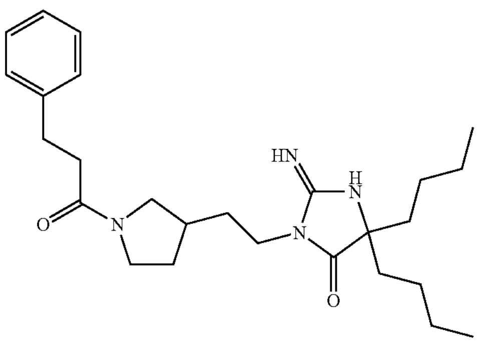 | 440 | 441 |
| 1095 | 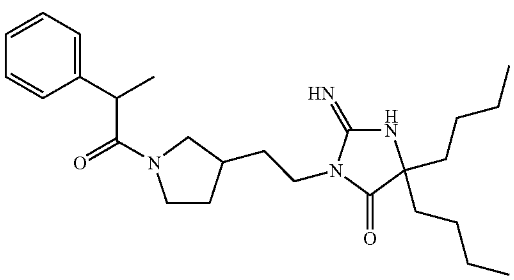 | 440 | 441 |
| 1096 | 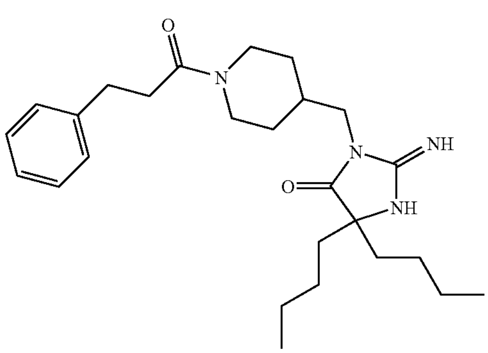 | 440 | 441 |

-continued
| # | Structure | MW | Obs. m/e |
|---|---|---|---|
| 1097 | 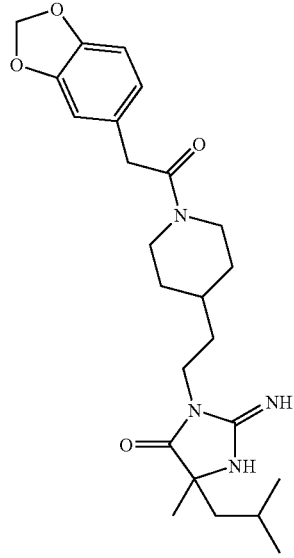 | 442 | 443 |
| 1098 | 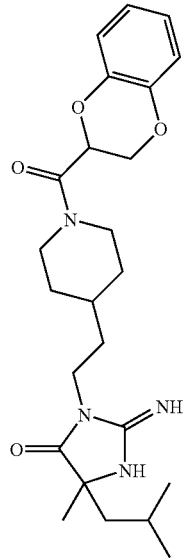 | 442 | 443 |
| 1099 | 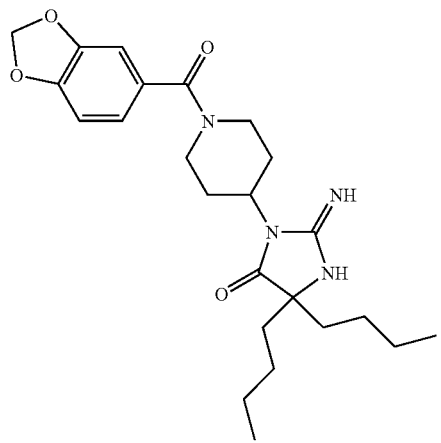 | 442 | 443 |

-continued
| # | Structure | MW | Obs. m/e |
|---|---|---|---|
| 1100 | 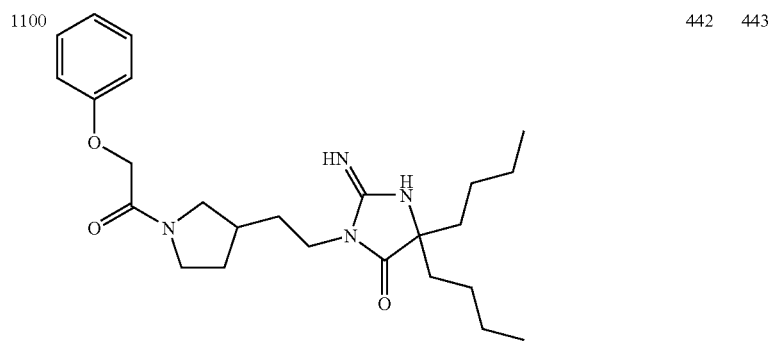 | 442 | 443 |
| 1101 | 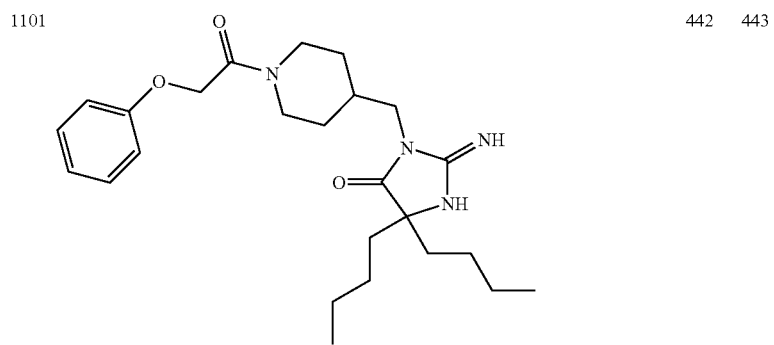 | 442 | 443 |
| 1102 | 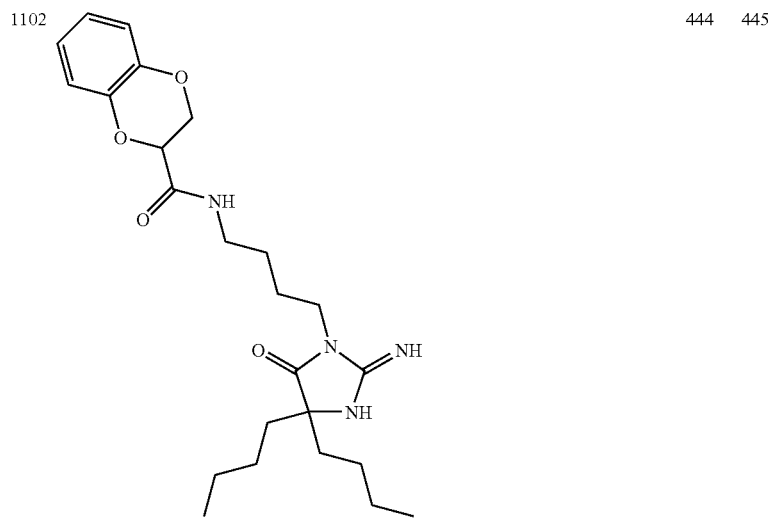 | 444 | 445 |

-continued
| # | Structure | MW | Obs. m/e |
|---|---|---|---|
| 1103 | 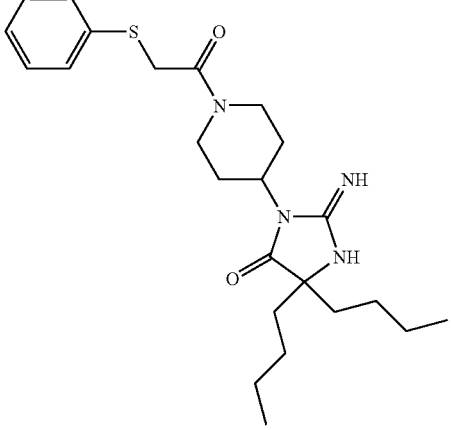 | 444 | 445 |
| 1104 | 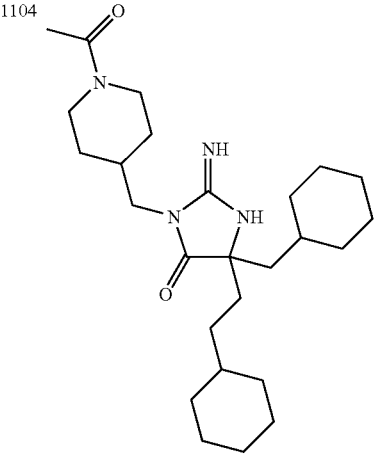 | 444 | 445 |
| 1105 | 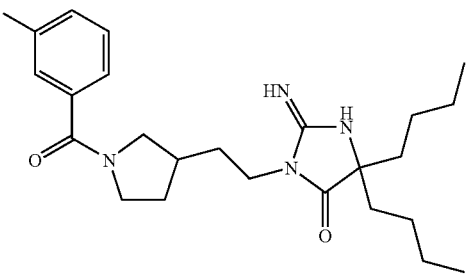 | 446 | 447 |
| 1106 | 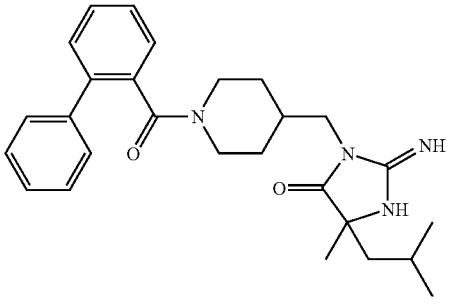 | 446 | 447 |

-continued
| # | Structure | MW | Obs. m/e |
|---|---|---|---|
| 1107 | 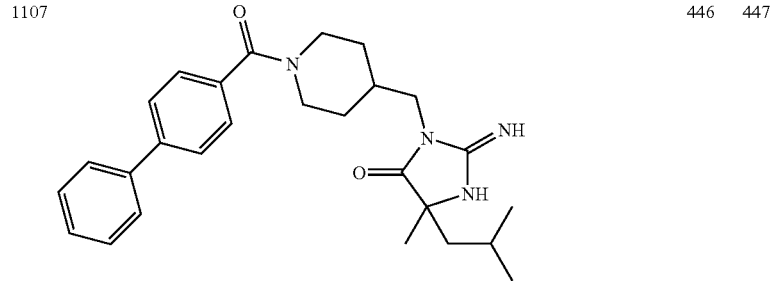 | 446 | 447 |
| 1108 | 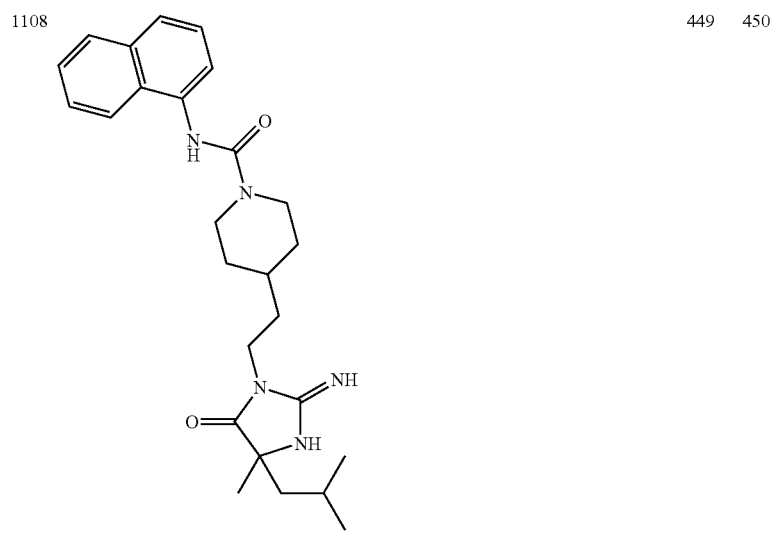 | 449 | 450 |
| 1109 | 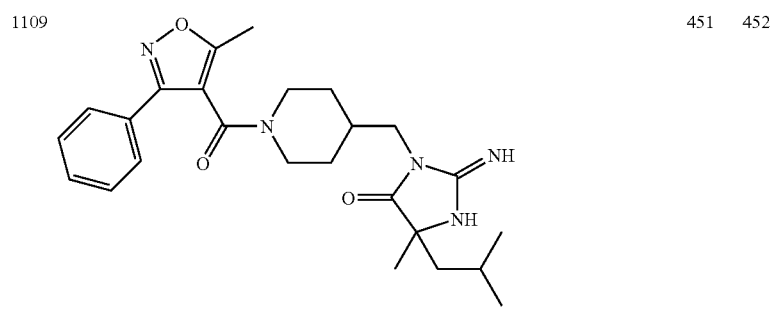 | 451 | 452 |

-continued

| # | Structure | MW | Obs. m/e |
|---|---|---|---|
| 1110 | 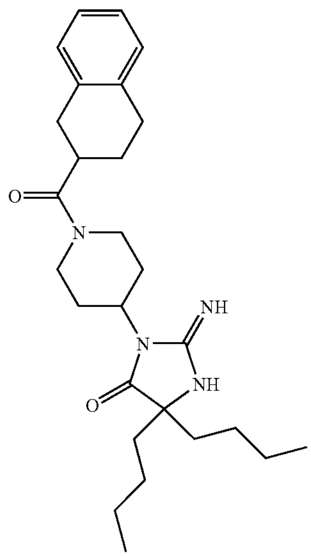 | 452 | 453 |
| 1111 | 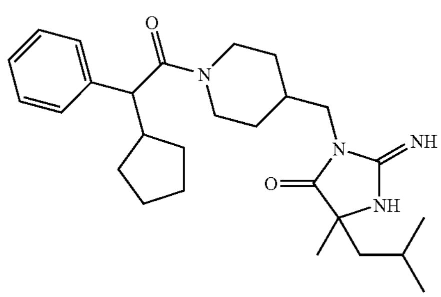 | 452 | 453 |
| 1112 | 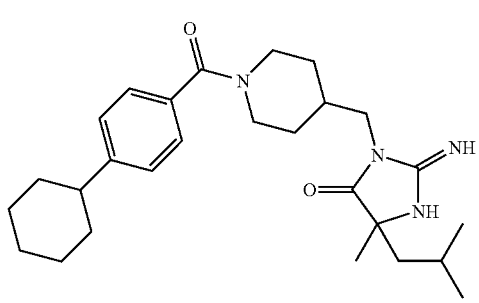 | 452 | 453 |

-continued

| # | Structure | MW | Obs. m/e |
|---|---|---|---|
| 1113 | 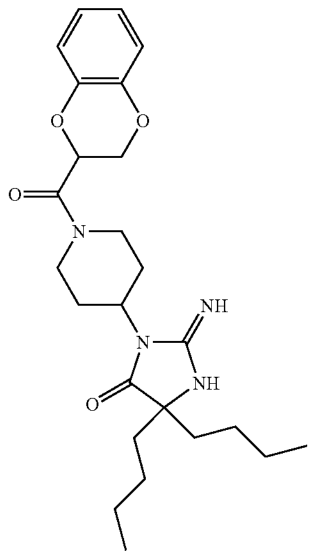 | 456 | 457 |
| 1114 | 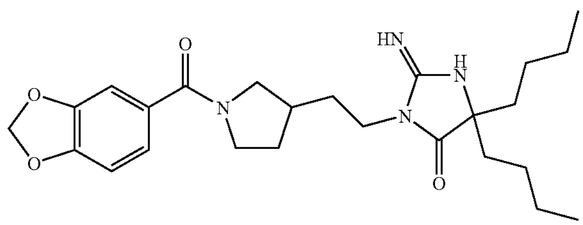 | 456 | 457 |
| 1115 | 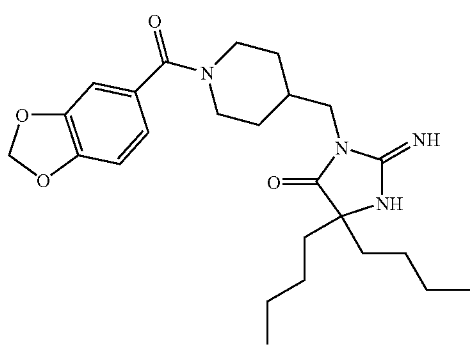 | 456 | 457 |
| 1116 | 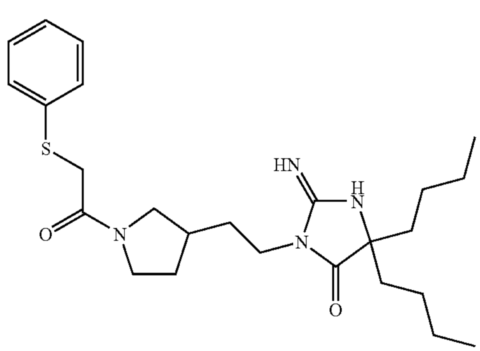 | 458 | 459 |

-continued

| # | Structure | MW | Obs. m/e |
|---|---|---|---|
| 1117 | 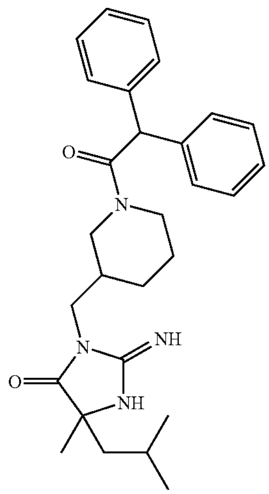 | 460 | 461 |
| 1118 | 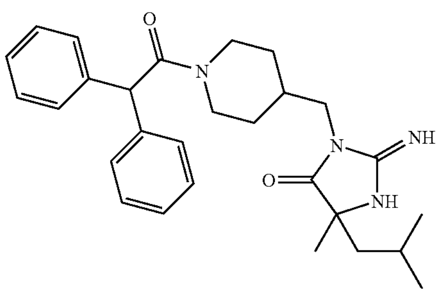 | 460 | 461 |
| 1119 | 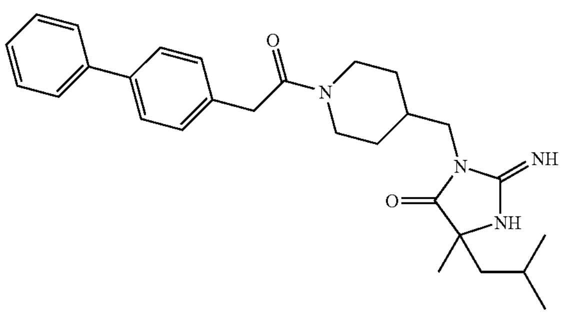 | 460 | 461 |
| 1120 | 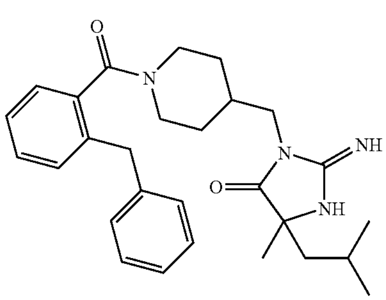 | 460 | 461 |

-continued
| # | Structure | MW | Obs. m/e |
|---|---|---|---|
| 1121 | 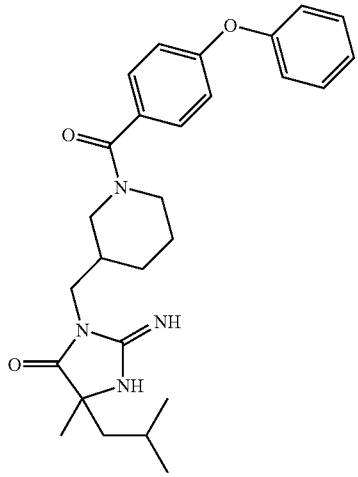 | 462 | 463 |
| 1122 | 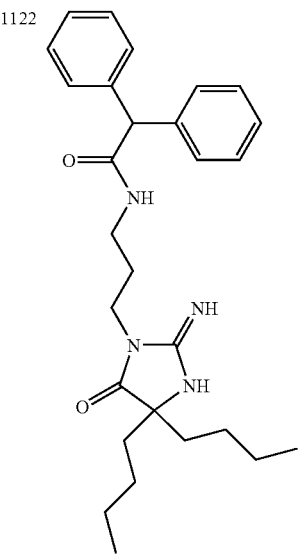 | 462 | 463 |
| 1123 | 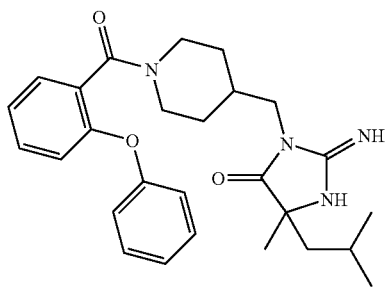 | 462 | 463 |

-continued

| # | Structure | MW | Obs. m/e |
|---|---|---|---|
| 1124 | 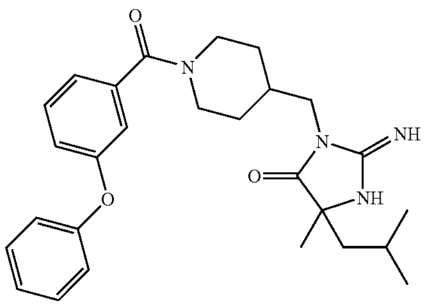 | 462 | 463 |
| 1125 | 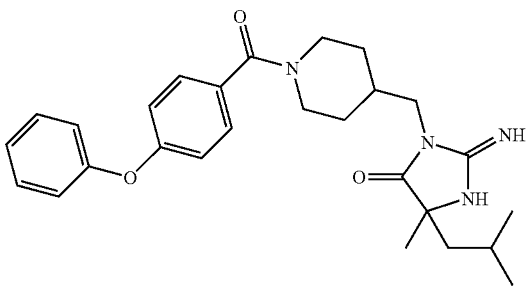 | 462 | 463 |
| 1126 | 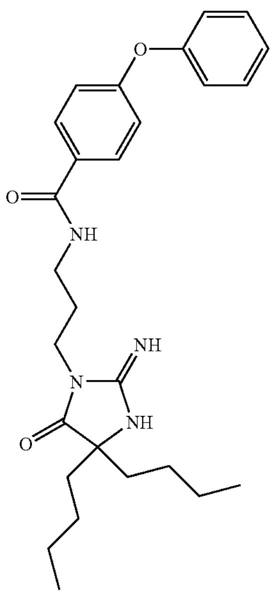 | 464 | 465 |
| 1127 | 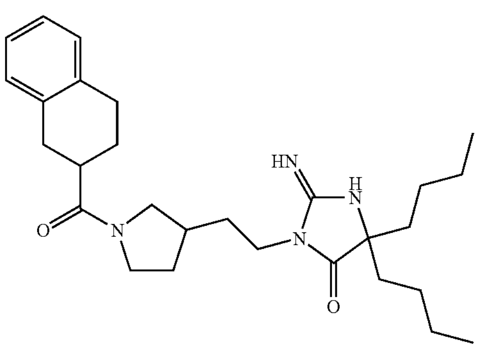 | 466 | 467 |

|   |   |   | Obs. |
|---|---|---|---|
| # | Structure | MW | m/e |
| 1128 | | 466 | 467 |
| 1129 | | 470 | 471 |
| 1130 | | 472 | 473 |

-continued
| # | Structure | MW | Obs. m/e |
|---|---|---|---|
| 1131 | 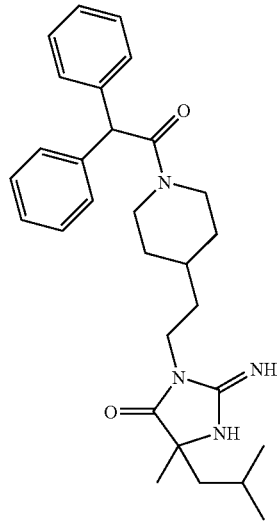 | 474 | 475 |
| 1132 | 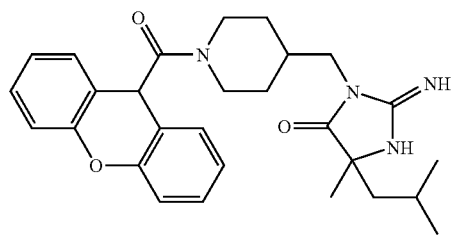 | 474 | 475 |
| 1133 | 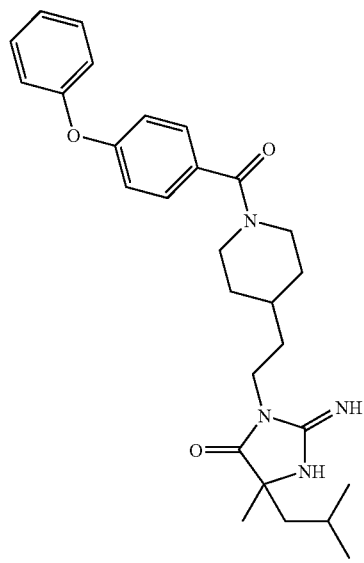 | 476 | 477 |

-continued

| # | Structure | MW | Obs. m/e |
|---|---|---|---|
| 1134 | 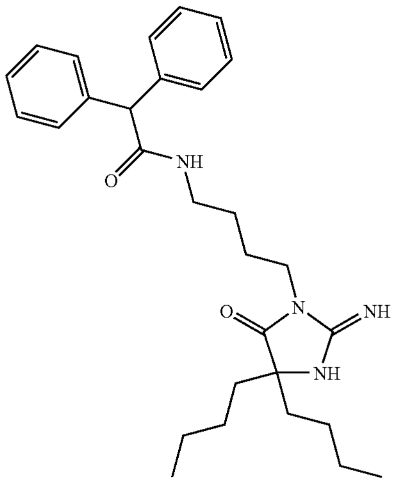 | 476 | 477 |
| 1135 | 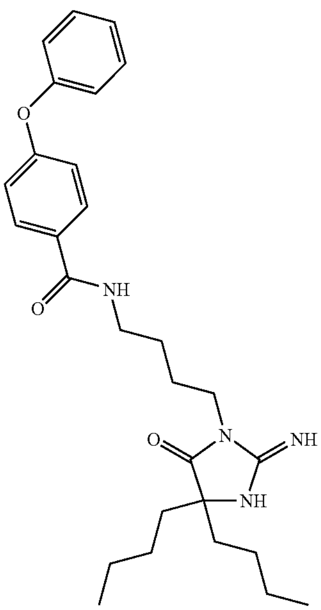 | 478 | 479 |
| 1136 | 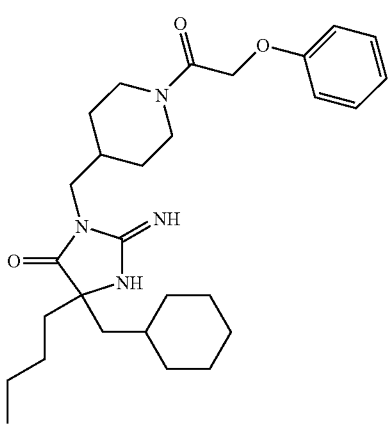 | 482 | 483 |

-continued
| # | Structure | MW | Obs. m/e |
|---|---|---|---|
| 1137 | 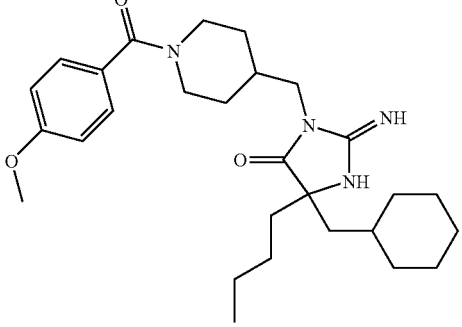 | 482 | 483 |
| 1138 | 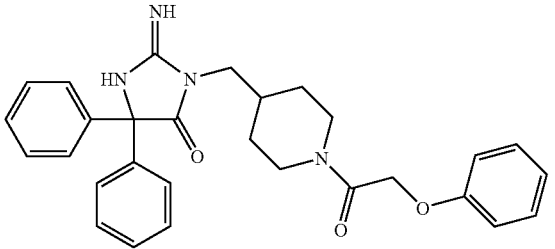 | 482 | 483 |
| 1139 | 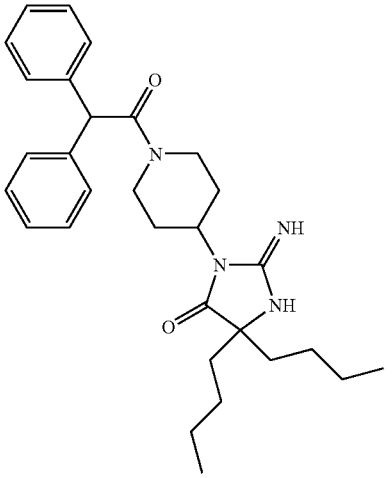 | 488 | 489 |
| 1140 | 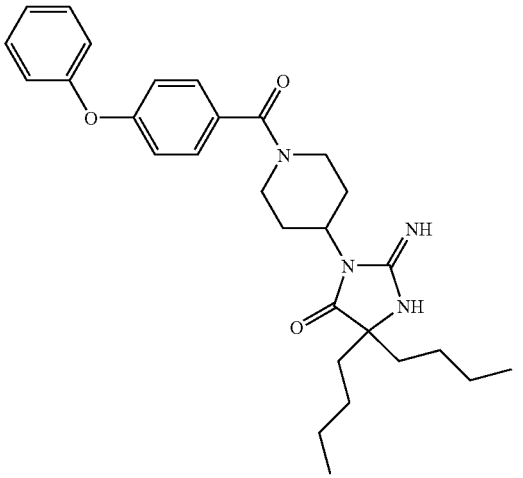 | 490 | 491 |

-continued
| # | Structure | MW | Obs. m/e |
|---|---|---|---|
| 1141 | 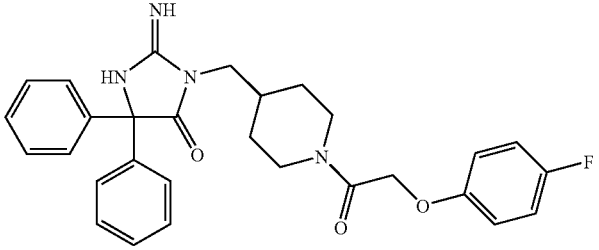 | 500 | 501 |
| 1142 | 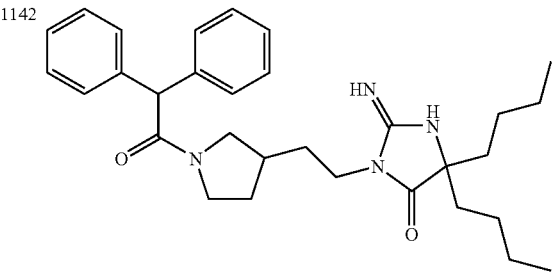 | 502 | 503 |
| 1143 | 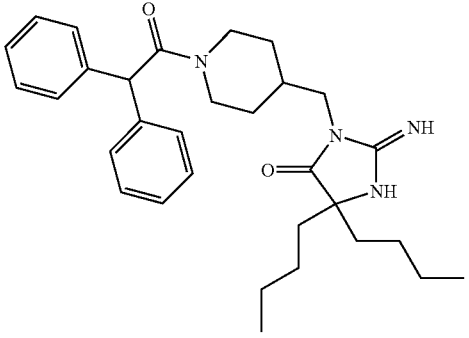 | 502 | 503 |
| 1144 | 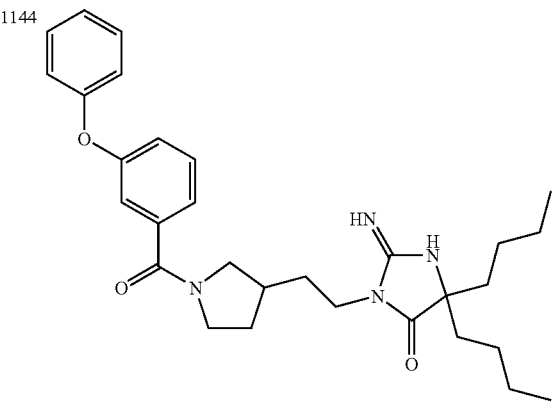 | 504 | 505 |

-continued

| # | Structure | MW | Obs. m/e |
|---|---|---|---|
| 1145 | 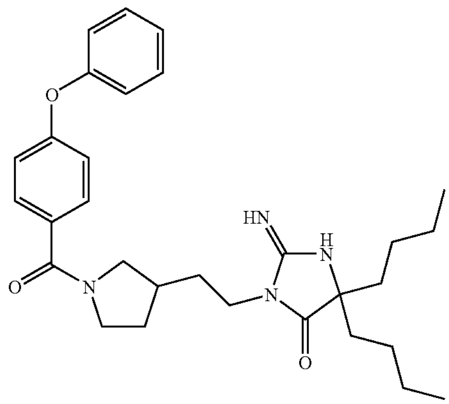 | 504 | 505 |
| 1146 | 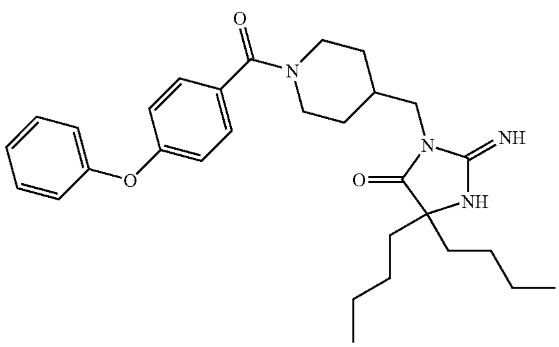 | 504 | 505 |
| 1147 | 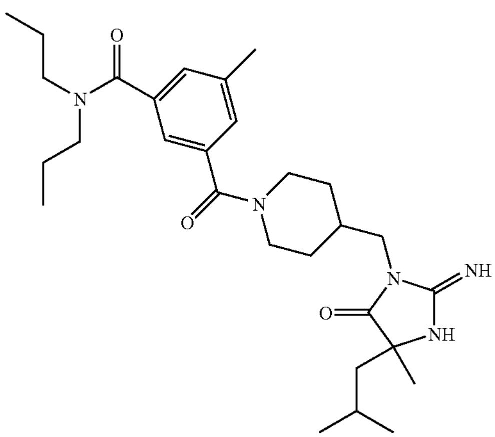 | 511 | 512 |
| 1148 | 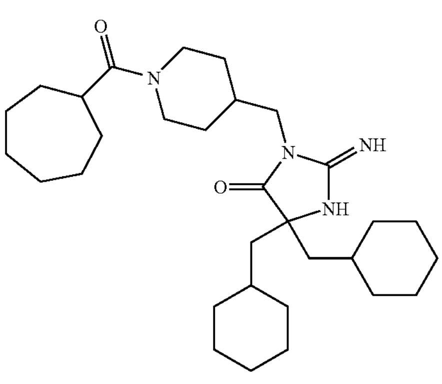 | 512 | 513 |

-continued

| # | Structure | MW | Obs. m/e |
|---|---|---|---|
| 1149 | 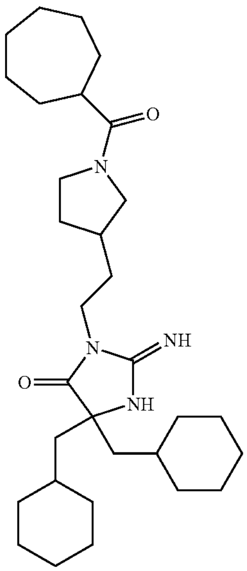 | 512 | 513 |
| 1150 | 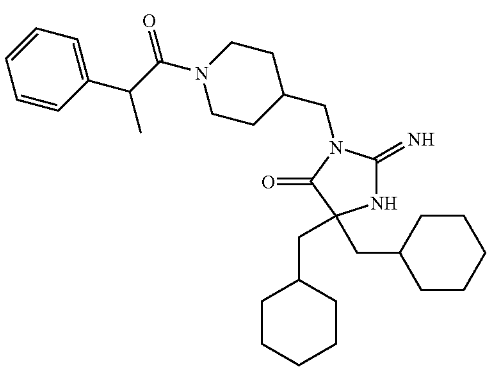 | 520 | 521 |
| 1151 | 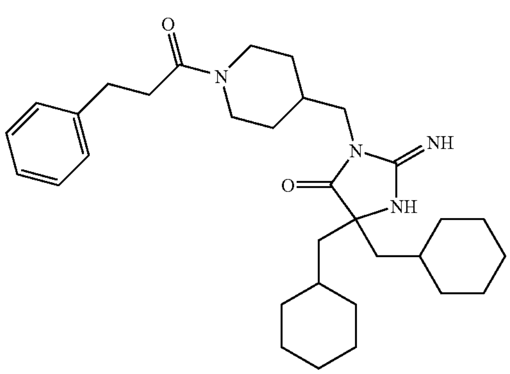 | 520 | 521 |

-continued

| # | Structure | MW | Obs. m/e |
|---|---|---|---|
| 1152 | 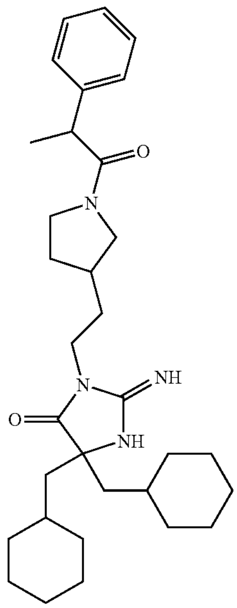 | 520 | 521 |
| 1153 | 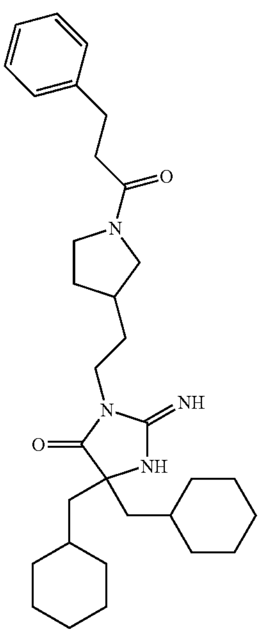 | 520 | 521 |

-continued

| # | Structure | MW | Obs. m/e |
|---|---|---|---|
| 1154 | 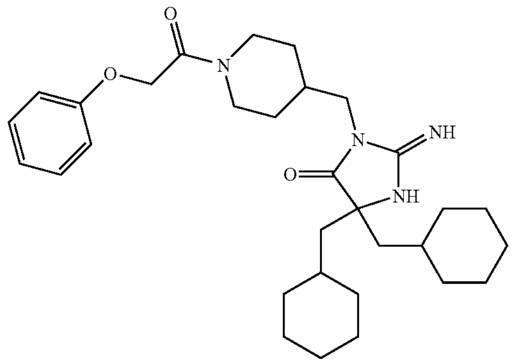 | 522 | 523 |
| 1155 | 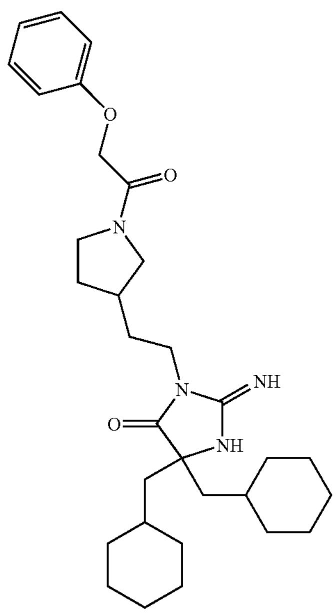 | 522 | 523 |
| 1156 | 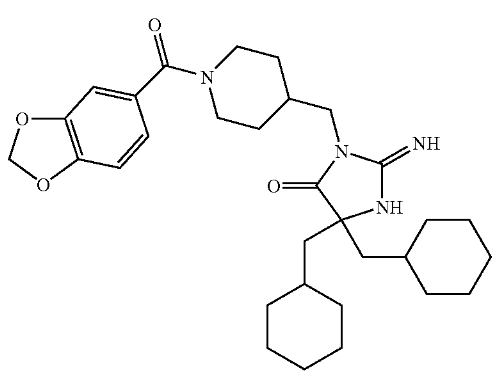 | 536 | 537 |

-continued
| # | Structure | MW | Obs. m/e |
|---|---|---|---|
| 1157 | 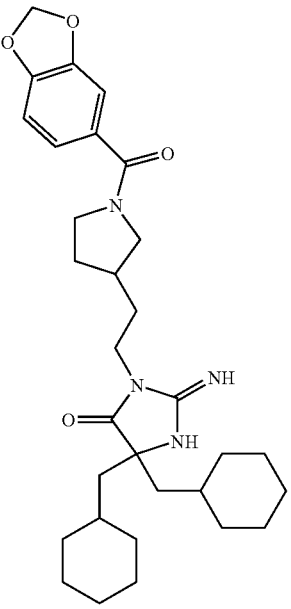 | 536 | 537 |
| 1158 | 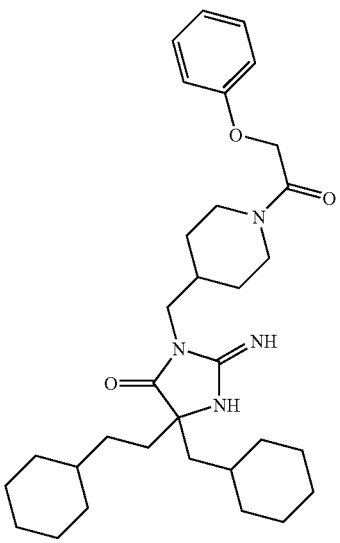 | 536 | 537 |
| 1159 | 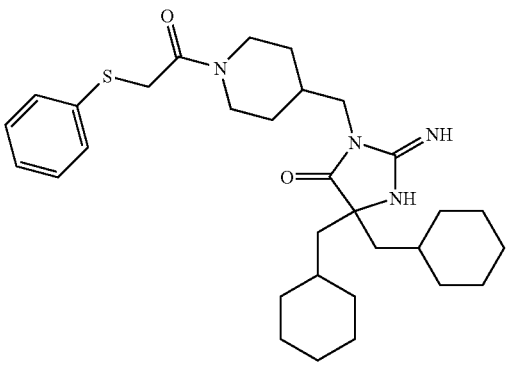 | 538 | 539 |

| # | Structure | MW | Obs. m/e |
|---|---|---|---|
| 1160 | 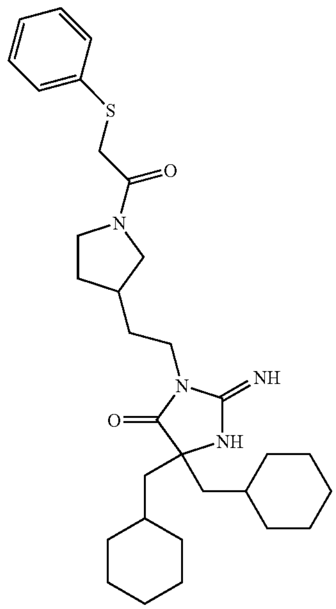 | 538 | 539 |
| 1161 | 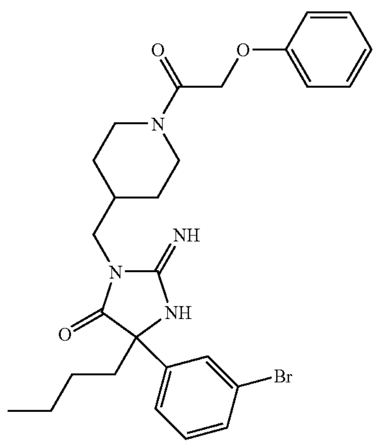 | 540 | 541 |
| 1162 | 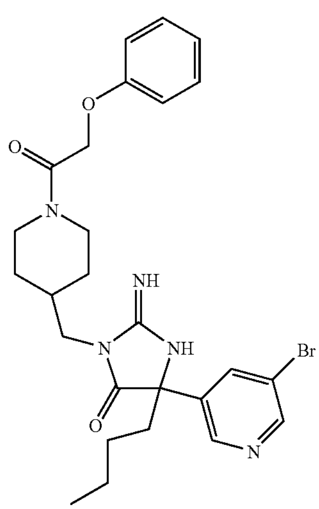 | 541 | 542 |

| # | Structure | MW | Obs. m/e |
|---|-----------|-----|----------|
| 1163 | 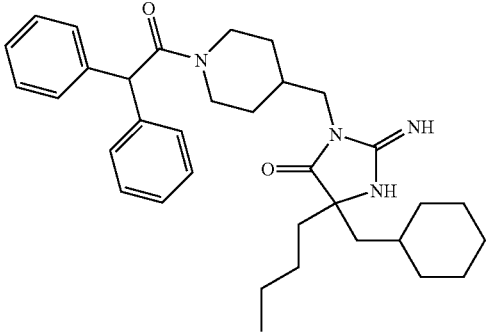 | 542 | 543 |
| 1164 | 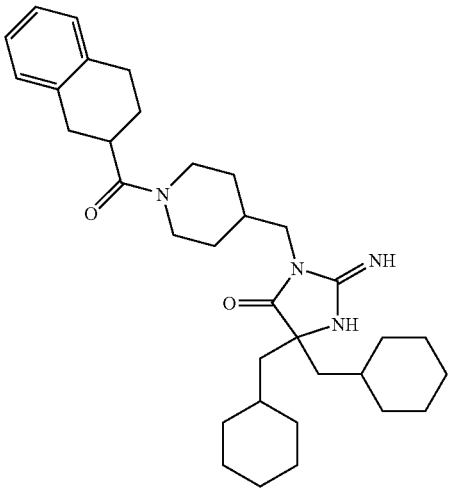 | 546 | 547 |
| 1165 | 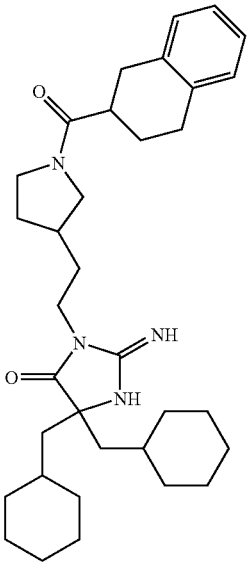 | 546 | 547 |

-continued

| # | Structure | MW | Obs. m/e |
|---|---|---|---|
| 1166 | 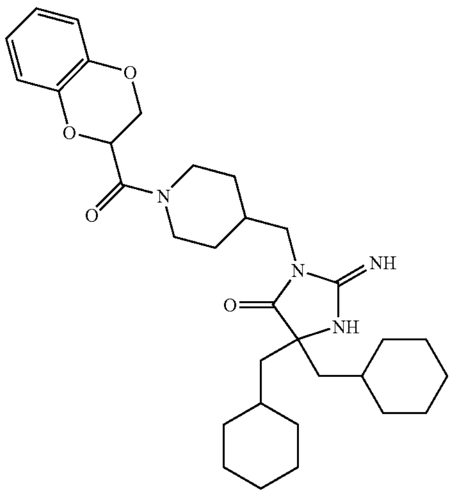 | 550 | 551 |
| 1167 | 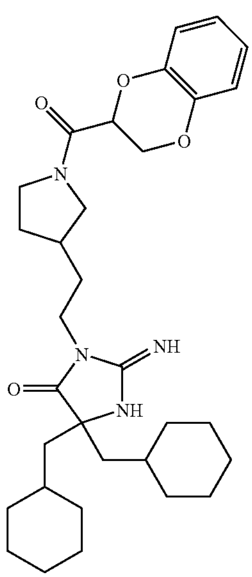 | 550 | 551 |

-continued

| # | Structure | MW | Obs. m/e |
|---|---|---|---|
| 1168 | 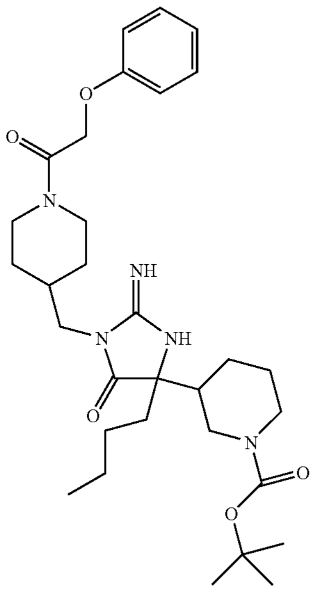 | 569 | 570 |
| 1169 | 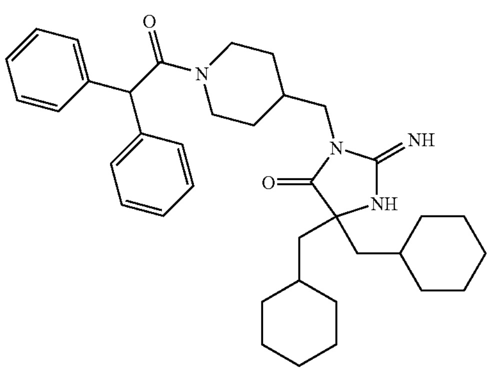 | 582 | 583 |
| 1170 | 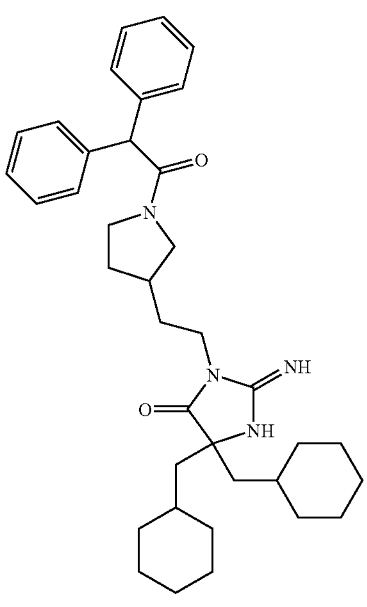 | 582 | 583 |

-continued

| # | Structure | MW | Obs. m/e |
|---|---|---|---|
| 1171 | 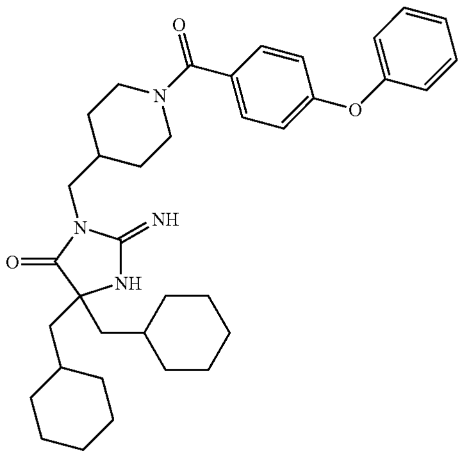 | 584 | 585 |
| 1172 | 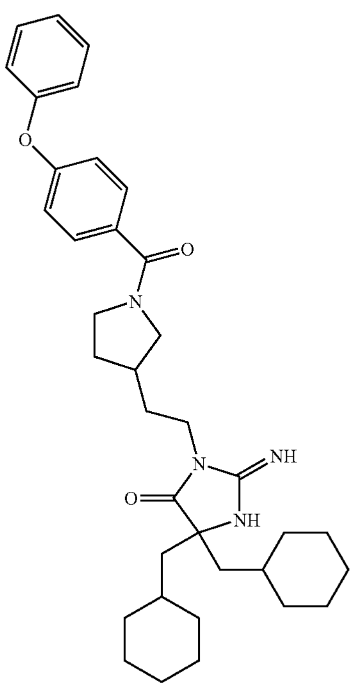 | 584 | 585 |

-continued
| # | Structure | MW | Obs. m/e |
|---|---|---|---|
| 1173 | 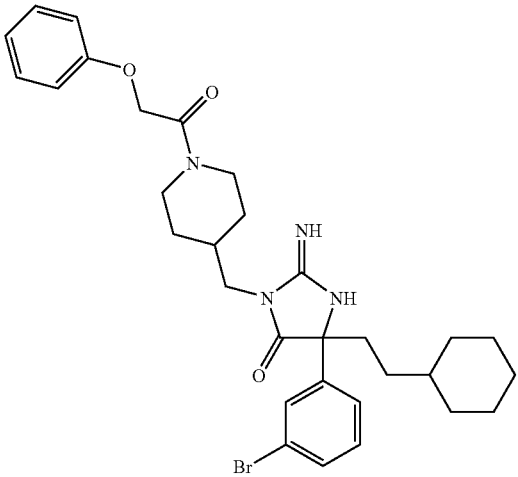 | 594 | 595 |
| 1174 | 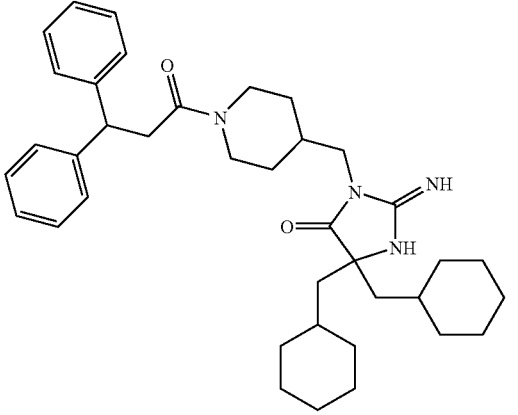 | 596 | 597 |
| 1175 | 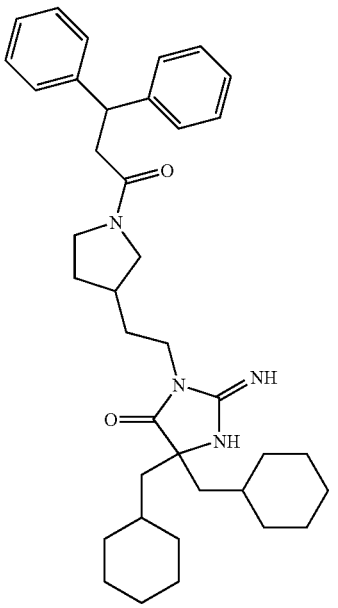 | 596 | 597 |

Method R

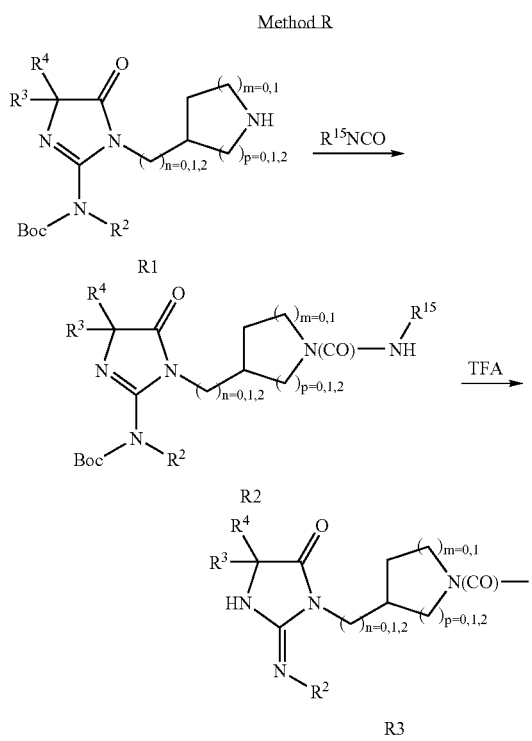

Method R, Step 1.

A solution of $R^1$ (n=1, p=2, m=1, $R^2$=H, $R^3$=Me; $R^4$=$^i$Bu) (0.010 g) in acetonitrile (0.85 mL) and dichloroethane (0.15 mL) was put into a microtiter plate well followed by addition of 0.12 ml of 0.5M phenylisocyanate solution in dichloroethane. The well was sealed and the plate shaken for 20 h before the mixture was filtered and the solid washed with acetonitrile (0.5 ml). The combined solution was treated with Trisamine resin (0.050 g, 6 eq., 4.23 mmol/g) and Isocyanate resin (0.067 g, 3 eq., 1.53 mmol/g) and the mixture was shaken for 18 h. The mixture was filtered and the solution was evaporated to give $R^2$ (n=1, p=2, m=1, $R^2$=H, $R^3$=Me; $R^4$=$^i$Bu and $R^{15}$=Ph).

Method R, Step 2.

Procedure similar to Method Q, step 6 was used for the transformation of $R^2$ (n=1, p=2, m=1, $R^2$=H, $R^3$=Me; $R^4$=$^i$Bu and $R^{15}$=Ph) to $R^3$ (n=1, p=2, m=1, $R^2$=H, $R^3$=Me; $R^4$=$^i$Bu and $R^5$=Ph).

The following compounds were prepared using similar methods:

| # | Structure | MW | Obs. m/e |
|---|-----------|----|----|
| 1176 | 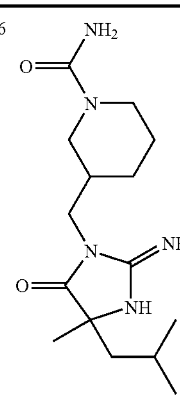 | 309 | 310 |
| 1177 | 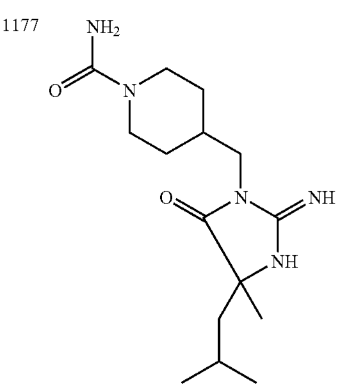 | 309 | 310 |

-continued

| # | Structure | MW | Obs. m/e |
|---|---|---|---|
| 1178 | 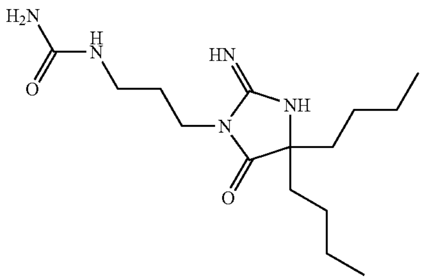 | 311 | 312 |
| 1179 | 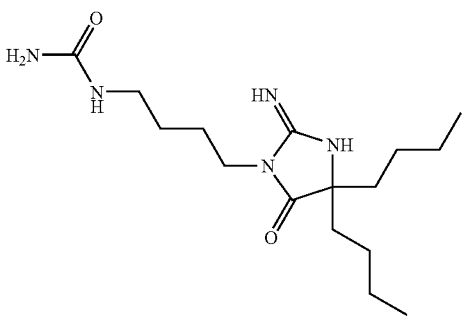 | 325 | 326 |
| 1180 | 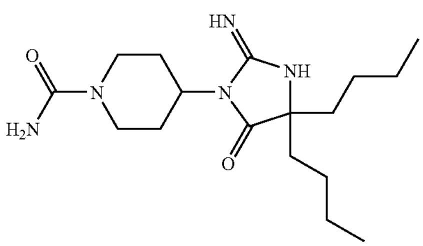 | 337 | 338 |
| 1181 | 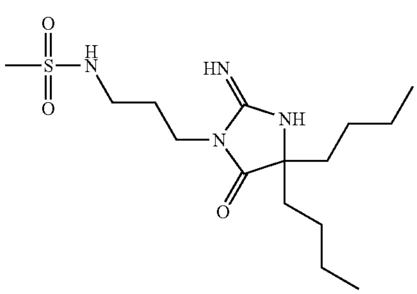 | 346 | 347 |
| 1182 | 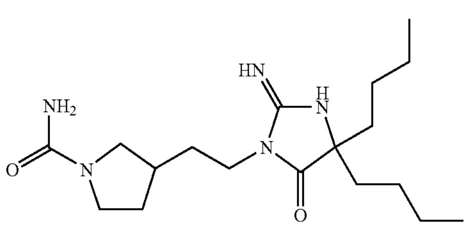 | 351 | 352 |

-continued
| # | Structure | MW | Obs. m/e |
|---|---|---|---|
| 1183 | 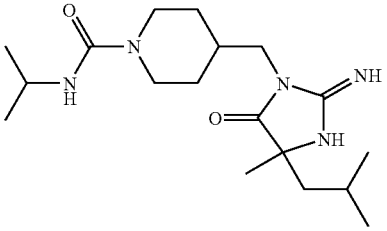 | 351 | 352 |
| 1184 | 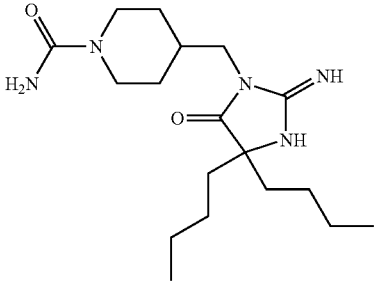 | 351 | 352 |
| 1185 | 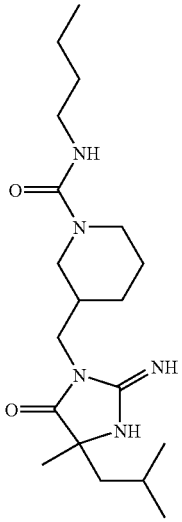 | 365 | 366 |
| 1186 | 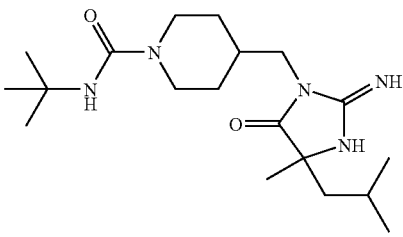 | 365 | 366 |
| 1187 | 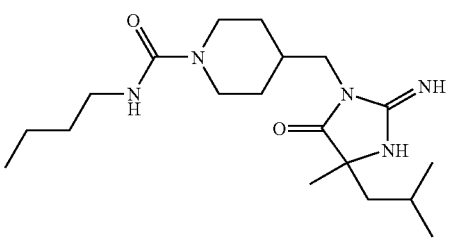 | 365 | 366 |

| # | Structure | MW | Obs. m/e |
|---|---|---|---|
| 1188 | 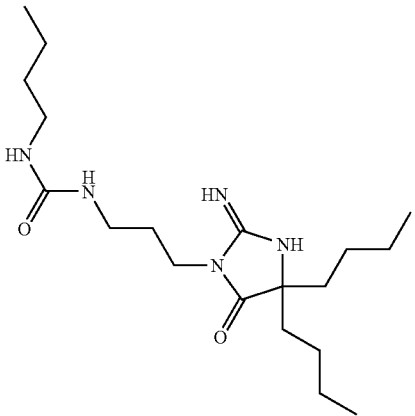 | 367 | 368 |
| 1189 | 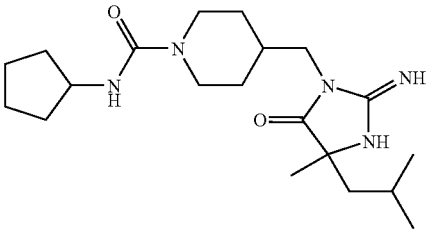 | 377 | 378 |
| 1190 | 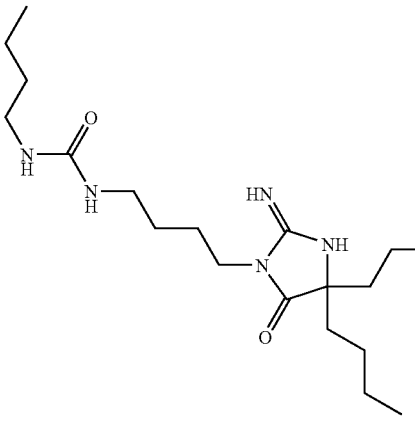 | 381 | 382 |
| 1191 | 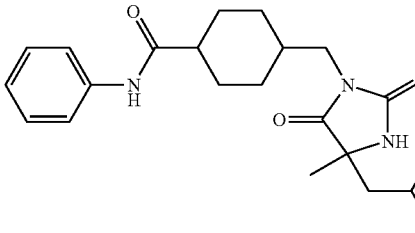 | 385 | 386 |
| 1192 | 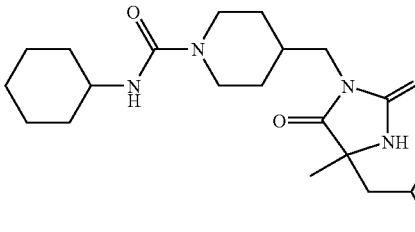 | 391 | 392 |

-continued

| # | Structure | MW | Obs. m/e |
|---|---|---|---|
| 1193 | 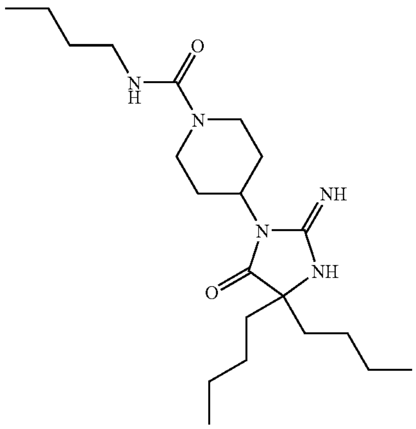 | 393 | 394 |
| 1194 | 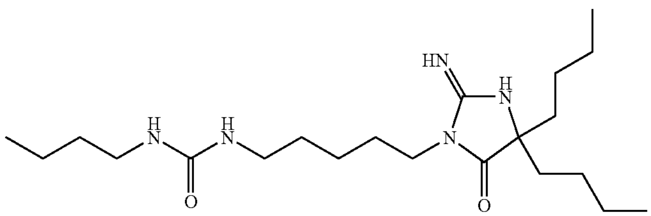 | 395 | 396 |
| 1195 | 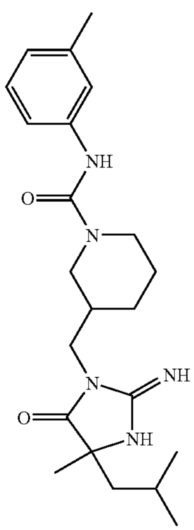 | 399 | 400 |
| 1196 | 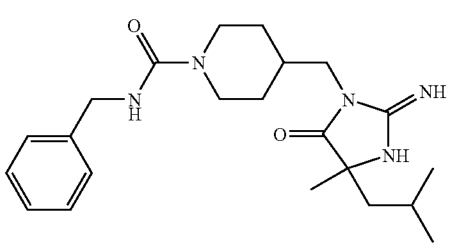 | 399 | 400 |

-continued

| # | Structure | MW | Obs. m/e |
|---|---|---|---|
| 1197 | 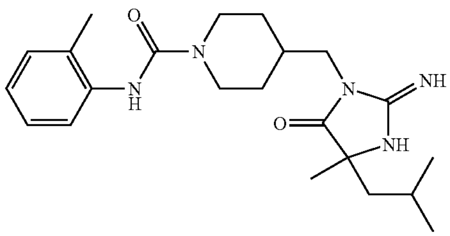 | 399 | 400 |
| 1198 | 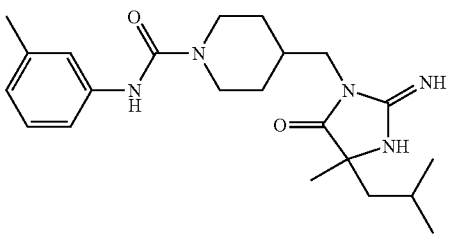 | 399 | 400 |
| 1199 | 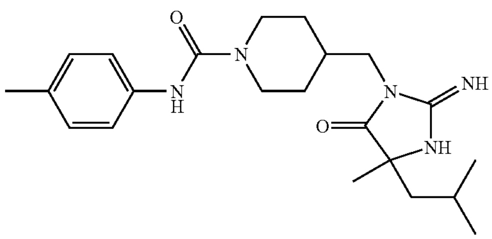 | 399 | 400 |
| 1200 | 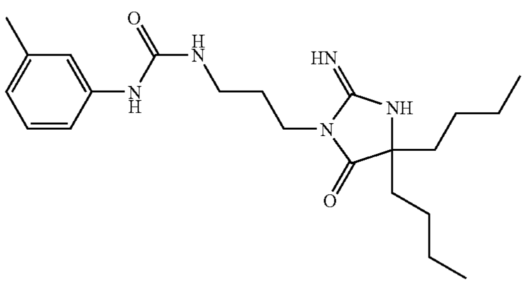 | 401 | 402 |
| 1201 | 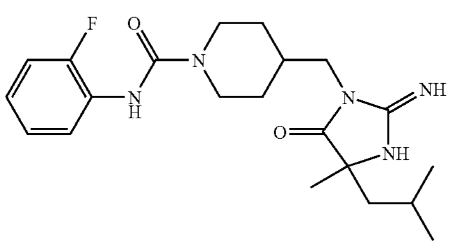 | 403 | 404 |
| 1202 | 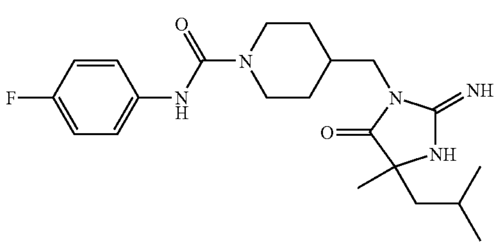 | 403 | 404 |

-continued
| # | Structure | MW | Obs. m/e |
|---|---|---|---|
| 1203 | 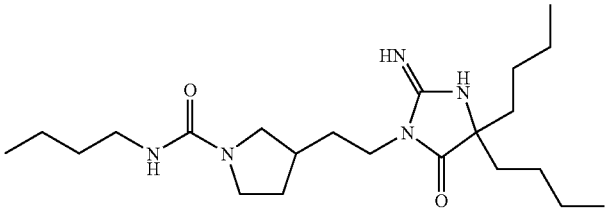 | 407 | 408 |
| 1204 | 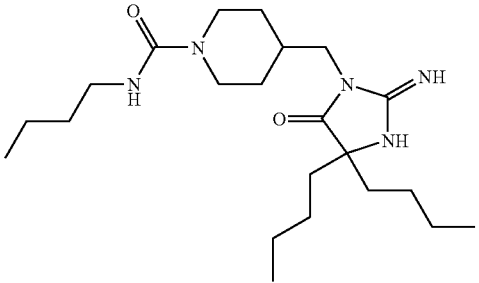 | 407 | 408 |
| 1205 | 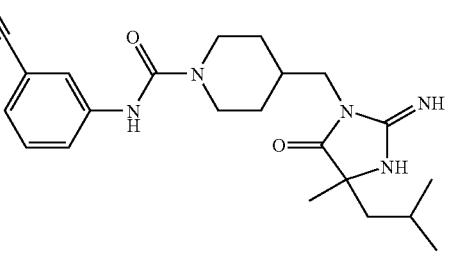 | 410 | 411 |
| 1206 | 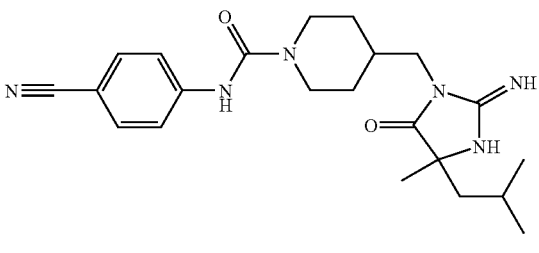 | 410 | 411 |

-continued

| # | Structure | MW | Obs. m/e |
|---|---|---|---|
| 1207 | 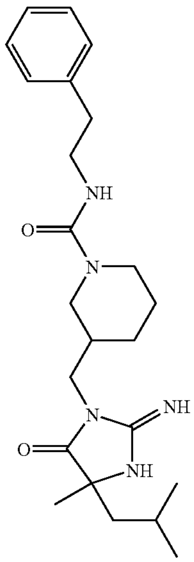 | 413 | 414 |
| 1208 | 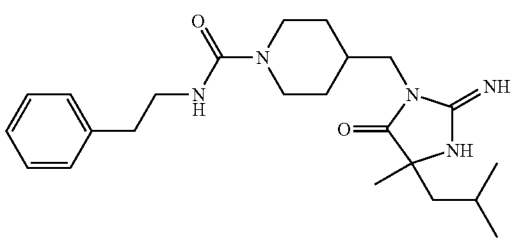 | 413 | 414 |
| 1209 | 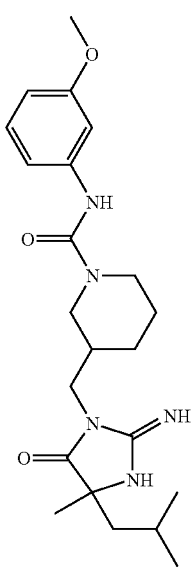 | 415 | 416 |

| # | Structure | MW | Obs. m/e |
|---|---|---|---|
| 1210 | 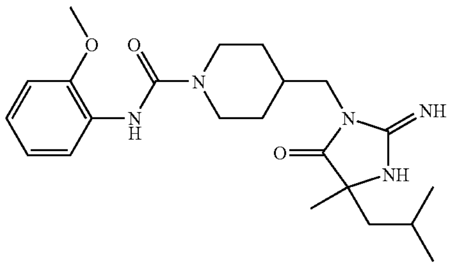 | 415 | 416 |
| 1211 | 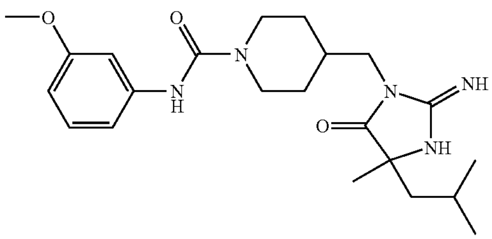 | 415 | 416 |
| 1212 | 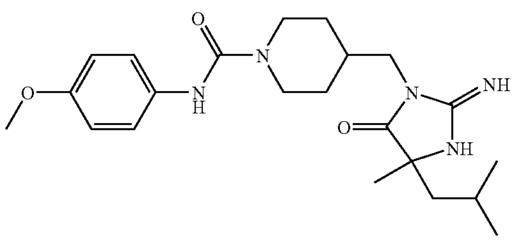 | 415 | 416 |
| 1213 | 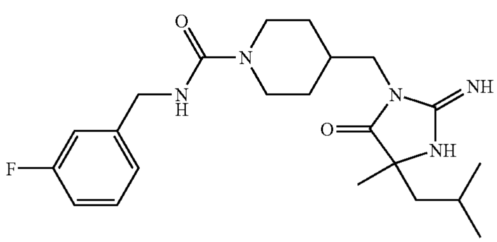 | 417 | 418 |
| 1214 | 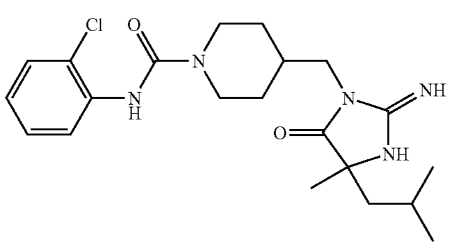 | 419 | 420 |
| 1215 | 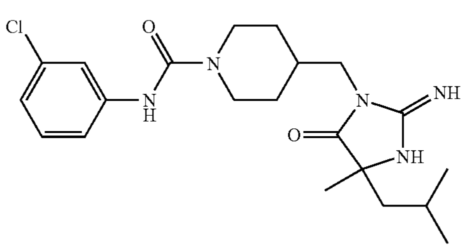 | 419 | 420 |

-continued

| # | Structure | MW | Obs. m/e |
|---|---|---|---|
| 1216 | 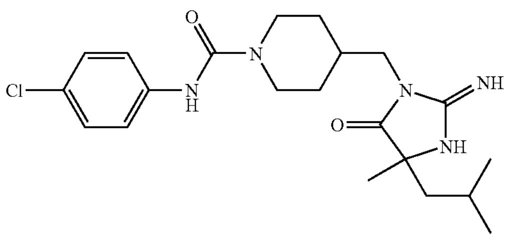 | 419 | 420 |
| 1217 | 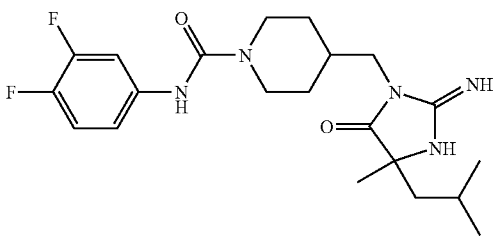 | 421 | 422 |
| 1218 | 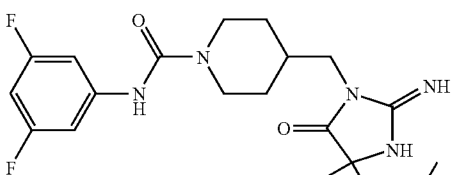 | 421 | 422 |
| 1219 | 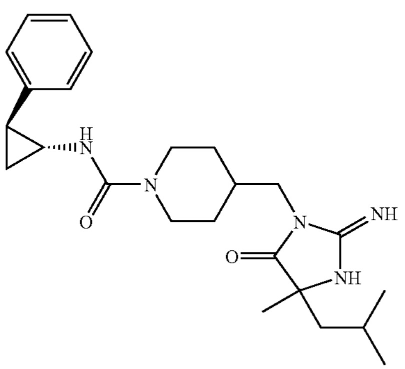 | 425 | 426 |
| 1220 | 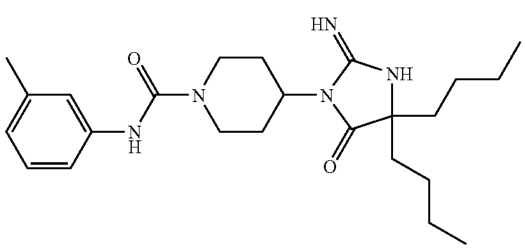 | 427 | 428 |

-continued

| # | Structure | MW | Obs. m/e |
|---|---|---|---|
| 1221 | 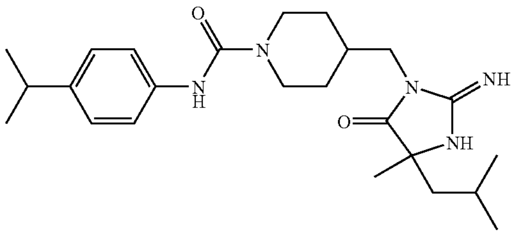 | 427 | 428 |
| 1222 | 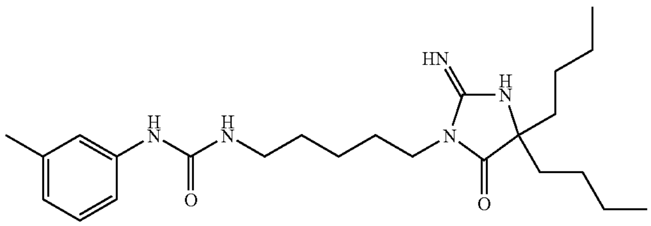 | 429 | 430 |
| 1223 | 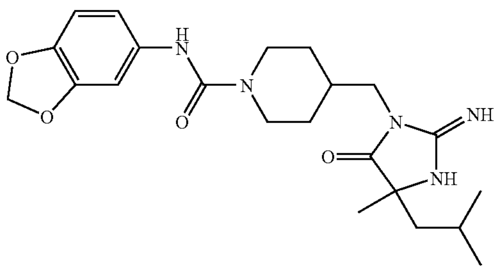 | 429 | 430 |
| 1224 | 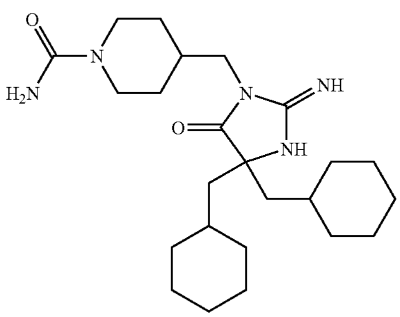 | 431 | 432 |
| 1225 | 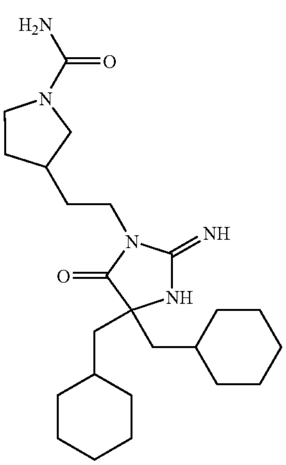 | 431 | 432 |

| # | Structure | MW | Obs. m/e |
|---|-----------|-----|----------|
| 1226 | 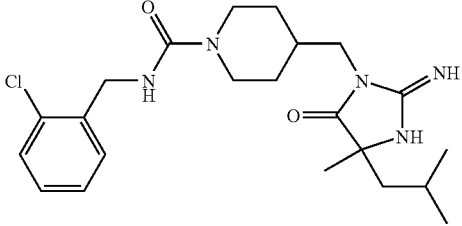 | 433 | 434 |
| 1227 | 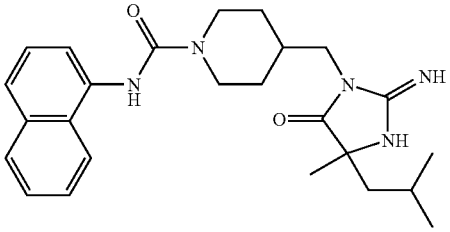 | 435 | 436 |
| 1228 | 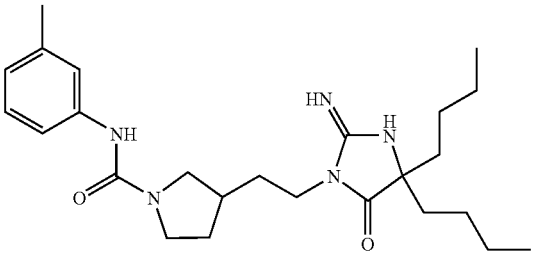 | 441 | 442 |
| 1229 | 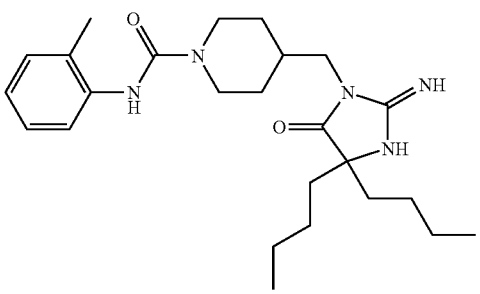 | 441 | 442 |
| 1230 | 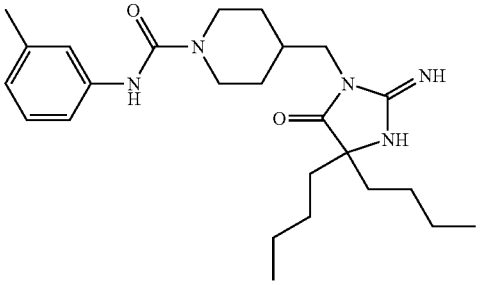 | 441 | 442 |

| # | Structure | MW | Obs. m/e |
|---|---|---|---|
| 1231 | 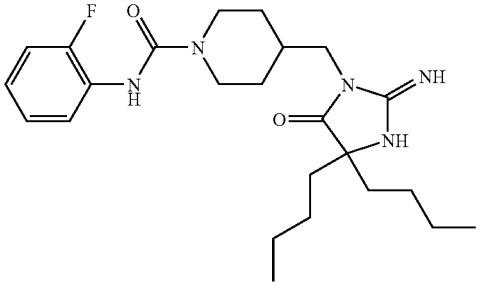 | 445 | 446 |
| 1232 | 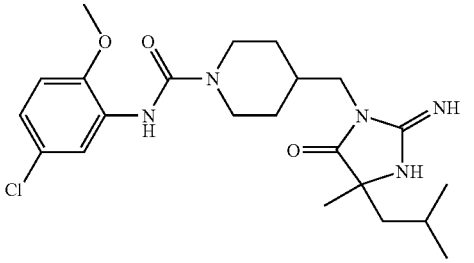 | 449 | 450 |
| 1233 | 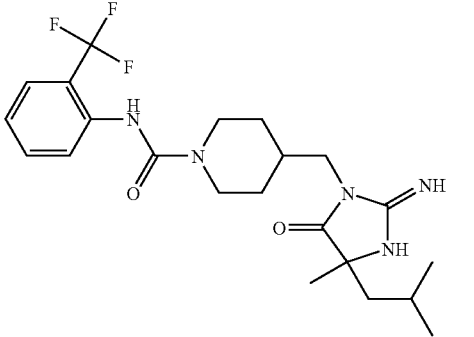 | 453 | 454 |
| 1234 | 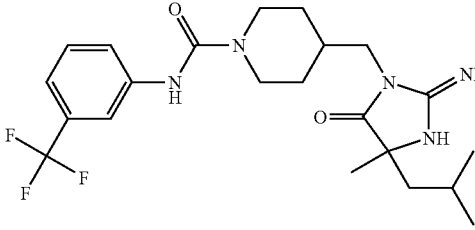 | 453 | 454 |
| 1235 | 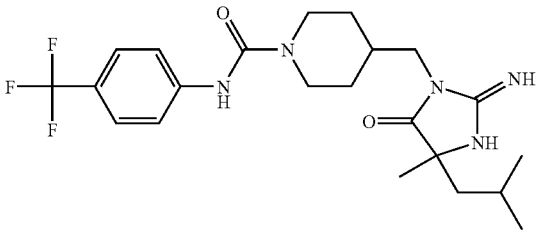 | 453 | 454 |

| # | Structure | MW | Obs. m/e |
|---|---|---|---|
| 1236 | 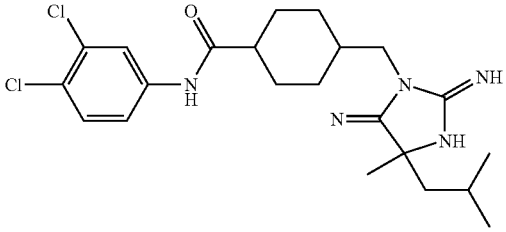 | 453 | 454 |
| 1237 | 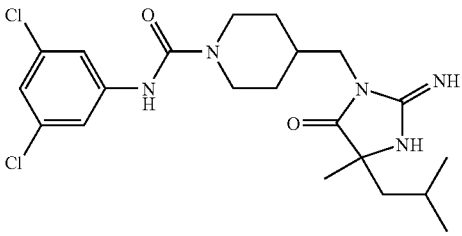 | 453 | 454 |
| 1238 | 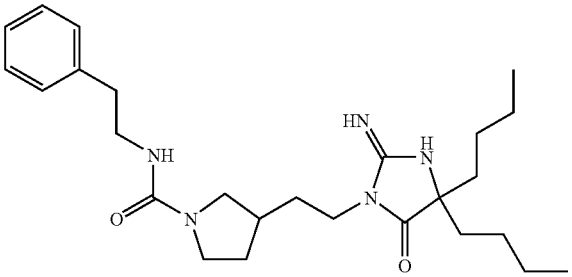 | 455 | 456 |
| 1239 | 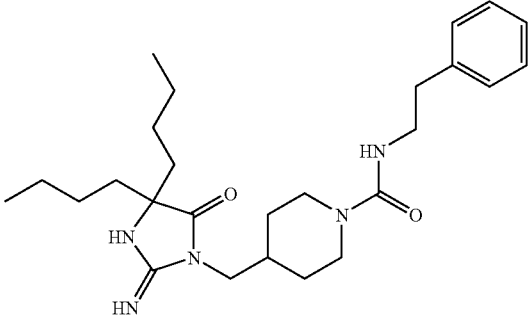 | 455 | 456 |
| 1240 | 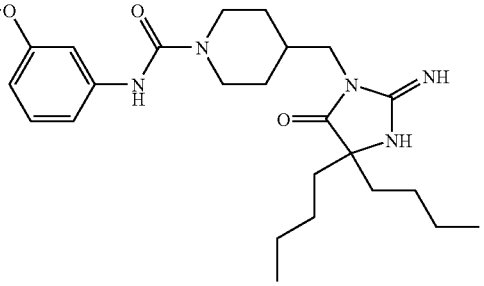 | 457 | 458 |

-continued

| # | Structure | MW | Obs. m/e |
|---|---|---|---|
| 1241 | 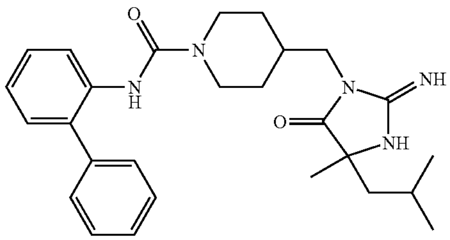 | 461 | 462 |
| 1242 | 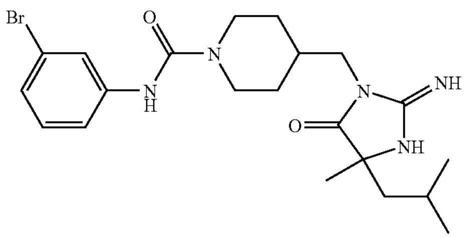 | 463 | 464 |
| 1243 | 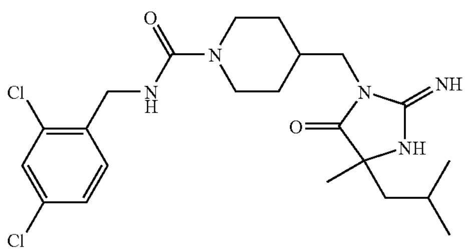 | 467 | 468 |
| 1244 | 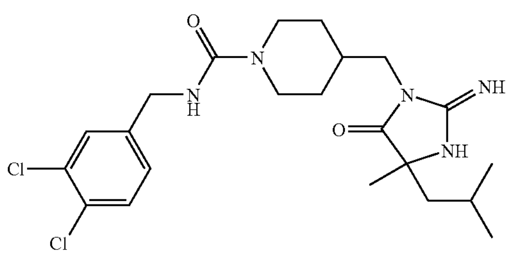 | 467 | 468 |
| 1245 | 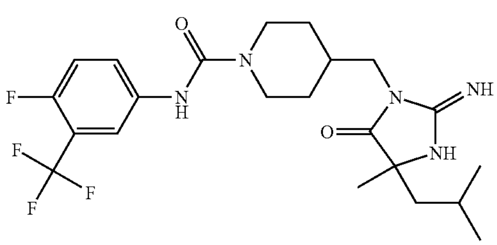 | 471 | 472 |
| 1246 | 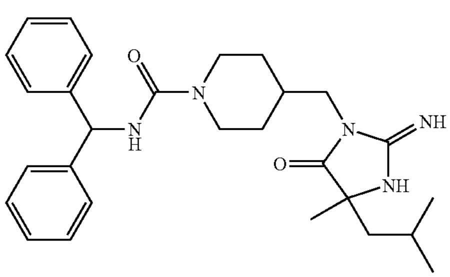 | 475 | 476 |

| # | Structure | MW | Obs. m/e |
|---|---|---|---|
| 1247 | 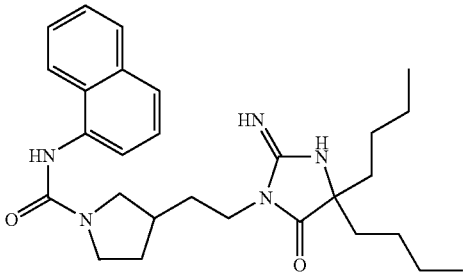 | 477 | 478 |
| 1248 | 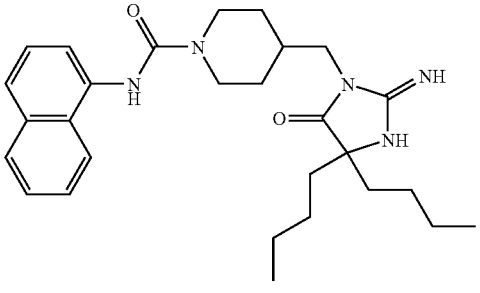 | 477 | 478 |
| 1249 | 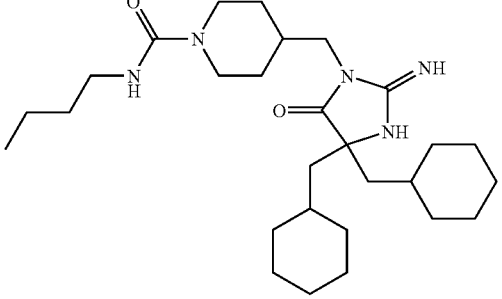 | 487 | 488 |
| 1250 | 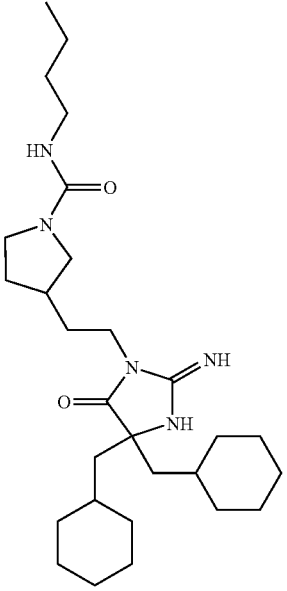 | 487 | 488 |

-continued

| # | Structure | MW | Obs. m/e |
|---|---|---|---|
| 1251 | 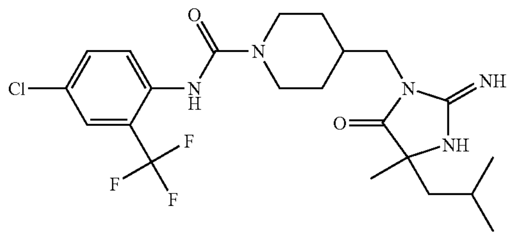 | 487 | 488 |
| 1252 | 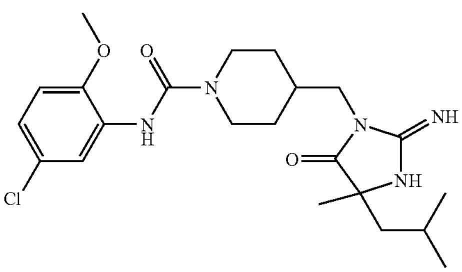 | 491 | 492 |

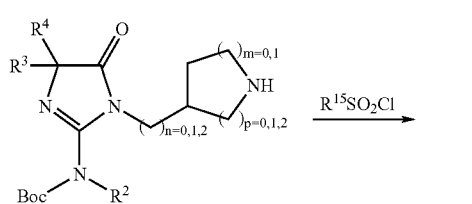

Method S

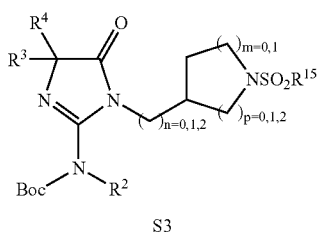

Method S, Step 1.

A solution of S1 (n=1, p=2, m=1, $R^2$=H, $R^3$=Me; $R^4$=iBu) (0.010 g) in acetonitrile (0.85 mL) and dichloroethane (0.15 mL) was put into a microtiter plate followed by addition of DIPEA-MP resin (0.030 g, 4 eq) and phenylsulfonyl chloride in dioxane (1M, 45 μL, 0.045 mmol. The well was capped and shaken for 18 h before it was filtered and residue washed with acetonitrile (0.5 mL). The combined solution was treated with Trisamine resin (0.040 g, 6 eq., 4.23 mmol/g) and Isocyanate resin (0.060 g, 3 equiv., 1.53 mmol/g) and shaken for 18 h before the mixture was filtered and the solvent removed to give S2 (n=1, p=2, m=1, $R^2$=H, $R^3$=Me; $R^4$=iBu and $R^{15}$=Ph).

Method S, Step 2.

Procedure similar to Method Q, step 6 was used for the transformation of S2 to S3 (n=1, p=2, m=1, $R^2$=H, $R^3$=Me; $R^4$=Bu and $R^{15}$=Ph).

The following compounds were prepared using similar methods:

| # | Structure | MW | Obs. m/e |
|---|---|---|---|
| 1253 | 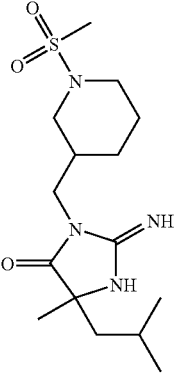 | 344 | 345 |
| 1254 | 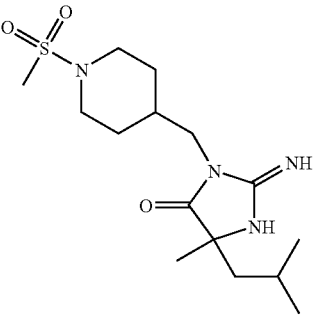 | 344 | 345 |
| 1255 | 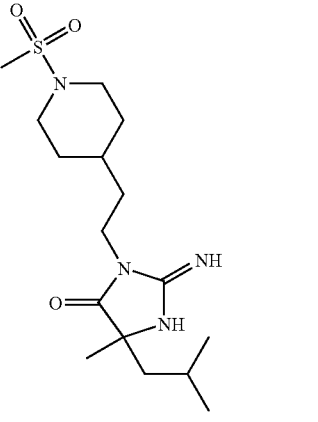 | 358 | 359 |
| 1256 | 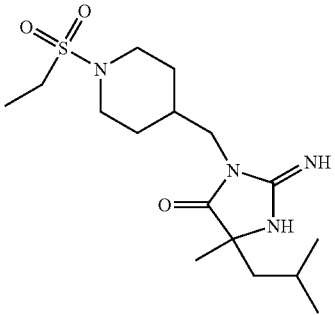 | 358 | 359 |

-continued

| # | Structure | MW | Obs. m/e |
|---|---|---|---|
| 1257 | 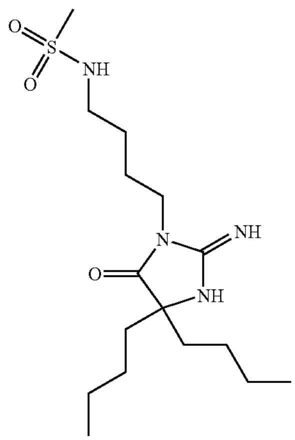 | 360 | 361 |
| 1258 | 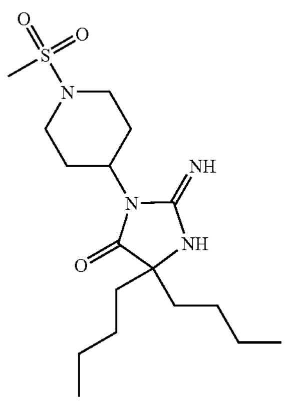 | 372 | 373 |
| 1259 | 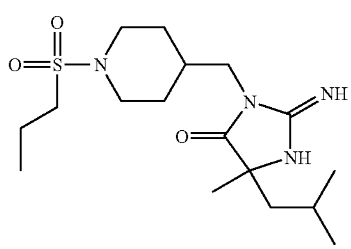 | 372 | 373 |
| 1260 | 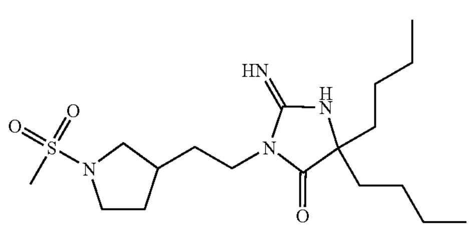 | 386 | 387 |

-continued

| # | Structure | MW | Obs. m/e |
|---|---|---|---|
| 1261 | 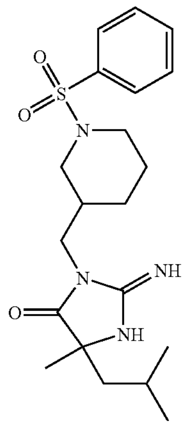 | 406 | 407 |
| 1262 | 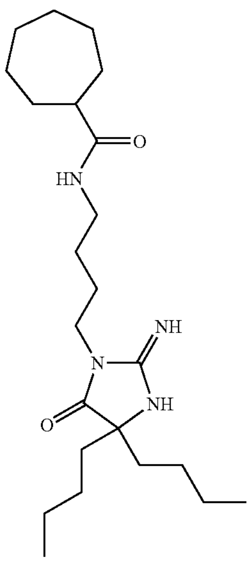 | 406 | 407 |
| 1263 | 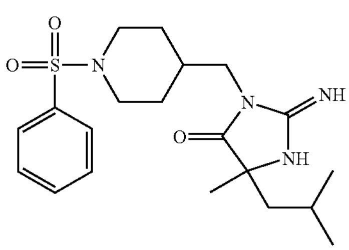 | 406 | 407 |
| 1264 | 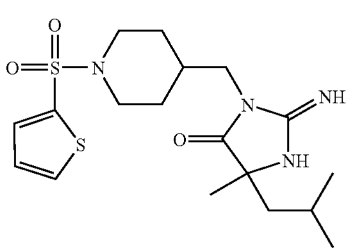 | 412 | 413 |

-continued

| # | Structure | MW | Obs. m/e |
|---|---|---|---|
| 1265 | 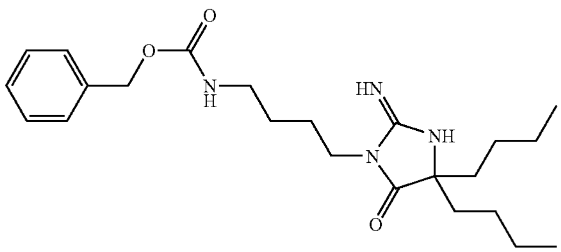 | 416 | 417 |
| 1266 | 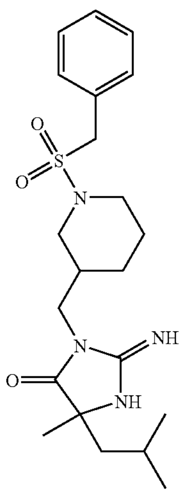 | 420 | 421 |
| 1267 | 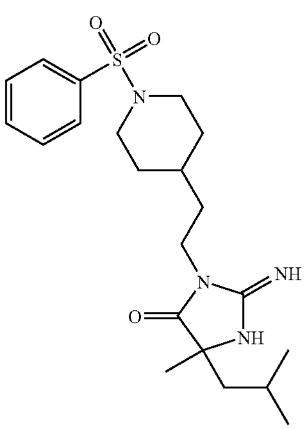 | 420 | 421 |
| 1268 | 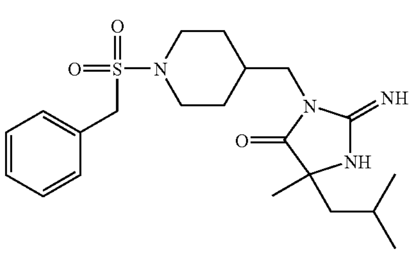 | 420 | 421 |

-continued

| # | Structure | MW | Obs. m/e |
|---|---|---|---|
| 1269 | 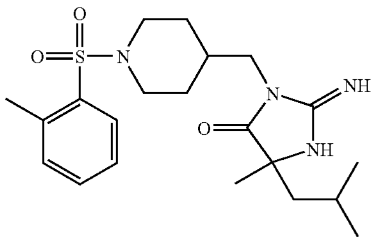 | 420 | 421 |
| 1270 | 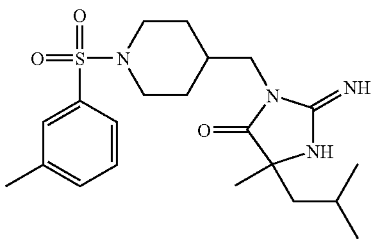 | 420 | 421 |
| 1271 | 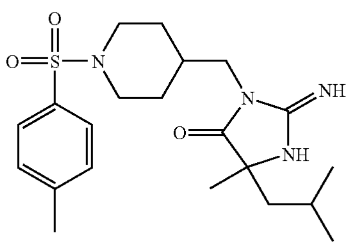 | 420 | 421 |
| 1272 | 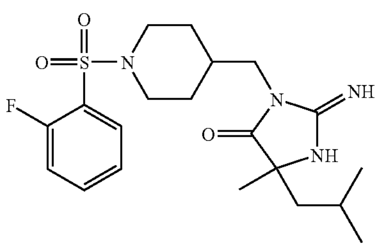 | 424 | 425 |
| 1273 | 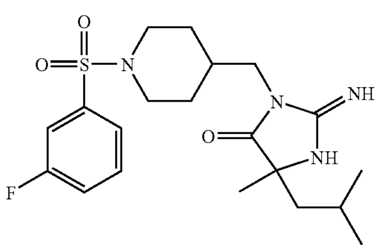 | 424 | 425 |
| 1274 | 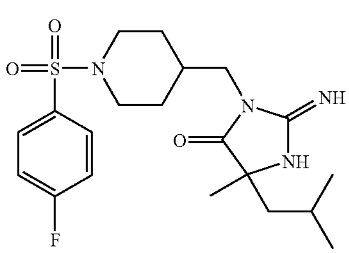 | 424 | 425 |

-continued

| # | Structure | MW | Obs. m/e |
|---|---|---|---|
| 1275 | 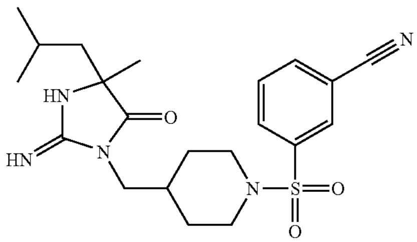 | 431 | 432 |
| 1276 | 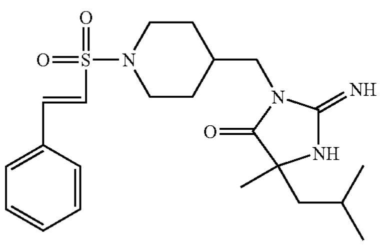 | 432 | 433 |
| 1277 | 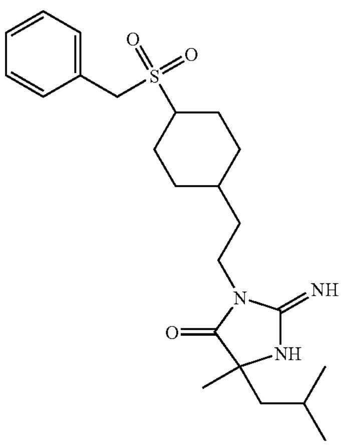 | 434 | 435 |
| 1278 | 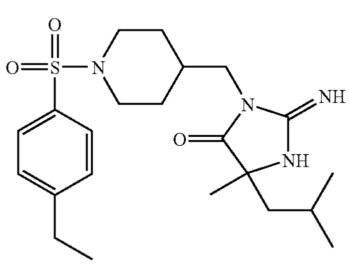 | 434 | 435 |
| 1279 | 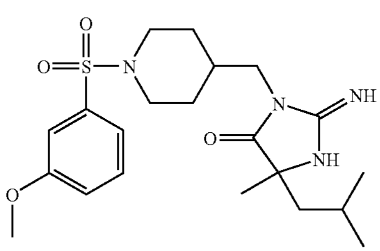 | 436 | 437 |

-continued

| # | Structure | MW | Obs. m/e |
|---|---|---|---|
| 1280 | 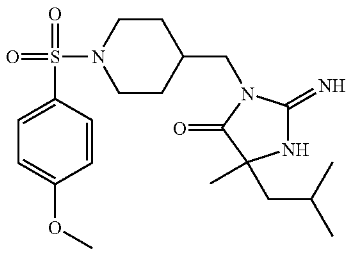 | 436 | 437 |
| 1281 | 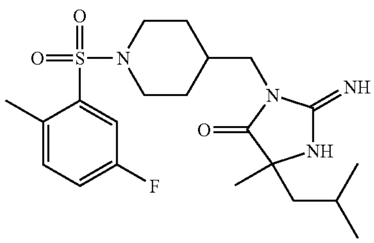 | 438 | 439 |
| 1282 | 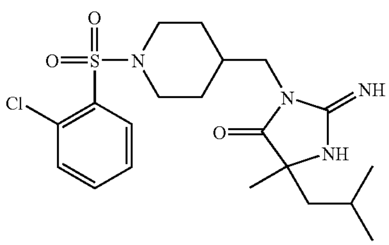 | 440 | 441 |
| 1283 | 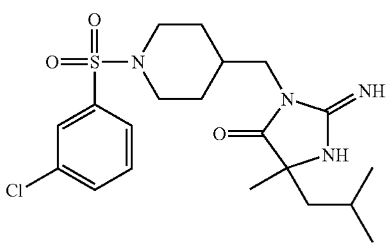 | 440 | 441 |
| 1284 | 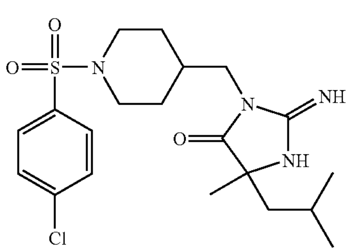 | 440 | 441 |
| 1285 | 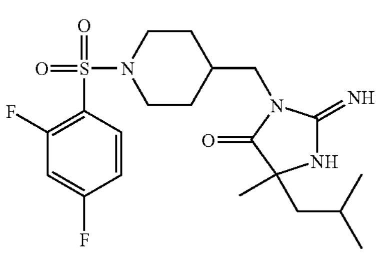 | 442 | 443 |

-continued

| # | Structure | MW | Obs. m/e |
|---|---|---|---|
| 1286 | 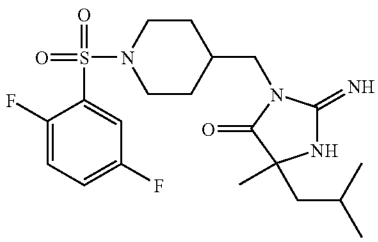 | 442 | 443 |
| 1287 | 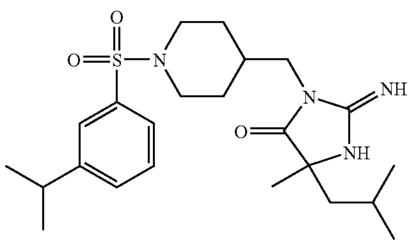 | 442 | 443 |
| 1288 | 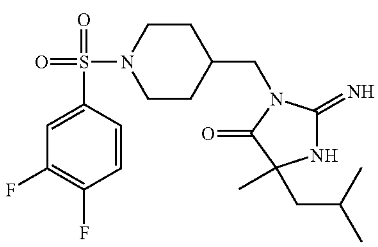 | 442 | 443 |
| 1289 | 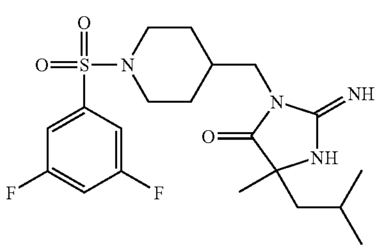 | 442 | 443 |
| 1290 | 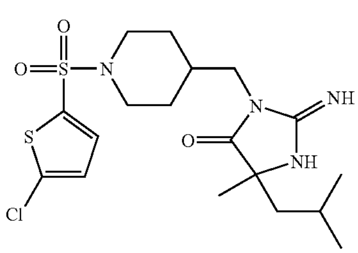 | 446 | 447 |
| 1291 | 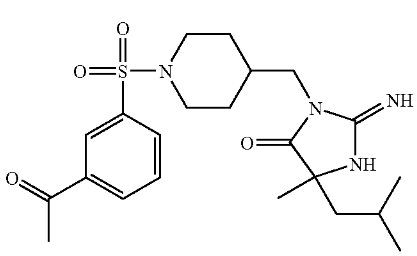 | 448 | 449 |

-continued

| # | Structure | MW | Obs. m/e |
|---|---|---|---|
| 1292 | 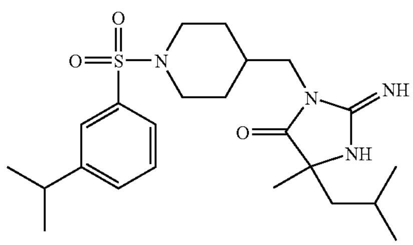 | 448 | 449 |
| 1293 | 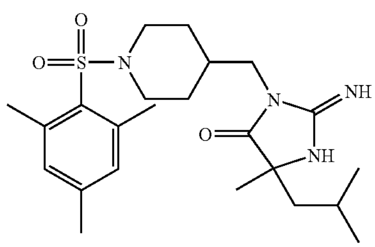 | 448 | 449 |
| 1294 | 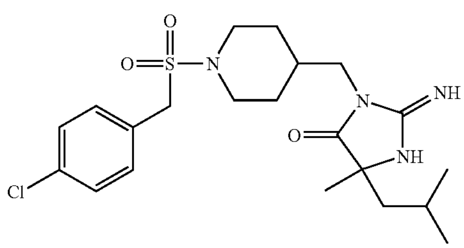 | 454 | 455 |
| 1295 | 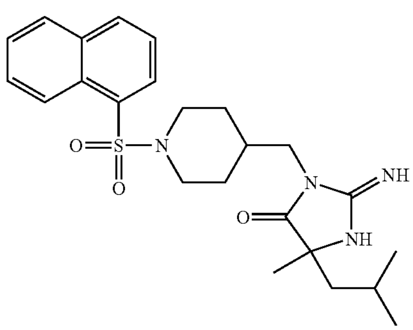 | 456 | 457 |
| 1296 | 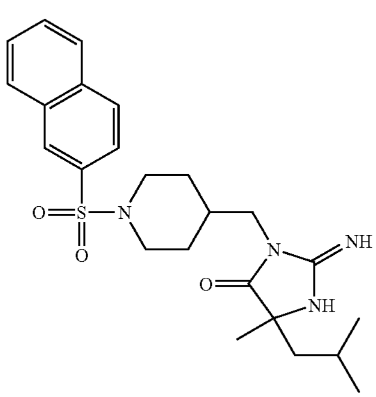 | 456 | 457 |

-continued

| # | Structure | MW | Obs. m/e |
|---|---|---|---|
| 1297 | 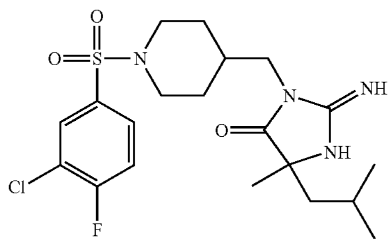 | 458 | 459 |
| 1298 | 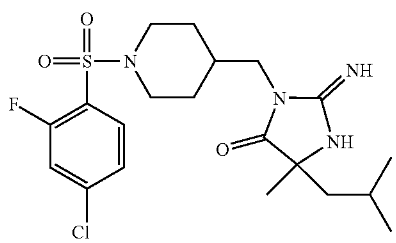 | 458 | 459 |
| 1299 | 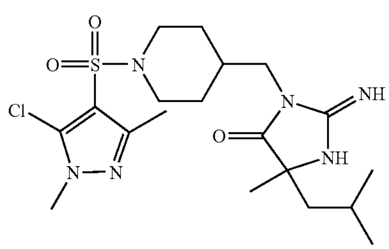 | 458 | 459 |
| 1300 | 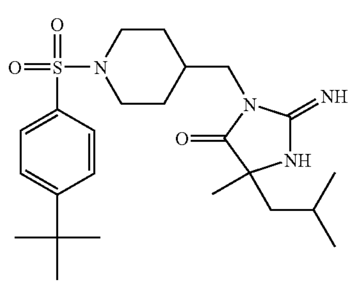 | 462 | 463 |
| 1301 | 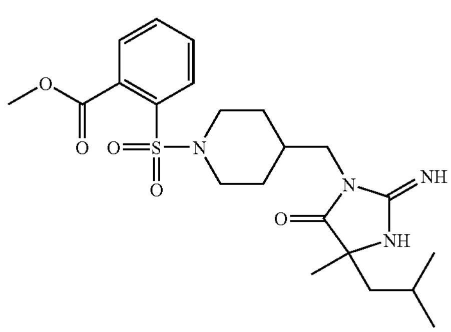 | 464 | 465 |

-continued
| # | Structure | MW | Obs. m/e |
|---|---|---|---|
| 1302 | 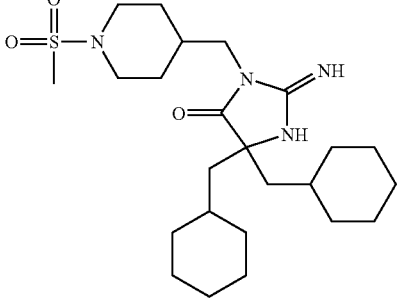 | 466 | 467 |
| 1303 | 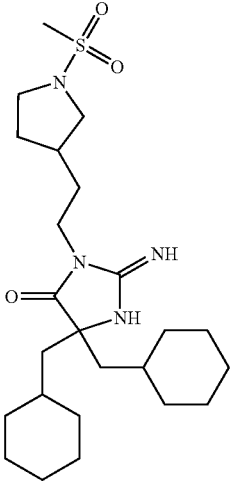 | 466 | 467 |
| 1304 | 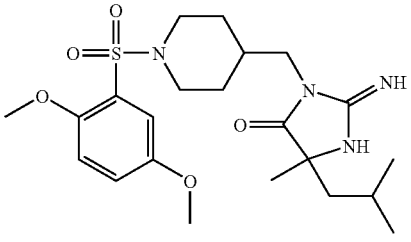 | 466 | 467 |
| 1305 | 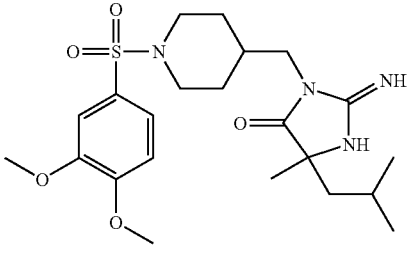 | 466 | 467 |
| 1306 | 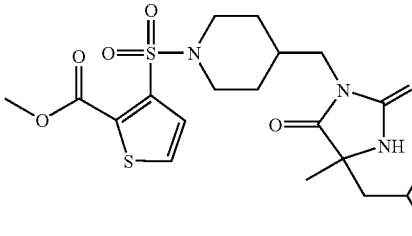 | 470 | 471 |

-continued

| # | Structure | MW | Obs. m/e |
|---|-----------|----|----|
| 1307 | 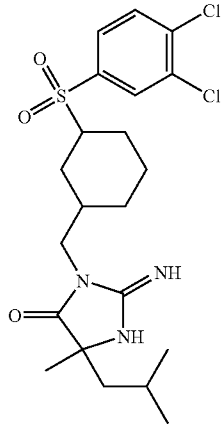 | 474 | 475 |
| 1308 | 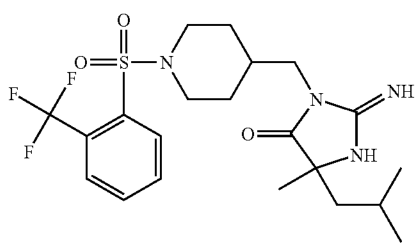 | 474 | 475 |
| 1309 | 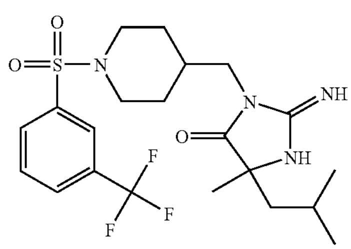 | 474 | 475 |
| 1310 | 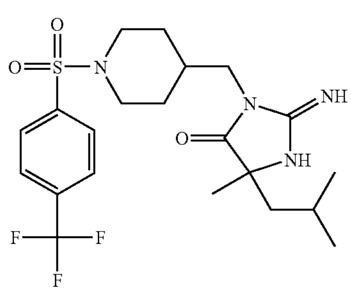 | 474 | 475 |
| 1311 | 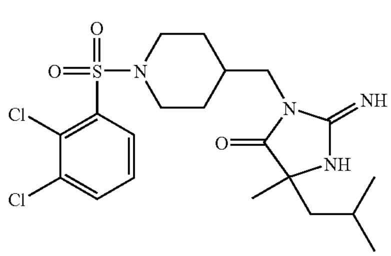 | 474 | 475 |

| # | Structure | MW | Obs. m/e |
|---|---|---|---|
| 1312 | 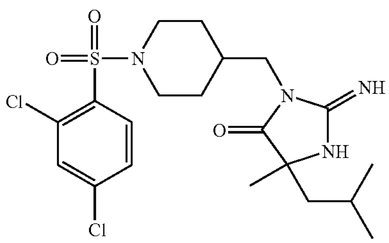 | 474 | 475 |
| 1313 | 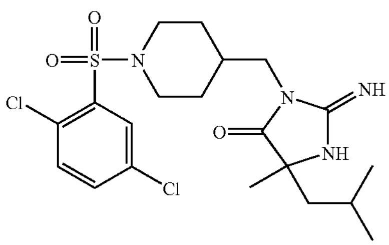 | 474 | 475 |
| 1314 | 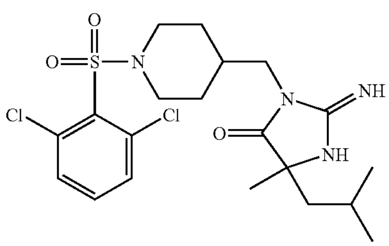 | 474 | 475 |
| 1315 | 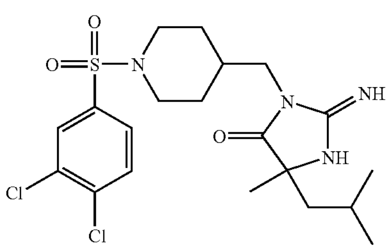 | 474 | 475 |
| 1316 | 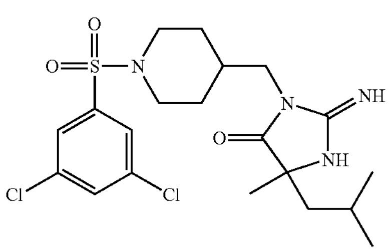 | 474 | 475 |
| 1317 | 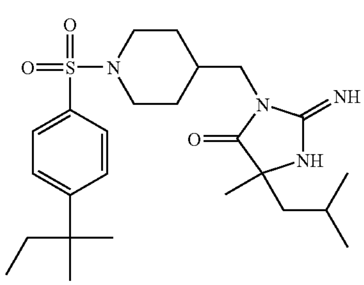 | 476 | 477 |

-continued

| # | Structure | MW | Obs. m/e |
|---|---|---|---|
| 1318 | 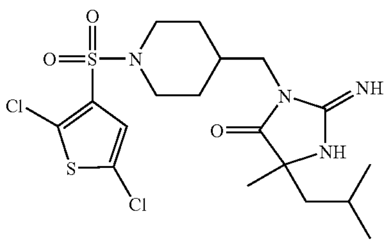 | 480 | 481 |
| 1319 | 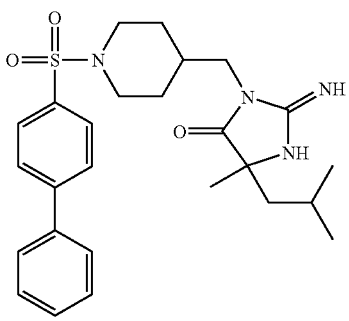 | 482 | 483 |
| 1320 | 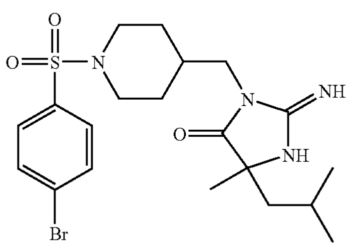 | 484 | 485 |
| 1321 | 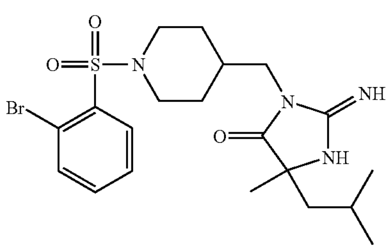 | 484 | 485 |
| 1322 | 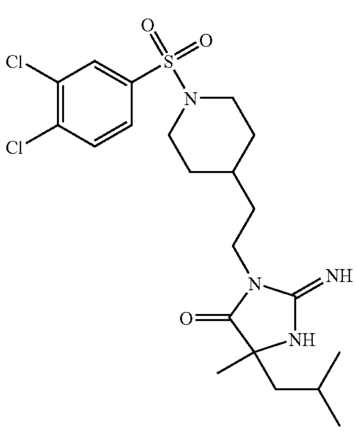 | 488 | 489 |

| # | Structure | MW | Obs. m/e |
|---|---|---|---|
| 1323 | 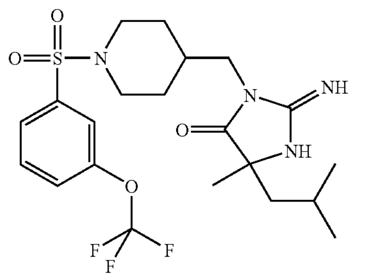 | 490 | 491 |
| 1324 | 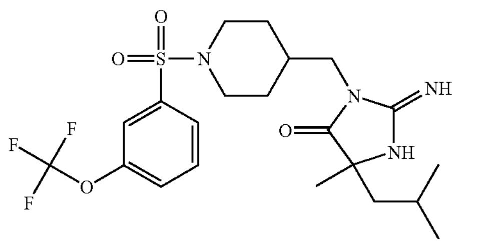 | 490 | 491 |
| 1325 | 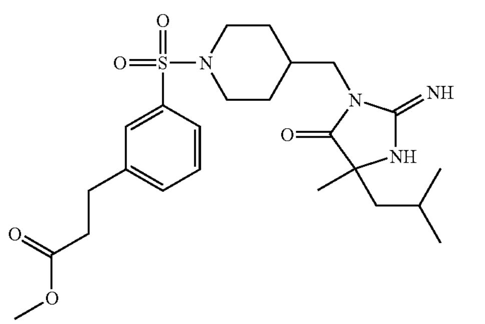 | 492 | 493 |
| 1326 | 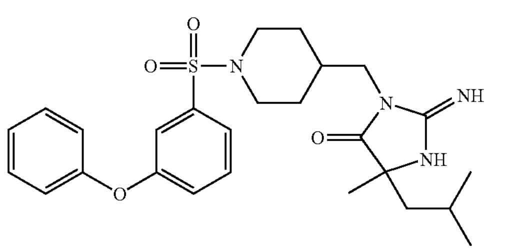 | 498 | 499 |
| 1327 | 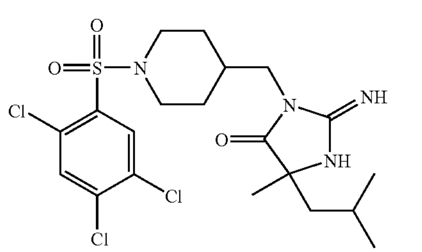 | 508 | 509 |

-continued
| # | Structure | MW | Obs. m/e |
|---|---|---|---|
| 1328 | 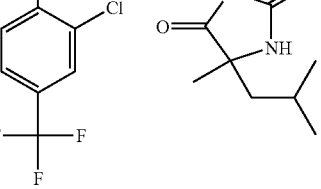 | 508 | 509 |
| 1329 | 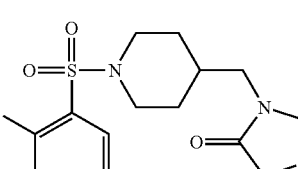 | 508 | 509 |
| 1330 | 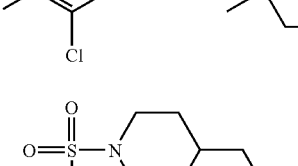 | 508 | 509 |
| 1331 | 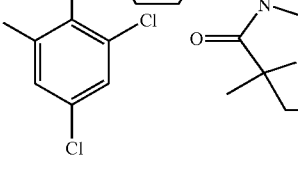 | 542 | 543 |
| 1332 | 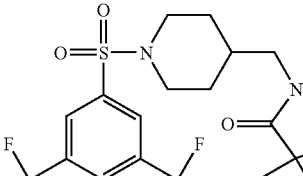 | 557 | 558 |

Method T

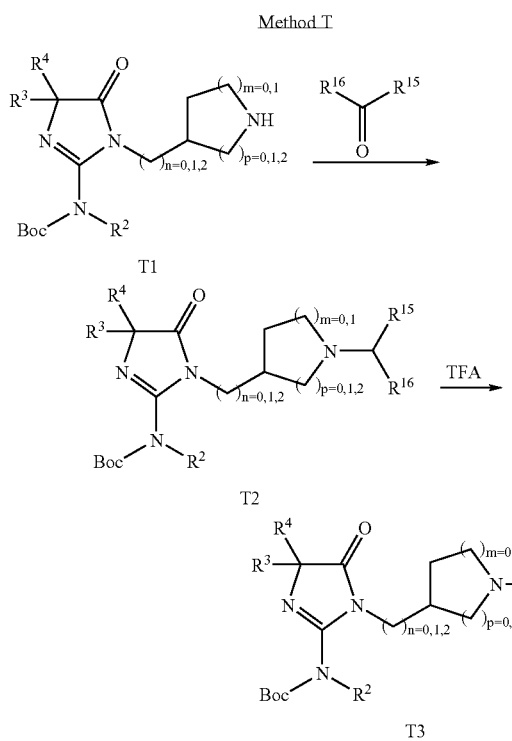

Method T, Step 1.

To a microtiter plate well containing 1 ml solution of T1 (n=1, p=2, m=1, $R^2$=H, $R^3$=Me; $R^4$=iBu) in DCM (0.010 g) and $R^{15}$C(O)$R^{16}$ (5 equiv, $R^{15}$=H, $R^{16}$=Ph) was added Sodium cyanoborohydride in dichloroethane (14.3 mg/mL, 2 equiv.). The well was capped and shaken for 20 h before MP-TsOH Resin (100 mg, 1.29 mmol/g) was added to the well followed by additional MP-TsOH resin (50 mg) after 2 h. After the mixture was shaken for another 1 h, the mixture was filtered and the resin washed with dichloroethane (1 mL) (3×), then MeOH (1 mL) (2×). The resin was treated with 7N ammonia in MeOH (1 mL) for 30 min (2×) followed by filtration and evaporation of solvent to give T2 (n=1, p=2, m=1, $R^2$=H, $R^3$=Me; $R^4$=Bu and $R^{15}$=Ph and $R^{16}$=H).

Method T, Step 2.

Procedure similar to Method Q, step 6 was used for the transformation of T2 (n=1, p=2, m=1, $R^2$=H, $R^3$=Me; $R^4$=iBu and $R^{15}$=Ph and $R^{15}$=H) to T3 (n=1, p=2, m=1, $R^2$=H, $R^3$=Me; $R^4$==Bu and $R^{15}$=Ph and $R^{16}$=H).

The following compounds were prepared using similar methods:

| # | Structure | MW | Obs. m/e |
|---|---|---|---|
| 1333 | 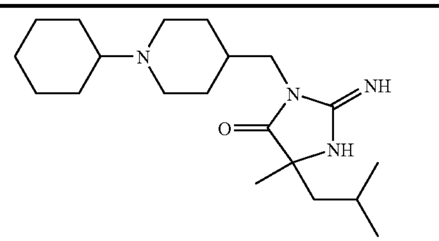 | 348 | 349 |
| 1334 | 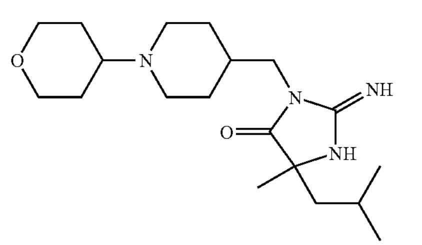 | 350 | 351 |
| 1335 | 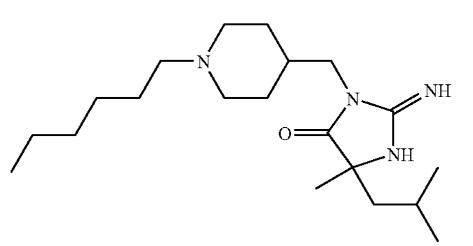 | 350 | 351 |

| # | Structure | MW | Obs. m/e |
|---|---|---|---|
| 1336 | 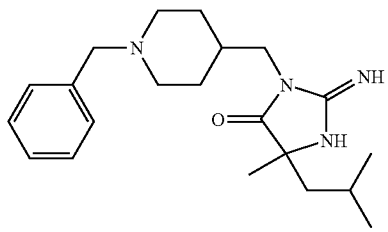 | 356 | 357 |
| 1337 | 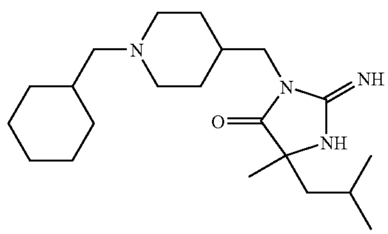 | 362 | 363 |
| 1338 | 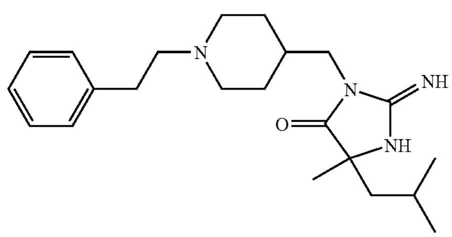 | 370 | 371 |
| 1339 | 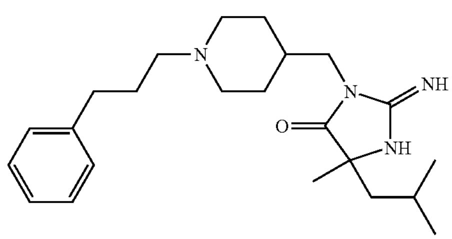 | 384 | 385 |
| 1340 | 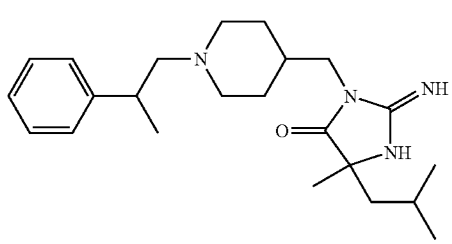 | 384 | 385 |
| 1341 | 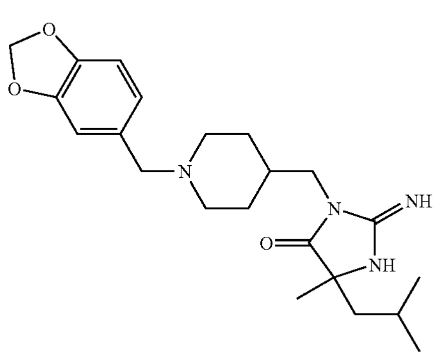 | 400 | 401 |

-continued

| # | Structure | MW | Obs. m/e |
|---|-----------|-----|----------|
| 1342 | 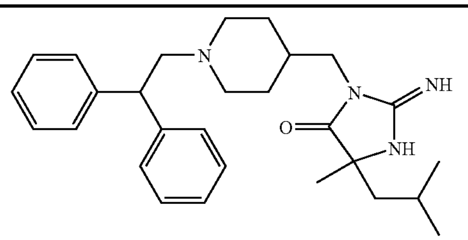 | 446 | 447 |
| 1343 | 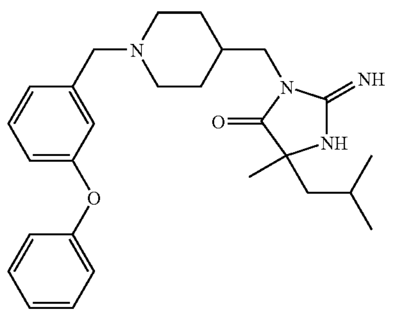 | 448 | 449 |

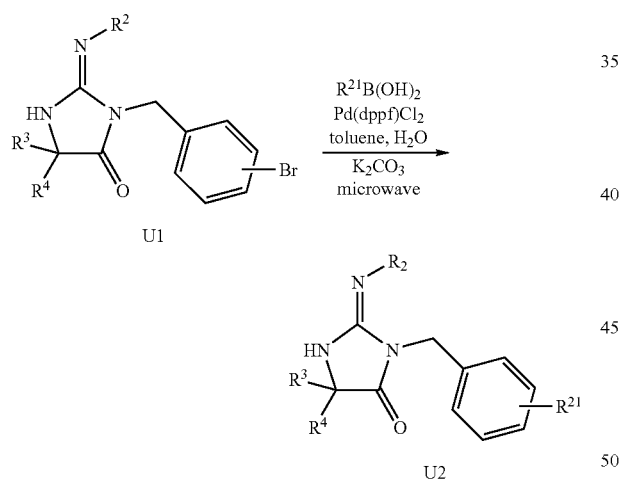

Method U

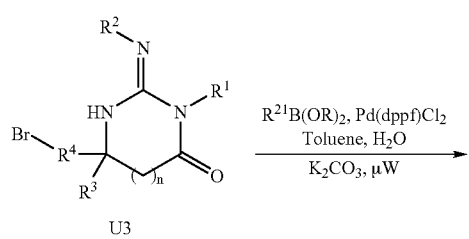

Alternatively, similar synthetic method can be used for the generation of other types of compounds. i.e.

-continued

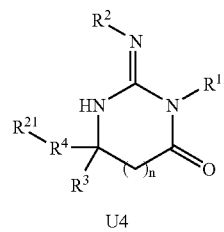

In a microwave vial was charged U1 ($R^2$=H; $R^3$=i-Bu, $R^4$=Me) (0.025 g) in toluene (4 mL), potassium carbonate (0.035 g), Pd(dppf)Cl$_2$ (0.020 g). water (0.02 mL) and $R^{21}$B(OH)$_2$ ($R^{21}$=m-Methoxyphenyl) (3 eq.) were placed. The vial was placed in a microwave for 10 min. at 150° C. The reaction mixture was diluted with dichloromethane and extracted with 2.5N NaOH. The dried (MgSO$_4$) dichloromethane solution was concentrated in vacuo to give a brown residue which was purified via a RP Prep LCMS system to give product U2 ($R^2$=H; $R^3$=$^i$Bu: $R^4$=Me; $R^2$=m-methoxyphenyl).

The following compounds were prepared using similar methods:

| # | Structure | MW | Obs. m/e |
|---|---|---|---|
| 1344 | 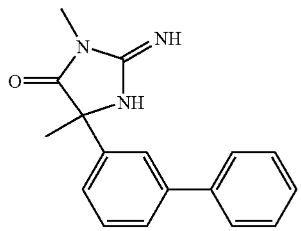 | 279 | 280 |
| 1345 | 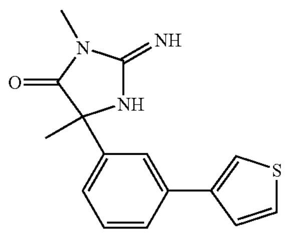 | 285 | 286 |
| 1346 | 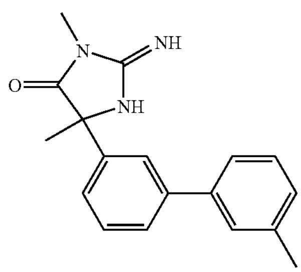 | 293 | 294 |
| 1347 | 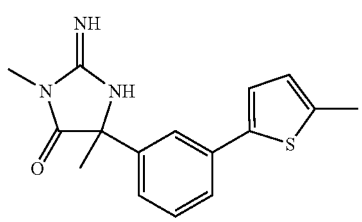 | 299 | 300 |
| 1348 | 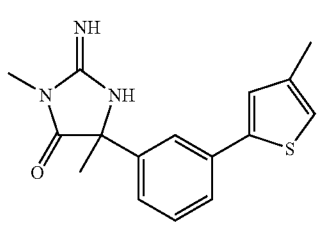 | 299 | 300 |
| 1349 | 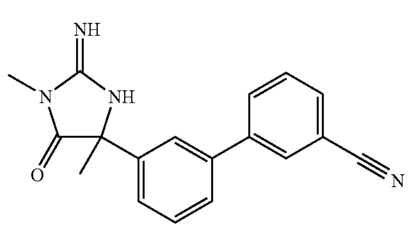 | 304 | 305 |

-continued

| # | Structure | MW | Obs. m/e |
|---|---|---|---|
| 1350 | 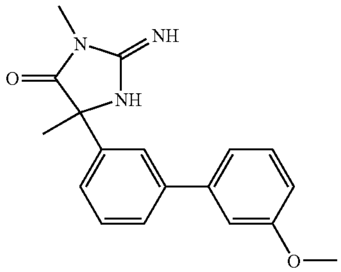 | 309 | 310 |
| 1351 | 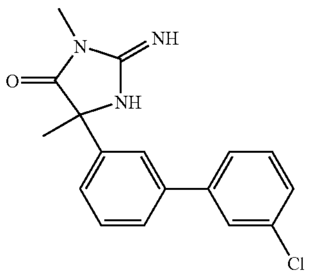 | 313 | 314 |
| 1352 | 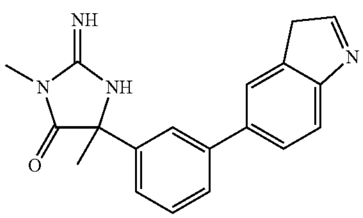 | 318 | 319 |
| 1353 | 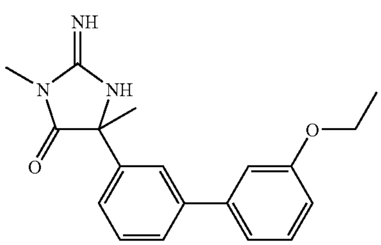 | 323 | 324 |
| 1354 | 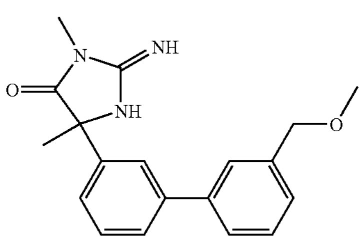 | 323 | 324 |
| 1355 | 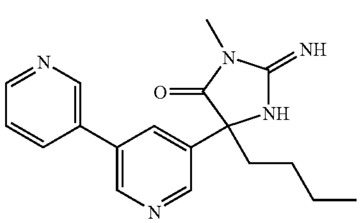 | 323 | 324 |

| # | Structure | MW | Obs. m/e |
|---|---|---|---|
| 1356 | 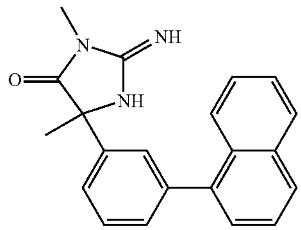 | 329 | 330 |
| 1357 | 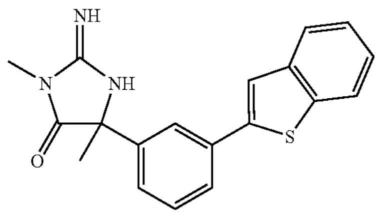 | 335 | 336 |
| 1358 | 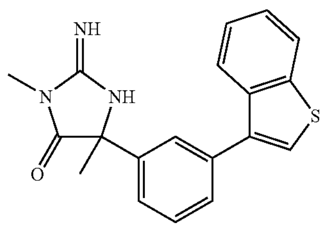 | 335 | 336 |
| 1359 | 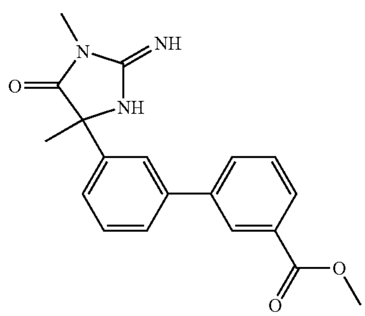 | 337 | 338 |
| 1360 | 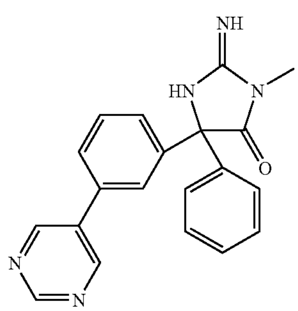 | 343 | 344 |
| 1361 | 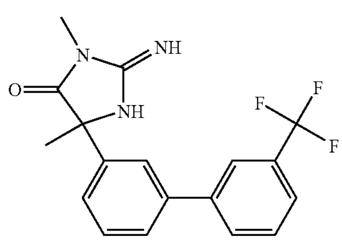 | 347 | 348 |

| # | Structure | MW | Obs. m/e |
|---|---|---|---|
| 1362 | 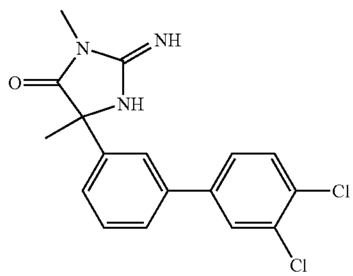 | 347 | 348 |
| 1363 | 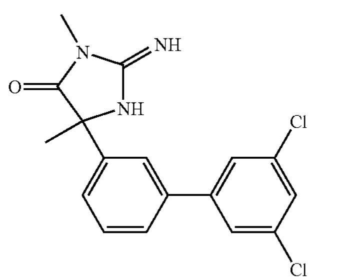 | 347 | 348 |
| 1364 | 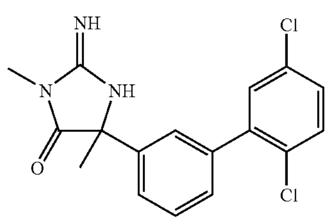 | 347 | 348 |
| 1365 | 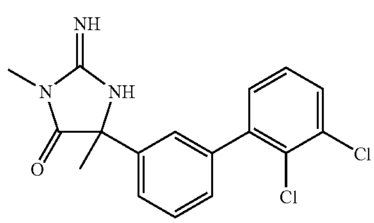 | 347 | 348 |
| 1366 | 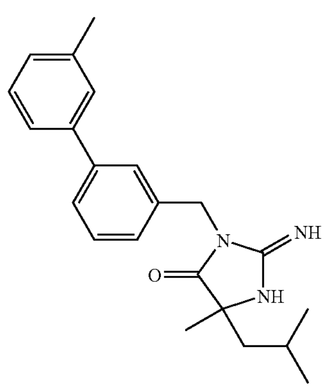 | 349 | 350 |

| # | Structure | MW | Obs. m/e |
|---|---|---|---|
| 1367 | 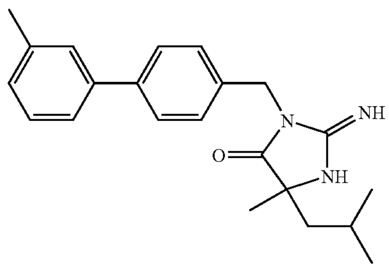 | 349 | 350 |
| 1368 | 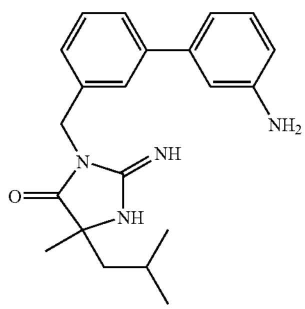 | 350 | 351 |
| 1369 | 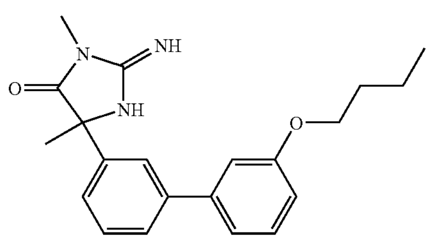 | 351 | 352 |
| 1370 | 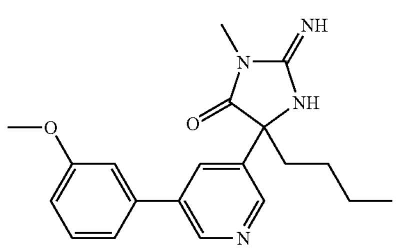 | 352 | 353 |
| 1371 | 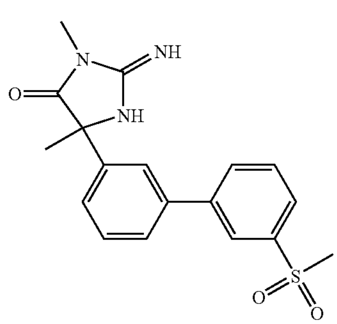 | 357 | 358 |

-continued

| # | Structure | MW | Obs. m/e |
|---|---|---|---|
| 1372 | 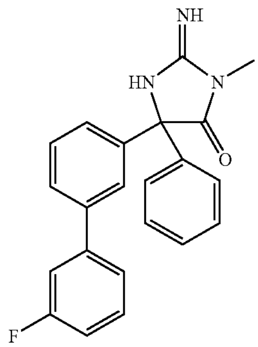 | 359 | 360 |
| 1373 | 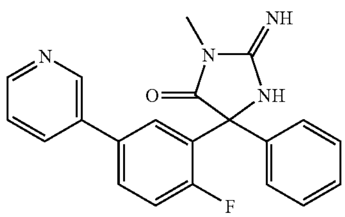 | 360 | 361 |
| 1374 | 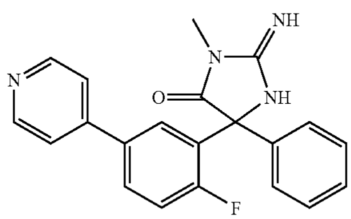 | 360 | 361 |
| 1375 | 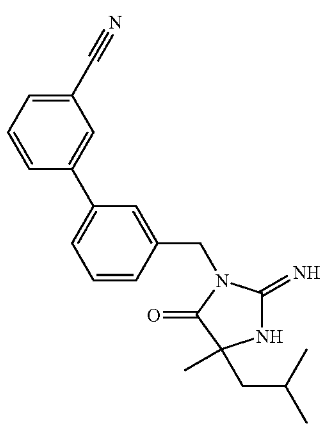 | 360 | 361 |
| 1376 | 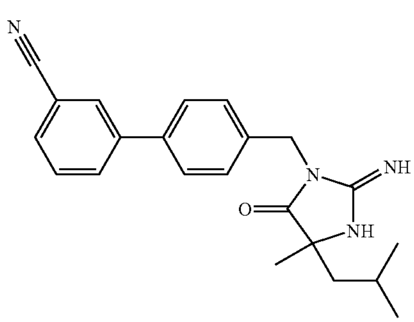 | 360 | 361 |

-continued

| # | Structure | MW | Obs. m/e |
|---|---|---|---|
| 1377 | 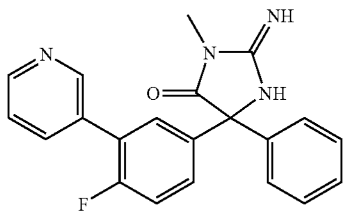 | 360 | 361 |
| 1378 | 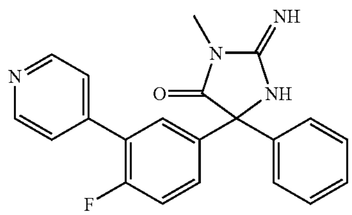 | 360 | 361 |
| 1379 | 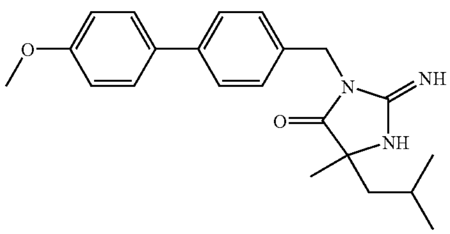 | 365 | 366 |
| 1380 | 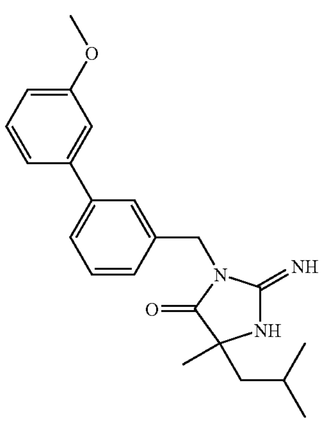 | 365 | 366 |
| 1381 | 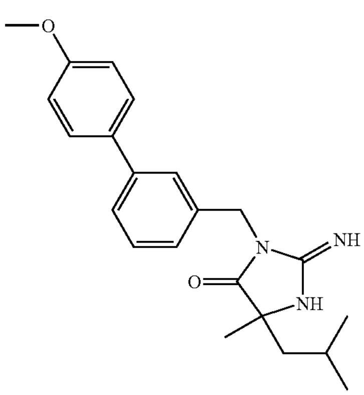 | 365 | 366 |

| # | Structure | MW | Obs. m/e |
|---|---|---|---|
| 1382 | 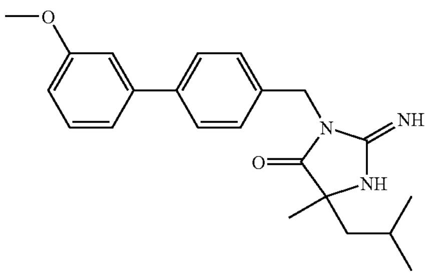 | 365 | 366 |
| 1383 | 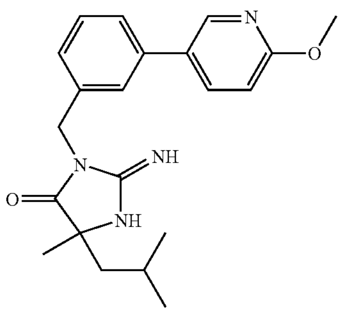 | 366 | 367 |
| 1384 | 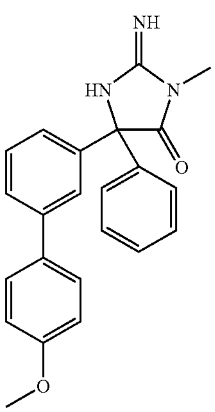 | 371 | 372 |
| 1385 | 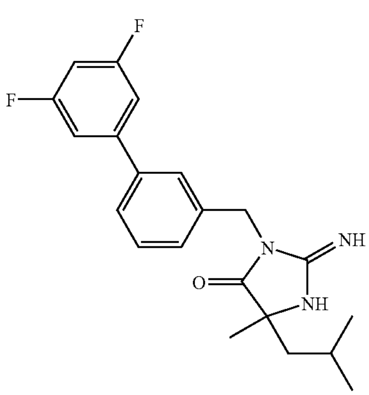 | 371 | 372 |

-continued

| # | Structure | MW | Obs. m/e |
|---|---|---|---|
| 1386 | 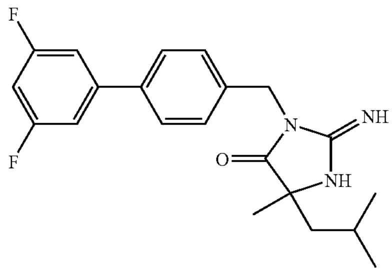 | 371 | 372 |
| 1387 | 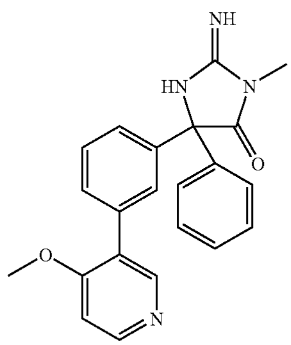 | 372 | 373 |
| 1388 | 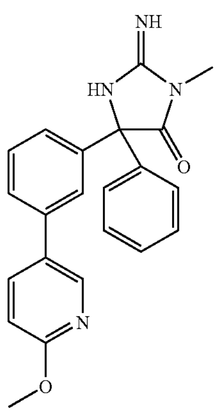 | 372 | 373 |
| 1389 | 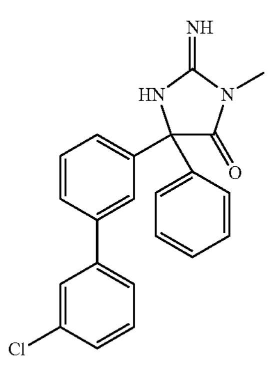 | 375 | 376 |

| # | Structure | MW | Obs. m/e |
|---|-----------|-----|----------|
| 1390 | 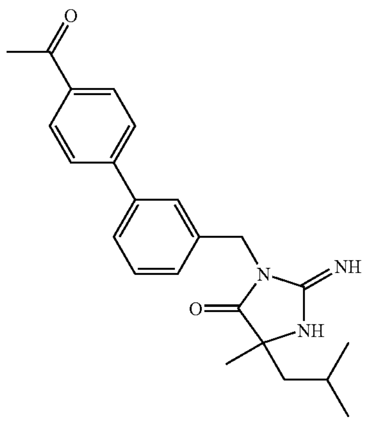 | 377 | 378 |
| 1391 | 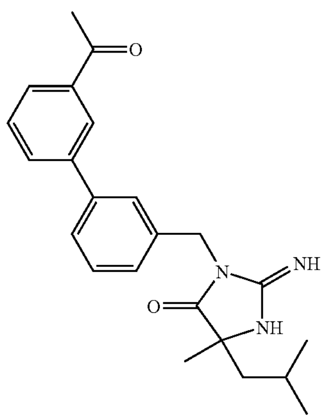 | 377 | 378 |
| 1392 | 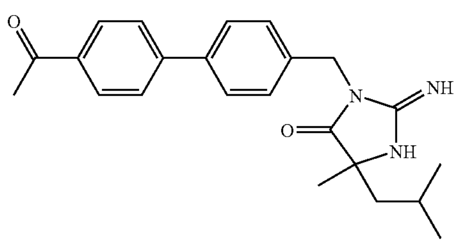 | 377 | 378 |
| 1393 | 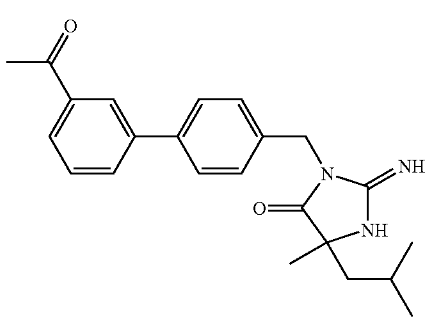 | 377 | 378 |

-continued

| # | Structure | MW | Obs. m/e |
|---|---|---|---|
| 1394 | 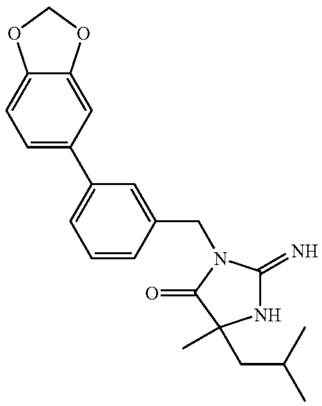 | 379 | 380 |
| 1395 | 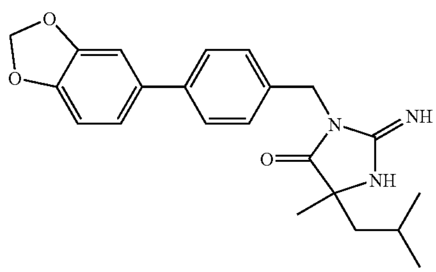 | 379 | 380 |
| 1396 | 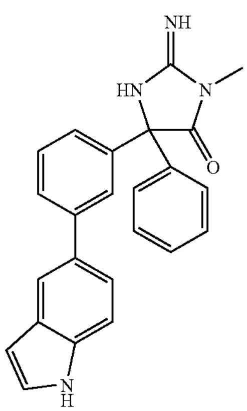 | 380 | 381 |
| 1397 | 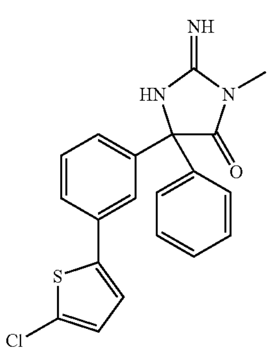 | 381 | 382 |

-continued

| # | Structure | MW | Obs. m/e |
|---|---|---|---|
| 1398 | 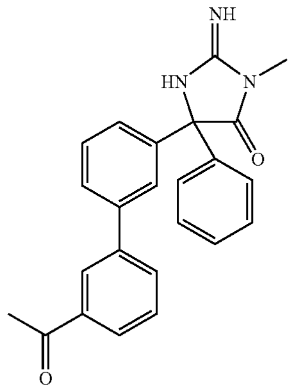 | 383 | 384 |
| 1399 | 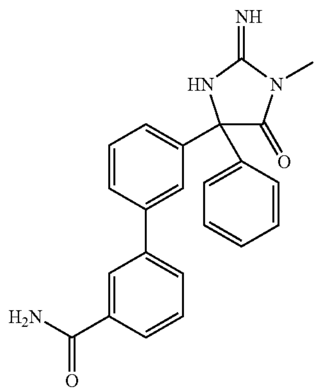 | 384 | 385 |
| 1400 | 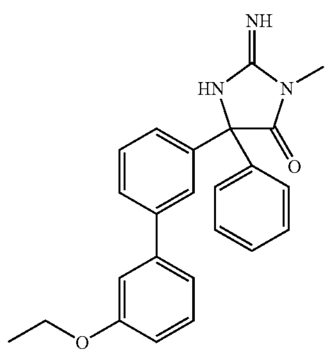 | 385 | 386 |
| 1401 | 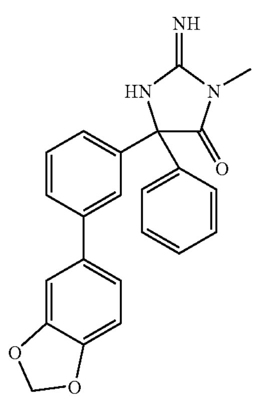 | 385 | 386 |

|   |           |     | Obs. |
|---|-----------|-----|------|
| # | Structure | MW  | m/e  |
| 1402 | | 386 | 387 |
| 1403 | | 387 | 388 |
| 1404 | | 389 | 390 |
| 1405 | | 389 | 390 |
| 1406 | | 392 | 393 |

-continued

| # | Structure | MW | Obs. m/e |
|---|---|---|---|
| 1407 | 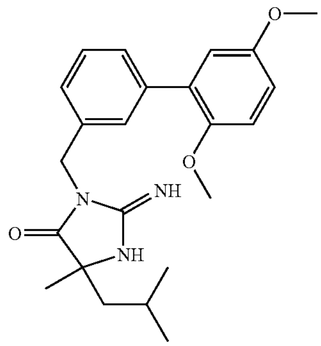 | 395 | 396 |
| 1408 | 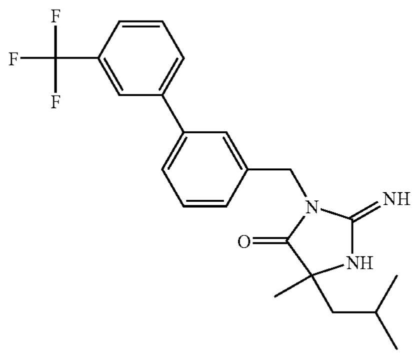 | 403 | 404 |
| 1409 | 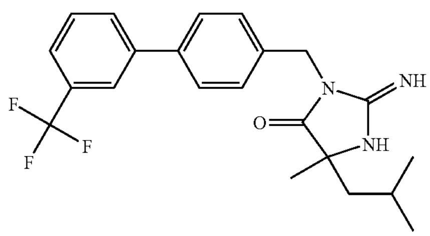 | 403 | 404 |
| 1410 | 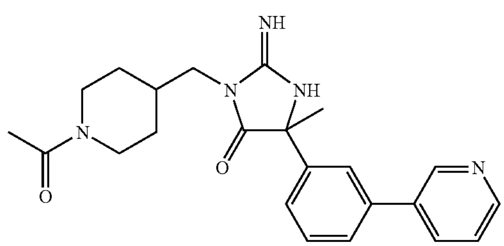 | 405 | 406 |
| 1411 | 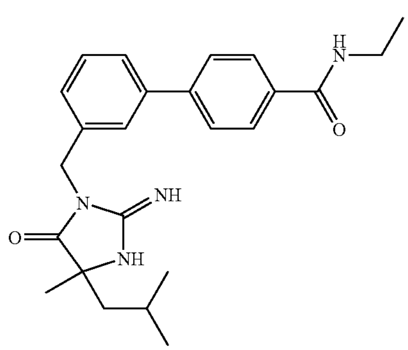 | 406 | 407 |

-continued

| # | Structure | MW | Obs. m/e |
|---|---|---|---|
| 1412 | 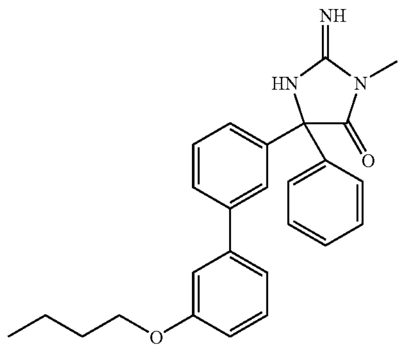 | 413 | 414 |
| 1413 | 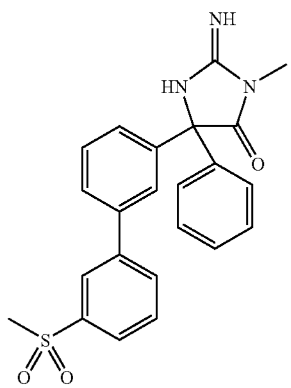 | 419 | 420 |
| 1414 | 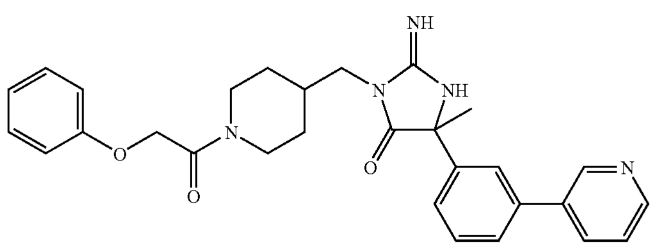 | 497 | 498 |
| 1415 | 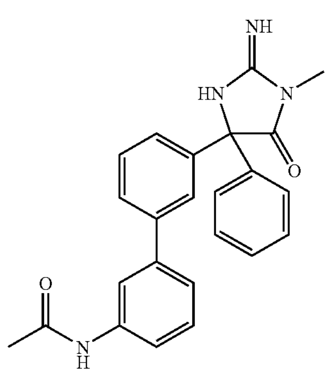 | 398 | TBD |

-continued

| # | Structure | MW | Obs. m/e |
|---|---|---|---|
| 1416 | 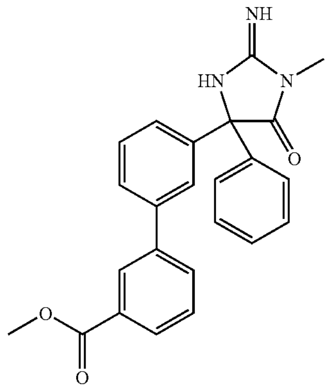 | 399 | TBD |

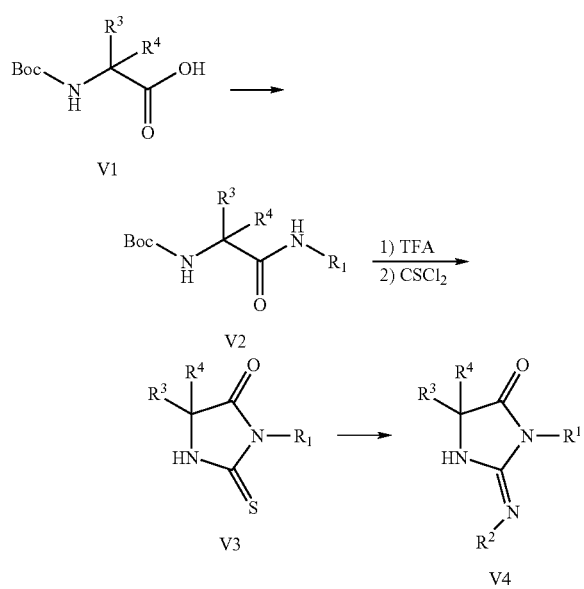

Method V, Step 1:

Compound V1 ($R^3=R^4=Me$) (14.76 mmole), EDCl (14.76 mmole), HOAt mmole), and DIEA (14.76 mmole) were mixed with 36 ml DCM. This mixture was stirred at RT for 15 min before 3-chlorobenzylamine was added. After the reaction solution was stirred at RT overnight, it was washed with sodium carbonate (3×), water, 1N HCl (4×), and aq sodium bicarbonate and dried over anhydrous sodium sulfate. The solvent was evaporated and the residue was purified on flash column to give the amide product V2 ($R^1$=3-chlorobenzyl; $R^3=R^4=Me$).

Method V, Step 2

Compound V2 ($R^1$=3-chlorobenzyl; $R^3=R^4=Me$) (8.33 mmole) was dissolved in 35 ml anhydrous DCM, and cooled to 0-5° C. Thiophosgene (9.16 mmole) in 10 ml DCM was added dropwise under $N_2$ followed by addition of DIEA (11.96 mmole). The solution was stirred in ice bath for 0.5 h before the reaction mixture was washed with saturated sodium bicarbonate (3×), brine, and dried over anhydrous sodium sulfate. The solvent was evaporated and residue purified on flash column using ethylacetate/hexane to give the thiohydantoin V3 ($R^1$=3-chlorobenzyl; $R^3=R^4=Me$).

Method V, Step 3:

The thiohydantoin V3 ($R^1$=3-chlorobenzyl; $R^3=R^4=Me$) was treated with t-butyl hydroperoxide and ammonium hydroxide in MeOH at RT for 48 h to give compound V4 ($R^1$=3-chlorobenzyl; $R^2$=H; $R^3=R^4=Me$).

The following compounds were prepared using similar method.

| # | Structure | MW | Obs. m/e |
|---|---|---|---|
| 1417 | 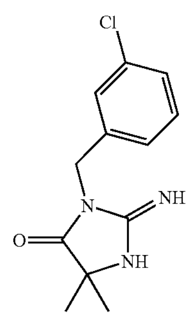 | 251 | 252 |
| 1418 | 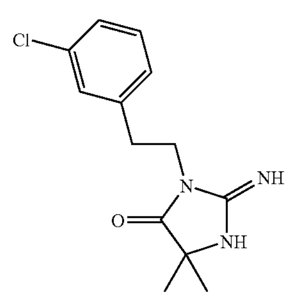 | 265 | 266 |

-continued
| # | Structure | MW | Obs. m/e |
|---|---|---|---|
| 1419 | 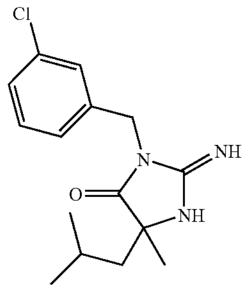 | 293 | 294 |
| 1420 | 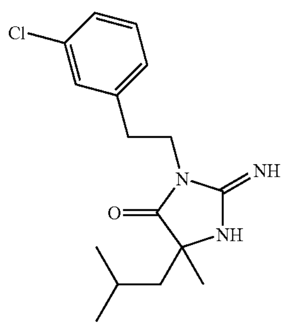 | 307 | 308 |
| 1421 | 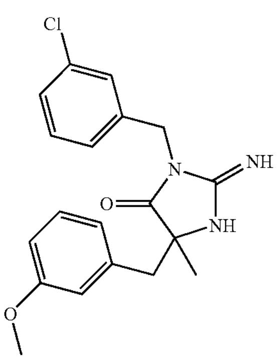 | 357 | 358 |
| 1422 | 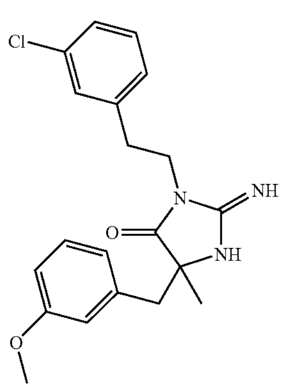 | 371 | 372 |
Method W
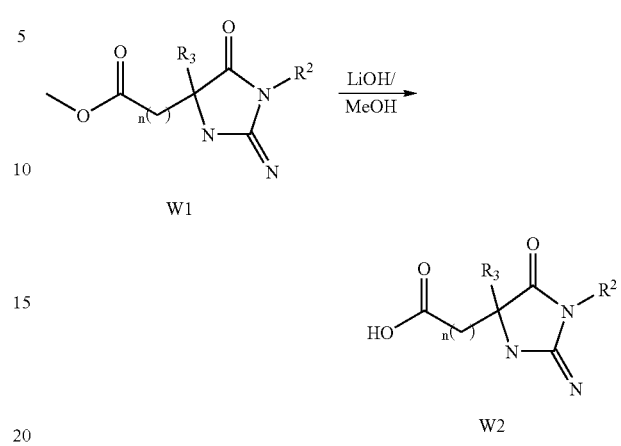
Compound W1 obtained using method A (n=1, $R^2$=m-Cl-Bn, $R^3$=Me) was hydrolyzed to W2 (n=1, $R^2$=m-Cl-Bn, $R^3$=Me) using two equivalent of LiOH in MeOH.
The following compounds were synthesized in similar fashion:
| # | Structure | MW | Obs. m/e |
|---|---|---|---|
| 1423 | 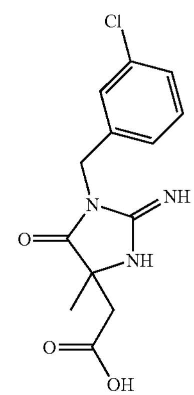 | 295 | 296 |
| 1424 | 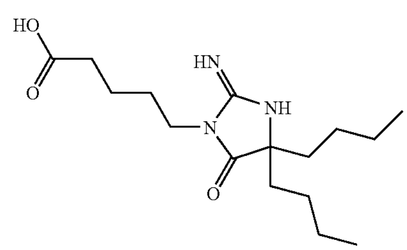 | 311 | 312 |
| 1425 | 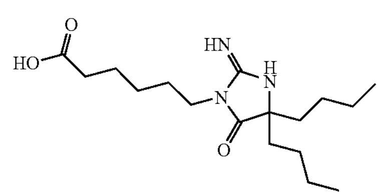 | 325 | 326 |

-continued

| # | Structure | MW | Obs. m/e |
|---|---|---|---|
| 1426 | 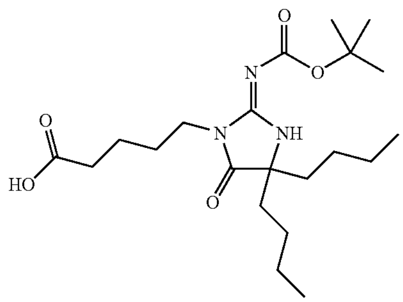 | 411 | 412 |
| 1427 | 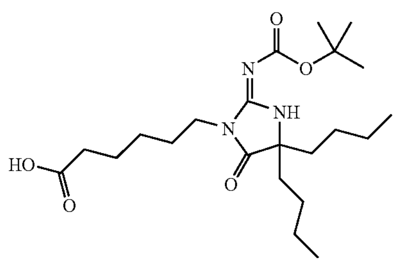 | 425 | 426 |

Method X

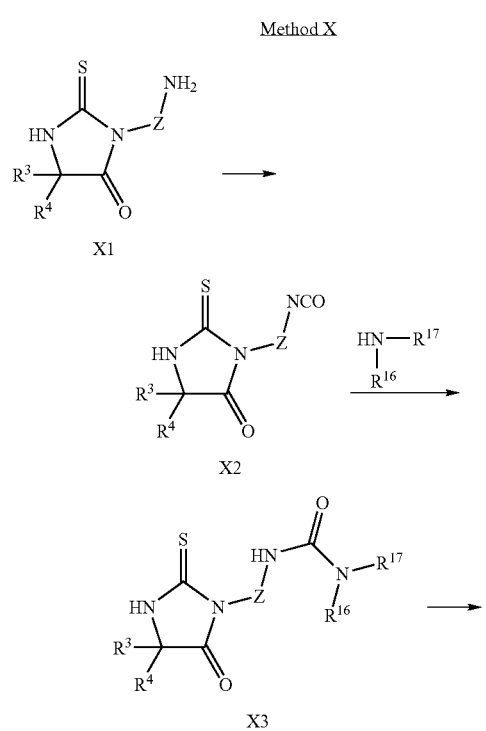

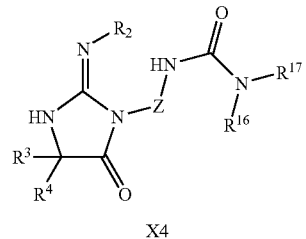

X4

(In the scheme, -Z-NH—C(O)—N($R^{16}$)($R^{17}$)— is equivalent to $R^1$ substituted by $R^{21}$, or $R^1$ Subsitituted by alkyl-$R^{22}$, wherein $R^{21}$ and $R^{22}$ are —NH—C(O)—N($R^{16}$)($R^{17}$) and $R^{15}$ is H, and wherein Z is optionally substituted alkylene-arylene, alkylene-arylene-alkylene, alkylene-heteroarylene, alkylene-heteroarylene-alkylene, alkylene-cycloalkylene, alkylene-cycloalkylene-alkylene, alkylene-heterocycloalkylene, alkylene-heterocycloalkylene-alkylene, arylene, heteroarylene, cycloalkylene or heterocycloalkylene)

Method X, Step 1:

To a mixture of the amine X1 obtained using method L ($R^3$=Me; $R^4$=Bu; Z=para-($CH_2$)$C_6H_4$($CH_2$)—) (10 mg) in DCM and sat. $NaHCO_3$ (1:1 by volume) was added triphosgene (0.33 eq) at r.t. The solution was stirred vigorously for 40 minutes before the organic layer was separated and dried over anhydrous $Na_2SO_4$. The organic solution was evaporated to give compound X2 ($R^3$=Me; $R^4$=i-Bu; Z=para-($CH_2$)$C_6H_4$($CH_2$)—).

Method X, Step 2:

Compound X3 ($R^{15}$=H; $R^{16}$=cyclopropylmethyl; $R^3$=Me; $R^4$=$^i$Bu; Z=para-($CH_2$)$C_6H_4$($CH_2$)—) was prepared from X2 ($R^3$=Me; $R^4$=i-Bu; Z=para-($CH_2$)$C_6H_4$($CH_2$)—) using method similar to method M, step 1.

Method X, Step 3:

Compound X4 ($R^{16}$=H; $R^{17}$=cyclopropylmethyl; $R^{12}$=H; $R^3$=Me; $R^4$=$^i$Bu; Z=para-($CH_2$)$C_6H_4$($CH_2$)—) was prepared from X3 ($R^{16}$=H; $R^{17}$=cyclopropylmethyl; $R^2$=H; $R^3$=Me; $R^4$=$^i$Bu; Z=para-($CH_2$)$C_6H_4$($CH_2$)—) using method similar to method A Step 3. NMR ($CD_3OD$): δ 7.25, s, 4H; δ 4.8, m, 2H; δ 4.25, s, 2H; δ 2.9, m, 2H; δ 1.68, m, 2H; δ 1.44, m, 1H; δ 1.36, s, 3H, δ 0.9, m, 1H; δ 0.82, m, 3H; δ 0.66, m, 3H; δ 0.4, m, 2H; δ 0.12, m, 2H. ES_LCMS (m/e) 386.1.

The following compounds were prepared using a similar method.

| # | Structure | MW | Obs. m/e |
|---|---|---|---|
| 1428 | 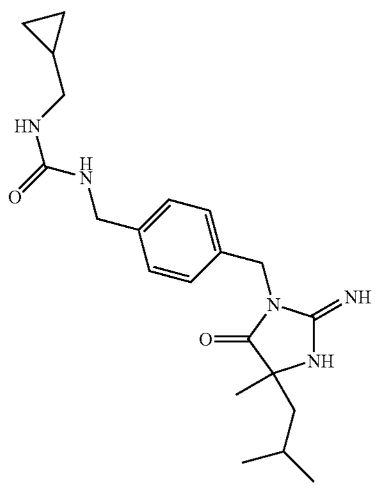 | 385 | 386 |
| 1429 | 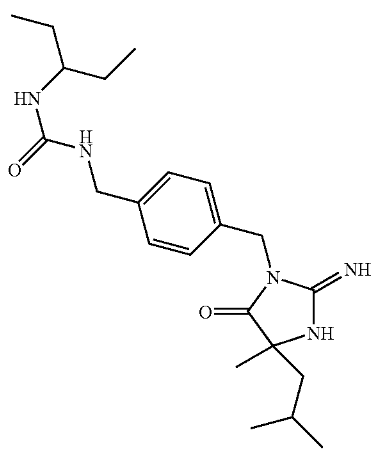 | 401 | 402 |
| 1430 | 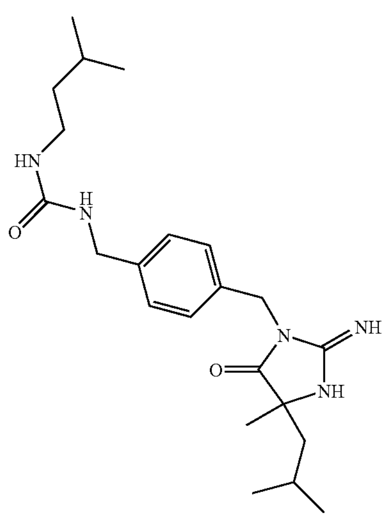 | 401 | 402 |

-continued

| # | Structure | MW | Obs. m/e |
|---|---|---|---|
| 1431 | 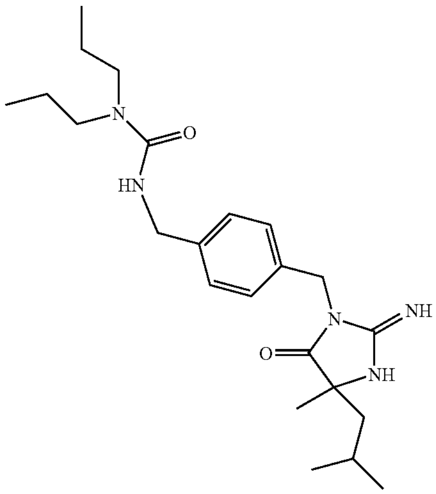 | 415 | 416 |
| 1432 | 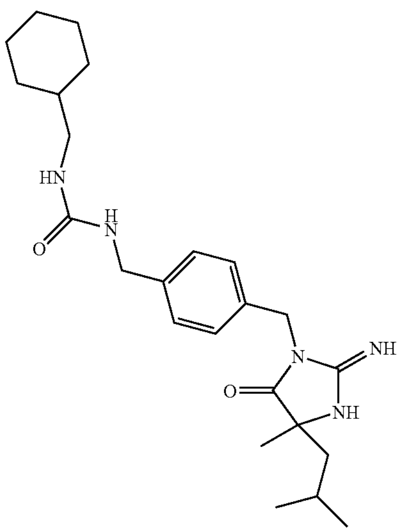 | 427 | 428 |
| 1433 | 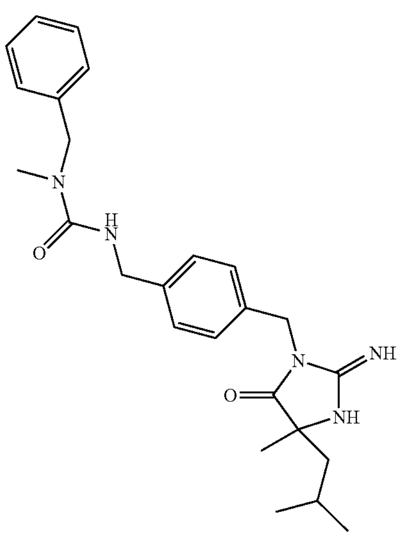 | 435 | 436 |

-continued

| # | Structure | MW | Obs. m/e |
|---|---|---|---|
| 1434 | 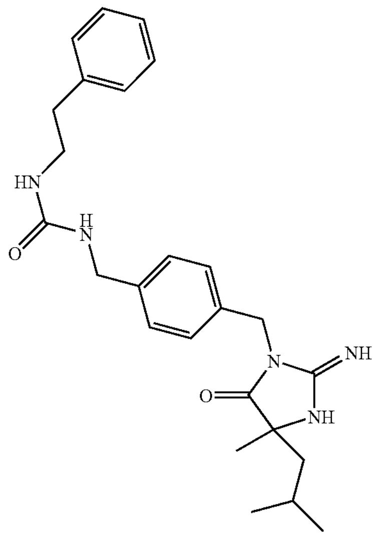 | 435 | 436 |
| 1435 | 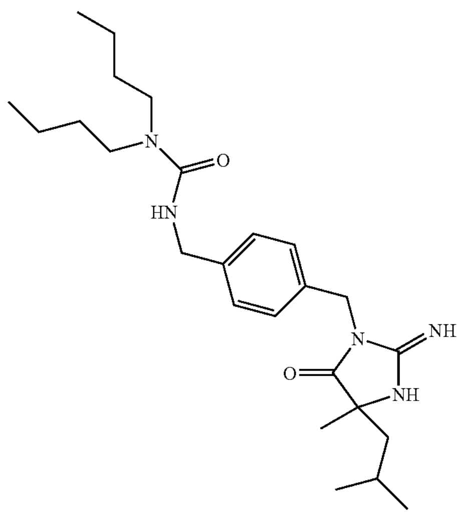 | 443 | 444 |
| 1436 | 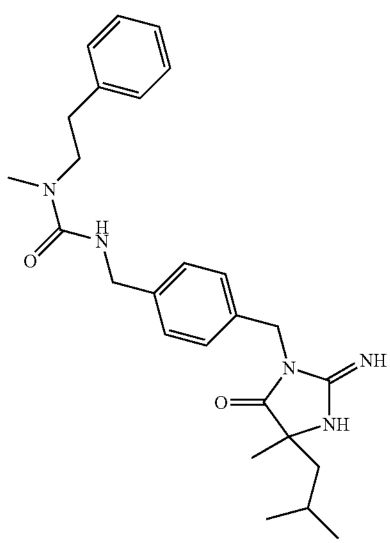 | 449 | 450 |

| # | Structure | MW | Obs. m/e |
|---|---|---|---|
| 1437 | 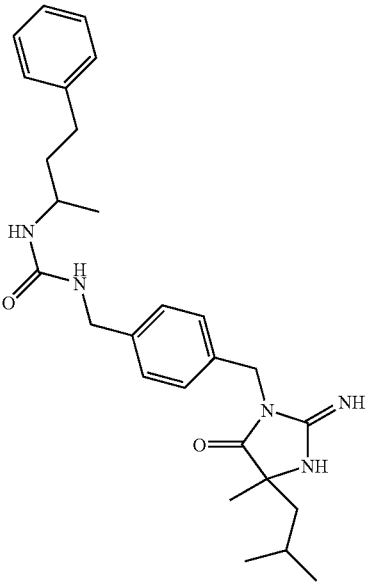 | 463 | 464 |
| 1438 | 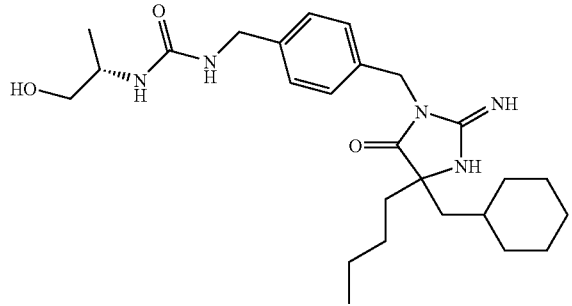 | 471 | 472 |
| 1439 | 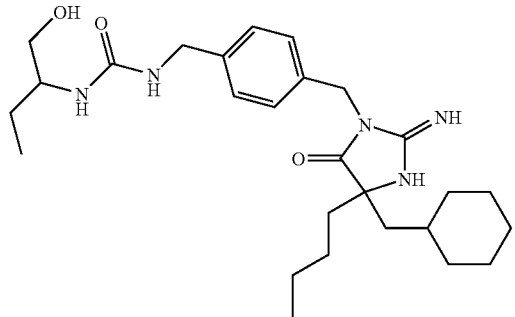 | 485 | 486 |

-continued

| # | Structure | MW | Obs. m/e |
|---|---|---|---|
| 1440 | 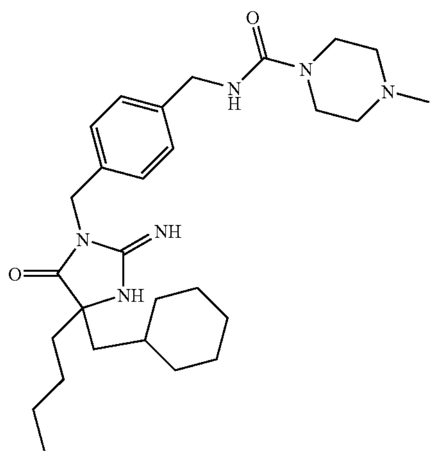 | 496 | 497 |
| 1441 | 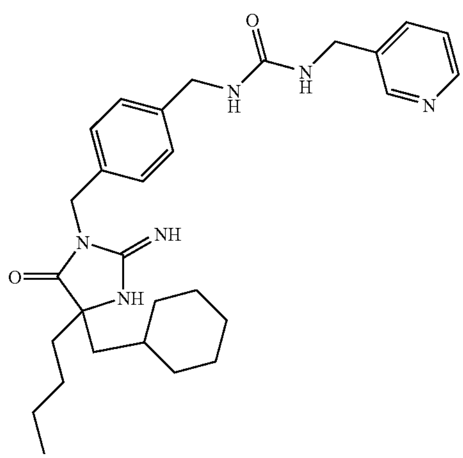 | 504 | 505 |
| 1442 | 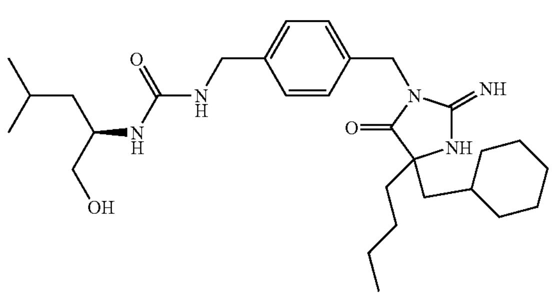 | 513 | 514 |

-continued

| # | Structure | MW | Obs. m/e |
|---|---|---|---|
| 1443 | 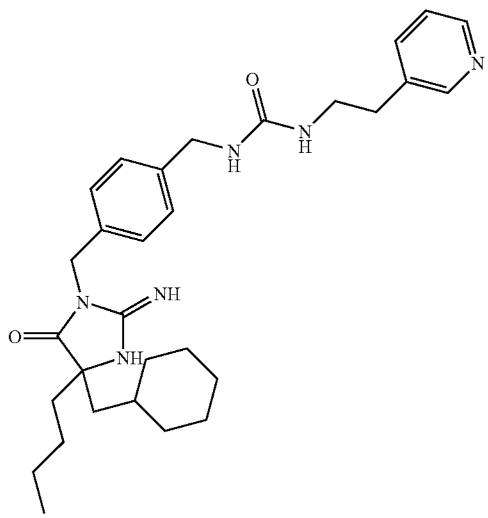 | 518 | 519 |
| 1444 | 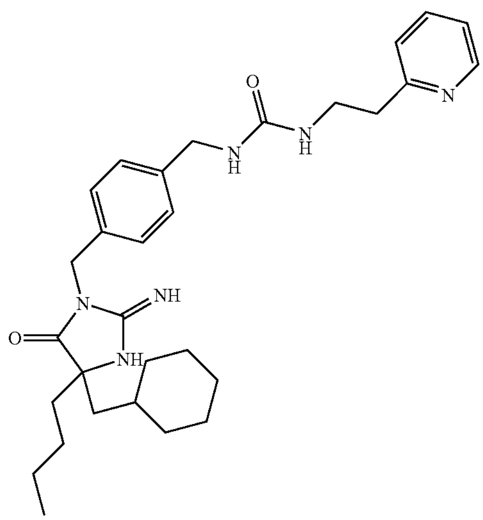 | 518 | 519 |
| 1445 | 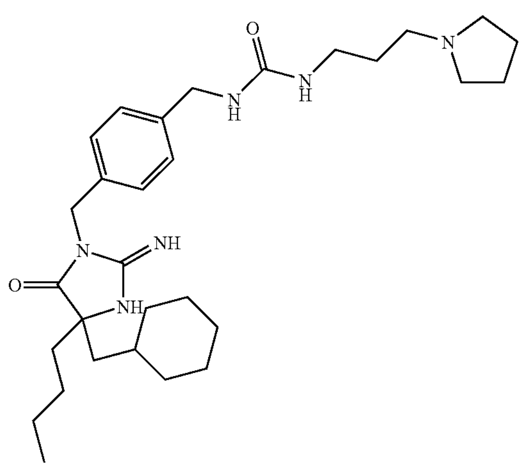 | 524 | 525 |

-continued
| # | Structure | MW | Obs. m/e |
|---|---|---|---|
| 1446 | 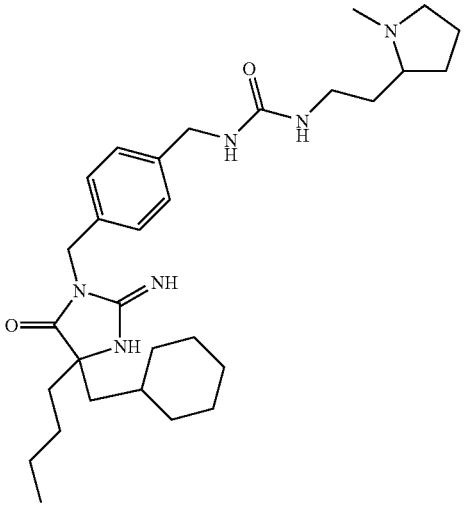 | 524 | 525 |
| 1447 | 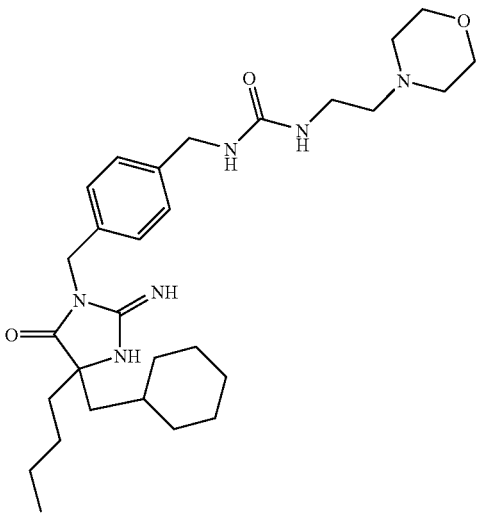 | 526 | 527 |
| 1448 | 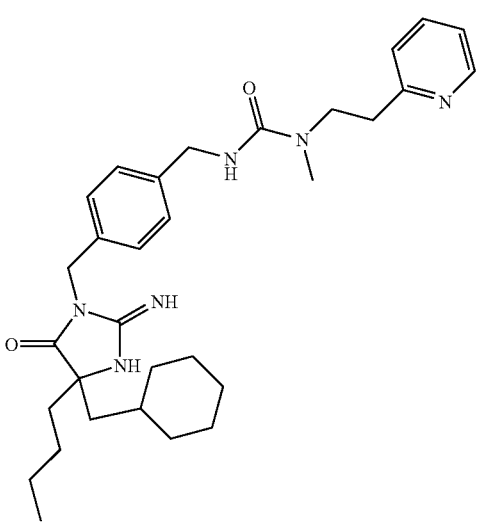 | 532 | 533 |

-continued
| # | Structure | MW | Obs. m/e |
|---|---|---|---|
| 1449 | 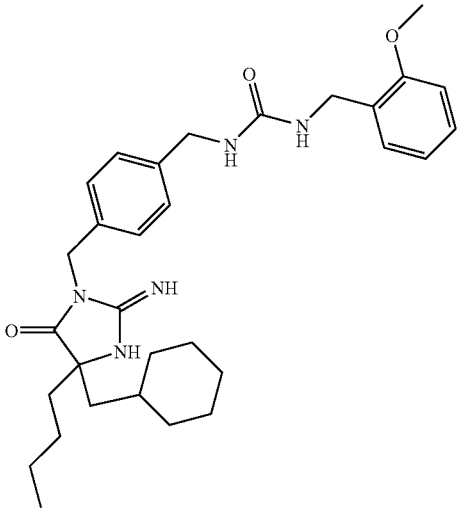 | 533 | 534 |
| 1450 | 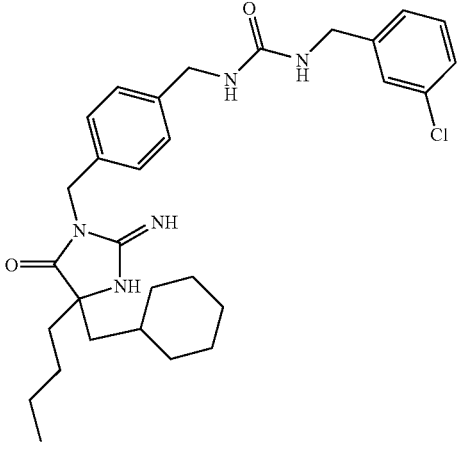 | 537 | 538 |
| 1451 | 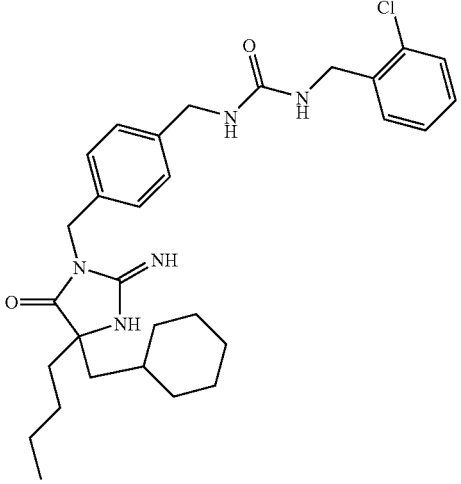 | 537 | 538 |

-continued
| # | Structure | MW | Obs. m/e |
|---|---|---|---|
| 1452 | 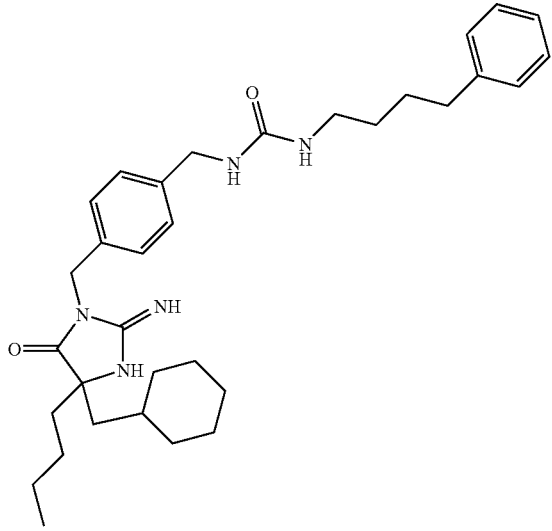 | 545 | 546 |
| 1453 | 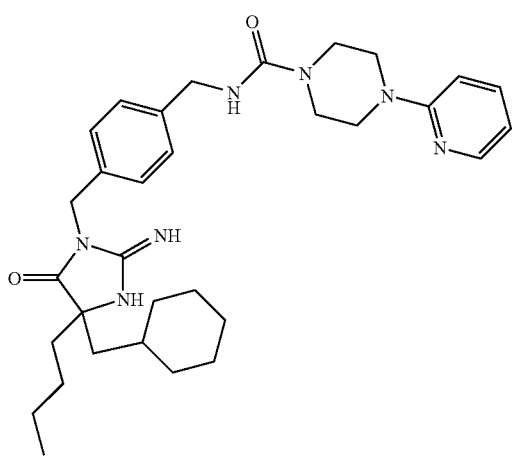 | 559 | 560 |
| 1454 | 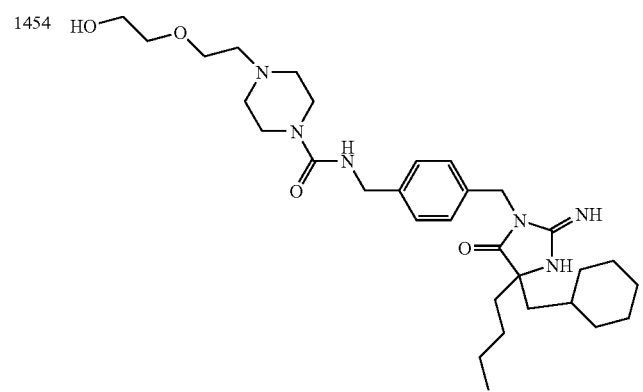 | 570 | 571 |

-continued
| # | Structure | MW | Obs. m/e |
|---|---|---|---|
| 1455 | 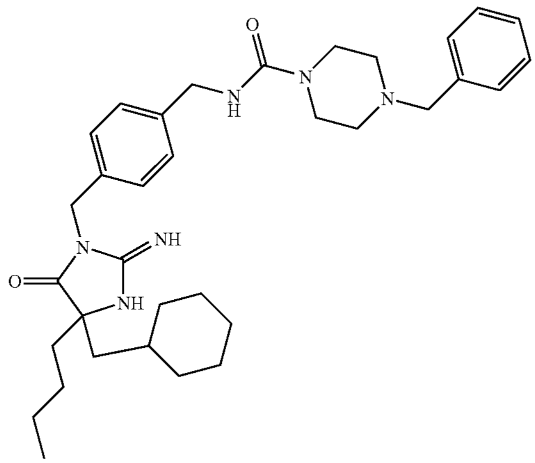 | 572 | 573 |
| 1456 | 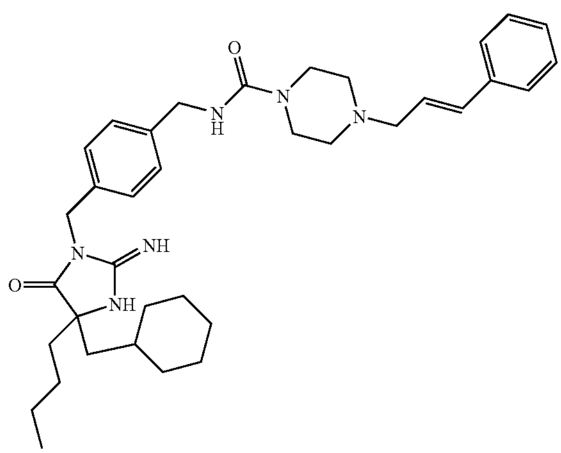 | 598 | 599 |
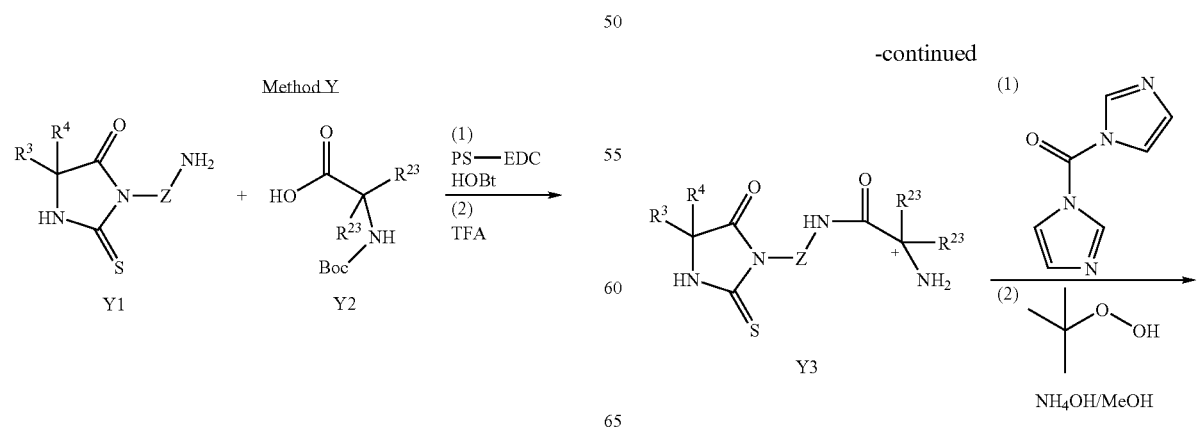

-continued

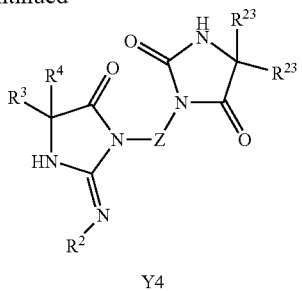

Y4

(In the scheme,

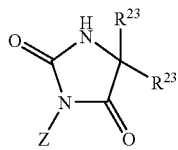

is equivalent to $R^1$ substituted by $R^2$, or $R^1$ Subsitituted by alkyl-$R^{22}$, wherein $R^{21}$ and $R^{22}$ are —N($R^{15}$)—C(O)—N($R^{16}$)($R^{17}$) and $R^{15}$ and $R^{16}$ form a ring as defined above, and wherein Z is optionally substituted alkylene-arylene, alkylene-arylene-alkylene, alkylene-heteroarylene, alkylene-heteroarylene-alkylene, alkylene-cycloalkylene, alkylene-cycloalkylene-alkylene, alkylene-heterocycloalkylene, alkylene-heterocycloalkylene-alkylene, arylene, heteroarylene, cycloalkylene or heterocycloalkylene)

Method Y, Step 1:

The reaction mixture of compound Y1 obtained from Method L ($R^3$=Me; $R^4$=i-Bu; Z=para-(CH$_2$)C$_6$H$_4$(CH$_2$)—) (0.1639 mmole), Y2 ($R^{23}$=H; $R^{23}$=Pr) (0.1967 mmole), PS-EDC resin (0.4917 mmole) and HOBT (0.2459 mmole) in 3.5 ml of mixture of THF, MeCN and DMF (1:1:0.3) was shaken overnight at RT before 6 eq of PS-trisamine resin 3 eq of PS-isocyanate resin were added. After 6 hrs the reaction mixture was filtered and the resin was washed with THF, DCM and MeOH. The combined filtrate was evaporated and the crude was treated with 40% TFA in DCM for 40 min before the solvent was evaporated and residue purified on RP HPLC system to give product Y3 ($R^3$=Me; $R^4$=i-Bu; Z=para-(CH$_2$)C$_6$H$_4$(CH$_2$)—, $R^{23}$=H; $R^{23}$=Pr).

Method Y, Step 2:

The reaction solution of Y3 ($R^3$=Me; $R^4$=i-Bu; Z=para-(CH$_2$)C$_6$H$_4$(CH$_2$)—, $R^{23}$=H; $R^{23}$=Pr) (0.030 mmole), carbonyl diimidazole (0.032 mmole), and DIEA (0.09 mmole) in 0.5 ml DCM was shaken overweekend at RT. The crude was then purified on reverse column to give the thiohydantoin product which was converted into Y4 ($R^2$=H; $R^3$=Me; $R^4$=$^i$Bu; Z=para-(CH$_2$)C$_6$H$_4$(CH$_2$)—, $R^{23}$=H; $R^{23}$=Pr).

The following compounds were prepared using similar method.

| # | Structure | MW | Obs. m/e |
|---|---|---|---|
| 1457 | 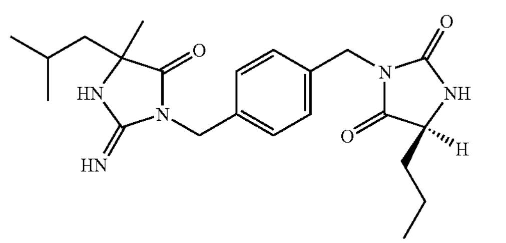 | 413 | 414 |
| 1458 | 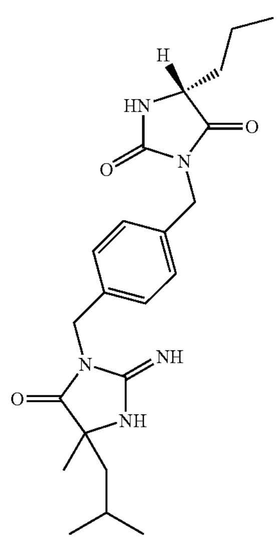 | 413 | 414 |

-continued

| # | Structure | MW | Obs. m/e |
|---|---|---|---|
| 1459 | 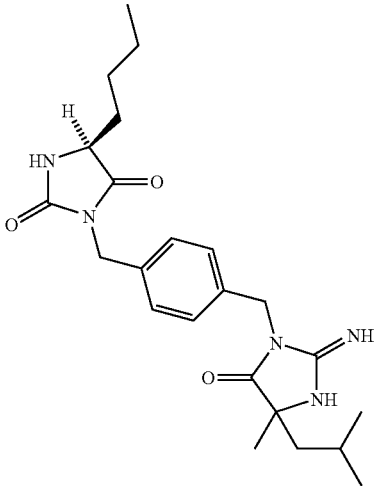 | 427 | 428 |

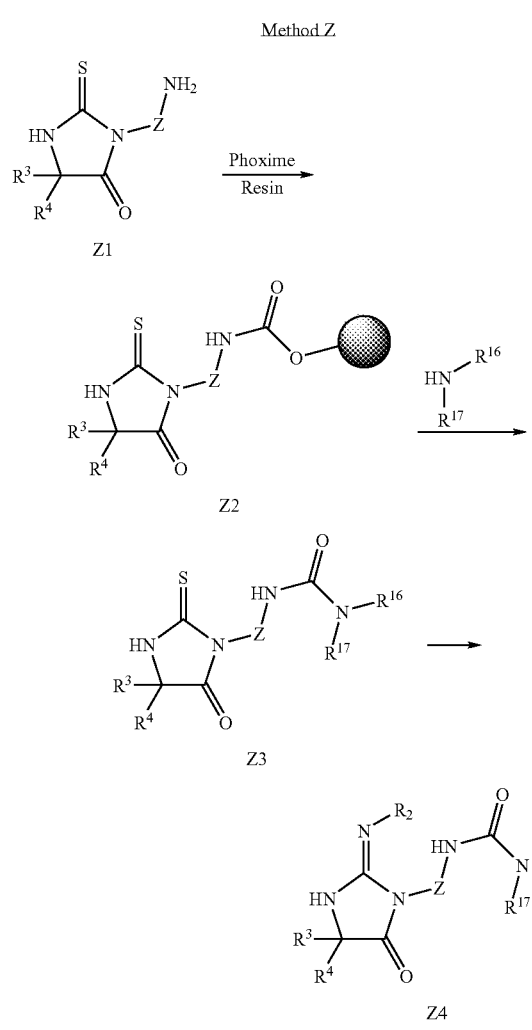

(In the scheme, -Z-NH—C(O)—N($R^{16}$)($R^{17}$)— is equivalent to $R^1$ substituted by $R^{21}$, or $R^1$ Subsitituted by alkyl-$R^{22}$, wherein $R^{21}$ and $R^{22}$ are —N($R^{15}$)—C(O)—N($R^{16}$)($R^{17}$) and $R^{15}$ is H, and wherein Z is optionally substituted alkylene-arylene, alkylene-arylene-alkylene, alkylene-heteroarylene, alkylene-heteroarylene-alkylene, alkylene-cycloalkylene, alkylene-cycloalkylene-alkylene, alkylene-heterocycloalkylene, alkylene-heterocycloalkylene-alkylene, arylene, heteroarylene, cycloalkylene or heterocycloalkylene)

Method Z, Step 1:

To the solution of the Phoxime™ resin (1.23 mmol/g) in DCM was added the amine Z1 obtained from method L ($R^3$=Me; $R^4$=$^i$Bu; Z=para-($CH_2$)$C_6H_4$($CH_2$)—) (2 eq). The mixture was shaken overnight before the resin was filtered and washed with DCM, MeOH, THF (3 cycles), then DCM (×2), dried in vacuum to get resin Z2 ($R^3$=Me; $R^4$=Bu; Z=para-($CH_2$)$C_6H_4$($CH_2$)—).

Method Z, Step 2:

To the resin Z2 ($R^3$=Me; $R^4$=$^i$Bu; =para-($CH_2$)$C_6H_4$($CH_2$)—), swelled in DCM, in toluene was added N-methylbenzylamine (4 eq). The mixture was heated at 80-90° C. overnight before MP-TSOH resin (1.3 mmol/g, 12 eq) was added. The mixture was shaken for 1.5 hours, the solution was filtered and the resin washed with DCM and MeOH. The combined organic solution was concentrated in vacuo to get Z3 ($R^3$=Me; $R^4$=$^i$Bu; Z=para-($CH_2$)$C_6H_4$($CH_2$)—; $R^{16}$=Me; $R^{17}$=Bn).

Method Z, Step 3:

Compound Z4 ($R^3$=Me; $R^4$=$^i$Bu; Z=para-($CH_2$)$C_6H_4$($CH_2$)—; $R^{16}$=Me; $R^{17}$=Bn) was generated from Z3 ($R^3$=Me; $R^4$=$^i$Bu; Z=para-($CH_2$)$C_6H_4$($CH_2$)—; $R^{16}$=Me; $R^{17}$=Bn) using method similar to Method A step 3.

The following compounds were prepared using similar method.

| # | Structure | MW | Obs. m/e |
|---|---|---|---|
| 1460 | 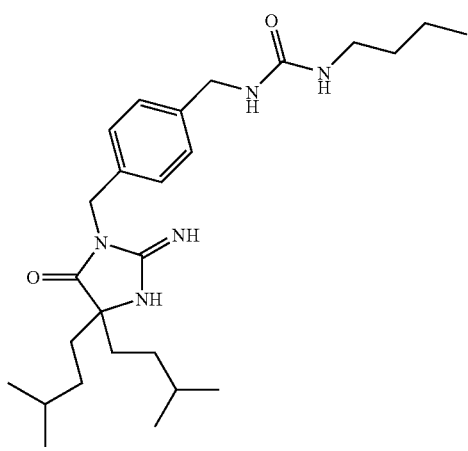 | 457 | 458 |
| 1461 | 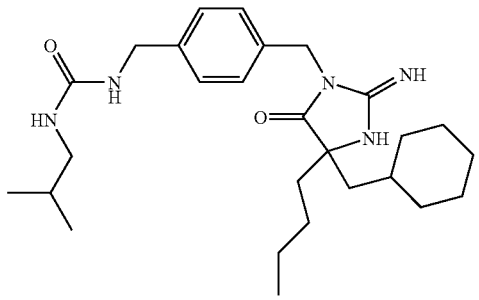 | 469 | 470 |
| 1462 | 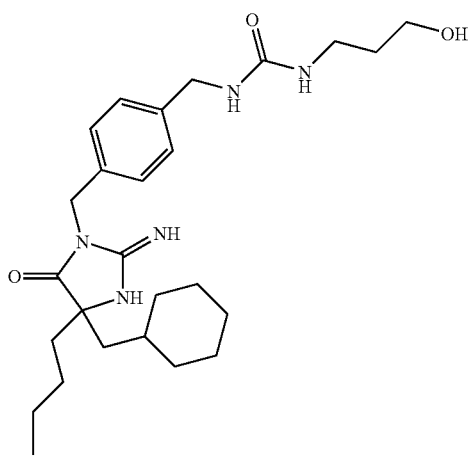 | 471 | 472 |

-continued

| # | Structure | MW | Obs. m/e |
|---|---|---|---|
| 1463 | 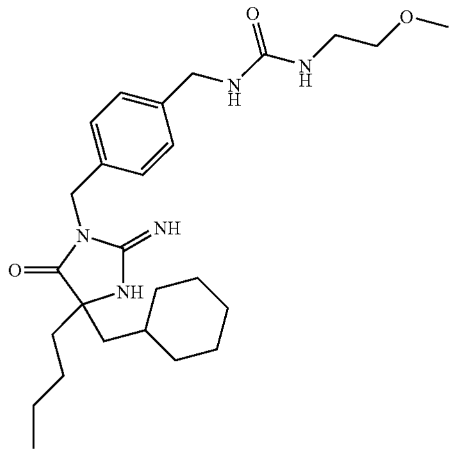 | 471 | 472 |
| 1464 | 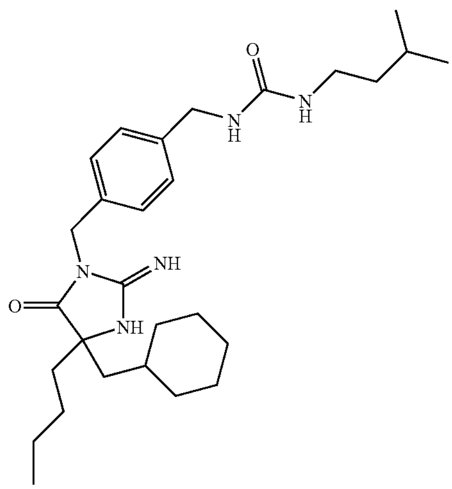 | 483 | 484 |
| 1465 | 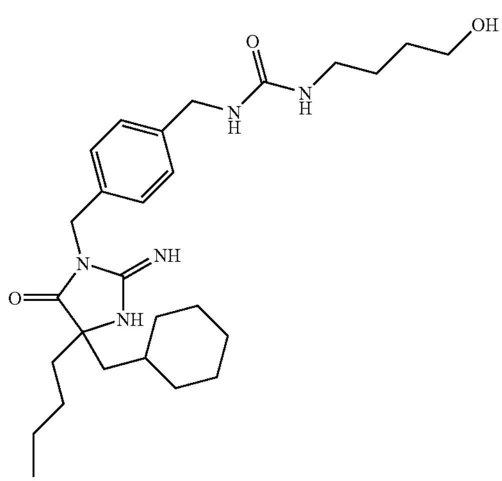 | 485 | 486 |

-continued

| # | Structure | MW | Obs. m/e |
|---|---|---|---|
| 1466 | 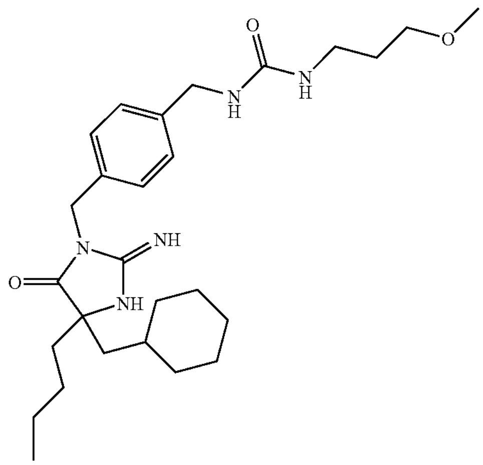 | 485 | 486 |
| 1467 | 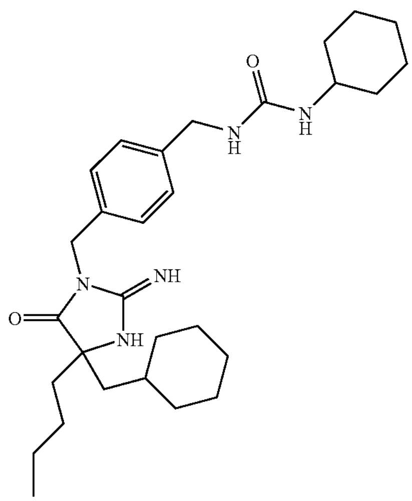 | 495 | 496 |
| 1468 | 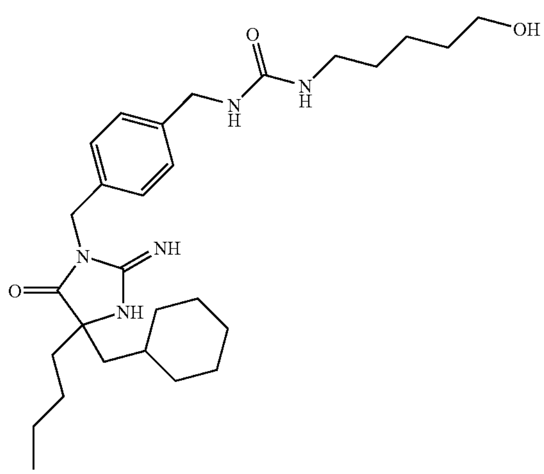 | 499 | 500 |

-continued
| # | Structure | MW | Obs. m/e |
|---|---|---|---|
| 1469 | 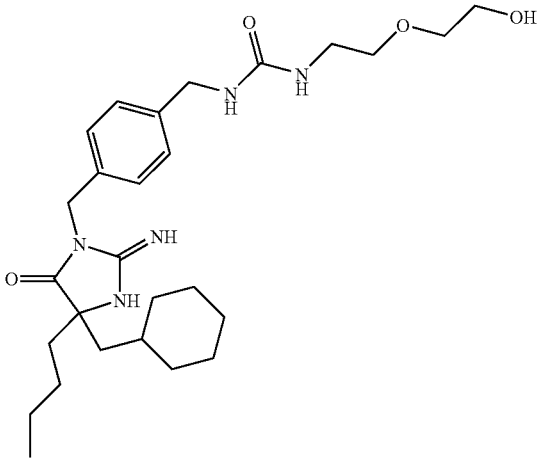 | 501 | 502 |
| 1470 | 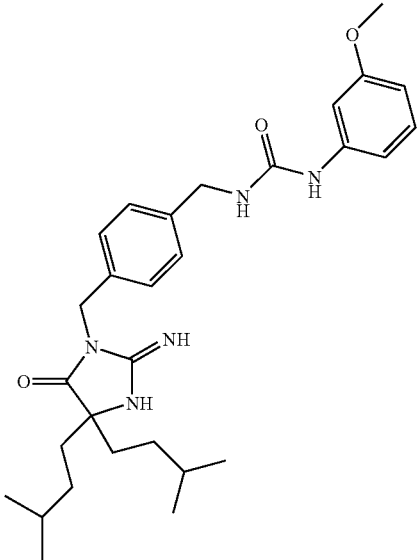 | 507 | 508 |

-continued
| # | Structure | MW | Obs. m/e |
|---|---|---|---|
| 1471 | 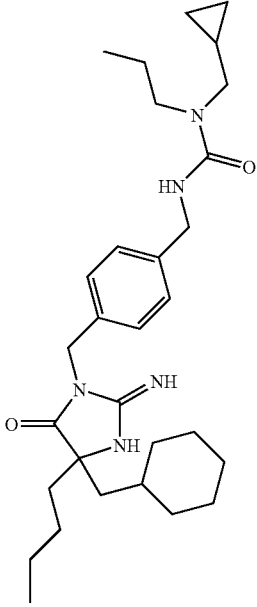 | 509 | 510 |
| 1472 | 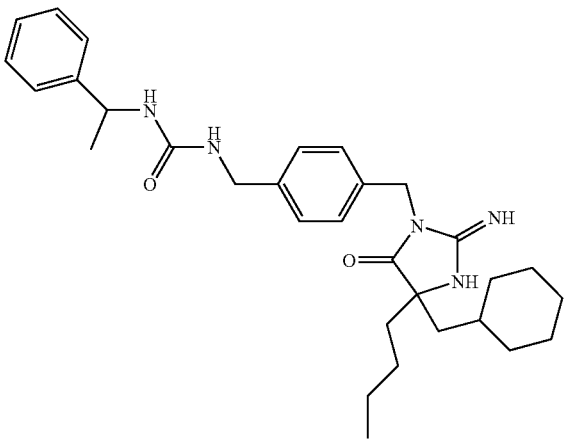 | 517 | 518 |
| 1473 | 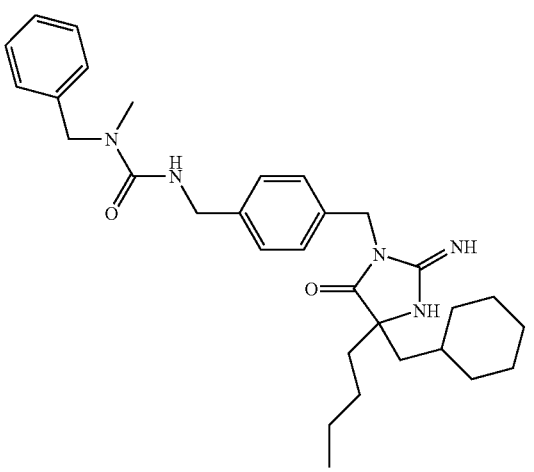 | 517 | 518 |

-continued
| # | Structure | MW | Obs. m/e |
|---|---|---|---|
| 1474 | 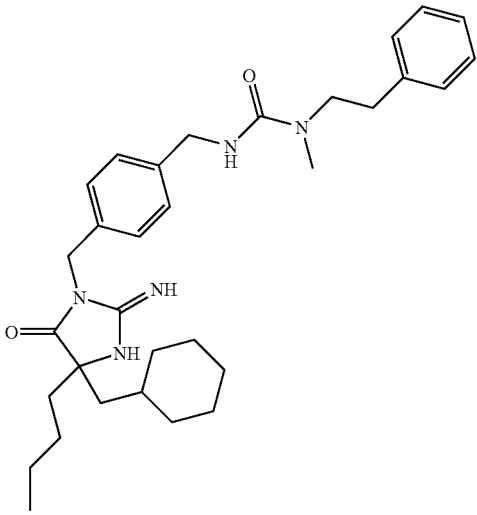 | 531 | 532 |
| 1475 | 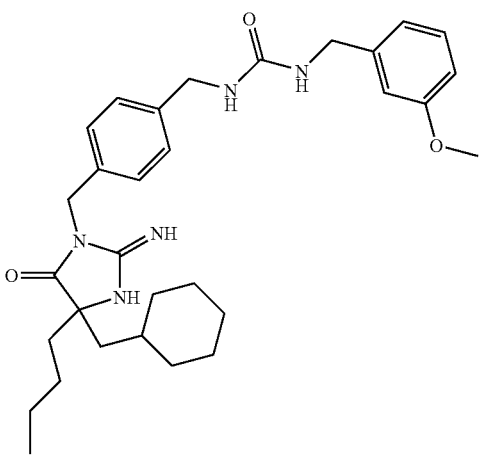 | 533 | 534 |
| 1476 | 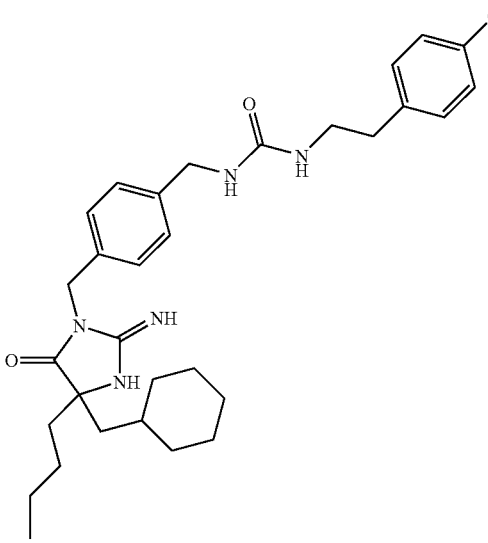 | 533 | 534 |

-continued
| # | Structure | MW | Obs. m/e |
|---|---|---|---|
| 1477 | 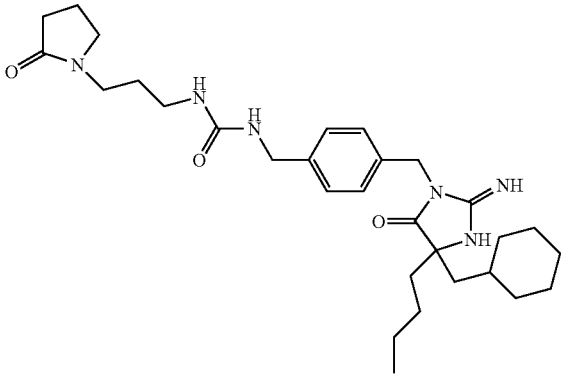 | 538 | 539 |
| 1478 | 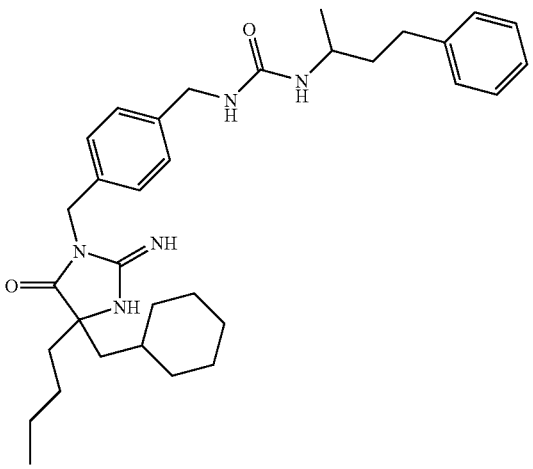 | 545 | 546 |
| 1479 | 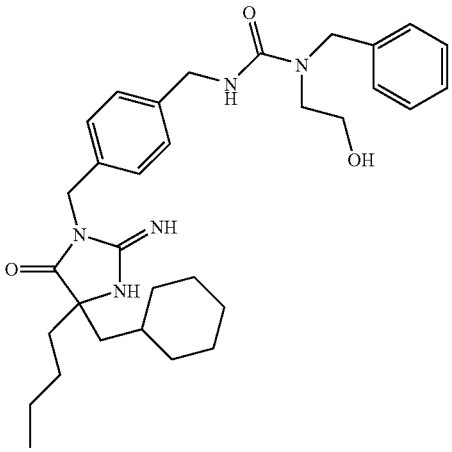 | 547 | 548 |

-continued

| # | Structure | MW | Obs. m/e |
|---|---|---|---|
| 1480 | 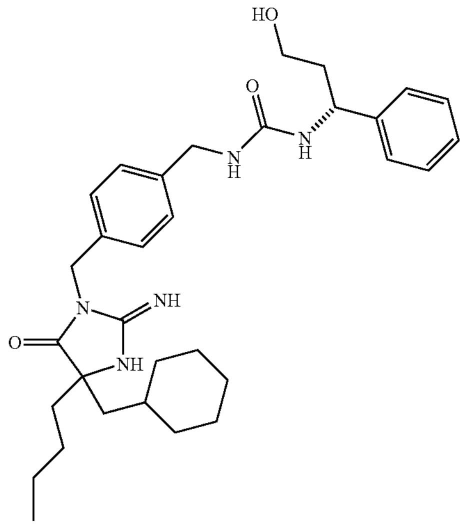 | 547 | 548 |
| 1481 | 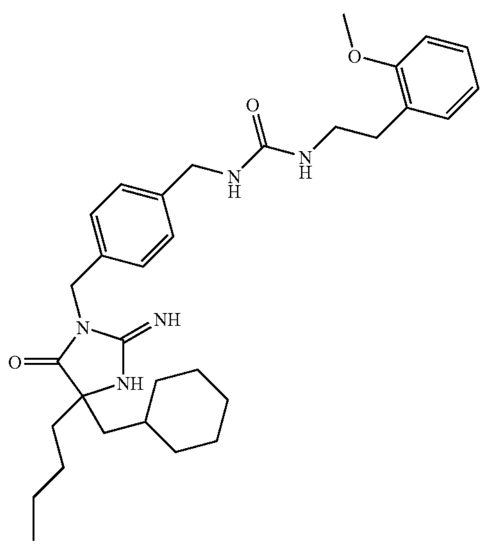 | 547 | 548 |

| # | Structure | MW | Obs. m/e |
|---|---|---|---|
| 1482 | 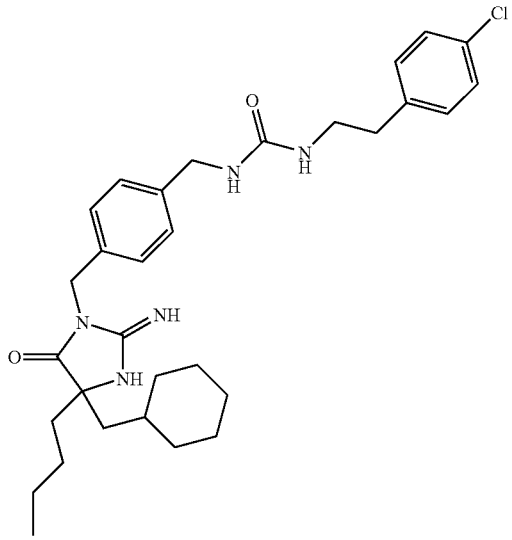 | 551 | 552 |
| 1483 | 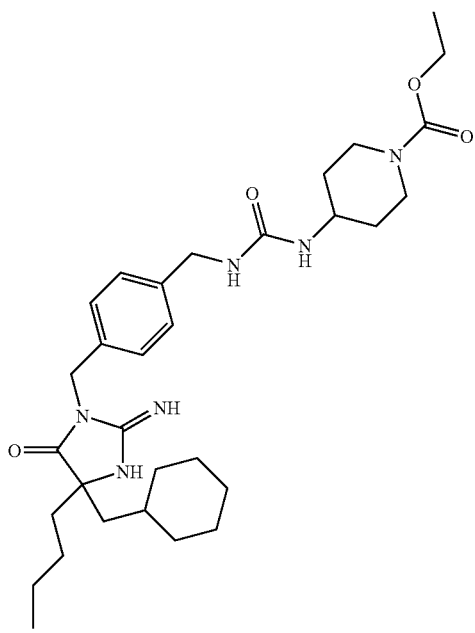 | 568 | 569 |

-continued
| # | Structure | MW | Obs. m/e |
|---|---|---|---|
| 1484 | 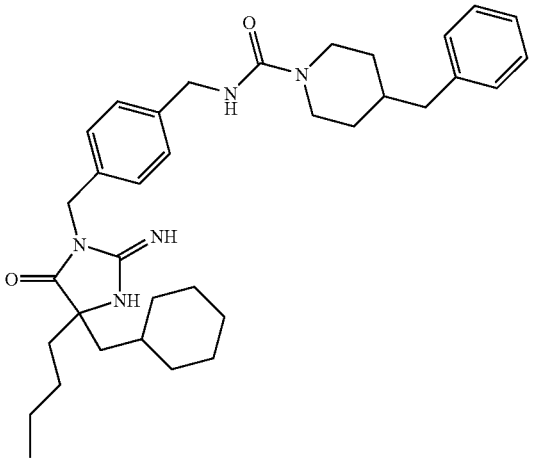 | 571 | 572 |
| 1485 | 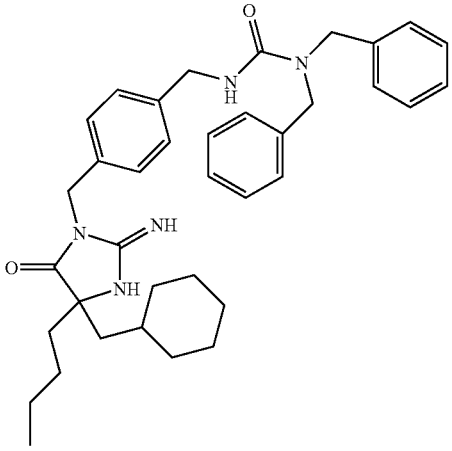 | 593 | 594 |
| 1486 | 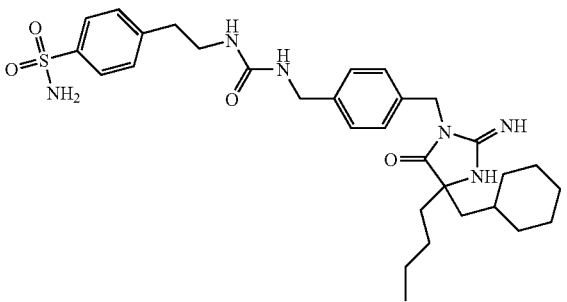 | 596 | 597 |

-continued
| # | Structure | MW | Obs. m/e |
|---|---|---|---|
| 1487 | 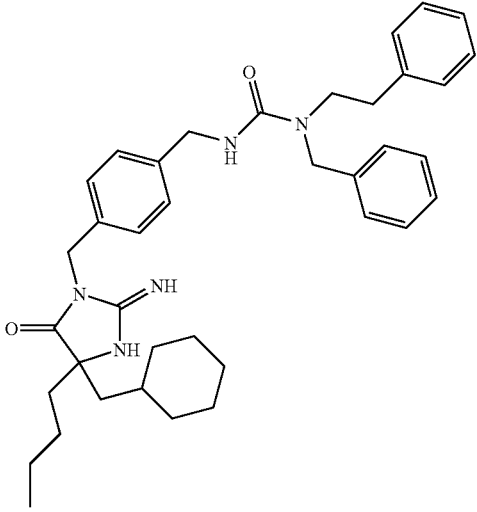 | 607 | 608 |
| 1488 | 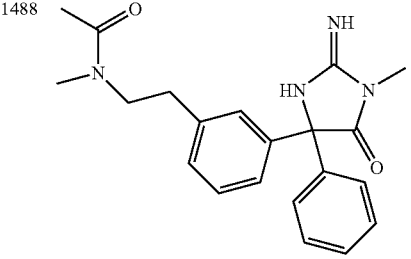 | 364 | 365 |
| 1489 | 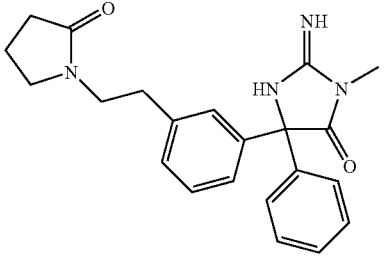 | 377 | 377 |
| 1490 | 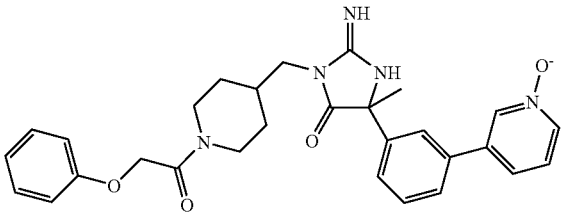 | 513 | 514 |

Method AA

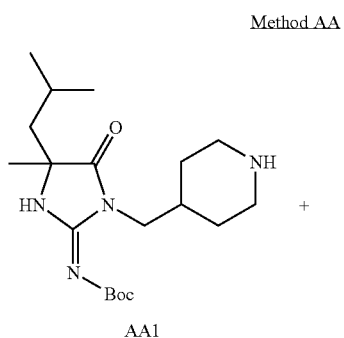

8,11-Dichloro-6,11-dihydro-5H-benzo[5,6]cyclohepta[1,2-b]pyridine (AA2) (18 mg) was reacted with AA1, obtained from method Q, and diisopropylethylamine (14 uL) in acetonitrile (2.5 mL). The resulting mixture was heated at 65° C. for 18 h. The reaction mixture was placed on a preparative silica gel plate and eluted with hexane:ethyl acetate 3:1 to give the desired product which was treated with 40% TFA. Evaporation of the solvent followed by purification afforded compound AA3.

The following compounds were prepared by similar methods:

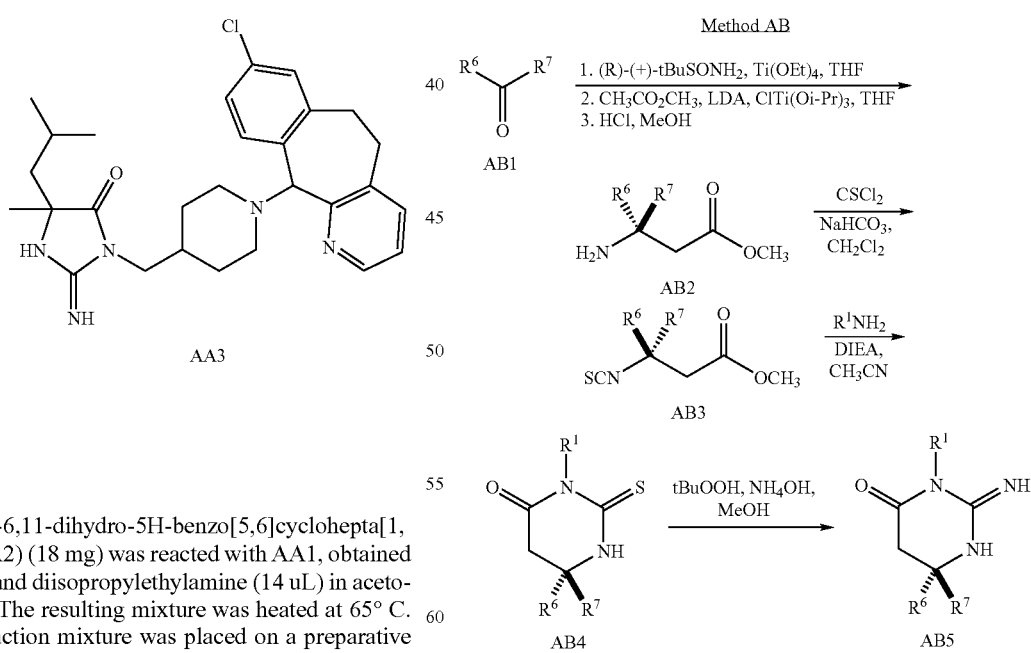

Method AB, Step 1:

To a solution of (R)-(+)-2-methyl-2-propane sulfinamide (1.0 g, 8.3 mmol, 1 eq) and AB1 ($R^6$=Ph, $R^7$=n-Bu) (3 mL, 9.1 mmol, 1.1 eq) in anhydrous THF (30 mL) at room temperature was added Ti(OEt)₄ (7 mL, 17 mmol, 2 eq). The mixture was heated at 70° C. for 24 h. After cooling to room temperature, the mixture was poured into 30 mL of brine under vigourous stirring. The resulting suspension was filtered through a pad of Celite and the solid was washed with EtOAc (2×20 mL). The filtrate was washed with brine (30 mL), dried (Na₂SO₄), and concentrated in vacuo. The residue was chromatographed on silica by eluting with hexane/Et₂O (5:1) to give 1.9 g (85%) of (R)-2-methyl-N-(1-phenylpentylidene)propane-2-sulfinamide. ¹HNMR (CDCl₃, 300 MHz): δ 7.91 (m, 2H), 7.52-7.37 (m, 3H), 3.27 (m, 1H), 3.15 (m, 1H), 1.73-1.61 (m, 2H), 1.47-1.38 (m, 2H), 1.31 (s, 9H), 0.95 (m, 3H). MS (ESI): MH⁺=265.9. HPLC $t_R$=7.24, 7.58 min (E/Z=5.5:1).

To a solution of methyl acetate (0.6 mL, 6.9 mmol, 2 eq) in THF (5 mL), LDA (2M in heptane/THF, 3.4 mL, 6.9 mmol, 2 eq) was added dropwise via a syringe at −78° C. After stirring at −78° C. for 30 min, a solution of ClTi(Oi-Pr)₃ (1.8 mL, 7.6 mmol, 2.2 eq) in THF (5 mL) was added dropwise. After stirring for another 30 min, a solution of (R)-2-methyl-N-(1-phenylpentylidene)propane-2-sulfinamide (0.9 g, 3.4 mmol, 1 eq) in THF (2 mL) was added dropwise via a syringe. The mixture was stirred at −78° C. for 3 h and TLC showed no starting material left. A saturated aqueous solution of NH₄Cl (10 eq) was added and the suspension was warmed to room temperature. The mixture was diluted with H₂O (50 mL) and stirred for 10 min. The mixture was then partitioned between H₂O (50 mL) and EtOAc (50 mL). The organic layer was separated and the aqueous layer was extracted with EtOAc (3×50 mL). The combined organic layers were washed with brine, dried (MgSO₄) and concentrated to give 1.1 g of a brown oil. Chromatography on silica gel using 50% EtOAc/hexanes as eluent gave 0.8 g (76%) of methyl 3-((R)-2-methylpropan-2-ylsulfinamido)-3-phenylheptanoate as a yellow oil. ¹HNMR (CDCl₃, 300 MHz): 87.15-7.07 (m, 5H), 3.35 (s, 1H), 3.19 (dd, J=16, 5.6 Hz, 1H), 3.01 (dd, J=15.8, 5.5 Hz, 1H), 2.07 (m, 2H), 1.71 (m, 2H), 1.35-1.26 (m, 4H), 1.17 (s, 9H), 0.89 (m, 3H). MS (ESI): MH⁺=339.9. HPLC $t_R$=7.50, 7.6 min (E/Z=1.5:1)

To a solution of methyl 3-((R)-2-methylpropan-2-ylsulfinamido)-3-phenylheptanoate (0.4 g, 1.1 mmol) in 12 mL of MeOH was added 16 mL of 4N HCl/dioxane. After stirring for 30 min, the volatiles were removed in vacuo. The residue was re-dissolved in MeOH (6 mL), stirred for 5 min, and evaporated again to afford 0.30 g (97%) of AB2 (R⁶=Ph, R⁷=n-Bu) as a yellow solid. ¹HNMR (CDCl₃, 300 MHz): 69.01 (brs, 2H), 7.37-7.12 (m, 5H), 3.64 (m, 1H), 3.54 (s, 3H), 3.31 (m, 1H), 2.09 (m, 2H), 1.8 (m, 2H), 1.1 (m, 4H), 1.07 (s, 9H), 0.7 (m, 3H). MS (ESI): MH⁺=235.9. HPLC $t_R$=4.72 min.

Method AB, Step 2:

Treatment of compound AB2 (R⁶=Ph, R⁷=n-butyl) with thiophosgene in CH₂Cl₂ in the presence of aqueous NaHCO₃ at 0° C. generates isothiocyanate AB3 (R⁶=Ph, R⁷=n-butyl) which was converted into final product using method similar to Method A Step 2 and Method A Step 3 to give product AB5 (R⁶=Ph, R⁷=n-butyl, R¹=Me). ¹HNMR (CDCl₃, 300 MHz): δ 10.4 (brs, 1H), 7.25-7.11 (m, 5H), 3.23 (dd, J=16, 5.6 Hz, 1H), 3.03 (s, 3H), 2.8 (dd, J=15.8, 5.5 Hz, 1H), 2.49 (s, 1H), 1.78 (m, 2H), 1.1-1.0 (m, 4H), 0.99 (m, 3H). MS (ESI): MH⁺=260.2. HPLC $t_R$=5.09 min.

The following compounds were synthesized using similar methods:

| # | Structure | MW | Obs. m/e |
|---|-----------|----|----|
| 189 | 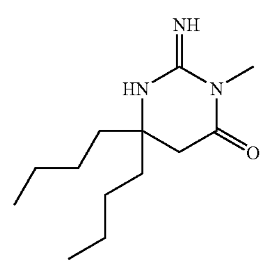 | 239 | 240 |
| 190 | 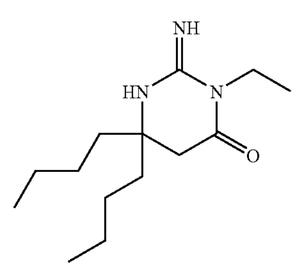 | 253 | 254 |

-continued

| # | Structure | MW | Obs. m/e |
|---|-----------|-----|----------|
| 191 | 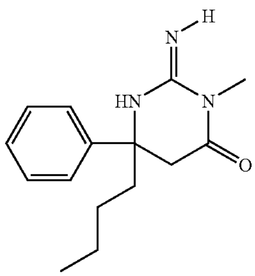 | 259 | 260 |
| 192 | 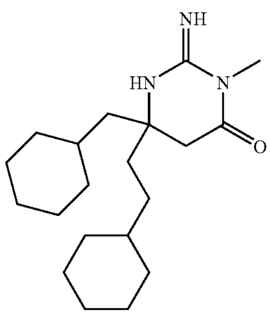 | 333 | 334 |
| 193 | 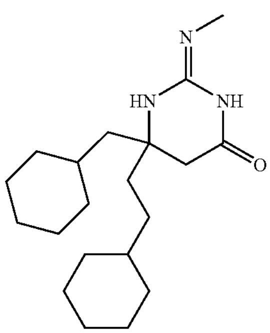 | 333 | 334 |
| 194 | 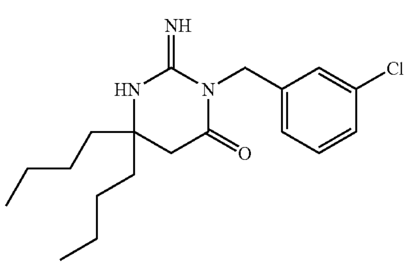 | 349 | 350 |

-continued
| # | Structure | MW | Obs. m/e |
|---|---|---|---|
| 195 | 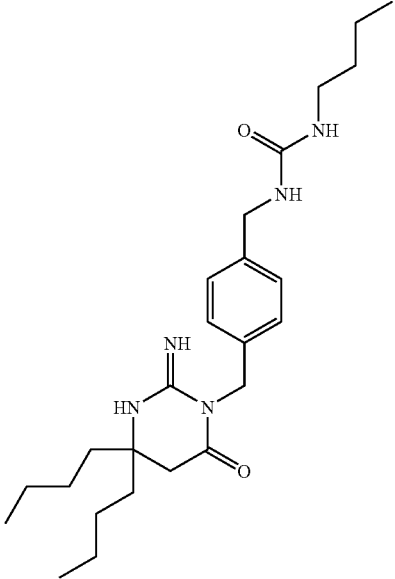 | 443 | 444 |
| 196 | 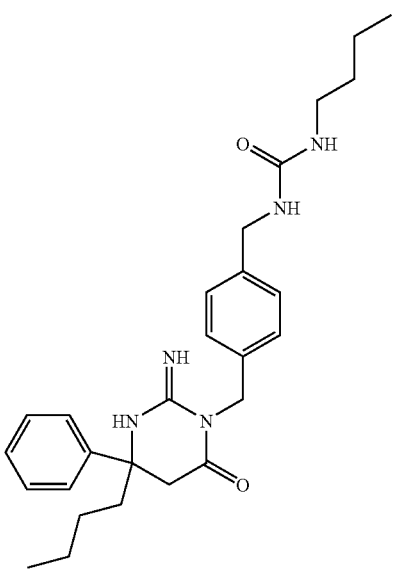 | 463 | 464 |

-continued
| # | Structure | MW | Obs. m/e |
|---|---|---|---|
| 197 | 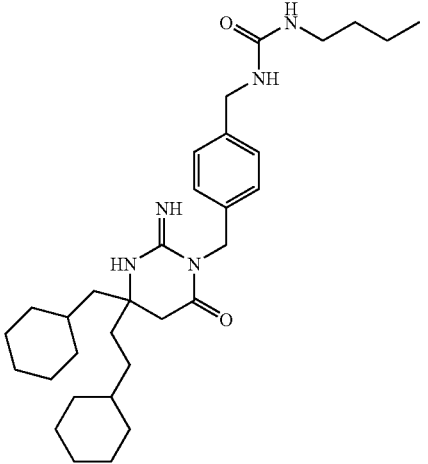 | 537 | 538 |
| 198 | 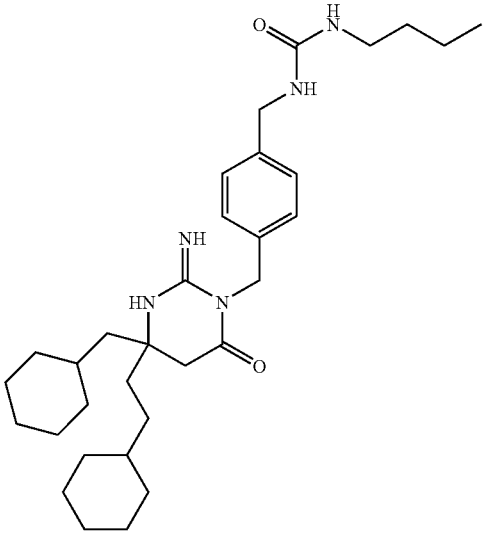 | 537 | 538 |
| 199 | 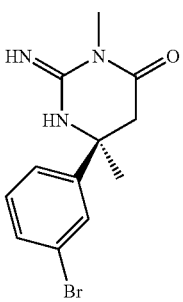 | 295 | 296 |

| # | Structure | MW | Obs. m/e |
|---|---|---|---|
| 200 | 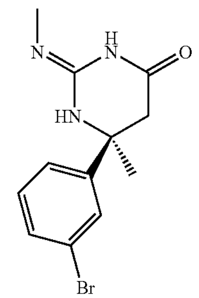 | 295 | 296 |

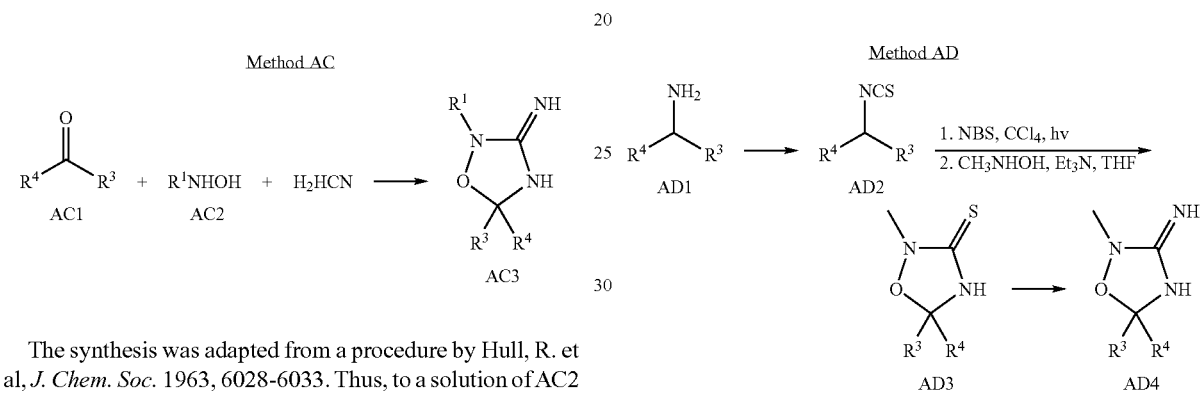

The synthesis was adapted from a procedure by Hull, R. et al, *J. Chem. Soc.* 1963, 6028-6033. Thus, to a solution of AC2 ($R^1$=Benzyl) (0.72 g, 5.9 mmol) in AC1 ($R^4$=Me, $R^3$=Me) (1.4 mL) was added a 50% aqueous solution of cyanamide (0.31 mL, 8.0 mmol). The reaction was heated with stirring at reflux (~40° C.) for 0.5 h, then cooled to 25° C. and stirred for an additional 16 h. The volatiles were removed in vacuo and the residue was partitioned between ether and $H_2O$. The organic layer was dried over $Na_2SO_4$, filtered and the volatiles were removed in vacuo. The residue was purified by column chromatography using 5-10% $CH_3OH/CH_2Cl_2$ as eluent followed by reverse phase preparative HPLC to give 0.15 g (8.0%) of AC3 ($R^1$=benzyl, $R^4$=Me and $R^3$=Me) as a white solid. $^1$H NMR ($CH_3OH$, 300 MHz): δ7.35-7.33 (m, 5H), 4.71 (s, 2H), 1.46 (s, 6H); $^{13}$C NMR ($CDCl_3$, 75 MHz) δ 157.8, 135.6, 129.1, 128.5, 127.9, 104.2, 59.6, 28.8. MS (ESI) m/e 206.1 $(M+H)^+$.

| # | Structure | MW | Obs. m/e |
|---|---|---|---|
| 201 | 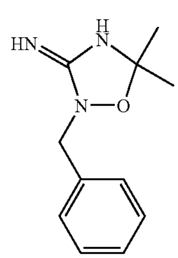 | 205 | 206 |

Method AD, Step 1:

AD2 ($R^3$=Ph, $R^4$=$^t$Butyl) was prepared from AD1 using method similar to Method AB, step 2.

Method AD, Step 2:

The synthesis was adapted from a procedure by Hussein, A. Q. et al, *Chem. Ber.* 1979, 112, 1948-1955. Thus, to a mixture of AD2 ($R^3$=Ph, $R^4$=tert-Butyl) (0.56 g, 2.7 mmol) and boiling chips in $CCl_4$ (25 mL) was added N-bromosuccinimide (0.49 g, 2.7 mmol). The mixture was irradiated with a 200 watt light source for 1 h. The reaction was cooled, the solid filtered off and the volatiles were removed in vacuo. Chromatography on silica gel by eluting with 5% EtOAc/hexane gave 0.57 g (73%) of 1-(1-bromo-1-isothiocyanato-2,2-dimethylpropyl)benzene as a beige powder. $^1$H NMR ($CDCl_3$, 300 MHz): δ 7.63-7.61 (m, 2H), 7.37-7.26 (m, 3H), 1.17 (s, 9H); $^{13}$C NMR ($CDCl_3$, 75 MHz): δ 139.1, 129.0, 128.9, 128.6, 127.5, 91.2, 45.6, 26.6. MS (ESI) m/e 284.9 $(M+H)^+$.

To a solution of 1-(1-bromo-1-isothiocyanato-2,2-dimethylpropyl)benzene (0.13 g, 0.47 mmol) and the hydrochloride salt of N-methylhydroxylamine (0.047 g, 0.57 mmol) in THF (3 mL) was added triethylamine (0.18 mL, 1.32 mmol). The mixture was stirred at 25° C. for 16 h, filtered and the volatiles were removed in vacuo. The residue was purified by column chromatography using $CH_3OH/CH_2Cl_2$ as eluent to give 0.050 g (42%) of AD3 ($R^3$=Ph, $R^4$=tert-Butyl) as a glassy solid. $^1$H NMR ($CDCl_3$, 300 MHz): δ 7.35-7.26 (m, 5H), 3.38 (s, 3H), 1.0 (s, 9H); MS (ESI) m/e 251.1 $(M+H)^+$.

Method AD, Step 3:

To a solution of AD3 ($R^3$=Ph, $R^4$=tert-Butyl) (0.065 g, 0.26 mmol) in $CH_3OH$ (5 mL) at 0° C. was added a solution of aqueous ammonia (2 mL) followed by a 70% aqueous solution of t-butylhydroperoxide (2 mL). The reaction was allowed to warm to 25° C. and stirred for 16 h, The volatiles were removed and the residue was purified by reverse phase HPLC to give 2.0 mg (2.2%) of AD4 ($R^3$=Ph, $R^4$=tert-Butyl) as a colorless oil. $^1$H NMR (CDCl$_3$, 300 MHz) δ 7.47-7.43 (m, 2H), 7.39-7.35 (m, 3H), 3.23 (s, 3H), 1.0 (s, 9H); MS (ESI) m/e 234.2 (M+H)$^+$.

The following compounds were synthesized using similar methods:

| # | Structure | MW | Obs. m/e |
|---|-----------|-----|----------|
| 202 | 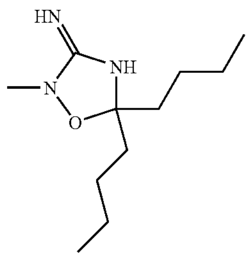 | 213 | 214 |
| 203 | 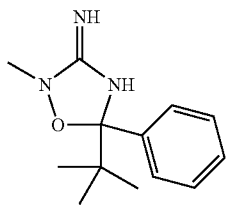 | 233 | 234 |
| 204 | 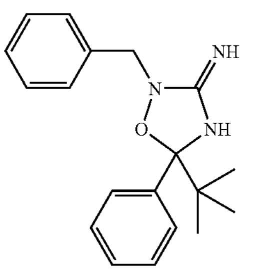 | 309 | 310 |

Method AE

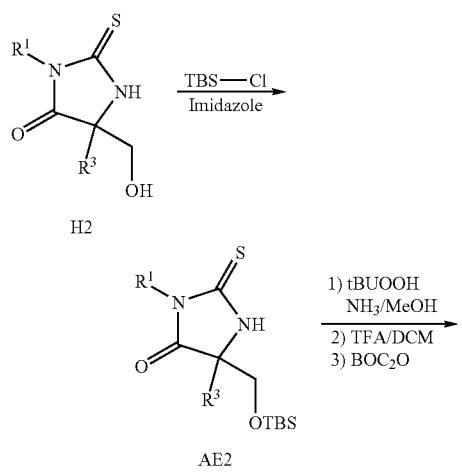

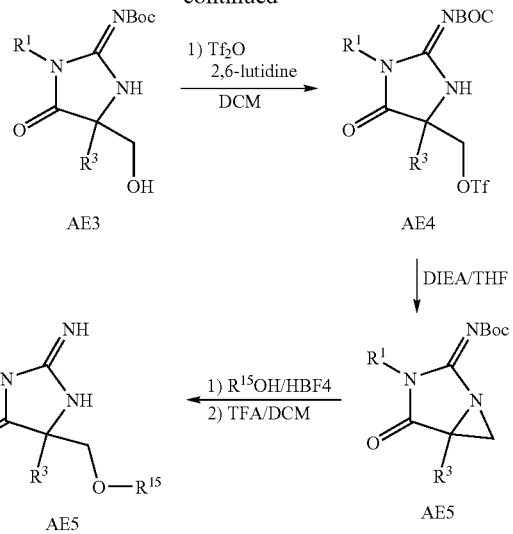

Method AE, Step 1:

TBDMS-Cl (5.3 g, 35.19 mmole) and imidazole (2.4 g, 35.19 mmole) were added to a suspension of H2 ($R^1$=Me, $R^3$=cyclohexylmethyl) (8.2 g, 31.99 mmole) in 220 ml DCM. The reaction mixture was stirred at room temperature overnight. The reaction mixture was filtered, and the filtrate was diluted with 1200 ml EtOAc. The organic phase was washed with saturated NaHCO$_3$ 3× and brine 3×, and dried over anhydrous Na$_2$SO$_4$ to give 12 g of AE2 ($R^1$=Me, $R^3$=cyclohexylmethyl), which was used for next step without further purification.

Method AE, Step 2:

AE2 ($R^1$=Me, $R^3$=cyclohexylmethyl; 12 grams crude) was converted to iminohydantoin using conditions similar to Method A Step 3, which was subsequently treated with 75% TFA in DCM at room temperature for 24 hrs. The solvent was evaporated in vacuo to give 13.6 g of a product that was reacted with Boc anhydride to give 5.8 g AE3 ($R^1$=Me, $R^3$=cyclohexylmethyl) after column purification.

Method AE, Step 3:

AE4 ($R^1$=Me, $R^3$=cyclohexylmethyl) (8.2 g) was obtained from AE3 (5.8 g) according to the step 4 of the method H.

Method AE, Step 4:

To a solution of AE4 ($R^1$=Me, $R^3$=cyclohexylmethyl) ((3.95 g, 8.38 mmol) in anhydrous THF (98 mL) was added diisopropylethylamine (7 mL, 40 mmol). The reaction was stirred under N$_2$ (gas) at room temperature. After 5.5 h, the reaction was concentrated and the crude material was purified via flash chromatography eluting with a gradient of 0 to 75% ethyl acetate in hexane to afford AE5 ($R^1$=Me, $R^3$=cyclohexylmethyl) (2.48 g, 92%).

Method AE, Step 4:

To a solution of $R^{15}$OH($R^{15}$=cyclobutyl) (10 µl) and HBF$_4$ (1 equiv) in anhydrous methylene chloride (0.5 mL) was added a solution of AE5 ($R^1$=Me, $R^3$=cyclohexylmethyl) (20 mg, 0.062 mmol) in methylene chloride (0.5 mL). The reaction was agitated overnight at rt. Trifluoroacetic acid (1 mL) was added to the reaction mixture and the solution was agitated for 1 h at rt. The reaction was concentrated and the crude material was purified via reverse phase preparative HPLC/MS eluting with a 7 min gradient of 5 to 95% CH$_3$CN in H$_2$O with 0.1% formic acid to afford AE5 ($R^1$=Me, $R^3$=cyclohexylmethyl, $R^{15}$=cyclobutyl).

The following compounds were synthesized using similar method:

| # | Structure | MW | Obs. m/e |
|---|-----------|----|----------|
| 205 | 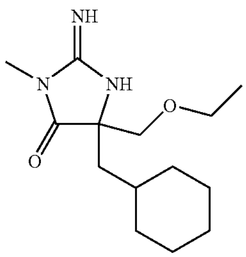 | 267 | 268 |
| 206 | 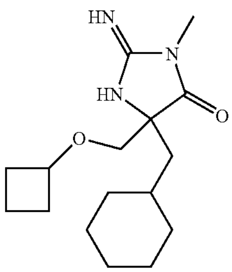 | 293 | 294 |
| 207 | 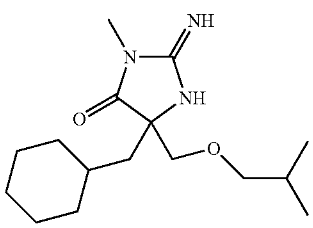 | 295 | 296 |
| 208 | Chiral | 295 | 296 |
| 209 | 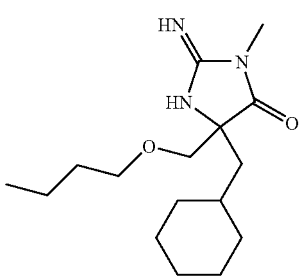 | 295 | 296 |

-continued

| # | Structure | MW | Obs. m/e |
|---|-----------|----|----------|
| 210 | Chiral | 295 | 296 |
| 211 | 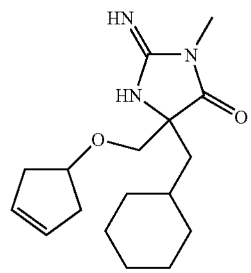 | 305 | 306 |
| 212 | 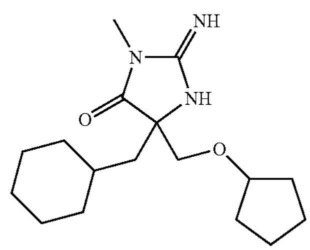 | 307 | 308 |
| 213 | 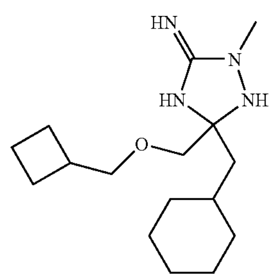 | 307 | 308 |
| 214 | Chiral | 309 | 310 |

-continued

| # | Structure | MW | Obs. m/e |
|---|---|---|---|
| 215 | Chiral | 309 | 310 |
| 216 | 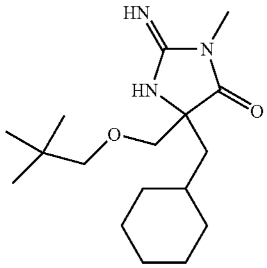 | 309 | 310 |
| 217 | 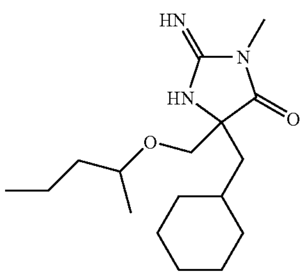 | 309 | 310 |
| 218 | 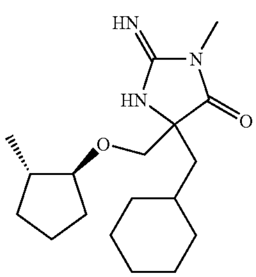 | 321 | 322 |
| 219 | 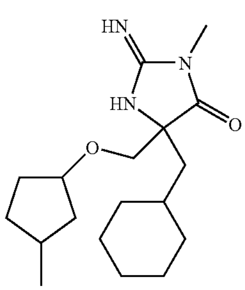 | 321 | 322 |

-continued

| # | Structure | MW | Obs. m/e |
|---|---|---|---|
| 220 | 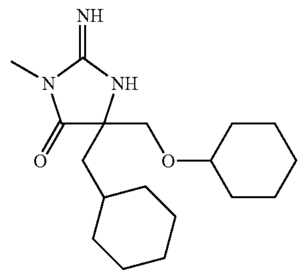 | 321 | 322 |
| 221 | 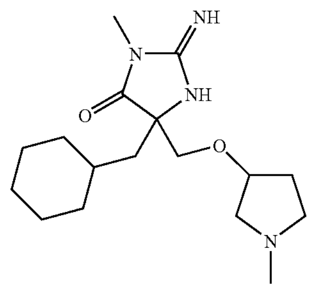 | 322 | 323 |
| 222 | 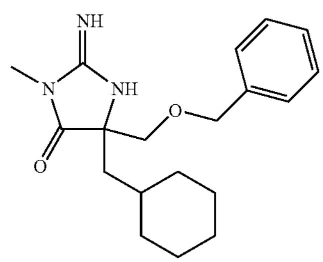 | 329 | 330 |
| 223 | 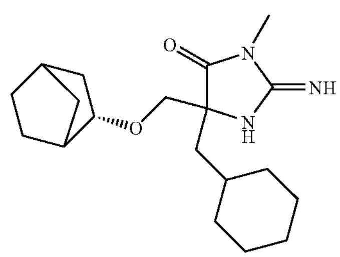 | 333 | 334 |
| 224 | 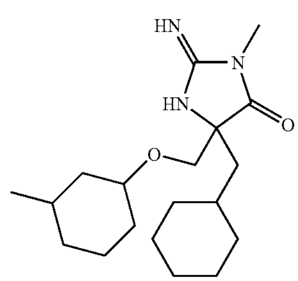 | 335 | 336 |

-continued

| # | Structure | MW | Obs. m/e |
|---|---|---|---|
| 225 | 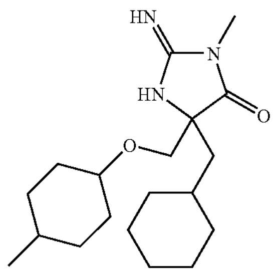 | 335 | 336 |
| 226 | 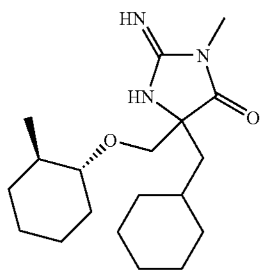 | 335 | 336 |
| 227 | 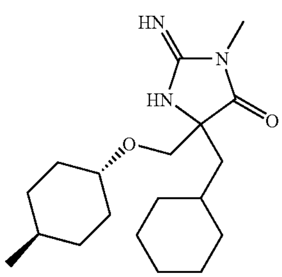 | 335 | 336 |
| 228 | 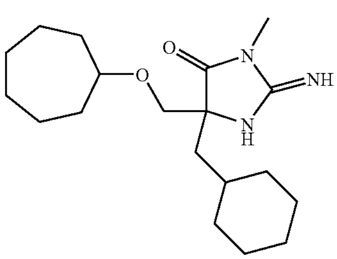 | 335 | 336 |
| 229 | 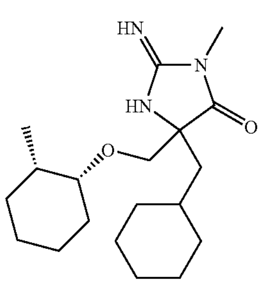 | 335 | 336 |

-continued

| # | Structure | MW | Obs. m/e |
|---|---|---|---|
| 230 | 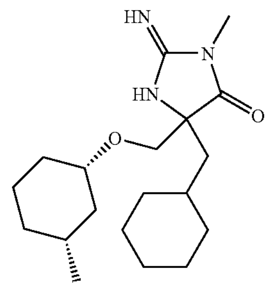 | 335 | 336 |
| 231 | 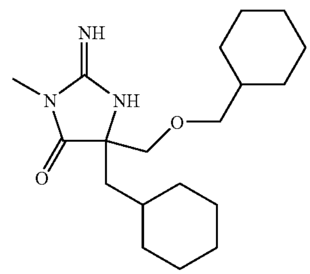 | 335 | 336 |
| 232 | 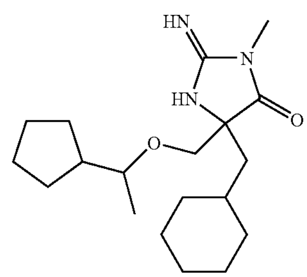 | 335 | 336 |
| 233 | 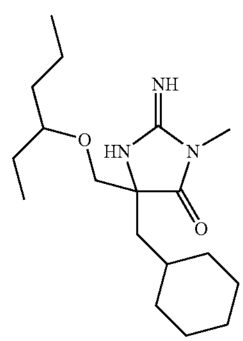 | 337 | 338 |
| 234 | 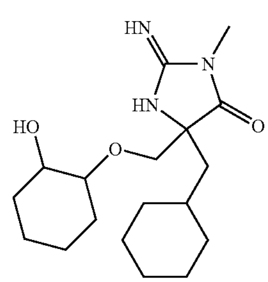 | 337 | 338 |

-continued
| # | Structure | MW | Obs. m/e |
|---|---|---|---|
| 235 | 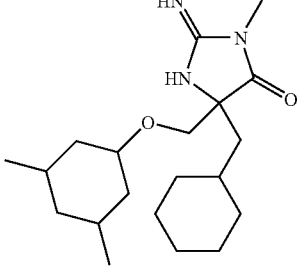 | 349 | 350 |
| 236 | 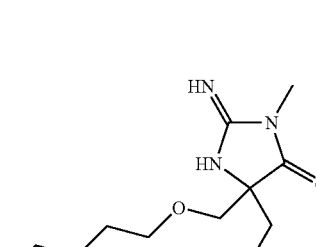 | 349 | 350 |
| 237 | 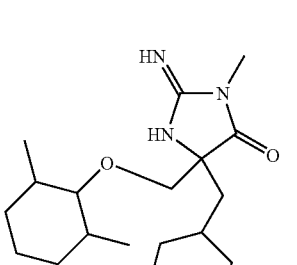 | 349 | 350 |
| 238 | 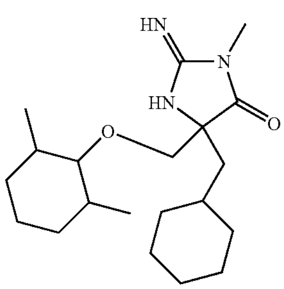 | 349 | 350 |
| 239 | 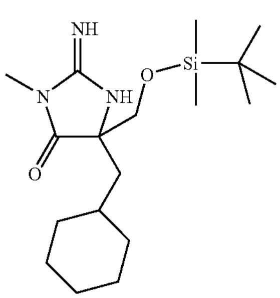 | 353 | 354 |
-continued
| # | Structure | MW | Obs. m/e |
|---|---|---|---|
| 240 | 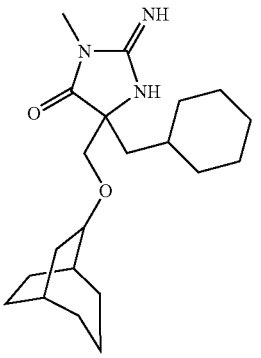 | 361 | 362 |
| 241 | 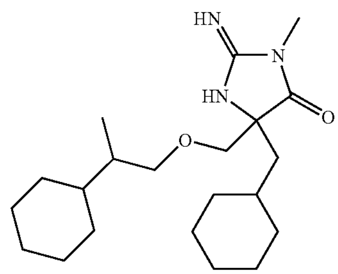 | 363 | 364 |
| 242 | 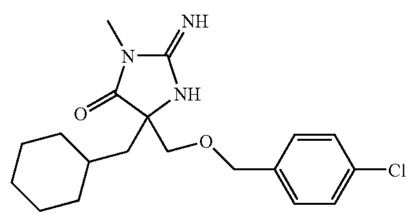 | 363 | 364 |
| 243 | 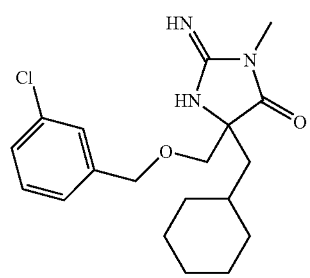 | 363 | 364 |
| 244 | 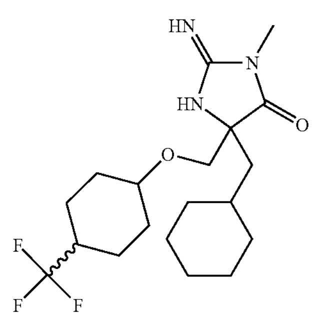 | 389 | 390 |

-continued

| # | Structure | MW | Obs. m/e |
|---|---|---|---|
| 245 | 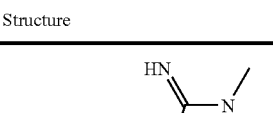 | 321 | NA |

Method AE

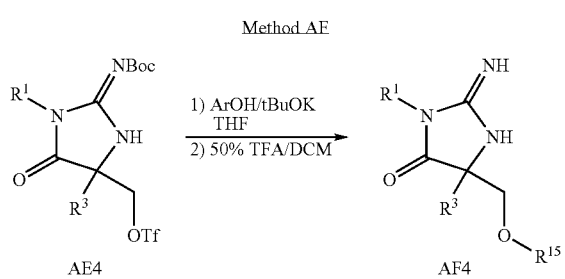

To a solution of tBuOK (9.5 mg, 0.0848 mmole) in 0.5 ml anhydrous THF was added ArOH (Ar=m-Chlorophenyl)(13 µl, 0.1273 mmole) in 0.5 ml anhydrous THF followed by addition of AE4 ($R^1$=Nem $R^3$=cyclohexylmethyl) (20 mg, 0.0424 mmole) in 0.5 ml anhydrous THF. The reaction mixture was stirred at room temperature for 2 days before it was diluted with 1 ml MeCN, treated with 100 mg MP-TsOH resin and 100 mg Amberlyst A26 resin. The resin was removed by filtration and the filtrate was evaporated down to give a product that was treated with 50% TFA for 1 hr. After evaporation of TFA in vacuo, the residue was dissolved in 2 ml MeCN, and treated with 100 mg MP-TsOH resin. The resin was washed thoroughly with THF, MeCN and MeOH, and then treated with 2M $NH_3$ in MeOH to give AF2 ($R^1$=Me, $R^3$=cyclohexylmethyl and $R^{15}$=3-chlorophenyl).

The following compounds were synthesized using similar method:

| # | Structure | MW | Obs. m/e |
|---|---|---|---|
| 246 | | 316 | 317 |
| 247 | 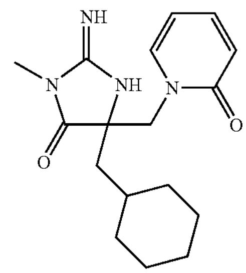 | 316 | 317 |
| 248 | 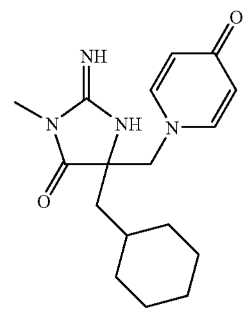 | 316 | 317 |
| 249 | 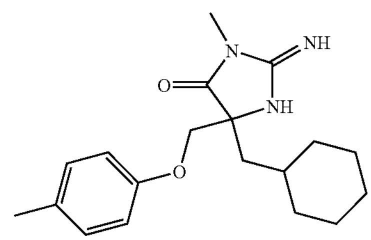 | 329 | 330 |
| 250 | 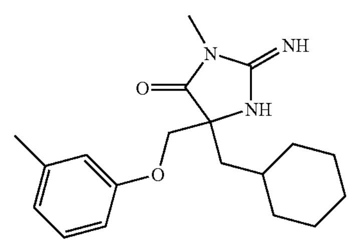 | 329 | 330 |
| 251 | 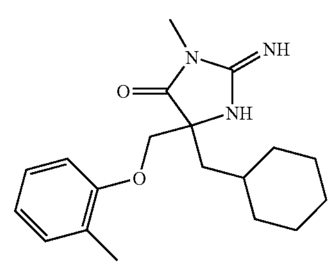 | 329 | 330 |
| 252 | 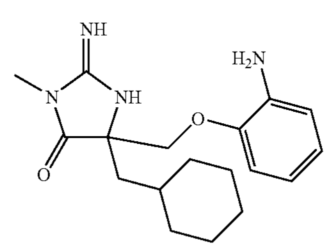 | 330 | 331 |

-continued

| # | Structure | MW | Obs. m/e |
|---|---|---|---|
| 253 | 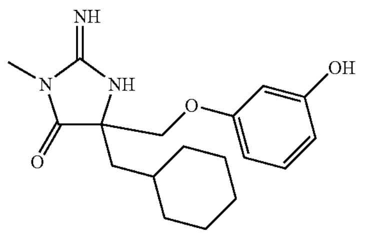 | 331 | 332 |
| 254 | 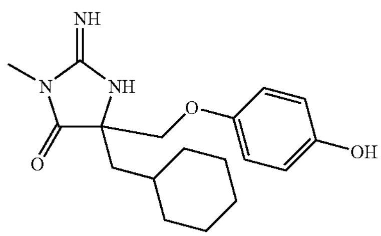 | 331 | 332 |
| 255 | 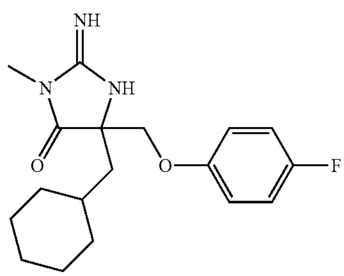 | 333 | 334 |
| 256 | 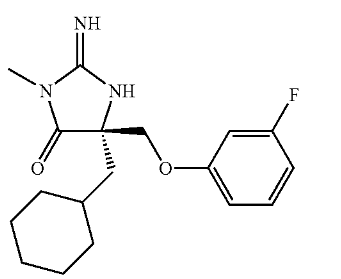 | 333 | 334 |
| 257 | 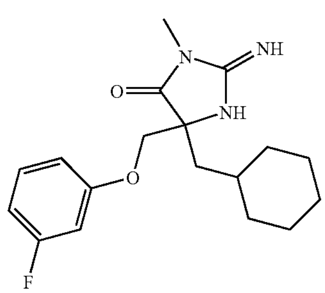 | 333 | 334 |
| 258 | 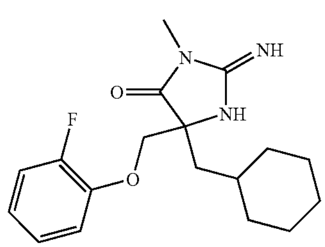 | 333 | 334 |

-continued

| # | Structure | MW | Obs. m/e |
|---|---|---|---|
| 259 | 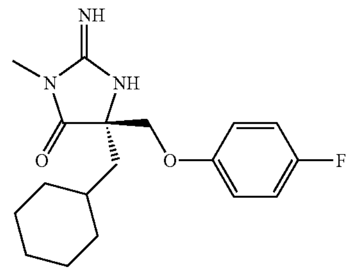 | 333 | 334 |
| 260 | 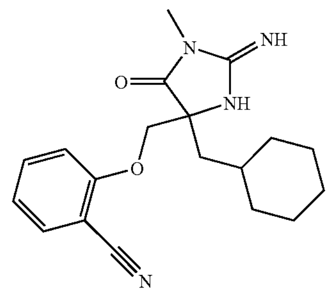 | 340 | 341 |
| 261 | 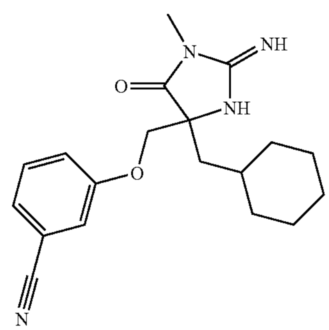 | 340 | 341 |
| 262 | 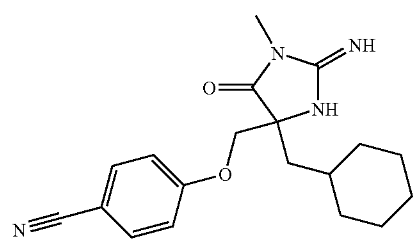 | 340 | 341 |
| 263 | 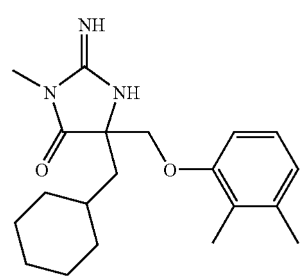 | 343 | 344 |

-continued

| # | Structure | MW | Obs. m/e |
|---|---|---|---|
| 264 | 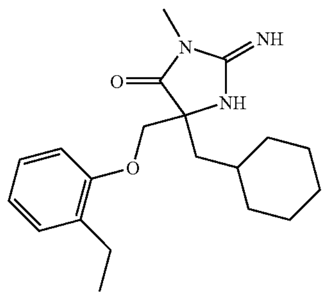 | 343 | 344 |
| 265 | 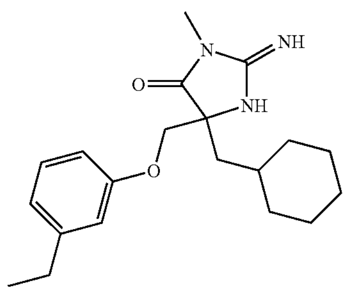 | 343 | 344 |
| 266 | 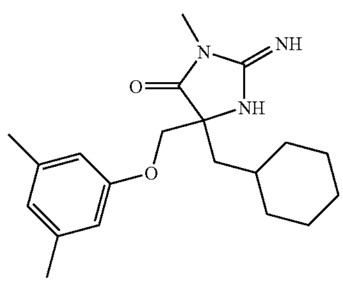 | 343 | 344 |
| 267 | 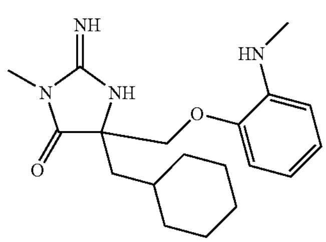 | 344 | 345 |
| 268 | 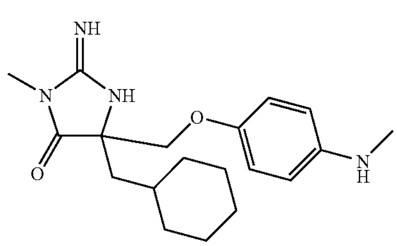 | 344 | 345 |

-continued

| # | Structure | MW | Obs. m/e |
|---|---|---|---|
| 269 | 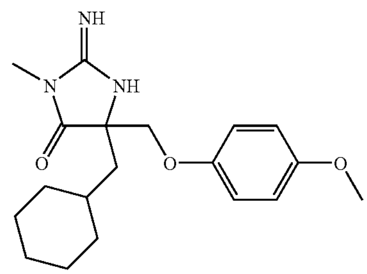 | 345 | 346 |
| 270 | 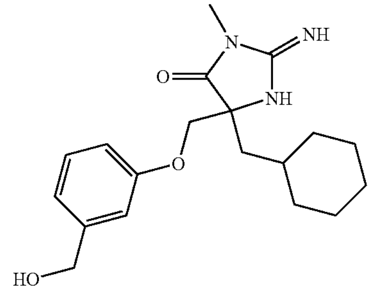 | 345 | 346 |
| 271 | 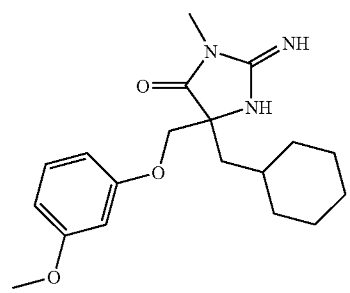 | 345 | 346 |
| 272 | 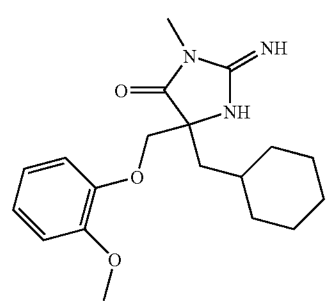 | 345 | 346 |
| 273 | 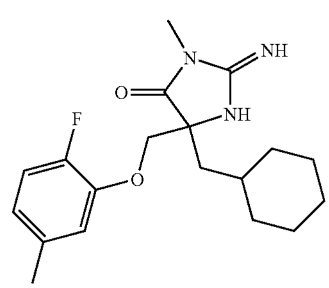 | 347 | 348 |

-continued
| # | Structure | MW | Obs. m/e |
|---|---|---|---|
| 274 | 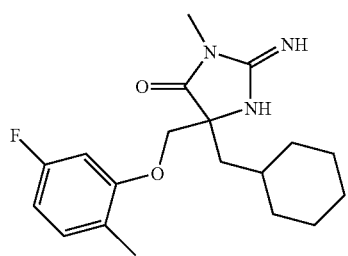 | 347 | 348 |
| 275 | 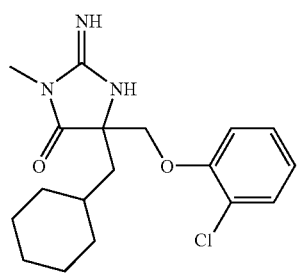 | 349 | 350 |
| 276 | 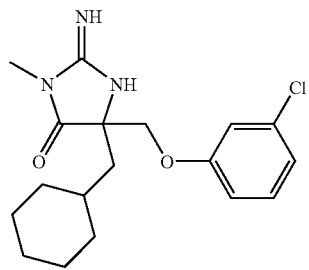 | 349 | 350 |
| 277 | 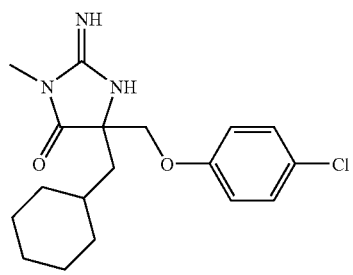 | 349 | 350 |
| 278 | 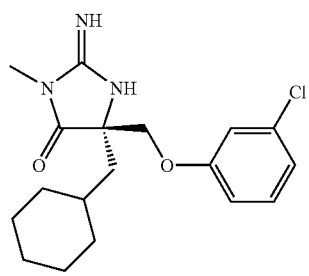 | 349 | 350 |
-continued
| # | Structure | MW | Obs. m/e |
|---|---|---|---|
| 279 | 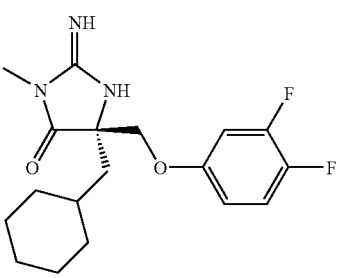 | 351 | 352 |
| 280 | 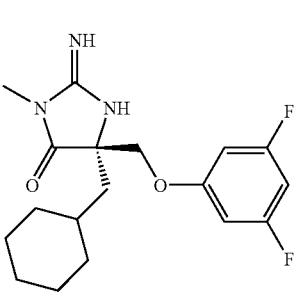 | 351 | 352 |
| 281 | 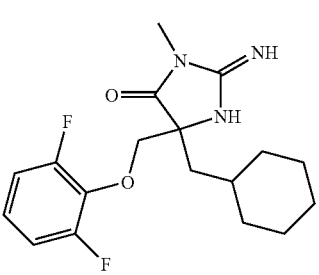 | 351 | 352 |
| 282 | 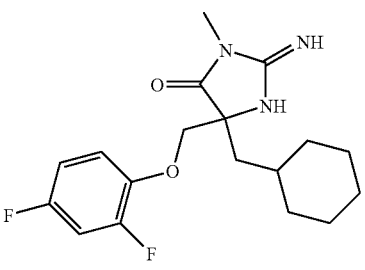 | 351 | 352 |
| 283 | 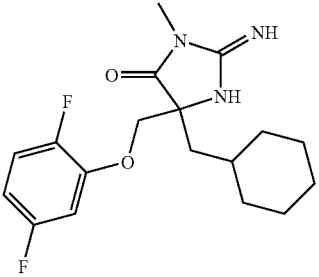 | 351 | 352 |

-continued
| # | Structure | MW | Obs. m/e |
|---|---|---|---|
| 284 | 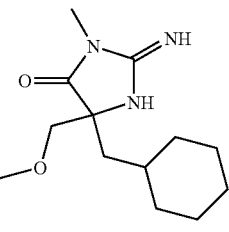 | 351 | 352 |
| 285 | 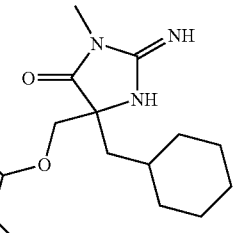 | 351 | 352 |
| 286 | 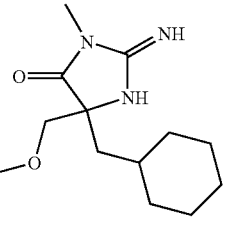 | 351 | 352 |
| 287 | 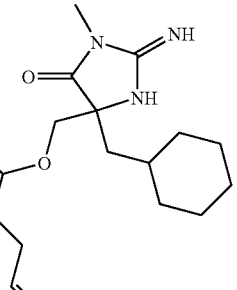 | 355 | 356 |
| 288 | 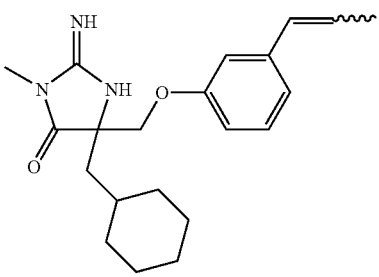 | 355 | 356 |
-continued
| # | Structure | MW | Obs. m/e |
|---|---|---|---|
| 289 | 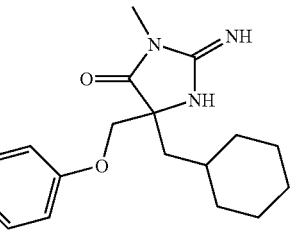 | 357 | 358 |
| 290 | 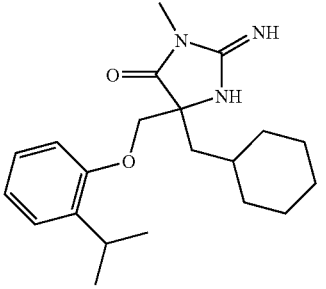 | 357 | 358 |
| 291 | 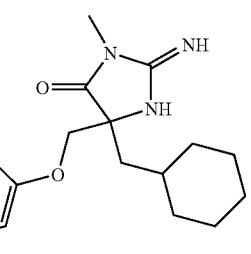 | 357 | 358 |
| 292 | 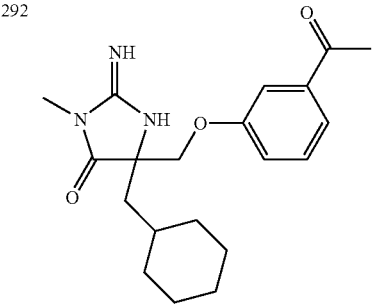 | 357 | 358 |
| 293 | 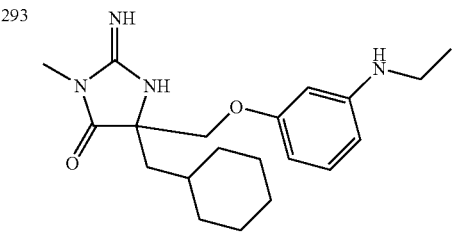 | 358 | 359 |

-continued

| # | Structure | MW | Obs. m/e |
|---|---|---|---|
| 294 | 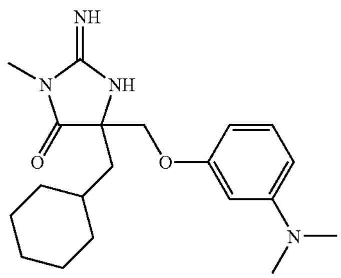 | 358 | 359 |
| 295 | 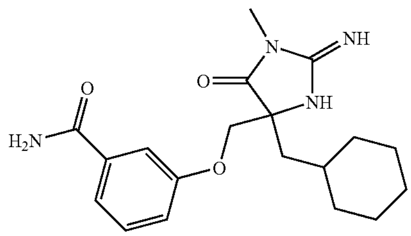 | 358 | 359 |
| 296 | 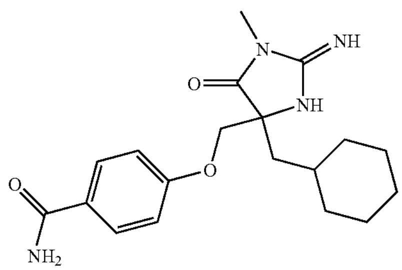 | 358 | 359 |
| 297 | 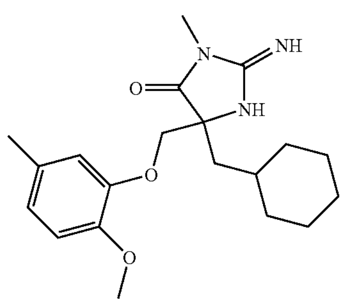 | 359 | 360 |
| 298 | 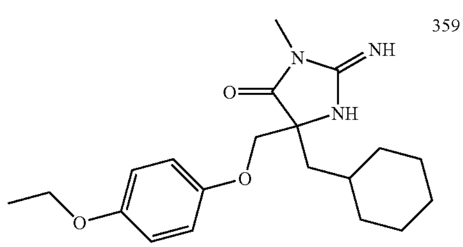 | 359 | 360 |

-continued

| # | Structure | MW | Obs. m/e |
|---|---|---|---|
| 299 | 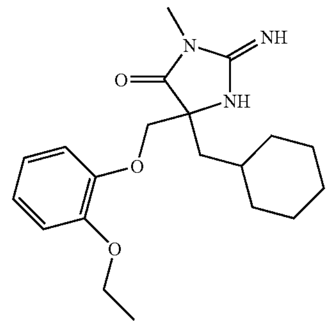 | 359 | 360 |
| 300 | 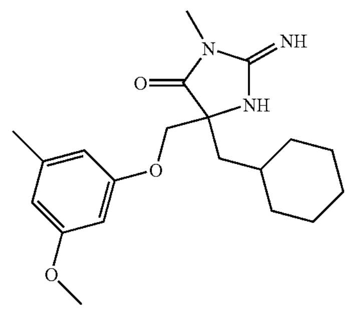 | 359 | 360 |
| 301 | 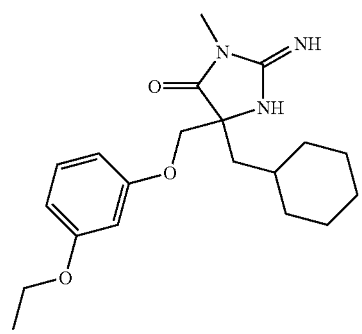 | 359 | 360 |
| 302 | 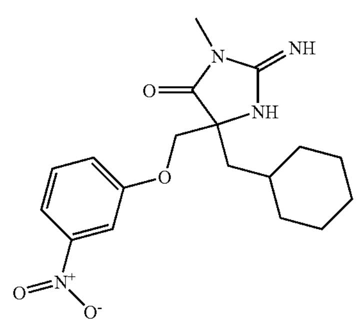 | 360 | 361 |

-continued
| # | Structure | MW | Obs. m/e |
|---|---|---|---|
| 303 | 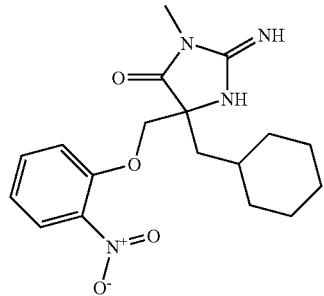 | 360 | 361 |
| 304 | 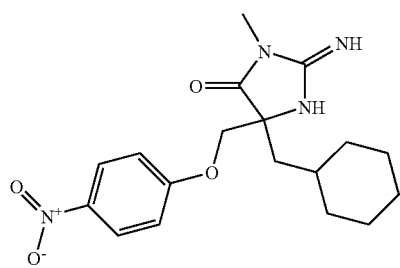 | 360 | 361 |
| 305 | 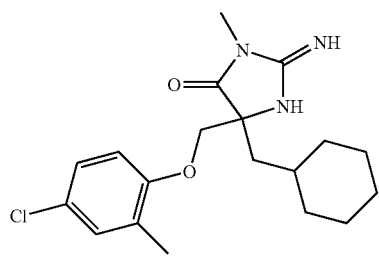 | 363 | 364 |
| 306 | 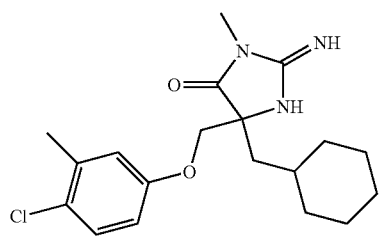 | 363 | 364 |
| 307 | 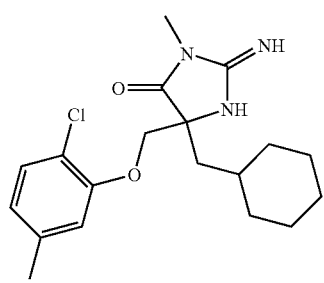 | 363 | 364 |
-continued
| # | Structure | MW | Obs. m/e |
|---|---|---|---|
| 308 | 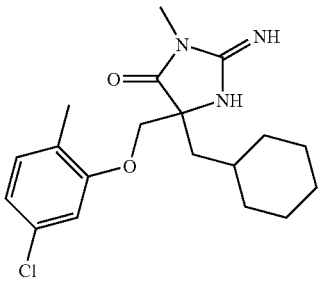 | 363 | 364 |
| 309 | 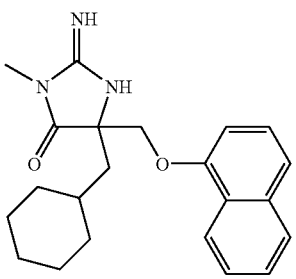 | 365 | 366 |
| 310 | 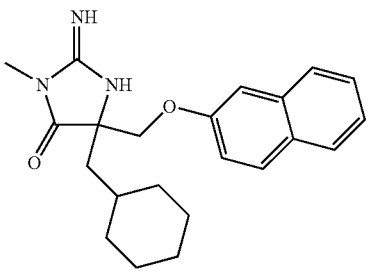 | 365 | 366 |
| 311 | 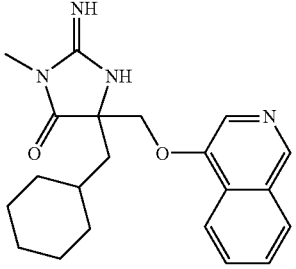 | 366 | 367 |
| 312 | 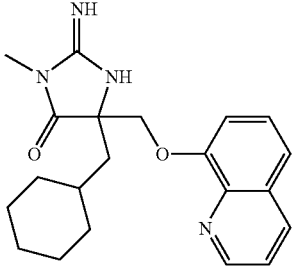 | 366 | 367 |

-continued
| # | Structure | MW | Obs. m/e |
|---|---|---|---|
| 313 | 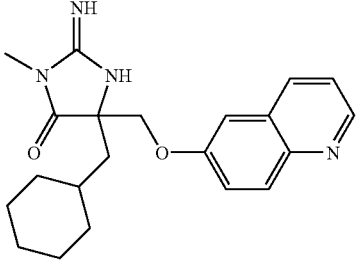 | 366 | 367 |
| 314 | 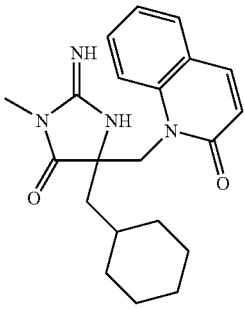 | 366 | 367 |
| 315 | 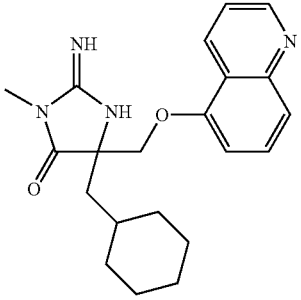 | 366 | 367 |
| 316 | 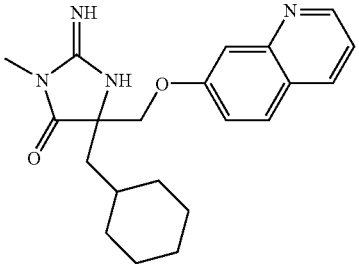 | 366 | 367 |
| 317 | 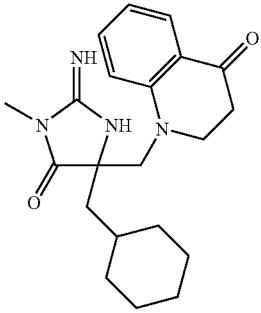 | 366 | 367 |
-continued
| # | Structure | MW | Obs. m/e |
|---|---|---|---|
| 318 | 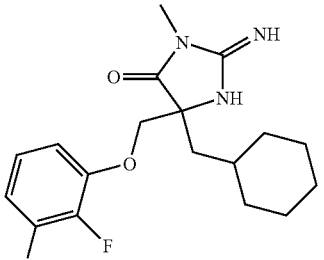 | 367 | 368 |
| 319 | 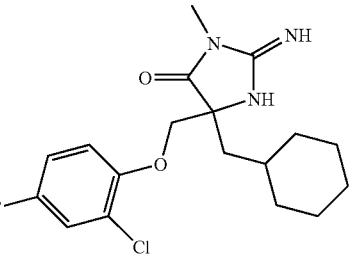 | 367 | 368 |
| 320 | 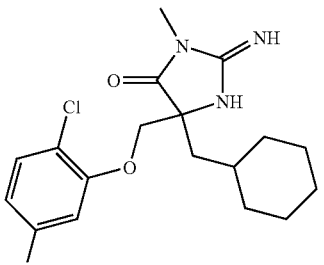 | 367 | 368 |
| 321 | 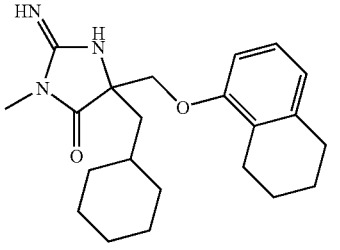 | 369 | 370 |
| 322 | 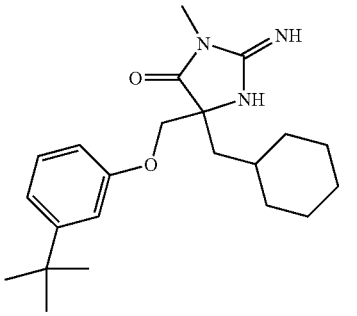 | 371 | 372 |

-continued
| # | Structure | MW | Obs. m/e |
|---|---|---|---|
| 323 | 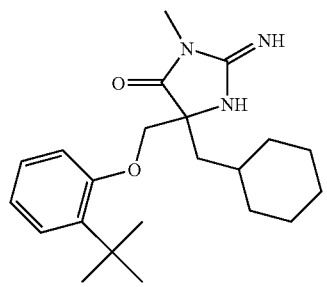 | 371 | 372 |
| 324 | 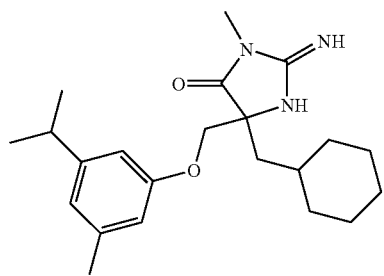 | 371 | 372 |
| 325 | 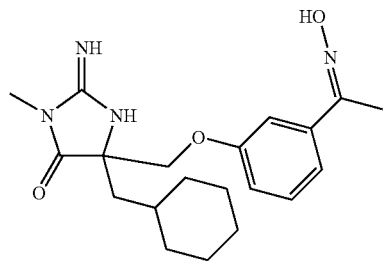 | 372 | 373 |
| 326 | 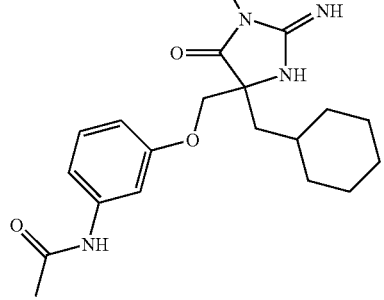 | 372 | 373 |
| 327 | 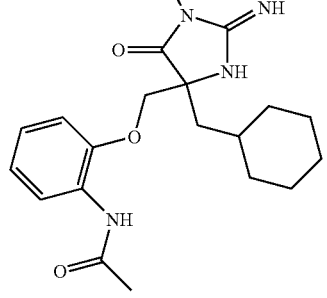 | 372 | 373 |
-continued
| # | Structure | MW | Obs. m/e |
|---|---|---|---|
| 328 | 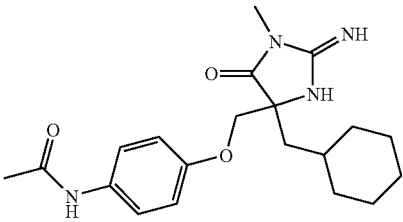 | 372 | 373 |
| 329 | 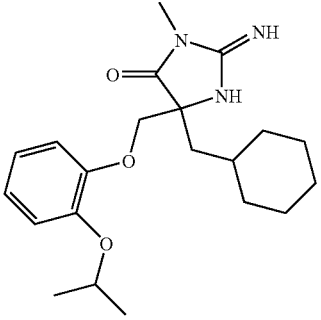 | 373 | 374 |
| 330 | 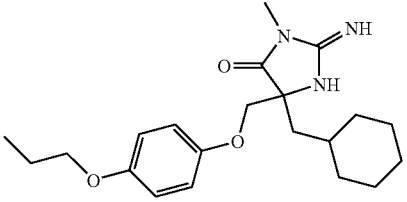 | 373 | 374 |
| 331 | 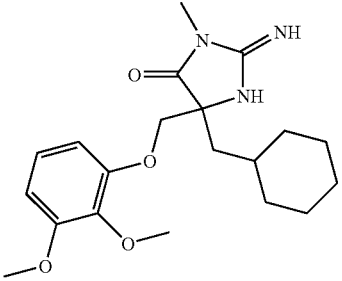 | 375 | 376 |
| 332 | 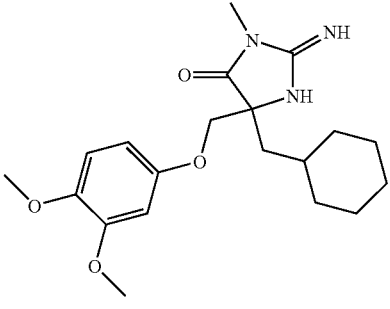 | 375 | 376 |

-continued

| # | Structure | MW | Obs. m/e |
|---|---|---|---|
| 333 | 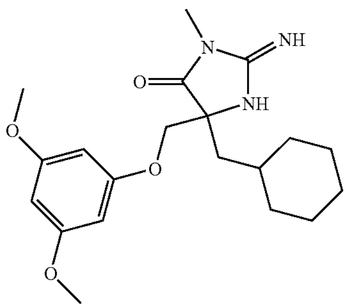 | 375 | 376 |
| 334 | 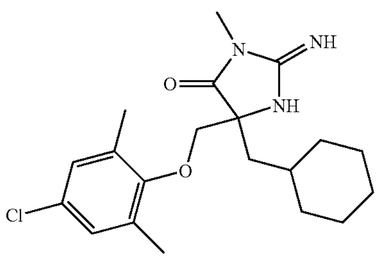 | 377 | 378 |
| 335 | 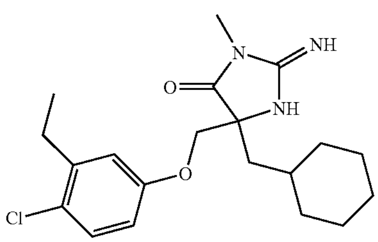 | 377 | 378 |
| 336 | 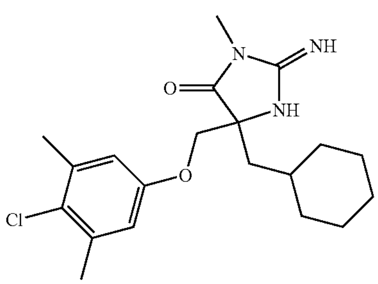 | 377 | 378 |
| 337 | 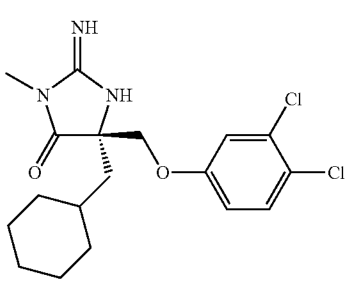 | 383 | 384 |

-continued

| # | Structure | MW | Obs. m/e |
|---|---|---|---|
| 338 | 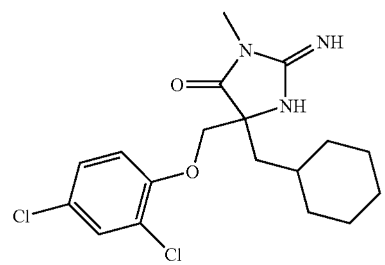 | 383 | 384 |
| 339 | 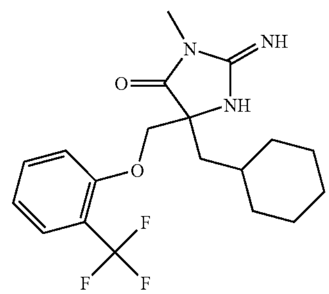 | 383 | 384 |
| 340 | 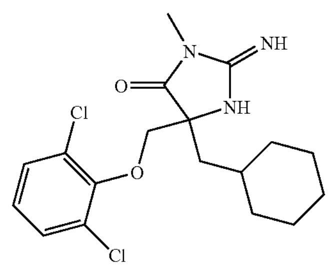 | 383 | 384 |
| 341 | 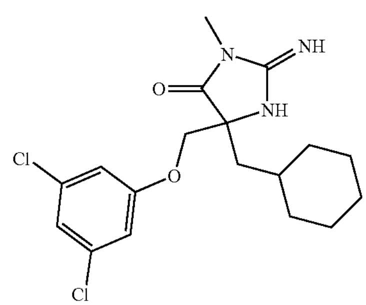 | 383 | 384 |
| 342 | 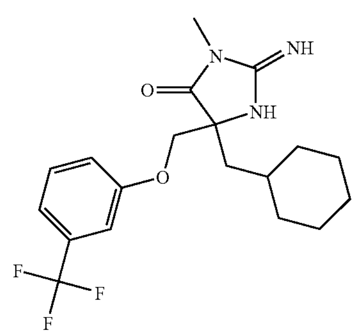 | 383 | 384 |

| # | Structure | MW | Obs. m/e |
|---|---|---|---|
| 343 | 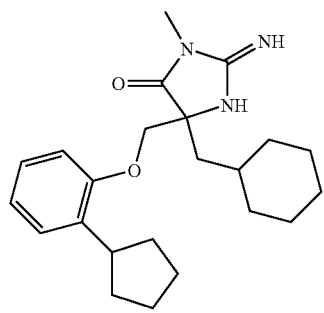 | 383 | 384 |
| 344 | 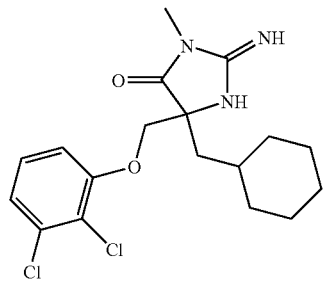 | 383 | 384 |
| 345 | 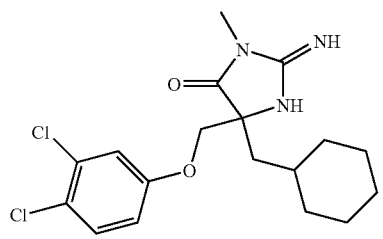 | 383 | 384 |
| 346 | 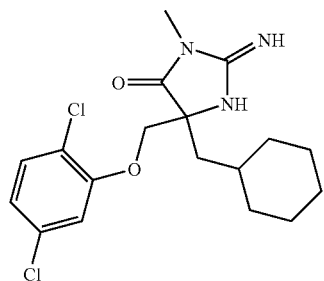 | 383 | 384 |
| 347 | 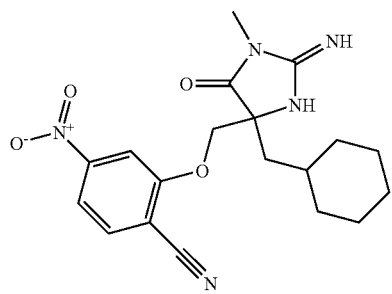 | 385 | 386 |
| # | Structure | MW | Obs. m/e |
|---|---|---|---|
| 348 | 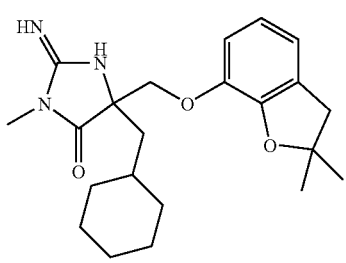 | 385 | 386 |
| 349 | 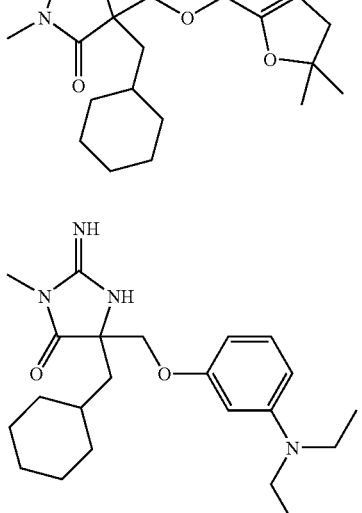 | 386 | 387 |
| 350 | 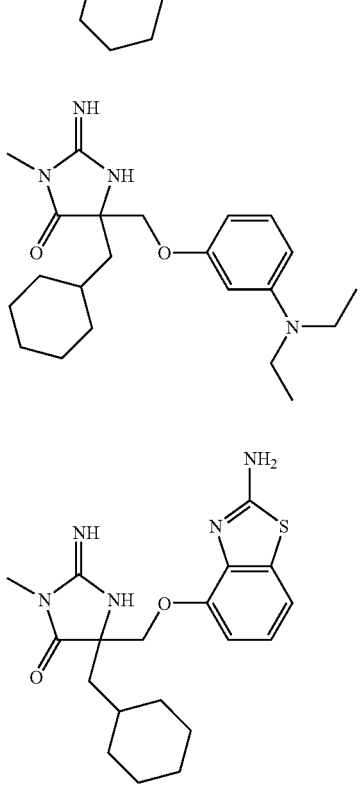 | 387 | 388 |
| 351 | 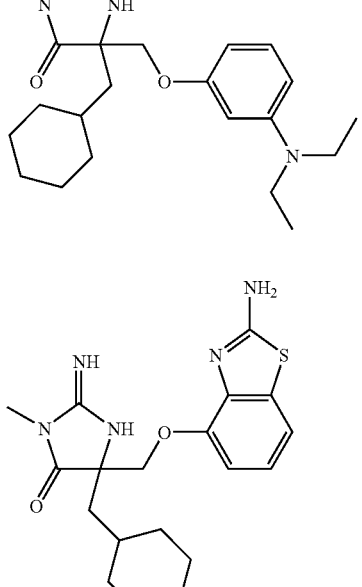 | 387 | 388 |
| 352 | 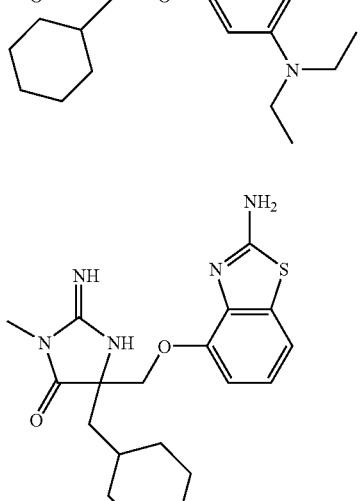 | 393 | 394 |

-continued
| # | Structure | MW | Obs. m/e |
|---|---|---|---|
| 353 | 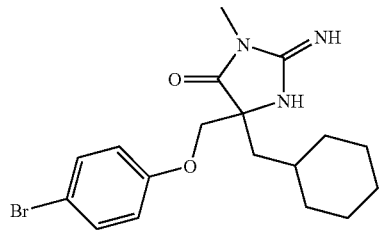 | 393 | 394 |
| 354 | 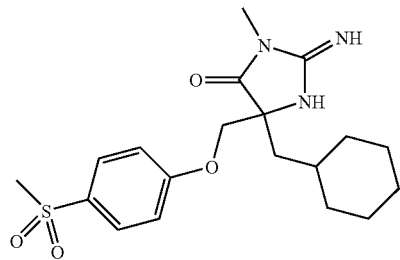 | 393 | 394 |
| 355 | 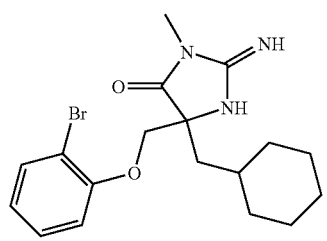 | 393 | 394 |
| 356 | 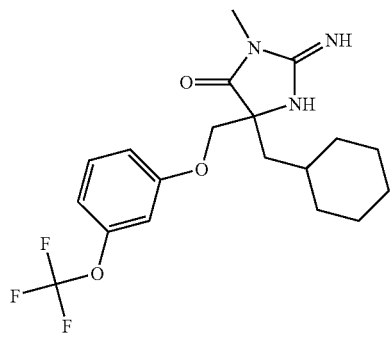 | 399 | 400 |
| 357 | 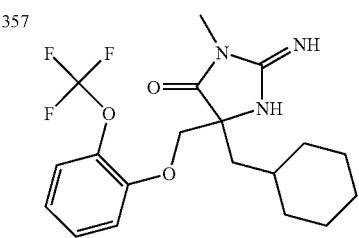 | 399 | 400 |
-continued
| # | Structure | MW | Obs. m/e |
|---|---|---|---|
| 358 | 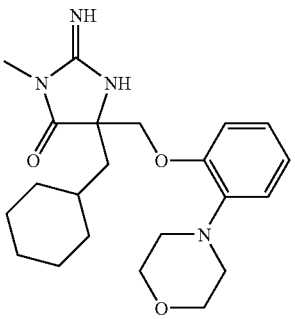 | 400 | 401 |
| 359 | 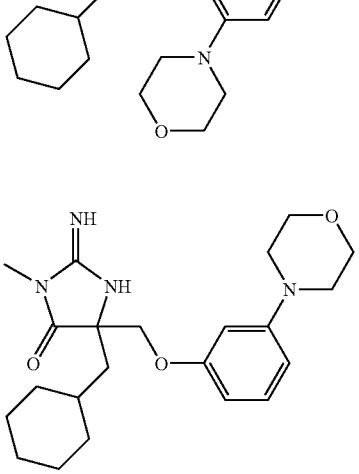 | 400 | 401 |
| 360 | 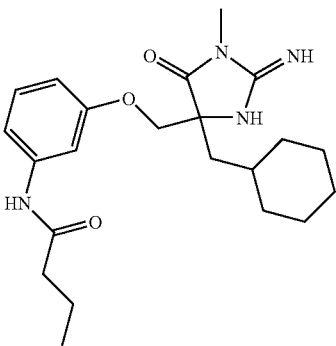 | 400 | 401 |
| 361 | 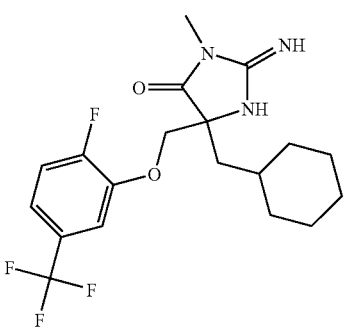 | 401 | 402 |

-continued
| # | Structure | MW | Obs. m/e |
|---|---|---|---|
| 362 | 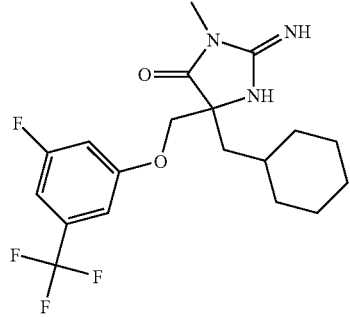 | 401 | 402 |
| 363 | 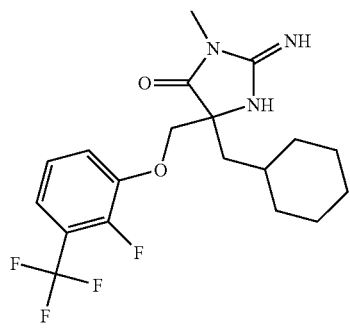 | 401 | 402 |
| 364 | 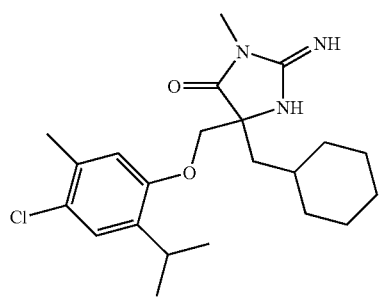 | 405 | 406 |
| 365 | 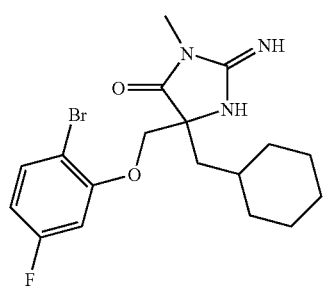 | 411 | 412 |
-continued
| # | Structure | MW | Obs. m/e |
|---|---|---|---|
| 366 | 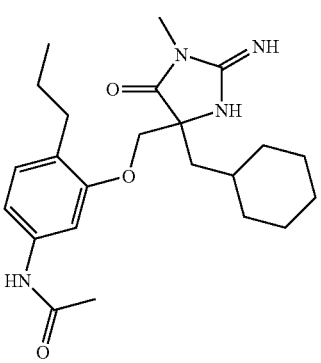 | 414 | 415 |
| 367 | 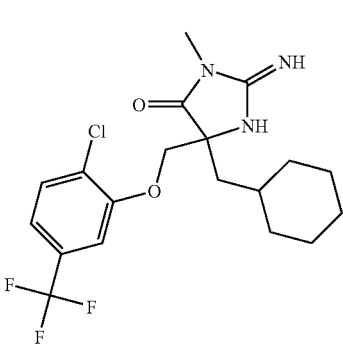 | 417 | 418 |
| 368 | 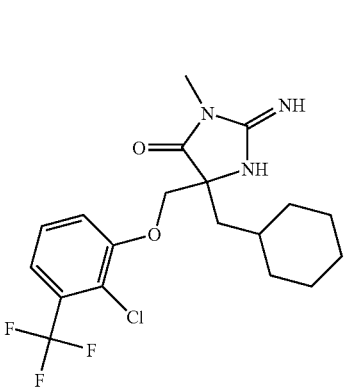 | 417 | 418 |
| 369 | 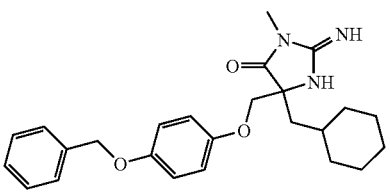 | 421 | 422 |

-continued

| # | Structure | MW | Obs. m/e |
|---|---|---|---|
| 370 | 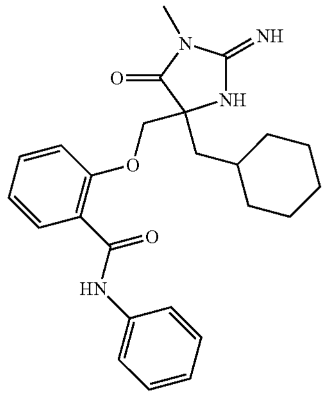 | 434 | 435 |
| 371 | 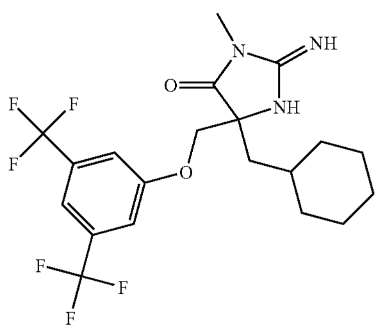 | 451 | 452 |

Method AG

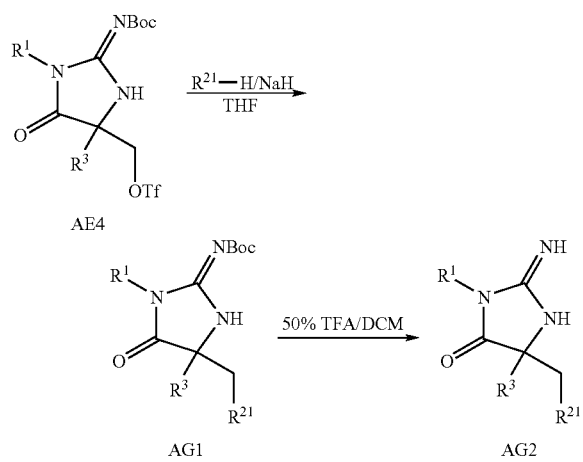

Method AG, Step 1:

$R^{21}$—H ($R^{21}$=PhS—) (33 μl, 0.318 mmole) was treated with NaH (10.2 mg, 60% in mineral oil) in 0.5 ml anhydrous THF. A solution of AE4 ($R^1$=Me, $R^3$=Cyclohexylmethyl) (20 mg, 0.0424 mmol) in 0.5 ml anhydrous THF was added. The reaction mixture was stirred at room temperature overnight before it was partitioned between ether and saturated NaHCO$_3$ water solution. The aqueous phase was extracted with ether 2 times. The combined organic phase was washed with brine 2 times, and dried over anhydrous NaSO$_4$. The crude was purified on flash column with EtOAc/hexane to give 9 mg of AG1 ($R^{21}$=PhS—, $R^1$=Me, $R^3$=cyclohexylmethyl) (49.2% yield).

Method AG, Step 2:

AG1 ($R^{21}$=PhS—, $R^1$=Me, $R^3$=cyclohexylmethyl) was treated with 50% TFA according to the Step 6 of the method H to give AG2 ($R^{21}$=PhS—, $R^1$=Me, $R^3$=cyclohexylmethyl).

The following compounds were synthesized using similar method:

| # | Structure | MW | Obs. m/e |
|---|---|---|---|
| 372 | 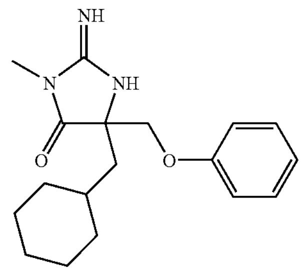 | 315 | 316 |
| 373 | 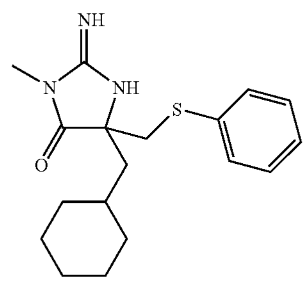 | 331 | 332 |
| 374 | 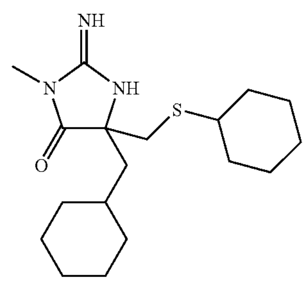 | 337 | 338 |

Method AH

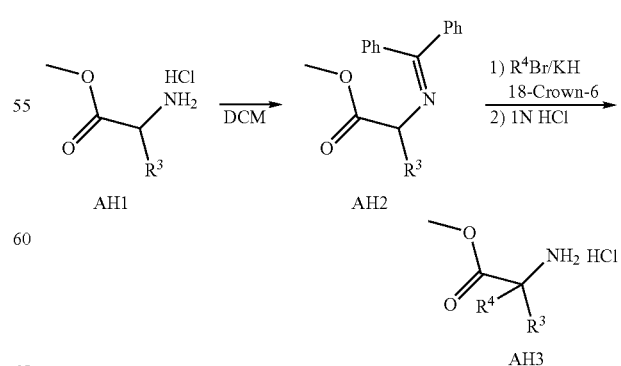

Method AH, Step 1:

Benzophenone imine (3.27 g, 18.04 mmole) was added to a suspension of AH1 ($R^3$=cyclohexylmethyl) (4 g, 18.04 mmole) in 65 ml DCM. The reaction mixture was stirred at room temperature overnight under $N_2$ before the solid was filtered, and the solvent was evaporated. The residue was dissolved in 100 ml ether, washed with water 2× and dried over anhydrous $MgSO_4$. The crude was purified on flash column to give 5.08 g (80.57% yield) of AH2 ($R^3$=cyclohexylmethyl).

Method AH, Step 2:

A solution of AH2 ($R^3$=cyclohexylmethyl) (1 g, 2.86 mmole) in 12 ml anhydrous THF was added to a suspension of 18-crown-6 (0.76 g, 2.86 mmole) and 30% KH in mineral oil (1.16 g, 8.58 mmole) in 4 ml anhydrous THF under N2. The mixture was cooled in ice-bath and $R^4$Br ($R^4$=3-pyridylmethyl, as a hydrobromide salt) was then added. The reaction mixture was stirred in ice-bath for 30 min and at room temperature for 2 more hrs before the reaction was quenched with 2 ml of $HOAc/THF/H_2O$ (0.25:0.75:1). The mixture was diluted with 40 ml $EtOAc/H_2O$ (1:1). The aqueous phase was extracted with EtOAc 3 times. The combined organic phase was washed with brine 3 times and dried over anhydrous MgSO4. The crude was purified on flash column to give 0.44 g (35.14% yield) of product which was treated with 1N HCl (2.2 ml, 2.22 mmole) in 3 ml ether in ice-bath followed by stirred at r.t. overnight. The aqueous phase was evaporated and purified on C-18 reverse phase column to give 0.22 g (66% yield) of AH3 ($R^4$=3-pyridylmethyl; $R^3$=cyclohexylmethyl).

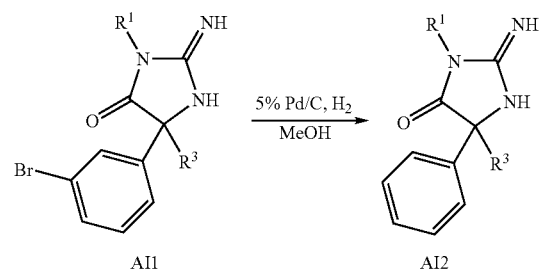

Method AI

To a solution of compound AI1 ($R^1$=Me, $R^3$=n-Bu) (34 mg, 0.105 mmol) in methanol (1 ml) was added 10% Pd/C (5 mg). The mixture was kept under an $H_2$ balloon for 1 hr. After filtration of the catalyst, the filtrate was concentrated to get crude product. This residue was purified by RP HPLC to get compound AI2 ($R^1$=Me, $R^3$=n-Bu) (25 mg, 100%). Observed MW (M+H) 246.1; exact mass 245.15. $^1$H NMR (400 MHz, $CD_3OD$): δ=7.59 (m, 2H), 7.36 (m, 3H), 3.17 (s, 3H), 2.17 (m, 2H), 1.27 (m, 4H), 0.86 (t, 3H, J=7.2 Hz).

The following compounds were synthesized using similar method:

| # | Structure | MW | Obs. m/e |
|---|---|---|---|
| 375 | 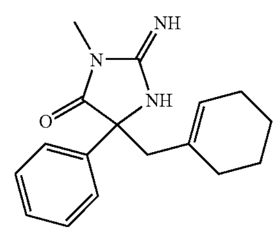 | 283 | 284 |
| 376 | 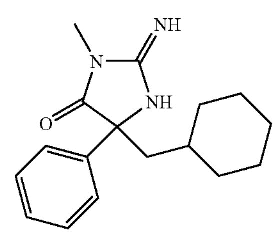 | 285 | 286 |
| 377 | 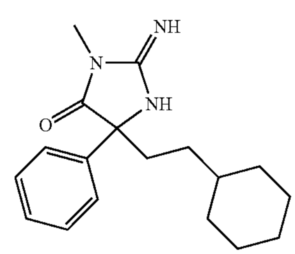 | 299 | 300 |

| # | Structure | MW | Obs. m/e |
|---|---|---|---|
| 378 | 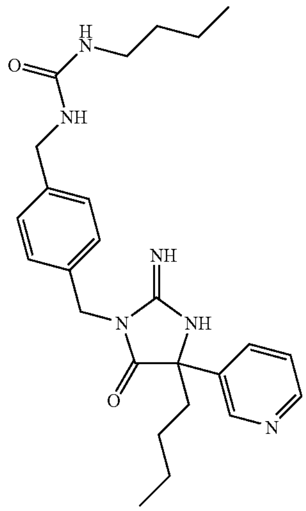 | 450 | 451 |
| 379 | 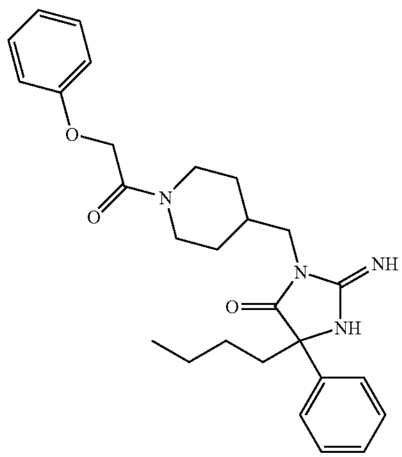 | 462 | 463 |
| 380 | 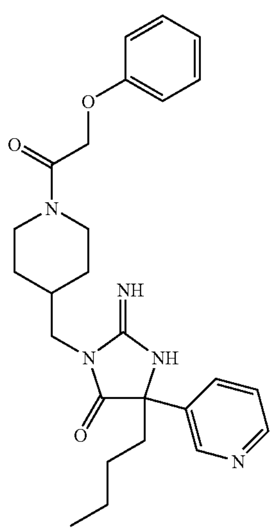 | 463 | 464 |

-continued
| # | Structure | MW | Obs. m/e |
|---|---|---|---|
| 381 | 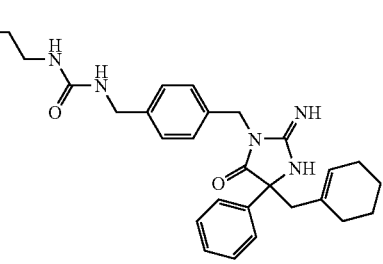 | 487 | 488 |
| 382 | 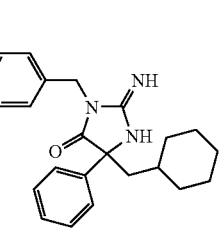 | 489 | 490 |
| 383 | 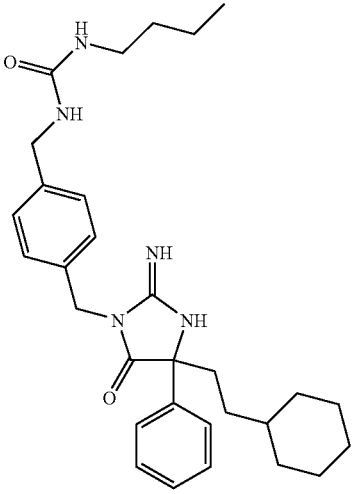 | 503 | 504 |
| 384 | 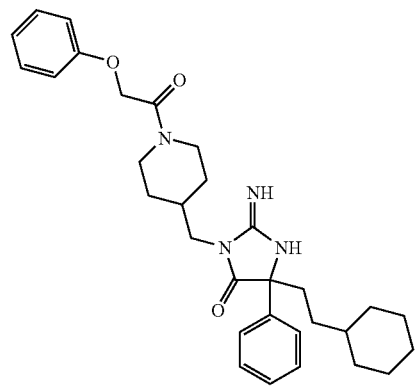 | 516 | 517 |

Method AJ

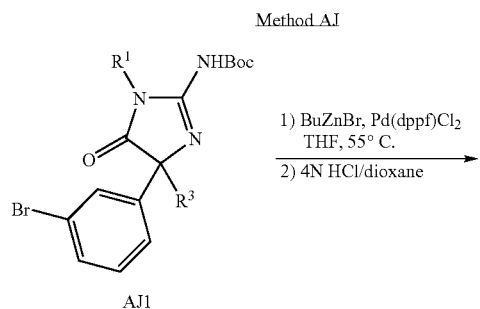

AJ1

1) BuZnBr, Pd(dppf)Cl₂
   THF, 55° C.
2) 4N HCl/dioxane

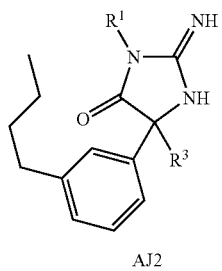

AJ2

To a mixture of compound AJ1 ($R^1$=Me, $R^3$=n-Bu) (70 mg, 0.165 mmol) and butylzincbromide (1.32 ml, 0.6 mmol) was added Pd(dppf)Cl₂. The mixture was degassed, sealed and heated at 55° C. for 1 day. The mixture was diluted with CH₂Cl₂ and NH₃/H₂O. The organic layer was separated, dried, concentrated, and purified by RP HPLC to get product which was then treated with 4N HCl/dioxane for 30 min to give compound AJ2 ($R^1$=Me, $R^3$=n-Bu) (12 mg, 25%). Observed MW (M+H) 302.1; ¹H NMR (400 MHz, CD₃OD): δ=7.32 (m, 3H), 7.22 (m, 1H), 3.19 (s, 3H), 2.65 (m, 2H), 2.20 (m, 2H), 1.60 (m, 2H), 1.38 (m, 4H), 1.24 (m, 2H), 0.92 (m, 6H).

The following compound was synthesized in a similar fashion:

| # | Structure | MW | Obs. m/e |
|---|-----------|-----|----------|
| 386 | 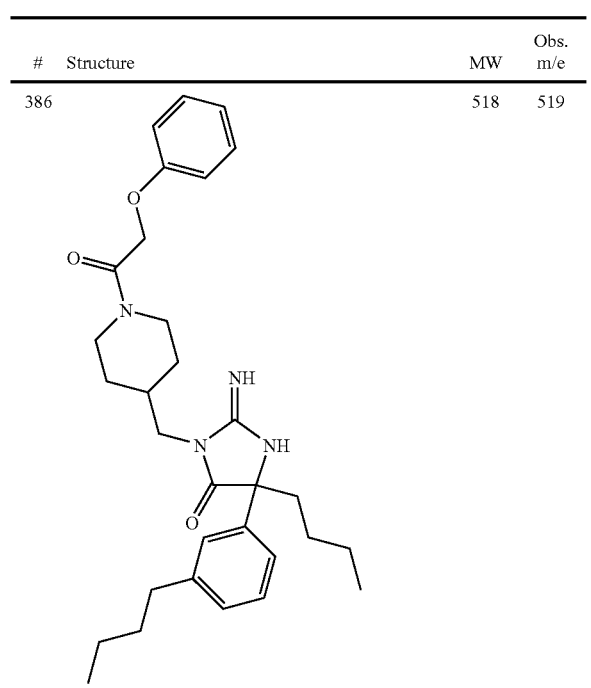 | 518 | 519 |

-continued

| # | Structure | MW | Obs. m/e |
|---|-----------|-----|----------|
| 385 | 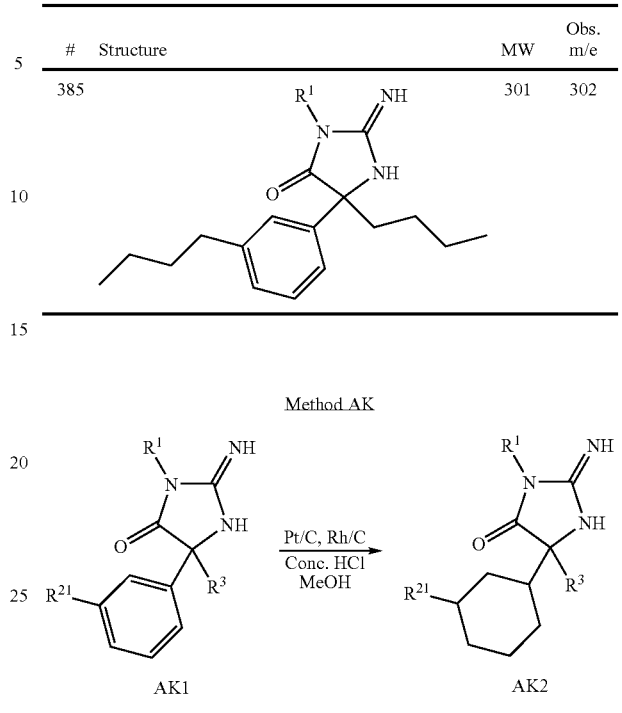 | 301 | 302 |

Method AK

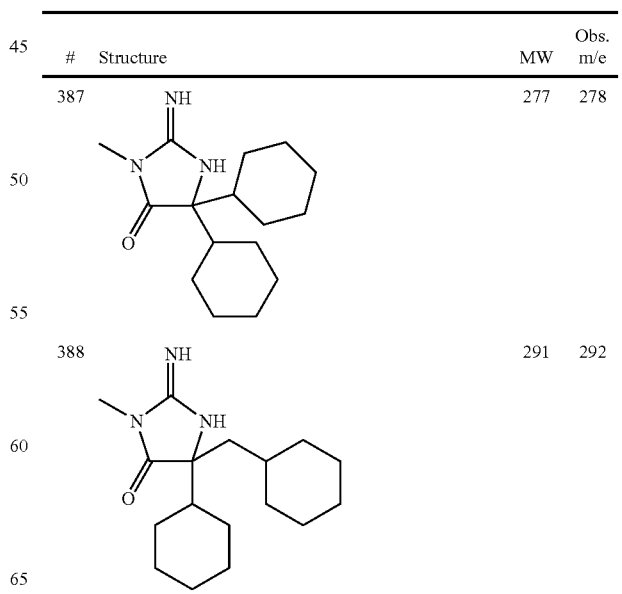

AK1 → AK2

Pt/C, Rh/C
Conc. HCl
MeOH

To a solution of AK1 ($R^1$=Me, $R^3$=n-Butyl, $R^{21}$=n-Bu) (9 mg, 0.03 mmol) in methanol (1 ml) was added 5% Pt/C (5 mg), Rh/C (5 mg) and conc. HCl (0.05 ml). The mixture was kept under H₂ (50 psi) for 2 days. After the filtration of the catalyst, the filtrate was concentrated to get compound AK2 ($R^1$=Me, $R^3$=n-butyl, $R^{21}$=n-Bu) Observed MW (M+H) 308.1. ¹H NMR (CD₃OD): δ=3.16 (s, 3H), 1.80 (m, 6H), 1.26 (m, 16H), 0.88 (m, 6H).

The following compounds were synthesized using similar method:

| # | Structure | MW | Obs. m/e |
|---|-----------|-----|----------|
| 387 | 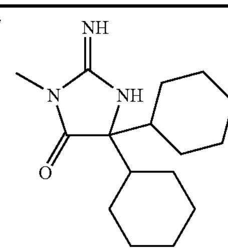 | 277 | 278 |
| 388 | 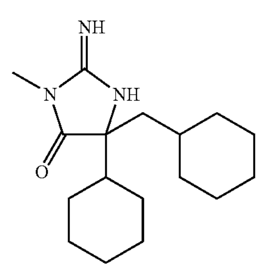 | 291 | 292 |

-continued

| # | Structure | MW | Obs. m/e |
|---|---|---|---|
| 389 | 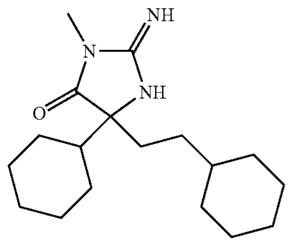 | 305 | 306 |
| 390 | 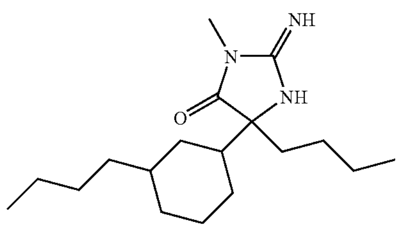 | 307 | 308 |
| 391 | 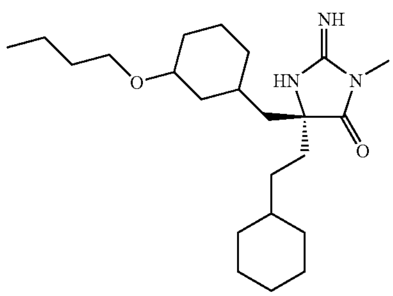 | 391 | 392 |
| 392 | 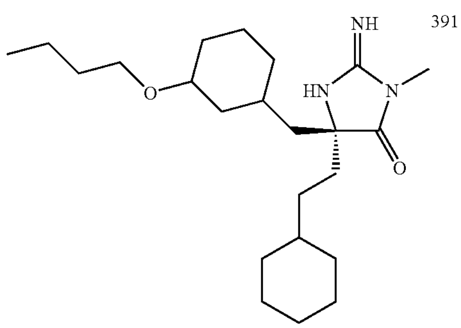 | 391 | 392 |

Method AL

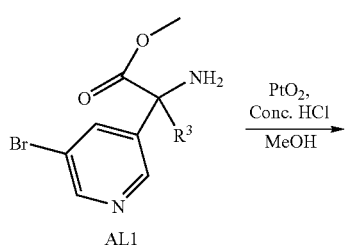

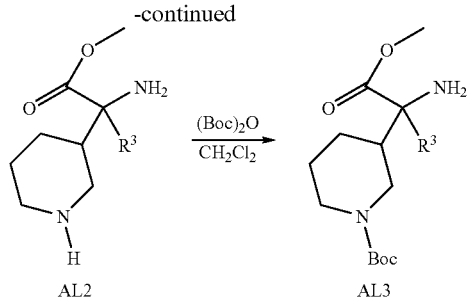

Method AL, Step 1:

To a solution of compound AL1 ($R^3$=n-Bu) (418 mg, 1.39 mmol) in methanol (8 ml) was added $PtO_2$ (40 mg) and conc. HCl (0.4 ml). The mixture was hydrogenated (50 psi) for 1 day. After filtration of the catalyst, the filtrate was concentrated. The crude residue was basified to pH=11-12 by 1N NaOH. This mixture was extracted with ethyl acetate. The organic layer was separated, dried and concentrated to get compound AL2 ($R^3$=n-Bu) (316 mg, 100%).

Method AL, Step 2:

To a solution of compound AL2 ($R^3$=n-Bu) (300 mg, 1.32 mmol) in dichloromethane (6 ml) was added $(BOC)_2O$ (316 mg, 1.45 mmol). The mixture was stirred at RT for 1.5 hr. It was diluted with water and dichloromethane. The organic layer was separated, dried and concentrated to get compound AL3 ($R^3$=n-Bu) (464 mg, 100%).

Method AM

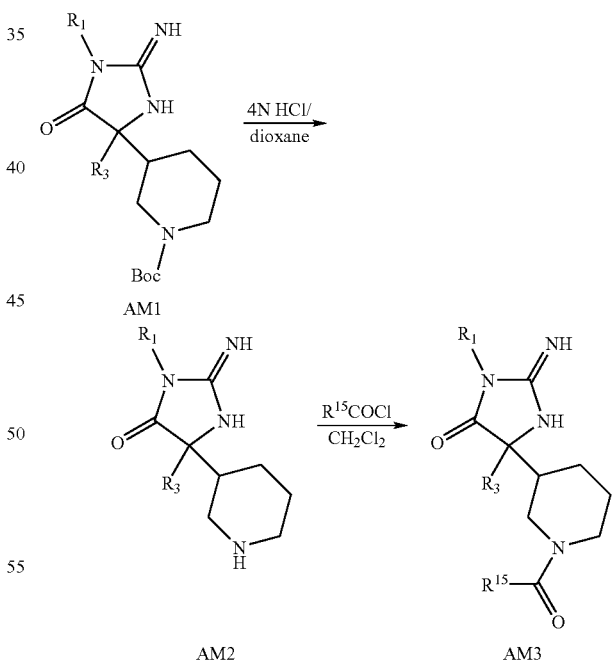

Method AM, Step 1:

Compound AM1 ($R^1$=Me, $R^3$=n-Butyl) was treated with 4N HCl in dioxane for 2 hr. The mixture was concentrated to get compound AM2 as an HCl salt ($R^1$=Me, $R^3$=n-Butyl). Observed MW (M+H) 470.1; $^1H$ NMR ($CD_3OD$): δ=7.28 (m, 2H), 6.96 (m, 3H), 4.80 (m, 2H), 4.56 (m, 1H), 4.00 (m, 1H), 3.64 (m, 4H), 3.37 (m, 2H), 3.12 (m, 1H), 3.00 (m, 1H), 2.90

(m, 1H), 2.72 (m, 1H), 2.38 (m, 1H), 2.12-1.62 (m, 8H), 1.35 (m, 6H), 1.12 (m, 1H), 0.91 (m, 3H).

Method AM, Step 2:

To a solution of compound AM2 ($R^1$=Me, $R^3$=n-Butyl) (32 mg, 0.068 mmol) in dichloromethane (1 ml) was added acetyl chloride (5 ul, 0.072 mmol). The mixture was stirred for 2 hr. It was then diluted with $CH_2Cl_2$ and water. The organic layer was separated, dried, concentrated and purified by RP HPLC to get compound AM3 ($R^1$=Me, $R^3$=n-Butyl and $R^{15}$=Me) Observed MW (M+H) 512.3; $^1$H NMR (400 MHz, $CDCl_3$): δ=7.27 (m, 2H), 6.98 (m, 1H), 6.92 (m, 2H), 4.65 (s, 2H), 4.50 (m, 2H), 3.98 (m, 1H), 3.70 (m, 1H), 3.41 (m, 2H), 2.98 (m, 2H), 2.62 (m, 1H), 2.50 (m, 1H), 2.47 (m, 1H), 2.02 (m, 5H), 1.75 (m, 6H), 1.26 (m, 7H), 0.84 (m, 3H).

The following compounds were synthesized using similar method:

| # | Structure | MW | Obs. m/e |
|---|-----------|----|---------:|
| 394 | 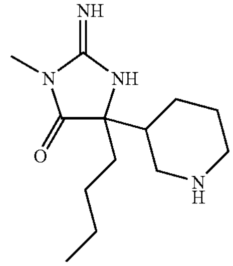 | 252 | 253 |
| 395 | 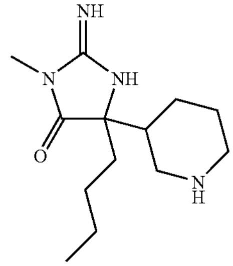 | 252 | 253 |
| 396 | 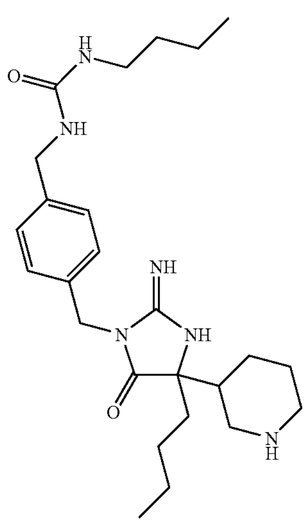 | 456 | 457 |
| 397 | | 469 | 470 |
| 398 | | 498 | 499 |

-continued

| # | Structure | MW | Obs. m/e |
|---|---|---|---|
| 399 | [structure] | 511 | 512 |

Method AN

[Reaction scheme: R16-C(O)-R15 + AN2 → with Et3N, NaBH(OAc)3, DCE]

AN2

-continued

[Structure AN3 with R1, R3, R15, R16 substituents]

To a solution of compound AN2 (R¹=4-N-(α-phenoxyacetyl)piperidinylmethyl, R3=n-Butyl) (28 mg, 0.06 mmol) in dichloroethane (2 ml) was added butyraldehyde (5.3 ul, 0.06 mmol), triethylamine (8.4 ul, 0.06 mmol) and NaBH(OAc)₃ (18 mg, 0.084 mmol). The mixture was stirred overnight. It was then diluted with dichloromethane and water. The organic layer was separated, dried, concentrated and purified by RP HPLC to get AN2 (R¹=4-N-(a-phenoxyacetyl)piperidinylmethyl, R³=n-Butyl, R¹⁵=propyl and R¹⁶=H) (5.4 mg, 17%). Observed MW (M+H) 526.1; exact mass 525.37. ¹H NMR (CD₃OD): δ=7.28 (m, 2H), 6.96 (m, 3H), 4.76 (m, 2H), 4.55 (m, 1H), 4.05 (m, 1H), 3.77 (m, 1H), 3.61 (m, 3H), 3.50 (m, 1H), 3.11 (m, 4H), 2.85 (m, 1H), 2.68 (m, 1H), 2.38 (m, 1H), 2.05 (m, 2H), 1.95 (m, 2H), 1.73 (m, 5H), 1.39 (m, 8H), 1.10 (m, 1H), 0.99 (m, 3H), 0.92 (m, 3H).

The following compound was synthesized using similar method:

| # | Structure | MW | Obs. m/e |
|---|---|---|---|
| 400 | [structure] | 308 | 309 |
| 401 | [structure] | 308 | 309 |

-continued

| # | Structure | MW | Obs. m/e |
|---|---|---|---|
| 402 | 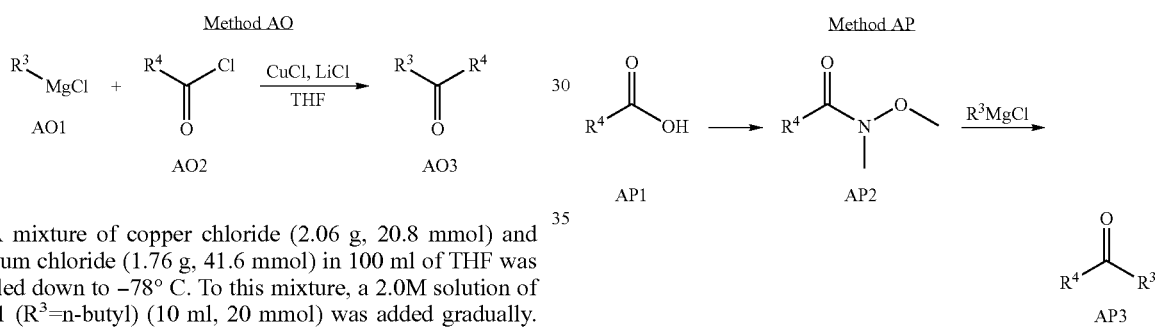 | 525 | 526 |

Method AO $R^3\text{-MgCl}$ (AO1) + $R^4\text{-C(=O)Cl}$ (AO2) $\xrightarrow{\text{CuCl, LiCl, THF}}$ $R^3\text{-C(=O)-}R^4$ (AO3)

A mixture of copper chloride (2.06 g, 20.8 mmol) and lithium chloride (1.76 g, 41.6 mmol) in 100 ml of THF was cooled down to −78° C. To this mixture, a 2.0M solution of AO1 ($R^3$=n-butyl) (10 ml, 20 mmol) was added gradually. The reaction was warmed up to −60° C., and AO2 ($R^4$=m-Br—Ph) (2.9 ml, 22 mmol) was injected. The mixture was stirred at −60° C. for 15 minutes and then quickly warmed up to RT by removing the dry-ice bath. The reaction was quenched with water and sat. NaHCO$_3$. After addition of diethyl ether, a lot of precipitate formed and was filtered. From the biphasic filtrate, the organic layer was separated, dried, concentrated and purified by silica gel chromatography (10% EtOAc/hexane) to get ketone AO3 ($R^4$=m-BrPh, $R^3$=n-Bu) (3.93 g, 82%). Observed MW (M+H) 241.1; exact mass 240.01. $^1$H NMR (400 MHz, CDCl$_3$): δ=8.07 (m, 1H), 7.88 (m, 1H), 7.64 (m, 1H), 7.34 (m, 1H), 2.94 (t, 3H, J=7.2 Hz), 1.71 (m, 2H), 1.40 (m, 2H), 0.95 (t, 3H, J=7.6 Hz).

The following ketones were made according to Method 9:

| Structure | Observed MW (M + H) | Exact mass |
|---|---|---|
| 4-Br-pyridin-3-yl pentanone | 242.1 | 241.01 |

Method AP $R^4\text{-C(=O)OH}$ (AP1) → $R^4\text{-C(=O)-N(OMe)(Me)}$ (AP2) $\xrightarrow{R^3\text{MgCl}}$ $R^4\text{-C(=O)-}R^3$ (AP3)

Method AP, Step 1:

To a solution of AP1 ($R^4$=3-Bromophenyl) (5 g, 25 mmol) in dichloromethane (10 ml) were added N,O-dimethylhydroxylamine hydrochloride (2.56 g, 26.25 mmol) and 4-methylmorpholine (2.95 ml, 26.25 mmol). EDCI (5.04 g, 26.25 mmol) was then added portionwise. The reaction mixture was stirred at RT overnight and was then quenched with 1N HCl (60 ml). The mixture was extracted with dichloromethane. The organic layer was washed with 1N HCl and brine, dried over Na$_2$SO$_4$, and concentrated to give the Weinreb amide AP2 ($R^4$=m-Bromophenyl) (5.96 g, 98%). Observed MW (M+H) 244.1; exact mass 243.99. $^1$H NMR (CDCl$_3$): δ=7.78 (m, 1H), 7.58 (m, 2H), 7.24 (m, 1H), 3.51 (s, 3H), 3.32 (s, 3H). This material was used in the next step without purification.

Method AP, Step 2:

To a suspension of magnesium turnings (1.19 g, 48.8 mmol) in 30 ml of THF was added dropwise a solution of $R^3$Br ($R^3$=cyclohexylethyl) (5.73 ml, 36.6 mmol) in 24 ml of THF. After addition of half of the solution of bromide, several crystals of iodine were added to initiate the reaction. The mixture became cloudy and heat evolved. The rest of the solution of bromide was added dropwise. The mixture was stirred at RT for 30 minutes and then was cooled to 0° C., and the AP2 (R⁴=m-Bromophenyl) (5.96 g, 24.4 mmol) was added. The mixture was stirred at RT for 3 hr and then quenched with 1N HCl until no residual Mg(0) was left. The phases was separated, and the water layer was extracted with ether. The combined organic layers were washed with brine, dried, and concentrated. The crude was purified by silica chromatography (15% EtOAc/hexane) to get ketone AP3 (R⁴=m-Bromophenyl, R³=Cyclohexylethyl) (8.06 g, 100%). Observed MW (M+H) 295.2; exact mass 294.06. ¹H NMR (400 MHz, CDCl₃): δ=8.18 (m, 1H), 7.85 (m, 1H), 7.64 (m, 1H), 7.33 (m, 1H), 2.94 (t, 3H, J=7.2 Hz), 1.70 (m, 9H), 1.63 (m, 4H).

Method AQ

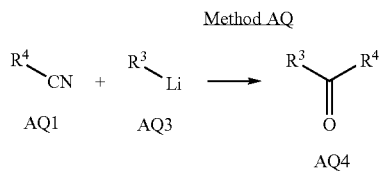

To a −78° C. solution of AQ1 (R⁴=cyclopropyl) (2.55 g, 38.0 mmol) in diethyl ether (100 ml) was added AO3 (R³=n-Bu) (38 ml, 1.5 M in hexanes, 57 mmol). After 45 min, the cooling bath was removed. After 3 h at RT, the reaction was quenched by dropwise addition of water and then diluted further with EtOAc and water. The phases were separated and the aqueous layer was extracted with EtOAc (2×). The organic portions were combined, washed with brine, dried over MgSO₄, and concentrated. This crude residue was subjected to column chromatography (silica gel, 0%→100% CH₂Cl₂/hexanes) to provide the desired ketone AQ4 (R⁴=cyclopropyl, R³=n-Butyl) (2.57 g, 20.4 mmol, 54%). ¹H NMR (CDCl₃) δ 2.52 (t, J=7.2 Hz, 2 H), 1.90 (m, 1 H), 1.57 (m, 2 H), 1.30 (m, 2 H), 0.98 (m, 2 H), 0.89 (t, J=7.6 Hz, 3 H), 0.83 (m, 2 H).

Method AR

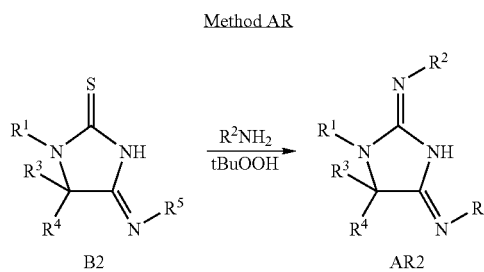

Method AR:

Compound B2 (R¹=m-Cl-Phenethyl, R³=Me, R⁴=i-butyl and R⁵=benzyl) was converted into AR2 (R¹=m-Cl-Phenethyl, R³=Me, R⁴=i-butyl and R⁵=benzyl) using method A step 3.

The following compounds were synthesized using similar methods:

| # | Structure | MW | Obs. m/e |
|---|---|---|---|
| 403 | 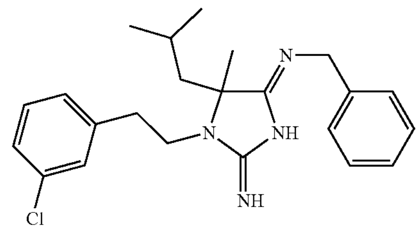 | 396 | 397 |
| 404 | 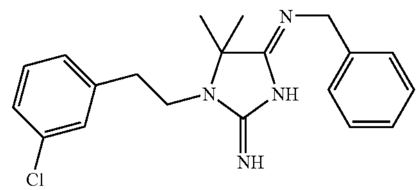 | 354 | NA |
| 405 | 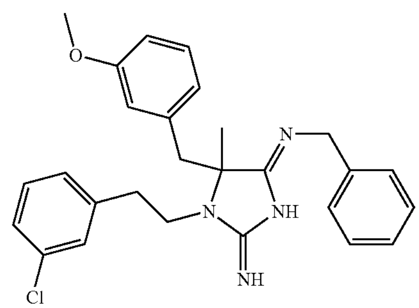 | 477 | NA |
| 406 | 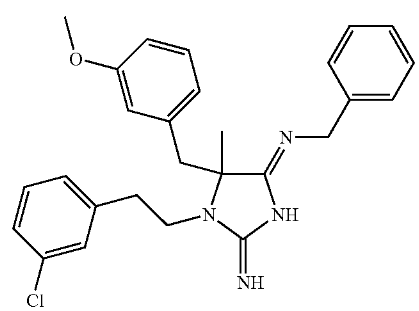 | 460 | NA |
| 407 | 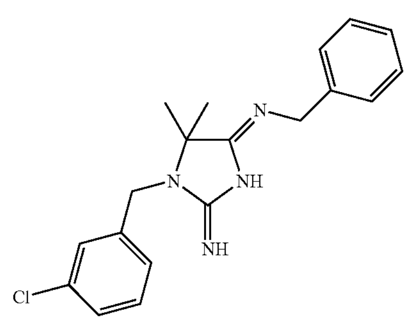 | 340 | NA |

-continued

| # | Structure | MW | Obs. m/e |
|---|---|---|---|
| 408 | 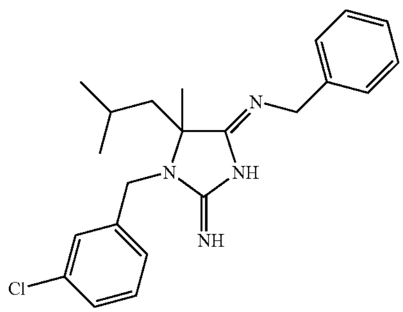 | 382 | NA |
| 409 | 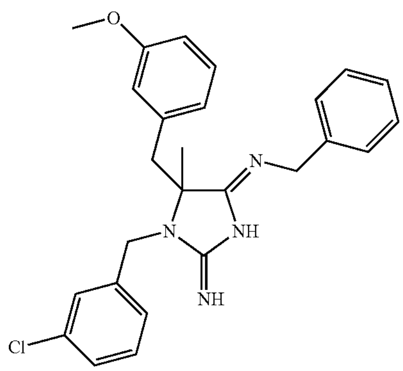 | 446 | NA |

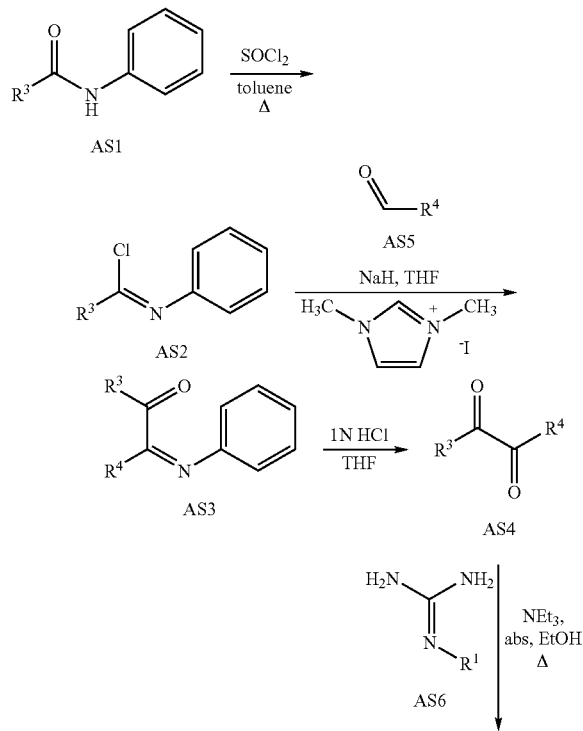

Method AS

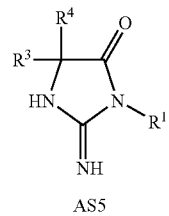

AS5

Method AS, Step 1:

To a mixture of AS1 ($R^3$=Ph) (3.94 g) in toluene (10 ml) was added thionyl chloride (1.61 ml) and the resulting mixture as heated under reflux for 6 h (until HCl evolution ceased). The reaction mixture was kept overnight at rt before it was concentrated in vacuo. Toluene (10 ml) was added and the mixture was concentrated in vacuo again. The reaction mixture was dissolved in $CH_2Cl_2$, solid sodium bicarbonate added, filtered and then the $CH_2Cl_2$ solution was concentrated in vacuo to give AS2 ($R^3$=Ph).

Method AS, Step 2:

To AS2 ($R^3$=Ph) (0.645 g) and AS5 ($R^4$=4-chlorophenyl) (0.464 g), and 1,3-dimethylimidazolium iodide (0.225 g) in anhydrous THF (20 ml) was added 60% sodium hydride in oil (0.132 g). The resulting mixture was stirred at rt for 18 h. The reaction mixture was concentrated and partitioned between $H_2O$ and $Et_2O$. The dried $Et_2O$ solution was concentrated in vacuo to give a yellow residue which was placed on preparative silica gel plates and eluted with $CH_2Cl_2$ to give AS3 ($R^3$=Ph, $R^4$=p-ClPh). (Miyashita, A., Matsuda, H., Hiagaskino, T., Chem. Pharm. Bull., 1992, 40 (10), 2627-2631).

Method AS, Step 3:

Hydrochloric acid (1N, 1.5 ml) was added to AS3 ($R^3$=Ph, $R^4$=p-ClPh) in THF (10 ml) and the resulting solution was stirred at rt for 20 h. The reaction mixture was concentrated in vacuo and then partitioned between $CH_2Cl_2$ and $H_2O$. The dried $CH_2Cl_2$ was concentrated in vacuo to give a residue which was placed on preparative silica gel plates and eluted with $CH_2Cl_2$:hexane 1:1 to afford AS4 ($R^3$=Ph, $R^4$=p-ClPh).

Method AS, Step 4:

AS4 ($R^3$=Ph, $R^4$=p-ClPh) (0.12 g) and methylguanidine, HCl (AS6, $R^1$=Me) (0.055 g) were mixed in absolute EtOH (5 ml) with triethylamine (0.2 ml) and then heated under reflux for 20 h. The resulting mixture was concentrated and then partitioned between $CH_2Cl_2$ and $H_2O$. The dried $CH_2Cl_2$ was concentrated in vacuo to give a residue which was placed on preparative silica gel plates and eluted with $CH_2Cl_2$:MeOH 9:1 to afford AS5 ($R^3$=Ph, $R^4$=p-ClPh and $R^1$=Me).

The following compounds were synthesized using similar methods:

| # | Structure | MW | Obs. m/e |
|---|---|---|---|
| 411 | 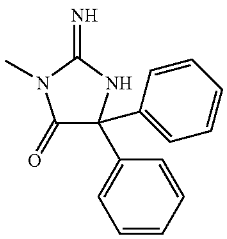 | 265 | 266 |
| 412 | 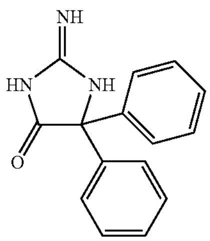 | 265 | 266 |
| 413 | 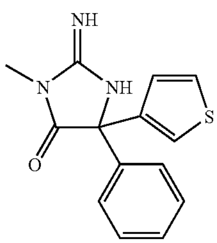 | 271 | 272 |
| 414 | 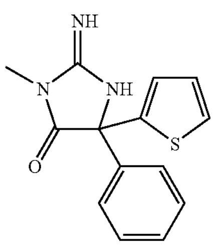 | 271 | 272 |
| 415 | 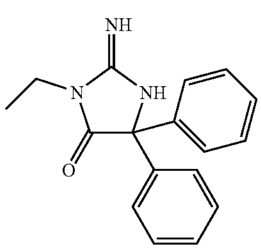 | 279 | 280 |
| 416 | 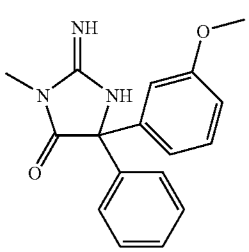 | 295 | 296 |

-continued

| # | Structure | MW | Obs. m/e |
|---|---|---|---|
| 417 | 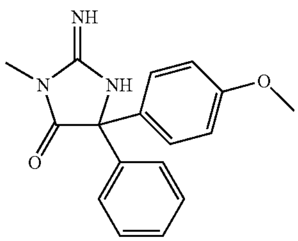 | 295 | 296 |
| 418 | 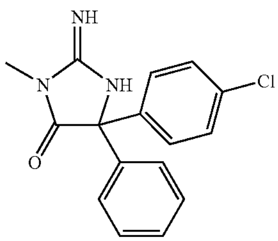 | 299 | 300 |
| 419 | 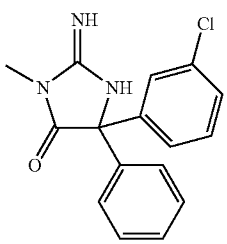 | 299 | 300 |
| 420 | 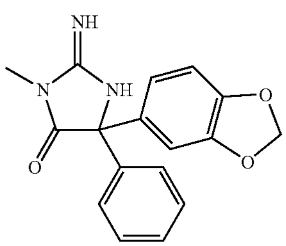 | 309 | 310 |
| 421 | 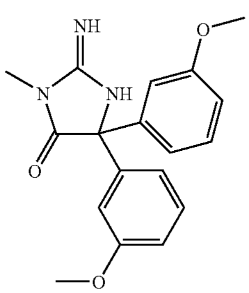 | 325 | 326 |
| 422 | 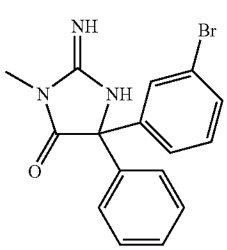 | 343 | 344 |

-continued
| # | Structure | MW | Obs. m/e |
|---|---|---|---|
| 423 | 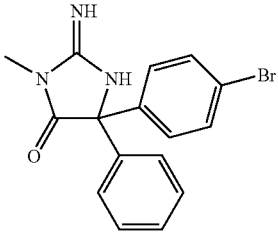 | 343 | 344 |
| 424 | 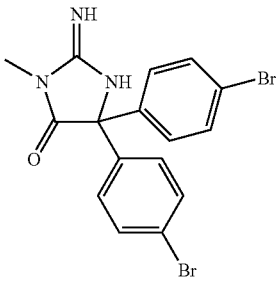 | 421 | 422 |
| 425 | 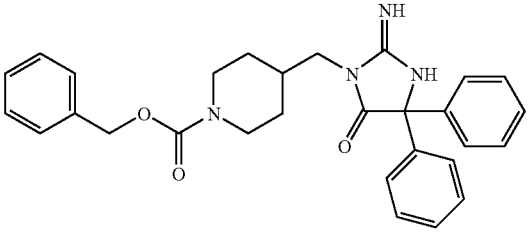 | 482 | 483 |
| 426 | 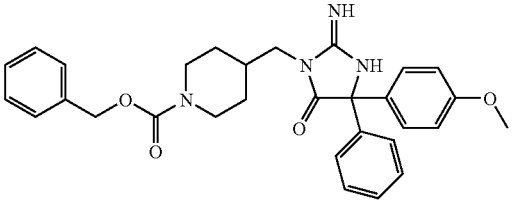 | 512 | 513 |
| 427 | 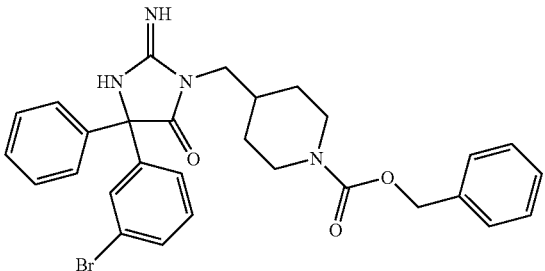 | 560 | 561 |

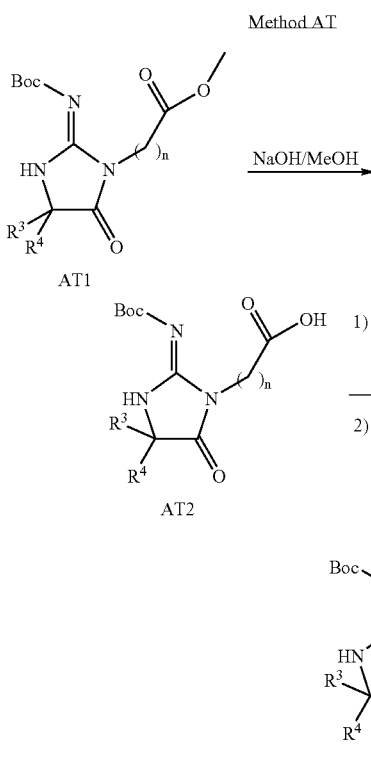

Method AT

Method AT, Step 1:

AT1, prepared using a method similar to Method H, Step 1, 2 and 3, (n=4, $R^3=R^4$=n-Bu) (0.146 g) in MeOH (3 ml) and 1N NaOH (0.727 ml) were stirred overnight at rt. The mixture was concentrated and then partitioned in water (pH ~3, adjusted using conc. HCl) and EtOAc. The dried EtOAc layer was concentrated in vacuo to afford AT2 (n=4, $R^3=R^4$=n-Bu).

Method AT, Step 2:

Compound AT2 (n=4, $R^3=R^4$=n-Bu) (0.012 g). in MeCN (1 ml) was treated with EDC resin (0.12 g, 1.44 mmol/g), HOBT (0.004 g) in THF (1 ml), and n-butylamine ($R^{15}$=H, $R^{16}$=n-butyl) (0.007 ml). The reaction was carried out overnight at rt. before Argonaut PS-NCO resin (0.150 g), PS-polyamine resin (0.120 g) and THF (2 ml) were added and the mixture shaken for 4 h. The reaction mixture was filtered and resin washed with THF (2 ml). The combined organic phase was concentrated in vacuo before the residue was treated with 1N HCl in MeOH (1 ml) for 4 h followed by evaporation of solvent to give AT3 (n=4, $R^3=R^4$=n-Bu, $R^{15}$=H and $R^{16}$=n-Butyl).

The following compounds were synthesized using similar method:

| # | Structure | MW | Obs. m/e |
|---|-----------|----|----------|
| 428 | 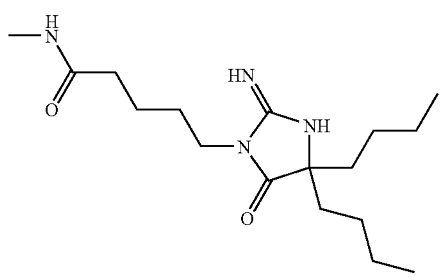 | 324 | 325 |
| 429 | 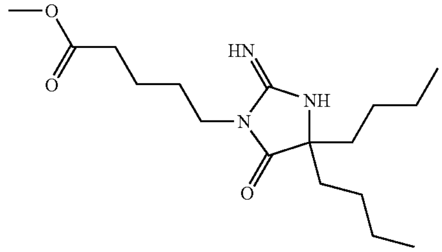 | 325 | 326 |

-continued
| # | Structure | MW | Obs. m/e |
|---|---|---|---|
| 430 | 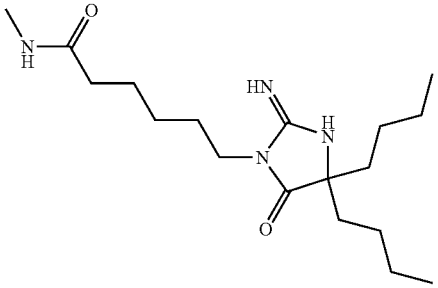 | 338 | 339 |
| 431 | 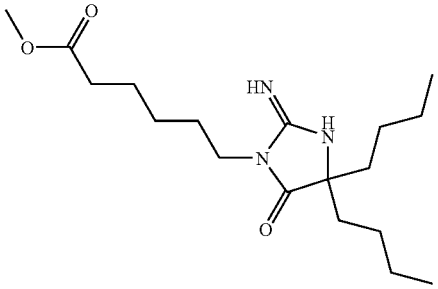 | 339 | 340 |
| 432 | 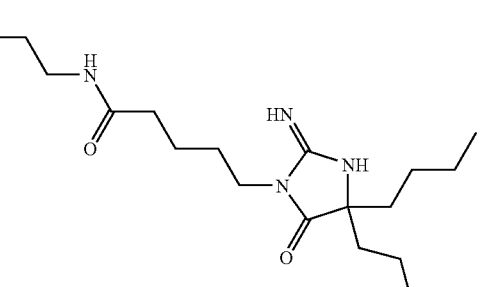 | 366 | 367 |
| 433 | 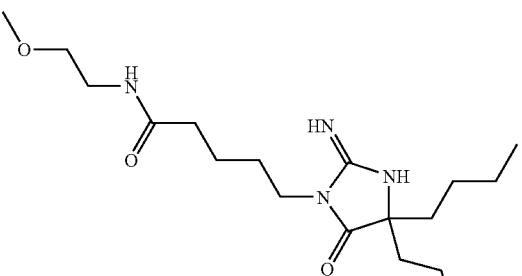 | 368 | 369 |
| 434 | 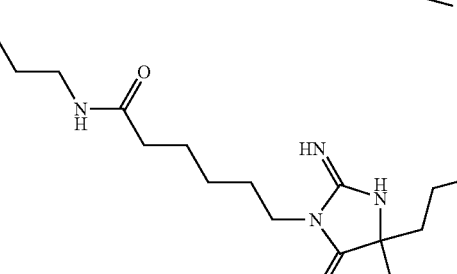 | 380 | 381 |

|   |           |     | Obs. |
|---|-----------|-----|------|
| # | Structure | MW  | m/e  |
| 435 | | 382 | 383 |
| 436 | | 400 | 401 |
| 437 | | 406 | 407 |
| 438 | | 414 | 415 |

-continued
| # | Structure | MW | Obs. m/e |
|---|---|---|---|
| 439 | 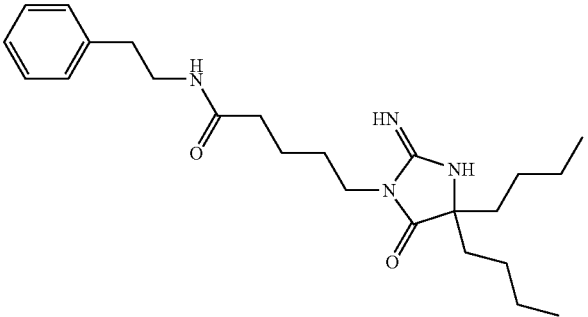 | 414 | 415 |
| 440 | 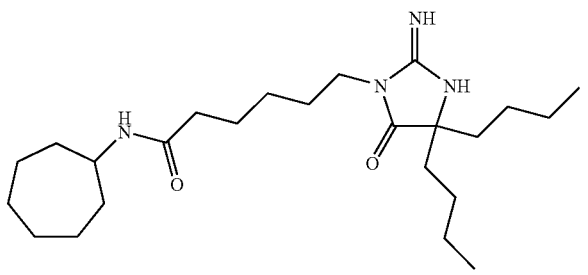 | 420 | 421 |
| 441 | 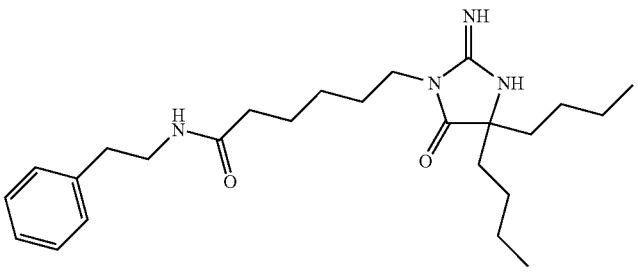 | 428 | 429 |
| 442 | 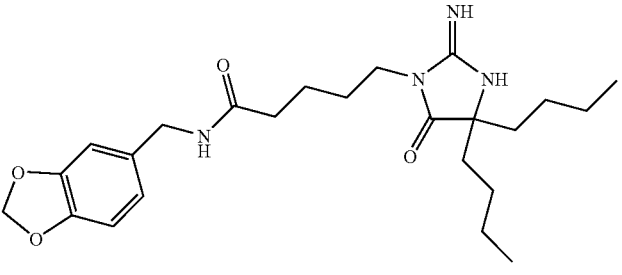 | 444 | 445 |
| 443 | 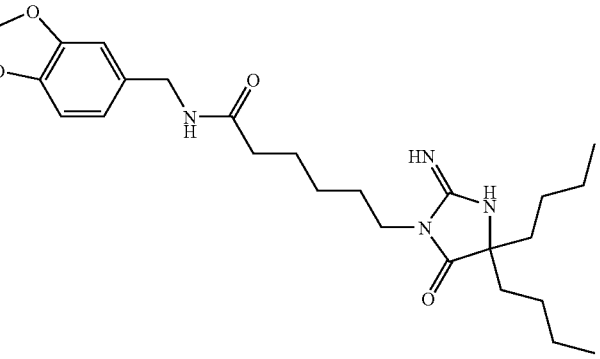 | 458 | 459 |

Method AU

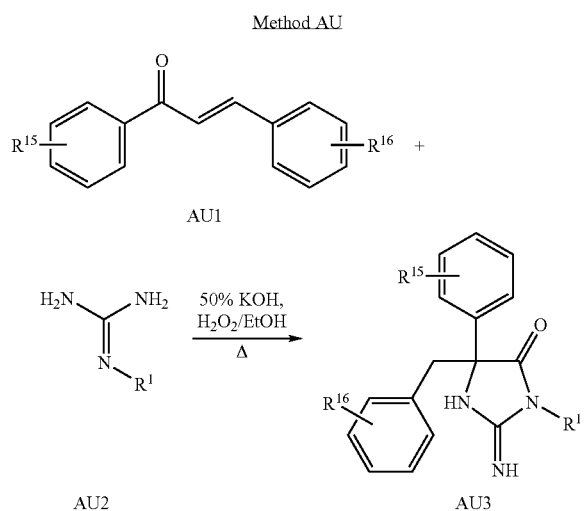

A published procedure was adapted (Varga, I.; Nagy, T.; Kovesdi, I.; Benet-Buchholz, J.; Dormab, G.; Urge, L.; Darvas, F. Tetrahedron, 2003, (59) 655-662).

AU1 ($R^{15}$=H, $R^{16}$=H) (0.300 g), prepared according to procedure described by Furniss, B. S.; Hannaford, A. J.; Smith, P. W. G.; Tatchell, A. R., (*Vogel's Textbook of Practical Organic Chemistry*. 5$^{th}$ ed. Longman: new York, 1989; pp 1034-1035), AU2 (HCl salt, $R^1$=Me) (0.237 g), 50% KOH (0.305 ml), 30% $H_2O_2$ (0.115 ml) and EtOH (4.6 ml) were heated in a sealed tube for 2 h. Reaction mixture was concentrated and extracted with $CH_2Cl_2$. The dried organic solution was concentrated in vacuo to give a residue which was placed on preparative silica gel plates eluting with $CH_2Cl_2$:MeOH 9:1 to afford AU3 ($R^{15}$=H, $R^{16}$=H, $R^1$=Me).

The following compounds were synthesized using similar method:

| # | Structure | MW | Obs. m/e |
|---|-----------|----|----|
| 444 | | 265 | 266 |
| 446 | | 280 | 281 |
| 447 | 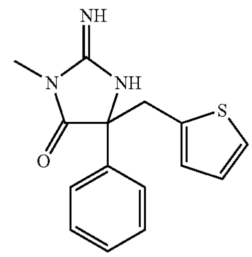 | 285 | 286 |
| 448 | 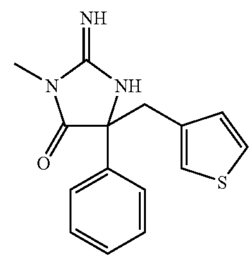 | 285 | 286 |
| 449 | 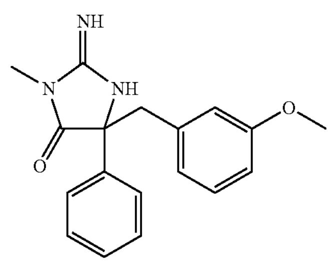 | 309 | 310 |
| 450 | 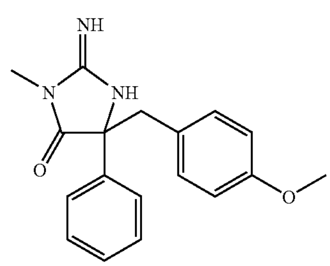 | 309 | 310 |

Method AV

-continued

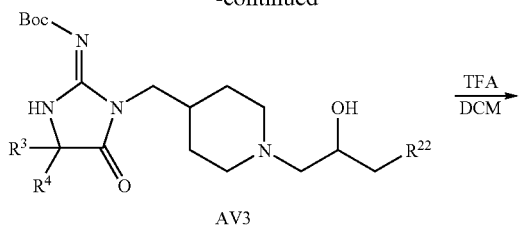

AV3

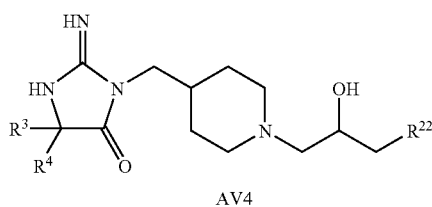

AV4

Method AV, Step 1:

In a microwave tube, AV1 ($R^3$=Me, $R^4$=Bu-i) (0.0012 g) and AV2 ($R^{22}$=OPh) (0.0059 ml) in isopropanol (2 ml) was placed in a microwave at 125° C. for 5 min. The reaction mixture was concentrated in vacuo to give AV3 ($R^3$=Me, $R^4$=i-Bu, $R^{22}$=OPh).

Method AV, Step 2:

AV3 ($R^3$=Me, $R^4$=i-Bu, $R^{22}$=OPh) in $CH_2Cl_2$ (1 ml) and TFA (1 ml) was shaken for 2 h and the concentrated in vacuo and purified on Prep LCMS to afford AV4 ($R^3$=Me, $R^4$=i-Bu, $R^{22}$=OPh).

The following compounds were synthesized in a simlar fashion.

| # | Structure | MW | Obs. m/e |
|---|---|---|---|
| 451 | 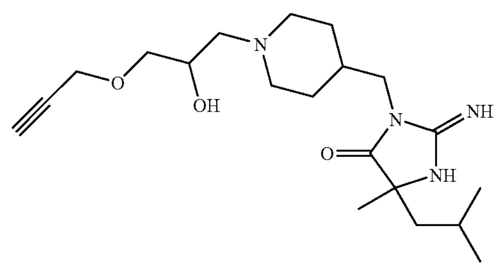 | 378 | 379 |
| 452 | 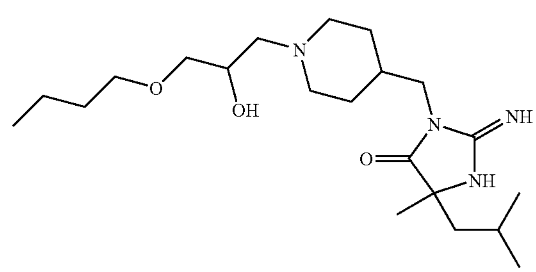 | 396 | 397 |
| 453 | 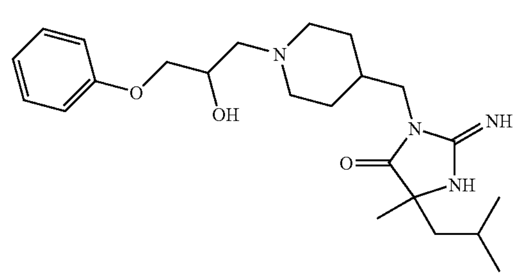 | 416 | 417 |

Method AW
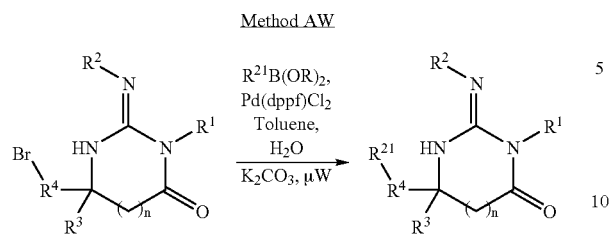
Method similar to Method U was used for this transformation. The following compounds were generated using similar methods.
The following compounds were synthesized in a similar fashion:
| # | Structure | MW | Obs. m/e |
|---|-----------|----|----|
| 454 | 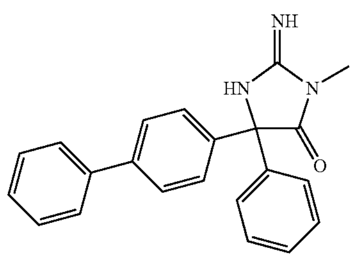 | 341 | 342 |
| 455 | 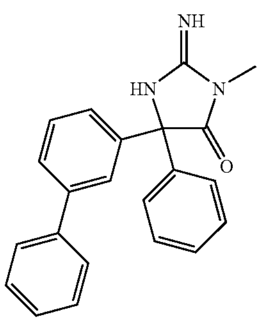 | 341 | 342 |
| 456 | 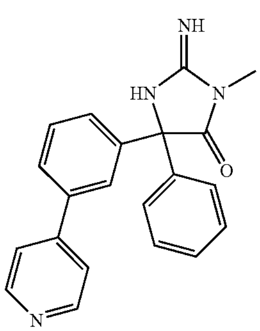 | 342 | 343 |
-continued
| # | Structure | MW | Obs. m/e |
|---|-----------|----|----|
| 457 | 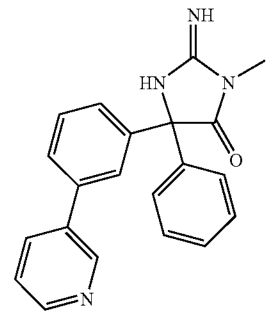 | 342 | 343 |
| 458 | 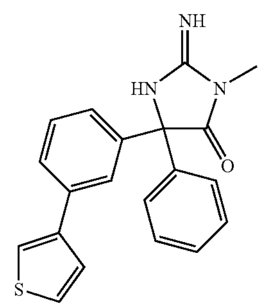 | 347 | 348 |
| 459 | 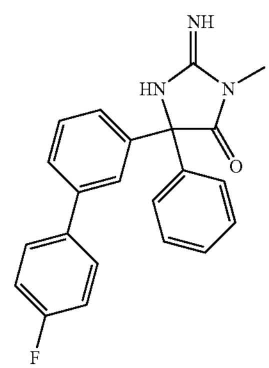 | 359 | 360 |
| 460 | 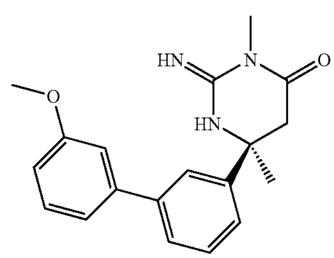 | 323 | 324 |
| 461 | 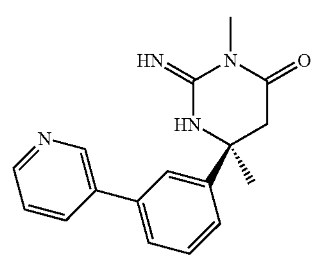 | 294 | 295 |

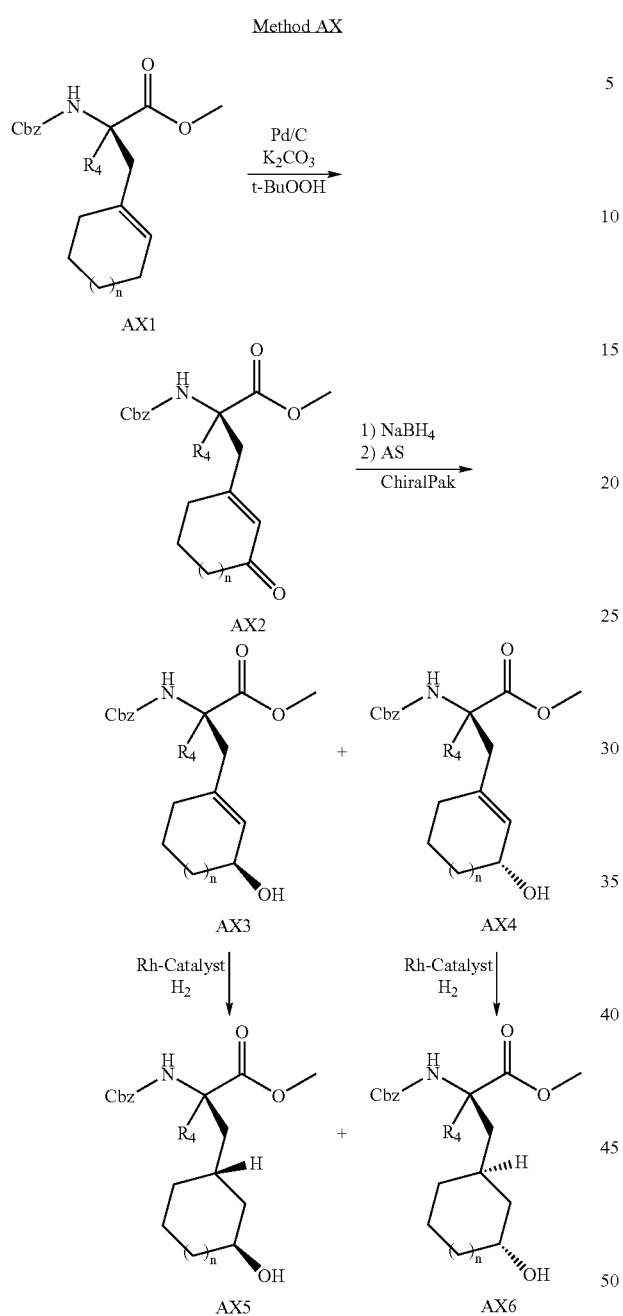

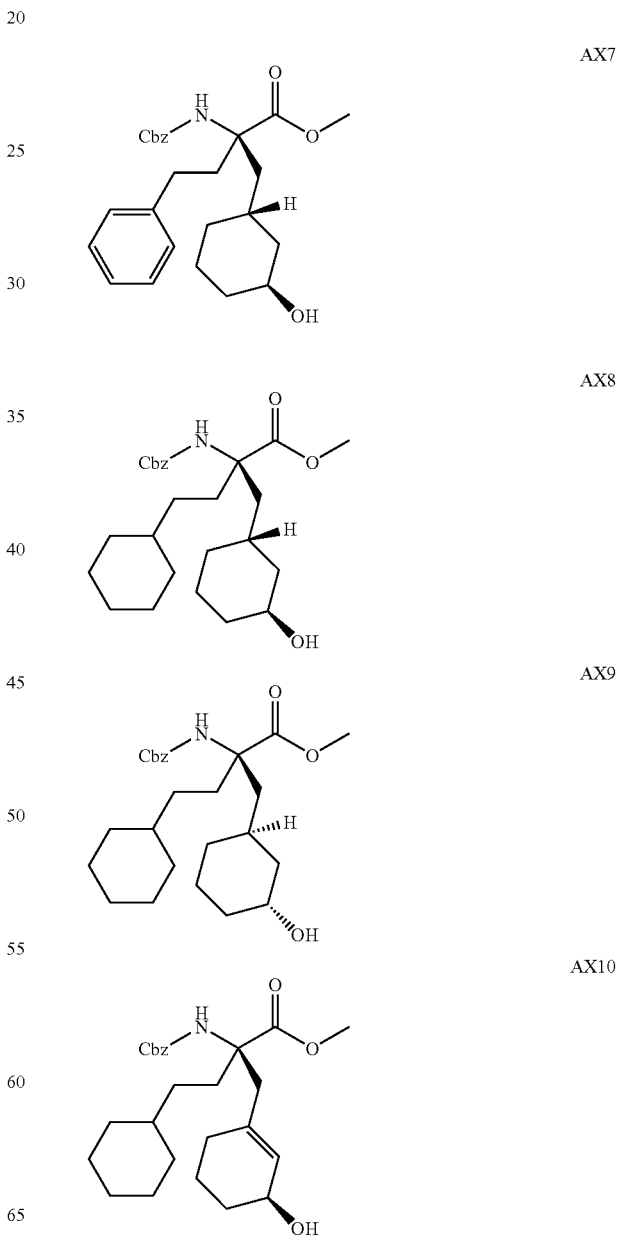

reaction was stirred for 30 min before the solvent was removed and residue chromatographed to give a mixtrue of AX3 (n=1, $R^4$=phenethyl) and AX4 (n=1, $R^4$=phenethyl) which was separated using an AS chiralpak column eluted with 8% IPA in Hexane (0.05% DEA) to give 2.1 g of AX3 (n=1, $R^4$=phenethyl) as the first fraction and 2.2 g of AX4 (n=1, $R^4$=phenethyl) as the second fraction.

Method AX, Step 3.

A 100 ml methanolic solution of AX4 (n=1, $R^4$=phenethyl) (2.2 g) and 1,1'-bis(di-1-propylphosphino)ferrocene (1,5-cyclooctadiene)rhodium (I) tetrafluoroborate (0.4 g, 0.57 mmol) was hydrogenated at 55 psi overnight. The reaction was concentrated, and the brown oil was purified by silica gel chromatography to yield AX6 (n=1, $R^4$=phenethyl) (1.79).

The following compounds were generated using similar method.

Method AX, Step 1.

A literature procedure was adapted. (J-Q Yu and E. J. Corey, *Organic Letters*, 2002, 4, 2727-2730).

To a 400 ml DCM solution of AX1 (n=1, $R^4$=phenethyl) (52 grams) in a ice bath was added 5 g of Pd/C (5% w/w), 50 g of potassium carbonate and 100 ml of anhydrous t-BuOOH. The mixture was stirred in air for overnight before it was diluted with DCM and washed with water. The residue after removal of organic solvent and drying was chromatographed using ethylacetate/hexane to give 25 g of AX2 (n=1, $R^4$=phenethyl).

Method AX, Step 2.

A solution of AX2 (4.5 g, n=1, $R^4$=phenethyl) in MeOH (50 ml) was treated with 0.4 g of Sodium borohydride and the AY3 was generated using similar method.

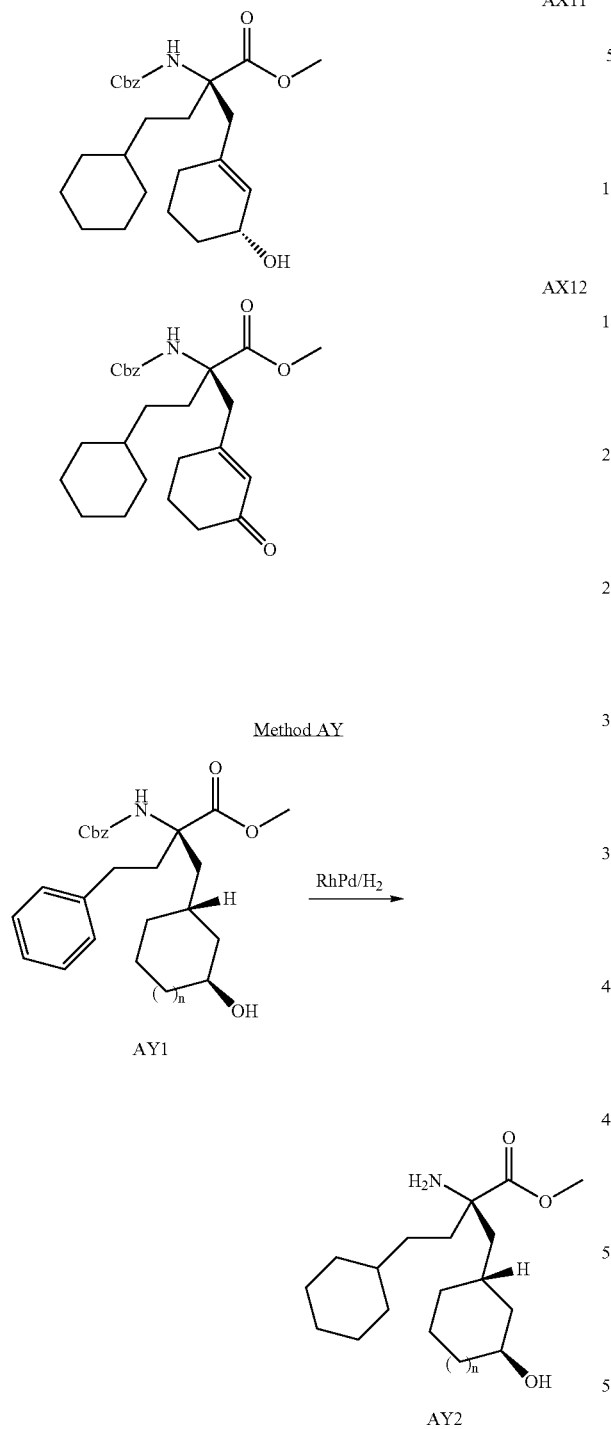

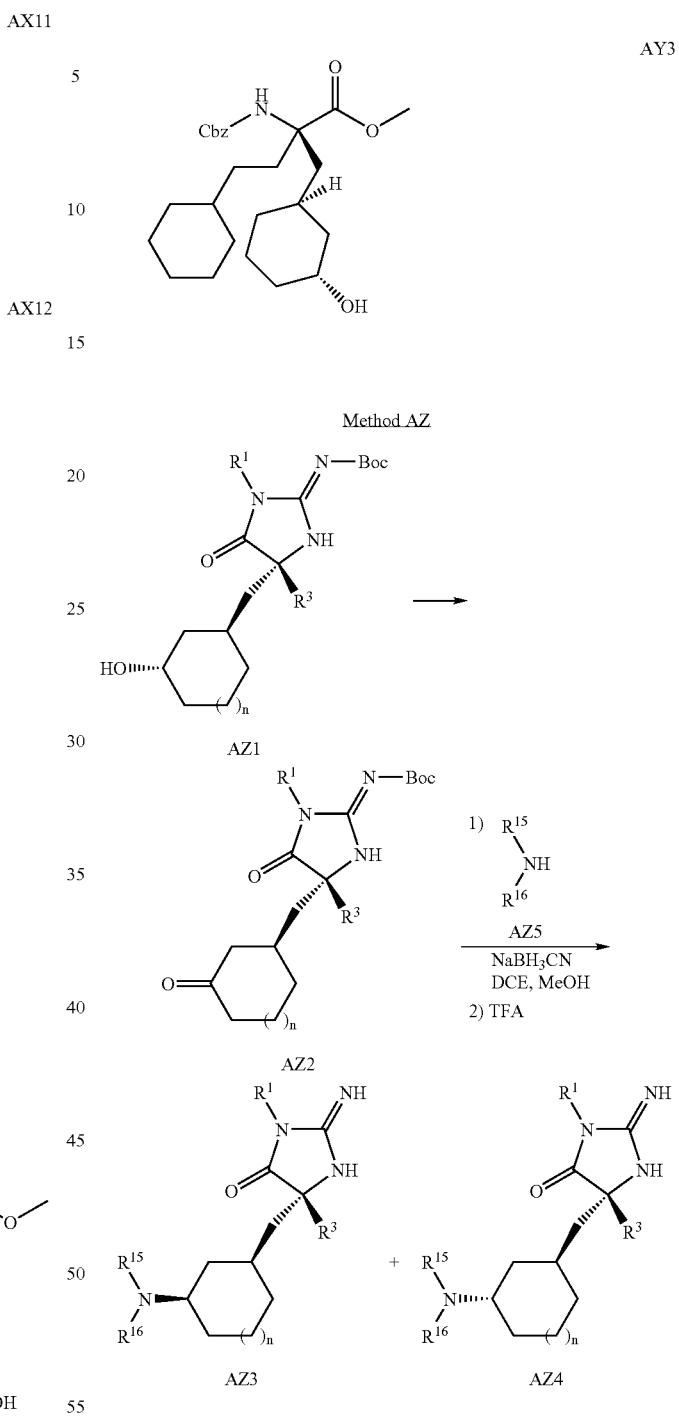

Method AZ, Step 1

To a solution of AZ1 (n=1, $R^1$=Me, $R^3$=2-cyclohexylethyl) (0.441 g, 1.01 mmol), generated from AY2 using Method C and Method H Step 3, in DCM was added Dess-Martin Periodinane (0.880 g, 2.07 mmol). The reaction was stirred for 3 hours at room temperature. The reaction was quenched with $H_2O$ and diluted with EtOAc. After removal of the organic phase, the aqueous layer was extracted with EtOAc (3×). The combined organics were dried ($Na_2SO_4$), filtered, and concentrated. The residue was purified by silica gel chromatog- A solution of AY1 (n=1; 1.5 g, 3.4 mmol), 5% Rh/C (1.5 g), 5% Pd/C (0.5 g) in AcOH (30 mL) was shaken in a Parr apparatus at 55 psi for 18 hours. The vessel was flushed with $N_2$, and the reaction was filtered through a pad of celite. After concentration AY2 was obtained which was carried on without purification. MS m/e: 312.0 (M+H).

raphy (0-100% EtOAc/hexanes) to yield AZ2 (n=1, R¹=Me, R³=2-cyclohexylethyl) (0.408 g, 0.94 mmol, 93% yield). MS m/e: 434.1 (M+H).

Method AZ Step 2:

To a solution of AZ2 (n=1, R¹=Me, R³=2-cyclohexylethyl) (0.011 g, 0.025 mmol) and AZ5 (R¹⁵=H and R¹⁶=m-pyridylmethyl) (0.0067 mL, 0.066 mmol) in DCE (1.8 mL) and MeOH (0.2 mL) was added AcOH (4 drops) and MP-cyanoborohydride resin (0.095 g, 2.42 mmol/g). The reaction was agitated for 40 hours at room temperature. The reaction was treated with 7N NH$_3$/MeOH, and solution was filtered.

After concentration, the residue was purified by silica gel HPLC (0-4% [(5% 7N NH$_3$/MeOH)/MeOH]/(50% DCM/hexanes) to furnish fraction 1 and fraction 2 which, after removal of solvent, were treated with 20% TFA in DCM for 3 h at r.t. to give AZ4 (n=1, R¹=Me, R³=2-cyclohexylethyl, R¹⁵=H and R¹⁶=m-pyridylmethyl) (0.005 g, 0.009 mmol) and the AZ3 (n=1, R¹=Me, R³=2-cyclohexylethyl, R¹⁵=H and R¹⁶=m-pyridylmethyl) (0.012 g, 0.022 mmol) respectively.

The following compounds were generated using similar methods:

| # | Structure | MW | Obs. m/e |
|---|-----------|----|----------|
| 462 | 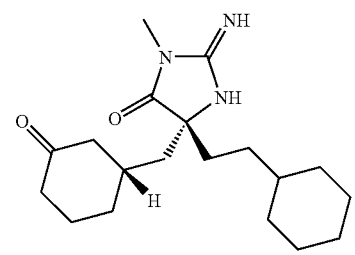 | 333 | 334 |
| 463 | 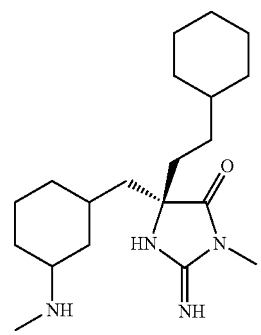 | 348 | 349 |
| 464 | 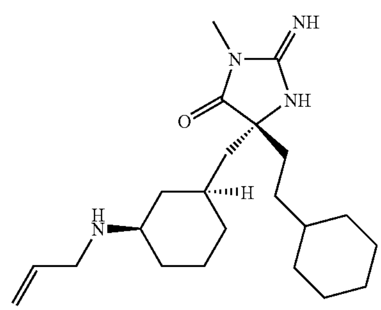 | 374 | 375 |
| 465 | 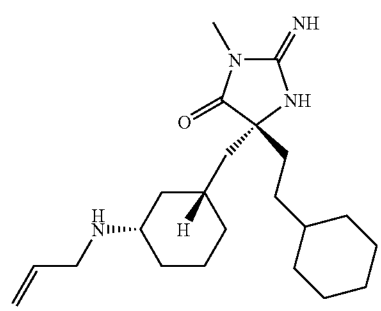 | 374 | 375 |

-continued

| # | Structure | MW | Obs. m/e |
|---|---|---|---|
| 466 | 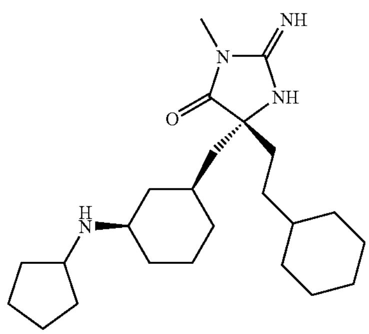 | 374 | 375 |
| 467 | 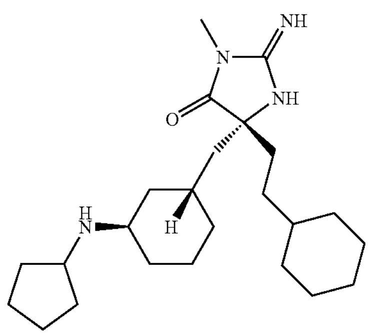 | 374 | 375 |
| 468 | 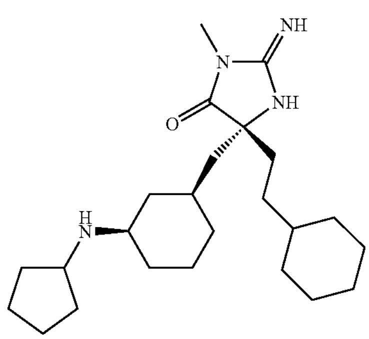 | 376 | 377 |
| 469 | 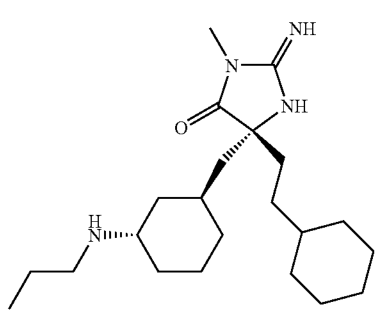 | 376 | 377 |

-continued

| # | Structure | MW | Obs. m/e |
|---|-----------|-----|----------|
| 470 | 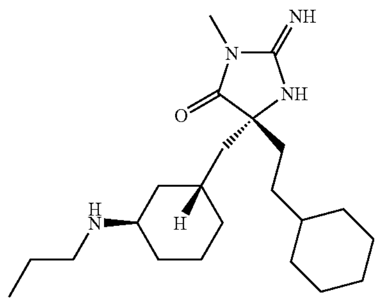 | 376 | 377 |
| 471 | 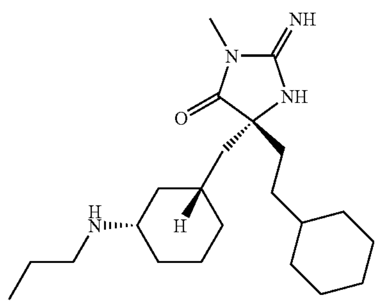 | 376 | 377 |
| 472 | 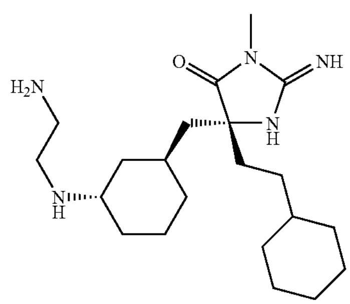 | 377 | 378 |
| 473 | 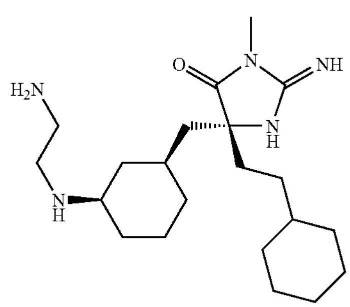 | 377 | 378 |
| 474 | 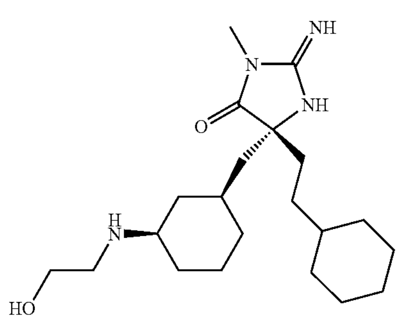 | 378 | 379 |

-continued

| # | Structure | MW | Obs. m/e |
|---|---|---|---|
| 475 | 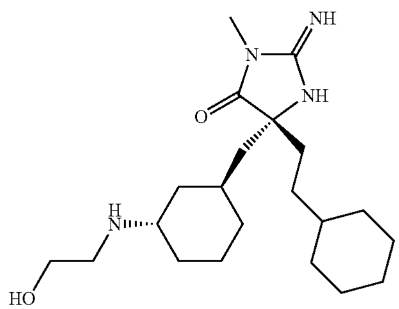 | 378 | 379 |
| 476 | 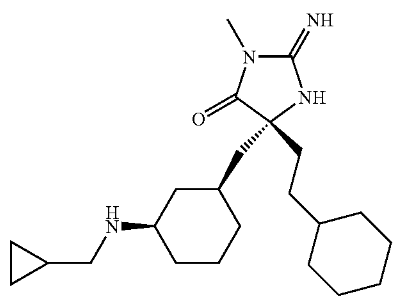 | 388 | 389 |
| 477 | 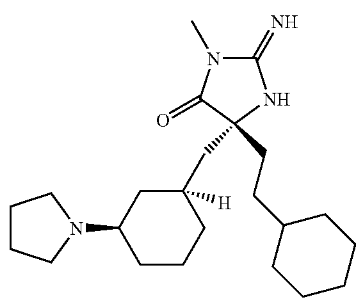 | 388 | 389 |
| 478 | 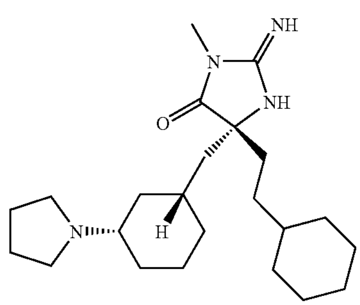 | 388 | 389 |
| 479 | 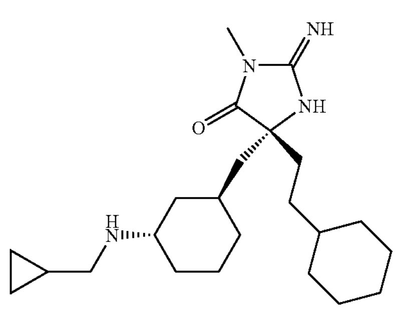 | 388 | 389 |

-continued

| # | Structure | MW | Obs. m/e |
|---|-----------|-----|----------|
| 480 | 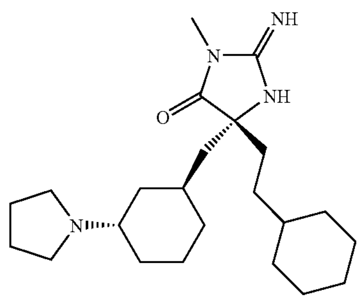 | 388 | 389 |
| 481 | 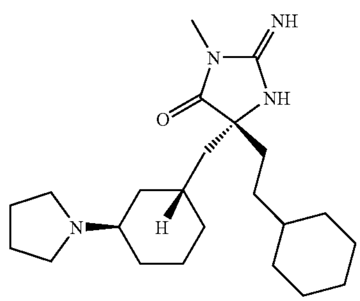 | 388 | 389 |
| 482 | 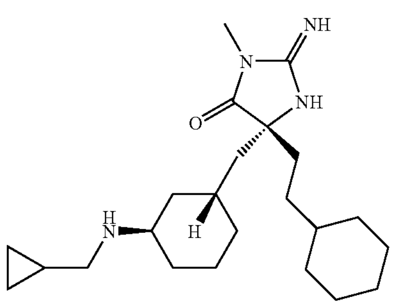 | 388 | 389 |
| 483 | 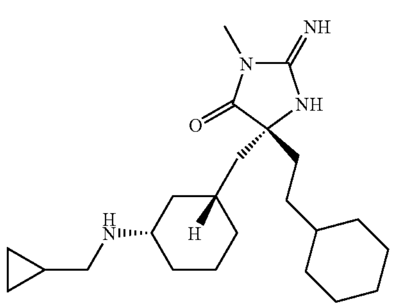 | 388 | 389 |
| 484 | 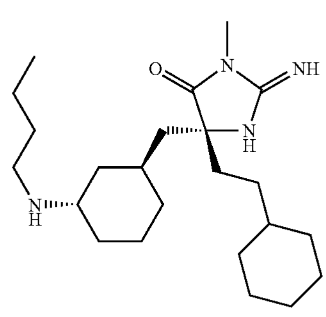 | 390 | 391 |

-continued

| # | Structure | MW | Obs. m/e |
|---|---|---|---|
| 485 | 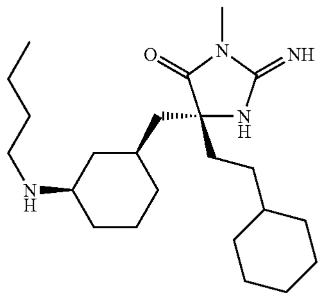 | 390 | 391 |
| 486 | 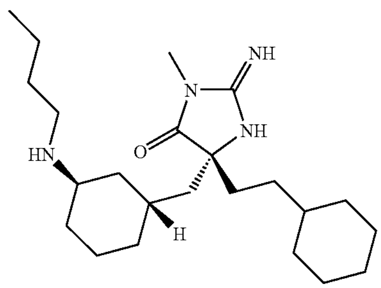 | 390 | 391 |
| 487 | 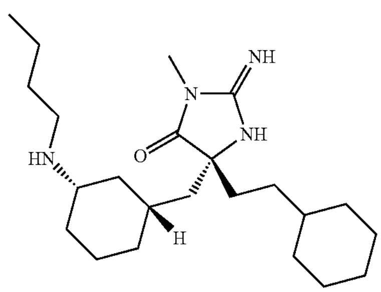 | 390 | 391 |
| 488 | 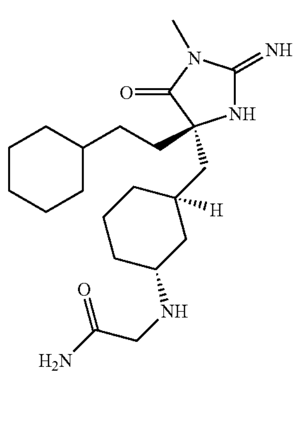 | 391 | 392 |

| # | Structure | MW | Obs. m/e |
|---|---|---|---|
| 489 | 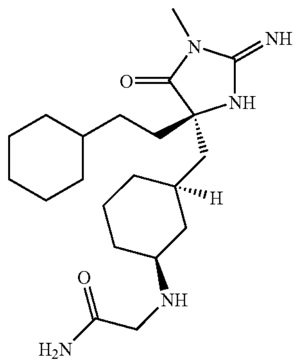 | 391 | 392 |
| 490 | 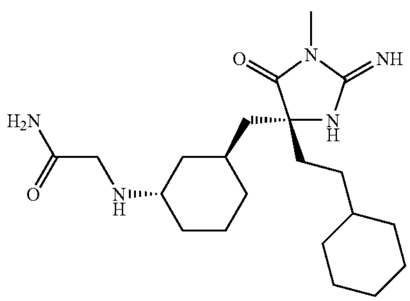 | 391 | 392 |
| 491 | 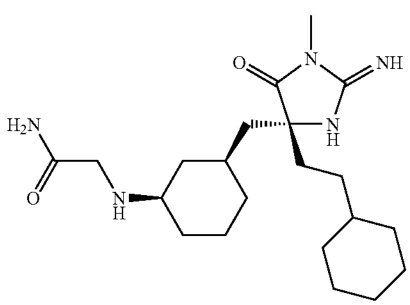 | 391 | 392 |
| 492 | 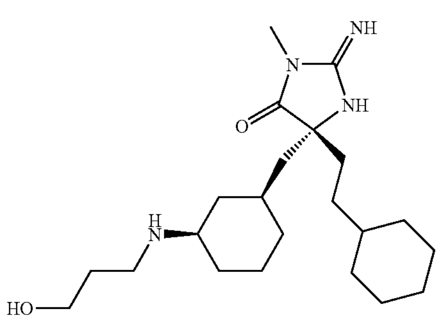 | 392 | 393 |

| # | Structure | MW | Obs. m/e |
|---|---|---|---|
| 493 | 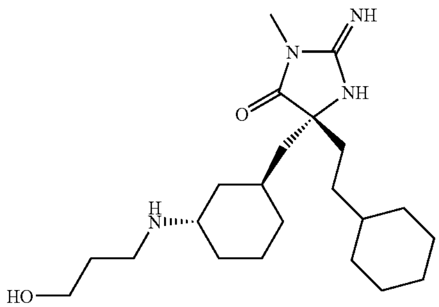 | 392 | 393 |
| 494 | 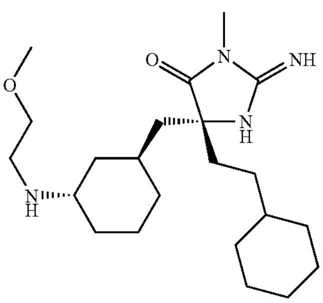 | 392 | 393 |
| 495 | 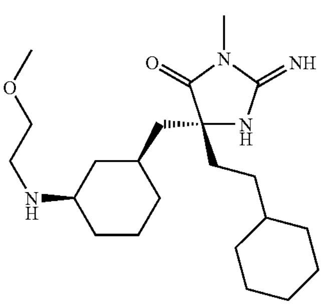 | 392 | 393 |
| 496 | 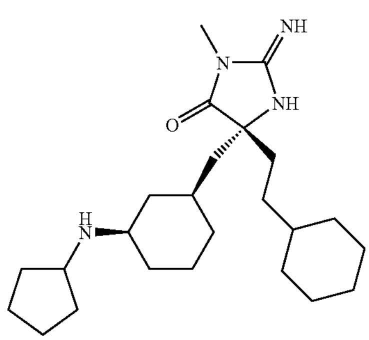 | 402 | 403 |

-continued

| # | Structure | MW | Obs. m/e |
|---|---|---|---|
| 497 | 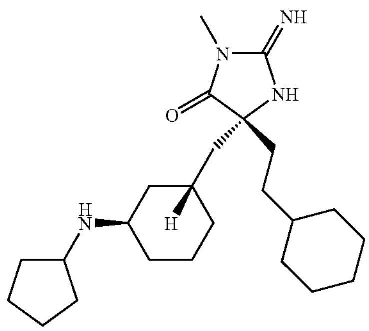 | 402 | 403 |
| 498 | 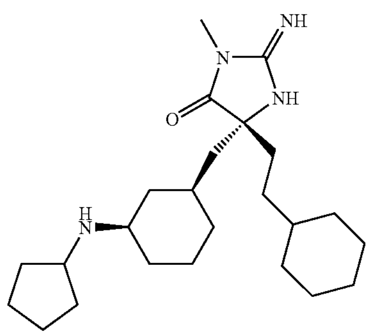 | 402 | 403 |
| 499 | 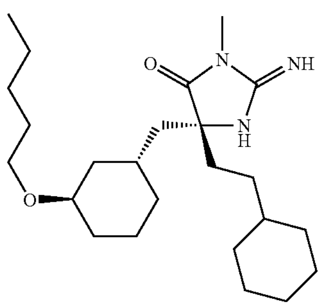 | 405 | 406 |
| 500 | 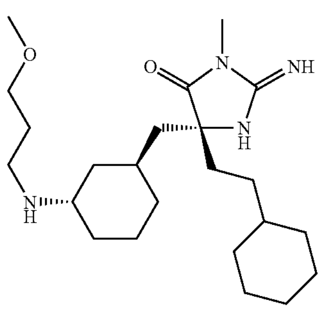 | 406 | 407 |

-continued

| # | Structure | MW | Obs. m/e |
|---|---|---|---|
| 501 | 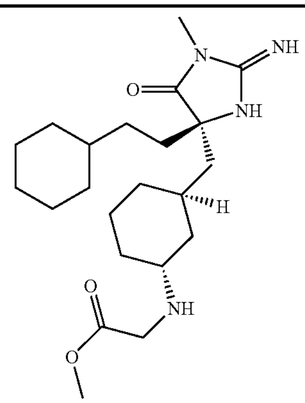 | 406 | 407 |
| 502 | 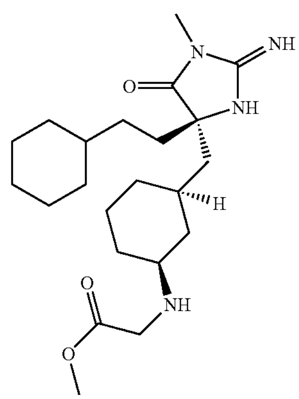 | 406 | 407 |
| 503 | 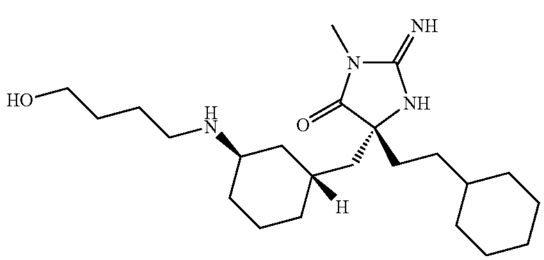 | 406 | 407 |
| 504 | 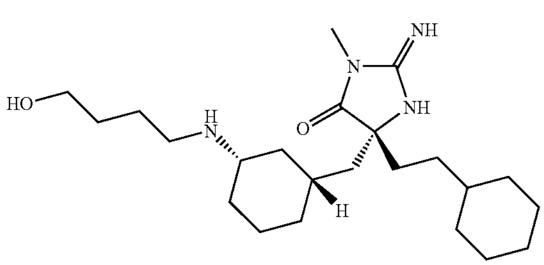 | 406 | 407 |

| # | Structure | MW | Obs. m/e |
|---|---|---|---|
| 505 | 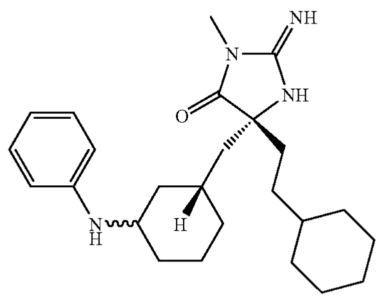 | 410 | 411 |
| 506 | 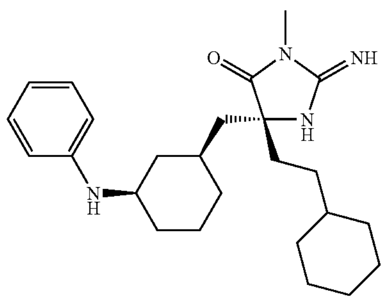 | 410 | 411 |
| 507 | 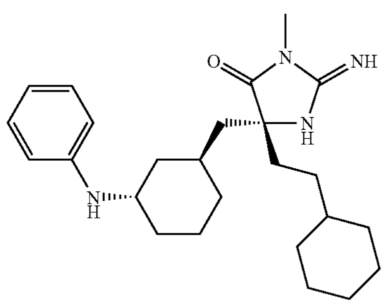 | 410 | 411 |
| 508 | 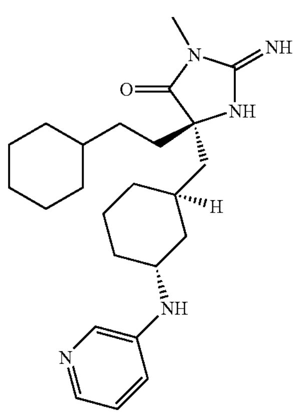 | 411 | 412 |

-continued

| # | Structure | MW | Obs. m/e |
|---|-----------|-----|----------|
| 509 | 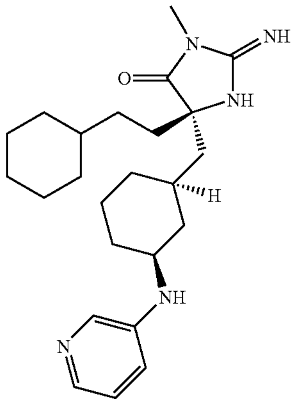 | 411 | 412 |
| 510 | 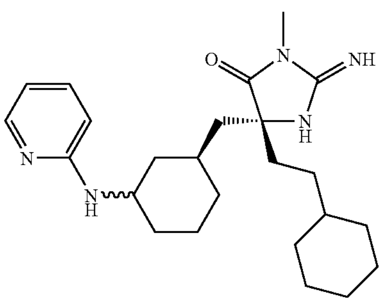 | 411 | 412 |
| 511 | 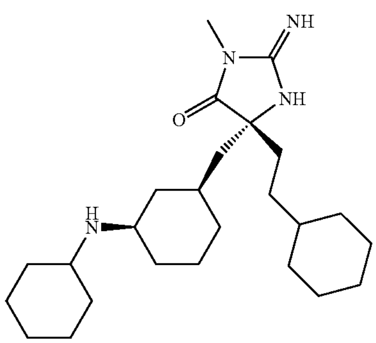 | 416 | 417 |
| 512 | 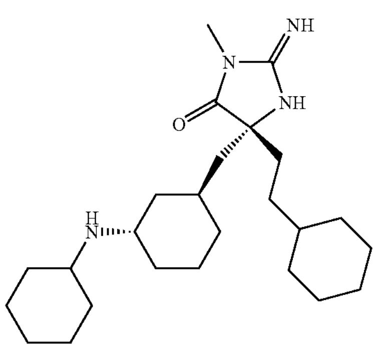 | 416 | 417 |

-continued

| # | Structure | MW | Obs. m/e |
|---|---|---|---|
| 513 | 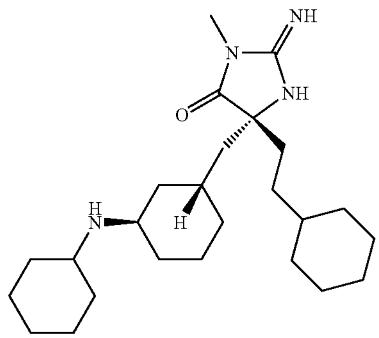 | 416 | 417 |
| 514 | 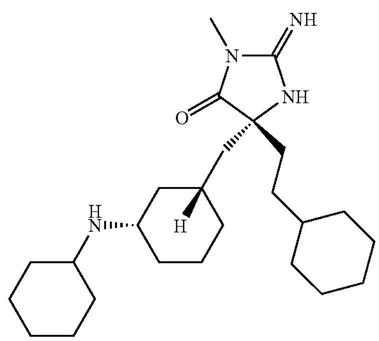 | 416 | 417 |
| 515 | 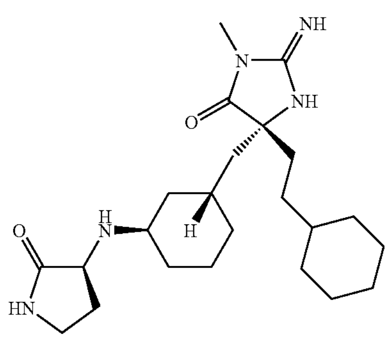 | 417 | 418 |
| 516 | 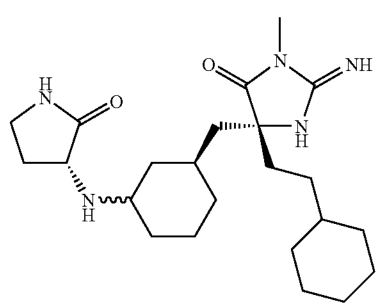 | 417 | 418 |

-continued

| # | Structure | MW | Obs. m/e |
|---|---|---|---|
| 517 | 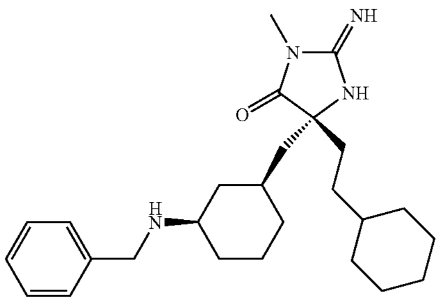 | 424 | 425 |
| 518 | 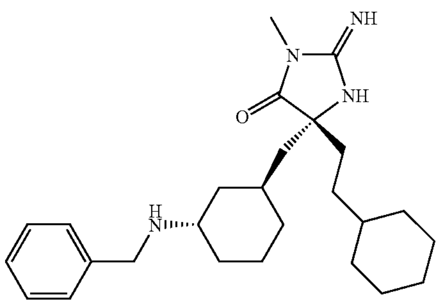 | 424 | 425 |
| 519 | 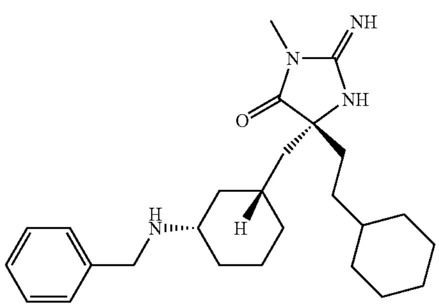 | 424 | 425 |
| 520 | 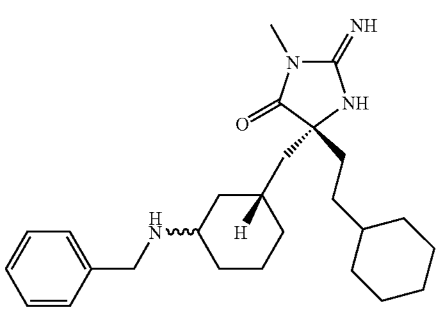 | 424 | 425 |

-continued

| # | Structure | MW | Obs. m/e |
|---|---|---|---|
| 521 | 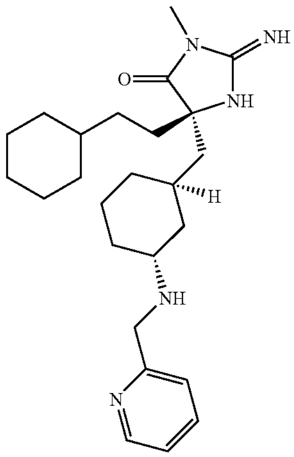 | 425 | 426 |
| 522 | 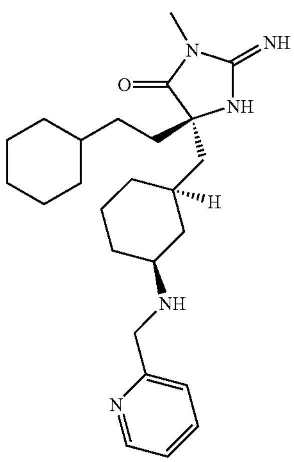 | 425 | 427 |
| 523 | 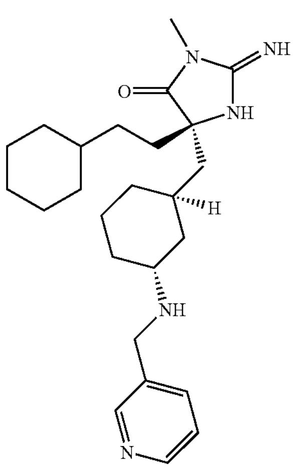 | 425 | 426 |

-continued

| # | Structure | MW | Obs. m/e |
|---|---|---|---|
| 524 | 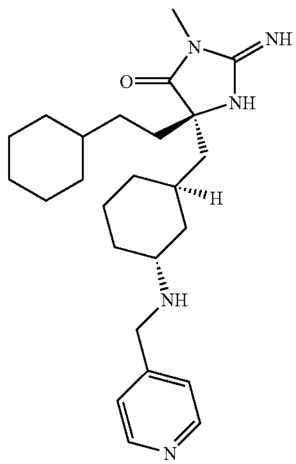 | 425 | 426 |
| 525 | 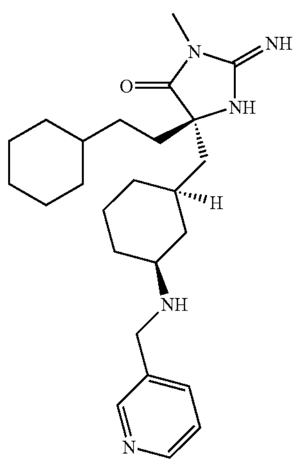 | 425 | 426 |
| 526 | 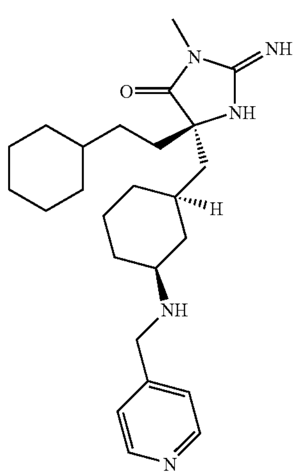 | 425 | 426 |

| # | Structure | MW | Obs. m/e |
|---|---|---|---|
| 527 | 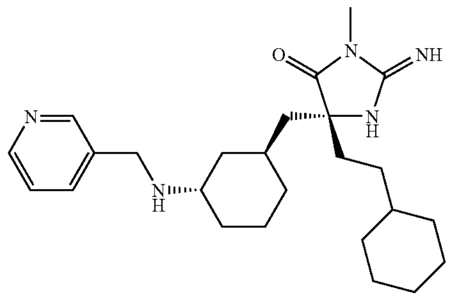 | 425 | 426 |
| 528 | 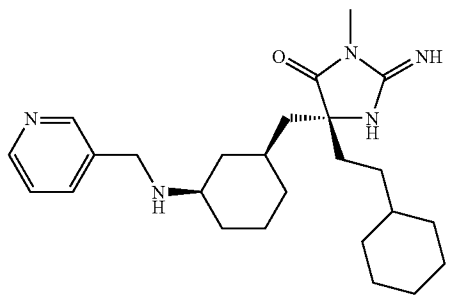 | 425 | 426 |
| 529 | 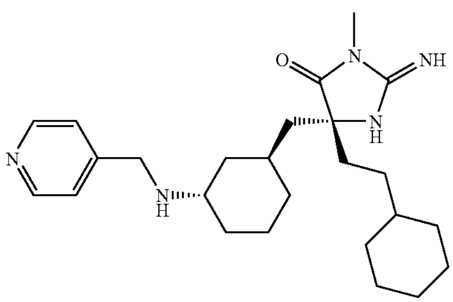 | 425 | 426 |
| 530 | 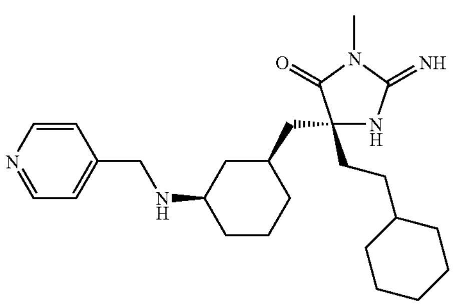 | 425 | 426 |
| 531 | 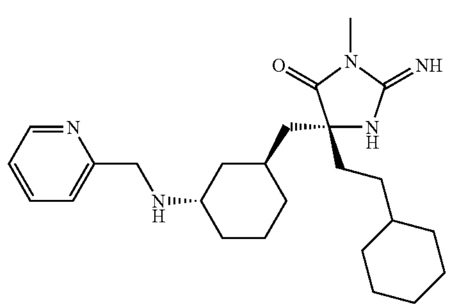 | 425 | 426 |

-continued

| # | Structure | MW | Obs. m/e |
|---|---|---|---|
| 532 | 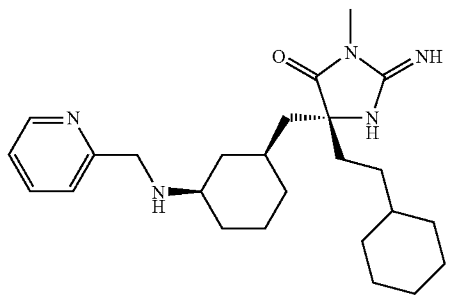 | 425 | 426 |
| 533 | 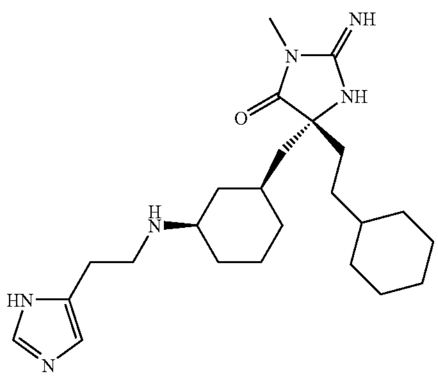 | 428 | 429 |
| 534 | 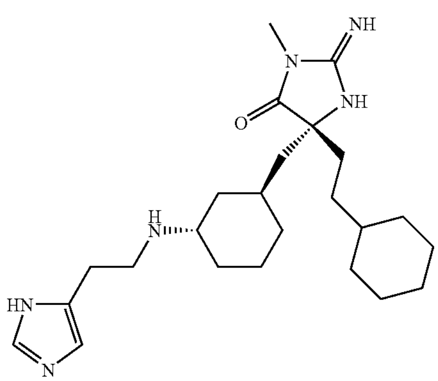 | 428 | 429 |
| 535 | 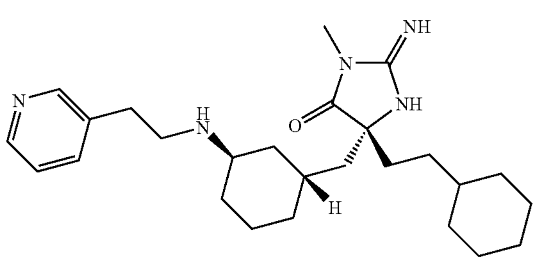 | 439 | 440 |
| 536 | 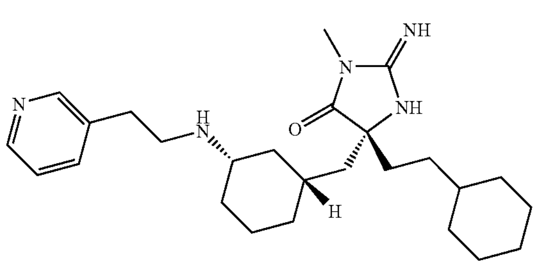 | 439 | 440 |

-continued

| # | Structure | MW | Obs. m/e |
|---|---|---|---|
| 537 | 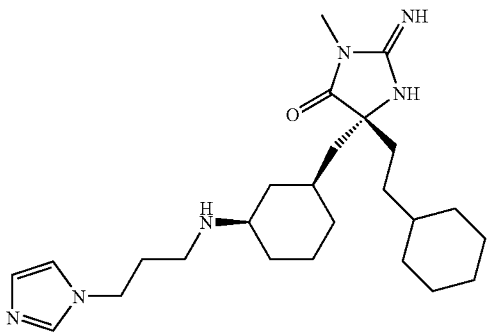 | 442 | 443 |
| 538 | 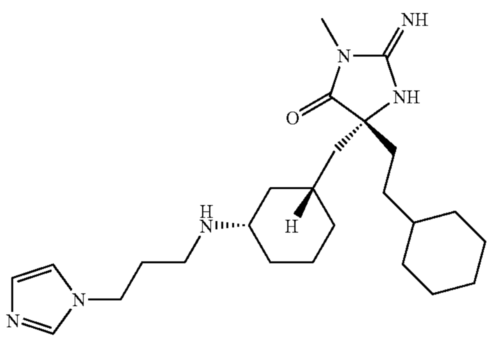 | 442 | 443 |
| 539 | 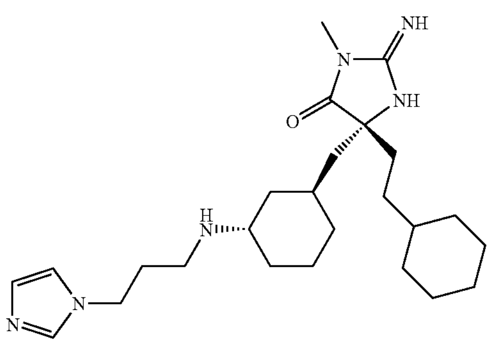 | 442 | 443 |
| 540 | 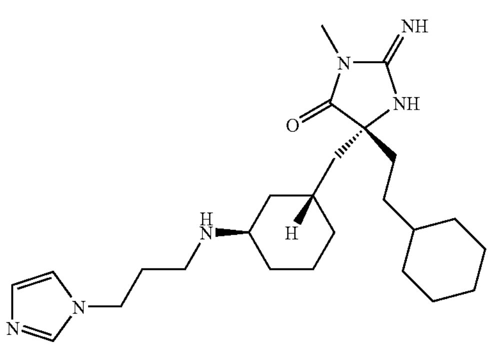 | 442 | 443 |

-continued

| # | Structure | MW | Obs. m/e |
|---|-----------|-----|----------|
| 541 | 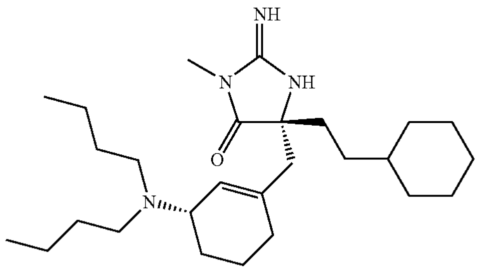 | 444 | 445 |
| 542 | 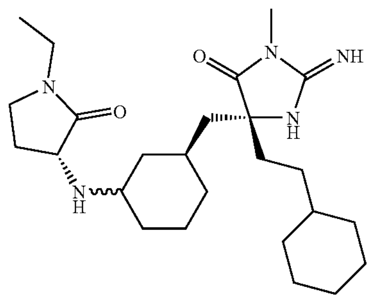 | 445 | 446 |
| 543 | 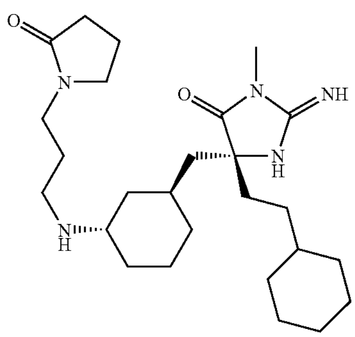 | 459 | 460 |
| 544 | 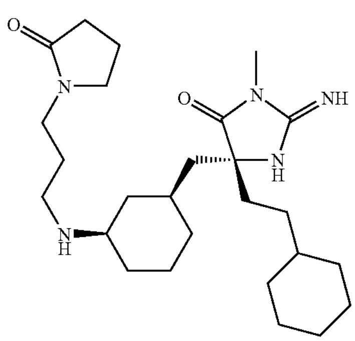 | 459 | 460 |

Method BA

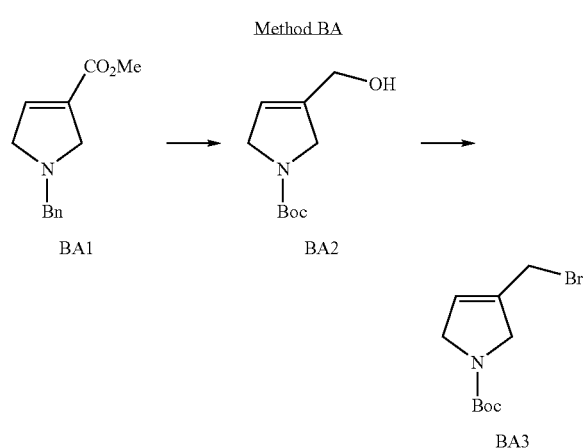

Method BA, Step 1:

BA1, prepared according to a literature procedure (Terao, Y; Kotaki, H; Imai, N and Achiwa K. *Chemical and Pharmaceutical Bulletin*, 33 (7), 1985, 2762-2766) was converted to BA2 using a procedure described by Coldham, I; Crapnell, K. M; Fernandez, J-C; Moseley J. D. and Rabot, R. (*Journal of Organic Chemistry*, 67 (17), 2002, 6185-6187).

$^1$H NMR(CDCl$_3$) for BA2: 1.42 (s, 9H), 4.06 (d, 4H), 4.09 (s, 1H), 4.18 (s, 2H), 5.62 (d, 1H).

Method BA, Step 2:

BA3 was generated from BA2 using a literature procedure described by Winkler J. D.; Axten J.; Hammach A. H.; Kwak, Y-S; Lengweiler, U.; Lucero, M. J.; Houk, K. N. (*Tetrahedron*, 54 1998, 7045-7056). Analytical data for compound BA3: MS m/e: 262.1, 264.1 (M+H). $^1$H NMR(CDCl$_3$) 1.43 (s, 9H), 3.98 (s, 2H), 4.11 (d, 4H), 5.78 (d, 1H).

Method BB, Step 1;

Compound BB1 (n=1, R$^1$=Me, R$^3$=cyclohexylethyl) was converted to BB2 (n=1, R$^1$=Me, R$^3$=cyclohexylethyl) and BB3 (n=1, R$^1$=Me, R$^3$=cyclohexylethyl) which were separated via a silica gel column eluted with EtOAc in Hexane (0-15%).

Method BB, Step 2;

Compound BB4 (n=1, R$^1$=Me, R$^3$=cyclohexylethyl) was generated from BB2 (n=1, R$^1$=Me, R$^3$=cyclohexylethyl) using 20% TFA in DCM.

The following compounds were generated using similar method:

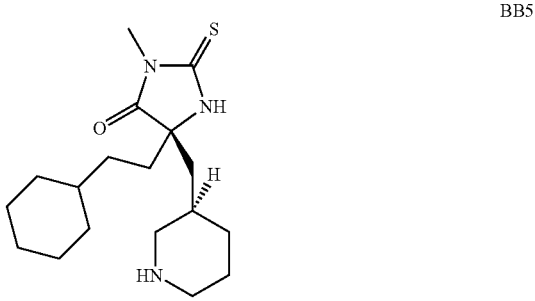

BB5

Method BB

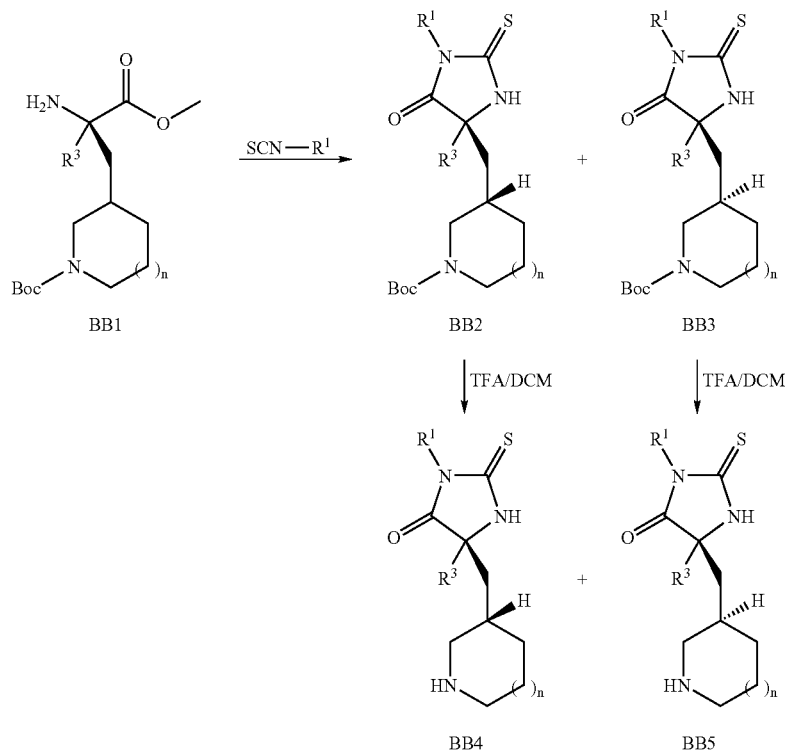

-continued

BB6

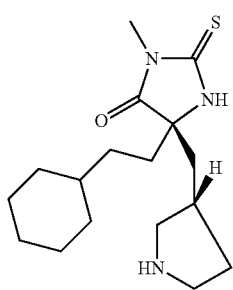

BB7

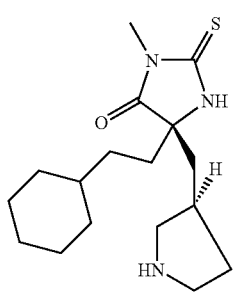

Method BC

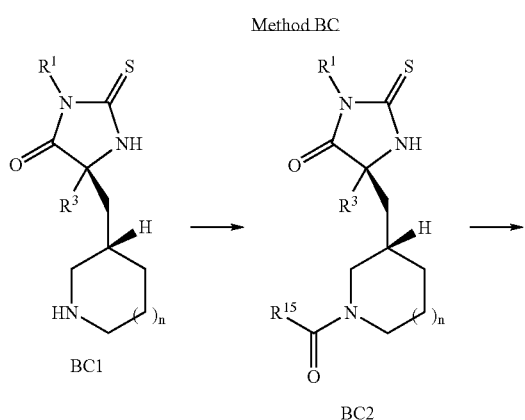

-continued

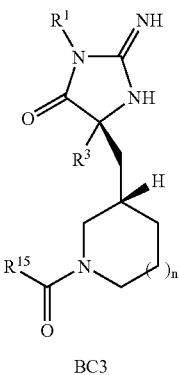
BC3

Method BC, Step 1;

Compound BC2 (n=1, $R^1$=Me, $R^3$=cyclohexylethyl and $R^{15}$=m-Pyridyl) was obtained from BC1 (n=1, $R^2$=Me, $R^3$=cyclohexylethyl) using method L step 2.

Method BC, Step 2;

Compound BC3 (n=1, $R^1$=Me, $R^3$=cyclohexylethyl and $R^{15}$=m-Pyridyl) was obtained from BC2(n=1, $R^1$=Me, $R^3$=cyclohexylethyl and $R^5$=m-Pyridyl) using method L step 3.

The following compounds were generated using a similar method:

| # | Structure | MW | Obs. m/e |
|---|---|---|---|
| 552 | 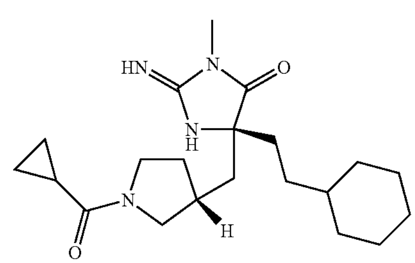 | 374 | 375 |

-continued

| # | Structure | MW | Obs. m/e |
|---|---|---|---|
| 553 | 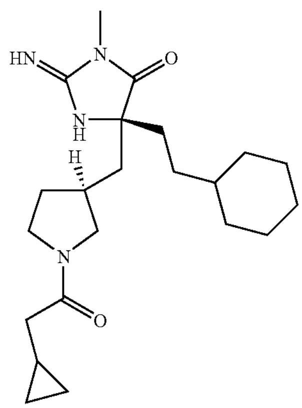 | 388 | 389 |
| 554 | 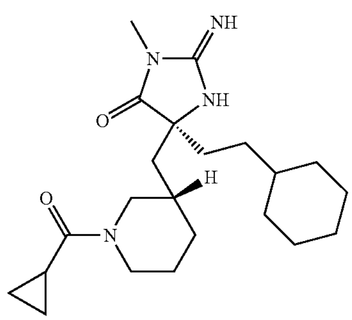 | 388 | 389 |
| 555 | 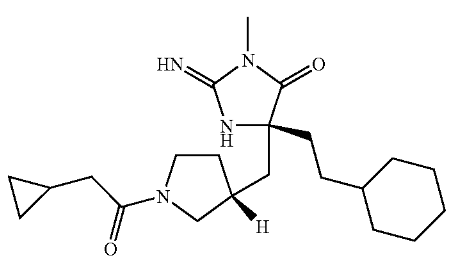 | 388 | 389 |
| 556 | 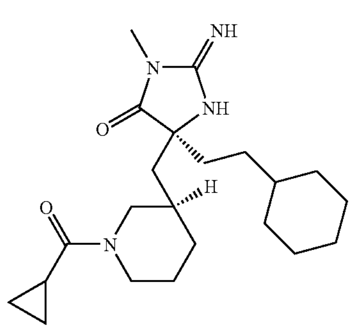 | 388 | 389 |

-continued

| # | Structure | MW | Obs. m/e |
|---|---|---|---|
| 557 | 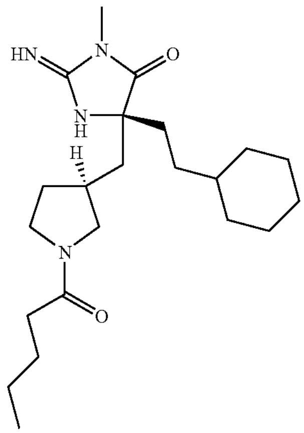 | 390 | 391 |
| 558 | 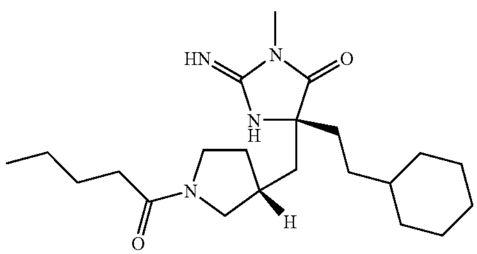 | 390 | 391 |
| 559 | 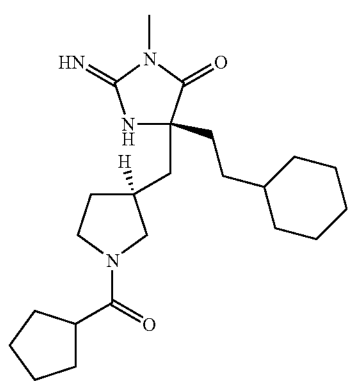 | 402 | 403 |
| 560 | 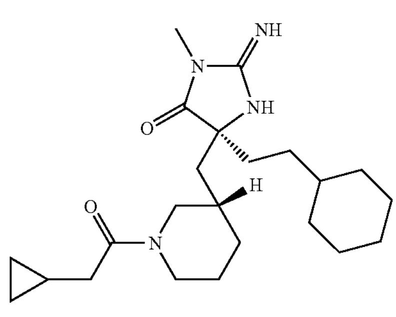 | 402 | 403 |

-continued

| # | Structure | MW | Obs. m/e |
|---|-----------|-----|----------|
| 561 | 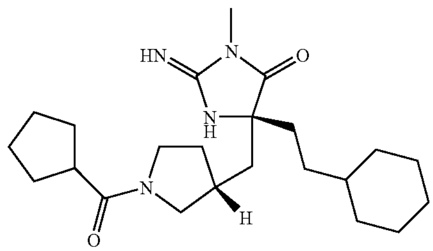 | 402 | 403 |
| 562 | 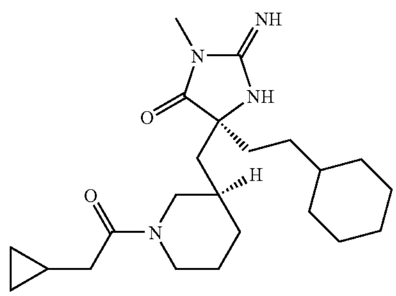 | 402 | 403 |
| 563 | 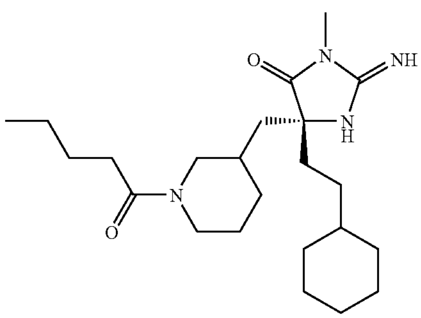 | 404 | 405 |
| 564 | 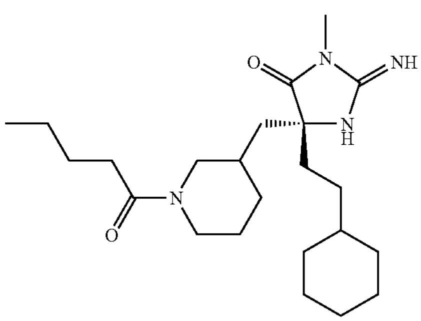 | 404 | 405 |
| 565 | 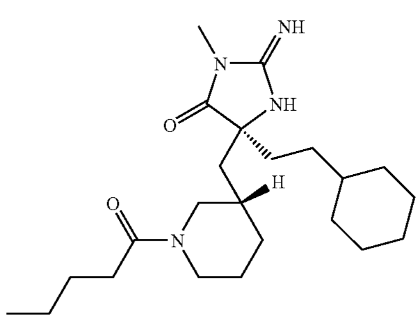 | 404 | 405 |

-continued

| # | Structure | MW | Obs. m/e |
|---|---|---|---|
| 566 | 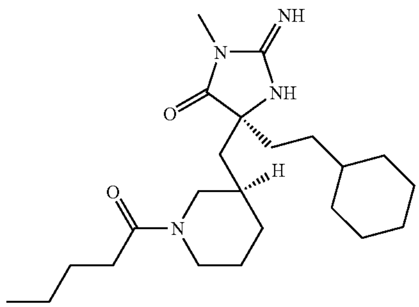 | 404 | 405 |
| 567 | 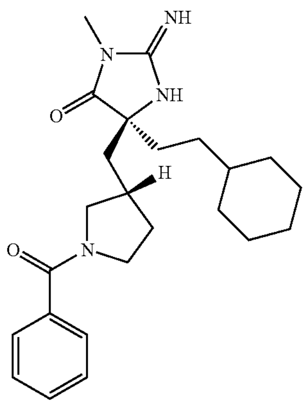 | 410 | 411 |
| 568 | 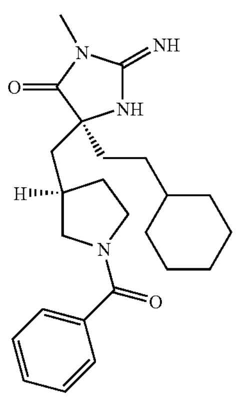 | 410 | 411 |
| 569 | 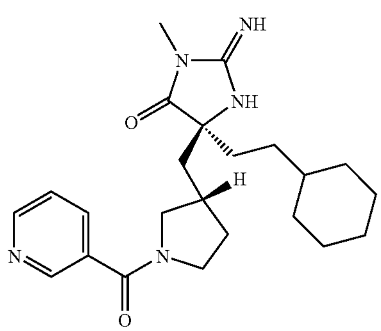 | 411 | 412 |

-continued

| # | Structure | MW | Obs. m/e |
|---|---|---|---|
| 570 | 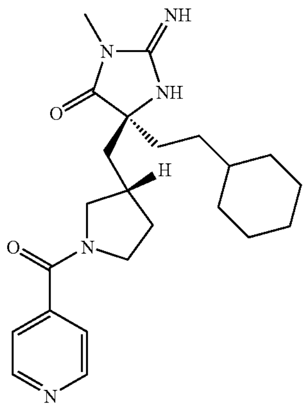 | 411 | 412 |
| 571 | 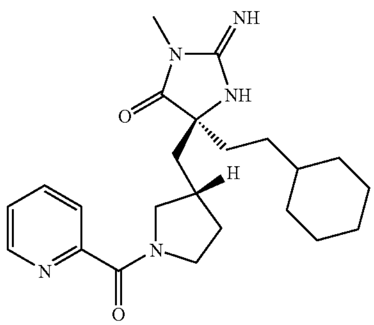 | 411 | 412 |
| 572 | 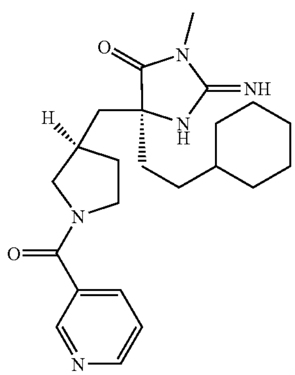 | 411 | 412 |
| 573 | 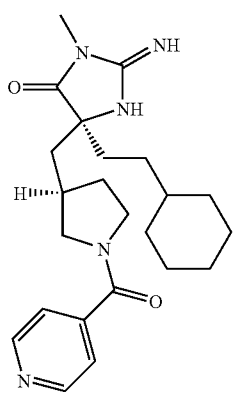 | 411 | 412 |

-continued

| # | Structure | MW | Obs. m/e |
|---|---|---|---|
| 574 | 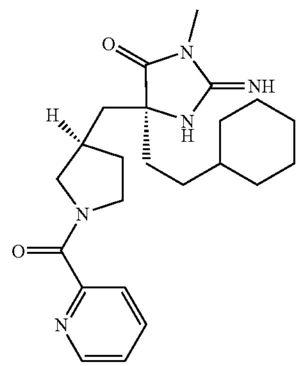 | 411 | 412 |
| 575 | 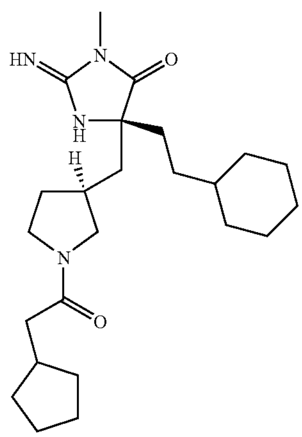 | 416 | 417 |
| 576 | 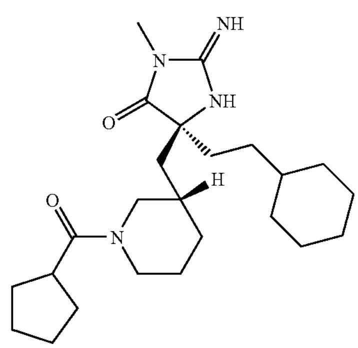 | 416 | 417 |
| 577 | 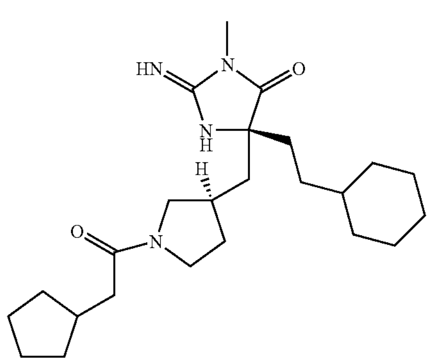 | 416 | 417 |

-continued

| # | Structure | MW | Obs. m/e |
|---|---|---|---|
| 578 | 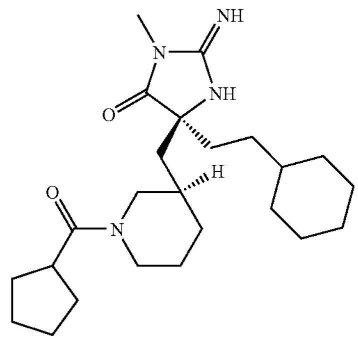 | 416 | 417 |
| 579 | 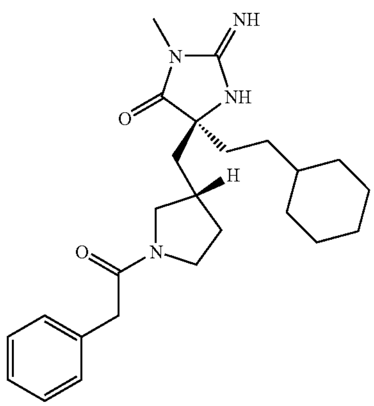 | 424 | 425 |
| 580 | 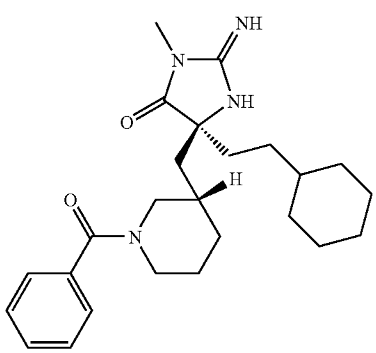 | 424 | 425 |
| 581 | 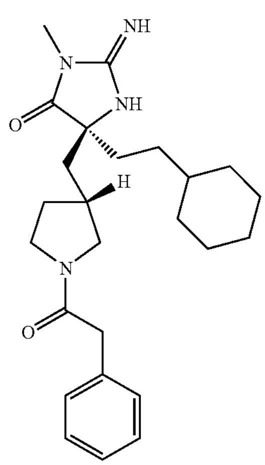 | 424 | 425 |

-continued
| # | Structure | MW | Obs. m/e |
|---|---|---|---|
| 582 | 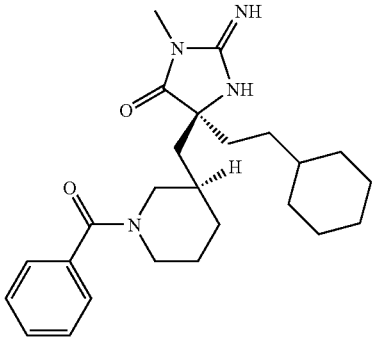 | 424 | 425 |
| 583 | 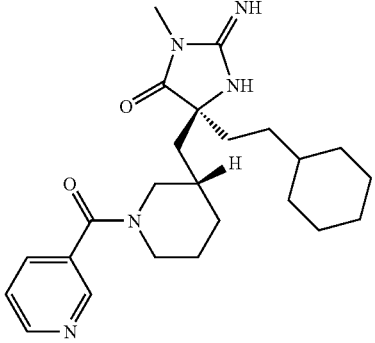 | 425 | 426 |
| 584 | 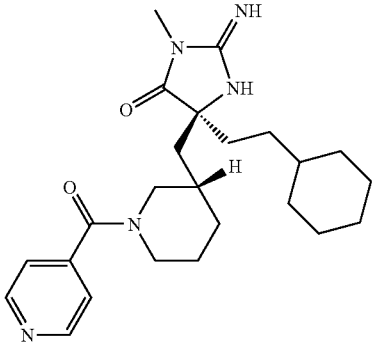 | 425 | 426 |
| 585 | 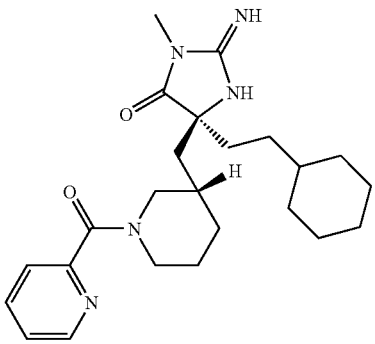 | 425 | 426 |

| # | Structure | MW | Obs. m/e |
|---|---|---|---|
| 586 | 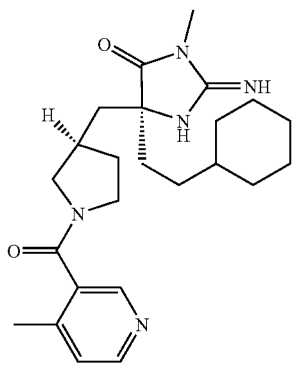 | 425 | 426 |
| 587 | 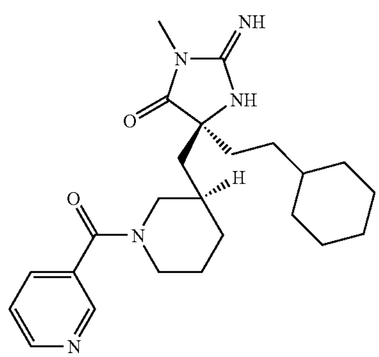 | 425 | 426 |
| 588 | 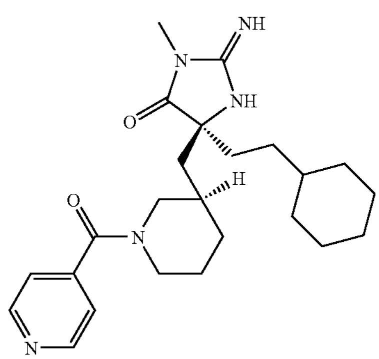 | 425 | 426 |
| 589 | 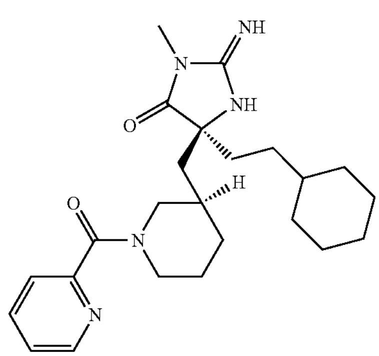 | 425 | 426 |

-continued

| # | Structure | MW | Obs. m/e |
|---|---|---|---|
| 590 | 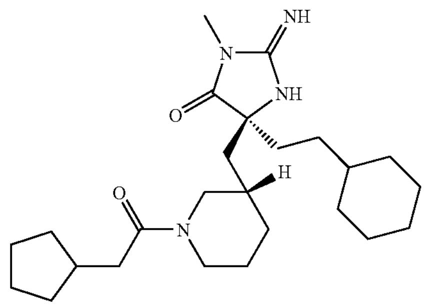 | 430 | 431 |
| 591 | 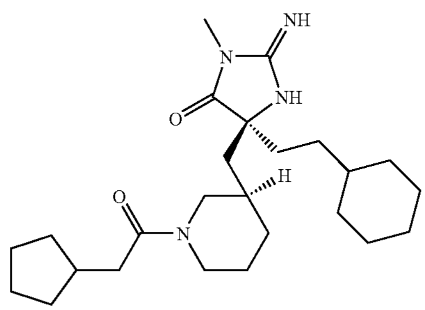 | 430 | 431 |
| 592 | 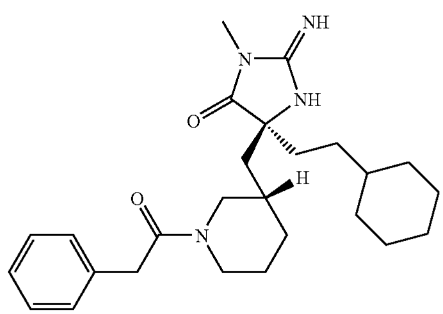 | 438 | 439 |
| 593 | 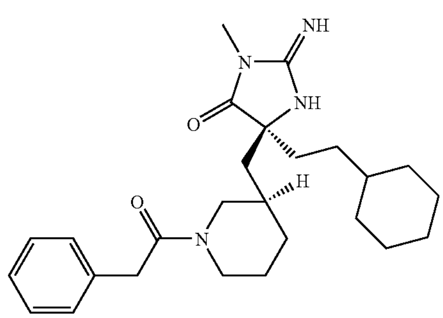 | 438 | 439 |

-continued

| # | Structure | MW | Obs. m/e |
|---|---|---|---|
| 594 | 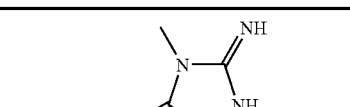 | 439 | 410 |

Method BD

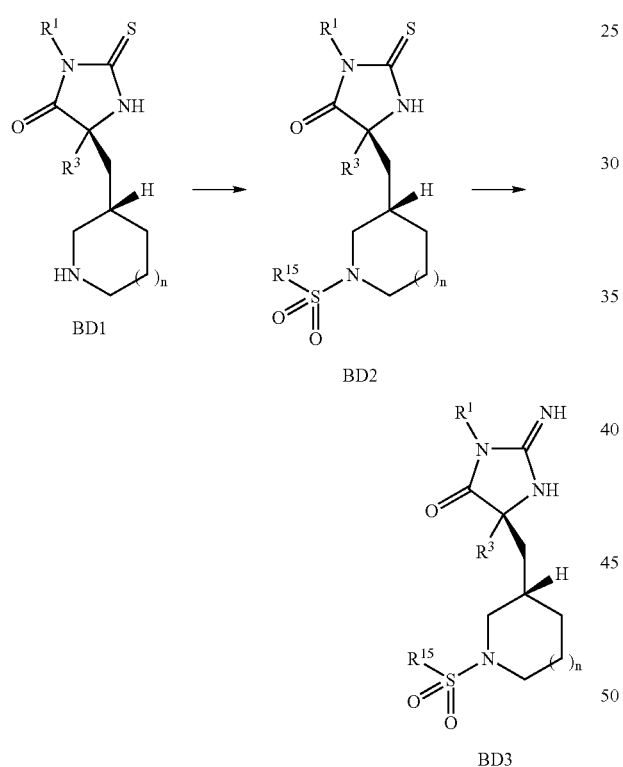

Method BD, Step 1;

Compound BD2 (n=1, R¹=Me, R³=cyclohexylethyl and R¹⁵=Ph) was obtained from BD1 (n=1, R²=Me, R³=cyclohexylethyl) using Method N, Step 1.

Method BD, Step 2;

Compound BD3 (n=1, R¹=Me, R³=cyclohexylethyl and R¹⁵=Ph) was obtained from BD2 (n=1, R¹=Me, R³=cyclohexylethyl and R¹⁵=m-Pyridyl) using Method N, Step 2.

The following compounds were generated using a similar method:

| # | Structure | MW | Obs. m/e |
|---|---|---|---|
| 595 | 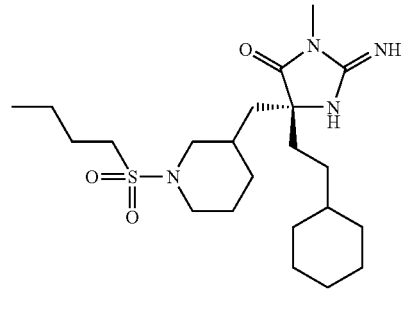 | 440 | 441 |
| 596 | 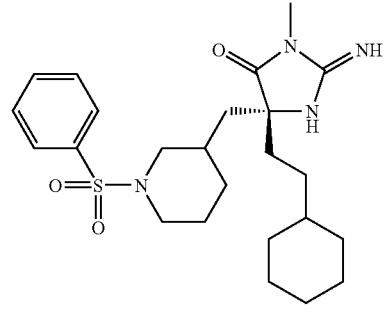 | 460 | 461 |

Method BE

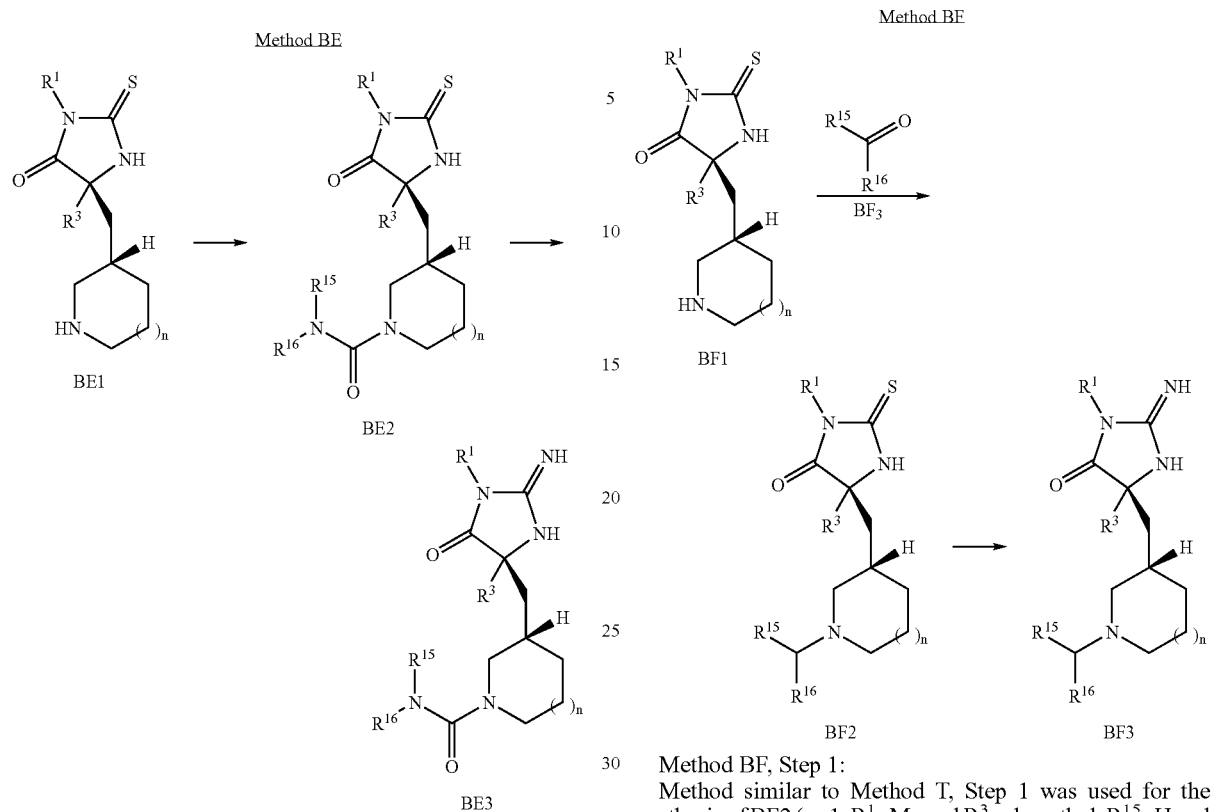

Method similar to Method M was adapted for these transformations. The following compounds were generated similar methods.

Method BF

Method BF, Step 1:
Method similar to Method T, Step 1 was used for the synthesis of BF2 (n=1, $R^1$=Me and $R^3$=phenethyl, $R^{15}$=H and $R^{16}$=n-propyl).

Method BF, Step 2:
Method similar to method L Step 3 was adapted for this transformation.

| # | Structure | MW | Obs. m/e |
|---|-----------|-----|----------|
| 597 | 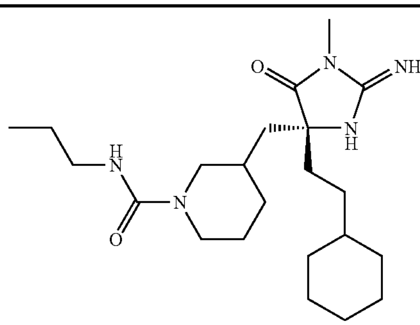 | 405 | 406 |
| 598 | 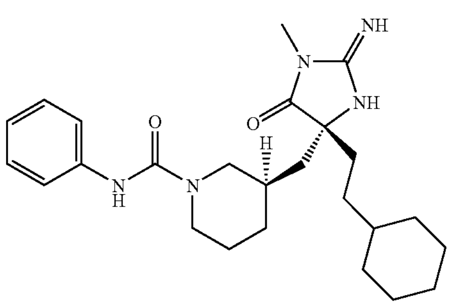 | 439 | 440 |

The following compounds were generated using similar methods.

| # | Structure | MW | Obs. m/e |
|---|---|---|---|
| 599 | 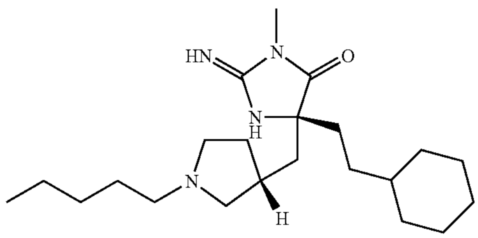 | 376 | 377 |
| 600 | 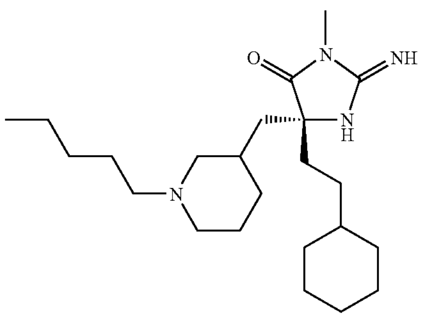 | 390 | 391 |
| 601 | 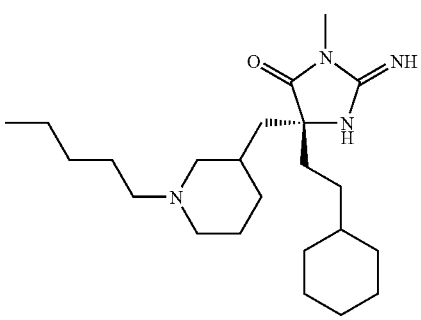 | 390 | 391 |
| 602 | 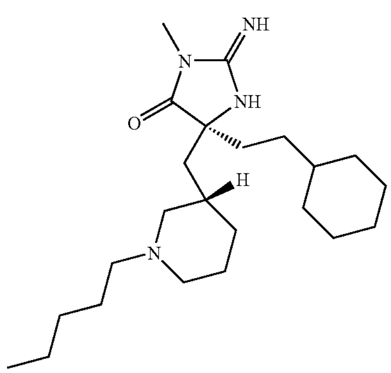 | 390 | 391 |

-continued

| # | Structure | MW | Obs. m/e |
|---|---|---|---|
| 603 | 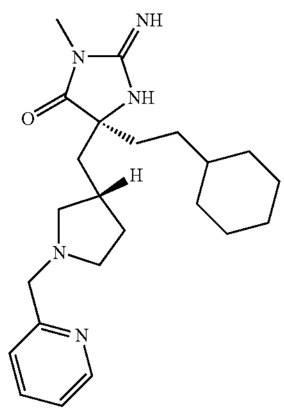 | 397 | 398 |
| 604 | 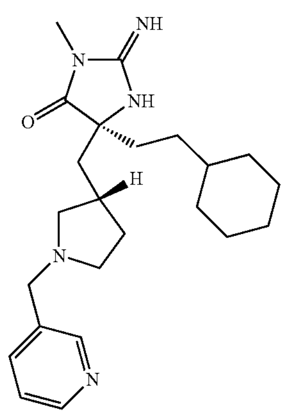 | 397 | 398 |
| 605 | 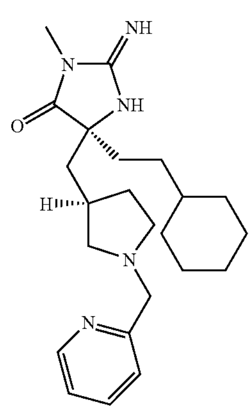 | 397 | 398 |

-continued

| # | Structure | MW | Obs. m/e |
|---|-----------|-----|----------|
| 606 | 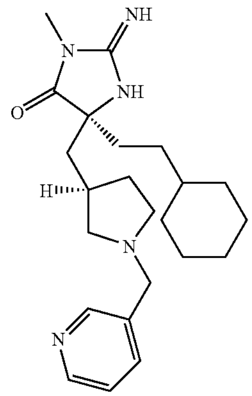 | 397 | 398 |
| 607 | 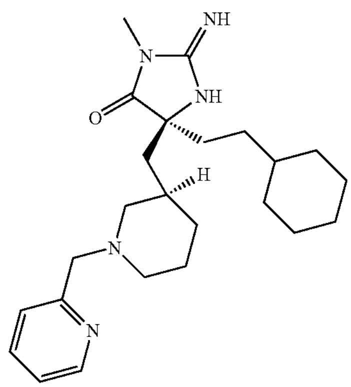 | 411 | 412 |

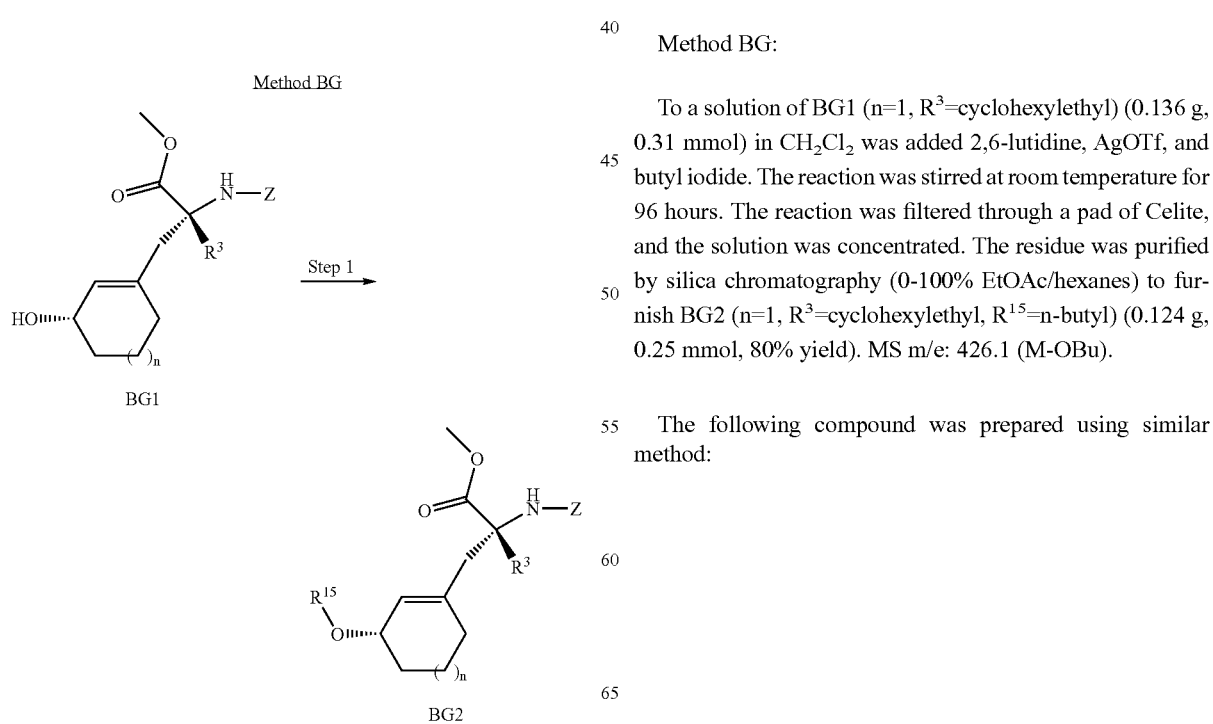

Method BG:

To a solution of BG1 (n=1, R$^3$=cyclohexylethyl) (0.136 g, 0.31 mmol) in CH$_2$Cl$_2$ was added 2,6-lutidine, AgOTf, and butyl iodide. The reaction was stirred at room temperature for 96 hours. The reaction was filtered through a pad of Celite, and the solution was concentrated. The residue was purified by silica chromatography (0-100% EtOAc/hexanes) to furnish BG2 (n=1, R$^3$=cyclohexylethyl, R$^{15}$=n-butyl) (0.124 g, 0.25 mmol, 80% yield). MS m/e: 426.1 (M-OBu).

The following compound was prepared using similar method:

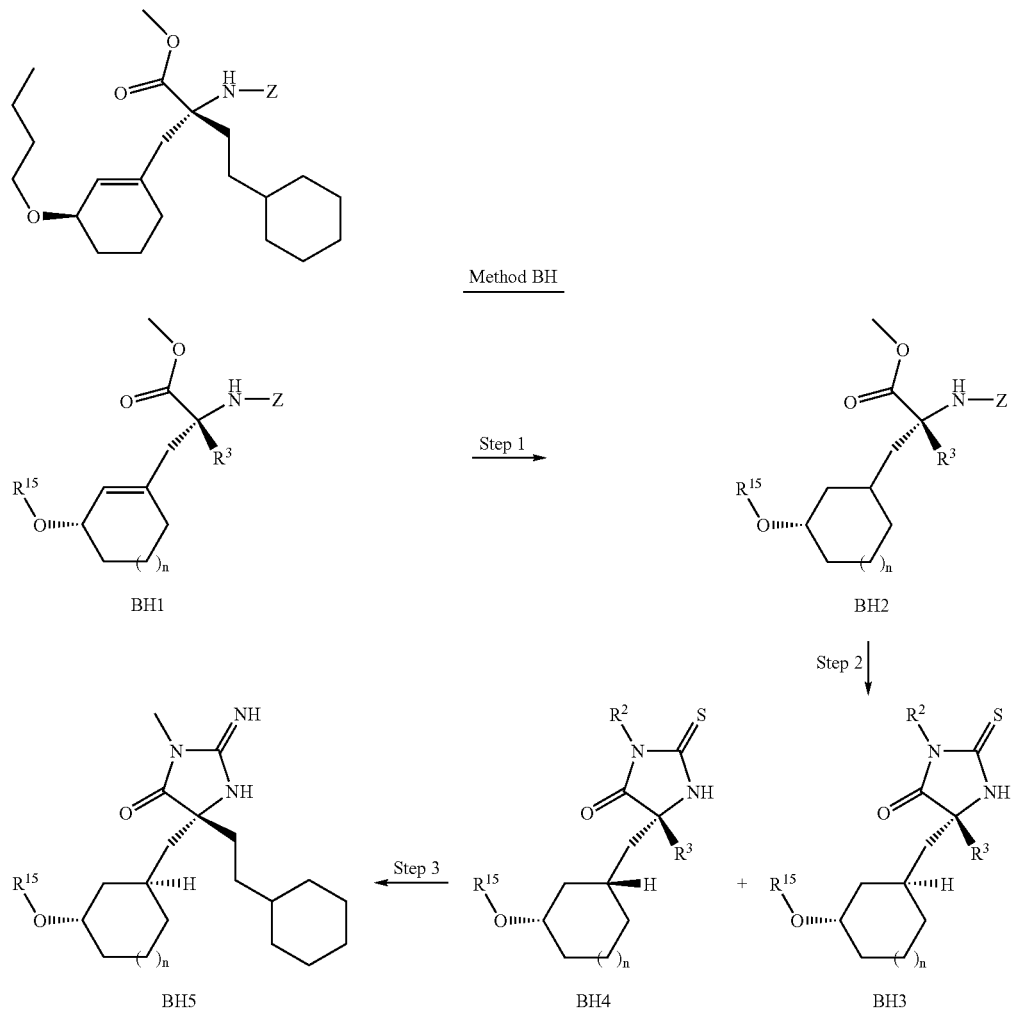

Method BH, Step 1.

Compound BH1 (n=1, $R^3$=cyclohexylethyl and $R^{15}$=n-butyl). (0.060 g, 0.12 mmol) and 5% Pd(OH)$_2$/C (0.040 g) in EtOAc (1 mL)/MeOH (0.2 mL) was stirred under an atmosphere of H$_2$ for 20 hours at room temperature. The reaction was filtered through a pad of Celite, and the solution was concentrated. The crude product mixture BH2 (n=1, $R^3$=cyclohexylethyl and $R^{15}$=n-butyl) was carried on to the next step without purification.

Method BH, Step 2.

A solution of BH2 (n=1, $R^3$=cyclohexylethyl and $R^{15}$=n-butyl) was converted to a product mixture of BH4 and BH3 using a method similar to Method C Step 1. The mixture was purified by silica gel chromatography using EtOAc/hexanes to yield BH4 (n=1, $R^2$=Me, $R^3$=cyclohexylethyl and $R^{15}$=n-butyl) (0.032 g, 0.078 mmol, 56% yield) and BH3 (n=1, $R^2$=Me, $R^3$=cyclohexylethyl and $R^{15}$=n-butyl) (0.008 g, 0.020 mmol, 14% yield). For BH4 (n=1, $R^2$=Me, $R^3$=cyclohexylethyl and $R^{15}$=n-butyl), MS m/e: 409.1M+H). For BH3 (n=1, $R^2$=Me, $R^3$=cyclohexylethyl and $R^{15}$=n-butyl), MS m/e: 409.1 (M+H).

Method BH, Step 3.

Compound BH4 (n=1, $R^2$=Me, $R^3$=cyclohexylethyl and $R^{15}$=n-butyl) (0.032 g, 0.078 mmol) was converted to BH5 (n=1, $R^2$=Me, $R^3$=cyclohexylethyl and $R^{15}$=n-butyl) (0.016 g, 0.043 mmol, 57% yield) using a method similar to Method A, step 3. MS m/e: 392.1 (M+H).

The following compound was generated using a similar method:

| # | Structure | MW | Obs. m/e |
|---|---|---|---|
| 608 | 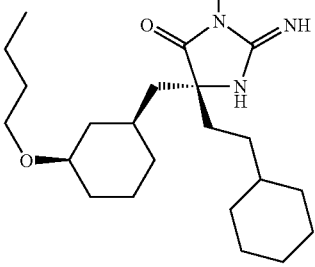 | 391 | 392 |

-continued

| # | Structure | MW | Obs. m/e |
|---|---|---|---|
| 609 | 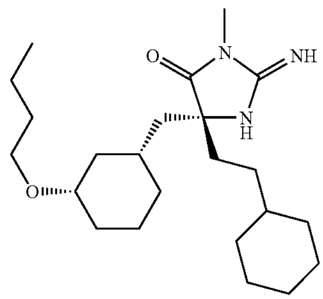 | 391 | 392 |
| 610 | 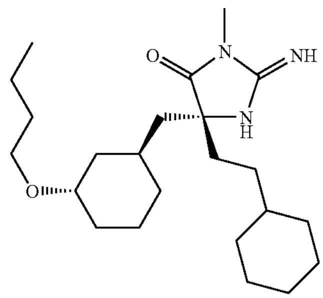 | 391 | 392 |

Method BI

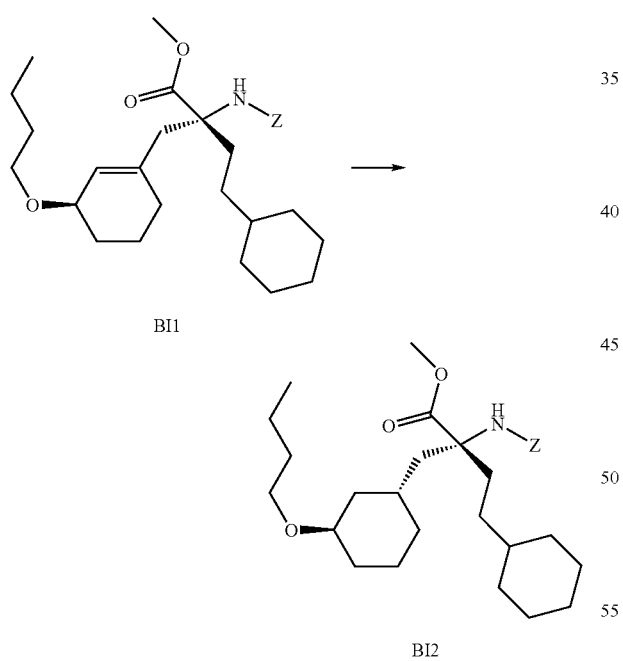

BI1

BI2

A solution of BI1 (0.020 g, 0.040 mmol) in DCM (1 mL) was degassed using freeze/pump/thaw (4×) method. At the end of the fourth cycle Crabtree's catalyst was added and the system was evacuated. While thawing, the system was charged with hydrogen gas, and the reaction was stirred at room temperature for 16 hours under an $H_2$ atmosphere. The reaction was concentrated, and the brown oil was purified by reverse phase HPLC to furnish BI2 (0.011 g, 0.022 mmol, 55% yield). MS m/e: 368.2 (M+H).

Method BJ

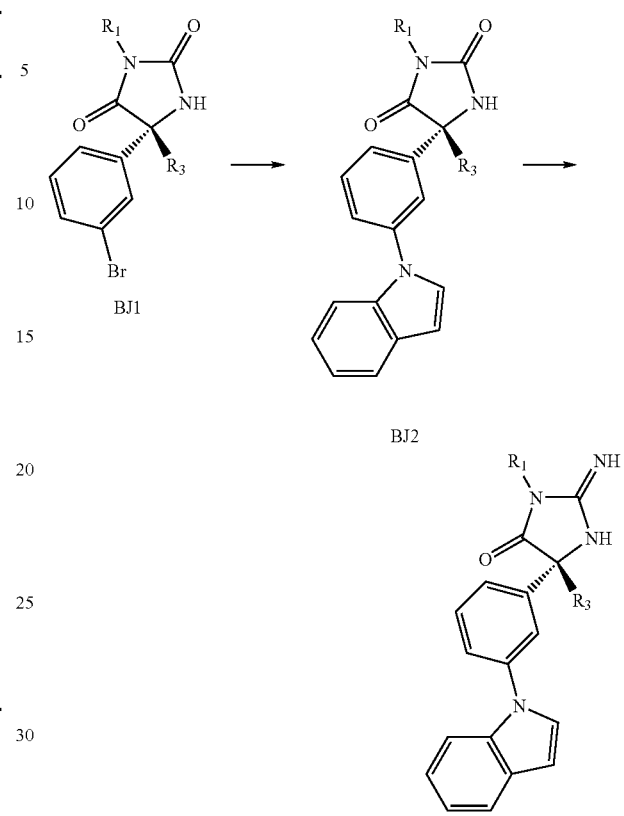

BJ1

BJ2

BJ3

Method BJ, Step 1

A mixture of 2 ml dioxane solution of BJ1 ($R^1$=Me, $R^3$=Me) (140 mg, 0.5 mmol) generated using Method BK Steps 1 & 2, indole (1.2 eq), potassium t-Butoxide (1.4 eq), $Pd_2(dba)_3$ (0.02 eq) and 2-di-t-butylphospinobiphenyl (0.04 eq) in a sealed tube was irradiated in a microwave oven at 120° C. for 10 min and the mixture was separated via a silica gel column to give BJ2 ($R^1$=Me, $R^3$=Me) (0.73 mg).

Method BJ, Step 2

BJ2 ($R^1$=Me, $R^3$=Me) was converted to BJ3 ($R^1$=Me, $R^3$=Me) using Method BK, Steps 3 & 4. Obs. Mass for BJ3 ($R^1$=Me, $R^3$=Me): 319.2.

| # | Structure | MW | Obs. m/e |
|---|---|---|---|
| 614 | 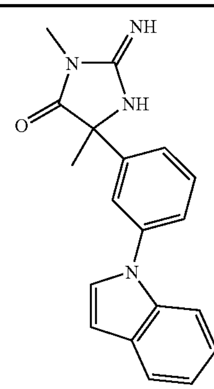 | 318 | 319 |

Method BK

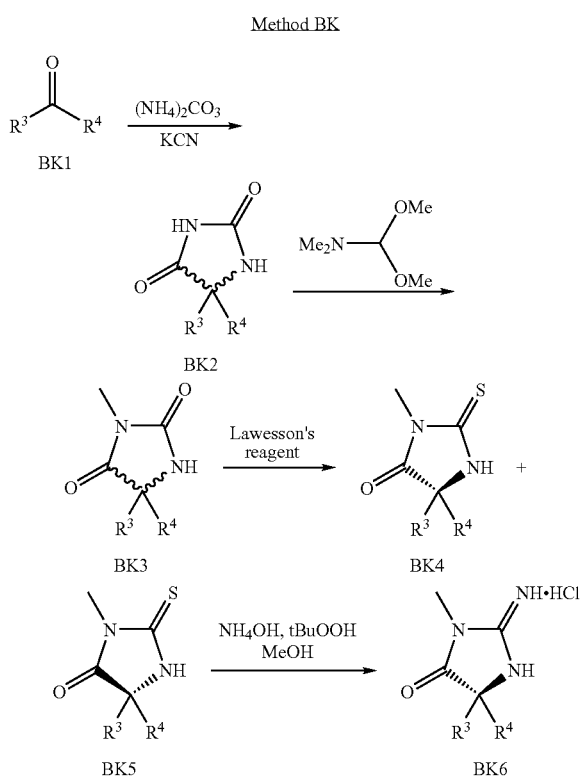

Method BK, Step 1:

Hydantoin BK2 (R³=N-benzyl-3-piperidyl, R⁴=n-Bu) was prepared, according to Method D, Step 1 from the corresponding ketone BK1 (R³=N-benzyl-3-piperidyl, R⁴=n-Bu). Analytical data for BK2 (R³=N-benzyl-3-piperidyl, R⁴=n-Bu): (M+H)=330.1.

Method BK, Step 2:

To a suspension of hydantoin BK2 (R³=N-benzyl-3-piperidyl, R⁴=n-Bu) (138 mg, 0.419 mmol) in DMF (1.5 ml) was added dimethylformamide dimethylacetal (0.11 ml, 0.84 mmol). The resulting mixture was heated in a 100° C. oil bath for 16 h and then cooled to RT and concentrated under vacuum. This crude residue was purified by column chromatography (MeOH/DCM) to give product BK3 (R³=N-benzyl-3-piperidyl, R⁴=n-Bu) (140 mg, 0.408 mmol, 97%), (M+H)=344.1.

Method BK, Step 3:

To a solution of a portion of BK3 (R³=N-benzyl-3-piperidyl, R⁴=n-Bu) (70 mg, 0.20 mmol) in toluene (1 ml) was added Lawesson's reagent (107 mg, 0.26 mmol). The resulting mixture was placed in an oil bath at 60° C. for 16 h and then at 100° C. for 24 h. After cooling to RT, the reaction was quenched by addition of several drops of 1 N HCl and then diluted with EtOAc and 1 N KOH. The phases were separated and the aqueous layer extracted with EtOAc (2×). The organic portions were combined, washed with brine, dried over MgSO₄, filtered, and concentrated. This crude residue was purified by preparative TLC (1000 μm silica, 15% EtOAc/DCM) to give two separated diastereomers BK4 (R³=N-benzyl-3-piperidyl, R⁴=n-Bu) (24 mg, 0.067 mmol, 33%, MS: (M+H)=360.2) and BK5 (R³=N-benzyl-m-piperidyl, R⁴=n-Bu) (22 mg, 0.062 mmol, 31%, MS: (M+H)=360.2).

Method BK, Step 4:

Diastereomer BK5 (R³=N-benzyl-3-piperidyl, R⁴=n-Bu) was treated with NH₄OH (2 ml) and t-butyl hydrogen peroxide (70% aqueous, 2 ml) in MeOH (4 ml) for 24 h. After concentration, the crude sample was purified by preparative TLC (1000 mm silica, 7.5% 7N NH₃/MeOH in DCM). The resulting sample was dissolved in DCM (1 ml), treated with 4N HCl in dioxane for 5 min, and finally concentrated to give diastereomeric products BK7 (R³=N-benzyl-3-piperidyl, R⁴=n-Bu) (12 mg, 0.029 mmol, 43%). ¹H NMR (CD₃OD) δ 7.60 (m, 2 H), 7.49 (m, 3 H), 4.39 (ABq, $J_{AB}$=12.8 Hz, $\Delta v_{AB}$=42.1 Hz, 2 H), 3.69 (m, 1 H), 3.39 (br d, J=13.6 Hz, 1 H), 3.20 (s, 3 H), 2.96 (m, 2 H), 2.45 (m, 1 H), 1.99 (m, 1 H), 1.92-1.78 (m, 3 H), 1.68 (br d, J=12.4 Hz, 1 H), 1.50 (dq, $J_d$=3.6 Hz, $J_q$=12.8 Hz, 1 H), 1.36-1.22 (m, 4 H), 1.03 (m, 1 H), 0.90 (t, J=7.2 Hz, 3 H). LCMS: $t_R$ (doubly protonated)=0.52 min, (singly protonated)=2.79 min; (M+H) for both peaks=343.2.

The following compounds were synthesized using similar methods:

| # | Structure | MW | Obs. m/e |
|---|---|---|---|
| 615 | ![structure] | 281 | 282 |

Method BL

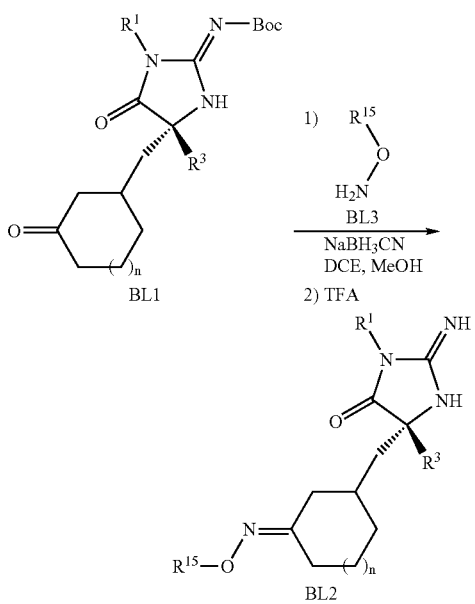

To a 2 ml Methanolic solution of BL1 (n=1, R³=cyclohexylethyl, R¹=Me) (10 mg) was added BL3 (HCl salt, R¹⁵=H, 2 eq) and NaOAc (2 eq) and the mixture was heated to 60 C for 16 h. After removal of solvent, the residue was treated with 20% TFA in DCM for 30 min before the solvent was evaporated and residue purified using a reverse phase HPLC to give BL2 (n=1, $R^3$=cyclohexylethyl, $R^1$=Me and $R^{15}$=H).

The following compounds were synthesized using similar methods.

| # | Structure | MW | Obs. m/e |
|---|---|---|---|
| 616 | 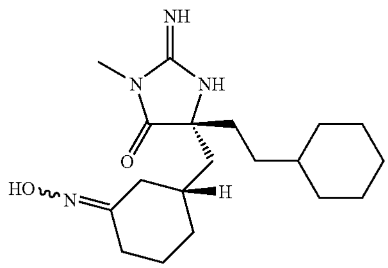 | 348 | 349 |
| 617 | 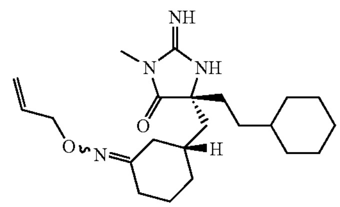 | 388 | 389 |

Method BM, Step 1:

To a toulene solution (3 ml) of BM1 (n=1, $R^3$=cyclohexylethyl, $R^2$=Me) (0.050 mg) was added 1.5 eq of diphenylphosphorylazide and 1.5 eq of DBU and the solution was stirred at r.t. overnight. The reaction mixture was diluted with EtOAc and washed with 1% aq HOAC before the organic layer was dried and solvent evaporated. The residue was chromatographed using EtOAc/Hex to give a product that was treated with triphenylphosphine (2 eq) in THF (1% water) overnight to give BM2 (n=1, $R^3$=cyclohexylethyl, $R^2$=Me) after reverse phase purification.

Method BM Step 2:

To a DCM solution of BM2 (n=1, $R^3$=cyclohexylethyl, $R^2$=Me) was added 1 eq of benzyloxycarbonyl-OSu and the reaction was stirred overnight before the solvent was evaporated and residue chromatographed to give BM3 (n=1, $R^3$=cyclohexylethyl, $R^2$=Me).

Compound BM4 (n=1, $R^3$=cyclohexylethyl, $R^2$=Me) and BM5 (n=1, $R^3$=cyclohexylethyl, $R^2$=Me) were generated from BM2 (n=1, $R^3$=cyclohexylethyl, $R^2$=Me) and BM3 (n=1, $R^3$=cyclohexylethyl, $R^3$=Me) through Boc-deprotection.

The following compounds were synthesized using similar method:

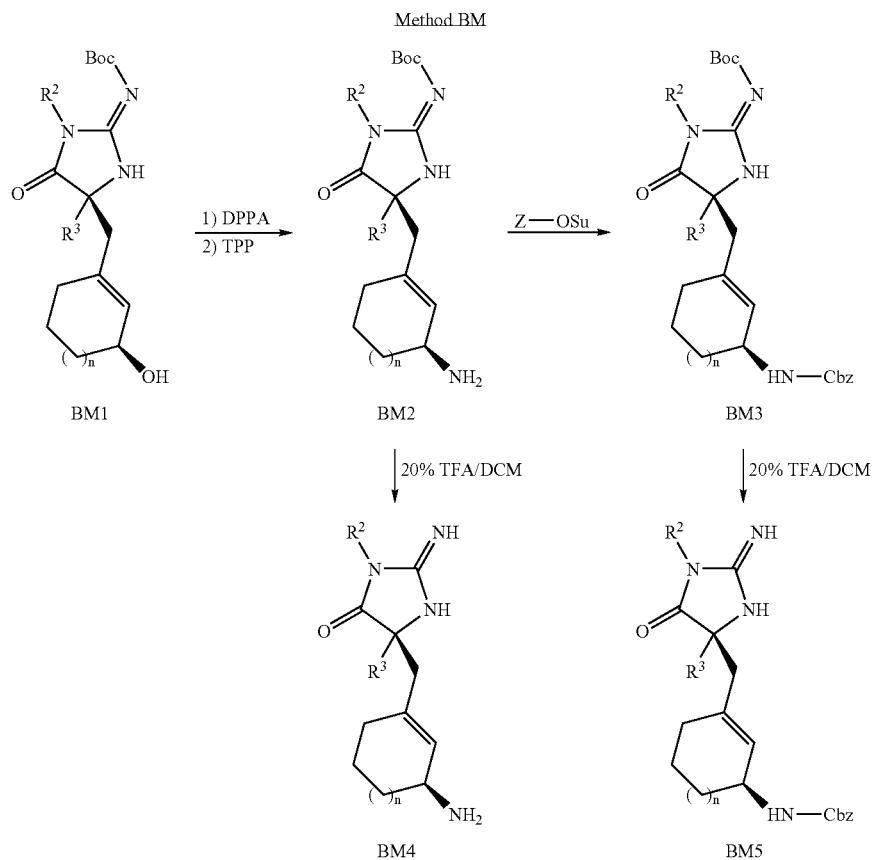

| # | Structure | MW | Obs. m/e |
|---|---|---|---|
| 618 | 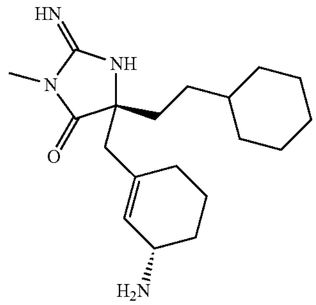 | 332 | 333 |
| 619 | 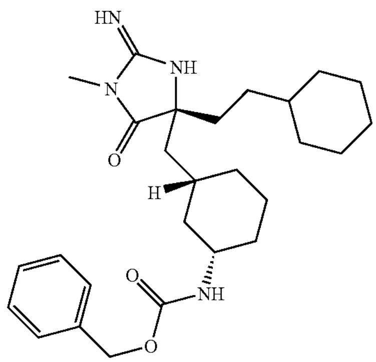 | 468 | 469 |

Method BN

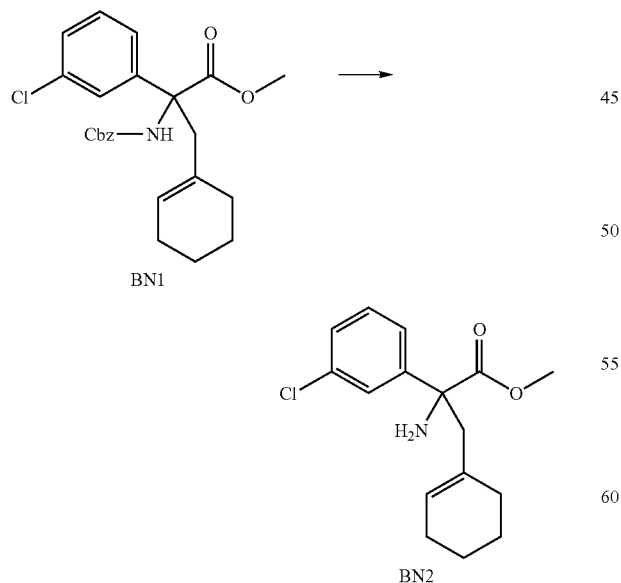

A mixture of Pd(OAc)$_2$ (9 mg), triethylamine (17 microliter), triethylsilane (11 microliter) and BN1 (20 mg) in DCM was hydrogenated at 1 atm at rt for 1.5 h before the reaction was filtered through a Celite pad to give BN2 after removal of solvent.

Method BO

The following compounds were generated through boc-deprotection of the corresponding starting material using 50% TFA in DCM, rt 30 min.

| # | Structure | MW | Obs. m/e |
|---|---|---|---|
| 620 | 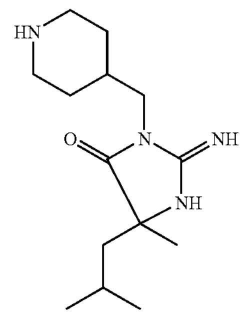 | 266 | 267 |
| 621 | 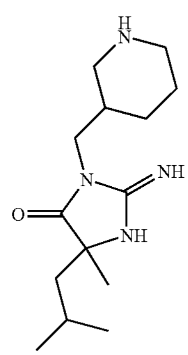 | 266 | 267 |
| 622 | 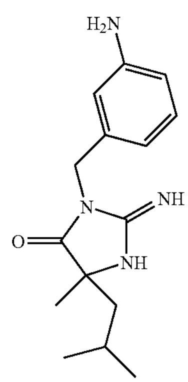 | 274 | 275 |

-continued

| # | Structure | MW | Obs. m/e |
|---|---|---|---|
| 623 | 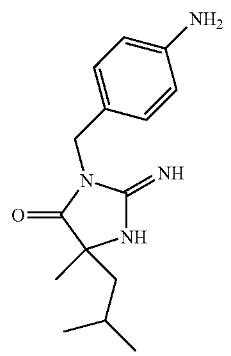 | 274 | 275 |
| 624 | 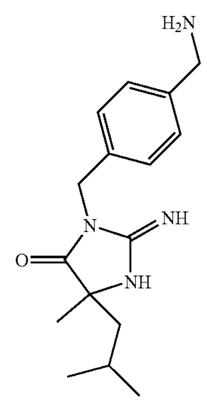 | 288 | 289 |
| 625 | 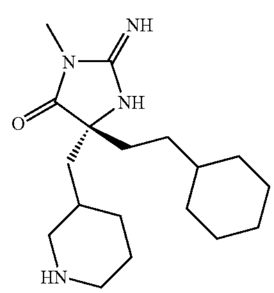 | 320 | 321 |
| 626 | 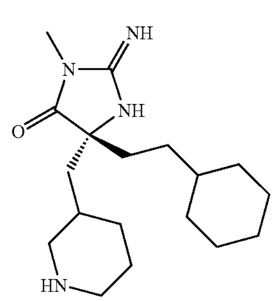 | 320 | 321 |

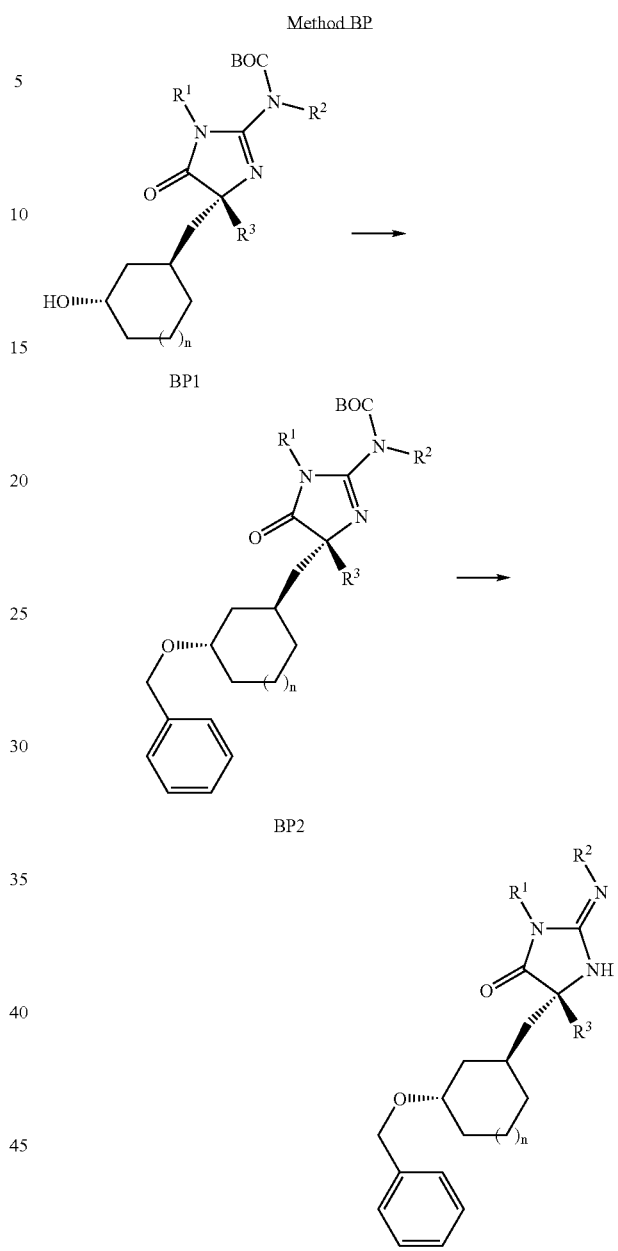

Method BP, Step 1

To a solution of BP1 (n=1, $R^1$=Me, $R^2$=H, $R^3$=cyclohexylethyl) (0.012 g, 0.028 mmol) in $CH_2Cl_2$ (0.5 mL) was added 2,6-lutidine (0.010 mL, 0.086 mmol), AgOTf (0.024 g, 0.093 mmol), and benzyl bromide (0.010 mL, 0.084 mmol). The reaction was stirred at room temperature for 16 hours. The solid was filtered, and after concentration the residue was purified by reverse phase HPLC to yield BP2 (n=1, $R^1$=Me, $R^2$=H, $R^3$=cyclohexylethyl) (0.010 g, 0.019 mmol). MS m/e: 526.1 (M+H).

Method BP, Step 2

BP3 (n=1, $R^1$=Me, $R^2$=H, $R^3$=cyclohexylethyl) was prepared from BP2 (n=1, $R^1$=Me, $R^2$=H, $R^3$=cyclohexylethyl) using 30% TFA/DCM. MS m/e: 426.1 (M+H).

| # | Structure | MW | Obs. m/e |
|---|---|---|---|
| 627 | 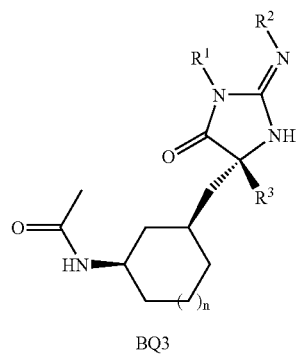 | 425 | 426 |

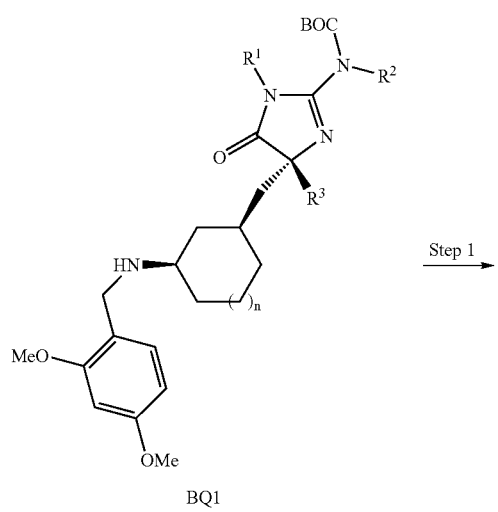

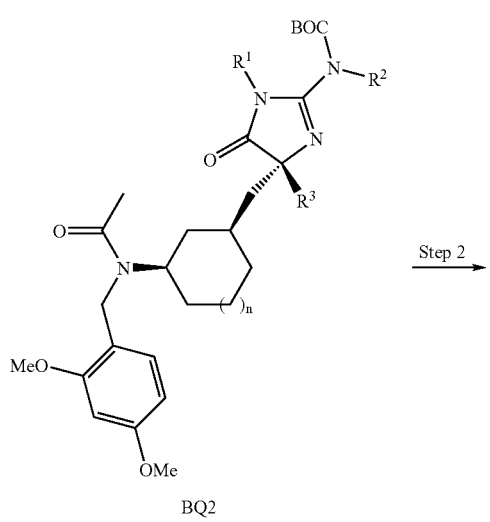

-continued

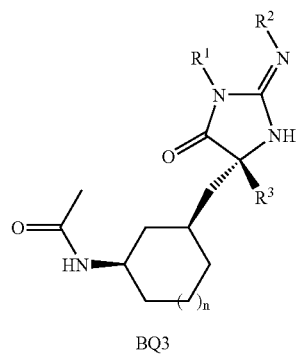

BQ3

Method BQ Step 1:

BQ1 was prepared according to Method AZ.

To a solution of BQ1 (n=1, R¹=Me, R²=H, R³=cyclohexylethyl) (0.004 g, 0.007 mmol) in $CH_2Cl_2$ (0.3 mL) was added DIEA (0.007 mL, 0.040 mmol), acetic acid (0.001 mL, 0.017 mmol), HOBt (0.003 g, 0.019 mmol), and EDCI (0.003 g, 0.016 mmol). The reaction was stirred at room temperature for 16 hours. The reaction was concentrated and purified by reverse phase HPLC to provide BQ2 (n=1, R¹=Me, R²=H, R³=cyclohexylethyl) (0.003 g, 0.005 mmol). MS m/e: 627.1 (M+H).

Method BQ Step 2:

BQ2 (n=1, R¹=Me, R²=H, R³=cyclohexylethyl) (0.003 g, 0.005 mmol) was treated with 20% $TFA/CH_2Cl_2$ (1 mL) in the presence of PS-thiophenol resin (0.030 g, 1.42 mmol/g) for 3 hours. The solution was filtered and concentrated to produce B03 (n=1, R¹=Me, R²=H, R³=cyclohexylethyl) (0.002 g, 0.005 mmol). MS m/e: 377.2 (M+H).

| # | Structure | MW | Obs. m/e |
|---|---|---|---|
| 628 | 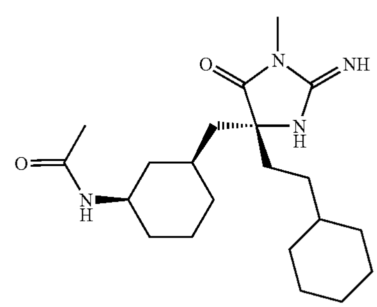 | 376 | 377 |

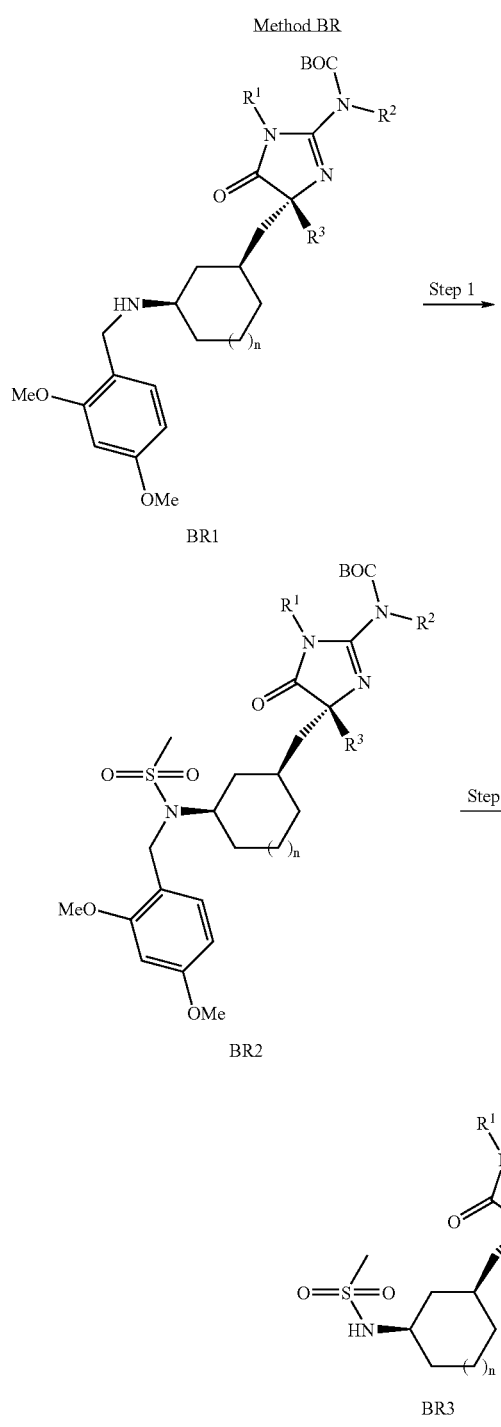

BR1

BR2

BR3

HPLC to yield BR2 (n=1, $R^1$=Me, $R^2$=H, $R^3$=cyclohexylethyl) (0.003 g, 0.004 mmol). MS m/e: 663.2 (M+H).

Method BR, Step 2:

BR3 (n=1, $R^1$=Me, $R^2$=H, $R^3$=cyclohexylethyl) was prepared from BR2 (n=1, $R^1$=Me, $R^2$=H, $R^3$=cyclohexylethyl) following a procedure similar to Method BQ Step 2. MS m/e: 413.1 (M+H).

| # | Structure | MW | Obs. m/e |
|---|---|---|---|
| 629 | 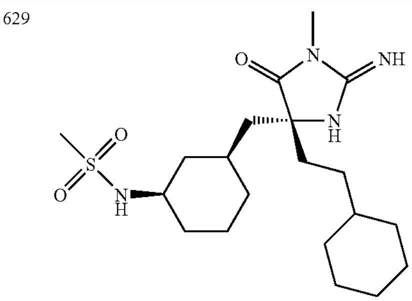 | 412 | 413 |

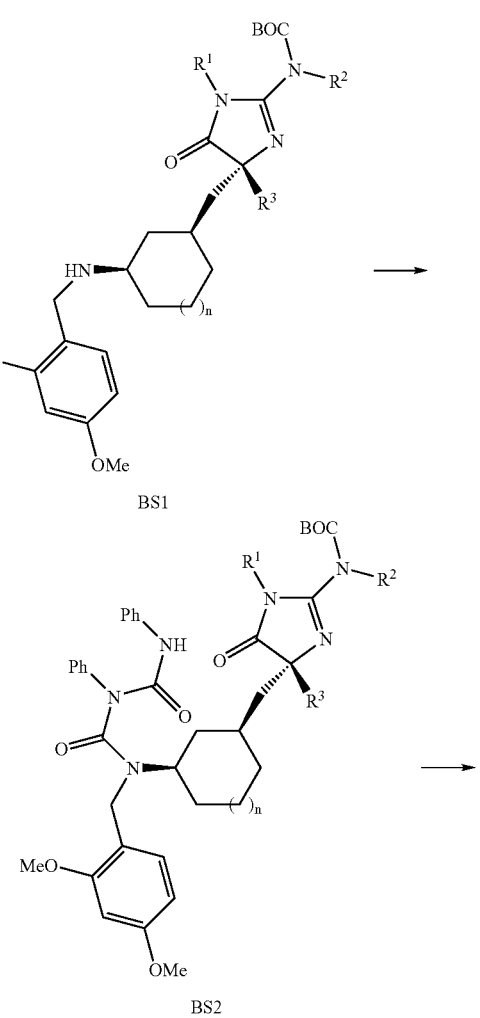

BS1

BS2

Method BR, Step 1:

To a solution of BR1 (n=1, $R^1$=Me, $R^2$=H, $R^3$=cyclohexylethyl) (0.004 g, 0.007 mmol) in pyridine (0.2 ml) was added DMAP (a few crystals) and methylsulfonyl chloride (3 drops). The reaction was stirred at room temperature for 6 days. The reaction was quenched with water and diluted with $CH_2Cl_2$. The organic layer was removed, and the aqueous phase was extracted with $CH_2Cl_2$ (3×). After concentration, the brown residue was purified by reverse phase

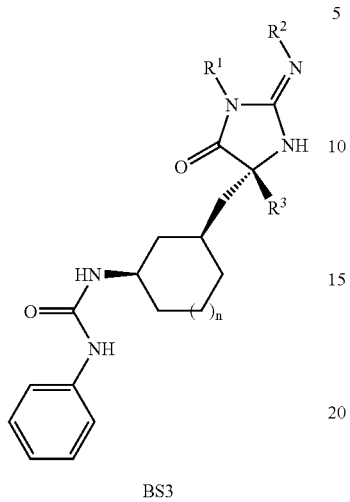

BS3

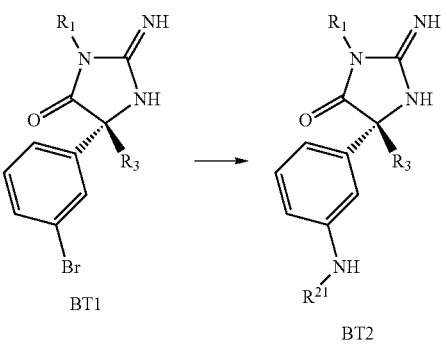

Method BT:

To a round bottom flask were added compound BT1 (R¹=Me, R³=Me) (100 mg, 0.29 mmol), anhydrous toluene (2 ml), 3-aminopyridine (55 mg, 0.58 mmol) and 2-(di-tert-butyl phosphino) biphenyl (17 mg, 0.058). The solution was then degassed by $N_2$ for 2 minutes before NaO-t-Bu (61 mg, 0.638 mmol) and $Pd_2(dba)_3$ (27 mg, 0.029 mmol) were added. The reaction was stirred at 80° C. for 22 hours. After cooling down to room temperature, the reaction was poured to cold water and extracted by $CH_2Cl_2$. The combined organic layer was then dried over $Na_2SO_4$. After the filtration, the concentrated residue was separated by TLC ($CH_3OH:CH_2Cl_2$=1:10) and reverse phase HPLC (10%-100% acetonitrile in water w/0.1% formic acid) to produce the desired compound BT2 (R¹=Me, R³=Me and R²¹=m-pyridyl) as a formate salt (23.6 mg, white solid, 20%). $^1$HNMR (CDCl$_3$) δ 7.50-6.90 (m, 13H), 3.14 (s, 3H) MS m/e 358 (M+H).

Method BS Step 1:

To a solution of BS1 (n=1, R¹=Me, R²=H, R³=cyclohexylethyl) (0.003 g, 0.006 mmol) in CH$_2$Cl$_2$ (0.3 mL) was added phenyl isocyanate (2 drops). The reaction was stirred at room temperature for 16 hours. The reaction was concentrated and purified by reverse phase HPLC to provide BS2 (n=1, R¹=Me, R²=H, R³=cyclohexylethyl) (0.002 g, 0.002 mmol). MS m/e: 823.5 (M+H).

Method BS Step 2:

Compound BS2 (n=1, R¹=Me, R¹²=H, R³=cyclohexylethyl) was subjected to the same conditions in Method BQ Step 2. The crude mixture prepared above was treated with LiOH (0.006 g, 0.25 mmol) in MeOH (0.3 mL) for 2 hours. The reaction was concentrated, and the residue was purified by reverse phase HPLC to furnish BS3 (n=1, R¹=Me, R²=H, R³=cyclohexylethyl) (0.0012 g, 0.002 mmol). MS m/e: 454.1 (M+H).

| # | Structure | MW | Obs. m/e |
|---|---|---|---|
| 630 | | 453 | 454 |
| 631 | 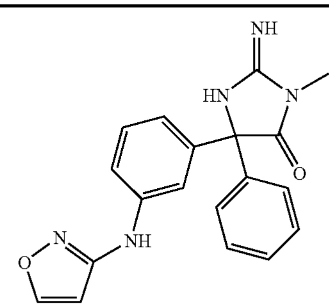 | 347 | 348 |
| 632 | 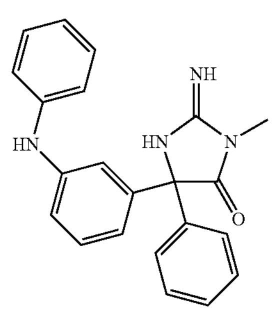 | 356 | 357 |

-continued
| # | Structure | MW | Obs. m/e |
|---|---|---|---|
| 633 | 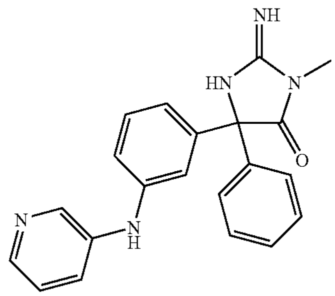 | 357 | 358 |
| 634 | 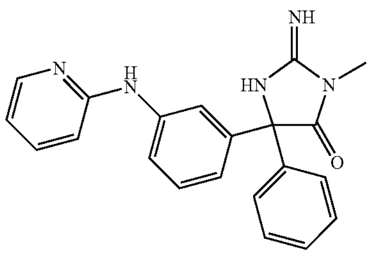 | 357 | 358 |
-continued
| # | Structure | MW | Obs. m/e |
|---|---|---|---|
| 635 | | 357 | 358 |
| 636 | | 358 | 359 |
Method BU
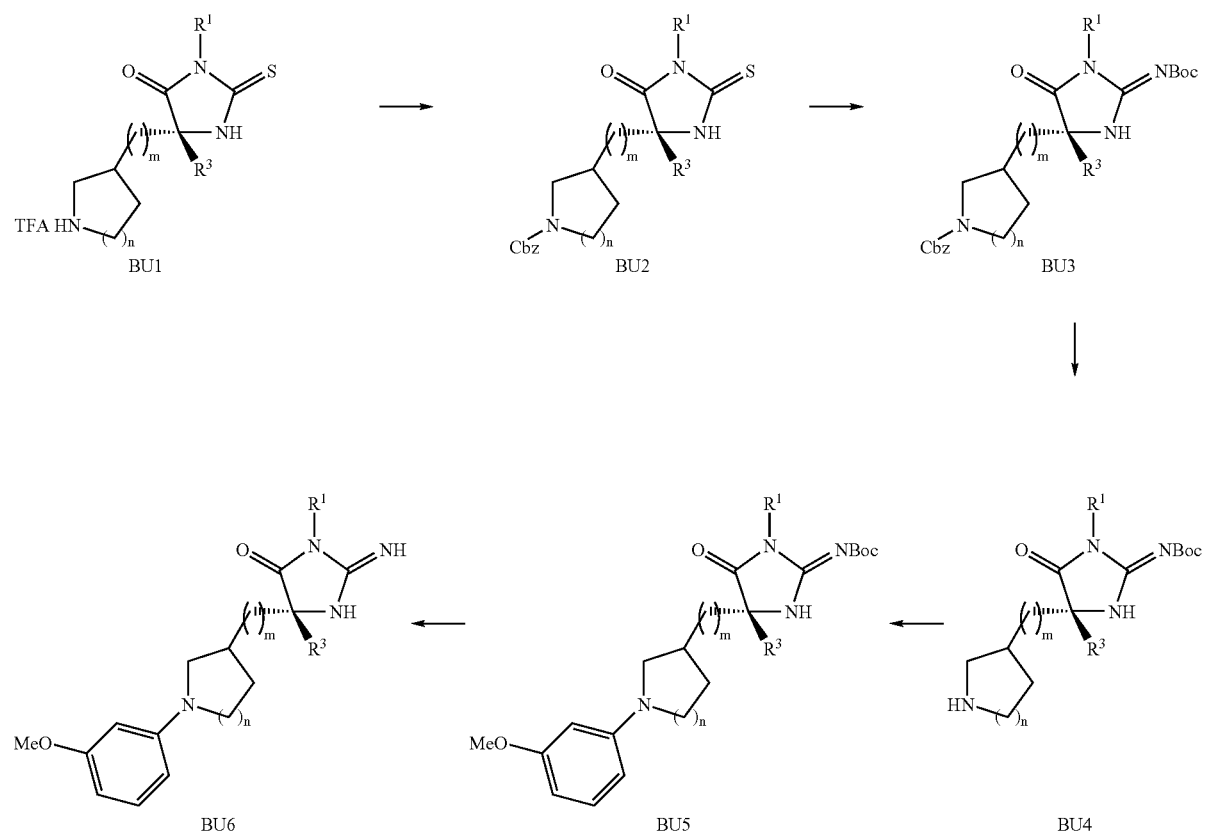

Method BU, Step 1,

To a round bottmed flask containing BU1 (m=1, n=1, R¹=Me, R³=Cyclohexylethyl) (99 mg, 0.307 mmol) of the trifluroacetic acid salt of pyrollidine derivative in 5 ml of DCM was added (86 µL, 0.614 mmol) of triethylamine followed by addition of (76 mg, 0.307 mmol) N-(benzyyloxycarbonyloxy)succinimide. Stir at room temperature for 18 h. Dilute the mixture with DCM and extract with sat'd NaHCO$_3$ soln, then water. Collect the organic portion and dry over Na$_2$SO$_4$, filter and concentrate in vacuo. Purify by silica gel chromatography (eluting with 0 to 60% EtOAc/hexanes) to yield BU2 (m=1, n=1, R¹=Me, R³=Cyclohexylethyl) (130 mg, 0.284 mmol, 93% yield). MS m/e: 458.1 (M+H).

Method BU, Step 2,

To a solution of BU2 (m=1, n=1, R¹=Me, R³=Cyclohexylethyl) (130 mg) in 1 ml of MeOH in a reaction vial was added 0.5 ml of a solution of 70% tBuOOH in water and 0.5 ml of NH$_4$OH. Seal the vial and shake at room temperature for 72 h. The mixture was concentrated in vacuo. The mixture was diluted with 1 ml of MeOH and a mixture 30 mg of NaHCO$_3$ and Boc$_2$O (87 mg, 0.398 mmol) were added. The solution mixture was stirred at room temperature for 18 h before it was concentrated and the residue purified by silica gel chromatography using EtOAc/hexanes to yield the BU3 (m=1, n=1, R¹=Me, R³=Cyclohexylethyl) (90 mg, 0.167 mmol, 58% yield). MS m/e: 541.1, 441.1 (M+H).

Method BU, Step 3,

A solution of BU3 (m=1, n=1, R¹=Me, R³=Cyclohexylethyl) (90 mg, 0.167 mmol) in 5 ml of MeOH was hydrogenated using 100 mg of Pd(OH)$_2$—C (20% w/w) at 1 atm for 1 h. The reaction mixture was filtered through a pad of diatomaceous earth and the pad was washed with MeOH. Concentration of the collected organic portions in vacuo yielded BU4 (m=1, n=1, R¹=Me, R³=Cyclohexylethyl) (47 mg 0.116 mmol, 70% yield). MS m/e: 407.1 (M+H).

Method BU, Step 4,

To a vial containing 10 mg of powdered 4 4' molecular sieves was added 3-methoxyphenyl boronic acid (60 mg, 0.395 mmol) then 3 ml of anhydrous MeOH. To this mixture was added pyridine (100 ml, 0.650 mmol), Cu(OAc)$_2$ (7 mg, 0.038 mmol), and BU4 (m=1, n=1, R¹=Me, R³=Cyclohexylethyl) (7.83 mg, 0.019 mmol) and the mixture was stirred at room temperature for 96 h before it was quenched with 0.25 ml of 7N ammonia in methanol solution. The reaction mixture was extracted with water and DCM and the organic layers were dried and concentrate in vacuo. The residue was purified via a reverse-phase HPLC to give a product which was treated with 5 ml of 40% of TFA in DCM for 5 h. After removal of the volatiles, the residue was purified using a reverse phase HPLC system to furnish BU5 (m=1, n=1, R¹=Me, R³=Cyclohexylethyl and R²=m-MeOPh) as the formic acid salt (0.7 mg, 0.0015 mmol, 30.1% yield). MS m/e: 413.1 (M+H).

| # | Structure | MW | Obs. m/e |
|---|---|---|---|
| 637 | 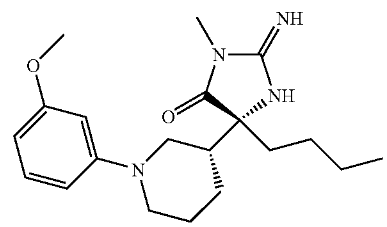 | 358 | 359 |
| 638 | 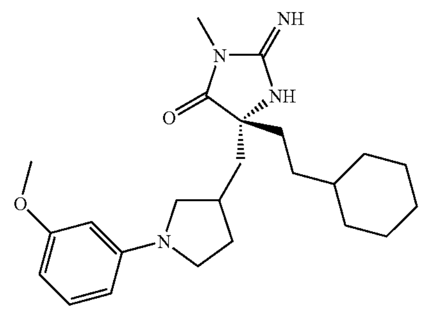 | 412 | 413 |

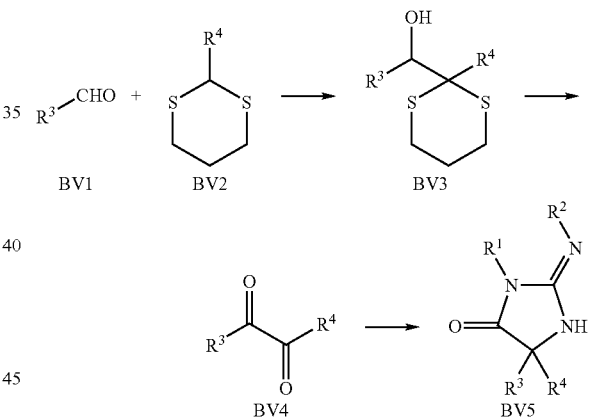

Method BV Step 1:

The method was adapted from a literature procedure (Page et al., *Tetrahedron* 1992, 35, 7265-7274)

A hexane solution of nBuLi (4.4 mL, 11 mmol) was added to a −78 C solution of BV2 (R⁴=phenyl) (2.0 g, 10 mmol) in THF (47 mL). After 60 minutes at −78 C, a solution of BV1 (R³=3-bromo-4-fluorophenyl) (2.24 g, 11 mmol) was added and the reaction slowly warmed to RT over 18 h. The reaction mixture was quenched with saturated ammonium chloride solution and extracted with CH$_2$Cl$_2$ (2×), dried over MgSO4 and concentrated under vacuum. The resulting oil was subjected to silica gel chromatography using 4-10% EtOAc/ Hexanes to give a white solid BV3: (R³=3-bromo-4-fluorophenyl and R⁴=phenyl) (1.69 g, 4.23 mmol, 42%). ¹H NMR (CDCl$_3$) δ 7.61 (m, 2 H), 7.27 (m, 3 H), 6.94 (m, 1 H), 6.92 (m, 1 H), 6.68 (m, 1 H), 3.15 (bs, 1 H), 2.57-2.73 (m, 4 H), 1.89 (m, 2 H).

Method BV Step 2:

A solution of BV3 (R³=3-bromo-4-fluorophenyl and R⁴=phenyl) (1.69 g, 4.23 mmol) in acetone (40 mL) was slowly added via addition funnel to a 0° C. solution of N-bromosuccinimide (NBS, 11.3 g, 63.3 mmol) in acetone (200 mL) and water (7.5 mL). The mixture was slowly warmed to RT, and quenched after 60 minutes with 10% aqueous Na₂SO₃. After diluting with CH₂Cl₂, the layers were separated, and the organic layer washed with water (2×), brine (1×) and dried over MgSO₄. Concentration under vacuum afforded an oil which was subjected to silica gel chromatography using 5% EtOAc/Hexanes to give a solid BV4 (R³=3-bromo-4-fluorophenyl and R⁴-phenyl) (690 mg, 2.24 mmol, 53%). ¹H NMR (CDCl₃) δ 8.19 (m, 1 H), 7.93 (m, 3 H), 7.66 (m, 1 H), 7.50 (m, 2 H), 7.20 (m, 1 H).

Method BV Step 3:

BV5 (R³=3-bromo-4-fluorophenyl and R⁴=phenyl and R¹=Me and R²=H) was prepared from BV4 (R³=3-bromo-4-fluorophenyl and R⁴=phenyl) using Method AS, Step 4.

| # | Structure | MW | Obs. m/e |
|---|---|---|---|
| 639 | 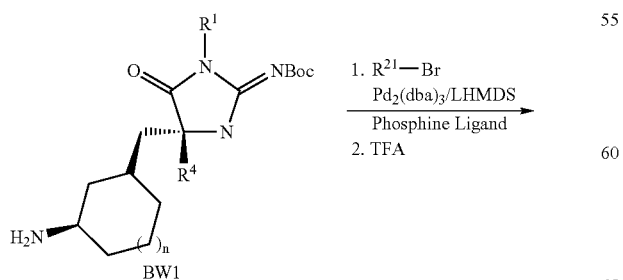 | 361 | 362 |
| 640 | 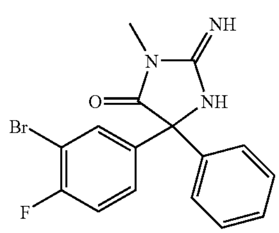 | 361 | NA |

Method BW

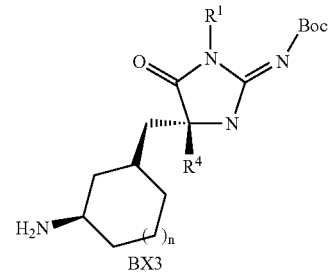

1. R²¹—Br
   Pd₂(dba)₃/LHMDS
   Phosphine Ligand
2. TFA

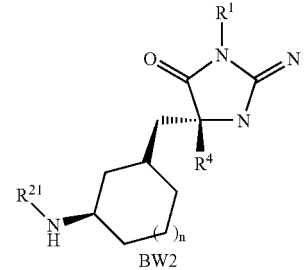

To an oven-dried vial was added Pd₂(dba)₃ (15.4 mg, 0.0168 mmol) and 2-(Di-t-butylphosphino)biphenyl (10.0 mg, 0.0336 mmol) followed by addition of a solution of BW1 (R⁴=Me; R¹=Me and n=1) (56.8 mg, 0.168 mmol) in 2 mL of anhydrous THF. 2-Bromopyridine (17.0 mL, 0.178 mmol) was added followed by addition of 0.80 mL of 1.0 N LHMDS solution in THF. The reaction mixtures was stirred at 35° C. for 90 min followed by addition of MeOH and filteration through a silica gel pad. Purification by silica gel chromatography (0 to 100% EtOAc in hexanes) yielded the product which was treated with 5 mL of a 30% TFA in DCM solution to give BW2 after concentration and purification via a reverse phase column (R⁴=Me; R¹=Me; R²⁼²-pyridyl and n=1) (69.3 mg, 99%). ES_LCMS (m/e): 416.2

Method BX

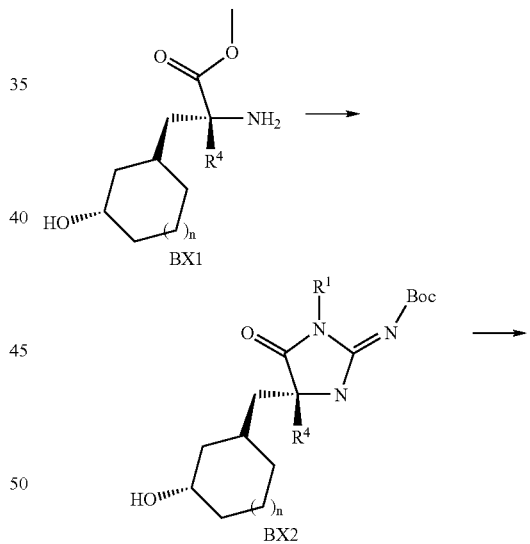

Method BX, Step 1
To a solution of BX1 (R⁴=Me and n=1) (0.78 g, 3.63 mmol) in 10 mL of anhydrous DMF, was added N-Boc-N'-methyl thiourea (0.70 g, 3.70 mmol), EDCI.HCl (0.90 g, 4.71 mmol), and diisopropylethylamine (2.5 mL). The mixture was stirred at RT for 16 h before it was quenched with water and extracted with EtOAc (3×50 mL). The organic solution was dried, concentrated and the residue chromatographed via a silica gel column to yield BX2 ($R^1=R^4$=Me and n=1) (1.23 g, 100%). ES_LCMS (m/e): 340.1

Method BX, Step 2

To a solution of BX2 ($R^1=R^4$=Me and n=1) (1.23 g, 3.63 mmol) in 40 mL of anhydrous THF was added triphenylphosphine (1.43 g, 5.44 mmol) and the mixture was cooled to 0° C. followed by slow addition of diisopropylcarbodiimide (1.07 mL, 5.44 mmol). After the mixture was stirred for 15 min at 0° C., nicotinoyl azide (Synthesis, 2004 (17), 2886) (0.66 g, 4.71 mmol) was added in one portion and the reaction was allowed to warm to RT and stir for 3 h. The reaction was diluted with EtOAc (200 mL) and washed with water (3×100 mL). The residue from the organic layer was purified through a silica gel column to yield the product azide which was hydrogenation using 20% $Pd(OH)_2$/C (0.64 mg) in MeOH to give BX3 ($R^1=R^4$=Me and n=1). ES_LCMS (m/e): 339.1.

Method BY

The following compounds were synthesized using methods similar to Methods AO or AP.

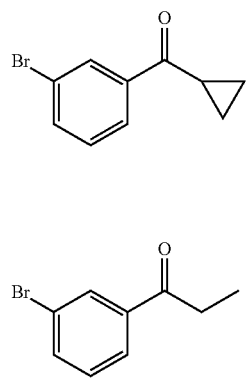

BY1

BY2

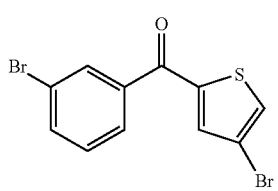

BY3

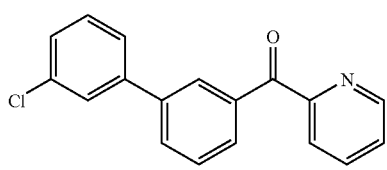

BY4

Method BZ

The following aminoacids were generated using methods similar to Method D

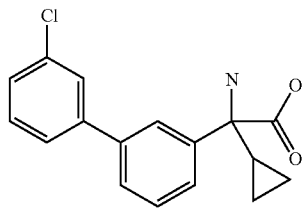

BZ1

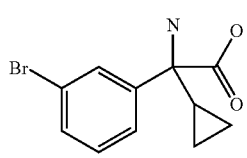

BZ2

Method CA

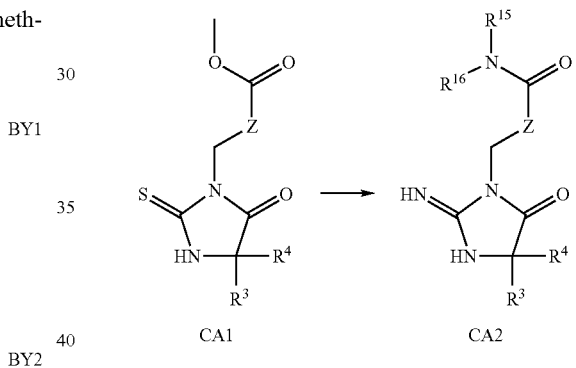

CA1            CA2

Compound CA2 ($R^3=R^4$=Ph; Z=m-phenylene, $R^{15}$=H and $R^{16}$=cyclopentyl) was obtained from CA1 ($R^3=R^4$=Ph; Z=m-phenylene, $R^{15}$=H and $R^{16}$=cyclopentyl) using a method similar to Method G.

Method CB

The following compounds were synthesized using methods similar to Method E and/or AX.

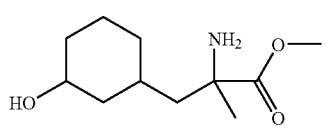

CB1

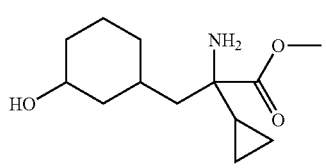

CB2

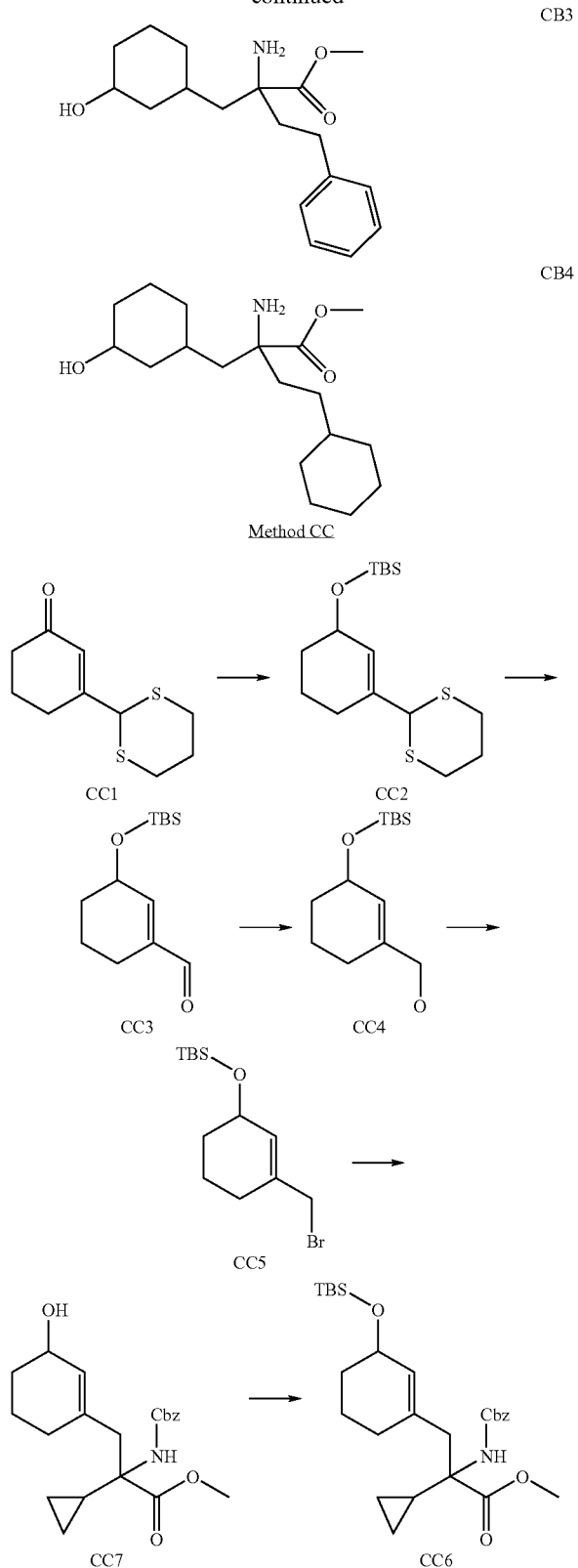

Method CC, Step 1.

To a methanol solution (20 mL) of CC1 (5 g) cooled to 0° C. was added sodium borohydride (1 eq) and the reaction was stirred for 30 min before the reaction mixture was evaporated to dryness then extracted with DCM/water. The DCM fractions were pooled, dried (MgSO$_4$), filtered and concentrated to dryness. The crude product was dissolved in 20 mL. of anhydrous DCM. To this solution was added t-butyldimethylchlorosilane (2 eq.) and imidazole (2 eq.). The reaction was stirred overnight at RT before it was quenched DCM and saturated NaHCO$_3$. The organic phase was dried (MgSO$_4$), filtered and evaporated to dryness to give crude product CC2.

Method CC, Step 2.

A literature procedure was adapted (Aust. J. Chem. 1990, 43(7), 1195). Compound CC2 (50 g) in 80 mL. THF was added to mercuric oxide (1.5 eq.) and borontrifluoride etherate (1.6 eq.) in 540 mL. of THF/H$_2$O (5:1) and the mixture was stirred under nitrogen for 2 h before the reaction was quenched with saturated NaHCO$_3$ (aq.) and ether. The ether phase was dried over anhyd. Na$_2$SO$_4$, filtered through a silica pad and concentrated to give crude CC3.

Method CC, Step 3.

To CC3 (10.4 grams) in 200 mL MeOH was added 1.1 eq. of sodium borohydride and the mixture was stirred for 30 min before the reaction mixture was concentrated and the residue partitioned in DCM/H$_2$O. The organic phase was dried over Na$_2$SO$_4$, filtered and concentrated. The residue was chromatographed to give product CC4.

Method CC, Step 4.

Compound CC4 (2.5) in 5 mL. anhydrous DCM was added Bis(1,2-diphenylphosphino)ethane (DPPE; 1.2 eq.) followed by carbon tetrabromide (1.1 eq.) at 0° C. and the reaction was stirred for 30 min. The reaction was quenched with hexane and poured over a silica pad. The organic solution was evaporated to give product CC5 as an oil. $^1$H-NMR (CDCl$_3$) δ 5.72, br s, 1H, 4.18, t, 1H, 3.83, q, 2H, 2.00-2.10, m, 2H, 1.76-1.81, m, 2H, 1.43-1.56, m, 2H, 0.84, s, 9H, 0.03, s, 6H.

Method CC, Step 5.

Compound CC6 was generated from CC5 using a similar procedure in Method E. Crude compound CC6 was purified by flash chromatography (gradient 0-10% EtOAc in hexane). Two isomers were isolated during purification isomer A which eluted first followed by isomer B.

ISOMER A: $^1$H-NMR (CDCl$_3$) δ 7.26-7.37, m, 5H, 5.57, s, 1H, 5.38, s, 1H, 5.02, q, 2H; 4.08, br s, 1H, 3.67, s, 3H, 3.08, d, 1H, 2.58, d, 1H, 1.80-1.92, m, 1H, 1.60-1.75, m, 3H, 1.32-1.44, m, 3H, 0.83, s, 9H, 0.35-0.45, m, 4H, 0.01, s, 6H.

ISOMER B: $^1$H-NMR (CDCl$_3$) δ 7.286-7.36, m, 5H, 5.56, s, 1H, 5.39, s, 1H, 5.06, q, 2H, 4.15, brs, 1H, 3.71, s, 3H, 3.06, d, 1H, 2.70, d, 1H, 1.60-1.90, m, 4H, 1.33-1.48, m, 3H, 0.87, s, 9H, 0.37-0.51, m, 4H, 0.03, s, 6H. Yield 26% isomer A and 22% isomer B.

Method CC, Step 6.

Compound CC7 was obtained from CC6 (isomer B) through treatment with 1 N TBAF in THF for 30 min followed by extraction with ether/water. The organic phase was separated and washed four times with water. The aqueous phase was pooled and washed once with Et$_2$O (pH ~6 to 7). The organic phase was dried over Na$_2$SO$_4$, filtered and evaporated to give product CC7 in 94% yield. $^1$H-NMR (CDCl$_3$) δ 7.28-7.39, m, 5H, 5.58, brs, 1H, 5.49, brs, 1H, 5.10, d, 1H, 5.02, d, 1H, 4.09, brs, 1H; 3.72, s, 3H, 3.14, d, 1H, 2.70, s, 1H, 1.79-1.87, m, 2H, 1.67-1.79, m, 1H, 1.53-1.67, m, 2H, 1.44-1.53, m, 2H.; 1.31-1.39, m, 1H, 0.35-0.54, m, 4H

Method CD

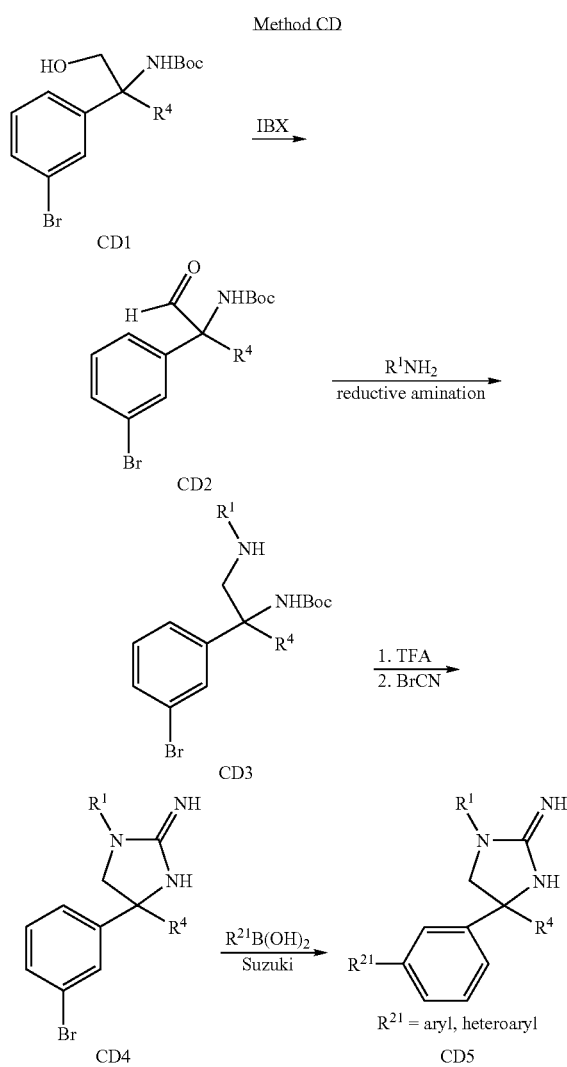

Step 1: tert-Butyl 2-(3-bromophenyl)-1-oxopropan-2-ylcarbamate

To a solution of tert-butyl 2-(3-bromophenyl)-1-hydroxypropan-2-ylcarbamate (CD1; $R^4$=Me) (1.5 g, 4.6 mmol) in EtOAc (150 mL) at reflux was added IBX (3.82 g, 13.6 mmol, 3 eq). Reflux was continued for another 2 h and then the mixture was cooled to RT. The white precipitate was filtered and the filtrate was concentrated. The residue was purified by chromatography on silica gel by eluting with EtOAc/hexanes to give 1.0 g (66%) of tert-butyl 2-(3-bromophenyl)-1-oxopropan-2-yl carbamate (CD2; $R^4$=Me) as a colorless oil. $^1$H NMR (CDCl$_3$) δ 9.42 (s, 1H), 7.69 (m, 1H), 7.60 (m, 1H), 7.55-7.40 (m, 2H), 5.85 (bs, 1H), 1.96 (s, 3H), 1.56 (s, 9H).

Step 2: tert-Butyl 2-(3-bromophenyl)-1-(methylamino)propan-2-ylcarbamate

To a solution of tert-butyl 2-(3-bromophenyl)-1-oxopropan-2-ylcarbamate (CD2; $R^4$=Me) (1.0 g, 3 mmol) in dichloroethane (50 mL) was added methylamine (0.48 g, 6.1 mmol, 2 eq) in water (40%) and 1 mL of AcOH. The solution was allowed to stir at RT for 1 h followed by the addition of sodium triacetoxyborohydride (1.8 g, 8.5 mmol, 2.8 eq). The resulting mixture was stirred at RT for 16 h and quenched with MeOH. After stirring for 30 min the mixture was concentrated in vacuo. The residue was purified by chromatography on silica gel by eluting with EtOAc/MeOH to give 0.62 g (60%) of tert-butyl 2-(3-bromophenyl)-1-(methylamino)propan-2-ylcarbamate (CD3; $R^1$=Me, $R^4$=Me) as a colorless oil. $^1$H NMR (CDCl$_3$) δ 7.47(bs, 1H), 7.37 (m, 1H), 7.27 (m, 1H), 7.23 (m, 1H), 5.97 (bs, 1H), 3.18-2.82 (m, 2H), 2.45 (s, 3H), 1.74 (s, 3H), 1.40 (s, 9H). MS (ESI) m/e 342.9 (M+H)$^+$.

Step 3: 4-(3-Bromophenyl)-1,4-dimethylimidazolidin-2-imine tert-Butyl 2-(3-bromophenyl)-1-(methylamino)propan-2-ylcarbamate (CD3; $R^1$=Me, $R^4$=Me) (0.62 g, 1.8 mmol) was dissolved in 25% TFA in DCM (25 mL) and the mixture was left stirring at RT for 1 h. The mixture was concentrated in vacuo and the residue was redissolved in CHCl$_3$ (20 mL). The solution was washed with 15% NaOH (10 mL) and the aqueous layer was extracted with CHCl$_3$ (3×10 mL). The combined organic layer was dried over MgSO$_4$ and concentrated in vacuo to give 0.33 g (76%) of crude 2-(3-bromophenyl)-$N^1$-methylpropan-1,2-diamine as a colorless oil. $^1$H NMR (CDCl$_3$) δ 7.65(t, J=1.7 Hz, 1H), 7.41-7.34 (m, 2H), 7.21 (t, J=7.8 Hz, 1H), 2.86 (dd, J=11.7, 0.6 Hz, 1H), 2.64 (dd, J=11.7, 0.6 Hz, 1H), 2.38 (s, 3H), 1.54 (bs, 3H), 1.43 (s, 9H). MS (ESI) m/e 242.9 (M+H)$^+$. The compound was used in the next step without further purification.

To a solution of 2-(3-bromophenyl)-$N^1$-methylpropan-1,2-diamine (0.12 g, 0.50 mmol) in EtOH (10 mL) was added BrCN (0.073 g, 0.70 mmol, 1.4 eq). The mixture was stirred at RT for 16 h and then concentrated in vacuo. The residue was redissolved in CHCl$_3$ (20 mL) and the solution was washed with 15% NaOH (10 mL). The aqueous layer was extracted with CHCl$_3$ (3×10 mL) and the combined organic layer was dried (MgSO$_4$), and concentrated to give 0.14 g (100%) of 4-(3-bromophenyl)-1,4-dimethylimidazolidin-2-imine (CD4; $R^1$=Me, $R^4$=Me) as a colorless oil. $^1$H NMR (CDCl$_3$) δ 7.42 (t, J=1.7 Hz, 1H), 7.35 (dd, J=8.1, 1.7 Hz, 2H), 7.15 (t, J=8.1 Hz, 1H), 3.62 (d, J=9.3 Hz, 1H), 3.53 (d, J=9.0 Hz, 1H), 3.08 (s, 3H), 1.56 (bs, 3H). MS (ESI) m/e 268.1, 270.1 (M+H)$^+$.

Step 4: 4-(3-(3,4-Difluorophenyl)phenyl)-1,4-dimethylimidazolidin-2-imine

A mixture of 4-(3-bromophenyl)-4-methyloxazolidin-2-imine (0.027 g, 0.1 mmol, 1 eq), 3,4-difluorophenyl boronic acid (0.020 g, 0.13 mmol, 1.3 eq), FibreCat (20 mg), anhydrous ethanol (2 mL), and a 1N K$_2$CO$_3$ aqueous solution (0.12 mL, 0.12 mmol, 1.2 eq) was heated in a microwave reactor (Emrys Optimizer) at 110° C. for 15 min. The mixture was transferred to a prepacked column of Si-carbonate (2 g, 0.79 mmol/g), which had been conditioned with MeOH/DCM (1:1). The column was eluted with 1:1 MeOH/DCM (3×3 mL) and the eluants were collected and concentrated to give 0.019 g (63%) of 4-(3-(3,4-difluorophenyl)phenyl)-1,4-dimethylimidazolidin-2-imine (CD5; $R^1$=Me, $R^4$=Me, $R^{21}$=3,4-difluorophenyl) as a white solid. $^1$H NMR (CDCl$_3$) δ 7.60 (s, 1H), 7.50-7.20 (m, 6H), 3.48 (m, 2H), 2.79 (s, 3H), 1.66 (s, 3H). MS (ESI) m/e 302.2 (M+H)$^+$, HPLC (A) R$_t$=5.48 min.

Alternative for Method CD for compound: $R^1$=OR$^{15}$

Alternative Method CD, Step 2: tert-Butyl 2-(3-bromophenyl)-1-(methoxyamino)propan-2-ylcarbamate To a solution of tert-butyl 2-(3-bromophenyl)-1-oxopropan-2-ylcarbamate (CD2; $R^4$=Me) (2.7 g, 8.2 mmol) in dichloroethane (40 mL) was added methoxylamine hydrochloride (0.89 g, 10.7 mmol, 1.3 eq) and 1 mL of AcOH. The solution was allowed to stir at RT for 16 h. The reaction mixture was concentrated to give the oxime intermediate. The oxime was dissolved in EtOH (20 mL) and borane-pyridine complex (0.74 g, 7.9 mmol) was added dropwise. After stirring at r.t for 20 min, the reaction mixture was concentrated in vacuo. The residue was redissolved in DCM (50 mL) and washed with water (3×20 mL). The organic layer was dried (Na$_2$SO$_4$) and concentrated to give 1.6 g (54%) of tert-butyl 2-(3-bromophenyl)-1-(methoxyamino)propan-2-ylcarbamate (CD3; R$^1$=OMe, R$^4$=Me). $^1$H NMR (CDCl$_3$) δ 7.60-7.10 (m, 4H), 5.82 (s, 1H), 3.90 (s, 3H), 3.70 (m, 2H) 1.80 (s, 3H), 1.40 (s, 9H). The crude compound was used in the next step without further purification.

Alternative Method CD, Step 3: 4-(3-Bromophenyl)-1-methoxy-4-methylimidazolidin-2-imine tert-Butyl 2-(3-bromophenyl)-1-(methoxyamino)propan-2-yl carbamate (CD3; R$^1$=OMe, R$^4$=Me) (1.6 g, 4.4 mmol) was dissolved in 25% TFA in DCM (25 mL) and the mixture was left stirring at RT for 1 h. The mixture was concentrated in vacuo. The residue was redissolved in CHCl$_3$ (20 mL) and washed with 15% NaOH (10 mL). The aqueous layer was extracted with CHCl$_3$ (3×10 mL). The combined organic layer was dried over MgSO$_4$ and concentrated in vacuo. The residue was dissolved in EtOH (10 mL) and BrCN (0.096 g, 0.91 mmol) was added. After stirring at RT for 16 h, the mixture was concentrated in vacuo. The residue was redissolved in CHCl$_3$ (20 mL) and washed with 15% NaOH (10 mL). The aqueous layer was extracted with CHCl$_3$ (3×10 mL). The combined organic layer was dried over MgSO$_4$ and concentrated to give 0.2 g (16%) of 4-(3-bromophenyl)-1-methoxy-4-methylimidazolidin-2-imine (CD4; R$^1$=OMe, R$^4$=Me) as a colorless oil. $^1$H NMR (CDCl$_3$) δ 7.65-7.35 (m, 4H), 4.02 (s, 3H), 3.98 (d, 1H), 3.91 (d, 1H), 1.94 (s, 3H).

Alternative Method CD, Step 4: 4-(3-(3-Chlorophenyl)phenyl)-1-methoxy-4-methylimidazolidin-2-imine A mixture of 4-(3-bromophenyl)-4-methyloxazolidin-2-imine (CD4; R$^1$=OMe, R$^4$=Me) (0.027 g, 0.1 mmol, 1 eq), 3-chloro phenylboronic acid (0.023 g, 0.13 mmol, 1.3 eq), FibreCat (0.020 g), anhydrous ethanol (2 mL), and 1N K$_2$CO$_3$ aqueous solution (0.12 mL, 0.12 mmol, 1.2 eq) was heated in a microwave reactor (Emrys Optimizer) at 110° C. for 15 min. The mixture was transferred to a prepacked column of Si-carbonate (2 g, 0.79 mmol/g), which had been conditioned with MeOH/DCM (1:1). The column was eluted with 1:1 MeOH/DCM (3×3 mL) and the eluants were collected and concentrated to give 0.008 g (25%) of 4-(3-(3-chlorophenyl)phenyl)-1-methoxy-4-methylimidazolidin-2-imine (CD5; R$^1$=OMe, R$^4$=Me, R$^{21}$=3-ClC$_6$H$_4$) as a white solid. $^1$H NMR (CDCl$_3$) δ 7.75-7.60 (m, 5H), 7.58-7.42 (m, 3H), 4.00 (m, 2H), 3.97 (s, 3H), 1.97 (s, 3H). MS (ESI) m/e 316.0, 318.0 (M+H)$^+$, HPLC (A) R$_t$=5.64 min.

Method CE

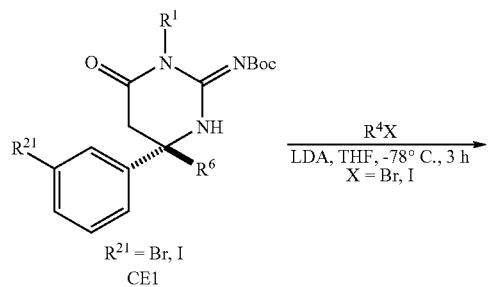

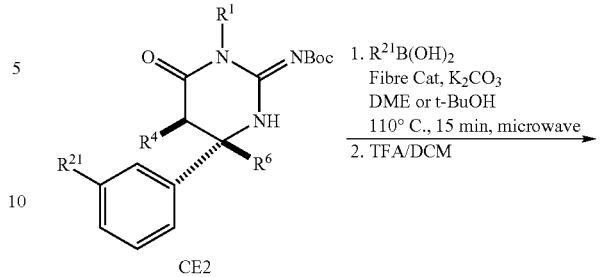

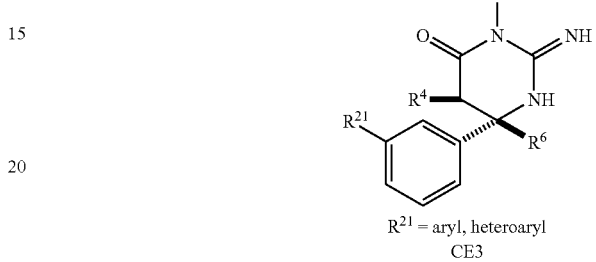

R$^{21}$ = aryl, heteroaryl
CE3

Method CE, Step 1

The synthesis of CE2 (R$^1$=R$^4$=Me, R$^{21}$=Br and R$^4$=Me) was adapted from the procedure of Spanu, P. et. al., Tet. Lett., 2003, 44, 671-675. Thus, to a solution of (S)-tert-butyl 4-(3-bromophenyl)-1,4-dimethyl-6-oxo-tetrahydropyrimidin-2 (1H)-ylidenecarbamate (CE1; R$^1$=R$^6$=Me, R$^{21}$=Br) (0.24 g, 0.6 mmol, 1 eq) in THF (4 mL), LDA (2M in heptane/THF, 0.6 mL, 0.12 mmol, 2 eq) was added dropwise via a syringe at −78° C. After stirring at −78° C. for 30 min, a solution of iodomethane (0.080 mL, 0.12 mmol, 2 eq) in THF (4 mL) was added dropwise to form an orange-colored enolate solution. The mixture was stirred at −78° C. for 3 h. Water was added to quench the reaction and the suspension was warmed to RT. The mixture was then partitioned between H$_2$O and Et$_2$O. The organic layer was separated and the aqueous layer was extracted with Et$_2$O (3×25 mL).

The combined organic layers were washed with brine, dried (MgSO$_4$) and concentrated to give 0.38 g of a brown oil. Chromatography on silica gel using 50% EtOAc/hexanes as eluent gave 0.14 g (54%) of tert-butyl (4S,5R)-4-(3-bromophenyl)-1,4,5-trimethyl-6-oxo-tetrahydropyrimidin-2 (1H)-ylidenecarbamate (CE2; R$^1$=R$^4$=Me, R$^{21}$=Br and R$^6$=Me) as a white solid. $^1$HNMR (CDCl$_3$, 300 MHz): δ 10.16 (s, 1H), 7.46 (m, 2H), 7.26 (m, 2H), 3.21 (s, 1H), 3.01 (m, 3H), 3.02 (m, 1H), 1.51 (s, 12H), 1.17 (d, J=7.1 Hz, 3H). MS (ESI): MH$^+$=441.7 HPLC (A) R$_t$=7.20 min.

Method CE, Step 2

A mixture of (S)-tert-butyl 4-(3-bromophenyl)-1,4-dimethyl-6-oxo-tetrahydropyrimidin-2(1H)-ylidene carbamate (CE2; R$^1$=R$^4$=Me, R$^6$=Me, R$^{21}$=Br) (0.25 g, 0.6 mmol), 5-cyanothien-1-ylboronic acid (0.2 g, 1.3 mmol, 2 eq), Fibrecat (4.26% Pd, 0.7 g), and 1N aq. K$_2$CO$_3$ (0.5 mL) was heated at 110° C. in a 20 mL Smith process vial using the Emrys microwave synthesizer. After cooling, the reaction mixture was transferred to a pre-packed column of Si-Carbonate column and eluted with with MeOH/CH$_2$Cl$_2$ (1:1). The eluent was concentrated to give 0.32 g of a yellow oil, which was purified by silica gel chromatography (20-50% EtOAc/hexanes to give 0.13 g (0.3 mmol, 48% yield, syn:anti ratio: 5:1) of (S)-tert-butyl 4-(3-(5-cyanothien-1-yl)phenyl)-1,4-dimethyl-6-oxotetrahydro-pyrimidin-2(1H)-ylidenecarbamate as a white solid. $^1$HNMR (CDCl$_3$, 300 MHz): δ 10.15 (s, 1H), 7.58-7.53 (m, 3H), 7.53-7.38 (m, 2H), 7.23 (m, 1H), 3.32 (s, 3H), 3.16 (m, 1H), 1.57 (s, 9H), 1.23 (d, J=6.9 Hz, 3H). MS (ESI): MH$^+$=438.7; M$^+$−56=383.1. HPLC R$_t$=7.28 min (syn isomer).

(S)-tert-Butyl 4-(3-(5-cyanothien-1-yl)phenyl)-1,4-dimethyl-6-oxo-tetrahydropyrimidin-2(1H)-ylidenecarbamate (23 mg, 0.05 mmol) was treated with 1 mL of 30% TFA/CH$_2$Cl$_2$ at RT for 30 min. The volatiles were removed in vacuo and the residue was re-dissolved in acetonitrile (5 mL) and evaporated again to afford 17 mg of crude iminopyrimidinone as a yellow solid. The crude product was purified by reverse phase HPLC (B) to provide 10 mg (60%) of (S)-6-(3-(5-cyanothien-1-yl)phenyl)-6-ethyl-2-imino-3-methyl-tetrahydropyrimidin-4(1M-one (CE3; R$^1$=R$^4$=Me, R$^6$=Me, R$^{21}$=5-cyanothien-1-yl) as a white solid. $^1$HNMR (CDCl$_3$, 300 MHz): δ 11.1 (brs, 1H), 10.0 (s, 1H), 7.58-7.53 (m, 3H), 7.44 (m, 1H), 7.40-7.26 (m, 2H), 3.30 (m, 1H), 3.16(s, 3H), 1.60 (s, 3H), 1.27 (d, J=7.2 Hz, 3H). MS (ESI): MH$^+$=438.7; M+−56=339.1. HPLC R$_t$=7.24 min (syn isomer).

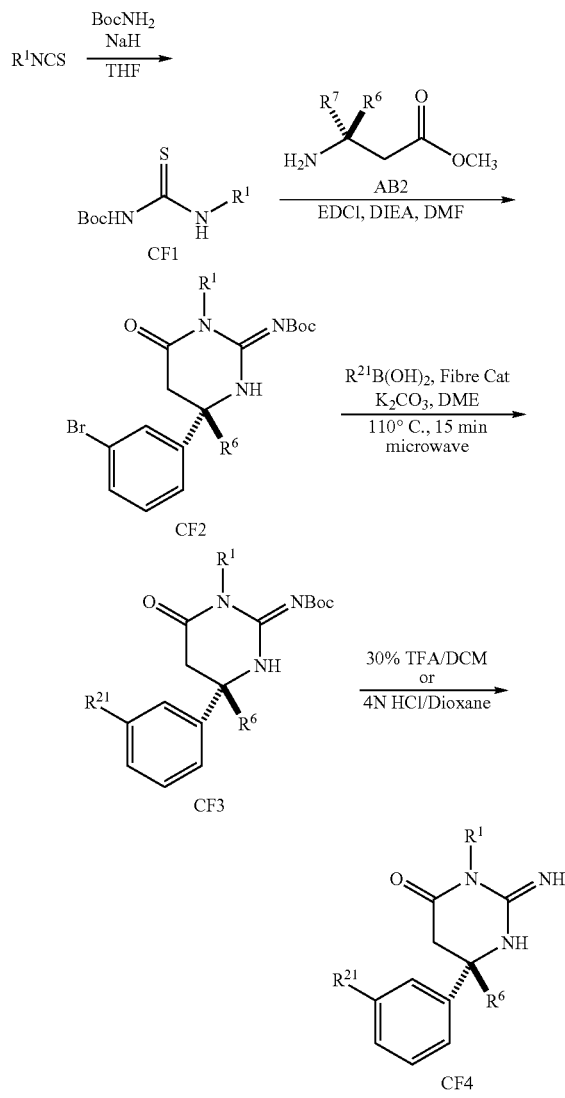

Method CF, Step 1.

To a solution of t-butylcarbamate (0.5 g, 4.3 mmol, 1 eq) in anhydrous THF (5.0 mL) at RT was added NaH (0.17 g, 4.3 mmol, 1 eq). The mixture was stirred at RT for 15 min. Then a solution of methyl isocyanate (0.3 g, 4.2 mmol, 1 eq.) in anhydrous THF (5.0 mL) was added dropwise. The reaction mixture was allowed to stir at 25° C. for 15 min. The mixture was then poured into 30 mL of ice-water under vigorous stirring. The reaction solution was extracted with Et$_2$O (2×25 mL). The organic layers were combined and washed with brine (30 mL), dried (Na$_2$SO$_4$), and concentrated in vacuo to give 0.42 g (50% yield) of tert-butyl methylcarbamothioyl-carbamate CF1 (R$^1$=Me) as a white solid 1 HNMR (CDCl$_3$, 300 MHz): δ 8.3 (br s, 1H), 3.19 (d, 3H, J=4.8 Hz), 1.8 (br s, 1H), 1.5 (s, 9H).

Method CF, Step 2.

To a solution of an HCl salt of AB2 (R$^6$=3-bromophenyl and R$^7$=Me) (0.2 g, 0.7 mmol) and CF1 (R$^1$=Me) in DMF (2 mL) at RT was added DIEA (0.5 mL, 2.8 mmol, 4 eq) and 1-[3-(dimethylamino)propyl]-3-ethylcarbodiimide HCl (EDCI, 0.2 g, 1.0 mmol, 1.4 eq). After stirring at RT for 16 h, the mixture was diluted with EtOAc (10 mL), washed with brine, dried (MgSO$_4$), and filtered. The filtrate was evaporated under reduced pressure to afford 0.34 g of crude product as a yellow oil which was purified using silica gel chromatography by eluting with 20% EtOAc/hexanes to give 0.17 g (0.4 mmol, 60%) of (S)-tert-butyl 4-(3-bromophenyl)-1,4-dimethyl-6-oxo-tetrahydropyrimidin-2(1H)-ylidenecarbamate (CF2; R$^1$=R$^6$=Me) as a white solid.

$^1$HNMR (CDCl$_3$, 300 MHz): δ 10.63 (s, 1H), 7.42 (m, 2H), 7.24 (m, 2H), 3.21 (s, 3H), 3.2 (d, 1H, J=16.3 Hz), 2.87 (d, 1H, J=16.1 Hz), 1.65 (s, 3H), 1.55 (s, 9H). MS (ESI): MH$^+$=395.7, 398.7. HPLC R$_t$=7.11 min.

Method CF, Step 3.

A mixture of (S)-tert-butyl 4-(3-bromophenyl)-1,4-dimethyl-6-oxo-tetrahydropyrimidin-2(1H)-ylidenecarbamate (CF2; R$^1$=R$^6$=Me) (0.25 g, 0.6 mmol), 5-chloro-2-hydroxyphenylboronic acid (R$^{21}$=5-chloro-2-hydroxyphenyl; 0.2 g, 1.2 mmol, 2 eq), Fibrecat (4.26% of Pd, 0.7 g) and 1N aq. K$_2$CO$_3$ (0.5 mL) in dimethoxyethane (DME, 10 mL) or tert-butanol (10 mL) in a 20 mL Smith process vial equipped with stir a bar was sealed and heated in an Emrys optimizer at 110° C. for 15 min. After cooling, the reaction mixture was transferred to a pre-packed Si-Carbonate column and eluted with MeOH/CH$_2$Cl$_2$ (1:1). The eluant was collected and concentrated under reduced pressure to give 0.32 g of the crude product as an oil. The crude product was purified by silica gel chromatography (20-50% EtOAc/hexanes gradient) to yield 0.13 g (0.3 mmol, 48%) of (S)-tert-butyl 4-(3-(3-chloro-6-hydroxyphenyl)-phenyl)-1,4-dimethyl-6-oxo-tetrahydropyrimidin-2(1H)-ylidenecarbamate (CF3; R$^1$=R$^6$=Me, R$^{21}$=3-chloro-6-hydroxyphenyl) as a white solid. $^1$HNMR (CDCl$_3$, 300 MHz): δ 7.48-4.32 (m, 2H), 7.20 (m, 3H), 6.84 (m, 2H), 5.68 (br s, 1H), 3.28 (d, J=15.7 Hz, 1H), 3.21 (s, 3H), 2.96(d, J=15.3 Hz, 1H), 1.68 (s, 3H), 1.53 (s, 9H). MS (ESI): MH$^+$=443.7, 445.7; M$^+$-56=388.0. HPLC Rt (A)=6.99 min.

Method CF, Step 4.

(S)-tert-butyl 4-(3-(3-chloro-6-hydroxyphenyl)phenyl)-1,4-dimethyl-6-oxo-tetrahydropyrimidin-2(1H)-ylidenecarbamate (CF3; R$^1$=R$^6$=Me, R$^{21}$=3-chloro-6-hydroxyphenyl) (23 mg, 0.05 mmol) was treated with 1 mL of 30% TFA/CH$_2$Cl$_2$ at RT for 30 min. The volatiles were removed in vacuo. The residue was redissolved in acetonitrile (5 mL) and evaporated again to afford 17 mg of the crude product as a yellow solid. The crude product was purified via reverse phase HPLC to provide 10 mg (60%) of (S)-6-(3-(3-chloro- 6-hydroxy-phenyl)phenyl)-6-ethyl-2-imino-3-methyl-tetrahydropyrimidin-4(1''-one (CF4; $R^1=R^6=Me$, $R^{21}=3$-chloro-6-hydroxyphenyl) as a white solid. $^1$HNMR (CDCl$_3$, 300 MHz): 611.4 (br s, 1H), 7.6-4.25 (m, 3H), 7.24-6.84 (m, 3H), 3.68 (brs, 1H), 5.18 (brs, 1H), 3.39 (d, J=16.1 Hz, 1H), 3.20 (s, 3H), 2.95(d, J=15.8 Hz, 1H), 1.74 (s, 3H). MS (ESI): MH$^+$=344.1. HPLC (A) R$_t$=5.07 min.

The resulting material was subjected to silica gel chromatography (0%-40% EtOAc/hexanes) to give CG3 ($R^{21}$=Br, $R^{15}=R^{16}$=Pr, 3.62 g, 24%).

Method CG, Step 3;

A mixture of CG3 ($R^{21}$=Br, $R^{15}=R^{16}$=Pr, 3.6 g, 10.5 mmol), HN(Me)SO$_2$Me (1.4 mL, 16.3 mmol), Pd(OAc)$_2$ (355 mg, 1.58 mmol), Xantphos (1.41 g, 2.44 mmol), Cs$_2$CO$_3$

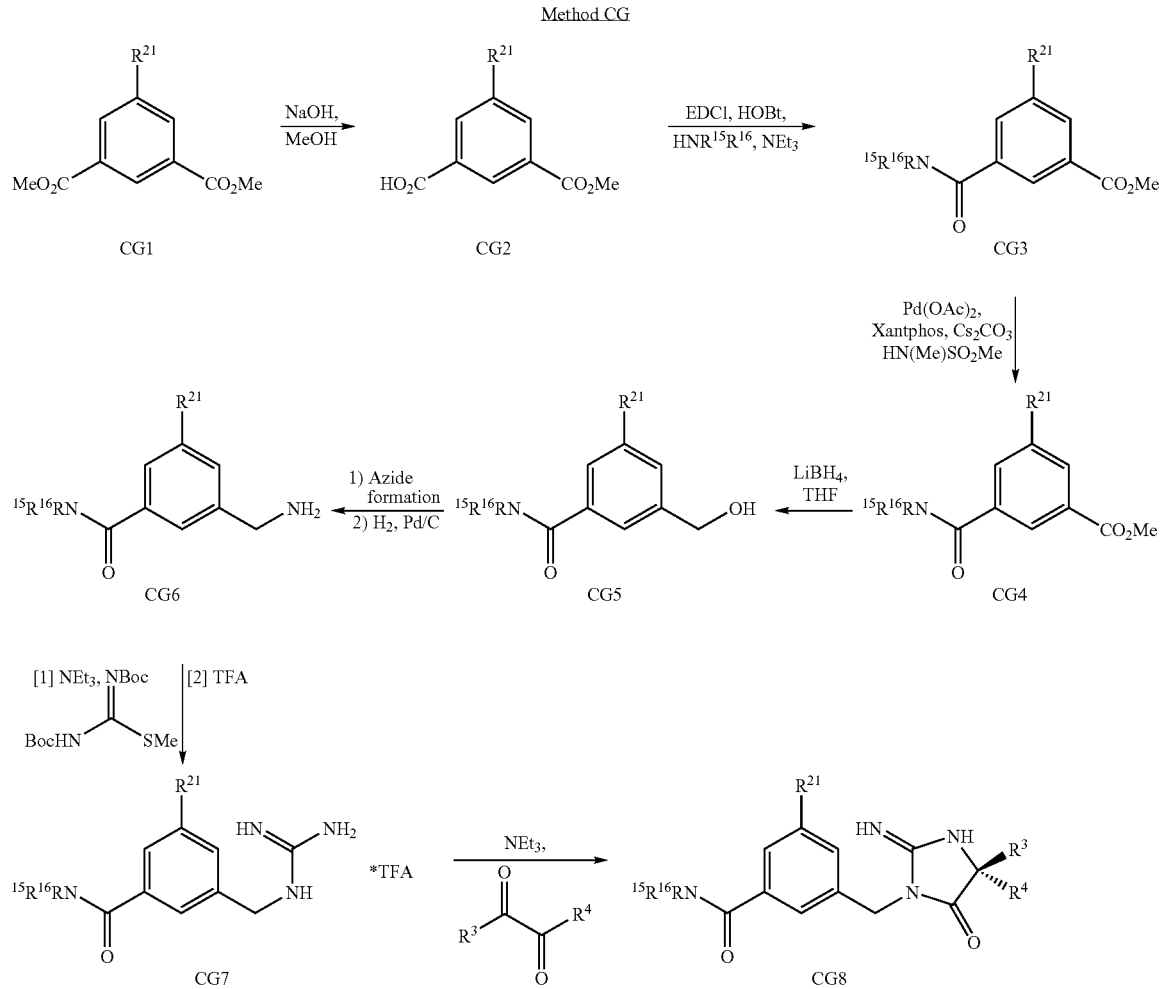

Method CG

Method CG, Step 1;

A solution of CG1 ($R^{21}$=Br, 12.29 g, 45 mmol) and NaOH (1.93 g, 49 mmol) in MeOH (70 mL) and water (10 mL) was refluxed for 3 h. After removal of MeOH under vacuum, the aqueous residue was adjusted to pH 3 and the resulting solid filtered off, dried under vacuum to give CG2 ($R^{21}$=Br, 11.41 g, 98%). $^1$H NMR (400 MHz, CD$_3$OD) δ 8.49 (m, 1 H), 8.27 (m, 1 H), 3.90 (s, 3 H).

Method CG, Step 2;

A mixture of CG2 ($R^{21}$=Br, 11.41 g, 44 mmol), EDCI (8.6 g, 45 mmol), dipropylamine (6.2 mL, 44.8 mmol), HOBt (6.0 g, 44.4 mmol) and NEt$_3$ (10 mL, 72 mmol) in CH$_2$Cl$_2$ (100 mL) was stirred at RT for 48 h. The reaction was washed with sat. NaHCO$_3$, water (1×), NH$_4$Cl (1×), water (1×), brine (1×), dried over MgSO$_4$, filtered and concentrated under vacuum.

(5.17 g, 15.8 mmol) in toluene (40 mL) was degassed under a stream of N$_2$ for 10 min, then heated at 95° C. for 18 h. The reaction was cooled to RT, filtered through celite, and the filtrate partitioned between EtOAc and water. The organic layer was washed with water (1×), brine (1×), dried over MgSO$_4$, filtered, and evaporated under vacuum. The resulting residue was subjected twice to silica gel chromatography (0%→3% MeOH/CH$_2$Cl$_2$) to give CG4 ($R^{21}$=N(Me)SO$_2$Me, $R^{15}=R^{16}$=Pr, 2.65 g, 68%).

Method CG, Step 4;

LiBH$_4$ (2 M THF, 8 mL, 16 mmol) was added to a solution of CG4 ($R^{21}$=N(Me)SO$_2$Me, $R^{15}=R^{16}$=Pr, 2.65 g, 7.15 mmol) in THF (40 mL) at 0° C. After 18 h at RT, the reaction was quenched with 1M HCl and extracted with EtOAc. The organic layer was washed with brine (1×), dried over MgSO$_4$, filtered, and evaporated under vacuum. The resulting residue was subjected to silica gel chromatography (0%) 5% MeOH/CH$_2$Cl$_2$) to give CG5 (R$^{21}$=N(Me)SO$_2$Me, R$^{15}$=R$^{16}$=Pr, 1.77 g, 72%).

Method CG, Step 5;

A mixture of CG5 (R$^{21}$=N(Me)SO$_2$Me, R$^5$=R$^{16}$=Pr, 1.77 g, 5.17 mmol), sodium azide (404 mg, 6.21 mmol), and PPh$_3$ (2.85 g, 10.87 mmol) in CCl$_4$ (5 mL) and DMF (20 mL) was stirred at 90° C. for 5 h, then at RT for 18 h. The reaction was stirred with water (10 mL) for 10 min, then diluted with Et$_2$O. The organic layer was triturated with water, filtered, dried over MgSO$_4$, and evaporated under vacuum. The resulting material was directly used in the next step (azide reduction).

Method CG, Step 6;

The product from method CG, step 5 was dissolved in EtOH (5 mL) and stirred in the presence of 10% Pd/carbon under an atmosphere of hydrogen (50 psi) for 18 h at RT. The reaction mixture was passed through a PTFE-filter, and the filtrate evaporated under reduced pressure. The resulting material was subjected to preparative thin layer chromatography (5% MeOH/CH$_2$Cl$_2$) to give CG6 (R$^{21}$=N(Me)SO$_2$Me, R$^{15}$=R$^{16}$=Pr, 130 mg, 7.5% from CG5).

Method CG, Step 7;

A mixture of CG6 (R$^{21}$=N(Me)SO$_2$Me, R$^{15}$=R$^1$=Pr, 130 mg, 0.38 mmol), 1,3-di(tert-butoxycarbonyl)-2-methyl-isothiourea (110 mg, 0.38 mmol), NEt$_3$ (55 µL, 0.38 mmol) in DMF (1.5 mL) was stirred at RT for 48 h. After removal of the volatiles in vacuo, the resulting material was subjected to preparative thin layer chromatography (5% MeOH/CH$_2$Cl$_2$ as eluent). The resulting intermediate (140 mg, 0.24 mmol) was treated with 50% TFA/CH$_2$Cl$_2$ at RT for 3 h, followed by removal of all volatiles under vacuum to give CG7 (R$^{21}$=N(Me)SO$_2$Me, R$^{15}$=R$^{16}$=Pr, 140 mg, 74% from CG6).

Method CG, Step 8;

A mixture of CG7 (R$^{21}$=N(Me)SO$_2$Me, R$^{15}$=R$^{16}$=Pr, 120 mg, 0.24 mmol), benzil (50 mg, 0.24 mmol) and NEt$_3$ (134 µL, 0.96 mmol) in EtOH (5 mL) was heated at 100° C. for 18 h. After evaporating all volatiles, the residue was partitioned between water and CH$_2$Cl$_2$. The organic layer was washed with brine (1×), dried over MgSO$_4$, filtered and evaporated. The resulting material was subjected to preparative thin layer chromatography (10% MeOH/CH$_2$Cl$_2$ as eluent) to give CG8 (R$^{21}$=N(Me)SO$_2$Me, R$^{15}$=R$^{16}$=Pr, R$^3$=R$^4$=Ph, 69 mg, 50%) as the formate salt. $^1$H NMR (400 MHz, CDCl$_3$) δ 7.10-7.40 (m, 13 H), 4.72 (m, 2 H), 3.34 (m, 2 H), 3.08 (s, 3 H), 3.00 (m, 2 H), 2.60 (s, 3 H), 1.59 (m, 2 H), 1.39 (m, 2 H), 0.92 (m, 3 H), 0.64 (m, 3 H); LCMS: 576.3 (M+H).

Method CH

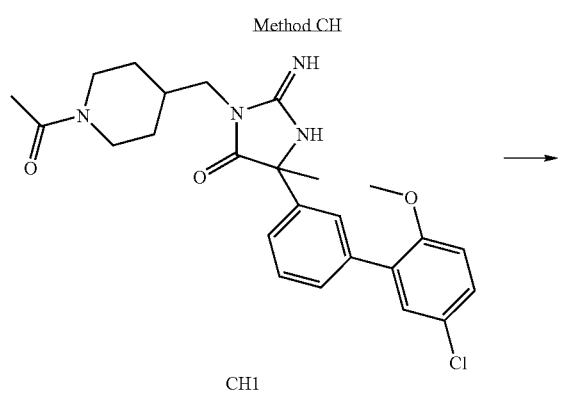

CH1

-continued

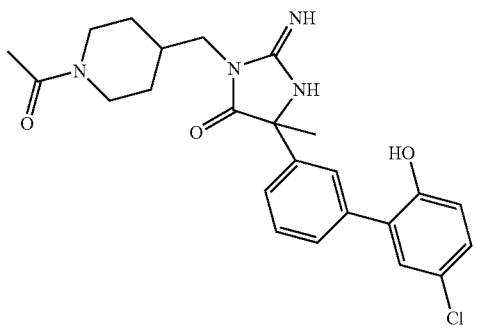

CH2

A solution of 0.35 mL of 1M BBr$_3$ in DCM (0.35 mmole) was added dropwise to a solution of CH1 (52 mg, 0.11 mole) in 1.5 mL anhydrous DCM in ice bath. The reaction solution was stirred in ice bath for 10 min. and 2 hrs at RT. The reaction was quenched with 5 mL MeOH in ice bath. After concentration the crude was purified on C18 reverse phase column to give CH2 (37.3 mg, 67. % yield) as a formate.

Method CI

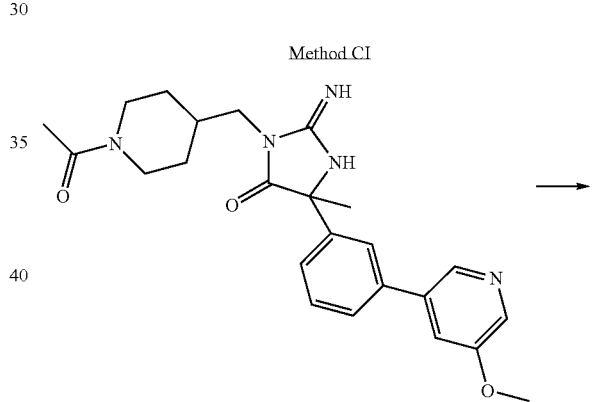

CI1

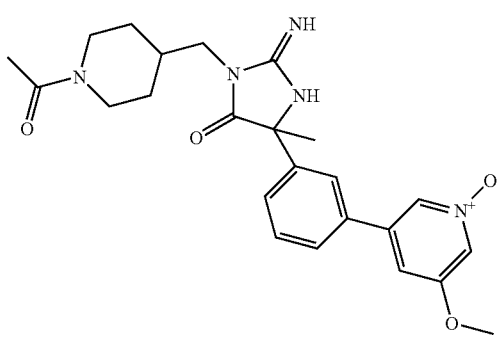

CI2

A solution of CI1 (20 mg as a formate; 0.042 mmole) in 4 mL of DCM was treated with mCPBA (0.42 mmole) at RT for 2 hrs. The crude mixture was purified on C18 reverse phase column to give compound C12.

Method CJ

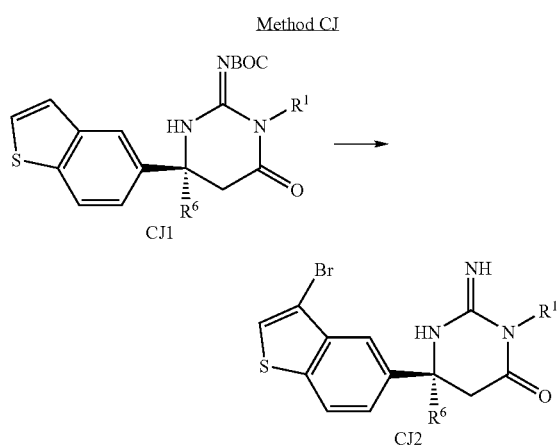

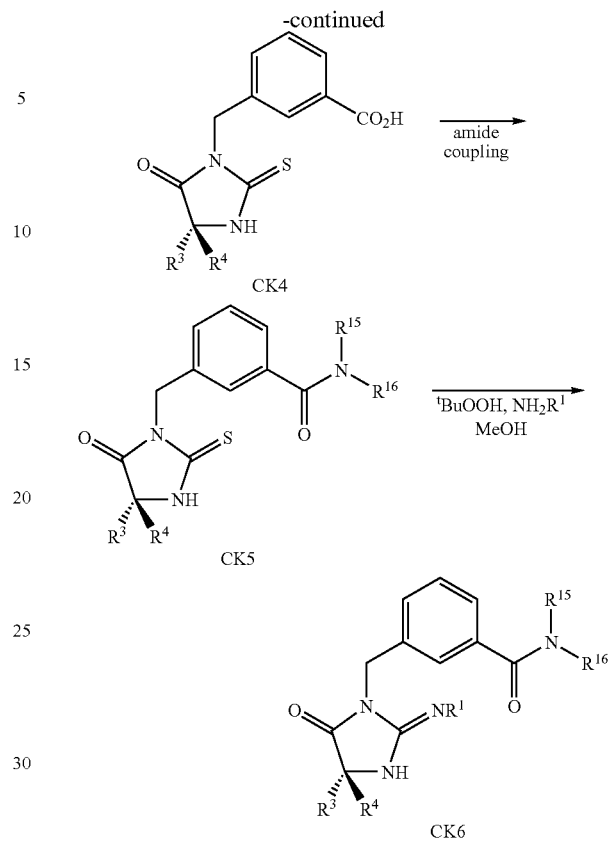

To a solution of CJ1 ($R^1=R^6=Me$; 324 mg, 0.87 mmole) in 2.5 mL $CHCl_3$ and 2.5 mL HOAc in ice bath was added NBS (312 mg, 1.75 mmole) and the reaction mixture was stirred at RT. Upon reaction completion, the crude mixture was diluted with DCM, and washed with saturated aqueous $Na_2S_2O_3$, aqueous $NaHCO_3$ and brine. The crude was purified on flash column to give a product which was treated with 50% TFA in DCM to give CJ2 ($R^1=R^6=Me$ 220 mg, 56. % yield) after evaporation.

Method CK

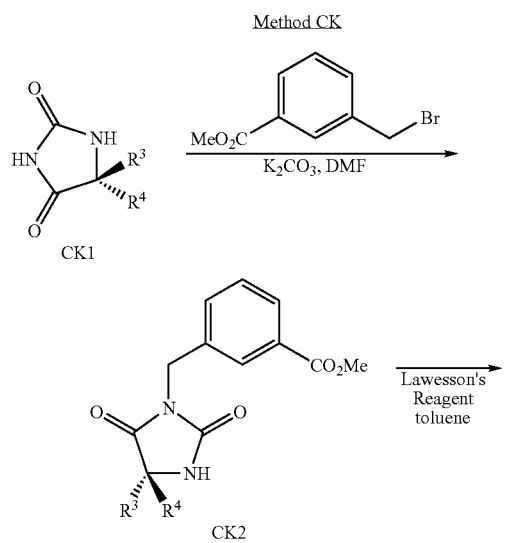

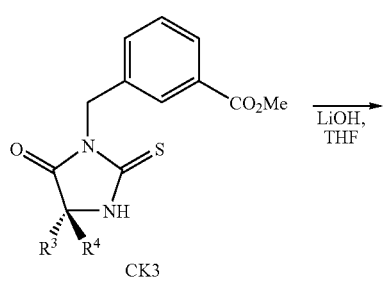

Method CK, Step 1;

Similar to a literature procedure (Moloney et al., *J. Med. Chem.* 1997, 2347-2362), methyl bromomethylbenzoate (7.00 g, 30.5 mmol) was added to a suspension of CK1 ($R^3=R^4=Ph$, 7.00 g, 27.8 mmol) and $K_2CO_3$ (3.85 g, 27.8 mmol) in DMF (50 mL) at RT. After 18 h, the reaction mixture was diluted with water and extracted with $CH_2Cl_2$ (3×). The combined organic layers were washed with $NaHCO_3$ (1×), water (3×), dried over $MgSO_4$, filtered and concentrated under vacuum to give compound CK2 (12.7 g, 100%)

Method CK, Step 2;

Compound CK3 was obtained from CK2 using method BK, step 3.

Method CK, Step 3;

CK3 (1.18 g, 2.83 mmol) in THF (15 mL) and 2 N LiOH (4 mL, 8 mmol) was stirred overnight at RT. The mixture was quenched with 6 N HCl (2 mL, 12 mmol) and then partitioned between water and EtOAc. The dried EtOAc layer was concentrated in vacuo and the residue subjected to reverse-phase HPLC (gradient from 10% 95% $CH_3CN/H_2O$ with 0.1% $HCO_2H$, 30 mL/min flow rate on a preparative C18 reverse-phase column) to afford CK4.

Method CK, Step 4;

Compounds CK5 were obtained from CK4 using method G, step 2.

Method CK, Step 5;

Compounds CK6 were obtained from CK5 using method A, step 3.

813

Method CL

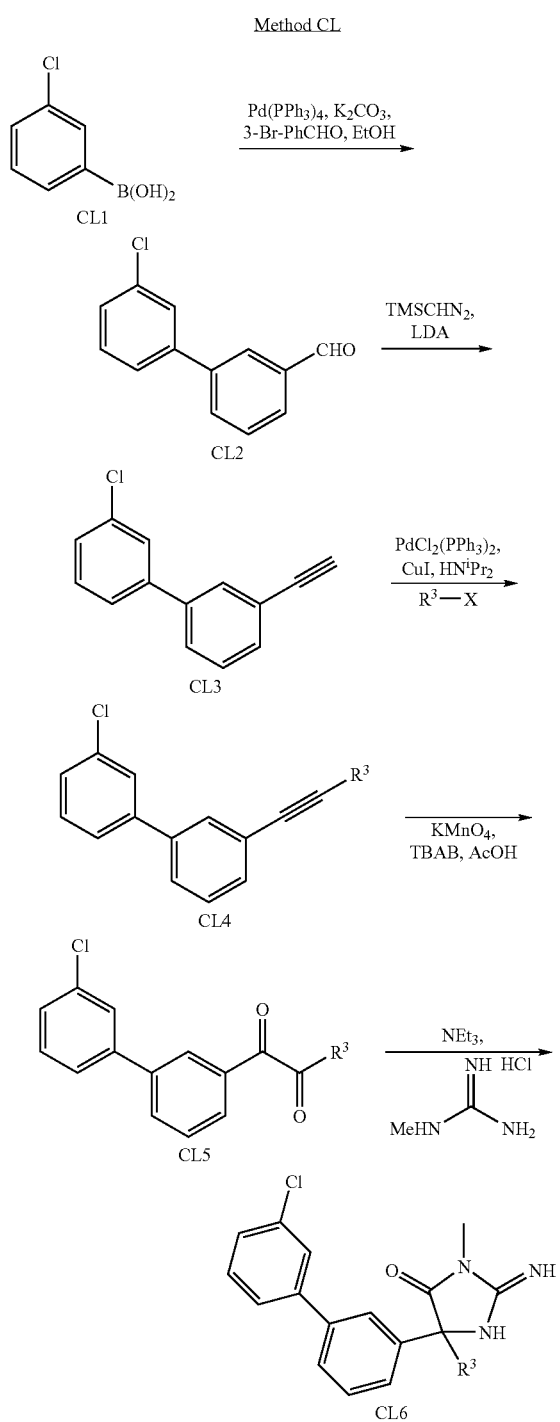

Method CL, Step 1;

CL2 was obtained from CL1 (3-chlorophenyl boronic acid) following method AW.

Method CL, Step 2;

Trimethylsilyldiazomethane (2 M hexanes, 2.5 mL, 5.0 mmol) was added to a solution of LDA (freshly prepared from DIPA and $^n$BuLi) in THF at −78° C. After 30 min at −78° C., a solution of aldehyde CL2 (900 mg, 4.13 mmol) in THF (5 mL) was added and the reaction warmed slowly to RT over 3 h. The reaction was quenched with water, then extracted with Et$_2$O (2×100 mL). The combined organic layers were washed with brine (1×), dried over MgSO$_4$, filtered, and evaporated under vacuum. The resulting material was subjected to silica gel chromatography (100% hexanes) to give CL3 (752 mg, 86%). $^1$H NMR (400 MHz, CDCl$_3$) δ 7.21-7.65 (m, 8 H), 3.08 (s, 1 H).

Method CL, Step 3;

A mixture of CL3 (202 mg, 0.95 mmol), aryl bromide (Ar=3,5-pyrimidinyl, 181 mg, 1.14 mmol), Pd(dba)$_2$ (27 mg. 47.5 μmol), PPh$_3$ (25 mg, 95 μmol), CuI (18 mg, 95 μmol) and DIPA (400 μL, 285 μmol) in DMF (2 mL) was degassed for 10 min under a stream of N$_2$, then heated at 100° C. for 30 min in a Smith Synthesizer microwave. The reaction was cooled to RT, filtered and diluted with EtOAc. The organic layer was washed with water (1×), brine (1×), dried over MgSO$_4$, filtered, and evaporated under vacuum. The resulting material was subjected to silica gel chromatography (0→20% EtOAc/hexanes) to give CL4 (R$^3$=3,5-pyrimidinyl, 220 mg, 80%).

Method CL, Step 4;

A mixture of CL4 (R$^3$=3,5-pyrimidinyl, 210 mg, 0.72 mmol), KMnO$_4$ (297 mg, 1.88 mmol), tetrabutylammonium bromide (TBAB, 55 mg, 0.17 mmol) in AcOH (263 μL) and CH$_2$Cl$_2$ (5 mL) was stirred for 3 h at RT. The reaction mixture was filtered through a plug of silica gel, eluting with MeOH, and the filtrate was concentrated under vacuum. The residue was subjected to preparative thin layer chromatography (5% MeOH/DCM) to give CL5 (R$^3$=3,5-pyrimidinyl, 154 mg, 66%).

Method CL, Step 5;

Diketone CL5 was converted into CL6 as described in Method CG, step 8. LCMS (CL6, R$^3$=3,5-pyrimidinyl): 378.2 (M+H).

Method CM

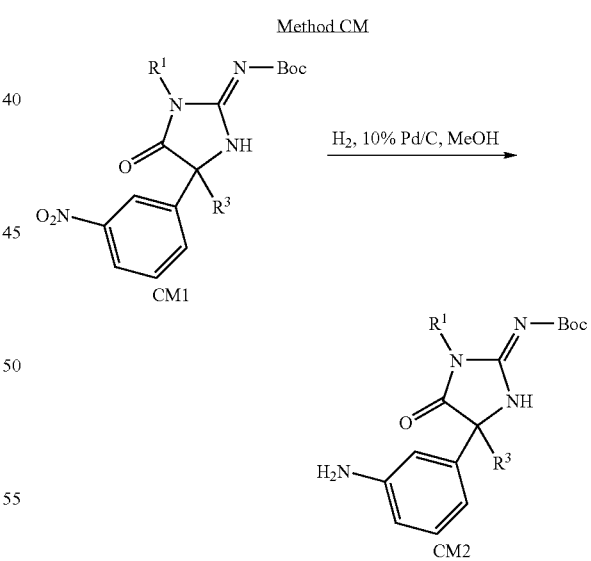

Method CM, Step 1

To a round bottom flask were added CM1 (R$^1$=Me, R$^3$=Ph; 500 mg, 1.22 mmol), methanol (20 mL) and 10% Pd/C (200 mg). The mixture was hydrogenated by a hydrogen balloon for 3 hour 40 min at stirring. After filtration, the concentrated residue was purified by Analogix flash column chromatography (EtOAc/Hexane=0%-50%) to produce CM2 (R$^1$=Me, R$^3$=Ph; 443 mg, 92%) as white solid. Observed MW (M+H)

381.2. (400 MHz, CD$_3$OD): δ=9.13 (s, br, 1H), 7.36-7.26 (m, 5H), 7.09 (m, 1H), 6.68-6.57 (m, 3H), 3.13 (s, 3H), 1.49 (s, 9H).

Method CN

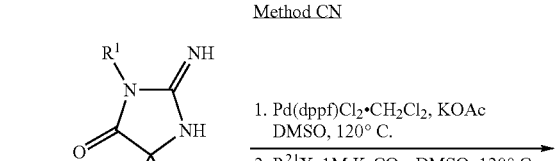

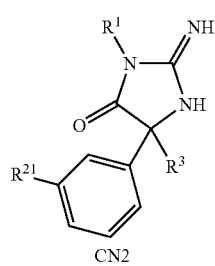

To an Ace pressure tube were added CN1 (R$^3$=phenyl; R$^1$=Me; 100 mg, 0.290 mmol), bis(pinacolato)diboron (81.0 mg, 0.319 mmol), KOAc (85.0 mg, 0.87 mmol), PdCl$_2$(dppf)$_2$·CH$_2$Cl$_2$ (24 mg, 0.029 mmol) and anhydrous DMSO (1.0 mL). The reaction was then heated to 120° C. (oil bath temperature) at stirring for 2 hour 15 min. After cooling down to RT, the reaction were added 3,5-dibromo pyridine (206 mg, 0.87 mmol), anhydrous DMSO (1.0 mL) and 1M aq. K$_2$CO$_3$ (1.45 mL, 1.45 mmol). The reaction was then heated to 120° C. at stirring for 45 min. After cooling down to RT, the reaction was poured to cold water. The aqueous layer was extracted by DCM (3×50 mL) and the combined organic layer was dried over Na$_2$SO$_4$. The concentrated residue was purified first by preparative TLC (7M NH$_3$/MeOH:DCM=1:10) and then preparative HPLC (reverse phase, C-18 column, 0.1% HCOOH/CH$_3$CN: 0.1% HCOOH/H$_2$O=10%-100%) to afford the desired product CN2 (formic acid salt; R$^3$=phenyl; R$^1$=Me; R$^{21}$=3'-(5-bromopyridyl); 53.5 mg, 40%) as a white solid. Observed MW (M+H) 421.1. (400 MHz, CD$_3$OD): δ=8.83-8.50 (m, br. 2H), 8.21 (s, 1H), 7.65 (m, 2H), 7.50 (m, 2H), 7.37 (m, 5H), 3.22 (s, 3H).

Method CO

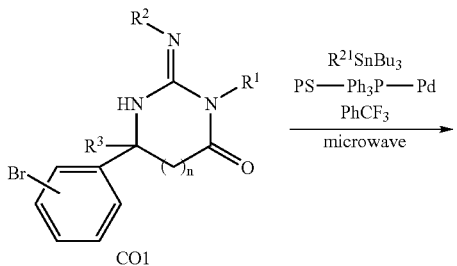

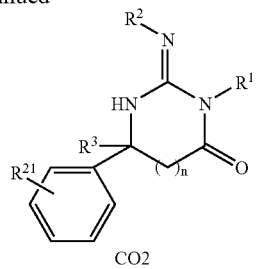

A microwave tube was charged with CO1 (R$^1$=Me, R$^2$=H; R$^3$=cyclopropyl, n=0) (30 mg, 0.097 mmol), PS-Ph$_3$P—Pd (49 mg, 0.12 mmol), and R$^{21}$SnBu$_3$ (R$^{21}$=2-pyrazinyl) (43 mg, 0.12 mmol) as a solution in 1 mL of PhCF$_3$. The tube was sealed, and evacuated and back-filled with N$_2$ (5×). The mixture was then exposed to microwave irradiation (110° C., 30 min). The resulting mixture was filtered with copious MeOH washes. Concentration of the filtrate gave a crude product that was subjected to RP-HPLC to give CO$_2$ (R$^1$=Me, R$^2$=H; R$^3$=c-Pr, n=0, R$^{21}$=2-pyrazinyl) as a formate salt (12 mg, 0.063 mmol, 35%). LCMS R$_t$=3.58 min, m/e=308.2 (M+H).

Method CP

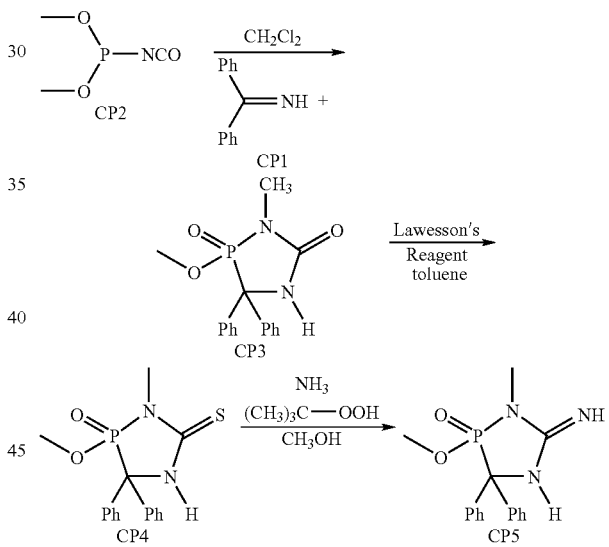

Method CP; Step 1: 1,4,2-Diazaphospholidin-5-one, 2-methoxy-1-methyl-3,3-diphenyl-2-oxide (CP3)

Using methods similar to those described by 1. V. Konovalova et al. (Zhurnal Obshchei Khimii, 50(7), 1653-1654), 1.0 equivalent of phosphorisocyanatidous acid dimethyl ester (CP2), is added to a solution of benzophenone imine (CP1) in toluene and the mixture is warmed to reflux for 4 h. Removal of solvent and purification by flash chromatography provides the title compound (CP3).

Method CP, Step 2: 1,4,2-Diazaphospholidin-5-thione, 2-methoxy-1-methyl-3,3-diphenyl-2-oxide (CP4)

To a solution of CP3 in toluene (or xylene) is added Lawesson's reagent (1.2 equivalents), and the mixture is stirred at reflux for 2 h. The mixture is cooled and poured into cold water. The organic phase is dried (MgSO$_4$) and filtered, and solvent is removed. The crude product is purified by flash chromatography to provide the title compound (CP4).

Method P1, Step 3: 1,4,2-Diazaphospholidin-5-imine, 2-methoxy-1-methyl-3,3-diphenyl-2-oxide (CP5)

Using a route similar to that described in Method A, step 3, CP4 is used to prepare the title compound (CP5).

As a variant of Method CP, benzophenone imine (CP1) is treated with 1.0 equivalent of phosphorisocyanatidous acid dimethyl ester [(CH$_3$O)$_2$P—N=C=S], giving directly CP4, which is coverted to CP5 as described in Method CP, Step 3.

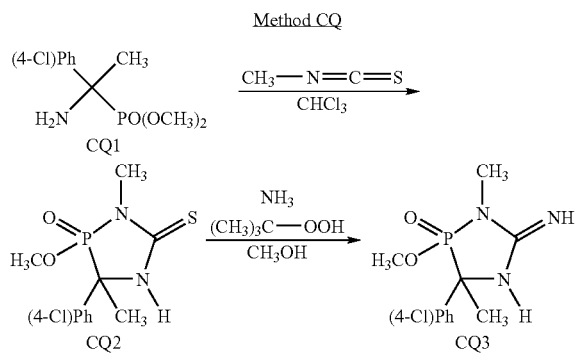

Method CO, Step 1: 1,4,2-Diazaphospholidin-5-thione, 2-methoxy-1-methyl-3-methyl-3-(4-chloro)phenyl-2-oxide (CQ2)

Using an approach similar to that described by R. Merten et al. [(Chem. Ber., 102, 2143 (1969)], methylisothiocyanate (1.2 equivalents) is added to a solution of dimethyl [1-amino-1-(4-chloro)phenyl]ethylphosphonate (CQ1) in chloroform and the mixture is gradually warmed to reflux. After 2 h at reflux, the mixture is cooled and solvent is removed by evaporation. Purification of the crude product by flash chromatography provides the title compound.

Method CQ, Step 2: 1,4,2-Diazaphospholidin-5-imine, 2-methoxy-1-methyl-3-methyl-3-(4-chloro)phenyl-2-oxide (CQ3)

Using a route similar to that described in Method A, step 3, CQ2 is used to prepare the title compound.

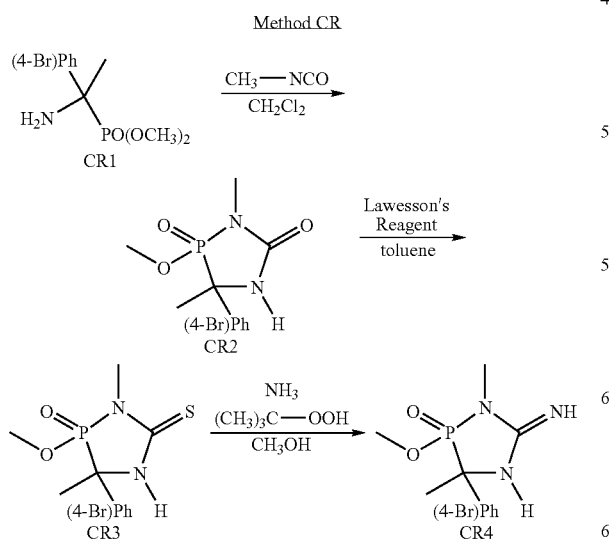

Method CR, Step 1: 1,4,2-Diazaphospholidin-5-one, 2-methoxy-1-methyl-3-methyl-3-(4-bromo)phenyl-2-oxide (CR2)

Using an approach similar to that described by R. Merten et al. [(Chem. Ber., 102, 2143 (1969)], methylisocyanate (1.2 equivalents) is added to a solution of dimethyl [1-amino-1-(4-bromo)phenyl]ethylphosphonate (CR1) in chloroform and the mixture is gradually warmed to reflux. After 2 h at reflux, the mixture is cooled and solvent is removed by evaporation. Purification of the crude product by flash chromatography provides the title compound (CR2).

Method CR, Step 2: 1,4,2-Diazaphospholidin-5-thione, 2-methoxy-1-methyl-3-methyl-3-(4-bromo)phenyl-2-oxide (CR3)

To a solution of CR2 in toluene or xylene is added Lawesson's reagent (1.2 equivalents), and the mixture is stirred at reflux for 2 h. The mixture is cooled and poured into cold water. The organic phase is dried (MgSO$_4$) and filtered, and solvent is removed. The crude product is purified by flash chromatography to provide the title compound.

Method CR, Step 3: 1,4,2-Diazaphospholidin-5-imine, 2-methoxy-1-methyl-3-methyl-3-(4-bromo)phenyl-2-oxide (CR4)

Using a route similar to that described in Method A, step 3, CR3 is used to prepare the title compound.

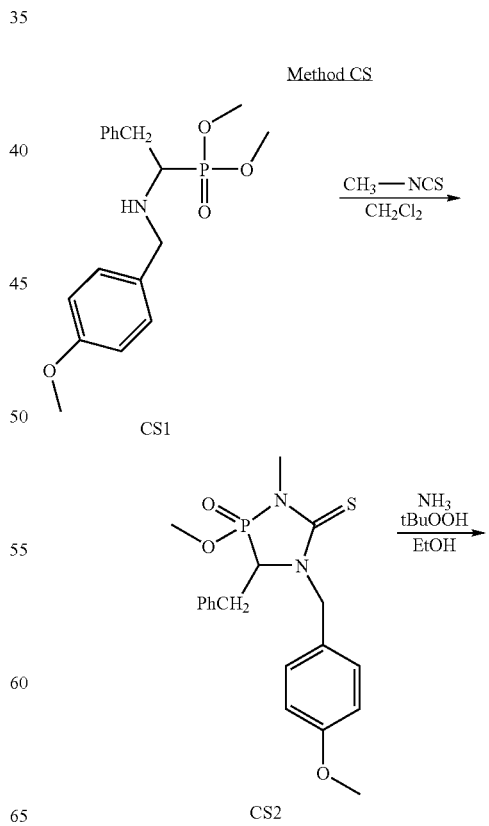

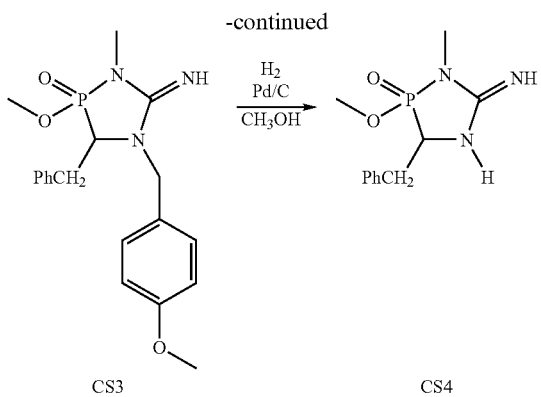

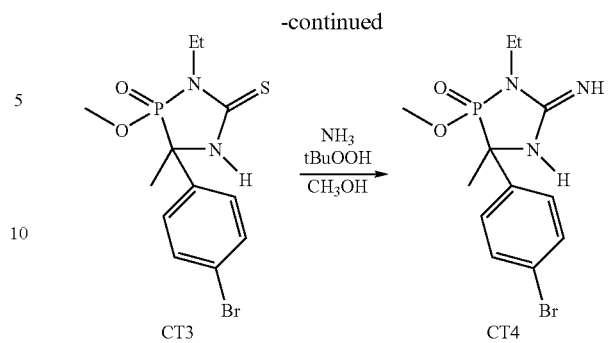

Method CS, Step 1: 1,4,2-Diazaphospholidin-5-thione, 2-methoxy-4-(4-methoxy)phenylmethyl)-1-methyl-3-phenylmethyl-2-oxide (CS2)

Using an approach similar to that described by R. Merten et al. [(Chem. Ber., 102, 2143 (1969)), methylisothiocyanate (1.2 equivalents) is added to a solution of dimethyl [1-(4-methoxy)phenylmethylamino-2-(4-bromo)phenyl]ethylphosphonate (CS1) in chloroform and the mixture is gradually warmed to reflux. After 2 h at reflux, the mixture is cooled and solvent is removed by evaporation. Purification of the crude product by flash chromatography provide the title compound.

Method CS, Step 2: 1,4,2-Diazapholidin-5-imine, 2-methoxy-4-(4-methoxy)phenylmethyl)-1-methyl-3-phenylmethyl-2-oxide (CS3)

Using a route similar to that described in Method A, step 3, CS2 is used to prepare the title compound.

Method CS, Step 3: 1,4,2-Diazaphospholidin-5-imine, 2-methoxy-1-methyl-3-phenylmethyl-2-oxide (CS4)

A solution of CS3 in methanol is hydrogenated at 1 atm in the presence of 5 mol % Pd/C, yielding the title compound after filtration and purification by flash chromatography.

Method CT

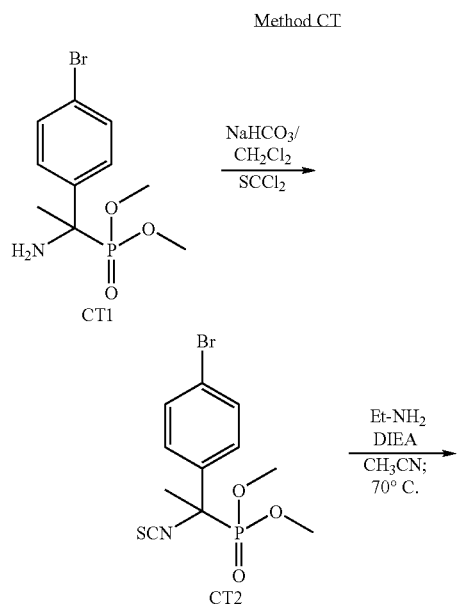

Method CT, Step 1: Dimethyl-[(4-bromophenyl)-1-isothiocyanato]ethylphosphonate

To a mixture of CT1 in DCM and 0.1 N aqueous sodium bicarbonate (1.0 equivalent) is added thiophosgene (1.5 equivalents), and the mixture is stirred for 4 h at RT. Water is added, and the organic phase is dried (MgSO$_4$), filtered and concentrated to give the product CT2 which is used without purification.

Method CT, Step 2: 1,4,2-Diazaphospholidin-5-thione, 2-methoxy-1-ethyl-3-(4-bromo)phenyl-2-oxide (CT3)

To a solution of CT2 in acetonitrile is added ethylamine (2 equivalents) and diisopropylethylamine (2 equivalents) and the solution is slowly warmed to reflux for 2 h. After removal of solvent, the product is purified by flash chromatography to give the title product.

Method CT Step 3: 1,4,2-Diazaphospholidin-5-imine, 2-methoxy-1-ethyl-3-(4-bromo)phenyl-2-oxide (CT4)

Using a route similar to that described in Method A, step 3, CT3 is used to prepare the title compound.

Method CU

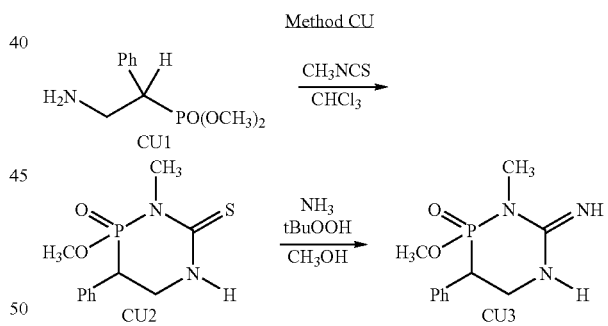

Method CU, Step 1: 1,5,2-Diazaphosphorine-6(1H)-thione, 1-methyl-2-methoxy-3-phenyl-2-oxide (CU2)

Using an approach similar to that described by R. Merten et al. [(Chem. Ber., 102, 2143 (1969)), methylisothiocyanate (1.2 equivalents) is added to a solution of dimethyl (2-amino-1-phenyl)ethylphosphonate (CU1) in chloroform and the mixture is gradually warmed to reflux. After 2 h at reflux, the mixture is cooled and solvent is removed by evaporation. Purification of the crude product by flash chromatography provides the title compound.

Method CU, Step 2: 1,5,2-Diazaphosphorine-6(1H)-imine, 1-methyl-2-methoxy-3-phenyl-2-oxide (CU3)

Using a route similar to that described in Method A, step 3, CU2 is used to prepare the title compound.

Method CV

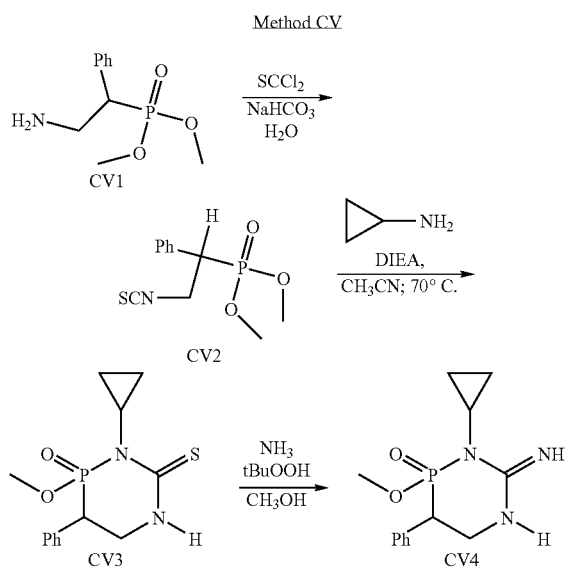

Method CV, Step 1: Dimethyl (2-isothiocyanato-1-phenyl) ethylphosphonate (CV2)

To a mixture of CV1 in methylene chloride and 0.1 N aqueous sodium bicarbonate (1.0 equivalent) is added thiophosgene (1.5 equivalents), and the mixture is stirred for 4 h at RT. Water is added, and the organic phase is dried (MgSO$_4$), filtered and concentrated to give the product which is used without purification.

Method CV, Step 2: 1,5,2-Diazaphosphorine-6(1H)-thione, 1-cyclopropyl-2-methoxy-3-phenyl-2-oxide (CV3)

To a solution of CV2 in acetonitrile is added cyclopropylamine (2 equivalents) and diisopropylethylamine (2 equivalents) and the solution is heated at reflux for 2 h. After removal of solvent, the product is purified by flash chromatography to give the title product.

Method CV Step 3: 1,4,2-Diazaphospholidin-5-imine, 2-methoxy-1-cyclopropyl-3-(4-bromo)phenyl-2-oxide (CV4)

Using a route similar to that described in Method A, step 3, CV3 is used to prepare the title compound.

Method CW

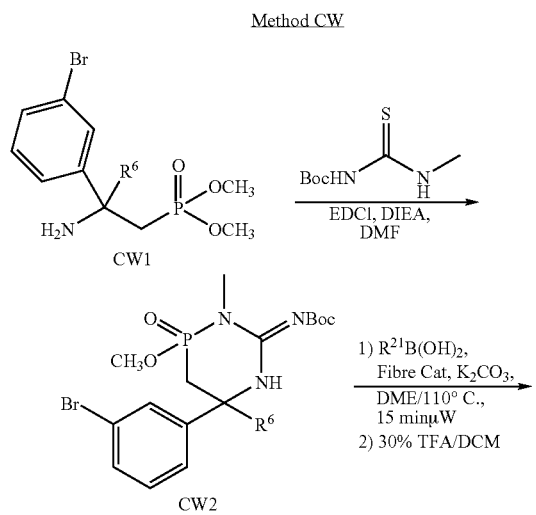

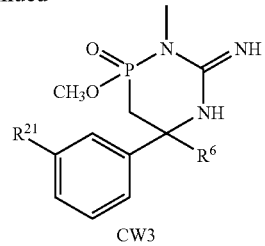

Method CW; Step 1: Boc-1,5,2-diazaphosphorine-5-imine, 2-methoxy-1-methyl-4-(3-arylphenyl)-2-oxides (CW2)

Reaction of tert-butyl methylcarbamothioylcarbamate with CW1 (R$^6$=Me) using EDCI and DIEA in DMF affords CW2 (R$^6$=Me) after purification.

Method CW; Step 2: 1,5,2-Diazaphosphorine-5-imine, 2-methoxy-1-methyl-4-(3-(m-cyanopheny)phenyl)-2-oxides (CW3)

Following the procedure of Sauer, D. R. et al, *Org. Lett.,* 2004, 6, 2793-2796, Suzuki reaction of CW2 (R$^6$=Me) with aryl boronic acids using polymer-support Pd catalysts such as Fibre Cat or PS-PPh3-Pd under microwave heating conditions provides CW3 (R$^6$=Me and R$^{21}$=m-CN-Ph) of the invention after subsequent Boc-deprotection.

Method CX

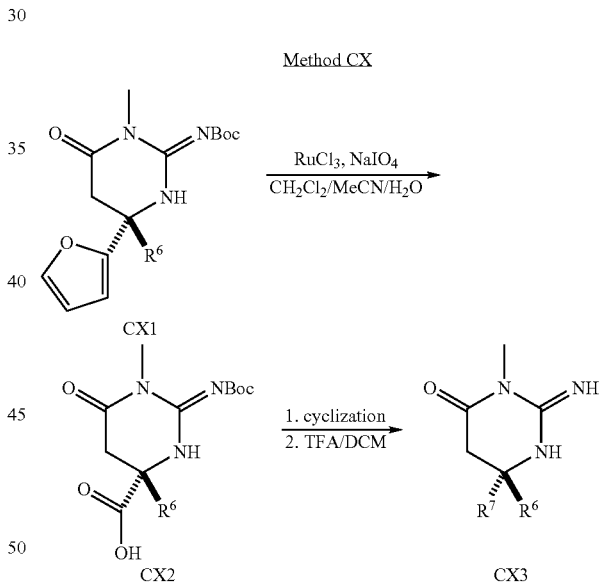

Method CX, Step 1, (S)-2-(tert-Butoxycarbonyl)-1,4-dimethyl-6-oxo-hexahydropyrimidine-4-carboxylic acid To a solution of (S)-tert-butyl 4-(furan-2-yl)-1,4-dimethyl-6-oxo-tetrahydropyrimidin-2(1H)-ylidenecarbamate CX1 (R$^6$=Me) (1.12 g, 3.64 mmol, prepared using Method CF) in DCM (7 mL) was added MeCN (7 mL) and H$_2$O (10.5 mL), followed by RuCl$_3$·H$_2$O (7.6 mg, 0.036 mmol, 1 mol %), and NaIO$_4$ (11.6 g, 54.2 mmol, 15 eq). The mixture was stirred at RT for 2 h. The mixture was diluted with DCM (100 mL) and the organic layer was separated, dried (Na$_2$SO$_4$), and concentrated to give 0.90 g (86%) of (S)-2-(tert-butoxycarbonyl)-1,4-dimethyl-6-oxo-hexahydropyrimidine-4-carboxylic acid CX2 (R$^6$=Me) as a brown solid. $^1$H NMR (CD$_3$OD): δ 3.17 (s, 3H), 3.02 (m, 2H), 1.63 (s, 9H), 1.57 (s, 3H).

Method CX, Step 2, (6S)-2-Imino-3,6-dimethyl-6-(3-(3-(trifluoromethyl)phenyl)-1,2,4-oxadiazol-5-yl)-tetrahydropyrimidin-4(1H)-one (CX3)

To a solution of (S)-2-(tert-butoxycarbonyl)-1,4-dimethyl-6-oxo-hexahydropyrimidine-4-carboxylic acid (CX2, $R^6$=Me, 0.035 g, 0.12 mmol) in DMF (0.24 mL) was added TBTU (0.040 mg, 0.12 mmol, 1 eq), HOBt (0.0035 mg, 0.024 mmol, 0.2 eq), and DIEA (0.107 mL, 0.60 mmol, 5 eq). The mixture was stirred at RT for 10 min and then N'-hydroxy-3-(trifluoromethyl)benzamidine (0.028 mg, 0.13 mmol, 1.1 eq) was added. After stirring for another 2 h, the reaction mixture was diluted with EtOAc (20 mL), washed with $H_2O$ (10 mL) and saturated brine (10 mL), and concentrated in vacuo. The crude residue was dissolved in THF (0.4 mL) and then TBAF (1M in THF, 0.099 mL, 0.9 eq) was added. The mixture was stirred at RT for 2 h. EtOAc (20 mL) was added to the reaction mixture, which was washed with $H_2O$ (10 mL) and saturated brine (10 mL), and concentrated in vacuo. The residue was treated with 30% TFA/DCM (1 mL) at RT for 1. The reaction mixture was concentrated in vacuo and the crude product was purified on reverse phase HPLC (B) to give 0.015 g (26%) of (6S)-2-imino-3,6-dimethyl-6-(3-(3-(trifluoromethyl)phenyl)-1,2,4-oxadiazol-5-yl)-tetrahydropyrimidin-4(1H)-one (CX3; $R^6$=Me, $R^7$=3-(3-(trifluoromethyl)phenyl)-1,2,4-oxadiazol-5-yl)) as a white solid. $^1$H NMR (CD$_3$OD): δ 8.40 (m, 2H), 8.04 (d, 1H, J=6.9 Hz), 7.90 (t, 1H, J=8.1 Hz), 3.81 (m, 2H), 3.39 (s, 3H), 1.82 (s, 3H). MS (ESI): MH$^+$=354.2, HPLC (A) $R_t$=6.234 min.

Method CY

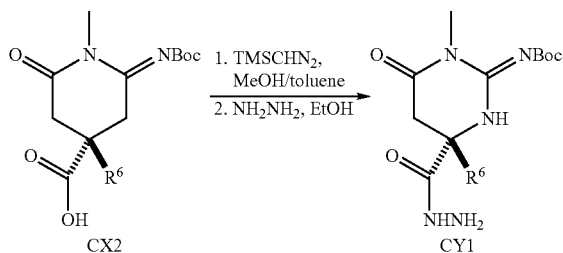

(S)-2-(tert-Butoxycarbonyl)-1,4-dimethyl-6-oxo-hexahydropyrimidine-4-carbohydrazide To a solution of (S)-2-(tert-butoxycarbonyl)-1,4-dimethyl-6-oxo-hexahydropyrimidine-4-carboxylic acid CX2 ($R^6$=Me) (0.357 g, 1.25 mmol) in 1:5 MeOH/toluene (3 mL) was added TMSCHN$_2$ (2M in hexane, 1.9 mL, 3.8 mmol, 3 eq). The mixture was stirred at RT for 2 h. The mixture was concentrated in vacuo to give 0.37 g (100%) of (S)-methyl 2-(tert-butoxycarbonyl)-1,4-dimethyl-6-oxo-hexahydropyrimidine-4-carboxylate as a brown solid. $^1$H NMR (CDCl$_3$): δ 8.80 (s, 1H), 3.70 (s, 3H), 3.14 (s, 1H), 2.79 (s, 2H), 1.53 (s, 9H), 1.50 (s, 3H).

To a solution of (S)-methyl 2-(tert-butoxycarbonyl)-1,4-dimethyl-6-oxo-hexahydropyrimidine-4-carboxylate (0.074 g, 0.25 mmol) in EtOH (0.5 mL) was added NH$_2$NH$_2$ (0.023 mL, 0.75 mmol, 3 eq) and the mixture was stirred at RT for 4 h. The mixture was concentrated in vacuo to give 0.074 g (100%) of (S)-2-(tert-butoxycarbonyl)-1,4-dimethyl-6-oxo-hexahydropyrimidine-4-carbohydrazide (CY1, $R^6$=Me) as a yellow solid. $^1$H NMR (CDCl$_3$) δ 8.95 (s, 1H), 3.11 (s, 3H), 2.28 (m, 2H), 1.50 (s, 9H), 1.47 (s, 3H).

Method CZ

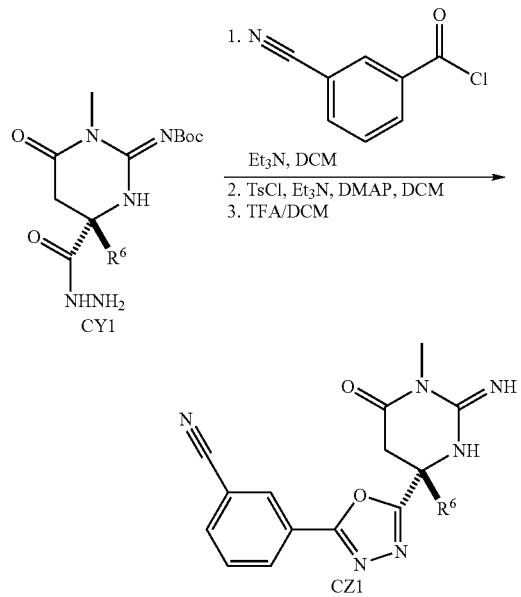

3-(5-((S)-2-Imino-1,4-dimethyl-6-oxo-hexahydropyrimidin-4-yl)-1,3,4-oxadiazol-2-yl)benzonitrile To a solution of (S)-2-(tert-butoxycarbonyl)-1,4-dimethyl-6-oxo-hexahydropyrimidine-4-carbohydrazide (CY1; $R^6$=Me, 0.037 g, 0.12 mmol) in DCM (0.3 mL) at 0° C. was added Et$_3$N (0.035 mL, 0.24 mmol, 2 eq) followed by 3-cyanobenzoyl chloride (0.027 g, 0.16 mmol, 1.3 eq). The mixture was stirred at RT for 6 h. The mixture was diluted with DCM (20 mL), washed with $H_2O$ (10 mL) and saturated brine (10 mL), and concentrated in vacuo. The residue was then treated with TsCl (0.035 g, 0.18 mmol, 1.5 eq), Et$_3$N (0.046 mL, 0.31 mmol, 2.6 eq), and DMAP (0.002 g, 0.016 mmol, 0.13 eq) in DCM (0.25 mL) at RT for 16 h. The mixture was diluted with DCM (20 mL), washed with $H_2O$ (10 mL) and saturated brine (10 mL), and concentrated in vacuo. The residue was treated with 30% TFA/DCM (1 mL) at RT for 1 h. The mixture was concentrated in vacuo and the residue was purified on reverse phase HPLC (B) to give 0.006 g (12%) of 3-(5-((S)-2-imino-1,4-dimethyl-6-oxo-hexahydropyrimidin-4-yl)-1,3,4-oxadiazol-2-yl)benzonitrile as a white solid (CZ1; $R^6$=Me). $^1$HNMR (CD$_3$OD, 300 MHz): δ 8.49 (m, 2H), 8.12 (d, 1H), 7.92 (t, 1H), 3.75 (m, 2H), 3.36 (s, 3H), 1.82 (s, 3H). MS (ESI): MH$^+$=311.2, HPLC (A) $R_t$=4.175 min.

Method DA

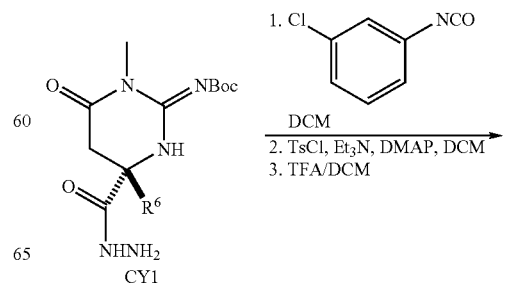

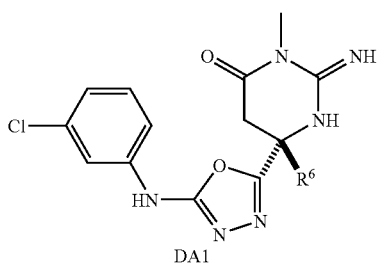

DA1

(S)-6-(5-(3-Chlorophenylamino)-1,3,4-oxadiazol-2-yl)-2-imino-3,6-dimethyl-tetrahydropyrimidin-4(1H)-one To a solution of (S)-2-(tert-butoxycarbonyl)-1,4-dimethyl-6-oxo-hexahydropyrimidine-4-carbohydrazide (CY1, $R^6$=Me, 0.030 g, 0.10 mmol) in DCM (0.25 mL) was added 3-chlorophenylisocyanate (0.015 mL, 0.20 mmol, 2 eq). The mixture was stirred at RT for 3 h and volatiles were then removed in vacuo. The residue was treated with TsCl (0.020 g, 0.10 mmol, 1 eq), Et$_3$N (0.083 mL, 0.60 mmol, 6 eq), and DMAP (0.002 g, 0.016 mmol, 0.16 eq) in DCM (0.25 mL) at RT for 16 h. The mixture was diluted with DCM (20 mL), washed with H$_2$O (10 mL) and saturated brine (10 mL), and concentrated in vacuo. The residue was treated with 30% TFA/DCM (1 mL) at RT for 1 h. The mixture was concentrated in vacuo and the residue was purified on reverse phase HPLC (B) to give 0.006 g (10%) of (S)-6-(5-(3-chlorophenylamino)-1,3,4-oxadiazol-2-yl)-2-imino-3,6-dimethyl-tetrahydropyrimidin-4(1H)-one (DA1; $R^6$=Me). $^1$HNMR (CD$_3$OD, 300 MHz): 67.78 (t, 1H), 7.47 (m, 2H), 7.17 (dt, 1H), 3.53 (m, 2H), 3.36 (s, 3H), 1.78 (s, 3H). MS (ESI): MH$^+$=335.3, HPLC (A) R$_t$=5.710 min.

Method DB

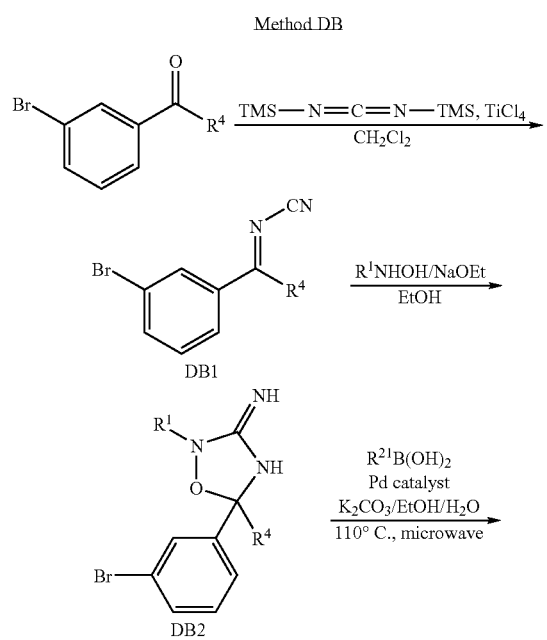

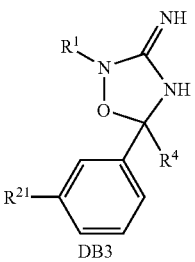

DB3

Method DB, Step 1; (1-(3-Bromophenyl)ethylidene)cyanamide (DB1, $R^4$=Me)

Following the procedure of Cuccia, S. J.; Fleming, L. B.; France, D. J. Synth. Comm. 2002, 32 (19), 3011-3018: 3-Bromoacetophenone (2.0 g, 10 mmol, 1 eq), was dissolved in 20 mL DCM. A 1.0 N solution of titanium tetrachloride in DCM (20 mL, 20 mmol, 2 eq) was added dropwise over 15 min and the resulting mixture was stirred at 25° C. for 1 h. Bis-trimethylsilylcarbodiimide (5.0 mL, 22 mmol, 2.2 eq) in 5 mL of DCM was added over 15 min and the reaction was stirred for 16 h under argon. The reaction was poured onto 200 mL of an ice/water mixture and extracted with 3×200 mL of DCM. The combined organic phase was dried over MgSO$_4$, filtered, and concentrated to give 2.3 g (100%) of (1-(3-bromophenyl)ethylidene)cyanamide (DB1, $R^4$=Me) as a white solid: $^1$H NMR (CDCl$_3$) δ 8.16 (t, J=1.8 Hz, 1H), 7.94 (dd, J=1.7, 1.1 Hz, 1H), 7.76 (dd, J=1.7, 1.1 Hz, 1H), 7.38 (t, J=8.0 Hz, 1H), 2.82 (s, 3H).

Method DB, Step 2; 5-(3-Bromophenyl)-2,5-dimethyl-1,2,4-oxadiazolidin-3-imine (DB2, $R^4$=Me)

To a solution of the HCl salt of methylhydroxylamine (0.19 g, 2.2 mmol, 1 eq) in ethanol (25 mL) at 25° C. was added a 21% solution of NaOEt in ethanol (0.75 mL, 2.0 mmol, 0.9 eq) followed by (1-(3-bromophenyl) ethylidene) cyanamide (0.50 g, 2.2 mmol, 1 eq). After stirring at 25° C. for 10 min, the solvent was removed in vacuo. The residue was redissolved in CH$_2$Cl$_2$ (25 mL), the mixture was filtered, and the solvent was removed in vacuo to give 0.5 g (83%) of 5-(3-bromophenyl)-2,5-dimethyl-1,2,4-oxadiazolidin-3-imine (DB2, $R^1$=Me, $R^4$=Me) as a colorless oil: $^1$H NMR (CDCl$_3$) δ 7.63 (t, J=1.8 Hz, 1H), 7.52. (dd, J=2.0, 1.1 Hz, 1H), 7.38 (dd, J=2.0, 1.1 Hz, 1H), 7.29 (t, J=7.9 Hz, 1H), 3.28 (s, 3H), 1.88 (s, 3H). MS (ESI) m/e 270.0, 272.0 (M$^+$H)$^+$.

Method DB, Step 3; 5-(3-(3-Chlorophenyl)phenyl)-2,5-dimethyl-1,2,4-oxadiazolidin-3-imine To a solution of 5-(3-bromophenyl)-2,5-dimethyl-1,2,4-oxadiazolidin-3-imine (25 mg, 0.093 mmol) and 3-chlorophenyl boronic acid (17 mg, 0.11 mmol) in ethanol (1 mL) was added a 1 M aqueous solution of K$_2$CO$_3$ (0.22 mL, 0.22 mmol) and PS-PPh$_3$-Pd (46 mg, 0.0046 mmol). The sample was heated in an Emrys Optimizer Microwave at 110° C. for 10 min. The resin was filtered off and rinsed alternately three times with CH$_2$Cl$_2$ (5 mL) and CH$_3$OH (5 mL). The combined filtrates were concentrated and the residue was purified by reverse phase prep-HPLC to give 12.3 mg (44%) of 5-(3-(3'-chlorophenyl)-phenyl)-2,5-dimethyl-1,2,4-oxadiazolidin-3-imine (DB3; $R^1$=Me, $R^4$=Me, $R^{21}$=3-chlorophenyl) as a colorless oil: $^1$H NMR (CDCl$_3$) δ 7.69 (s, 1H), 7.58 (m, 2H), 7.49 (m, 3H), 7.37 (m, 2H), 3.29 (s, 3H), 1.94 (s, 3H). MS (ESI) m/e 302.0, 304.0 (M+H)$^+$.

Using a similar procedure, the following compounds were also prepared.

827

5-(3-(3-Methoxyphenyl)phenyl)-2,5-dimethyl-1,2,4-oxadiazolidin-3-imine

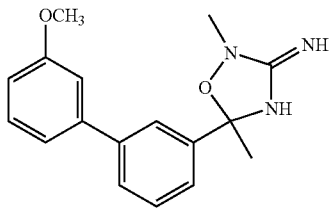

¹H NMR (CDCl₃) δ 7.72 (s, 1H), 7.62 (dt, 1H), 7.49 (m, 2H), 7.38 (t, J=8.2 Hz, 1H), 7.20 (m, 1H), 7.14 (t, 1H), 6.93 (m, 1H), 3.88 (s, 3H), 3.27 (s, 3H), 1.95 (s, 3H). MS m/e 298.1 (M+H)

5-(3-(2,5-Dimethoxyphenyl)phenyl)-2,5-dimethyl-1,2,4-oxadiazolidin-3-imine

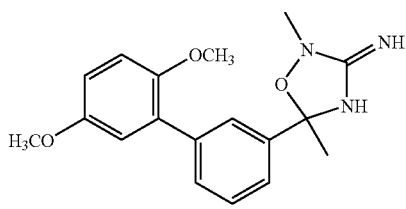

¹H NMR (CDCl₃) δ 7.67 (s, 1H), 7.57 (m, 1H), 7.45 (m, 2H), 6.92 (m, 3H), 3.82 (s, 3H), 3.77 (s, 3H), 3.27 (s, 3H), 1.95 (s, 3H). MS m/e 328.1 (M+H)

5-(3-(3-Fluorophenyl)phenyl)-2,5-dimethyl-1,2,4-oxadiazolidin-3-imine

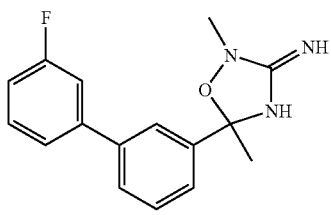

¹H NMR (CDCl₃) δ 7.71 (s, 1H), 7.60 (m, 1H), 7.50 (m, 2H), 7.41 (m, 2H), 7.31 (m, 1H), 7.08 (m, 1H), 3.29 (s, 3H), 1.94 (s, 3H). MS m/e 286.0 (M+H)

828

5-(3-(3-Trifluoromethoxyphenyl)phenyl)-2,5-dimethyl-1,2,4-oxadiazolidin-3-imine

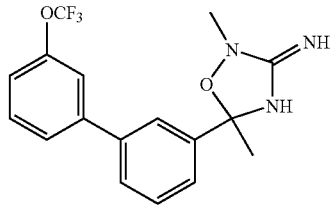

¹H NMR (CDCl₃) δ 7.70 (s, 1H), 7.59 (m, 1H), 7.55 (m, 1H), 7.50 (m, 2H), 7.46-7.48 (m, 2H), 7.26 (m, 1H), 3.29 (s, 3H), 1.95 (s, 3H). MS m/e 352.1 (M+H)

5-(3-(3-Pyridyl)phenyl)-2,5-dimethyl-1,2,4-oxadiazolidin-3-imine

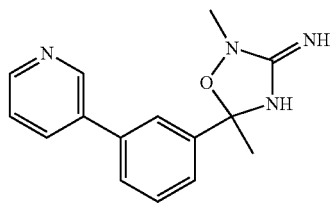

¹H NMR (CD₃OD) δ 9.17 (s, 1H), 8.84 (m, 2H), 8.08 (m, 1H), 7.99 (s, 1H), 7.88 (m, 1H), 7.72 (m, 2H), 3.37 (s, 3H), 2.00 (s, 3H). MS m/e 269.1 (M+H)

5-(3-(3,5-Dichlorophenyl)phenyl)-2,5-dimethyl-1,2,4-oxadiazolidin-3-imine

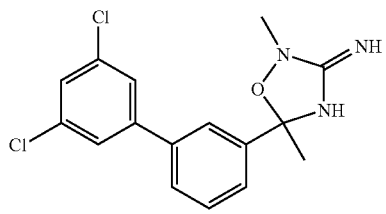

¹H NMR (CDCl₃) δ 7.66 (s, 1H), 7.54 (m, 1H), 7.52 (m, 2H), 7.47 (m, 2H), 7.38 (m, 1H), 3.30 (s, 3H), 1.94 (s, 3H). MS m/e 336.1 (M+H)

5-(3-(2-Chlorophenyl)phenyl)-2,5-dimethyl-1,2,4-oxadiazolidin-3-imine

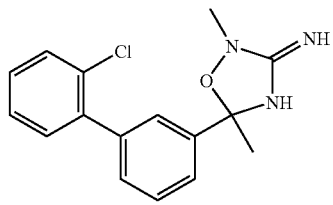

¹H NMR (CDCl₃) δ 7.59 (m, 1H), 7.50 (m, 4H), 7.34 (m, 3H), 3.28 (s, 3H), 1.95 (s, 3H). MS m/e 302.1 (M+H)

5-(3-(3-Chloro-4-fluorophenyl)phenyl)-2,5-dimethyl-1,2,4-oxadiazolidin-3-imine

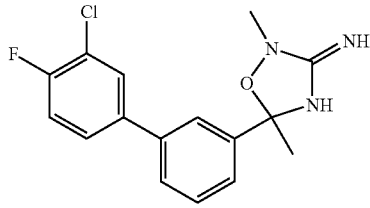

$^1$H NMR (CDCl$_3$) δ 7.65 (m, 2H), 7.48-7.54 (m, 4H), 7.22 (m, 1H), 3.30 (s, 3H), 1.94 (s, 3H). MS m/e 320.1 (M+H)

$^1$H NMR (CD$_3$OD) δ 7.64 (s, 1H), 7.45 (t, J=9.7 Hz, 2H), 7.26 (t, J=7.6 Hz, 1H), 1.68 (s, 3H).

Method DC, Step 2, 2-Amino-2-(3-bromophenyl)propanoic acid 5-(3-Bromophenyl)-5-methylimidazolidine-2,4-dione (DC1; R$^6$=Me) (1.5 g, 5.6 mmol) was dissolved in 15 mL of 1N KOH, heated to 185° C. in a microwave reactor (Emrys Optimizer) for 2 h. Afterward, the mixture was carefully acidified using conc. HCl to pH ~2. The mixture was extracted once with Et$_2$O (20 mL). The aqueous layer was concentrated in vacuo to give 1.6 g (100%) of 2-amino-2-(3-bromophenyl)-2-propanoic acid (DC2; R$^6$=Me) as an off white solid. $^1$H NMR (CD$_3$OD) δ 7.75 (t, J=2.0, 1H), 7.66 (m, 1H), 7.56 (m, 1H), 7.45 (t, J=8.1 Hz, 1H), 1.99 (s, 3H).

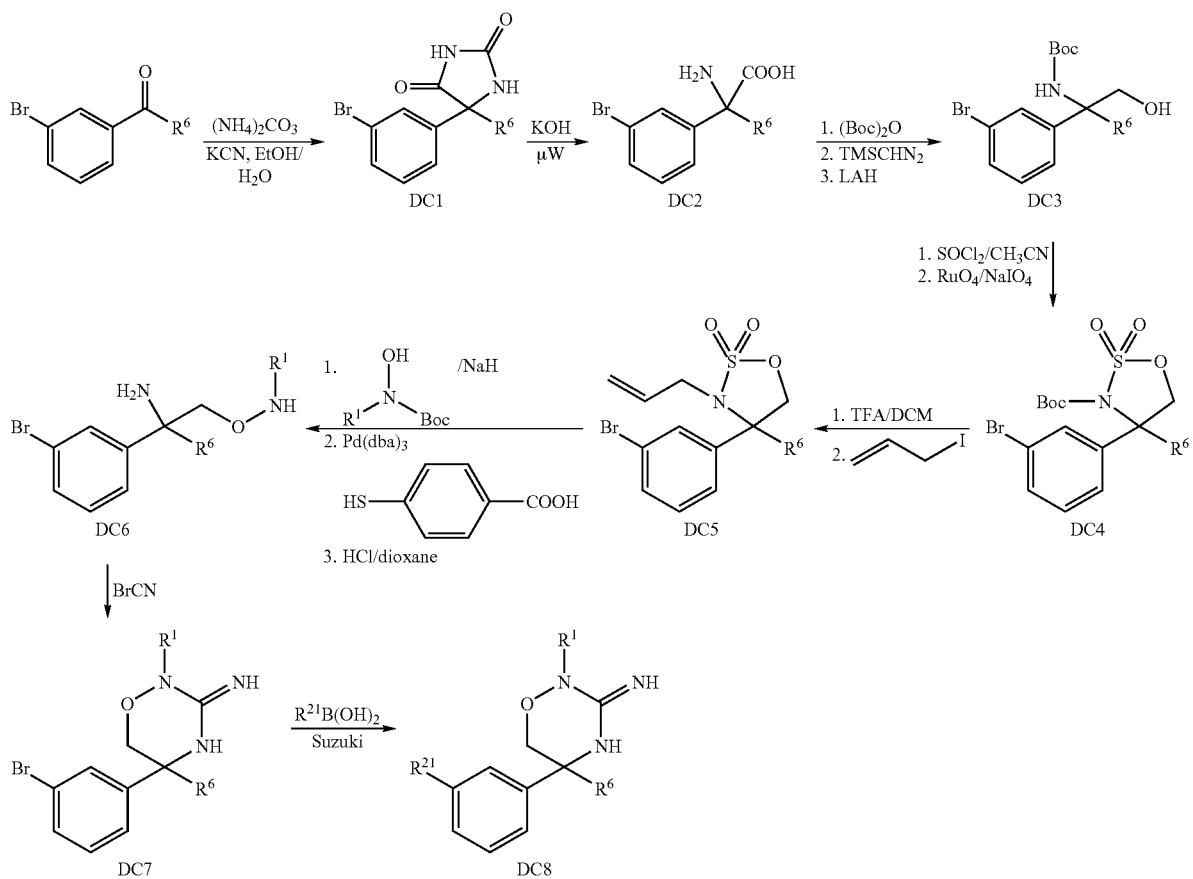

Method DC, Step 1, 5-(3-Bromophenyl)-5-methylimidazolidine-2,4-dione

A mixture of 3-bromoacetophenone (10 g, 50 mmol), KCN (8.16 g, 130 mmol, 2.5 eq) and (NH$_4$)$_2$CO$_3$ (21.7 g, 225 mmol, 4.5 eq) in EtOH/H$_2$O (1:1, 110 mL) was heated at 60° C. for 16 h. The reaction mixture was cooled to 0° C. The resulting precipitate was filtered, washed with water, hexane, and then dried to give 12.6 g (93%) of 5-(3-bromophenyl)-5-methylimidazolidine-2,4-dione as an off-white solid (DC1; R$^6$=Me).

Method DC, Step 3, 2-(3-Bromophenyl)-2-(tert-butoxycarbonyl)propanoic acid

To a solution of 2-amino-2-(3-bromophenyl)-propanoic acid (DC2; R$^6$=Me) (10.5 g, 43 mmol) in 1N KOH (105 mL) and dioxane (70 mL) at 0° C. was added (Boc)$_2$O (20.6 g, 95 mmol, 2.2 eq). The mixture was stirred at RT for 16 h. The reaction mixture was concentrated to 100 mL. EtOAc (100 mL) was added and the mixture was cooled to 0° C. After acidifying with 2N KHSO$_4$ to pH 2-3, the aqueous layer was extracted with EtOAc (3×50 mL). The combined EtOAc layer was washed with H$_2$O (2×50 mL), dried (Na$_2$SO$_4$), and concentrated to give 11.7 g (79%) of 2-(3-bromophenyl)-2-(tert-butoxycarbonyl) propanoic acid as a white solid. $^1$H NMR (CDCl$_3$) δ 7.61 (s, 1H), 7.41 (m, 2H), 7.24 (m, 1H), 1.98 (s, 3H), 1.44 (s, 9H).

To a solution of 2-(3-bromophenyl)-2-(tert-butoxycarbonyl) propanoic acid (11.3 g, 32.8 mmol) in MeOH (35 mL) was added toluene (175 mL) followed by TMSCHN$_2$ (2M in hexane, 44 mL, 98 mmol, 3 eq). The mixture was stirred at RT for 16 h. Solvents were evaporated and the residue was chromatographed on silica by eluting with EtOAc/hexanes to give 11.8 g (100%) of methyl 2-(3-bromophenyl)-2-(tert-butoxycarbonyl)propanoate as a yellow oil. $^1$H NMR (CDCl$_3$) δ 7.59 (t, J=1.8 Hz, 1H), 7.36-7.44 (m, 2H), 7.21 (t, J=8.0 Hz, 1H), 5.92 (s, 1H), 3.70 (s, 3H), 1.97 (s, 3H), 1.36 (br s, 9H).

To a solution of methyl 2-(3-bromophenyl)-2-(tert-butoxycarbonyl) propanoate (11.8 g, 33 mmol) in THF (150 mL) at −78° C. was added LAH powder (3.1 g, 82.0 mmol, 2.5 eq). The mixture was stirred at −78° C. and allowed to warm to RT over 16 h. The mixture was cooled to 0° C. and the reaction was quenched by slowly adding 3 mL of H$_2$O. The mixture was diluted with DCM (500 mL) followed by the addition of 1N NaOH (6 mL) and H$_2$O (9 mL). After stirring at 0° C. for 30 min, the mixture was filtered and the filtrate was concentrated to give 10 g (95%) of tert-butyl 2-(3-bromophenyl)-1-hydroxypropan-2-ylcarbamate (DC3; R$^6$=Me) as a colorless oil. $^1$H NMR (CDCl$_3$) δ 7.49 (t, J=1.8 Hz, 1H), 7.35-7.39 (m, 1H), 7.27-7.30 (m, 1H), 7.21 (t, J=7.8 Hz, 1H), 3.72 (m, 2H), 1.57 (s, 3H), 1.41 (br s, 9H).

Method DC, Step 4; 3-(tert-Butoxycarbonyl)-4-(3-bromophenyl)-4-methyl-[1,2,3]-oxathiazolidine-2,2-dioxide To a solution of SOCl$_2$ (5.7 mL, 2.5 eq) in dry CH$_3$CN (37 mL) under argon was cooled to −40° C. was added tert-butyl 2-(3-bromophenyl)-1-hydroxypropan-2-ylcarbamate (DC3; R$^4$=Me) (10.3 g, 31 mmol) in dry CH$_3$CN (27 mL) was added dropwise, followed by the addition of dry pyridine (12.4 mL, 160 mmol, 5 eq). The mixture was then allowed to warm to RT in 1 h. The mixture was concentrated to about 30 mL. EtOAc (30 mL) was added and the precipitate was filtered off. The filtrate was concentrated in vacuo to give 10.4 g (89%) of 3-(tert-butoxycarbonyl)-4-(3-bromophenyl)-4-methyl-[1,2,3]-oxathiazolidine-2-oxide as a colorless oil. $^1$H NMR (CDCl$_3$) δ 7.64 (t, J=2.0 Hz, 1H), 7.36-7.53 (m, 2H), 7.24 (m, 1H), 4.52 (q, J=9.5 Hz, 2H), 1.86 (s, 3H), 1.42 (br s, 9H).

To a solution of 3-(tert-butoxycarbonyl)-4-(3-bromophenyl)-4-methyl-[1,2,3]-oxathiazolidine-2-oxide (10.4 g, 28 mmol) in CH$_3$CN (50 mL) at 0° C. was added RuO$_4$ (0.5% in stabilized aq., 50 mg, 0.1% by weight) in H$_2$O (10 mL) amd NaIO$_4$ (8.9 g, 41.5 mmol, 1.5 eq) in H$_2$O (35 mL). The mixture was stirred at RT for 2 h. The mixture was partitioned between Et$_2$O (200 mL) and H$_2$O (50 mL). The organic layer was separated and the aqueous layer was extracted with Et$_2$O (3×50 mL). The combined organic layer was dried (Na$_2$SO$_4$), and concentrated to give 10.8 g (100%) of 3-(tert-butoxycarbonyl)-4-(3-bromophenyl)-4-methyl-[1,2,3]-oxathiazolidine-2,2-dioxide (DC4; R$^6$=Me) as a white solid (~10.8 g, yield: 100%). $^1$H NMR (CDCl$_3$) S 7.56 (t, J=1.8 Hz, 1H), 7.48-7.52 (m, 1H), 7.38-7.44 (m, 1H), 7.30 (t, J=8.0 Hz, 1H), 4.41 (dd, J1=9.3 Hz, J2=20.4 Hz, 2H), 2.01 (s, 3H), 1.39 (s, 9H).

Method DC, Step 5; 3-Allyl-4-(3-bromophenyl)-4-methyl-[1,2,3]-oxathiazolidine-2,2-dioxide 3-(tert-Butoxycarbonyl)-4-(3-bromophenyl)-4-methyl-[1,2,3]-oxathiazolidine-2,2-dioxide (DC4; R$^6$=Me) (10.8 g, 28 mmol) was dissolved in 25% TFA in DCM (40 mL, 5 eq) and the mixture was left standing at RT for 3 h. The mixture was concentrated in vacuo to give 7.3 g (91%) of 4-(3-bromophenyl)-4-methyl-[1,2,3]-oxathiazolidine-2,2-dioxide as a yellow oil. $^1$H NMR (CDCl$_3$) δ 7.59 (t, J=1.8 Hz, 1H), 7.48-7.52 (m, 1H), 7.39-7.42 (m, 1H), 7.30 (t, J=8.1 Hz, 1H), 4.59 (m, 2H), 1.82 (s, 3H).

To a solution of 4-(3-bromophenyl)-4-methyl-[1,2,3]-oxathiazolidine-2,2-dioxide (7.3 g, 25 mmol) in DCM (77 mL) was added allyl iodide (9.1 mL, 100 mmol, 4 eq), followed by BnBu$_3$NCl (0.39 g, 1.3 mmol) and 40% NaOH (28 mL). The mixture was stirred at RT for 16 h. The organic layer was separated and the solvent was evaporated. Silica gel chromatography using 5-20% EtOAc/hexanes gave 8.3 g (100%) of 3-allyl-4-(3-bromophenyl)-4-methyl-[1,2,3]-oxathiazolidine-2,2-dioxide (DC5; R$^6$=Me) as a colorless oil. $^1$H NMR (CDCl$_3$) δ 7.64 (t, J=1.8 Hz, 1H), 7.46-7.54 (m, 2H), 7.31 (t, J=8.0 Hz, 1H), 5.77-5.89 (m, 1H), 5.19-5.33 (m, 2H), 4.38 (dd, J1=8.7 Hz, J2=23.7 Hz, 2H), 3.46-3.68 (m, 2H), 1.83 (s, 3H).

Method DC, Step 6; N-(2-(3-bromophenyl)-2-amino) prop-1-oxy)-methylamine

To a suspension of NaH (60%, 0.14 g, 1.5 eq) in 0.5 mL of anhydrous DMF was added tert-butyl hydroxy(methyl)carbamate (0.52 g, 1.5 eq) in 1.5 mL of DMF. After stirring at RT for 15 min, a solution of 3-allyl-4-(3-bromophenyl)-4-methyl-[1,2,3]-oxathiazolidine-2,2-dioxide (DC5; R$^6$=Me) (0.78 g, 2.3 mmol) in 6 mL of anhydrous DMF was added dropwise. The mixture was stirred at RT for 16 h. The mixture was partitioned between EtOAc (10 mL) and 1N HCl (3 mL). The organic layer was separated and the aqueous layer was extracted with EtOAc (3×5 mL). The combined organic layer was dried over Na$_2$SO$_4$ and concentrated to give 0.45 g (41%) of a product which was used without purification.

To a solution of the above product (3.86 g, 8.1 mmol) in THF (30 mL) was added a pre-stirred (15 min) mixture of Pd$_2$(dba)$_3$ (0.51 g, 0.41 mmol) and 1,4-bis(diphenylphosphio)butane (0.25 g, 0.41 mmol) in THF (5 mL), followed by thiosalicyliacid (2.2 g, 1.2 eq). The mixture was stirred at RT for 16 h. Solvent was evaporated and the residue was chromatographed on silica by eluting with 50% EtOAc/hexanes to give 1.3 g (37%) product as a oil which was dissolved in 4M HCl/dioxane (11 mL) and the mixture was stirred at RT for 2 h. Solvent was evaporated in vacuo and the residue was diluted with CHCl$_3$ (10 mL) followed by treatment with 1N NaOH tol pH ~12. The organic layer was separated and the aqueous layer was extracted with CHCl$_3$ (3×10 mL). The combined organic layer was dried (Na$_2$SO$_4$) and concentrated to give 0.56 g (76%) of N-(2-(3-bromophenyl)-2-amino)prop-1-oxy)-methylamine (DC6; R$^6$=Me, R$^1$=Me) as a colorless oil. $^1$H NMR (CDCl$_3$) δ 7.74 (t, J=1.8 Hz, 1H), 7.41-7.50 (m, 2H), 7.26 (t, J=8.0 Hz, 1H), 3.85 (dd, J1=9.6 Hz, J2=28.8 Hz, 2H), 2.72 (s, 3H), 1.48 (s, 3H).

Method DC, Step 7; 5-(3-Bromophenyl)-2,5-dimethyl-1,2,4-oxadiazinan-3-imine

To a solution of N-(2-(3-bromophenyl)-2-amino)prop-1-oxy)-methylamine (DC6; R$^6$=Me, R$^1$=Me) (0.76 g, 2.9 mmol) in EtOH (10 mL) was added BrCN (0.46 g, 4.4 mmol, 1.5 eq). After stirring at RT for 16 h, the mixture was concentrated. The residue was redissolved in CHCl$_3$ (20 mL) and washed with 2N NaOH (10 mL). The aqueous layer was extracted with CHCl$_3$ (3×10 mL). The combined organic layer was dried over Na$_2$SO$_4$ and concentrated to give 0.82 g (100%) of 5-(3-bromophenyl)-2,5-dimethyl-1,2,4-oxadiazinan-3-imine (DC7; R$^6$=Me, R$^1$=Me) as a light yellow oil. $^1$H NMR (CDCl$_3$) δ 10.59 (S, 1H), 8.12 (brs, 1H), 7.46 (m, 2H), 7.29 (m, 2H), 4.14 (dd, J1=11.5 Hz, J2=57.7 Hz, 2H), 3.39 (s, 3H), 1.69 (s, 3H).

Method DC, Step 8; 5-(3-(3-Cyanophenyl)phenyl)-2,5-dimethyl-1,2,4-oxadiazinan-3-imine A mixture of 5-(3-bromophenyl)-2,5-dimethyl-1,2,4-oxadiazinan-3-imine (DC7; $R^6$=Me, $R^1$=Me) (0.025 g, 0.088 mmol, 1 eq), 3-cyanophenylboronic acid (0.019 g, 0.13 mmol, 1.5 eq), FibreCat (40 mg), anhydrous ethanol (1.5 mL), and a 1N $K_2CO_3$ aqueous solution (0.12 mL, 0.12 mmol, 1.4 eq) in a microwave vial was heated in a microwave reactor (Emrys Optimizer) at 110° C. for 15 min. The mixture was filtered, concentrated and purified by prep HPLC (B) to give 0.012 g (44%) of 5-(3-(3-cyanophenyl)phenyl)-2,5-dimethyl-1,2,4-oxadiazinan-3-imine (DC8; $R^6$=Me, $R^1$=Me, $R^{21}$=3-cyanophenyl) as a white solid. $^1$H NMR (CDCl$_3$) δ 10.67 (s, 1H), 8.05 (br s, 1H), 7.85 (m, 2H), 7.50-7.66 (m, 5H), 7.35 (m, 1H), 4.22 (dd, J1=11.8 Hz, J2=48.6 Hz, 2H), 3.40 (s, 3H), 1.76 (s, 3H). MS m/e 307.3 (M+H)

Using a similar procedure, the following compounds were also prepared:

5-(3-(3-Pyridyl)phenyl)-2,5-dimethyl-1,2,4-oxadiazinan-3-imine

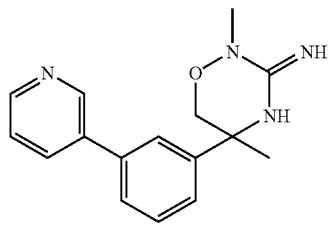

$^1$H NMR (CDCl$_3$) 10.85 (s, 1H), 9.13 (s, 1H), 8.76 (m, 1H), 8.65 (m, 1H), 7.92 (m, 2H), 7.81 (s, 1H), 7.60 (m, 2H), 7.44 (m, 1H), 4.26 (dd, J1=11.8 Hz, J2=37.4 Hz, 2H), 3.41 (s, 3H), 1.77 (s, 3H). MS m/e 283.2 (M+H)

5-(3-(5-Pyrimidyl)phenyl)-2,5-dimethyl-1,2,4-oxadiazinan-3-imine

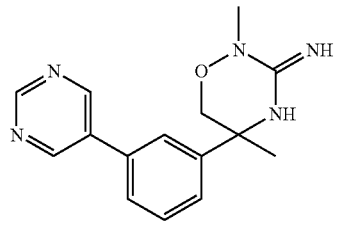

$^1$H NMR (CDCl$_3$) δ 10.77 (br s, 1H), 10.42 (s, 1H), 9.26 (s, 1H), 9.07 (s, 1H), 7.84 (br s, 1H), 7.57-7.63 (m, 3H), 7.46 (m, 1H), 4.23 (dd, J1=11.5 Hz, J2=45.9 Hz, 2H), 3.41 (s, 3H), 1.77 (s, 3H). MS m/e 284.2 (M+H)

5-(3-(3-Chlorophenyl)phenyl)-2,5-dimethyl-1,2,4-oxadiazinan-3-imine

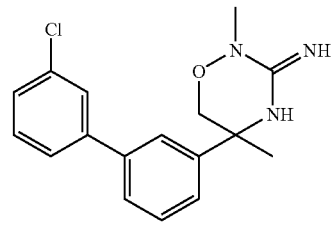

$^1$H NMR (CDCl$_3$) δ 10.63 (s, 1H), 8.00 (br S, 1H), 7.46-7.55 (m, 5H), 7.31-7.7.40 (m, 3H), 4.20 (dd, J1=11.5 Hz, J2=54.4 Hz, 2H), 3.39 (s, 3H), 1.76 (s, 3H). MS m/e 316.2 (M+H)

5-(3-(3-Trifluoromethoxyphenyl)phenyl)-2,5-dimethyl-1,2,4-oxadiazinan-3-imine

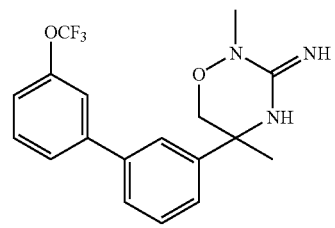

$^1$H NMR (CDCl$_3$) δ 10.72 (s, 1H), 8.03 (br s, 1H), 7.55 (m, 1H), 7.51 (m, 2H), 7.46 (m, 2H), 7.41 (m, 1H), 7.32-7.34 (dt, J1=1.6 Hz, J2=7.2 Hz, 1H), 7.21-7.23 (m, 1H), 4.21 (dd, J1=11.8 Hz, J2=53.0 Hz, 2H), 3.39 (s, 3H), 1.76 (s, 3H). MS m/e 366.2 (M+H)

5-(3-(3-Toluyl)phenyl)-2,5-dimethyl-1,2,4-oxadiazinan-3-imine

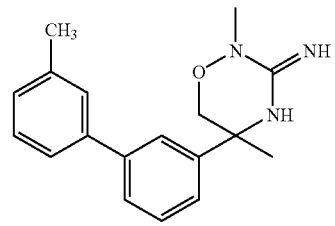

$^1$H NMR (CDCl$_3$) δ 10.61 (s, 1H), 8.07 (br s, 1H), 7.53 (m, 2H), 7.45 (m, 1H), 7.33-7.37 (m, 3H), 7.28-7.32 (m, 1H), 7.17-7.19 (m, 1H), 4.20 (dd, J1=11.8 Hz, J2=58.2 Hz, 2H), 3.38 (s, 3H), 2.42 (s, 3H), 1.76 (s, 3H). MS m/e 296.4 (M+H)

5-(3-(3,5-Dichlorophenyl)phenyl)-2,5-dimethyl-1,2,4-oxadiazinan-3-imine

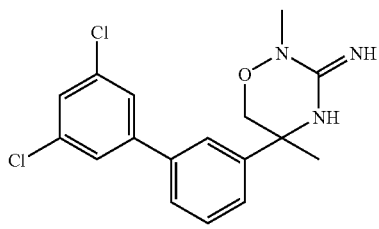

$^1$H NMR (CDCl$_3$) δ10.71 (s, 1H), 8.06 (br s, 1H), 7.47 (m, 3H), 7.43 (m, 2H), 7.35 (m, 2H), 4.20 (dd, J1=11.7 Hz, J2=54.9 Hz, 2H), 3.40 (s, 3H), 1.76 (s, 3H). MS m/e 350.2 (M+H)

5-(3-(2-Fluoro-5-cyanophenyl)phenyl)-2,5-dimethyl-1,2,4-oxadiazinan-3-imine

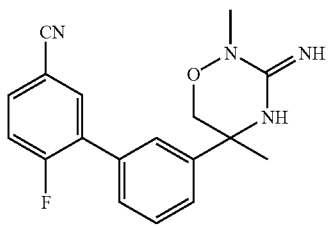

$^1$H NMR (CDCl$_3$) δ10.50 (s, 1H), 7.86 (br s, 1H), 7.77 (dd, J1=2.1 Hz, J2=6.9 Hz, 1H), 7.65 (m, 1H), 7.50 (m, 2H), 7.42 (m, 1H), 7.27 (t, J=5.0 Hz, 2H), 4.20 (dd, J1=12.0 Hz, J2=50.4 Hz, 2H), 3.40 (s, 3H), 1.76 (s, 3H). MS m/e 325.1 (M+H)

5-(3-(2-Fluoro-5-methoxyphenyl)phenyl)-2,5-dimethyl-1,2,4-oxadiazinan-3-imine

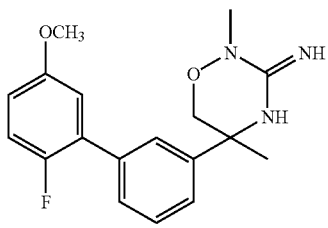

$^1$H NMR (CDCl$_3$) δ10.53 (s, 1H), 7.94 (brs, 1H), 7.47 (m, 3H), 7.37 (m, 1H), 7.07 (t, J=9.5 Hz, 1H), 6.93 (m, 1H), 6.86 (m, 1H), 4.19 (dd, J1=11.7 Hz, J2=58.5 Hz, 2H), 3.82 (s, 3H), 3.38 (s, 3H), 1.75 (s, 3H). MS m/e 330.1 (M+H)

5-(3-(3-Dimethylaminocarbonylphenyl)phenyl)-2,5-dimethyl-1,2,4-oxadiazinan-3-imine

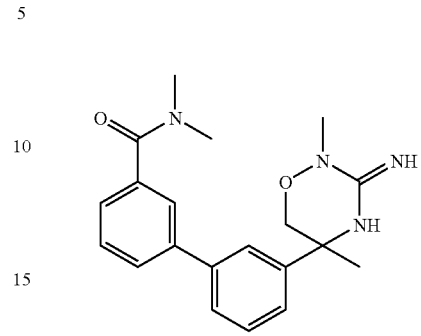

$^1$H NMR (CDCl$_3$) δ10.58 (s, 1H), 7.95 (brs, 1H), 7.26-7.65 (m, 8H), 4.20 (dd, J1=11.5 Hz, J2=54.7 Hz, 2H), 3.38 (s, 3H), 3.14 (s, 3H), 3.02 (s, 3H), 1.75 (s, 3H). MS m/e 353.2 (M+H)

5-(3-(2,5-Dimethoxyphenyl)phenyl)-2,5-dimethyl-1,2,4-oxadiazinan-3-imine

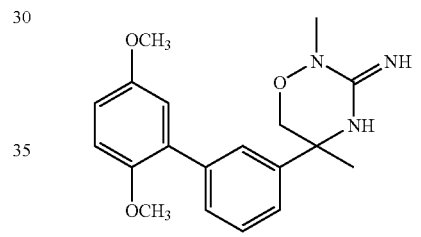

$^1$H NMR (CDCl$_3$) δ 10.50 (s, 1H), 7.99 (brs, 1H), 7.40-7.50 (m, 3H), 7.29-7.33 (m, 1H), 6.84-6.94 (m, 3H), 4.18 (dd, J1=11.5 Hz, J2=65.4 Hz, 2H), 3.80 (s, 3H), 3.74 (s, 3H), 3.37 (s, 3H), 1.74 (s, 3H). MS m/e 342.2 (M+H)

5-(3-(3-Hydroxyphenyl)phenyl)-2,5-dimethyl-1,2,4-oxadiazinan-3-imine

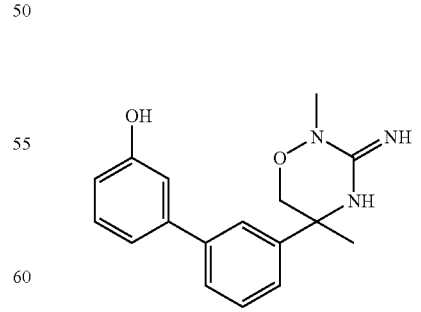

$^1$H NMR (CDCl$_3$) δ 9.75 (s, 1H), 7.39-7.54 (m, 3H), 7.21-7.30 (m, 2H), 7.10-7.12 (m, 2H), 6.82-6.84 (m, 1H), 5.83 (br s, 2H), 4.15 (dd, J1=11.5 Hz, J2=35.7 Hz, 2H), 3.36 (s, 3H), 1.74 (s, 3H). MS m/e 298.3 (M+H)

837
5-(3-(3-Fluorophenyl)phenyl)-2,5-dimethyl-1,2,4-oxadiazinan-3-imine
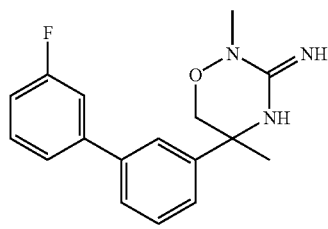
$^1$H NMR (CDCl$_3$) δ 10.77 (s, 1H), 8.15 (s, 1H), 7.25-7.56 (m, 7H), 7.01-7.08 (m, 1H), 4.20 (dd, J1=11.5 Hz, J2=53.0 Hz, 2H), 3.40 (s, 3H), 1.76 (s, 3H). MS m/e 300.2 (M+H)
5-(3-(4-Cyanophenyl)phenyl)-2,5-dimethyl-1,2,4-oxadiazinan-3-imine
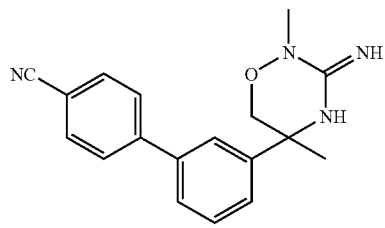
838
$^1$H NMR (CDCl$_3$) δ 10.67 (s, 1H), 8.01 (br s, 1H), 7.74 (s, 4H), 7.63 (s, 1H), 7.48-7.56 (m, 2H), 7.33-7.35 (m, 1H), 4.23 (dd, J1=11.5 Hz, J2=47.2 Hz, 2H), 3.40 (s, 3H), 1.76 (s, 3H). MS m/e 307.2 (M+H)
5-(3-(4-Methoxy-3-pyridyl)phenyl)-2,5-dimethyl-1,2,4-oxadiazinan-3-imine
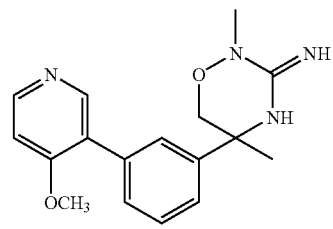
$^1$H NMR (CDCl$_3$) δ 10.55 (s, 1H), 8.74 (d, J=6.0 Hz, 1H), 8.64 (s, 1H), 7.83 (br s, 1H), 7.49-7.53 (m, 3H), 7.37-7.42 (m, 2H), 4.20 (dd, J1=11.5 Hz, J2=49.4 Hz, 2H), 4.11 (s, 3H), 3.39 (s, 3H), 1.76 (s, 3H). MS m/e 313.2 (M+H)
Method DD
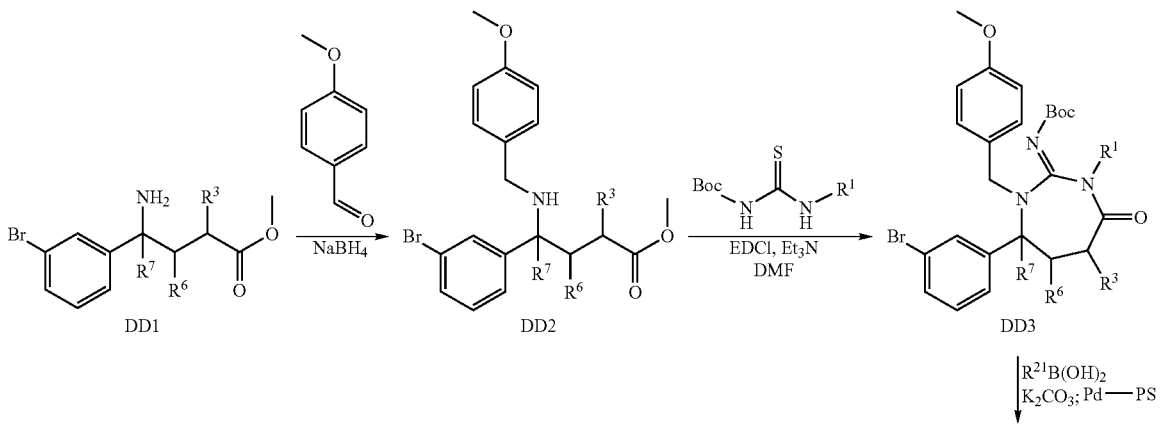
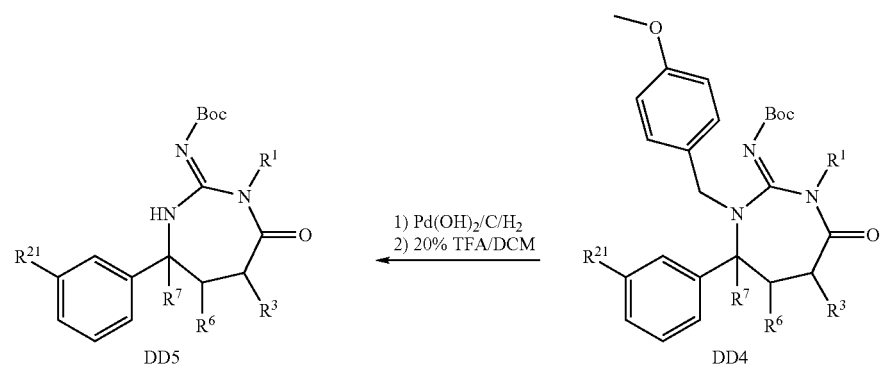

Method DD, Step 1;

To a 10 mL MeOH solution of DD1 ($R^3=R^6=H$. $R^7=Me$, 1 g) was added p-methoxybenzaldehyde (1 eq) and 4 A molecular sieves (4 g). The solution was stirred overnight before sodium borohydride (1 eq) was added and reaction stirred for 1 h. The reaction mixture was filted and solvent evaporated. The residue was chromatographed using MeOH/DCM to afford compound DD2 ($R^3=R^6=H$, $R^7=Me$).

Method DD, Step 2;

Procedure similar to Method CF, step 2 was used for generation of DD3 ($R^1=Me$, $R^3=R^6=H$. $R^7=Me$,).

Method DD, Step 3;

Procedure similar to Method CF, step 3 was used for generation of DD4 ($R^1=Me$, $R^3=R^6=H$, $R^7=Me$) from DD3

Method DD, Step 4;

Compound DD4 was hydrogenated using $Pd(OH)_2$/C in Methanol. After removal of the catalyst and solvent the crude product was treated with 20% TFA in DCM to give product DD5 ($R^1=Me$, $R^3=R^6=H$ $R^7=Me$) after purification.

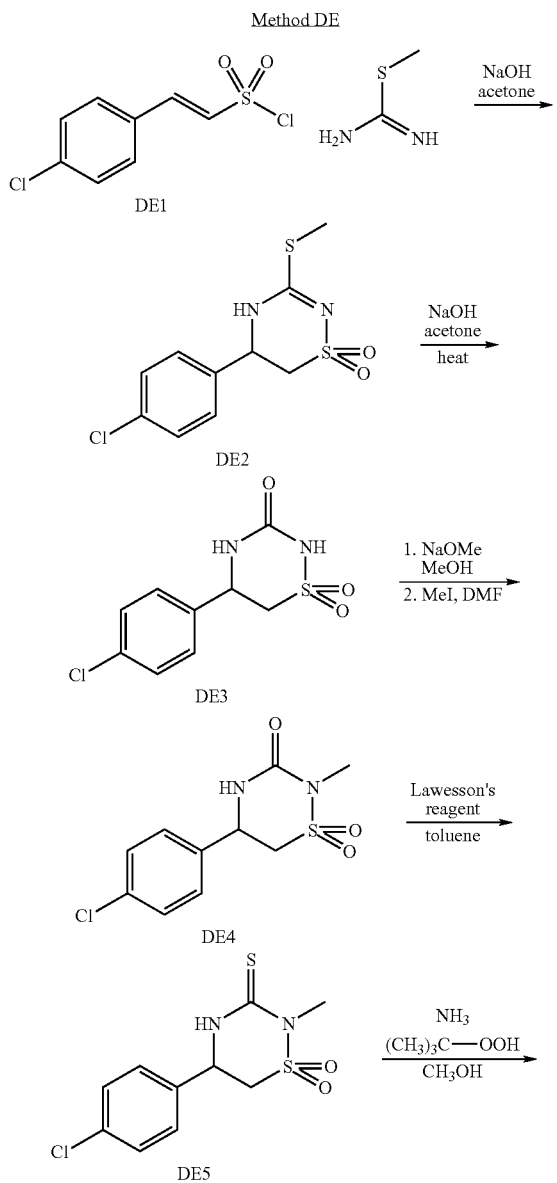

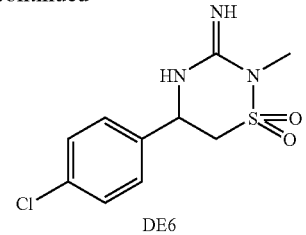

Method DE, Step 1: 5-(4-Chlorophenyl)-3-methylsulfanyl-5,6-dihydro-4H-[1,2,4]thiadiazine 1,1-dioxide 2-(4-Chlorophenyl)ethenesulfonyl chloride DE1 is treated with 1.2 equivalents of S-methyl isothiourea hemisulfate and a slight excess of 1N NaOH in acetone. After 12 h at RT the mixture is concentrated in vacuo and the precipitate collected to give the title compound.

Method DE, Step 2: N-(2-(4-Chlorophenyl)ethene-1-sulfonyl)-S-methylisothiourea

Using a method similar to that described by K. Hasegawa and S. Hirooka (Bull. Chem. Soc. Jap., 1972, 45, 1893), N-(2-(4-clorophenyl)ethylene-1-sulfonyl)thiourea DE2 in DMF is treated with 1N NaOH (2.4 equivalents) and dimethyl sulfate (1.2 equivalents) at 0-10° C. After 3 h at RT, the reaction mixture is poured into ice water. The precipitate is collected, washed with water and dried to give the title compound DE3.

Method DE, Step 2: 5-(4-Chlorophenyl)-1,1-dioxo-[1,2,4]thiadiazinan-3-one

Using a method similar to that described by K. Hasegawa and S. Hirooka (Bull. Chem. Soc. Jap., 1972, 45, 1893), 5-(4-chlorophenyl)-3-methylsulfanyl-5,6-dihydro-4H-[1,2,4]thiadiazine 1,1-dioxide DE2 in acetone is treated with 1N NaOH and the mixture is refluxed for 2 h. The acetone is evaporated and the mixture is acidified with conc. HCl to afford the title compound DE3.

Method DE, Step 3: 5-(4-Chlorophenyl)-2-methyl-1,1-dioxo-[1,2,4]thiadiazinan-3-one Using a method similar to that described by A. Etienne et al. (Bull. Soc. Chim. Fr., 1974, 1395) 5-(4-chlorophenyl)-1,1-dioxo-[1,2,4]thiadiazinan-3-one DE3 is treated with sodium methoxide (1 equivalent) in methanol. Add methyl iodide (1.2 equivalent) in DMF and allow to stir for 12 h. Pour the mixture into ice water and collect the precipitate of the title compound DE4.

Method DE, Step 4: 5-(4-Chlorophenyl)-2-methyl-1,1-dioxo-[1,2,4]thiadiazinan-3-thione To a solution of DE4 in toluene (or xylene) is added Lawesson's reagent (1.2 equivalents), and the mixture is stirred at reflux for 2 h. The mixture is cooled and poured into cold water. The organic phase is dried ($MgSO_4$) and filtered, and solvent is removed. The crude product is purified by flash chromatography to provide the title compound (DE5).

Method DE, Step 5: 5-(4-Chlorophenyl)-2-methyl-1,1-dioxo-[1,2,4]thiadiazinan-3-ylideneamine Using a route similar to that described in Method A, step 3, DE5 is used to prepare the title compound (DE6).

As a variant of this method, DE2 is treated with ammonia and the resultant product is treated with sodium hydride and methyl iodide in DMF to give the product DE6

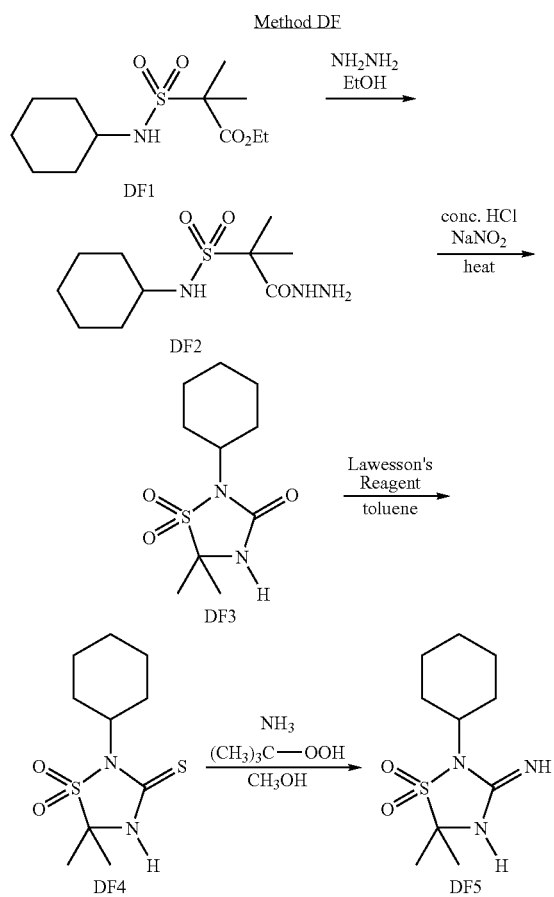

Method DF, Step 1: 2-Hydrazinocarbonylpropane-2-sulfonic acid cyclohexylamide

Using a method similar to that described by S. Paik and E. H. White (Tetrahedron, 1996, 52, 5303), 2-cyclohexylsulfamoyl-2-methylpropionic acid ethyl ester DF1 (which is prepared by the method of A. De Blic et al. (Synthesis, 1982, 281)) in ethanol is treated with 1.2 equivalent of 95% hydrazine under $N_2$ and the mixture is allowed to stand at RT for 12 h. The reaction mixture is concentrated to give the title compound DF2 which is used directly in Step 2.

Method DF, Step 2: 2-Cyclohexyl-5,5-dimethyl-1,2,4-thiadiazolidin-3-one-1,1-dioxide A solution of DF2 in $CH_2Cl_2$ is refluxed under a $N_2$ for 10 h. The solvent is removed in vacuo and the crude product is purified by flash chromatography to provide the title compound DF3.

Method DF, Step 3: 2-Cyclohexyl-5,5-dimethyl-1,2,4-thiadiazolidin-3-thione-1,1-dioxide To a solution of DF3 in toluene (or xylene) is added Lawesson's reagent (1.2 equivalents), and the mixture is stirred at reflux for 2 h. The mixture is cooled and poured into cold water. The organic phase is dried ($MgSO_4$) and filtered, and solvent is removed. The crude product is purified by flash chromatography to provide the title compound (DF4).

Method DF, Step 4: 2-Cyclohexyl-5,5-dimethyl-1,2,4-thiadiazolidin-3-imine-1,1-dioxide Using a route similar to that described in Method A, step 3, DF4 is used to prepare the title compound (DF5).

The following table contains example compounds which were synthesized with procedure(s) similar to methods listed in the corresponding column and whose LCMS data (obs. mass) are also listed.

| # | Compounds | Method | Obs. Mass |
|---|---|---|---|
| 1491 | | CF | 297 |
| 1492 | | CF | 333.9 |

-continued

| # | Compounds | Method | Obs. Mass |
|---|-----------|--------|-----------|
| 1493 | | CF | 329.9 |
| 1494 | | CF | 367.9 |
| 1495 | | AW | 281 |
| 1496 | | CF | 306 |
| 1497 | | AB | 307 |
| 1498 | | CF | 314 |

-continued

| # | Compounds | Method | Obs. Mass |
|---|-----------|--------|-----------|
| 1499 | | CF | 318 |
| 1500 | | CF | 325 |
| 1501 | | CF | 325 |
| 1502 | | CF | 330 |
| 1503 | | CF | 336 |

-continued

| # | Compounds | Method | Obs. Mass |
|---|---|---|---|
| 1504 | | CF | 336 |
| 1505 | | AB | 340 |
| 1506 | | CE | 342 |
| 1507 | | CF | 343 |
| 1508 | | CF | 344 |

-continued

| # | Compounds | Method | Obs. Mass |
|---|-----------|--------|-----------|
| 1509 | | CF | 344 |
| 1510 | | CF | 344 |
| 1511 | | AB | 354 |
| 1512 | | A | 354 |
| 1513 | | CF | 358 |

-continued

| # | Compounds | Method | Obs. Mass |
|---|-----------|--------|-----------|
| 1514 | | CF | 358 |
| 1515 | | BS | 358 |
| 1516 | | A | 364 |
| 1517 | | A | 366 |
| 1518 | | A | 366 |

-continued
| # | Compounds | Method | Obs. Mass |
|---|---|---|---|
| 1519 | 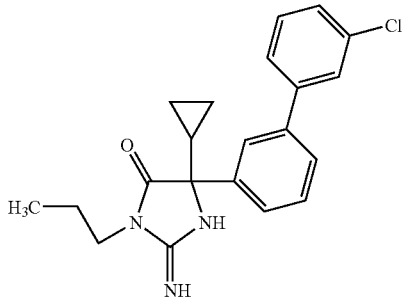 | A | 368 |
| 1520 | 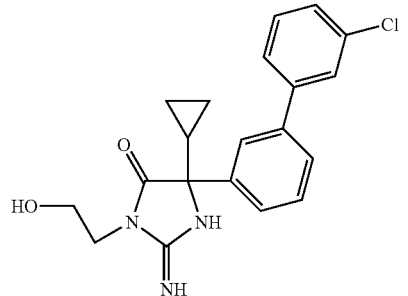 | A | 370 |
| 1521 | 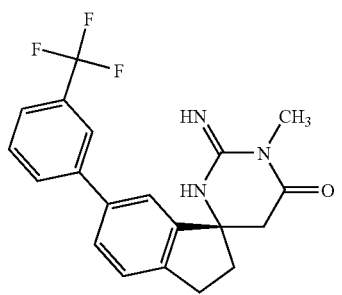 | AB | 374 |
| 1522 | 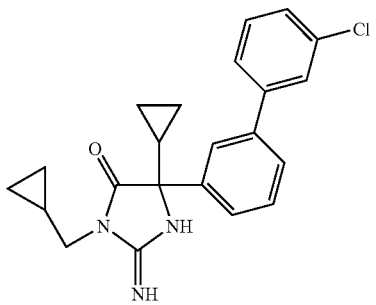 | A | 380 |
| 1523 | 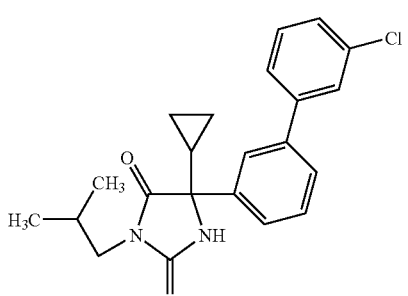 | A | 382 |

-continued

| # | Compounds | Method | Obs. Mass |
|---|---|---|---|
| 1524 | | A | 382 |
| 1525 | | BS | 383 |
| 1526 | | CF | 384 |
| 1527 | | A | 384 |
| 1528 | | A | 384 |

-continued

| # | Compounds | Method | Obs. Mass |
|---|---|---|---|
| 1529 | | A | 384 |
| 1530 | | A | 384 |
| 1531 | | A | 396 |
| 1532 | | A | 396 |
| 1533 | | A | 397 |

-continued
| # | Compounds | Method | Obs. Mass |
|---|---|---|---|
| 1534 | 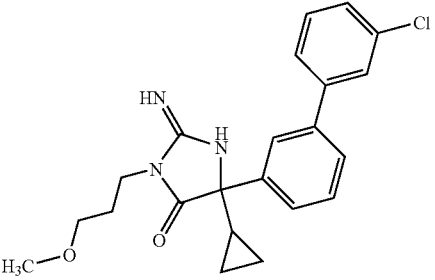 | A | 398 |
| 1535 | 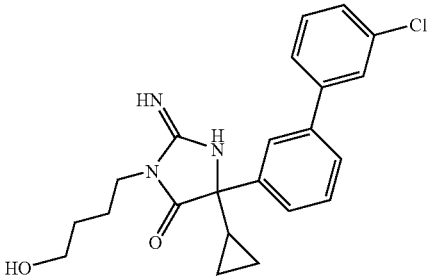 | A | 398 |
| 1536 | 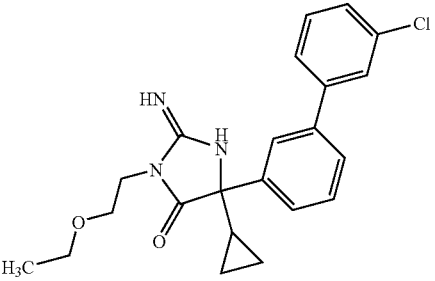 | A | 398 |
| 1537 | 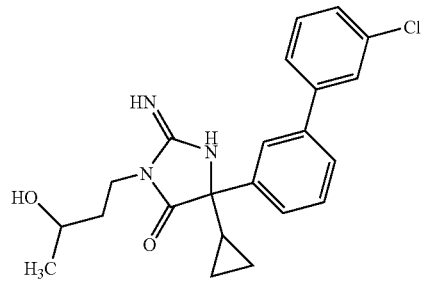 | A | 398 |
| 1538 | 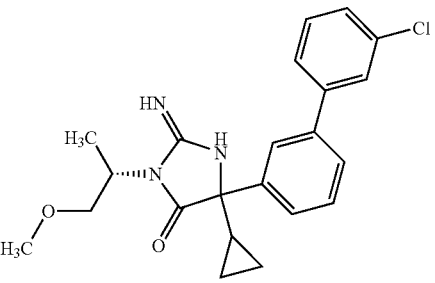 | A | 398 |

-continued
| # | Compounds | Method | Obs. Mass |
|---|---|---|---|
| 1539 | 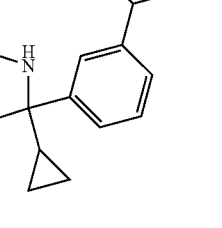 | A | 400 |
| 1540 | 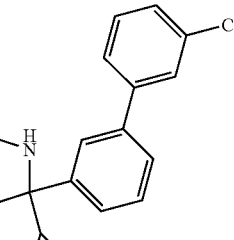 | A | 402 |
| 1541 | 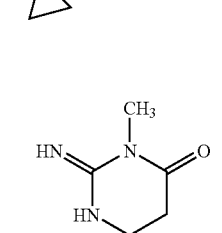 | AB | 404 |
| 1542 | 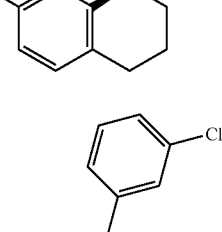 | A | 406 |
| 1543 | 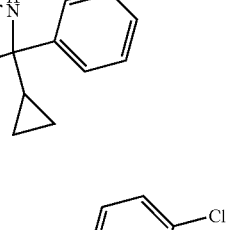 | A | 406 |

|   |   |   | Obs. |
|---|---|---|---|
| # | Compounds | Method | Mass |
| 1544 | | BS | 408 |
| 1545 | | A | 410 |
| 1546 | | A | 410 |
| 1547 | | A | 411 |

-continued

| # | Compounds | Method | Obs. Mass |
|---|---|---|---|
| 1548 | | A | 412 |
| 1549 | | A | 412 |
| 1550 | | A | 414 |
| 1551 | | CE | 415 |

-continued

| # | Compounds | Method | Obs. Mass |
|---|---|---|---|
| 1552 | | A | 416 |
| 1553 | | A | 417 |
| 1554 | | A | 417 |
| 1555 | | A | 419 |
| 1556 | | A | 420 |

-continued
| # | Compounds | Method | Obs. Mass |
|---|---|---|---|
| 1557 | 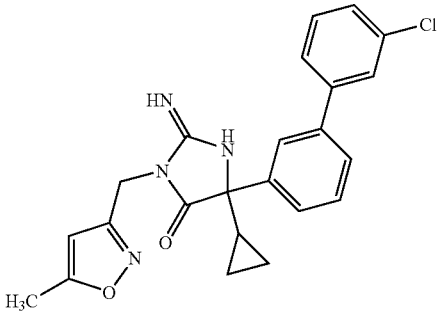 | A | 421 |
| 1558 | 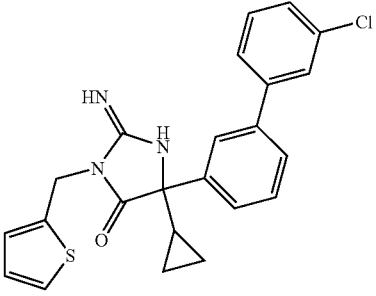 | A | 422 |
| 1559 | 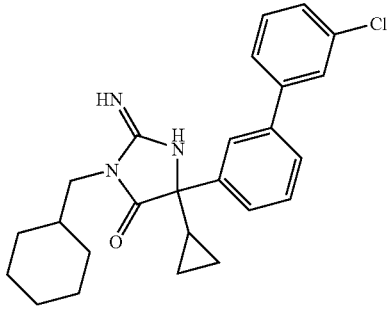 | A | 422 |
| 1560 | 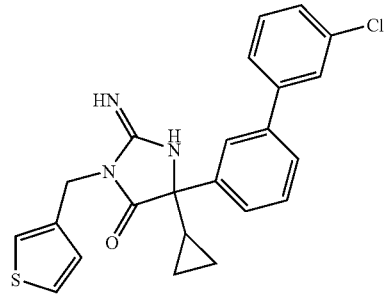 | A | 422 |
| 1561 | 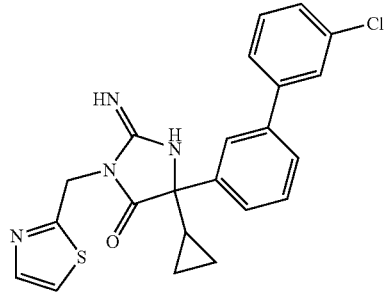 | A | 423 |

-continued

| # | Compounds | Method | Obs. Mass |
|---|---|---|---|
| 1562 | | A | 423 |
| 1563 | | CE | 424 |
| 1564 | | A | 425 |
| 1565 | | A | 426 |
| 1566 | | A | 426 |

-continued

| # | Compounds | Method | Obs. Mass |
|---|---|---|---|
| 1567 | | A | 426 |
| 1568 | | A | 431 |
| 1569 | | A | 431 |
| 1570 | | A | 431 |
| 1571 | | A | 433 |

-continued
| # | Compounds | Method | Obs. Mass |
|---|---|---|---|
| 1572 | 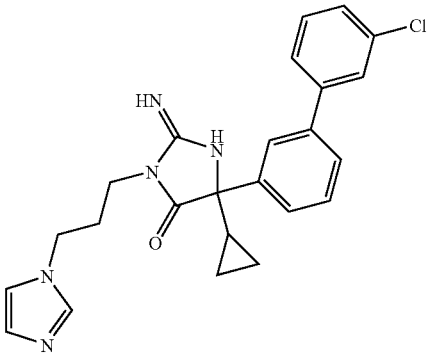 | A | 434 |
| 1573 | 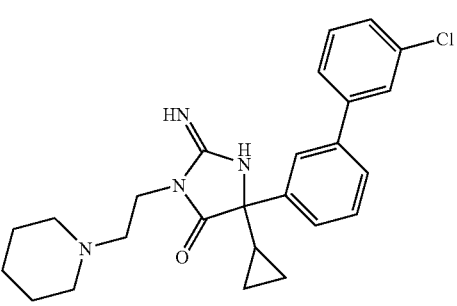 | A | 437 |
| 1574 | 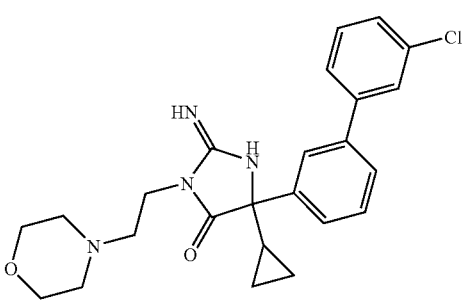 | A | 439 |
| 1575 | 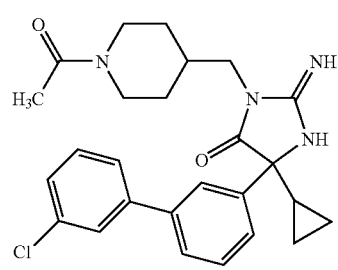 | A | 465 |
| 1576 | 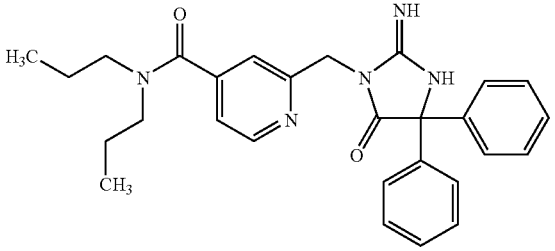 | CG | 470 |

-continued
| # | Compounds | Method | Obs. Mass |
|---|---|---|---|
| 1577 | 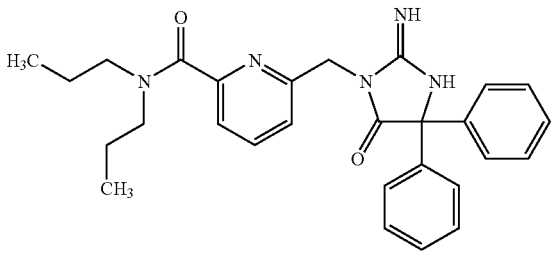 | CG | 470 |
| 1578 | 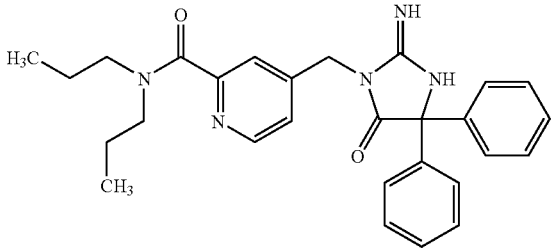 | CG | 470 |
| 1579 | 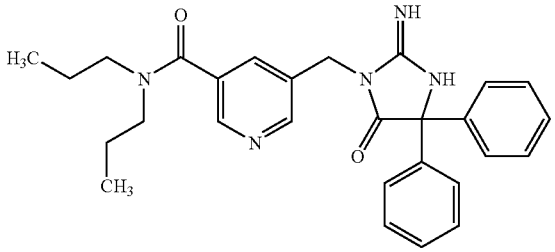 | CG | 470 |
| 1580 | 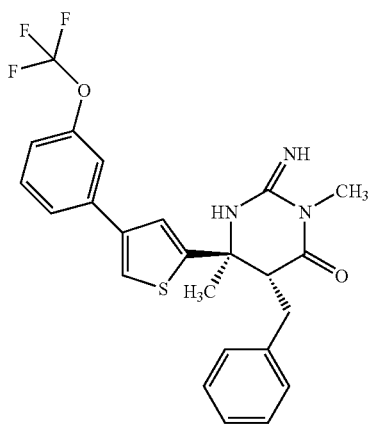 | CE | 474 |
| 1581 | 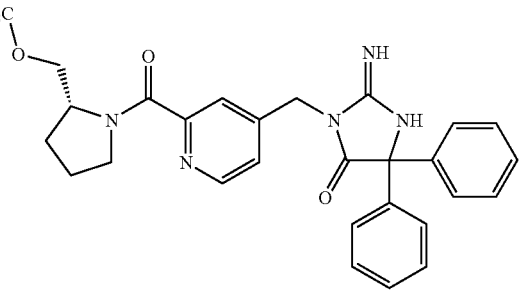 | CG | 484 |

-continued

| # | Compounds | Method | Obs. Mass |
|---|-----------|--------|-----------|
| 1582 | | CG | 484 |
| 1583 | | BR | 489 |
| 1584 | | CF | 274.1 |
| 1585 | | AW | 311.1 |
| 1586 | | AB | 312.1 |

-continued

| # | Compounds | Method | Obs. Mass |
|---|-----------|--------|-----------|
| 1587 | | AB | 319.1 |
| 1588 | | CF | 320.1 |
| 1589 | | CF | 325.1 |
| 1590 | | AB | 328.1 |
| 1591 | | AW | 332.1 |

| # | Compounds | Method | Obs. Mass |
|---|---|---|---|
| 1592 | | CE | 333.1 |
| 1593 | | CF | 336.1 |
| 1594 | | AW | 337.1 |
| 1595 | | CF | 337.1 |
| 1596 | | CF | 337.1 |
| 1597 | | CF | 337.1 |

-continued

| # | Compounds | Method | Obs. Mass |
|---|---|---|---|
| 1598 | | AB | 338.1 |
| 1599 | | AB | 338.1 |
| 1600 | | CE | 338.1 |
| 1601 | | CF | 339.1 |
| 1602 | | CE | 339.1 |

-continued

| # | Compounds | Method | Obs. Mass |
|---|---|---|---|
| 1603 | | AB | 342.1 |
| 1604 | | AW | 343.1 |
| 1605 | | AB | 345.1 |
| 1606 | | AB | 346.1 |
| 1607 | | AB | 350.1 |

-continued

| # | Compounds | Method | Obs. Mass |
|---|---|---|---|
| 1608 | | CF | 350.1 |
| 1609 | | AW | 356.1 |
| 1610 | | AW | 357.1 |
| 1611 | | AW | 359.1 |
| 1612 | | AB | 362.1 |

-continued
| # | Compounds | Method | Obs. Mass |
|---|---|---|---|
| 1613 | 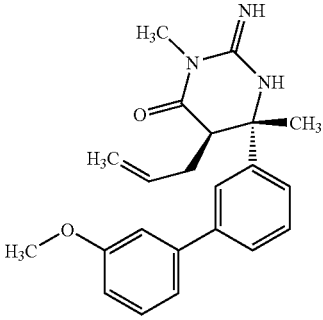 | CE | 364.1 |
| 1614 | 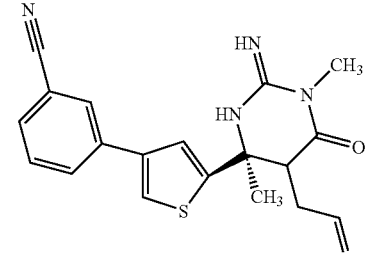 | CE | 365.1 |
| 1615 | 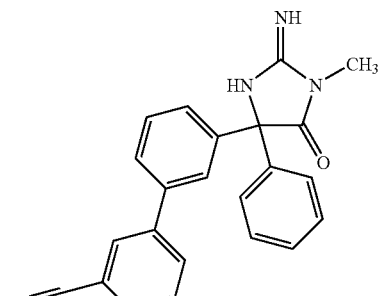 | AW | 367.1 |
| 1616 | 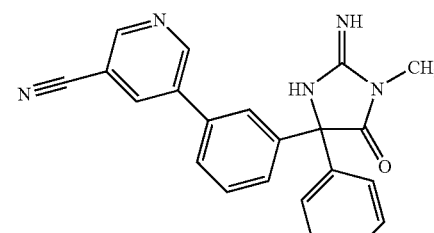 | AW | 368.1 |
| 1617 | 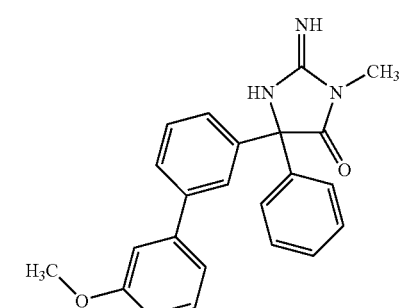 | AW | 372.1 |

-continued

| # | Compounds | Method | Obs. Mass |
|---|---|---|---|
| 1618 | | CF | 373.1 |
| 1619 | | AB | 378.1 |
| 1620 | | AW | 378.1 |
| 1621 | | CF | 379.1 |
| 1622 | | CF | 384.1 |

-continued

| # | Compounds | Method | Obs. Mass |
|---|---|---|---|
| 1623 | | BQ | 386.1 |
| 1624 | | BQ | 387.1 |
| 1625 | | AB | 388.1 |
| 1626 | | CO | 399.1 |
| 1627 | | BW | 412.1 |

| # | Compounds | Method | Obs. Mass |
|---|---|---|---|
| 1628 | | BW | 412.1 |
| 1629 | | CE | 414.1 |
| 1630 | | BQ | 419.1 |
| 1631 | | AW | 421.1 |
| 1632 | | AM | 425.1 |

| # | Compounds | Method | Obs. Mass |
|---|---|---|---|
| 1633 | | AW | 425.1 |
| 1634 | | BW | 426.1 |
| 1635 | | AW | 436.1 |
| 1636 | | BO | 439.1 |
| 1637 | | BQ | 440.1 |

-continued

| # | Compounds | Method | Obs. Mass |
|---|---|---|---|
| 1638 | | BQ | 453.1 |
| 1639 | | CH | 455.1 |
| 1640 | | BW | 463.1 |
| 1641 | | Q | 468.1 |
| 1642 | | BS | 478.1 |

-continued

| # | Compounds | Method | Obs. Mass |
|---|---|---|---|
| 1643 | | BS | 478.1 |
| 1644 | | BS | 484.1 |
| 1645 | | BS | 484.1 |
| 1646 | | BQ | 492.1 |

-continued
| # | Compounds | Method | Obs. Mass |
|---|---|---|---|
| 1647 | 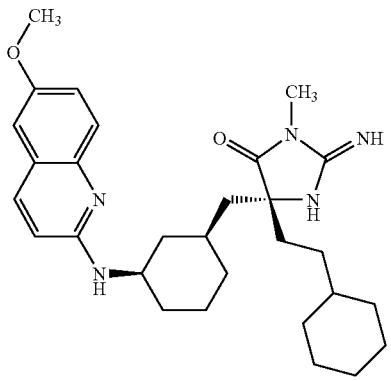 | BQ | 492.1 |
| 1648 | 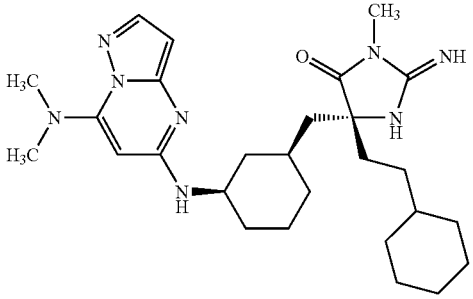 | BW | 495.1 |
| 1649 | 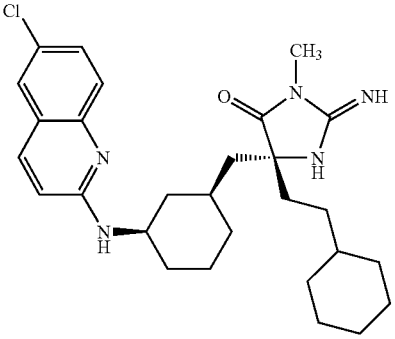 | BW | 496.1 |
| 1650 | 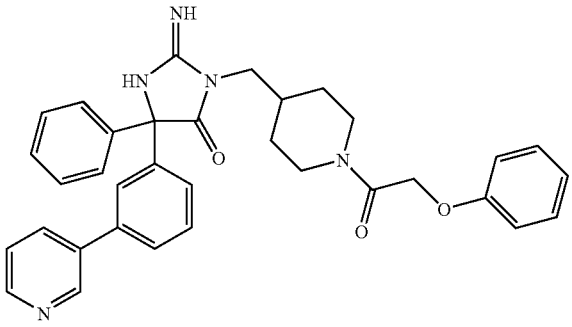 | Q | 560.1 |

-continued

| # | Compounds | Method | Obs. Mass |
|---|---|---|---|
| 1651 | | AW | 569.1 |
| 1652 | | BW | 573.1 |
| 1653 | | AW | 470.1 |
| 1654 | | AW | 307.2 |
| 1655 | | AW | 308.2 |

| # | Compounds | Method | Obs. Mass |
|---|---|---|---|
| 1656 | | CP | 308.2 |
| 1657 | | AW | 315.2 |
| 1658 | | AW | 321.2 |
| 1659 | | CO | 321.2 |
| 1660 | | AW | 325.2 |
| 1661 | | AW | 326.2 |

| # | Compounds | Method | Obs. Mass |
|---|---|---|---|
| 1662 | | AW | 328.2 |
| 1663 | | AW | 331.2 |
| 1664 | | CE | 335.2 |
| 1665 | | AW | 336.2 |
| 1666 | | AW | 337.2 |
| 1667 | | CF | 339.2 |

-continued

| # | Compounds | Method | Obs. Mass |
|---|-----------|--------|-----------|
| 1668 | | AW | 340.2 |
| 1669 | | CO | 341.2 |
| 1670 | | AW | 342.2 |
| 1671 | | AW | 346.2 |
| 1672 | | AW | 350.2 |
| 1673 | | CJ | 352.2 |
| 1674 | | AW | 354.2 |

| # | Compounds | Method | Obs. Mass |
|---|---|---|---|
| 1675 | | AW | 355.2 |
| 1676 | | CE | 359.2 |
| 1677 | | AW | 361.2 |
| 1678 | | AW | 361.2 |
| 1679 | | AW | 361.2 |

-continued

| # | Compounds | Method | Obs. Mass |
|---|---|---|---|
| 1680 | | AW | 362.2 |
| 1681 | | AW | 368.2 |
| 1682 | | AW | 372.2 |
| 1683 | | AW | 374.2 |
| 1684 | | BQ | 375.2 |

-continued

| # | Compounds | Method | Obs. Mass |
|---|---|---|---|
| 1685 | | CL | 377.2 |
| 1686 | | BK | 377.2 |
| 1687 | | AW | 377.2 |
| 1688 | | CG | 378.2 |
| 1689 | | AW | 383.2 |

-continued

| # | Compounds | Method | Obs. Mass |
|---|---|---|---|
| 1690 | | CO | 385.2 |
| 1691 | | BQ | 386.2 |
| 1692 | | AW | 406.2 |
| 1693 | | CL | 408.2 |
| 1694 | | BS | 409.2 |

-continued

| # | Compounds | Method | Obs. Mass |
|---|---|---|---|
| 1695 | | BW | 412.2 |
| 1696 | | BW | 413.2 |
| 1697 | | BS | 413.2 |
| 1698 | | BS | 420.2 |

-continued

| # | Compounds | Method | Obs. Mass |
|---|---|---|---|
| 1699 | | R | 425.2 |
| 1700 | | R | 425.2 |
| 1701 | | BQ | 429.2 |
| 1702 | | BQ | 430.2 |
| 1703 | | R | 434.2 |

-continued
| # | Compounds | Method | Obs. Mass |
|---|---|---|---|
| 1704 | 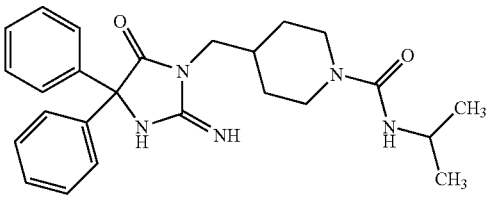 | R | 434.2 |
| 1705 | 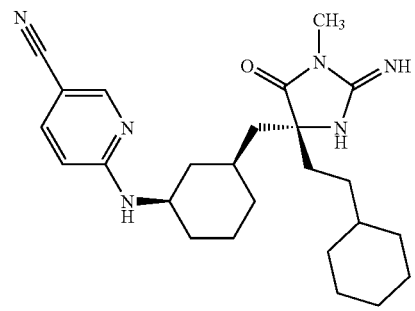 | BW | 437.2 |
| 1706 | 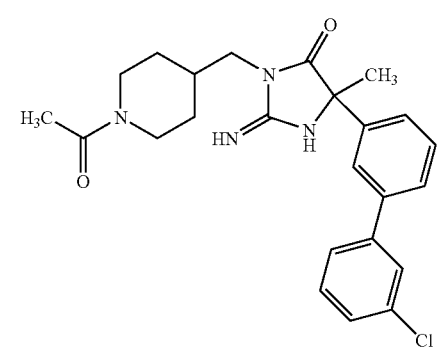 | AW | 439.2 |
| 1707 | 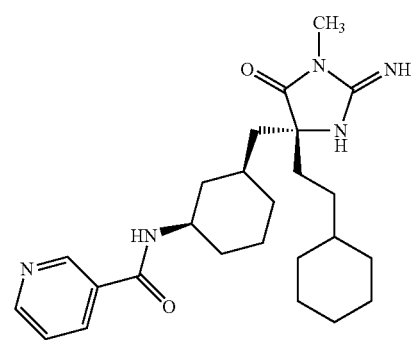 | BQ | 440.2 |

-continued

| # | Compounds | Method | Obs. Mass |
|---|---|---|---|
| 1708 | | BQ | 441.2 |
| 1709 | | BQ | 441.2 |
| 1710 | | BW | 442.2 |
| 1711 | | BQ | 445.2 |

| # | Compounds | Method | Obs. Mass |
|---|---|---|---|
| 1712 | | BQ | 446.2 |
| 1713 | | R | 446.2 |
| 1714 | | R | 446.2 |
| 1715 | | BS | 448.2 |

-continued

| # | Compounds | Method | Obs. Mass |
|---|---|---|---|
| 1716 | | R | 448.2 |
| 1717 | | BQ | 450.2 |
| 1718 | | BQ | 450.2 |
| 1719 | | BW | 451.2 |
| 1720 | | CI | 452.2 |

-continued

| # | Compounds | Method | Obs. Mass |
|---|---|---|---|
| 1721 | | BQ | 454.2 |
| 1722 | | BQ | 454.2 |
| 1723 | | AW | 419.2 |
| 1724 | | AW | 423.2 |

-continued
| # | Compounds | Method | Obs. Mass |
|---|---|---|---|
| 1725 | 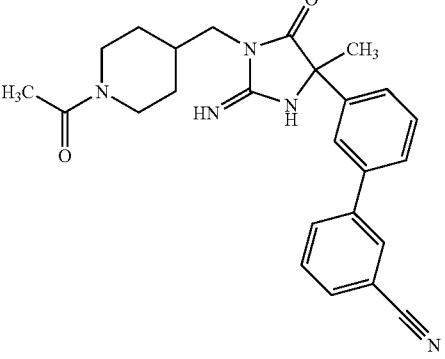 | AW | 430.2 |
| 1726 | 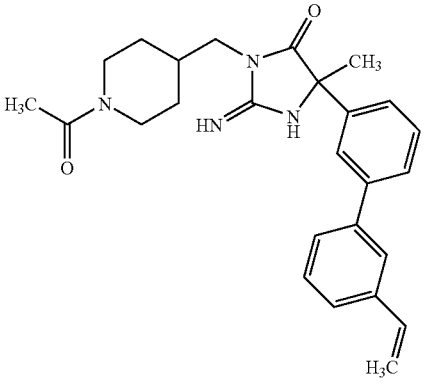 | AW | 431.2 |
| 1727 | 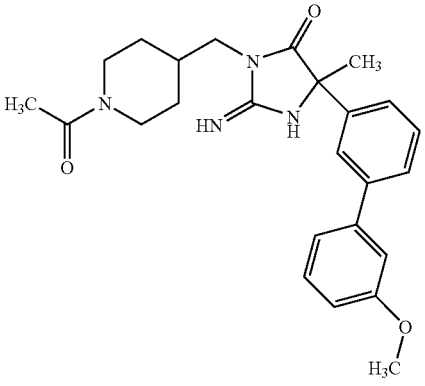 | AW | 435.2 |
| 1728 | 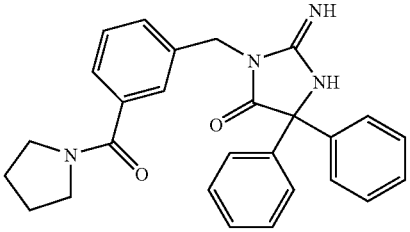 | CK | 439.2 |

-continued

| # | Compounds | Method | Obs. Mass |
|---|-----------|--------|-----------|
| 1729 | | AW | 441.2 |
| 1730 | | AW | 450.3 |
| 1731 | | CK | 453.3 |
| 1732 | | CK | 453.3 |

-continued

| # | Compounds | Method | Obs. Mass |
|---|---|---|---|
| 1733 | | AW | 453.3 |
| 1734 | | CK | 455.3 |
| 1735 | | L | 467.3 |
| 1736 | | L | 467.3 |

-continued
| # | Compounds | Method | Obs. Mass |
|---|---|---|---|
| 1737 | 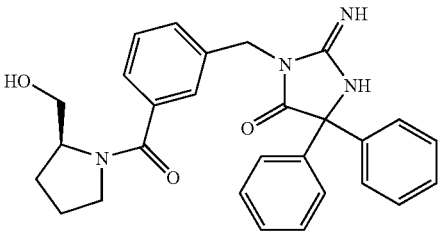 | CK | 469.3 |
| 1738 | 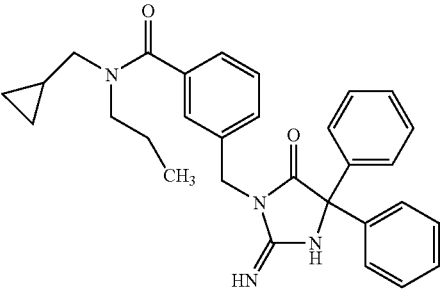 | CK | 481.3 |
| 1739 | 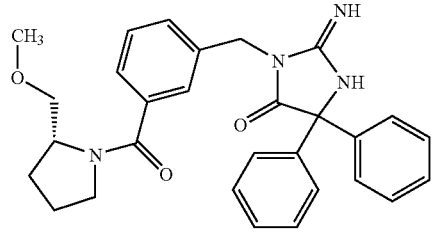 | CK | 483.3 |
| 1740 | 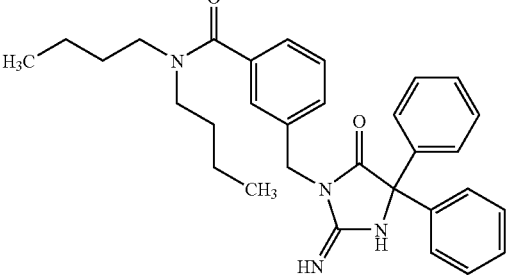 | CK | 497.3 |
| 1741 | 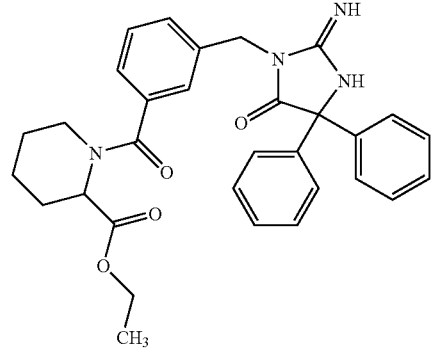 | CK | 525.3 |

| # | Compounds | Method | Obs. Mass |
|---|---|---|---|
| 1742 | 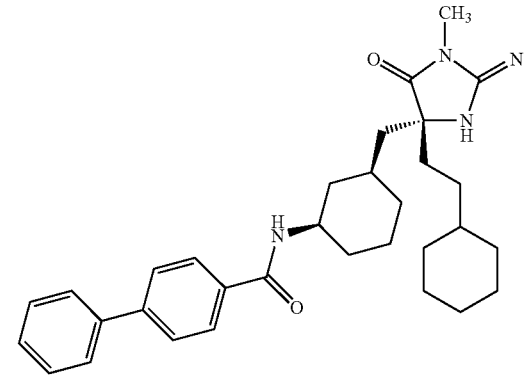 | BQ | 515.3 |
| 1743 | 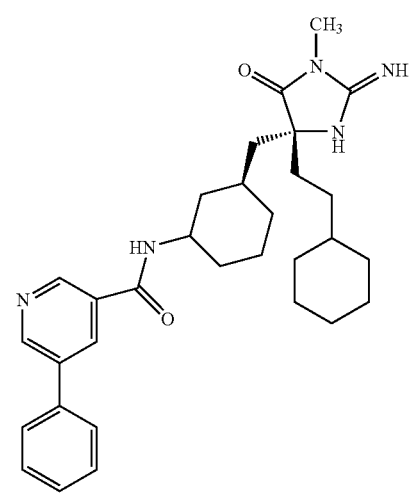 | BQ | 516.3 |
| 1744 | 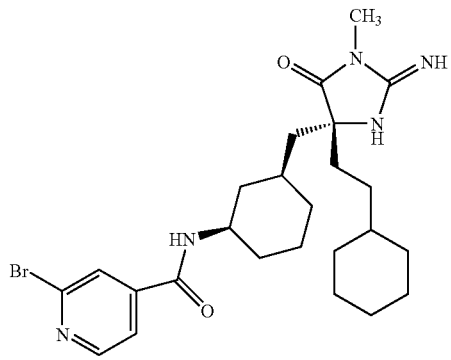 | BQ | 519.3 |

-continued

| # | Compounds | Method | Obs. Mass |
|---|-----------|--------|-----------|
| 1745 | | BS | 522.3 |
| 1746 | | BQ | 525.3 |
| 1747 | | BQ | 532.3 |
| 1748 | | CG | 576.3 |

-continued

| # | Compounds | Method | Obs. Mass |
|---|---|---|---|
| 1749 | | BQ | 455.3 |
| 1750 | | BW | 456.3 |
| 1751 | | BQ | 456.3 |
| 1752 | | BQ | 456.3 |

| # | Compounds | Method | Obs. Mass |
|---|---|---|---|
| 1753 | | BS | 456.3 |
| 1754 | | BQ | 456.3 |
| 1755 | | AW | 456.3 |
| 1756 | | BQ | 458.3 |

-continued

| # | Compounds | Method | Obs. Mass |
|---|---|---|---|
| 1757 | | BQ | 458.3 |
| 1758 | | BQ | 458.3 |
| 1759 | | BQ | 458.3 |
| 1760 | | BS | 460.3 |

-continued

| # | Compounds | Method | Obs. Mass |
|---|-----------|--------|-----------|
| 1761 | | R | 460.3 |
| 1762 | | BW | 462.3 |
| 1763 | | BW | 462.3 |
| 1764 | | BW | 463.3 |
| 1765 | | BQ | 464.3 |

|   |   | -continued |   |   |
|---|---|---|---|---|
| # | Compounds | | Method | Obs. Mass |
| 1766 | | | BQ | 464.3 |
| 1767 | | | BW | 465.3 |
| 1768 | | | BQ | 467.3 |
| 1769 | | | Q | 467.3 |

-continued
| # | Compounds | Method | Obs. Mass |
|---|---|---|---|
| 1770 | 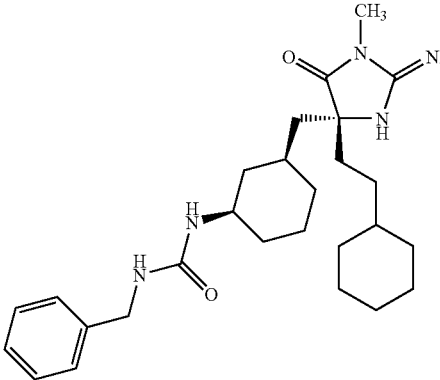 | BS | 468.3 |
| 1771 | 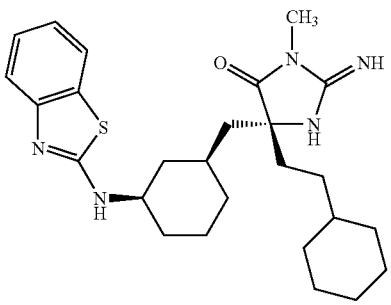 | BW | 468.3 |
| 1772 | 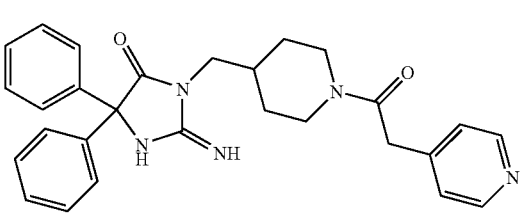 | Q | 468.3 |
| 1773 | 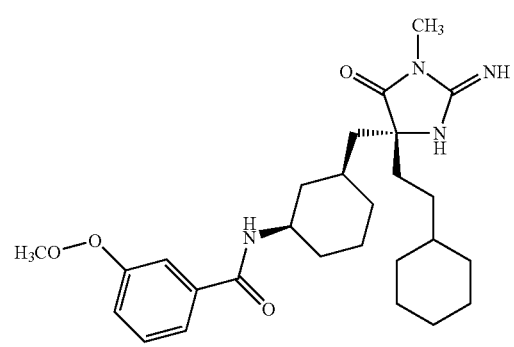 | BQ | 469.3 |

-continued

| # | Compounds | Method | Obs. Mass |
|---|---|---|---|
| 1774 | | BQ | 469.3 |
| 1775 | | CG | 469.3 |
| 1776 | | BQ | 470.3 |
| 1777 | | BQ | 470.3 |

-continued

| # | Compounds | Method | Obs. Mass |
|---|---|---|---|
| 1778 | | BS | 472.3 |
| 1779 | | BQ | 473.3 |
| 1780 | | BQ | 473.3 |
| 1781 | | BS | 473.3 |

-continued

| # | Compounds | Method | Obs. Mass |
|---|---|---|---|
| 1782 | | Q | 473.3 |
| 1783 | | AW | 473.3 |
| 1784 | | BQ | 474.3 |
| 1785 | | BQ | 478.3 |

-continued
| # | Compounds | Method | Obs. Mass |
|---|---|---|---|
| 1786 | 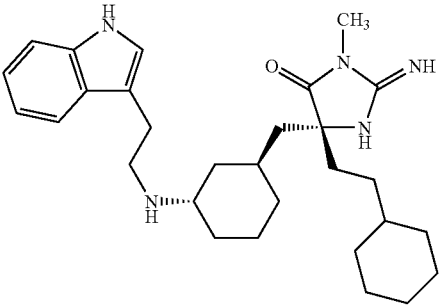 | AZ | 478.3 |
| 1787 | 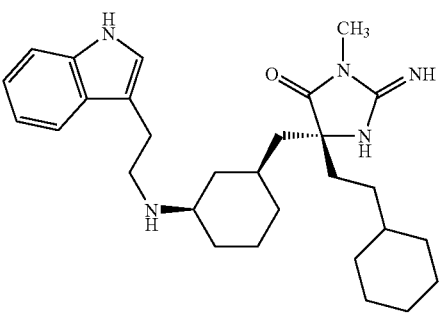 | AZ | 478.3 |
| 1788 | 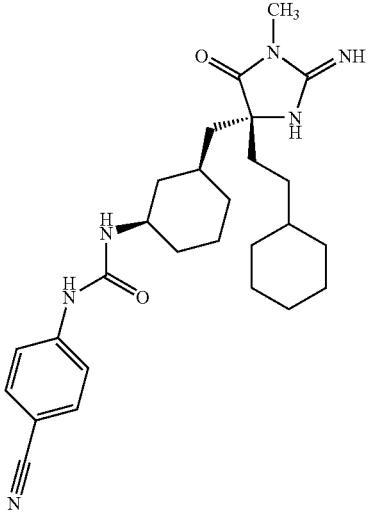 | BS | 479.3 |
| 1789 | 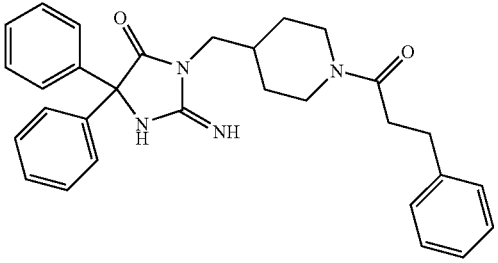 | Q | 481.3 |

| # | Compounds | Method | Obs. Mass |
|---|---|---|---|
| 1790 | | BS | 482.3 |
| 1791 | | Q | 482.3 |
| 1792 | | R | 482.3 |
| 1793 | | R | 482.3 |
| 1794 | | R | 482.3 |
| 1795 | | R | 482.3 |

-continued

| # | Compounds | Method | Obs. Mass |
|---|---|---|---|
| 1796 | | BS | 484.3 |
| 1797 | | R | 486.3 |
| 1798 | | R | 486.3 |
| 1799 | | CK | 487.3 |
| 1800 | | BS | 488.3 |

-continued
| # | Compounds | Method | Obs. Mass |
|---|-----------|--------|-----------|
| 1801 | 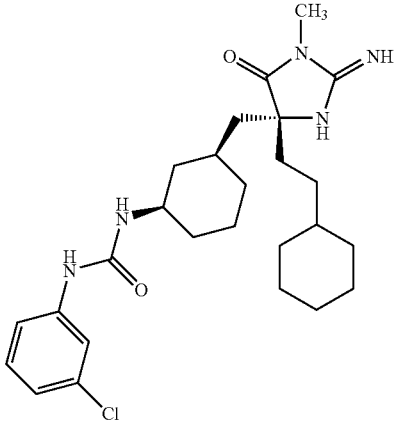 | BS | 488.3 |
| 1802 | 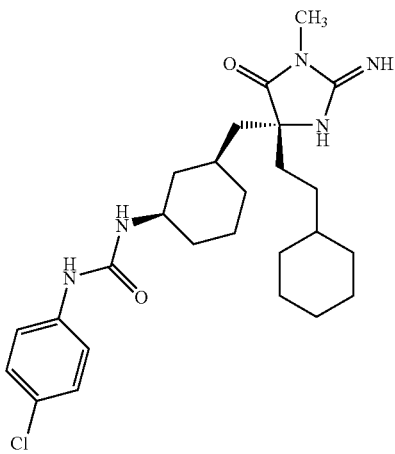 | BS | 488.3 |
| 1803 | 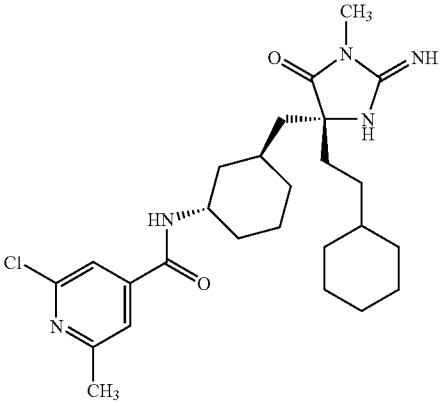 | BQ | 488.3 |

-continued
| # | Compounds | Method | Obs. Mass |
|---|-----------|--------|-----------|
| 1804 | 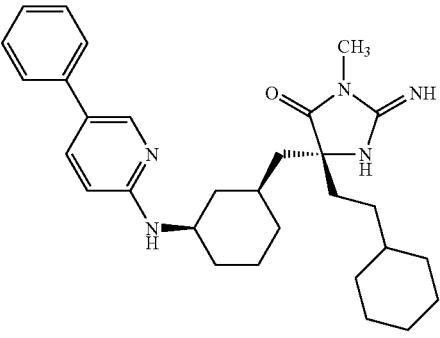 | BW | 488.3 |
| 1805 | 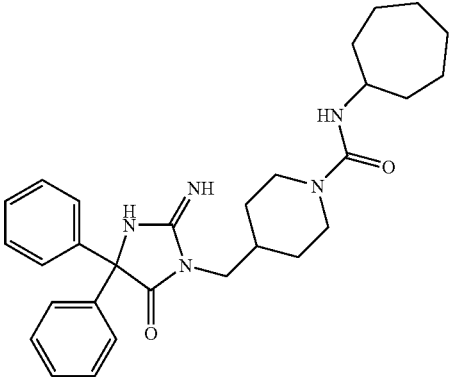 | R | 488.3 |
| 1806 | 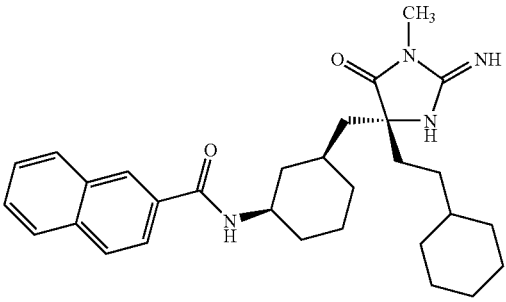 | BQ | 489.3 |
| 1807 | 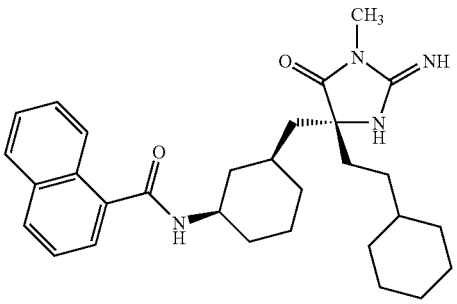 | BQ | 489.3 |

-continued
| # | Compounds | Method | Obs. Mass |
|---|-----------|--------|-----------|
| 1808 | 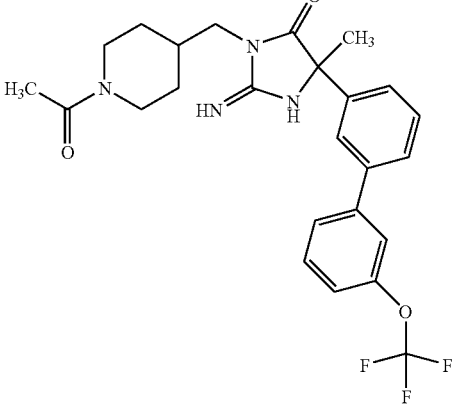 | AW | 489.3 |
| 1809 | 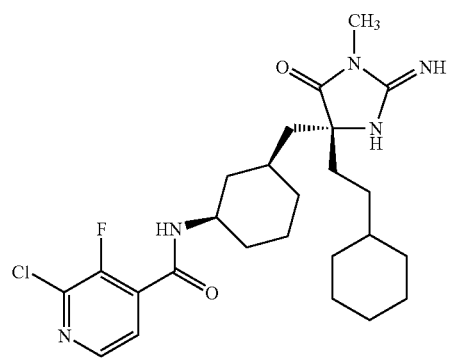 | BQ | 492.3 |
| 1810 | 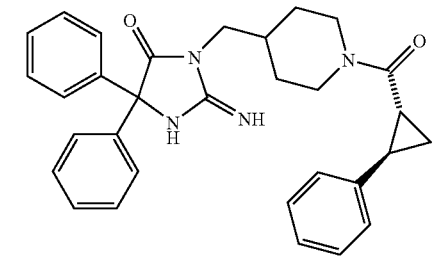 | Q | 493.3 |
| 1811 | 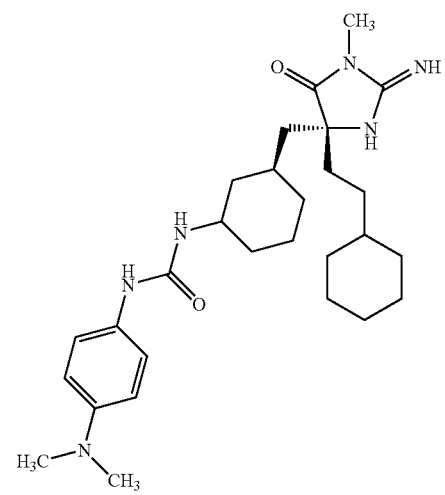 | BS | 497.3 |

-continued
| # | Compounds | Method | Obs. Mass |
|---|---|---|---|
| 1812 | 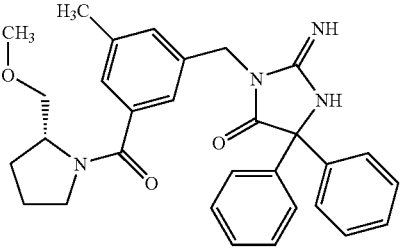 | CG | 497.3 |
| 1813 | 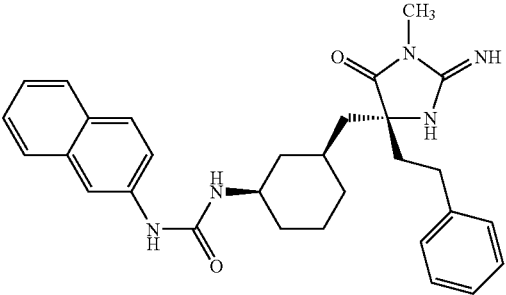 | BS | 498.3 |
| 1814 | 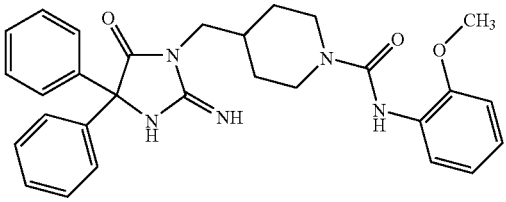 | R | 498.3 |
| 1815 | 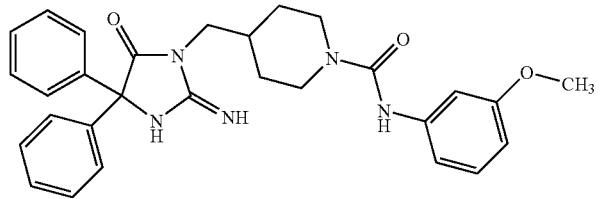 | | 498.3 |
| 1816 | 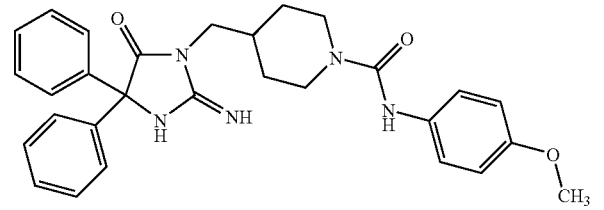 | | 498.3 |
| 1817 | 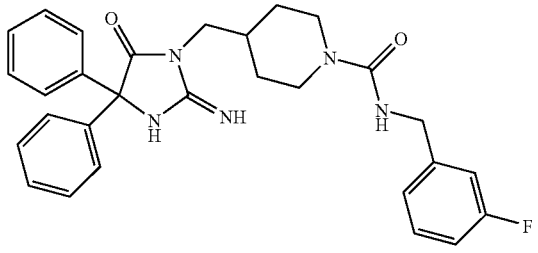 | R | 500.3 |

-continued

| # | Compounds | Method | Obs. Mass |
|---|---|---|---|
| 1818 | | R | 502.3 |
| 1819 | | R | 502.3 |
| 1820 | | BS | 504.3 |
| 1821 | | BS | 504.3 |

| # | Compounds | Method | Obs. Mass |
|---|---|---|---|
| 1822 | | BQ | 504.3 |
| 1823 | | BQ | 508.3 |
| 1824 | | CF | 329.1, 331.1 |
| 1825 | | CF | 334.0, 336.0 |

-continued

| # | Compounds | Method | Obs. Mass |
|---|---|---|---|
| 1826 | | CF | 342.1, 344.1 |
| 1827 | | CF | 352.0, 353.9 |
| 1828 | | CF | 358.1, 360.1 |
| 1829 | | CF | 363.1, 365.1 |
| 1830 | | CF | 367.9, 369.9 |

-continued

| # | Compounds | Method | Obs. Mass |
|---|---|---|---|
| 1831 | | A | 501.1 499 |
| 1832 | | CE | 309 |

Human Cathepsin D FRET Assay

This assay can be run in either continuous or endpoint format. The substrate used below has been described (Y. Yasuda et al., J. Biochem., 125, 1137 (1999)). Substrate and enzyme are commercially available.

The assay is run in a 30 ul final volume using a 384 well Nunc black plate. 8 concentrations of compound are pre-incubated with enzyme for 30 mins at 37 C followed by addition of substrate with continued incubation at 37 C for 45 mins. The rate of increase in fluorescence is linear for over 1 h and is measured at the end of the incubation period using a Molecular Devices FLEX station plate reader. Kis are interpolated from the IC50s using a Km value of 4 uM and the substrate concentration of 2.5 uM.

Reagents
Na-Acetate pH 5
1% Brij-35 from 10% stock (Calbiochem)
DMSO
Purified (>95%) human liver Cathepsin D (Athens Research & Technology Cat# 16-12-030104)
Peptide substrate (Km=4 uM) Mca-Gly-Lys-Pro-Ile-Leu-Phe-Phe-Arg-Leu-Lys(Dnp)-D-Arg-NH$_2$ Bachem Cat # M-2455
Pepstatin is used as a control inhibitor (Ki~0.5 nM) and is available from Sigma.
Nunc 384 well black plates Final Assay Buffer Conditions
100 mM Na Acetate pH 5.0
0.02% Brij-35
1% DMSO Compound is diluted to 3× final concentration in assay buffer containing 3% DMSO. 10 ul of compound is added to 10 ul of 2.25 nM enzyme (3×) diluted in assay buffer without DMSO, mixed briefly, spun, and incubated at 37 C for 30 mins. 3× substrate (7.5 uM) is prepared in 1× assay buffer without DMSO. 10 ul of substrate is added to each well mixed and spun briefly to initiate the reaction. Assay plates are incubated at 37 C for 45 mins and read on 384 compatible fluorescence plate reader using a 328 nm Ex and 393 nm Em.

Compounds of the present invention exhibit hCathD Ki data ranges from about 0.1 to about 500 nM, preferably about 0.1 to about 100 nM more preferably about 0.1 to about 75 nM.

The following are examples of compounds that exhibit hCathD Ki data under 75 nM.

structure

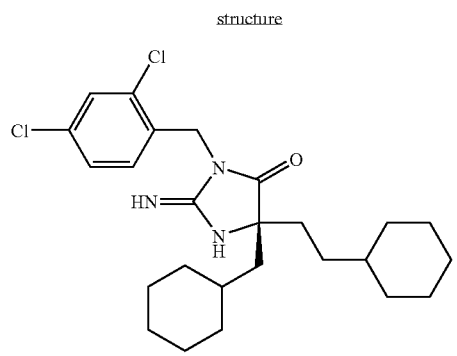

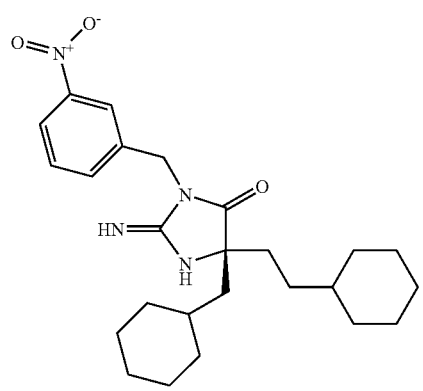

989
-continued
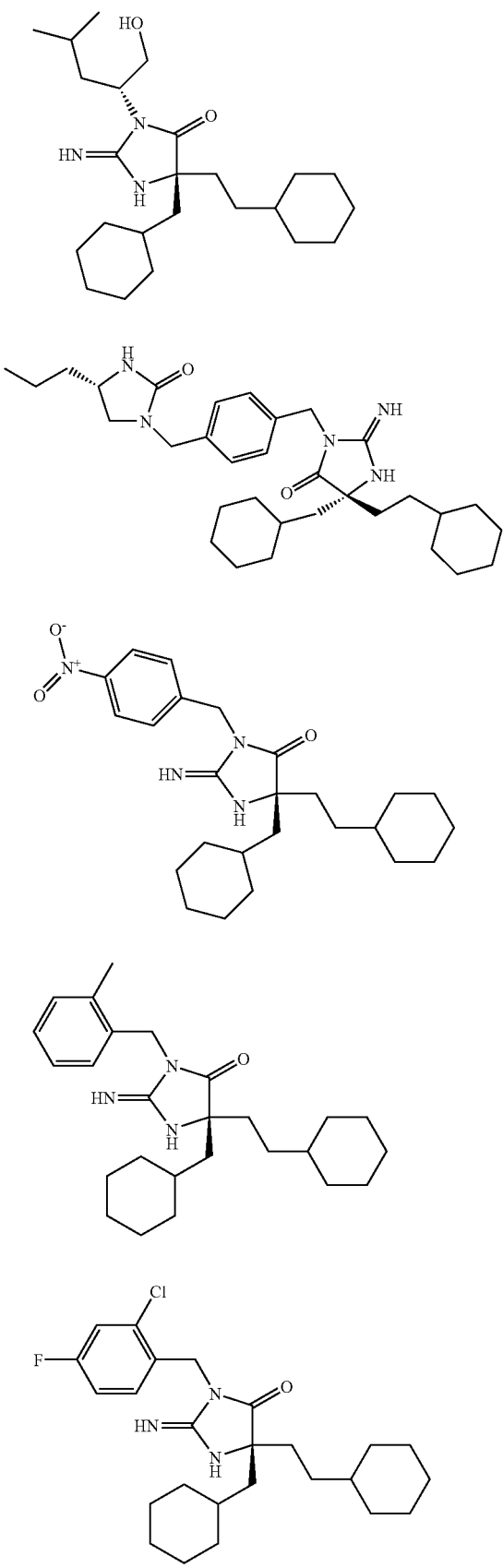
990
-continued
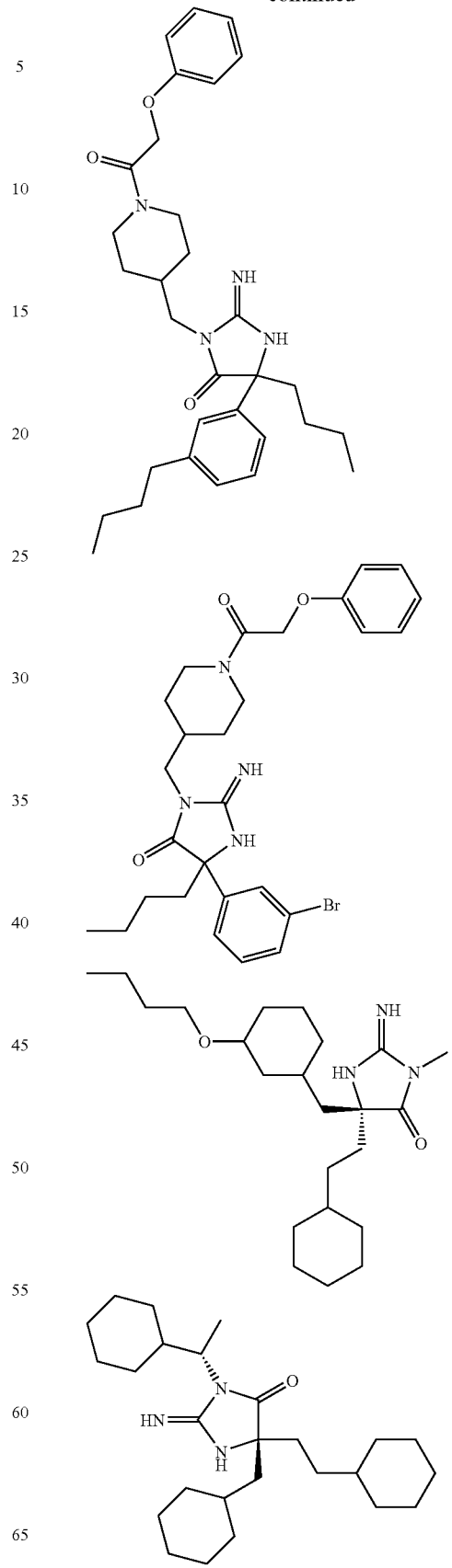

991
-continued
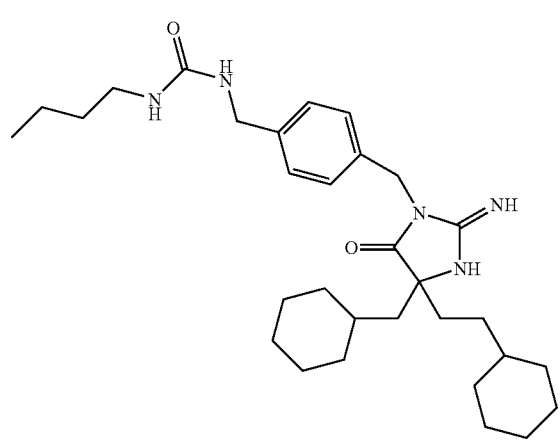
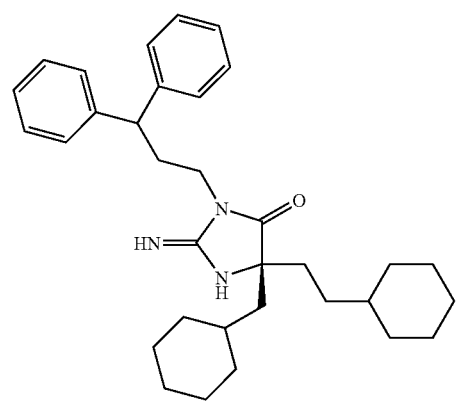
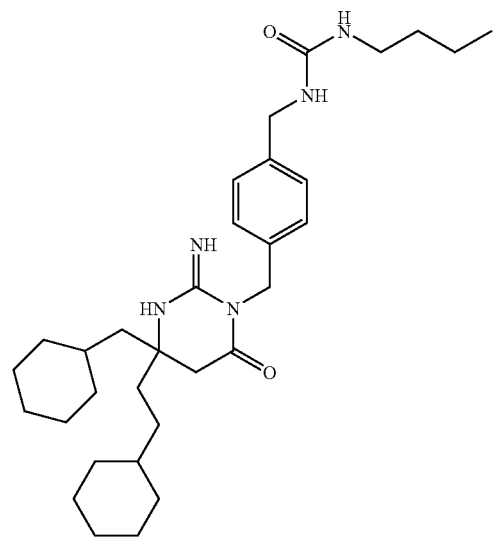
992
-continued
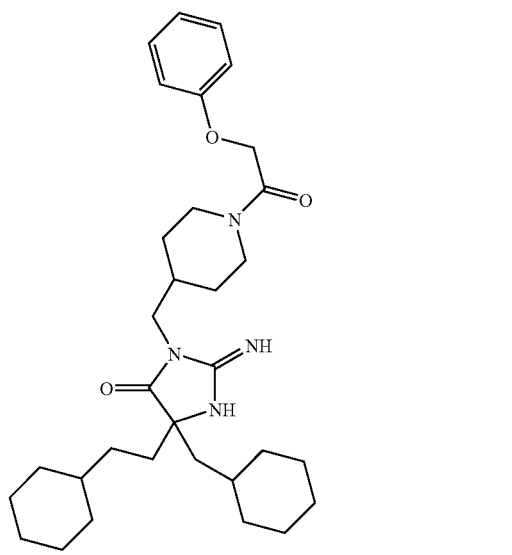
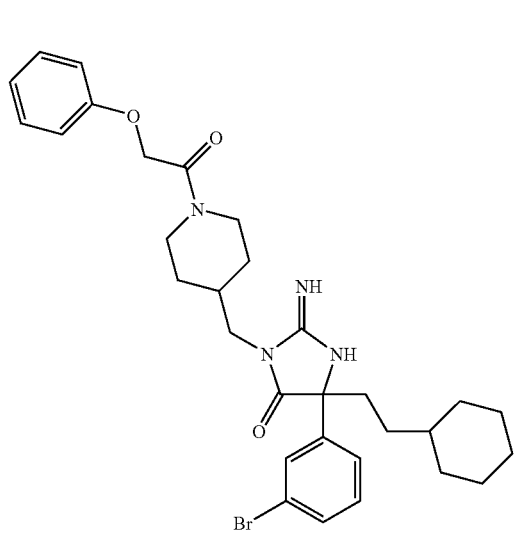
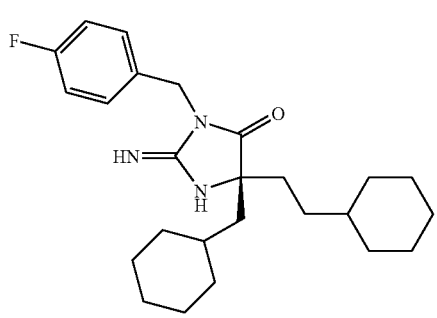

The following compound

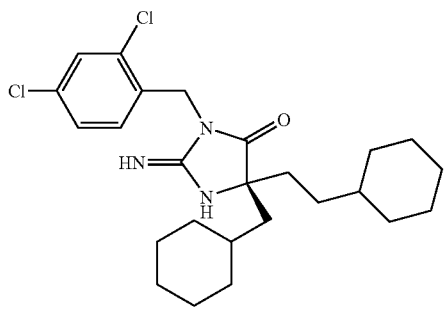

has a hCath D Ki value of 0.45 nM.

BACE-1 Cloning, Protein Expression and Purification

A predicted soluble form of human BACE1 (sBACE1, corresponding to amino acids 1-454) was generated from the full length BACE1 cDNA (full length human BACE1 cDNA in pCDNA4/mycHisA construct; University of Toronto) by PCR using the advantage-GC cDNA PCR kit (Clontech, Palo Alto, Calif.). A HindIII/PmeI fragment from pCDNA4-sBACE1 myc/His was blunt ended using Klenow and subcloned into the Stu I site of PFASTBACI(A) (Invitrogen). A sBACE1 mycHis recombinant bacmid was generated by transposition in DH10Bac cells (GIBCO/BRL). Subsequently, the sBACE1 mycHis bacmid construct was transfected into sf9 cells using CellFectin (Invitrogen, San Diego, Calif.) in order to generate recombinant baculovirus. Sf9 cells were grown in SF 900-II medium (Invitrogen) supplemented with 3% heat inactivated FBS and 0.5× penicillin/streptomycin solution (Invitrogen). Five milliliters of high titer plaque purified sBACEmyc/His virus was used to infect 1 L of logarithmically growing sf9 cells for 72 hours. Intact cells were pelleted by centrifugation at 3000×g for 15 minutes. The supernatant, containing secreted sBACE1, was collected and diluted 50% v/v with 100 mM HEPES, pH 8.0. The diluted medium was loaded onto a Q-sepharose column. The Q-sepharose column was washed with Buffer A (20 mM HEPES, pH 8.0, 50 mM NaCl).

Proteins, were eluted from the Q-sepharose column with Buffer B (20 mM HEPES, pH 8.0, 500 mM NaCl). The protein peaks from the Q-sepharose column were pooled and loaded onto a Ni-NTA agarose column. The Ni-NTA column was then washed with Buffer C (20 mM HEPES, pH 8.0, 500 mM NaCl). Bound proteins were then eluted with Buffer D (Buffer C+250 mM imidazole). Peak protein fractions as determined by the Bradford Assay (Biorad, CA) were concentrated using a Centricon 30 concentrator (Millipore). sBACE1 purity was estimated to be ~90% as assessed by SDS-PAGE and Commassie Blue staining. N-terminal sequencing indicated that greater than 90% of the purified sBACE1 contained the prodomain; hence this protein is referred to as sproBACE1.

Peptide Hydrolysis Assay

The inhibitor, 25 nM EuK-biotin labeled APPsw substrate (EuK-KTEEISEVNLDAEFRHDKC-biotin (SEQ ID NO: 1); CIS-Bio International, France), 5 µM unlabeled APPsw peptide (KTEEISEVNLDAEFRHDK; (SEQ ID NO: 2) American Peptide Company, Sunnyvale, Calif.), 7 nM sproBACE1, 20 mM PIPES pH 5.0, 0.1% Brij-35 (protein grade, Calbiochem, San Diego, Calif.), and 10% glycerol were pre-incubated for 30 min at 30° C. Reactions were initiated by addition of substrate in a 5 µl aliquot resulting in a total volume of 25 µl. After 3 hr at 30° C. reactions were terminated by addition of an equal volume of 2× stop buffer containing 50 mM Tris-HCl pH 8.0, 0.5 M KF, 0.001% Brij-35, 20 µg/ml SA-XL665 (cross-linked allophycocyanin protein coupled to streptavidin; CIS-Bio International, France) (0.5 µg/well). Plates were shaken briefly and spun at 1200×g for 10 seconds to pellet all liquid to the bottom of the plate before the incubation. HTRF measurements were made on a Packard Discovery® HTRF plate reader using 337 nm laser light to excite the sample followed by a 50 µs delay and simultaneous measurements of both 620 nm and 665 nm emissions for 400 µs.

$IC_{50}$ determinations for inhibitors, (1), were determined by measuring the percent change of the relative fluorescence at 665 nm divided by the relative fluorescence at 620 nm, (665/620 ratio), in the presence of varying concentrations of/and a fixed concentration of enzyme and substrate. Nonlinear regression analysis of this data was performed using Graph-Pad Prism 3.0 software selecting four parameter logistic equation, that allows for a variable slope. Y=Bottom+(Top-Bottom)/(1+10^((LogEC50-X)*Hill Slope)); X is the logarithm of concentration of 1, Y is the percent change in ratio and Y starts at bottom and goes to top with a sigmoid shape.

Compounds of the present invention have an $IC_{50}$ range from about 0.001 to about 500 µM, preferably about 0.001 to about 100 µM, more preferably about 0.001 to about 20 µM.

Examples of compounds with human BACE 1 IC50<1 µM are listed below:

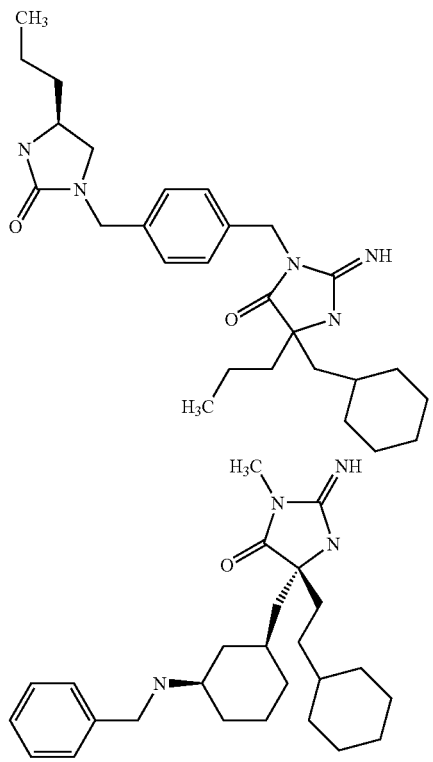

995 996
-continued
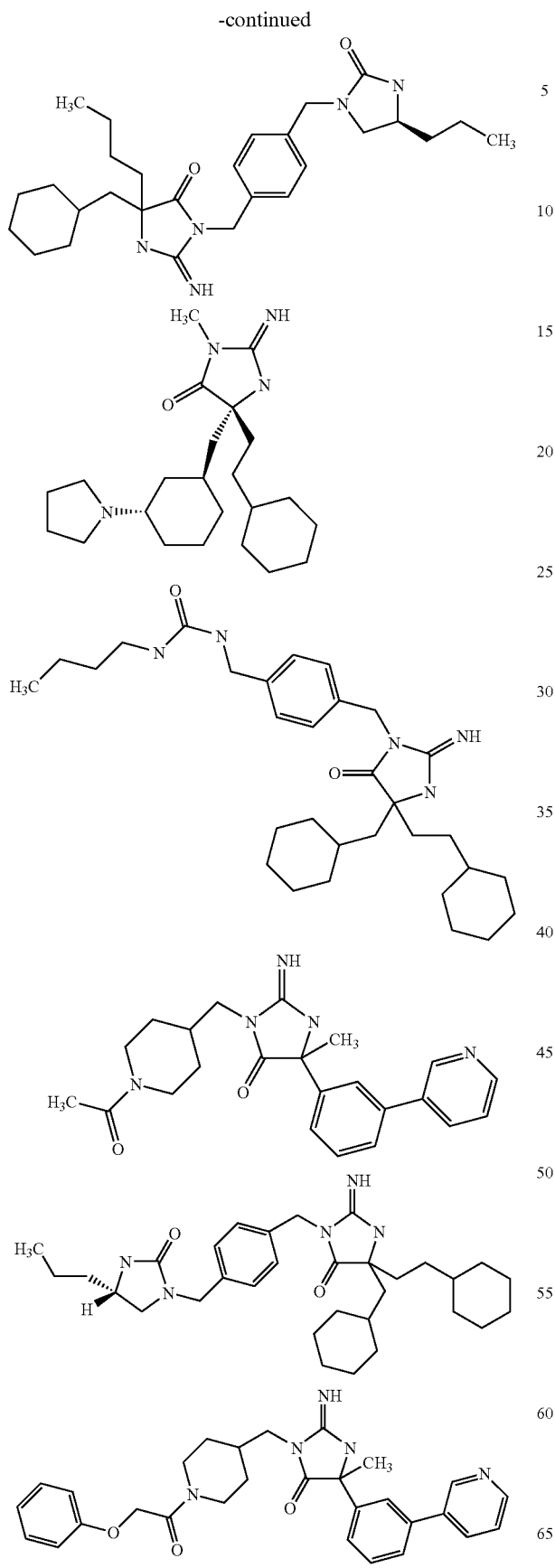
-continued
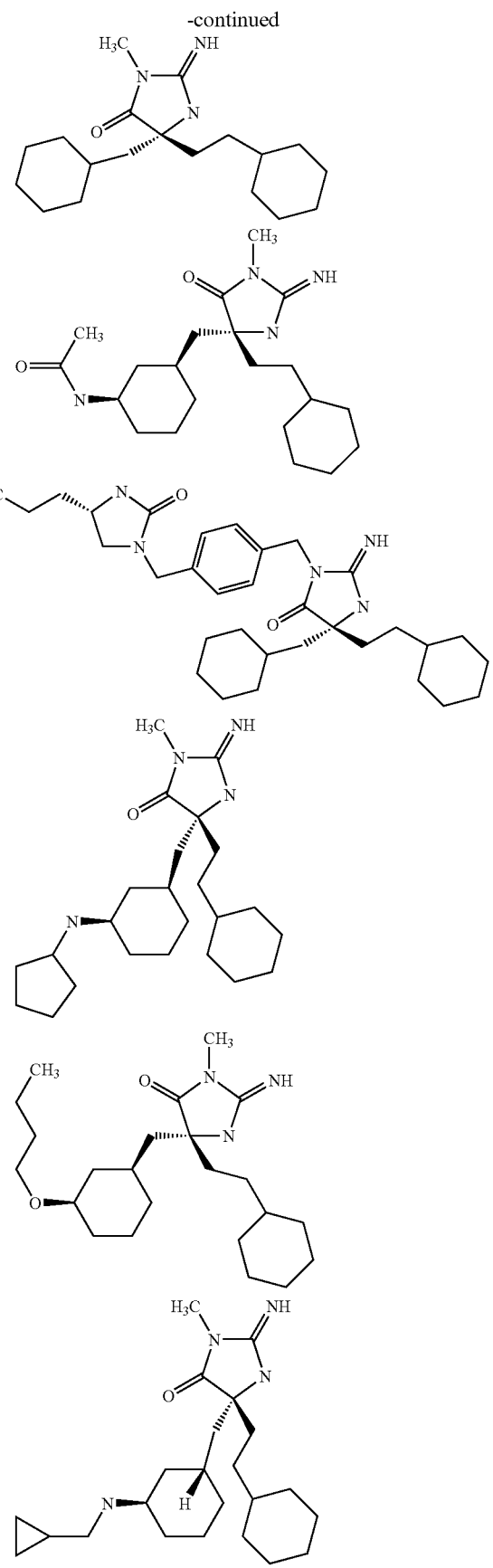

-continued
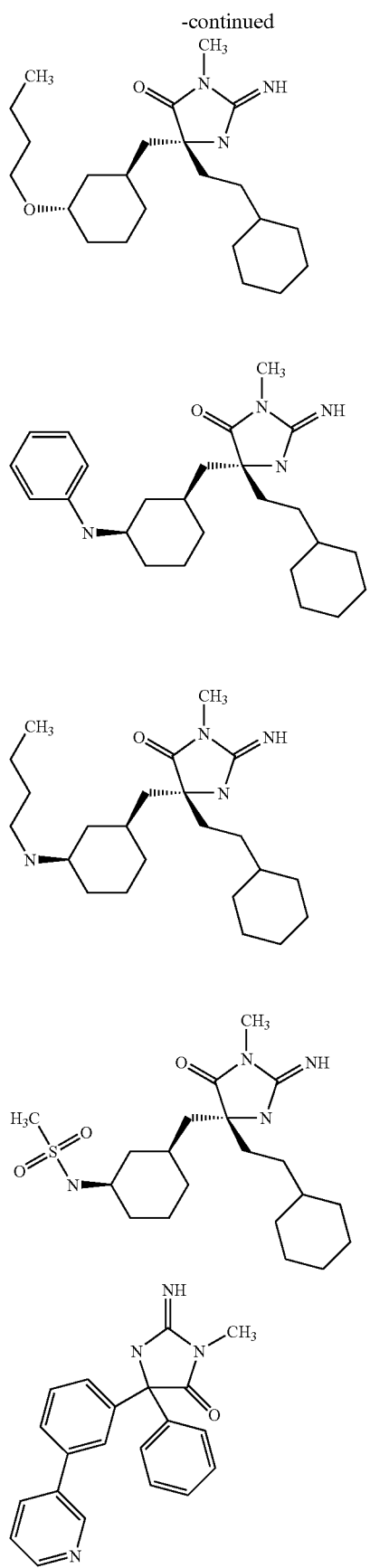
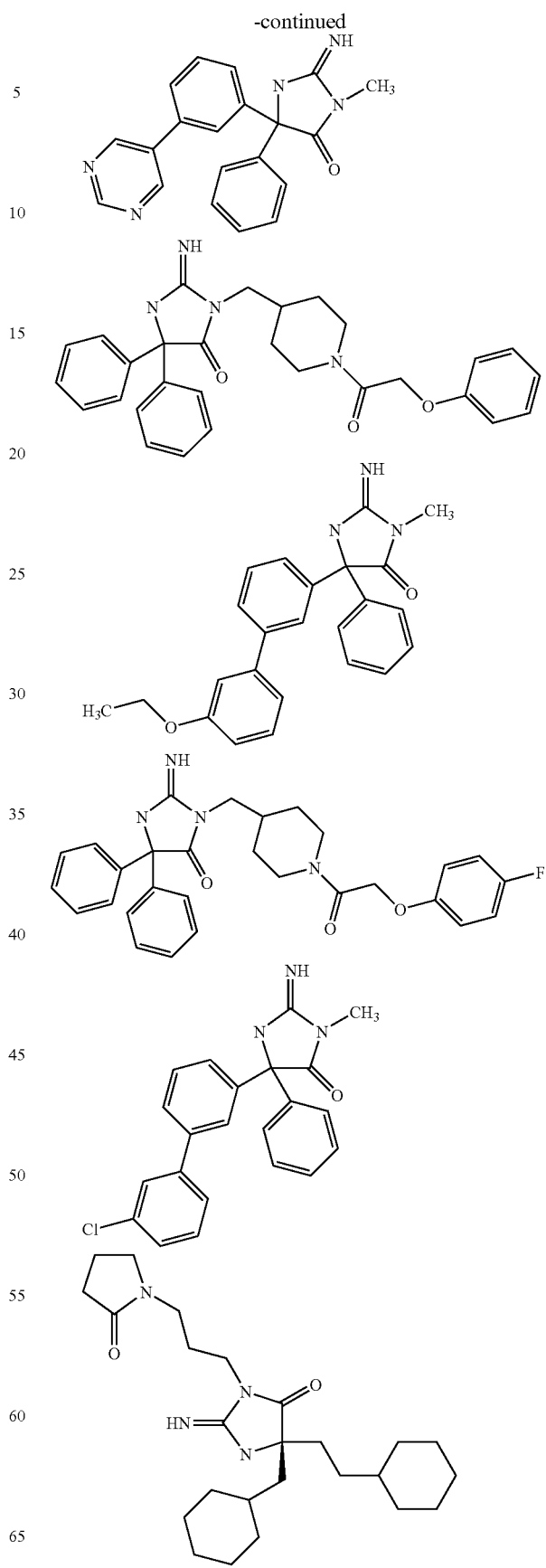

999
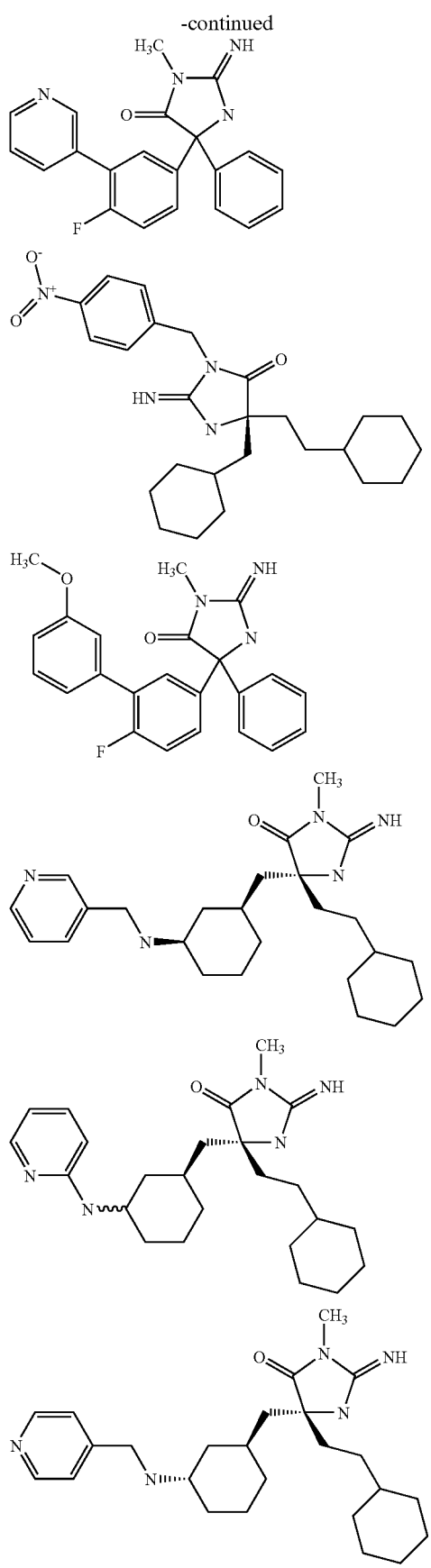
1000
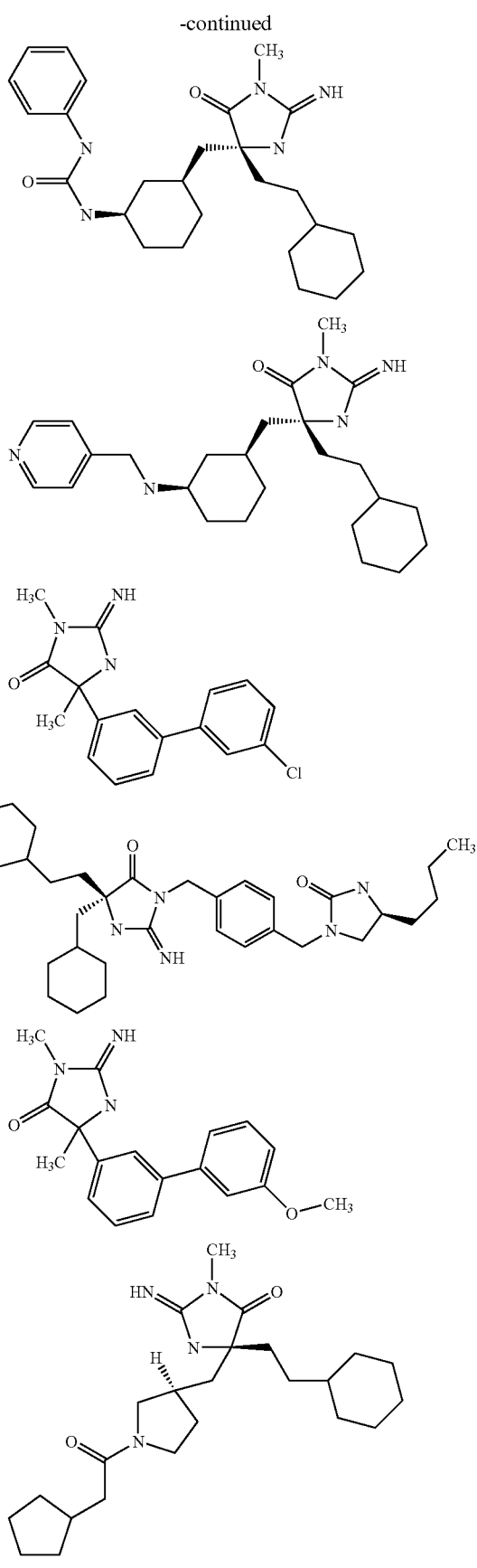

1001
-continued
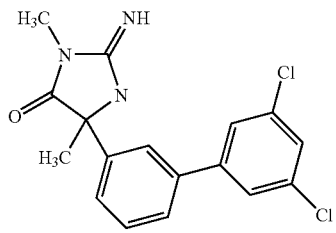
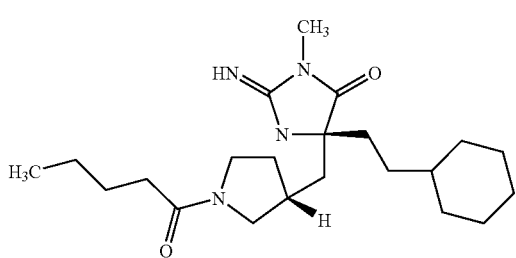
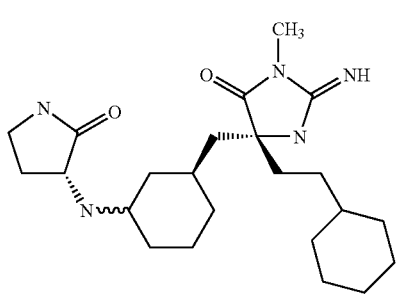
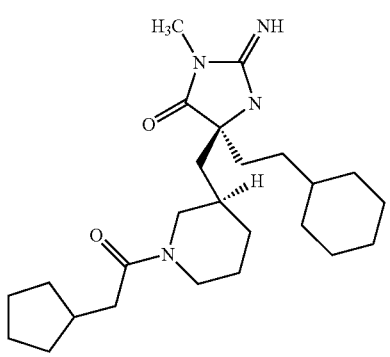
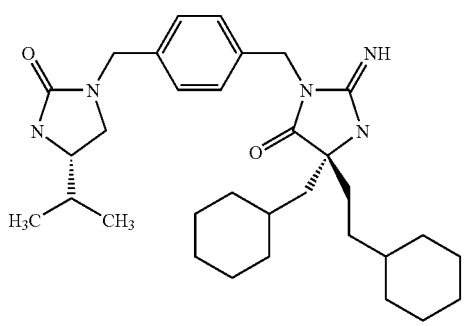
1002
-continued
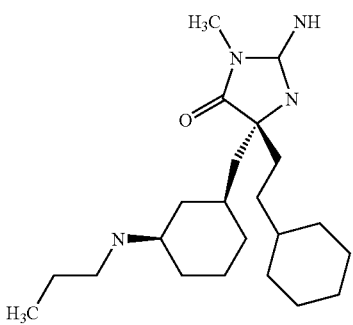
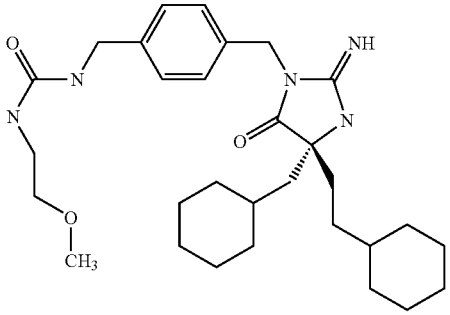
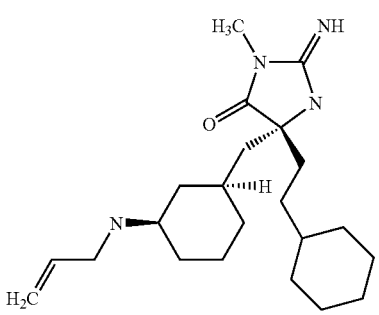
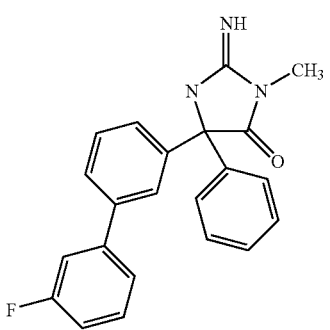

1003

-continued

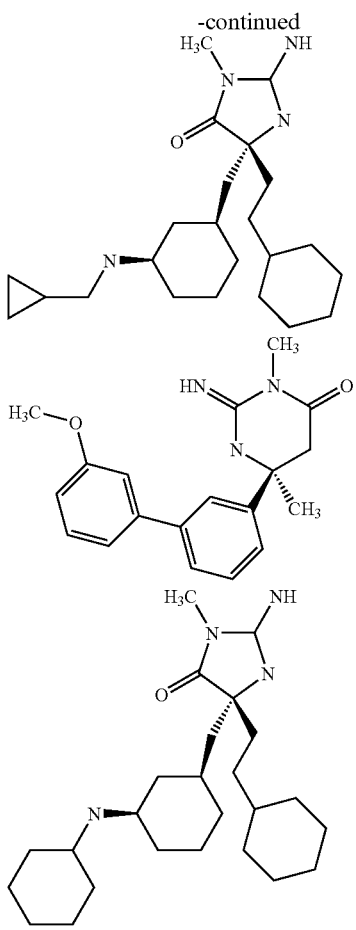

1004

-continued

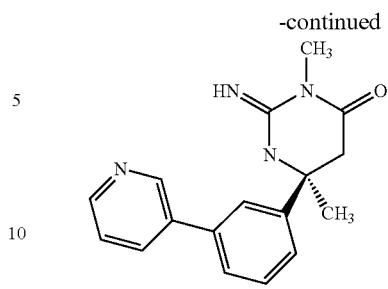

Human Mature Renin Enzyme Assay:

Human Renin was cloned from a human kidney cDNA library and C-terminally epitope-tagged with the V5-6His sequence into pCDNA3.1. pCNDA3.1-Renin-V5-6His was stably expressed in HEK293 cells and purified to >80% using standard Ni-Affinity chromatography. The prodomain of the recombinant human renin-V5-6His was removed by limited proteolysis using immobilized TPCK-trypsin to give mature-human renin. Renin enzymatic activity was monitored using a commercially available fluorescence resonance energy transfer (FRET) peptide substrate, RS-1 (Molecular Probes, Eugene, Oreg.) in 50 mM Tris-HCl pH 8.0, 100 mM NaCl, 0.1% Brij-35 and 5% DMSO buffer for 40 mins at 30 degrees celsius in the presence or absence of different concentrations of test compounds. Mature human Renin was present at approximately 200 nM. Inhibitory activity was defined as the percent decrease in renin induced fluorescence at the end of the 40 min incubation compared to vehicle controls and samples lacking enzyme.

| Compound | 1% of hRenin at 100 μM |
|---|---|
| | 68.8 |
| | 75.3 |

-continued

| Compound | 1% of hRenin at 100 μM |
|---|---|
| [chemical structure] | 76.9 |

In the aspect of the invention relating to a combination of at least one compound of formula I with at least one cholinesterase inhibitor, acetyl- and/or butyrylchlolinesterase inhibitors can be used. Examples of cholinesterase inhibitors are tacrine, donepezil, rivastigmine, galantamine, pyridostigmine and neostigmine, with tacrine, donepezil, rivastigmine and galantamine being preferred. Preferably, these combinations are directed to the treatment of Alzheimer's disease.

In the aspect of the invention relating to a combination of at least one compound of formula I with at least one muscarinic $m_1$ agonist or $m_2$ antagonist can be used. Examples of $m_1$ agonists are known in the art. Examples of $m_2$ antagonists are also known in the art; in particular, $m_2$ antagonists are disclosed in U.S. Pat. Nos. 5,883,096; 6,037,352; 5,889,006; 6,043,255; 5,952,349; 5,935,958; 6,066,636; 5,977,138; 6,294,554; 6,043,255; and 6,458,812; and in WO 03/031412, all of which are incorporated herein by reference.

In other aspects of the invention relating to a combination of at least one compound of formula I and at least one other agent, for example a beta secretase inhibitor; a gamma secretase inhibitor; an HMG-CoA reductase inhibitor such as atorvastatin, lovastatin, simvistatin, pravastatin, fluvastatin and rosuvastatin; non-steroidal anti-inflammatory agents such as, but not necessarily limited to ibuprofen, relafen or naproxen; N-methyl-D-aspartate receptor antagonists such as memantine; anti-amyloid antibodies including humanized monoclonal antibodies; vitamin E; nicotinic acetylcholine receptor agonists; CB1 receptor inverse agonists or CB1 receptor antagonists; antibiotics such as doxycycline; growth hormone secretagogues; histamine H3 antagonists; AMPA agonists; PDE4 inhibitors; GABAA inverse agonists; inhibitors of amyloid aggregation; glycogen synthase kinase beta inhibitors; promoters of alpha secretase activity. Preferably, these combinations are directed to the treatment of Alzheimer's disease.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

When a compound of formula I is used in combination with a cholinesterase inhibitor to treat cognitive disorders, these two active components may be co-administered simultaneously or sequentially, or a single pharmaceutical composition comprising a compound of formula I and a cholinesterase inhibitor in a pharmaceutically acceptable carrier can be administered. The components of the combination can be administered individually or together in any conventional oral or parenteral dosage form such as capsule, tablet, powder, cachet, suspension, solution, suppository, nasal spray, etc. The dosage of the cholinesterase inhibitor can be determined from published material, and may range from 0.001 to 100 mg/kg body weight.

When separate pharmaceutical compositions of a compound of formula I and a cholinesterase inhibitor are to be administered, they can be provided in a kit comprising in a single package, one container comprising a compound of formula I in a pharmaceutically acceptable carrier, and a separate container comprising a cholinesterase inhibitor in a pharmaceutically acceptable carrier, with the compound of formula I and the cholinesterase inhibitor being present in amounts such that the combination is therapeutically effective. A kit is advantageous for administering a combination when, for example, the components must be administered at different time intervals or when they are in different dosage forms.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound, or a stereoisomer, tautomer, or a pharmaceutically acceptable salt thereof, selected from the group consisting of:

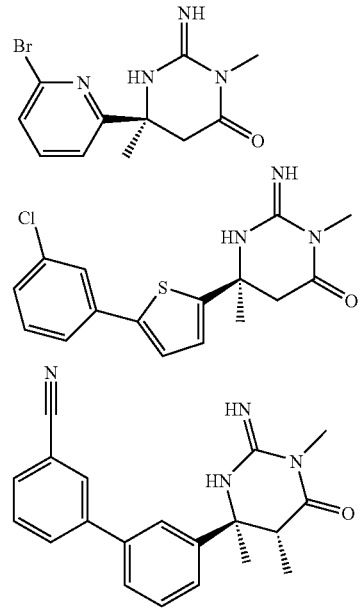

SEQUENCE LISTING

```
<160> NUMBER OF SEQ ID NOS: 2

<210> SEQ ID NO 1
<211> LENGTH: 19
<212> TYPE: PRT
<213> ORGANISM: Artificial Sequence
<220> FEATURE:
<223> OTHER INFORMATION: EuK-biotin labeled APPsw substrate
<220> FEATURE:
<221> NAME/KEY: MISC_FEATURE
<222> LOCATION: (1)..(1)
<223> OTHER INFORMATION: -EuK labeled residue
<220> FEATURE:
<221> NAME/KEY: MISC_FEATURE
<222> LOCATION: (19)..(19)
<223> OTHER INFORMATION: -biotinylated residue

<400> SEQUENCE: 1

Lys Thr Glu Glu Ile Ser Glu Val Asn Leu Asp Ala Glu Phe Arg His
1               5                   10                  15

Asp Lys Cys

<210> SEQ ID NO 2
<211> LENGTH: 18
<212> TYPE: PRT
<213> ORGANISM: Artificial Sequence
<220> FEATURE:
<223> OTHER INFORMATION: unlabeled APPsw peptide

<400> SEQUENCE: 2

Lys Thr Glu Glu Ile Ser Glu Val Asn Leu Asp Ala Glu Phe Arg His
1               5                   10                  15

Asp Lys
```

1009
-continued
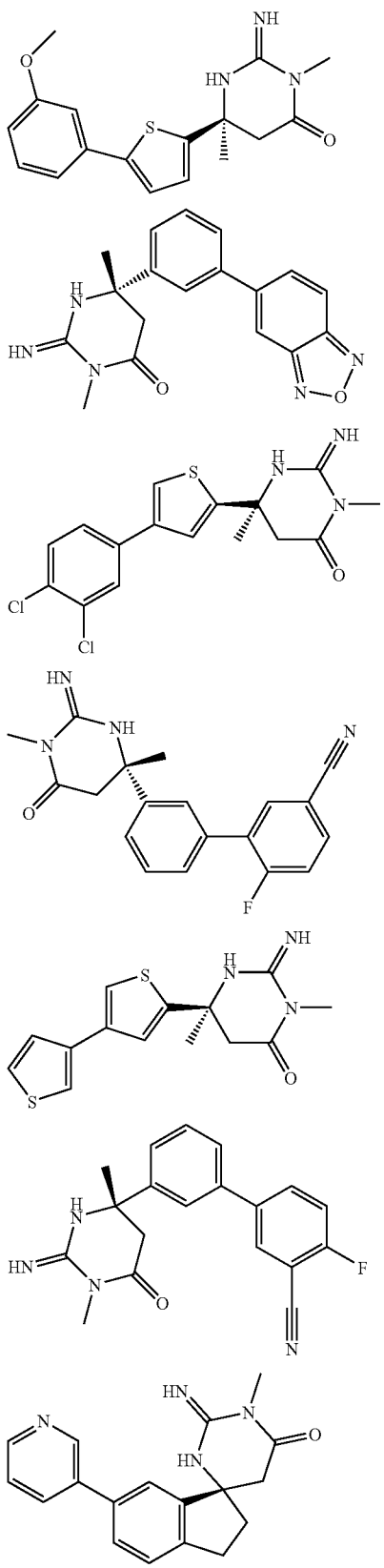
1010
-continued
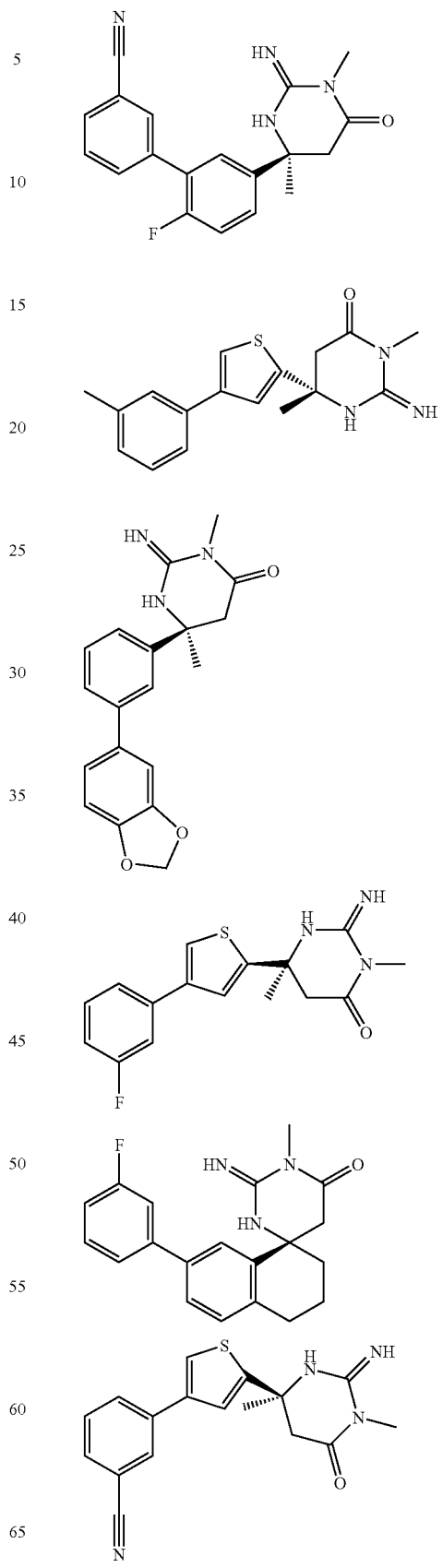

1011
-continued
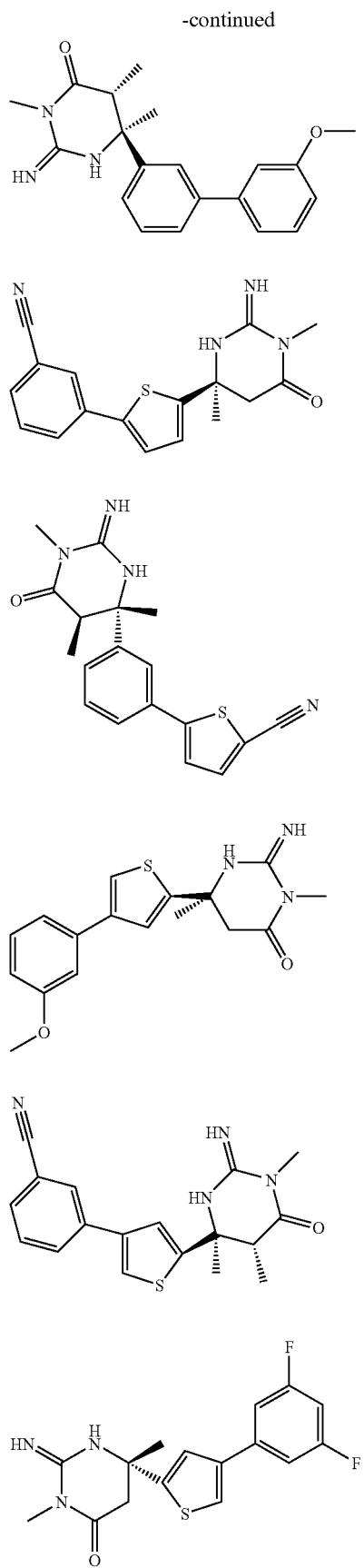
1012
-continued
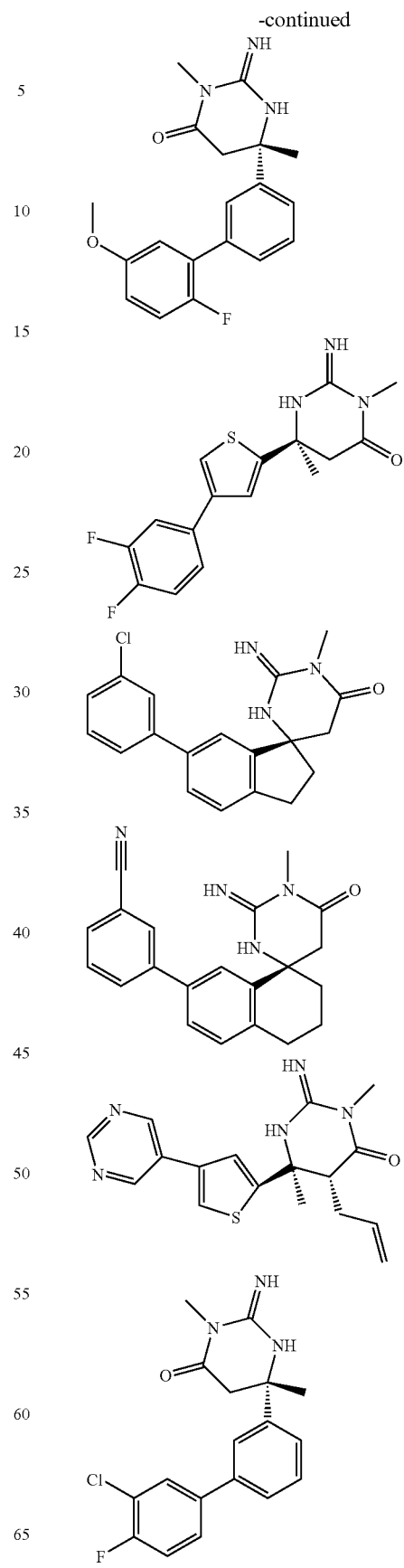

1013
-continued
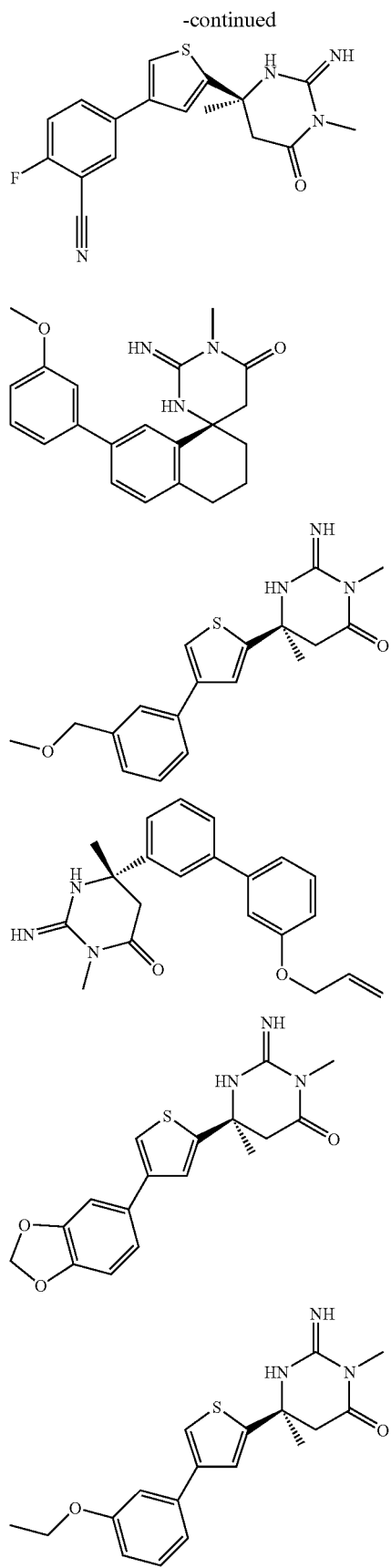
1014
-continued
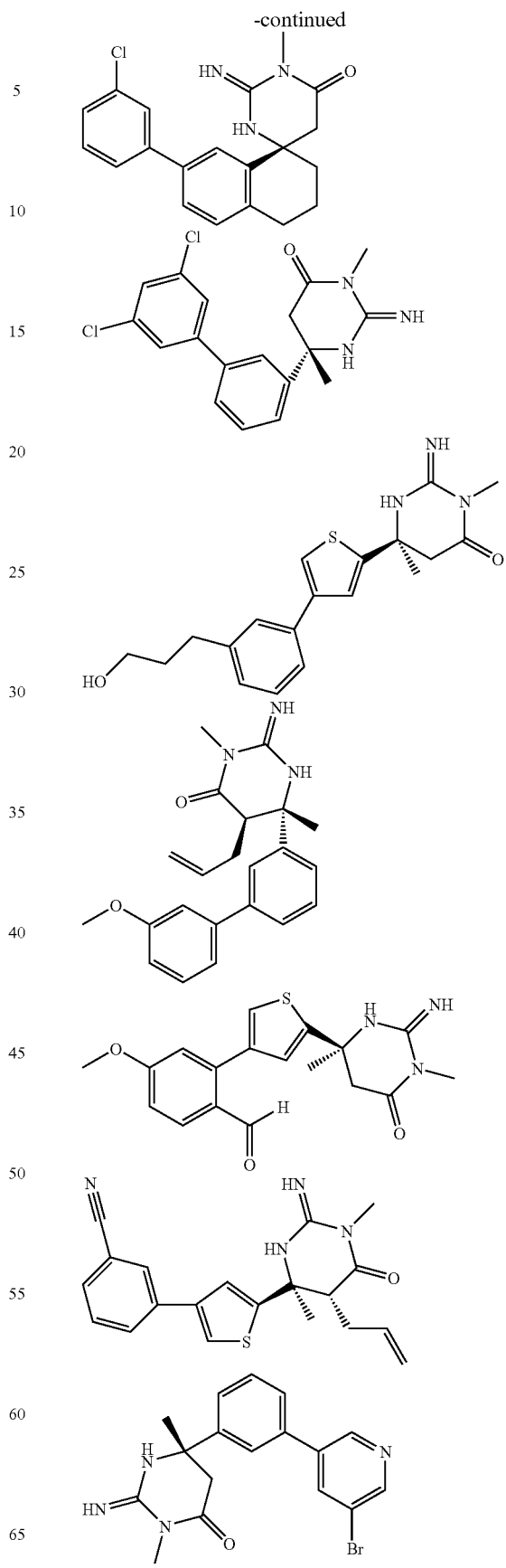

1015
-continued
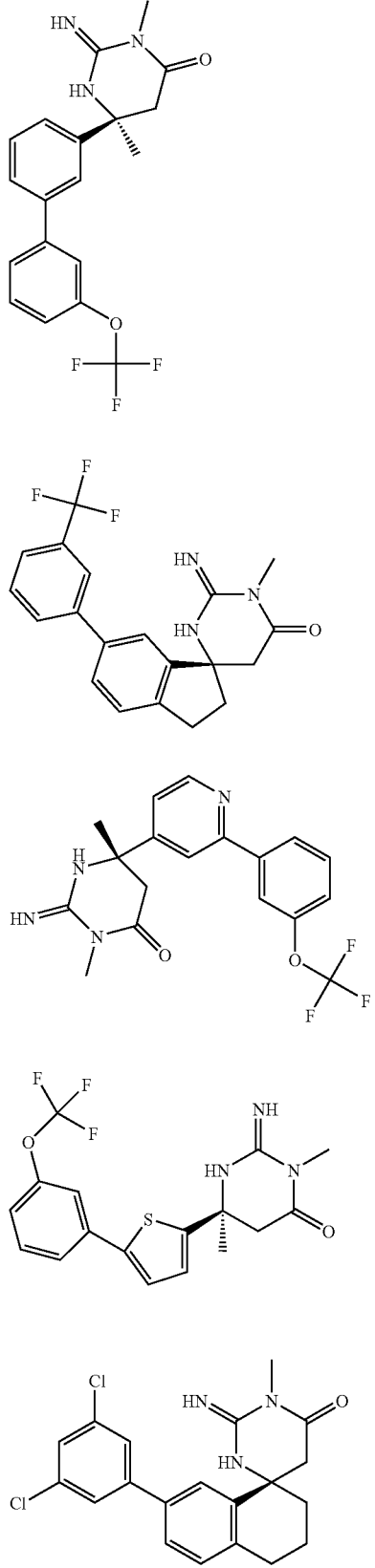
1016
-continued
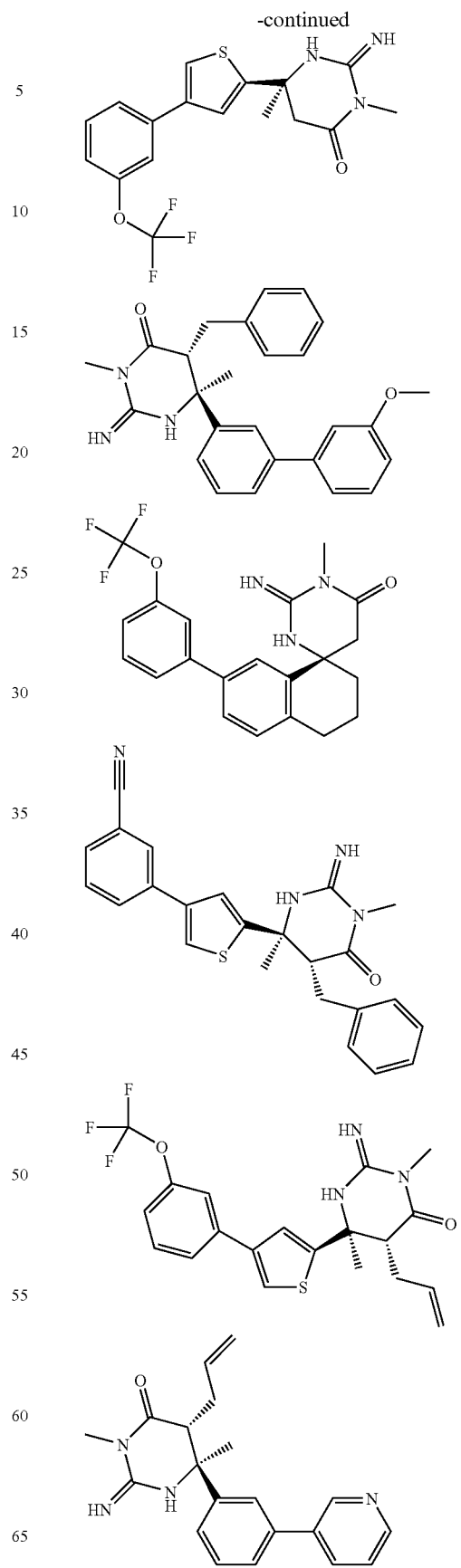

1017
-continued
1018
-continued
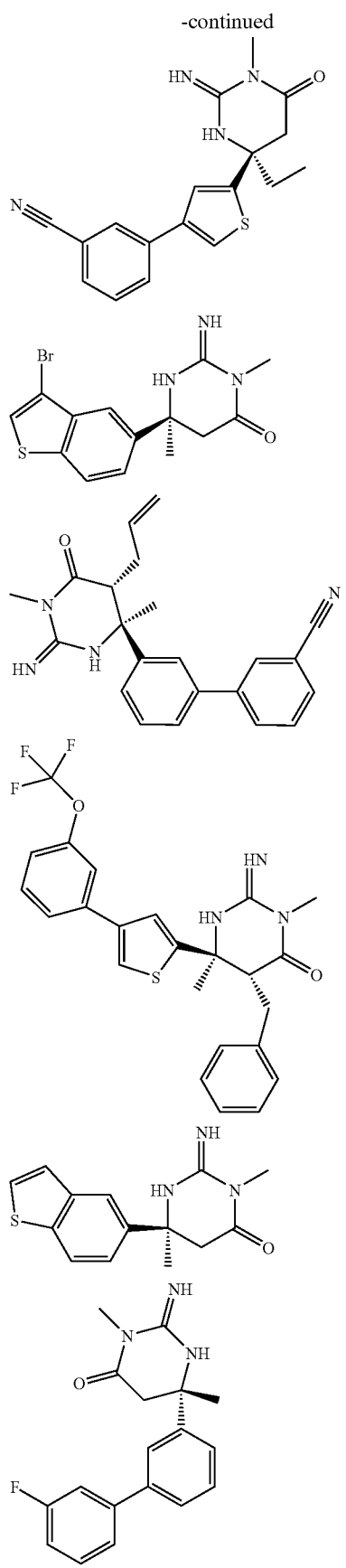
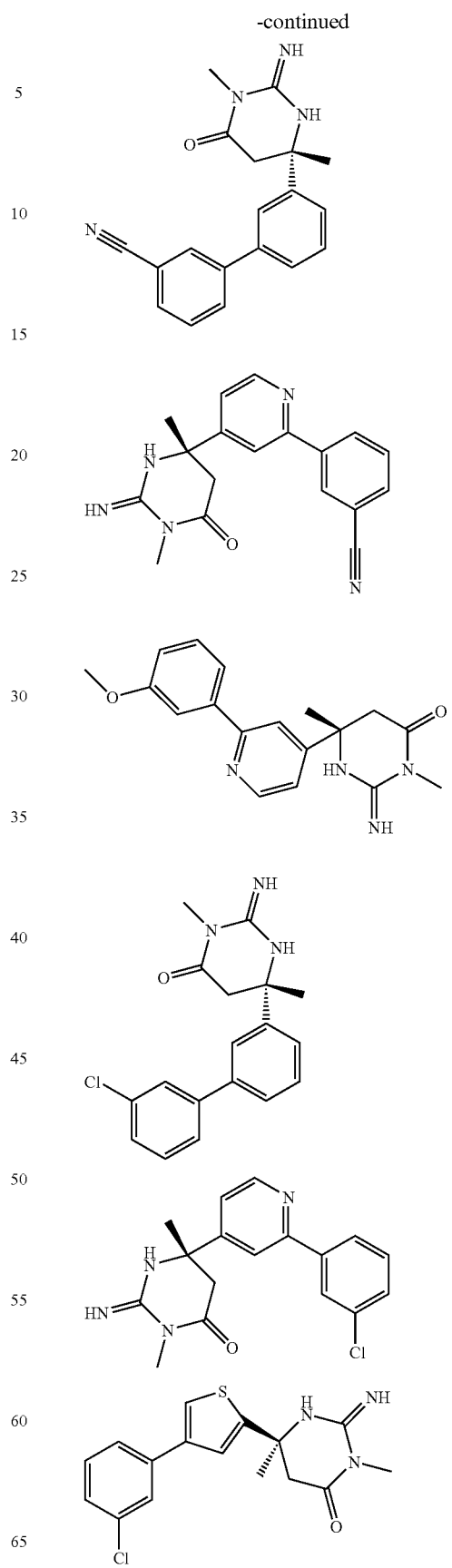

1019

-continued

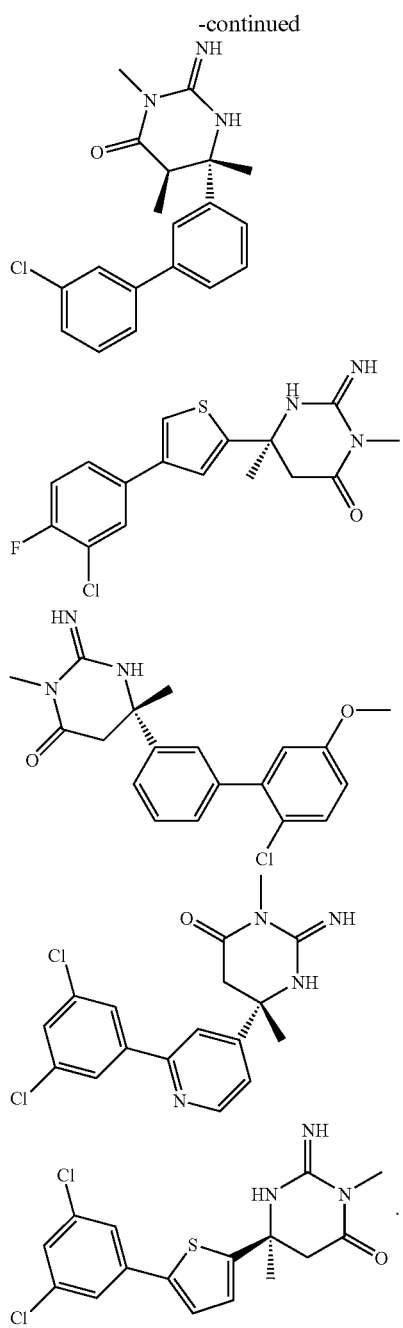

2. A pharmaceutical composition comprising an effective amount of a compound of claim 1, or a stereoisomer, tautomer, or a pharmaceutically acceptable salt thereof, and a pharmaceutically effective carrier.

3. A pharmaceutical composition comprising an effective amount of a compound of claim 1, or a stereoisomer, tautomer, or a pharmaceutically acceptable salt thereof, and an effective amount of a cholinesterase inhibitor or a muscarinic $m_1$ agonist or $m_2$ antagonist in a pharmaceutically effective carrier.

4. A pharmaceutical composition comprising an effective amount of a compound of claim 1, or a stereoisomer, tautomer, or a pharmaceutically acceptable salt thereof, and an effective amount of a gamma secretase inhibitor; an HMG-CoA reductase inhibitor or a non-steroidal anti-inflammatory agent.

5. A compound, or a stereoisomer, tautomer, or a pharmaceutically acceptable salt thereof, selected from the group consisting of:

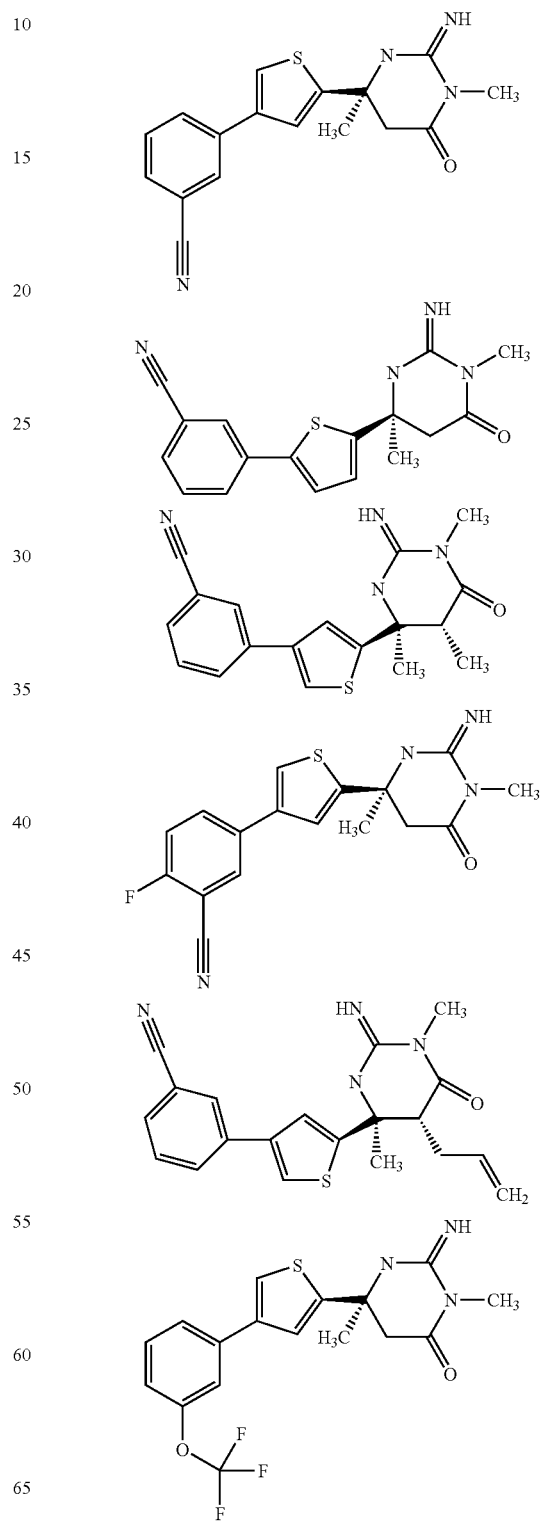

1021

-continued

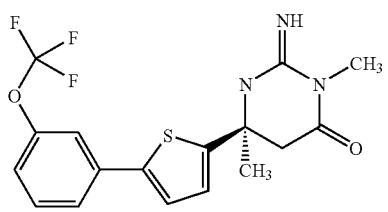

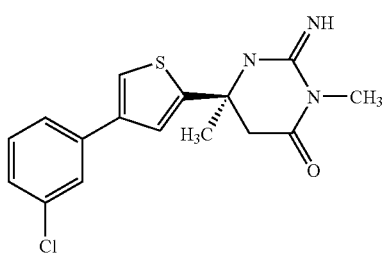

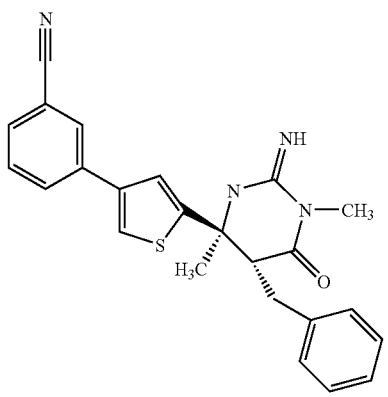

1022

-continued

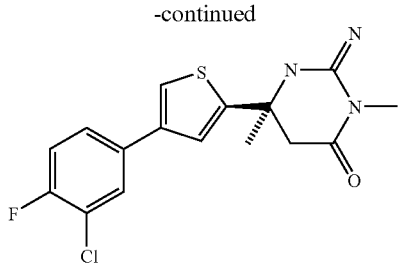

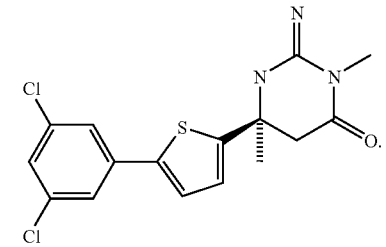

6. A pharmaceutical composition comprising an effective amount of a compound of claim 5, or a stereoisomer, tautomer, or a pharmaceutically acceptable salt thereof, and a pharmaceutically effective carrier.

7. A pharmaceutical composition comprising an effective amount of a compound of claim 5, or a stereoisomer, tautomer, or a pharmaceutically acceptable salt thereof, and an effective amount of a cholinesterase inhibitor or a muscarinic $m_1$ agonist or $m_2$ antagonist in a pharmaceutically effective carrier.

8. A pharmaceutical composition comprising an effective amount of a compound of claim 5, or a stereoisomer, tautomer, or a pharmaceutically acceptable salt thereof, and an effective amount of a gamma secretase inhibitor; an HMG-CoA reductase inhibitor or a non-steroidal anti-inflammatory agent.

* * * * *